(12) United States Patent
Wei et al.

(10) Patent No.: US 6,376,225 B1
(45) Date of Patent: Apr. 23, 2002

(54) ISOLATED HUMAN PHOSPHODIESTERASE PROTEINS, NUCLEIC ACID MOLECULES ENCODING HUMAN PHOSPHODIESTERASE PROTEINS, AND USES THEREOF

(75) Inventors: Ming-Hui Wei, Germantown; Xin Wang, Bethesda; Gennady V. Merkulov, Baltimore; Valentina Di Francesco, Rockville; Ellen M. Beasley, Darnestown, all of MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/754,250

(22) Filed: Jan. 5, 2001

(51) Int. Cl.$^7$ ............................. C12N 9/16; C12N 15/55
(52) U.S. Cl. ..................... 435/196; 435/6; 435/320.1; 536/23.2
(58) Field of Search .................. 435/6, 196, 320.1; 536/23.2

*Primary Examiner*—Charles L. Patterson, Jr.
(74) *Attorney, Agent, or Firm*—Celera Genomics; Lin Sun-Hoffman

(57) ABSTRACT

The present invention provides amino acid sequences of peptides that are encoded by genes within the human genome, the phosphodiesterase peptides of the present invention. The present invention specifically provides isolated peptide and nucleic acid molecules, methods of identifying orthologs and paralogs of the phosphodiesterase peptides, and methods of identifying modulators of the phosphodiesterase peptides.

10 Claims, 101 Drawing Sheets

```
   1 GGGCCGGCGG GCGGGCGGGC GGCTGCGAGC ATGGTCCTGG TGCTGCACCA
  51 CATCCTCATC GCTGTTGTCC AATTCCTCAG GCGGGGCCAG CAGGTCTTCC
 101 TCAAGCCGGA CGAGCCGCCG CCGCCGCCGC AGCCATGCGC CGACAGCCTG
 151 CAGCCAGCCT GGACCCCCTT GCAAAGGAGC CAGGACCCCC AGGGAGTAGA
 201 GACGACCGAC TGGAGGACGC CTTGCTGAGT CTGGGCTCTG TCATCGACAT
 251 TTCAGGCCTG CAACGTGCTG TCAAGGAGGC CCTGTCAGCT GTGCTCCCCC
 301 GAGTGGAAAC TGTCTACACC TACCTACTGG ATGGTGAGTC CCAGCTGGTG
 351 TGTGAGGACC CCCCACATGA GCTGCCCCAG GAGGGGAAAG TCCGGGAGGC
 401 TATCATCTCC CAGAAGCGGC TGGGCTGCAA TGGGCTGGGC TTCTCAGACC
 451 TGCCAGGGAA GCCCTTGGCC AGGCTGGTGG CTCCACTGGC TCCTGATACC
 501 CAAGTGCTGG TCATGCCGCT AGCGGACAAG GAGGCTGGGG CCGTGGCAGC
 551 TGTCATCTTG GTGCACTGTG GCCAGCTGAG TGATAATGAG GAATGGAGCC
 601 TGCAGGCGGT GGAGAAGCAT ACCCTGGTCG CCCTGCGGAG GGTGCAGGTC
 651 CTGCAGCAGC GCGGGCCCAG GGAGGCTCCC CGAGCCGTCC AGAACCCCCC
 701 GGAGGGGACG GCGGAAGACC AGAAGGGCGG GGCGGCGTAC ATCGACCGCG
 751 ACCGCAAGAT CCTCCAACTG TGCGGGGAAC TCTACGACCT GGATGCCTCT
 801 TCCCTGCAGC TCAAAGTGCT CCAATACCTG CAGCAGGAGA CCCGGGCATC
 851 CCGCTGCTGC CTCCTGCTGG TGTCGGAGGA CAATCTCCAG CTTTCTTGCA
 901 AGGTCATCGG AGACAAAGTG CTCGGGGAAG AGGTCAGCTT TCCCTTGACA
 951 GGATGCCTGG GCCAGGTGGT GGAAGACAAG AAGTCCATCC AGCTGAAGGA
1001 CCTCACCTCC GAGGATGTAC AACAGCTGCA GAGCATGTTG GGCTGTGAGC
1051 TGCAGGCCAT GCTCTGTGTC CCTGTCATCA GCCGGGCCAC TGACCAGGTG
1101 GTGGCCTTGG CCTGCGCCTT CAACAAGCTA GAAGGAGACT TGTTCACCGA
1151 CGAGGACGAG CATGTGATCC AGCACTGCTT CCACTACACC AGCACCGTGC
1201 TCACCAGCAC CCTGGCCTTC CAGAAGGAAC AGAAACTCAA GTGTGAGTGC
1251 CAGGCTCTTC TCCAAGTGGC AAAGAACCTC TTCACCCACC TGGATGACGT
1301 CTCTGTCCTG CTCCAGGAGA TCATCACGGA GGCCAGAAAC CTCAGCAACG
1351 CAGAGATCTG CTCTGTGTTC CTGCTGGATC AGAATGAGCT GGTGGCCAAG
1401 GTGTTCGACG GGGGCGTGGT GGATGATGAG AGCTATGAGA TCCGCATCCC
1451 GGCCGATCAG GGCATCGCGG ACACGTGGCC GACCACGGGC CAGATCCTGA
1501 ACATCCCTGA CGCATATGCC CATCCGCTTT TCTACCGCGG CGTGGACGAC
1551 AGCACCGGCT TCCGCACGCG CAACATCCTC TGCTTCCCCA TCAAGAACGA
1601 GAACCAGGAG GTCATCGGTG TGGCCGAGCT GGTGAACAAG ATCAATGGGC
1651 CATGGTTCAG CAAGTTCGAC GAGGACCTGG CGACGGCCTT CTCCATCTAC
1701 TGCGGCATCA GCATCGCCCA TTCTCTCCTA TACAAAAAAG TGAATGAGGC
1751 TCAGTATCGC AGCCACCTGG CCAATGAGAT GATGATGTAC CACATGAAGG
1801 TCTCCGACGA TGAGTATACC AAACTTCTCC ATGATGGGAT CCAGCCTGTG
1851 GCTGCCATTG ACTCCAATTT TGCAAGTTTC ACCTATACCC CTCGTTCCCT
1901 GCCCGAGGAT GACACGTCCA TGGCCATCCT GAGCATGCTG CAGGACATGA
1951 ATTTCATCAA CAACTACAAA ATTGACTGCC CGACCCTGGC CCGGTTCTGT
2001 TTGATGGTGA AGAAGGGCTA CCGGGATCCC CCCTACCACA ACTGGATGCA
2051 CGCCTTTTCT GTCTCCCACT TCTGCTACCT GCTCTACAAG AACCTGGAGC
2101 TCACCAACTA CCTCGAGGAC ATCGAGATCT TTGCCTTGTT TATTTCCTGC
2151 ATGTGTCATG ACCTGGACCA CAGAGGCACA AACAACTCTT TCCAGGTGGC
2201 CTCGAAATCT GTGCTGGCTG CGCTCTACAG CTCTGAGGGC TCCGTCATGG
2251 AGAGGCACCA CTTTGCTCAG GCCATTGCCA TCCTCAACAC CCACGGCTGC
2301 AACATCTTTG ATCATTTCTC CCGGAAGGAC TATCAGCGCA TGCTGGATCT
2351 GATGCGGGAC ATCATCTTGG CCACAGACCT GGCCCACCAT CTCCGCATCT
2401 TCAAGGACCT CCAGAAGATG GCTGAGGTGG CTACGACCG AAACAACAAG
2451 CAGCACCACA GACTTCTCCT CTGCCTCCTC ATGACCTCCT GTGACCTCTC
2501 TGACCAGACC AAGGGCTGGA AGACTACGAG AAAGATCGCG GAGCTGATCT
2551 ACAAAGAATT CTTCTCCCAG GGAGACCTGG AGAAGGCCAT GGGCAACAGG
2601 CCGATGGAGA TGATGGACCG GGAGAAGGCC TATATCCCTG AGCTGCAAAT
2651 CAGCTTCATG GAGCACATTG CAATGCCCAT CTACAAGCTG TTGCAGGACC
2701 TGTTCCCCAA AGCGGCAGAG CTGTATGAGC GCGTGGCCTC CAACCGTGAG
2751 CACTGGACCA AGGTGTCCCA CAAGTTCACC ATCCGCGGCC TCCCAAGTAA
2801 CAACTCGCTG GACTTCCTGG ATGAGGAGTA CGAGGTGCCT GATCTGGATG
2851 GCACTAGGGC CCCCATCAAT GGCTGCTGCA GCCTTGATGC TGAGTGATCC
```

FIGURE 1A

```
2901 CCTCCAGGGA CACTTCCCTG CCCAGGCCAC CTCCCACAGC CCTCCACTGG
2951 TCTGGCCAGA TGCACTGGGA ACAGAGCCAC GGGTCCTGGG TCCTAGACCA
3001 GGACTTCCTG TGTGACCCTG GACAAGTACT ACCTTCCTGG GCCTCAGCTT
3051 TCTCGTCTGT ATAATGGAAG CAAGACTTCC AACCTCACGG AGACTTTGTA
3101 ATTTGTTCTC TGAGAGCACA GGGGTGACCA ATGAGCAGTG GGCCCTACTC
3151 TGCACCTCTG ACCACACCTT GGCAAGTCTT TCCCAAGCCA TTCTTTGTCT
3201 GAGCAGCTTG ATGGTTTCTC CTTGCCCCAT TTCTGCCCCA CCAGATCTTT
3251 GCTCCTTTCC CTTTGAGGAC TCCCACCCTT TGGGGTCTCC AGGATCCTCA
3301 TGGAAGGGGA AGGTGAGACA TCTGAGTGAG CAGAGTGTGG CATCTTGGAA
3351 ACAGTCCTTA GTTCTGTGGG AGGACTAGAA ACAGCCGCGG GGCGAAGGCC
3401 CCCTGAGGAC CACTACTATA CTGATGGTGG GATTGGGACC TGGGGGATAC
3451 AGGGGCCCCA GGAAGAAGCT GCCAGAGGGG CAGCTCAGTG CTCTGCAGAG
3501 AGGGGCCCTG GGGAGAAGCA GGATGGGATT GATGGGCAGG AGGGATCCCC
3551 GCACTGGGAG ACAGGCCCAG GTATGAATGA GCCAGCCATG CTTCCTCCTG
3601 CCTGTGTGAC GCTGGGCGAG TCTCTTCCCC TGTCTGGGCC AAACAGGGAG
3651 CGGGTAAGAC AATCCATGCT CTAAGATCCA TTTTAGATCA ATGTCTAAAA
3701 TAGCTCTATC GCTCTGCGGA GTCCCAGCAG AGGCTATGGA ATGTTTCTGC
3751 AACCCTAAGG CACAGAGAGC CCAACCCTGA GTGTCTCAGA GGCCCCCTGA
3801 GTGTTCCCCT TGGCCTGAGC CCCTTACCCA TTCCTGCAGC CAGTGAGAGA
3851 CCTGGCCTCA GCCCTGGCAG GGCTCTCTCT TCAAGGCCAT ATCCACCTGT
3901 GCCCTGGGGC TTGGGAGACC CCATAGGGCC GGGACTCTTG GGTCAGCCCG
3951 GCCACTGGCT TCTCTCTTTT TCTCCGTTTC ATTCTGTGTG CGTTGTGGGG
4001 TGGGGGAGGG GGTCCACCTG CCTTACCTTT CTGAGTTGCC TTTAGAGAGA
4051 TGCGTTTTTC TAGGACTCTG TGCAACTGTC GTATATGGTC CCGTGGGCTG
4101 ACCGCTTTGT ACATGAGAAT AAATCTATTT CTTTCTACCA GAAAAAAAAA
4151 AAAAAAAAAA AAAAAAAAAA A (SEQ ID NO:1)
```

FEATURES:
5' UTR: 1-134
Start: 135
Stop: 2734
3" UTR: 2735-4171

Homologous proteins:
Top BLAST Hits

```
                                                                      Score     E
gi|4505657|ref|NP_002590.1| phosphodiesterase 2A, cGMP-stimulat...    1821    0.0
gi|116569|sp|P14099|CN2A_BOVIN CGMP-DEPENDENT 3',5'-CYCLIC PHOS...    1769    0.0
gi|1184300|gb|AAA87353.1| (L49503) cGMP-stimulated cyclic nucle...    1746    0.0
gi|11439394|ref|XP_006369.1| phosphodiesterase 2A, cGMP-stimula...    1712    0.0
gi|1705944|sp|Q01062|CN2A_RAT CGMP-DEPENDENT 3',5'-CYCLIC PHOSP...    1677    0.0
gi|280898|pir||A60179 3',5'-cyclic-nucleotide phosphodiesterase...    1245    0.0
gi|3868997|dbj|BAA34308.1| (AB017022) EFPDE2 [Ephydatia fluviat...     628   e-179
gi|10716052|dbj|BAB16371.1| (AB036704) phosphodiesterase 11A [H...     368   e-100
gi|7298454|gb|AAF53675.1| (AE003659) CG10231 gene product [Dros...     362    8e-99
gi|732209|sp|P30645|YNE6_CAEEL PROBABLE 3',5'-CYCLIC PHOSPHODIE...     358    2e-97
gi|102513|pir||S24462 probable 3',5'-cyclic-nucleotide phosphod...     358    2e-97
gi|10716054|dbj|BAB16372.1| (AB038041) phosphodiesterase 11A2 [...     354    2e-96
gi|6683035|dbj|BAA88997.1| (AB027156) PDE10A3 [Rattus norvegicus]      336    6e-91
gi|6683033|dbj|BAA88996.1| (AB027155) PDE10A2 [Rattus norvegicus]      336    6e-91
gi|10716139|dbj|BAB16383.1| (AB041798) phosphodiesterase 10A1 (...     333    7e-90
gi|8218102|emb|CAB92797.1| (AL117345) dJ416F21.1 (phosphodieste...     333    7e-90
gi|5902442|dbj|BAA84467.1| (AB026816) 3',5'-cyclic nucleotide p...     333    7e-90
```

FIGURE 1B

BLAST to dbEST:

```
                                                              Score    E
gb|AI333063|AI333063 qq17c03.x1 Soares_NhHMPu_S1 Homo sapiens c...  876   0.0
gb|AL119545|AL119545 DKFZp761B1623_r1 761 (synonym: hamy2) Homo... 763   0.0
gb|T33047|T33047 EST56468 Human Brain Homo sapiens cDNA 5' end ... 743   0.0
gb|AL046901|AL046901 DKFZp586G1217_r1 586 (synonym: hute1) Homo... 743   0.0
gb|T09162|T09162 EST07055 Infant Brain, Bento Soares Homo sapie... 692   0.0
gb|BE938766|BE938766 RC3-TN0093-280800-012-h11 TN0093 Homo sapi... 670   0.0
gb|BE543869|BE543869 601071557F1 NIH_MGC_12 Homo sapiens cDNA c... 658   0.0
gb|T66230|T66230 yc77d06.r1 Soares infant brain 1NIB Homo sapie... 620  e-175
gb|BE546407|BE546407 601070912F1 NIH_MGC_12 Homo sapiens cDNA c... 620  e-175
gb|BF346926|BF346926 602021761F1 NCI_CGAP_Brn67 Homo sapiens cD... 575  e-161
gb|AA188568|AA188568 zp78c04.s1 Stratagene HeLa cell s3 937216 ... 571  e-160
```

EXPRESSION INFORMATION FOR MODULATORY USE:
library source:
Expression information from BLAST dbEST hits:
gb|AI333063|AI333063  Pooled melanocyte, fetal heart, pregnant uterus
gb|AL119545|AL119545  Amygdala
gb|T33047|T33047  Brain
gb|AL046901|AL046901  Uterus
gb|T09162|T09162  Infant brain
gb|BE938766|BE938766  testis
gb|BE543869|BE543869  Placenta Choriocarcinoma
gb|T66230|T66230  Infant brain
gb|BE546407|BE546407  Placenta choriocarcinoma
gb|BF346926|BF346926  Brain
gb|AA188568|AA188568  Hela cells Expression information from PCR-based tissue screening panels:
whole brain

FIGURE 1C

```
  1 MRRQPAASLD PLAKEPGPPG SRDDRLEDAL LSLGSVIDIS GLQRAVKEAL
 51 SAVLPRVETV YTYLLDGESQ LVCEDPPHEL PQEGKVREAI ISQKRLGCNG
101 LGFSDLPGKP LARLVAPLAP DTQVLVMPLA DKEAGAVAAV ILVHCGQLSD
151 NEEWSLQAVE KHTLVALRRV QVLQQRGPRE APRAVQNPPE GTAEDQKGGA
201 AYIDRDRKIL QLCGELYDLD ASSLQLKVLQ YLQQETRASR CCLLLVSEDN
251 LQLSCKVIGD KVLGEEVSFP LTGCLGQVVE DKKSIQLKDL TSEDVQQLQS
301 MLGCELQAML CVPVISRATD QVVALACAFN KLEGDLFTDE DEHVIQHCFH
351 YTSTVLTSTL AFQKEQKLKC ECQALLQVAK NLFTHLDDVS VLLQEIITEA
401 RNLSNAEICS VFLLDQNELV AKVFDGGVVD DESYEIRIPA DQGIAGHVAT
451 TGQILNIPDA YAHPLFYRGV DDSTGFRTRN ILCFPIKNEN QEVIGVAELV
501 NKINGPWFSK FDEDLATAFS IYCGISIAHS LLYKKVNEAQ YRSHLANEMM
551 MYHMKVSDDE YTKLLHDGIQ PVAAIDSNFA SFTYTPRSLP EDDTSMAILS
601 MLQDMNFINN YKIDCPTLAR FCLMVKKGYR DPPYHNVVHA FSVSHFCYLL
651 YKNLELTNYL EDIEIFALFI SCMCHDLDHR GTNNSFQVAS KSVLAALYSS
701 EGSVMERHHF AQAIAILNTH GCNIFDHFSR KDYQRMLDLM RDIILATDLA
751 HHLRIFKDLQ KMAEVGYDRN NKQHHRLLLC LLMTSCDLSD QTKGWKTTRK
801 IAELIYKEFF SQGDLEKAMG NRPMEMMDRE KAYIPELQIS FMEHIAMPIY
851 KLLQDLFPKA AELYERVASN REHWTKVSHK FTIRGLPSNN SLDFLDEEYE
901 VPDLDGTRAP INGCCSLDAE (SEQ ID NO:2)
```

FEATURES:
Functional domains and key regions:
[1] PDOC00001 PS00001 ASN_GLYCOSYLATION
N-glycosylation site Number of matches: 3
    1    402-405 NLSN
    2    683-686 NNSF
    3    889-892 NNSL

[2] PDOC00005 PS00005 PKC_PHOSPHO_SITE
Protein kinase C phosphorylation site

Number of matches: 9
    1     92-94  SQK
    2    254-256 SCK
    3    585-587 TPR
    4    729-731 SRK
    5    797-799 TTR
    6    798-800 TRK
    7    869-871 SNR
    8    878-880 SHK
    9    882-884 TIR

[3] PDOC00006 PS00006 CK2_PHOSPHO_SITE
Casein kinase II phosphorylation site

Number of matches: 17
    1     21-24  SRDD
    2     35-38  SVID
    3    149-152 SDNE
    4    192-195 TAED
    5    291-294 TSED
    6    338-341 TDED
    7    384-387 THLD
    8    404-407 SNAE
    9    509-512 SKFD
   10    557-560 SDDE

FIGURE 2A

```
    11    588-591  SLPE
    12    703-706  SVME
    13    729-732  SRKD
    14    784-787  TSCD
    15    811-814  SQGD
    16    840-843  SFME
    17    869-872  SNRE
```

[4] PDOC00007 PS00007 TYR_PHOSPHO_SITE
Tyrosine kinase phosphorylation site

```
Number of matches: 6
    1    534-541  KKVNEAQY
    2    555-561  KVSDDEY
    3    627-634  KGYRDPPY
    4    652-659  KNLELTNY
    5    761-767  KMAEVGY
    6    799-806  RKIAELIY
```

[5] PDOC00008 PS00008 MYRISTYL
N-myristoylation site

```
Number of matches: 8
    1     41-46   GLQRAV
    2    100-105  GLGFSD
    3    135-140  GAVAAV
    4    452-457  GQILNI
    5    469-474  GVDDST
    6    524-529  GISIAH
    7    681-686  GTNNSF
    8    885-890  GLPSNN
```

[6] PDOC00116 PS00126 PDEASE_I
3'5'-cyclic nucleotide phosphodiesterases signature

```
          675-686  HDLDHRGTNNSF
```

Membrane spanning structure and domains:
```
  Helix  Begin   End   Score  Certainty
    1    297    317   0.713  Putative
    2    343    363   0.863  Putative
    3    514    534   1.277  Certain
    4    632    652   0.613  Putative
```

BLAST Alignment to Top Hit:
Alignment to human cyclic nucleotide phosphodiesterase PDE2A3:
>gi|4505657|ref|NP_002590.1| phosphodiesterase 2A, cGMP-stimulated;
       Human cGMP-stimulated 3',5'-cyclic nucleotide
       phosphodiesterase PDE2A3 (PDE2A) mRNA, complete cds
       [Homo sapiens]
  sp|O00408|CN2A_HUMAN CGMP-DEPENDENT 3',5'-CYCLIC PHOSPHODIESTERASE (CYCLIC GMP
       STIMULATED PHOSPHODIESTERASE) (CGS-PDE)
  gb|AAC51320.1| (U67733) PDE2A3 [Homo sapiens]
       Length = 941

Score = 1821 bits (4665), Expect = 0.0

FIGURE 2B

Identities = 897/905 (99%), Positives = 898/905 (99%)

```
Query:  16 PGPPGSRDDRLEDALLSLGSVIDISGLQRAVKEALSAVLPRVETVYTYLLDGESQLVCED  75
            P PP     D L+DALLSLGSVIDISGLQRAVKEALSAVLPRVETVYTYLLDGESQLVCED
Sbjct:  37 PPPPQPCADSLQDALLSLGSVIDISGLQRAVKEALSAVLPRVETVYTYLLDGESQLVCED  96

Query:  76 PPHELPQEGKVREAIISQKRLGCNGLGFSDLPGKPLARLVAPLAPDTQVLVMPLADKEAG 135
            PPHELPQEGKVREAIISQKRLGCNGLGFSDLPGKPLARLVAPLAPDTQVLVMPLADKEAG
Sbjct:  97 PPHELPQEGKVREAIISQKRLGCNGLGFSDLPGKPLARLVAPLAPDTQVLVMPLADKEAG 156

Query: 136 AVAAVILVHCGQLSDNEEWSLQAVEKHTLVALRRVQVLQQRGPREAPRAVQNPPEGTAED 195
            AVAAVILVHCGQLSDNEEWSLQAVEKHTLVALRRVQVLQQRGPREAPRAVQNPPEGTAED
Sbjct: 157 AVAAVILVHCGQLSDNEEWSLQAVEKHTLVALRRVQVLQQRGPREAPRAVQNPPEGTAED 216

Query: 196 QKGGAAYIDRDRKILQLCGELYDLDASSLQLKVLQYLQQETRASRCCLLLVSEDNLQLSC 255
            QKGGAAY DRDRKILQLCGELYDLDASSLQLKVLQYLQQETRASRCCLLLVSEDNLQLSC
Sbjct: 217 QKGGAAYTDRDRKILQLCGELYDLDASSLQLKVLQYLQQETRASRCCLLLVSEDNLQLSC 276

Query: 256 KVIGDKVLGEEVSFPLTGCLGQVVEDKKSIQLKDLTSEDVQQLQSMLGCELQAMLCVPVI 315
            KVIGDKVLGEEVSFPLTGCLGQVVEDKKSIQLKDLTSEDVQQLQSMLGCELQAMLCVPVI
Sbjct: 277 KVIGDKVLGEEVSFPLTGCLGQVVEDKKSIQLKDLTSEDVQQLQSMLGCELQAMLCVPVI 336

Query: 316 SRATDQVVALACAFNKLEGDLFTDEDEHVIQHCFHYTSTVLTSTLAFQKEQKLKCECQAL 375
            SRATDQVVALACAFNKLEGDLFTDEDEHVIQHCFHYTSTVLTSTLAFQKEQKLKCECQAL
Sbjct: 337 SRATDQVVALACAFNKLEGDLFTDEDEHVIQHCFHYTSTVLTSTLAFQKEQKLKCECQAL 396

Query: 376 LQVAKNLFTHLDDVSVLLQEIITEARNLSNAEICSVFLLDQNELVAKVFDGGVVDDESYE 435
            LQVAKNLFTHLDDVSVLLQEIITEARNLSNAEICSVFLLDQNELVAKVFDGGVVDDESYE
Sbjct: 397 LQVAKNLFTHLDDVSVLLQEIITEARNLSNAEICSVFLLDQNELVAKVFDGGVVDDESYE 456

Query: 436 IRIPADQGIAGHVATTGQILNIPDAYAHPLFYRGVDDSTGFRTRNILCFPIKNENQEVIG 495
            IRIPADQGIAGHVATTGQILNIPDAYAHPLFYRGVDDSTGFRTRNILCFPIKNENQEVIG
Sbjct: 457 IRIPADQGIAGHVATTGQILNIPDAYAHPLFYRGVDDSTGFRTRNILCFPIKNENQEVIG 516

Query: 496 VAELVNKINGPWFSKFDEDLATAFSIYCGISIAHSLLYKKVNEAQYRSHLANEMMMYHMK 555
            VAELVNKINGPWFSKFDEDLATAFSIYCGISIAHSLLYKKVNEAQYRSHLANEMMMYHMK
Sbjct: 517 VAELVNKINGPWFSKFDEDLATAFSIYCGISIAHSLLYKKVNEAQYRSHLANEMMMYHMK 576

Query: 556 VSDDEYTKLLHDGIQPVAAIDSNFASFTYTPRSLPEDDTSMAILSMLQDMNFINNYKIDC 615
            VSDDEYTKLLHDGIQPVAAIDSNFASFTYTPRSLPEDDTSMAILSMLQDMNFINNYKIDC
Sbjct: 577 VSDDEYTKLLHDGIQPVAAIDSNFASFTYTPRSLPEDDTSMAILSMLQDMNFINNYKIDC 636

Query: 616 PTLARFCLMVKKGYRDPPYHNWMHAFSVSHFCYLLYKNLELTNYLEDIEIFALFISCMCH 675
            PTLARFCLMVKKGYRDPPYHNWMHAFSVSHFCYLLYKNLELTNYLEDIEIFALFISCMCH
Sbjct: 637 PTLARFCLMVKKGYRDPPYHNWMHAFSVSHFCYLLYKNLELTNYLEDIEIFALFISCMCH 696

Query: 676 DLDHRGTNNSFQVASKSVLAALYSSEGSVMERHHFAQAIAILNTHGCNIFDHFSRKDYQR 735
            DLDHRGTNNSFQVASKSVLAALYSSEGSVMERHHFAQAIAILNTHGCNIFDHFSRKDYQR
Sbjct: 697 DLDHRGTNNSFQVASKSVLAALYSSEGSVMERHHFAQAIAILNTHGCNIFDHFSRKDYQR 756

Query: 736 MLDLMRDIILATDLAHHLRIFKDLQKMAEVGYDRNNKQHHRLLLCLLMTSCDLSDQTKGW 795
            MLDLMRDIILATDLAHHLRIFKDLQKMAEVGYDRNNKQHHRLLLCLLMTSCDLSDQTKGW
Sbjct: 757 MLDLMRDIILATDLAHHLRIFKDLQKMAEVGYDRNNKQHHRLLLCLLMTSCDLSDQTKGW 816

Query: 796 KTTRKIAELIYKEFFSQGDLEKAMGNRPMEMMDREKAYIPELQISFMEHIAMPIYKLLQD 855
            KTTRKIAELIYKEFFSQGDLEKAMGNRPMEMMDREKAYIPELQISFMEHIAMPIYKLLQD
Sbjct: 817 KTTRKIAELIYKEFFSQGDLEKAMGNRPMEMMDREKAYIPELQISFMEHIAMPIYKLLQD 876
```

FIGURE 2C

```
Query:  856 LFPKAAELYERVASNREHWTKVSHKFTIRGLPSNNSLDFLDEEYEVPDLDGTRAPINGCC 915
            LFPKAAELYERVASNREHWTKVSHKFTIRGLPSNNSLDFLDEEYEVPDLDGTRAPINGCC
Sbjct:  877 LFPKAAELYERVASNREHWTKVSHKFTIRGLPSNNSLDFLDEEYEVPDLDGTRAPINGCC 936

Query:  916 SLDAE 920
            SLDAE
Sbjct:  937 SLDAE 941 (SEQ ID NO:4)
```

Alignment to bovine cyclic nucleotide phosphodiesterase:
```
>gi|116569|sp|P14099|CN2A_BOVIN CGMP-DEPENDENT 3',5'-CYCLIC
            PHOSPHODIESTERASE (CYCLIC GMP STIMULATED
            PHOSPHODIESTERASE) (CGS-PDE)
  pir||A40981 3',5'-cyclic-nucleotide phosphodiesterase (EC 3.1.4.17),
            cGMP-stimulated - bovine
  gb|AAA74559.1| (M73512) cyclic nucleotide phosphodiesterase [Bos taurus]
            Length = 921

Score = 1769 bits (4532), Expect = 0.0
Identities = 872/921 (94%), Positives = 893/921 (96%), Gaps = 1/921 (0%)

Query:   1  MRRQPAASLDPLAKEPGPPGSRDDRLEDALLSLGSVIDISGLQRAVKEALSAVLPRVETV 60
            MRRQPAAS D A+EP PPGS D  L+DALLSLGSVID++GLQ+AVKEALSAVLP+VETV
Sbjct:   1  MRRQPAASRDLFAQEPVPPGSGDGALQDALLSLGSVIDVAGLQQAVKEALSAVLPKVETV 60

Query:  61  YTYLLDGESQLVCEDPPHELPQEGKVREAIISQKRLGCNGLGFSDLPGKPLARLVAPLAP 120
            YTYLLDGES+LVCE+PPHELPQEGKVREA+IS+KRLGCNGLG SDLPGKPLARLVAPLAP
Sbjct:  61  YTYLLDGESRLVCEEPPHELPQEGKVREAVISRKRLGCNGLGPSDLPGKPLARLVAPLAP 120

Query: 121  DTQVLVMPLADKEAGAVAAVILVHCGQLSDNEEWSLQAVEKHTLVALRRVQVLQQRGPRE 180
            DTQVLV+PL DKEAGAVAAVILVHCGQLSDNEEWSLQAVEKHTLVAL+RVQ LQQR
Sbjct: 121  DTQVLVIPLVDKEAGAVAAVILVHCGQLSDNEEWSLQAVEKHTLVALKRVQALQQRESSV 180

Query: 181  APRAVQNPPEGTAEDQKGGAAYIDRDRKILQLCGELYDLDASSLQLKVLQYLQQETRASR 240
            AP A QNPPE A DQKGG AY ++DRKILQLCGELYDLDASSLQLKVLQYLQQET+ASR
Sbjct: 181  APEATQNPPEEAAGDQKGGVAYTNQDRKILQLCGELYDLDASSLQLKVLQYLQQETQASR 240

Query: 241  CCLLLVSEDNLQLSCKVIGDKVLGEEVSFPLT-GCLGQVVEDKKSIQLKDLTSEDVQQLQ 299
            CCLLLVSEDNLQLSCKVIGDKVL EE+SFPLT G LGQVVEDKKSIQLKDLTSED+QQLQ
Sbjct: 241  CCLLLVSEDNLQLSCKVIGDKVLEEEISFPLTTGRLGQVVEDKKSIQLKDLTSEDMQQLQ 300

Query: 300  SMLGCELQAMLCVPVISRATDQVVALACAFNKLEGDLFTDEDEHVIQHCFHYTSTVLTST 359
            SMLGCE+QAMLCVPVISRATDQVVALACAFNKL GDLFTD+DEHVIQHCFHYTSTVLTST
Sbjct: 301  SMLGCEVQAMLCVPVISRATDQVVALACAFNKLGGDLFTDQDEHVIQHCFHYTSTVLTST 360

Query: 360  LAFQKEQKLKCECQALLQVAKNLFTHLDDVSVLLQEIITEARNLSNAEICSVFLLDQNEL 419
            LAFQKEQKLKCECQALLQVAKNLFTHLDDVSVLLQEIITEARNLSNAEICSVFLLDQNEL
Sbjct: 361  LAFQKEQKLKCECQALLQVAKNLFTHLDDVSVLLQEIITEARNLSNAEICSVFLLDQNEL 420

Query: 420  VAKVFDGGVVDDESYEIRIPADQGIAGHVATTGQILNIPDAYAHPLFYRGVDDSTGFRTR 479
            VAKVFDGGVV+DESYEIRIPADQGIAGHVATTGQILNIPDAYAHPLFYRGVDDSTGFRTR
Sbjct: 421  VAKVFDGGVVEDESYEIRIPADQGIAGHVATTGQILNIPDAYAHPLFYRGVDDSTGFRTR 480

Query: 480  NILCFPIKNENQEVIGVAELVNKINGPWFSKFDEDLATAFSIYCGISIAHSLLYKKVNEA 539
            NILCFPIKNENQEVIGVAELVNKINGPWFSKFDEDLATAFSIYCGISIAHSLLYKKVNEA
Sbjct: 481  NILCFPIKNENQEVIGVAELVNKINGPWFSKFDEDLATAFSIYCGISIAHSLLYKKVNEA 540
```

FIGURE 2D

```
Query: 540 QYRSHLANEMMMYHMKVSDDEYTKLLHDGIQPVAAIDSNFASFTYTPRSLPEDDTSMAIL 599
            QYRSHLANEMMMYHMKVSDDEYTKLLHDGIQPVAAIDSNFASFTYTPRSLPEDDTSMAIL
Sbjct: 541 QYRSHLANEMMMYHMKVSDDEYTKLLHDGIQPVAAIDSNFASFTYTPRSLPEDDTSMAIL 600

Query: 600 SMLQDMNFINNYKIDCPTLARFCLMVKKGYRDPPYHNWMHAFSVSHFCYLLYKNLELTNY 659
            SMLQDMNFINNYKIDCPTLARFCLMVKKGYRDPPYHNWMHAFSVSHFCYLLYKNLELTNY
Sbjct: 601 SMLQDMNFINNYKIDCPTLARFCLMVKKGYRDPPYHNWMHAFSVSHFCYLLYKNLELTNY 660

Query: 660 LEDIEIFALFISCMCHDLDHRGTNNSFQVASKSVLAALYSSEGSVMERHHFAQAIAILNT 719
            LED+EIFALFISCMCHDLDHRGTNNSFQVASKSVLAALYSSEGSVMERHHFAQAIAILNT
Sbjct: 661 LEDMEIFALFISCMCHDLDHRGTNNSFQVASKSVLAALYSSEGSVMERHHFAQAIAILNT 720

Query: 720 HGCNIFDHFSRKDYQRMLDLMRDIILATDLAHHLRIFKDLQKMAEVGYDRNNKQHHRLLL 779
            HGCNIFDHFSRKDYQRMLDLMRDIILATDLAHHLRIFKDLQKMAEVGYDR NKQHH LLL
Sbjct: 721 HGCNIFDHFSRKDYQRMLDLMRDIILATDLAHHLRIFKDLQKMAEVGYDRTNKQHHSLLL 780

Query: 780 CLLMTSCDLSDQTKGWKTTRKIAELIYKEFFSQGDLEKAMGNRPMEMMDREKAYIPELQI 839
            CLLMTSCDLSDQTKGWKTTRKIAELIYKEFFSQGDLEKAMGNRPMEMMDREKAYIPELQI
Sbjct: 781 CLLMTSCDLSDQTKGWKTTRKIAELIYKEFFSQGDLEKAMGNRPMEMMDREKAYIPELQI 840

Query: 840 SFMEHIAMPIYKLLQDLFPKAAELYERVASNREHWTKVSHKFTIRGLPSNNSLDFLDEEY 899
            SFMEHIAMPIYKLLQDLFPKAAELYERVASNREHWTKVSHKFTIRGLPSNNSLDFLDEEY
Sbjct: 841 SFMEHIAMPIYKLLQDLFPKAAELYERVASNREHWTKVSHKFTIRGLPSNNSLDFLDEEY 900

Query: 900 EVPDLDGTRAPINGCCSLDAE 920
            EVPDLDG RAPINGCCSLDAE
Sbjct: 901 EVPDLDGARAPINGCCSLDAE 921 (SEQ ID NO:5)
```

Hmmer search results (Pfam):

| Model | Description | Score | E-value | N |
|---|---|---|---|---|
| PF00233 | 3'5'-cyclic nucleotide phosphodiesterase | 521.5 | 1.6e-181 | 1 |
| PF01590 | GAF domain | 197.1 | 2.8e-55 | 2 |
| PF00872 | Transposase, Mutator family | 2.4 | 9.5 | 1 |

Parsed for domains:

| Model | Domain | seq-f | seq-t | hmm-f | hmm-t | score | E-value |
|---|---|---|---|---|---|---|---|
| PF01590 | 1/2 | 220 | 361 .. | 1 | 142 [] | 65.2 | 1.9e-16 |
| PF01590 | 2/2 | 388 | 532 .. | 1 | 142 [] | 132.1 | 9.8e-36 |
| PF00872 | 1/1 | 723 | 751 .. | 280 | 308 .. | 2.4 | 9.5 |
| PF00233 | 1/1 | 634 | 871 .. | 1 | 279 [] | 521.5 | 1.6e-181 |

FIGURE 2E

```
   1  ACGTGGATGA ACACCCACCC ACACACAGCT CTCTAGGAAA ATTGCTCCCC
  51  TTCCCTCCTG CTCCTCCTCC ACCCTGTCCT CCCACCACCA CCCACTTCCA
 101  AATGCTGAGA CCAAAGAGAT GGGCTGGACG GTGCCTCTCA CCACTTGTCA
 151  GCCTGGGACG CCCTCCTCCC TTTGTGACTA GCATGCCCTC CTCCCCCTGC
 201  CCGTCTGCCT CCCCAGCTCT CTCTGCCTCC CTGTCGCCCT GCCACCTCCC
 251  TGCGTTCCTG TGTATCTGCC CTCCACACAA GTCACTCTGA GGCCTCTCTT
 301  TGTTACTCTT GACTCTGAAG TGGAAACTGC TCCTCCCAGC TCTCCTGAGA
 351  GGCTCAGGAT GGGGACCTGA CCTCATAGGG CTGATGGAGG CATAGGGACA
 401  AGTGAAAGGG ACCCCAGGTC CCGAATCTCC TCAGCTCCTG TCACCTTCAG
 451  TCCCTCCTAT TGGGTTAGGG GAGGGCTGTG TGCCTGGCAC CATGGAGACC
 501  AGTGTCATGG CAACACAGTT CGGGTGGGCA CAGCTTCCTC CTCCTGGGGT
 551  GTGGGGTCCA TAAGAGGAGG TGCCGAGGAG GTGGGCCTTG TGCTGGTGCC
 601  CACCATGGCT GCCTCCAGCT CACCATTCCC AGGACAGCCC ACCCCCATCC
 651  CCCCAGCCAA CTTTGCTTGC CACTGCAGCT TCCAGTGCCA CAAGTCACTG
 701  ATCCCATTTG GGAAATCCTC TCTCAAACAC CAGCTCCAGA GCTGGGCGCC
 751  AGAGAGGGCA GGGGCTTGCC CAGGGTCACA CAGCAAGTCT GGCCAAGCTC
 801  CTGACTCTCA GACCTGTTTT CTCCTCCGGT CTCCCACCTT CCACCCAGAA
 851  AGGGGACTGG GGGCAGAGGG GTCAGTCCAA CCTCAGTTCC CACCACGATC
 901  TTCAGCCAGC CCTTAGAGTT GGCAGTGGGA GTGAAGATGC AAGTGATAGT
 951  GCCGAGAAAC CATCATGGGG CGCCCACCAC CTGCTGTGCC AAGGCTTTGC
1001  ATGTGTCATC CCATTTTATT CCAAGACCCA GGAGGAAGAT GACTGGTAAG
1051  TGGAGTAGCT GGGACAGGAA CACAGGTCCC TCTCAGATGG GGCAGGTGAG
1101  TCAAGGCTCG TGTGTATTGC TGTCTCCATC AGGCGCTCTT TTAAAAGAAT
1151  GGCAAAGCTT TTAATCCCAT CTTTATTACC GGTAAGAGTG TAGGGGGAGG
1201  ATCTGGGCA TAGCCTGGGT CTGGCCTTAG GGTTTCTAGA AACCAGGGGA
1251  TATTTTTCTA AGAAGATAGA GAATAGAGCT TTCCTAGTGT GGTTAGACCT
1301  AGGGAAGACC TTTCTTGCAG TGCAGCAATG CAGACCGACT TCCAATCCCT
1351  AGGTCAAGCT GGAGTCTAGG GACAGAGGGG AGGAGACCCC TGCCTCCTGT
1401  GCCCAGCCTC AACTTGTCTC CTGACCTTCA TGGAGTCACG TTGCAGCTGC
1451  CTCCCTCCTG GCTTATGTAA TAATTCAAAT ATAGCAGCTG CCTTTATCCC
1501  ACTGAGTCAC ACCCCCTGCA TCCCCCCTCA GGTGCGGGGA GTTATGGGGG
1551  AAGAGGTGGT TCAGGGCTGA GTGGGAGGTT CGGGGCCTCC TGGCAAGGAA
1601  GATCCCTAGT GTGCTGGATT GGAGGGTGGT GGTGGTGAGG GGGCTGGTGC
1651  TGAGGCCCCA AGAAGAGCAG AGCCTTCGCC AGAATATGAA GCCACAGGGG
1701  CCACTTCTGC CCTGACCCAT CCCTGCTGGA ATTCCACATT CCTGGGGGCC
1751  CTCCCCAGAG TCACAAGCTA TATGTACAGC CTTCTCTTGT GGGCTGCTGT
1801  CTCAGTTGGA GGAGGAAGGA GAGGTGGAAG AGTATGAAGA GGGGGAAGTA
1851  GTCCGGTGGG GCAATGGCCA CCGTCTTTGG TCCTAGGCTC AGCCTCGCCC
1901  TTCACTCACT GGGTTACCTG GCACCCCTC TGACCTCAGT TTTCCCATCT
1951  GCACAGTGAA GGATTAGATT AACTGGCTCT AGCGTCTCAT TCTCTCCGAT
2001  TTATAACCCT GGAGATGATC TCAACCTGAG GCTGAAGGCA CTTCCGAGTG
2051  TCTGGCCCAG CCGCGTTCCA GGCTGACTTC CCTCCCTCTT TTCTCTGCCA
2101  TCCCTCCTAG ACCAATGCAG CCACCCCCAC CCACAAGACA AAAGAGGCAG
2151  GAGAGGGCCC TGGACTCAGC TGGGGCTGGG CGGCTTCTCC CTTCCCTGAA
2201  CTCGCCATCT GTTCCAGCCC CCCAGCCCCC TGCCTAGCAG CCATGGGTAG
2251  GTCACTGCCC TCACCTGGGG TCACCCCTTC CTCCCCGGAG AGCTCTGACA
2301  GATATCCTGG AACCTGAAGT GGATCCTTCA TGCCCCATCC TGAATCCCAA
2351  AGCCACCTTC CTGAGGTGTT GAAGAAGCTG CTCCACCTTG GAACTACTAT
2401  AGGGGCTGTG GTGGCCTTTC ATTCCTTTAT CAGCAAAAGC TTTTGTCACT
2451  TGTGTGGTGG GGGACATGCT TAGTGTGAGA ATGCAGAGAC CCATGCCAGG
2501  CCCTACCCAA GGACATGGTG CTCCTTCAGC CATTGTCATC AGAGCCACAG
2551  AGGGGAGCTT CCTGGCAGAG GAGGAGTGGG GAGAAGCTGT GGAATGGCTC
2601  CTTGAGCTCC CCACTCCACC CCTTCCCCAT GCCTGGGCTC CCATTGCAAA
2651  GACCCAGATG TGGGCTTATC CTGTCCCCCA GCCAGAGGGA GTCACCCAGG
2701  GGTGTTCAGG CCAACCCTTT GTGAAATCCA TGTTCCACCA GTTACCAGCC
2751  TTTCTCCGGA GAGCTGAGGG CTGTCTCACA CTGGGTAGTC TCAGCCTGCC
2801  CTGGGGTTGG GGGGTGCTC ACAGAGCAGT AAGCGTCACT GCCTGCATCC
2851  CCACACACCT GCATTATCTT GTCTGCAAGA CACGTGTGCC CCTGAGCTGA
```

FIGURE 3-1

```
2901  GCTCTGTTGT GCACCACCCG ATTTCCGTCG GCCTCCTTTC TGACTTTTCT
2951  CCATCAACAT TTCCTGCTTG GGCCTGTTGC GGGCTGCCCA AAGGCTGTGG
3001  ACTGGGGCCG AGGTACATAG GACTTTGGCT TGTCTTTTGA GCTAACAGGA
3051  TCCTGTAGAA GAAATGAGAT GAGCCTGAGA GGGGGTCGGG GGGTGAGACA
3101  TTAGGGAAGG GAGAGGCCAC CAAGGGTCTC TAGCCCAGAA TCCAATGCCC
3151  CTTCCTGCCT ACCTGTCCTT GTGGGTGGGA GGCAGGGTGT GTGCTGACTG
3201  GCCCAGCAAT GGTGGGCTAG GATTTGGGAT AGGCAGAGAA AAGGAAGAGG
3251  AGGGGGAAGT CGGCCTGGGA GGAGAAACAC TGTACAAAGT CGAGGAGGAG
3301  AGAACCAGAG TGTGCTTAGG GACCAGACCT GGCCCCACCT GGAGCAGAGG
3351  ATGGTGAGGT CAGTCAGGGC TGGATCACAA GGGACCTCAA ATGCCAGGCT
3401  GAGGAGCTTG GCCTTTATCC TGAGGGCACT GGGGAGCCCT GCAAAGGTTT
3451  TGAGAGGGAA TTCCATTACC AGATAGATGT CTTTGGAAGC CGCCTCTAGG
3501  TGCAAGGAGG AGGTGGAGTA GAGAGGTTGA CCTGGGGTAA GGGTTGGAGC
3551  ATGACCAGGG GAGGGGGAAG GAAGCAGGGG GTGGGGATGG AGGGAGTGGA
3601  TGGATCTAAG AGAATCTACT GTCCTTTGGA ACAAACGATA CAGGAAGTGT
3651  AGGAGAGGGA TGGGGCAAGG CGACTTTGAA GTGTCCAGCT CAGAGATTGG
3701  AGGTTTGCTG ATGCCTTTGG GAGGCCAAGG CAGGCAGATC ACGAGGTCAG
3751  GAGTTGAAGA CCAGCCTGGC CAATATGGTG AAACCCCGTC TCTACTAAAA
3801  ATACAAAAAT TAGCCGGGCG TGGTGCGGGT GCCTGTAGTC CCAGCTACTT
3851  AGGAGGCTGA GGCAGGAGAA TTGCTTGAAC CCGGGAGGCA GAGGTTGCAG
3901  TGAGCCCAGA TCGCACCACT GCACTCCCCA CTCCACCCCT TCCCCATGCC
3951  TGGGTGACAG AGCGAGACTC CGTCTCAAAA ACAAAACAAA AACCCAAAAA
4001  ACAAAAAACT AAGAAGTTTG CTGATGCCTT TAATAGTAAC AAAAGGTGTA
4051  TTGATGTTC AATATTTGAG GGACCTACGG GTTGTTCCCA GAGGAGATGT
4101  CCAAGAGACA GCCTGGACAC CTGGAGCTCC AGGGAGAGGG ATGGGCAGCA
4151  GGGGACACCC GGAGTTGTTG GTATGCTGGG AGAAGGCTGC ATGCTCCGTG
4201  GGAGTAGGGT GGAGAATGAG GAGAGACAGG GCCGCCGTCC TGCAAGGAGC
4251  ATCCATATTG AGGGGGCGAA GATAGGGTGC ACCAGTGAGG GAGACAGAGG
4301  AGGGGCCGTC TGGAAGGTGG GAGGGAAACA GCCGCGCAGG ACGGGGCGGG
4351  GGCGGGCGCT GAGAAGAAGC CGCCTTCTTC GGCAAAGAGG TAGCTGAAGC
4401  CTGTGGAGCC TGCAGTCCTC TCAAGGCTAT GGGGGCAGCG CGGAGGCCGG
4451  ATTCCAGAAC TGAATCTTCC CATCGCTTTG GGCAGCCACC CTACCTCCCA
4501  GGAGCATCCT TCCTGCCATC CCACCTCCAG TTCCCCAGCT AACAAAAAAC
4551  GGTGTTTCTT GACTCCCGGC AGGGCGGCGG GGCGGGCAGG TCTTGTGAAC
4601  ACGGCTCGCA GGGTTCAGCA CCCTGGAGAG AGGCCTGTGG CCGGGGCGGG
4651  GCCTGCGGCG GGGGTAGGGG CGCGCAGTCA GAGCAGTCGG GCCTTTGGCT
4701  CCGTCTGGGA GCGGTCTTGC AGGCAGGCAA TTGGTGGAGG AGGGAAAAAC
4751  AATCTTGGAT TTTCTCCAGC TCTCTCCCCT TTATGCACCT CCCCCATCCC
4801  GGCACTGGCC TACAGGAGCC CCTATCCCAG CATTTGGGGC TATTACTCTC
4851  CTGACGACTT CAGGAAATGA GATGGGAGGA GAGGGGCAAC TATTTACTGG
4901  GAACTTTTCA GACATTCCCA AAACCTCACA ACCTTTTGAG CTTGGAATTC
4951  GTGACCCCAT ATTTCAGATG AGGAAACTAA ATTGAAGTTC AGGAAGGTGA
5001  AATACCTTGC CTAGGCACTT GGCAGAGCTG GGATTTGAAT TCCACCTGCC
5051  GGGCTCTAAG TCCTGAGTGC CCATTAGCCC TTCTGAGTCC TGAATCTTGC
5101  AGTTTGTTCC TGCAGACTCT CCACTTCTGG GTGGCTGTGG AGTCTGGTGT
5151  GGCAGTGGGA TGGGGAGGAG ACCTTCCCTT CCACCTGCTT GCTTGAGTGT
5201  ATTCCCAGGA GATTTCTGAA GATGAGGCCA CCACCATTGT TTCTGAAGTG
5251  GGAGGGCAGA AAGGAGGCTG AGGGCCAGGT GAGACCTCGT CACACCTGCA
5301  CCCATGCATG CCCAGGAGGA ACCCTCCTTT GAACTCTTCT GACTCAGCTT
5351  CTTGCTGCCA GGTTCCTCCG ACCAGTGAGC AGGTTCCCAG GACATGAAGG
5401  GGAGCTGTGA GGGAGCAGGA CGCCATGGTC CAGGGCTGCA GCTTCCTGAG
5451  CCCAGAGAAT GCCTTCCTAG CTGTCAGGAA TGGAGCAGCG AGGCCCCAGT
5501  GATAGGTGAG GTGGAGAAGC AAGACATGAG TTCTGGGCTG GCTCAGCTGC
5551  TTTACAACCA GCCTGGGCCT CGTTCCCTTT GAGAAAATGG TTTGCCCAGA
5601  GTTCAGAGAT CTAAAATTCT ATGATGCCTT CTGGGCCAC AGTGGGAAAC
5651  AAAGACTCCT CATATTTTCT TTCCTGACAC TTCCCAGGCC ACAAGACAAC
5701  TGCTTTCTGC AGCACCCAGC CTGGGCAGGC CATCTACACA AGCTCAGTCA
5751  TTTCTGACCT TGCCCCCTCC ACCGTGCACC CCCATGTTCT TCAACATGGG
```

FIGURE 3-2

```
5801  TCAGGTTTCT ATTCAGCCTC AGGGACTTCT CTGCTTGAAG CCTGTTGTGT
5851  GGCGGGGAGG TATTCTCCCC ACAGCTCAGA GAGATGGGGT TGCTGTGGAG
5901  GGTTTGCTGT AGCTCCTCTA CCCTGGAATA TACCCTCTTC TGCCTTAAAA
5951  GACCCAACTT GGACCCTCTC TTCCAGAAAT GCTTGCTAAC CGCCCCCCCA
6001  CCACCCAAAC TAGGTCAGGG GTCCCTCTGG GCTTCACAGA CCCTGTGCTT
6051  CTTTCTGTCA CAGCCTGCAA GTCTCCCCTC CCCACTCCCC AGCCCGAGTG
6101  CTTCTCTGAG ACAAGGGATA GTGTGAGCCA TGAGCTCAGC CACTGGTAGG
6151  CCAATGAATA AGTAAGTTAA TGGTGAAGCC AGGATCCAAA TCCCCATTTC
6201  CTGCCTCAAG GTGTGGAGCT GTTTCTCCTG CATACAATAG TAGCTCTGCT
6251  GTGACAACTC TCTATCTGTC CTAGGGCCTA AAATGCCTCT ATTTCACTAG
6301  GTTATAGCTT TATCCTAGGG AGTCCTCTTT GGAAGCAGGG TGGGGGTGCA
6351  ACAGGCCTTC CCCCATGCCT GTAGTCTGTG AGCAGCGAAG GCCATGTGGG
6401  GCAGGCTGTG GCCTAGGTCT CCACAGATCC TGGTAGAAGT CCATGCTCAC
6451  GCATCAGCTC CAAGTCCCAG CTAAACCAAG CCACCAAGAG GTGGGCCCTG
6501  TGACAAGGCT CTGAGTCCAA AGGCCATCAG TAAAGCCCCC TAAGTCTTCC
6551  GTGGACCCAG CTCCAGGCTG GGATGCACGC TAGGAGATGA TACACACCGG
6601  GTGAGGGAGC CCAGAGGAGA GGGCAGCTAG CTGTGCATGG AGGCCTGATC
6651  TCTCAGACTT GAGGGCACAA GCGTGTCCCC TCATCCTGAA GGCTTCTGCG
6701  ATGGGCAGC AGAGGGTCTG GGTCTGCTGC CCCTCAAGTC CCCAGCCCCA
6751  TCCTAGCCCA TGAGGATTGT AAATCCCTCG TCCTCTCCCC TCTCTCCTCT
6801  GTCAGCCACT CCCCTTTCCC CCTACCCCAC TCTCTTTCTA TTTCTGCCTC
6851  TGATTTTTTT TCCTTTTCTG CCTTTGTTCC TCTGTGTGTG TGTTTCTCTA
6901  TGCCTCTCTG ATCTCTTTGT ACTTCCATCT TGATCTCGCT AAGGCTCTGA
6951  TCCCTCTCTC CTCTCCCTCT TCATGTGTTA CTGTCCCCCT TCCTGTCTCT
7001  GTTTATCTCT CAGTCTCTCT GTCTGTGAGT CTTTTTTCCT CTCTCCCAGT
7051  CAGACTCTCT CTCTACCCCT CCCTCTCTCC CTCTCTCCCT CTCTGTCTGG
7101  GCCTCTCTCT GTTCCTCCTC CCTCCTCCCT CCCCCTTCTG CATTATCAGA
7151  CCTGCTCCAA CCTCCTCCCA GAGCCAGCCG AGCAGCAGAG GCAGTGGCAG
7201  CGGGAGAGGC GGGAGCAGCG GGGCAGCAGA GCTGGATTGG GGTGTTGAGT
7251  CCAGGCTGAG TAGGGGGCAG CCCACTGCTC TTGGTCCCTG TGCCTGCTGG
7301  GGGTGCCCTG CCCTGAACTC CAGGCAGCGG GGACAGGGCG AGGTGCCACC
7351  TTAGTCTGGC TGGGGAGGCG GACGATGAGG AGTGATGGGG CAGGCATGCG
7401  GCCACTCCAT CCTCTGCAGG AGCCAGCAGT ACCCGGCAGC GCGACCGGCT
7451  GAGCCGTGAG TATAGTGAGG GGCTGGGGTG GTGAGCGGCT GTGAGAGGTG
7501  CCACAGACAG GGTCCTGGGA GTCCCTCCAA GGAGCTGGGG CTGGCATGGA
7551  GCTGAGCCAC GTGGAAGGAT CGATCCTGTT CCTGGGCACC CCTCCTCCCC
7601  GCGTTGCCAG ACTGCAGCCT GGGGTGGGGG CAGGTTACCT CTGAGCAGAA
7651  TGAGGGTGTC TAACGTCAAC CTAGTAGGTG ATGAGGCTGG GGTCCCATGG
7701  AAGGGGCTGC TGGTTGGAGG AGGGGCTGAT AATGAACCTG AACCGCTTCT
7751  TCAAGGGCTG AGGGTGTATG TGGGGAGGGG GAGGTCTGCC AAGTAGTTGG
7801  GAGGAGCTCT CGGGGCTGCA ATAGGCTGGT TCAGGACCCT GGAGAGGGAG
7851  AGTGTCTTGG CCCACCAAGG CTATGTGTGT GTGAAGGAGG TGGGGAGGGG
7901  GAAAGATGGA GAAAATATGA ATAAGAGTGG CCCTGGAGCA AGAGAGGGTT
7951  AGAGGTAACC ACCTTCCATG GAATTGGGAA TTGGGGTTCA GGGACACCAC
8001  TTTATGAAAC TTTACCCCAA AGCGTCTGTC CCAGGATAGG GTTCTACGGA
8051  GCCAGATGGA ATATGGTGCC AGCCTCGTGT GTGTCCACGT GCAGGGGGGT
8101  GCATGTGCAA GTGAGTGGGG GGCGCCGTGG CGACACCCCT CTACTAAGGG
8151  CTGCCGAGGT GGTAGGCAGG GTGTGTGTGT GTGTGTGTGT GTGTGTGTGT
8201  ATACATGTGG AATGTAAGGG ACATGTTGGG TGTAGAGGGG CCTGTAGAGC
8251  TCTAGGGTCC TTGGTGGTTG GATGTAAAGC AGCCTGTCAG AGTTTGTGAT
8301  CATCCCTGTG TGAGTGAGAG TTTATTCGCA TGTGTCTGAG TGTGAGTGCA
8351  GGTTGGTCTG CATATGTATG TAGGTGTGTC TATTAGGTTG AGTTTGTATA
8401  TTATGTGTGT TGTGTCTGCA AAATAGAGTG AATCAGTGTG CATTTTTTAT
8451  CTGTTCCATG TGCATTTATG TGTGTGTATT TGTTAGTGTG TGAATAATAG
8501  CATTGCTGTG TGTGGAGGTG GATGTGGCTG TGTGCGTATA AGTATTCTGG
8551  TGTGGGTGTG TGATCATGGT GCTAGTGTGT ATATCGGTGC TTCTGTGGCT
8601  GGTGTGTGTG TGTATCTATA TGTGTGTATT CATCTGAGTG TGTGTGGGTG
8651  GCTGTTTCCT TCCCCTGGCA ATTGAGGATA CAGCTGGGAC ACCATGGCCC
```

FIGURE 3-3

```
 8701  ACTGATGCAG GGCAGGGAGG GGCTGAATGT ATGACCGCCT CTTTGAACTC
 8751  AGGACAATTC ATTCTACACC CTGTGGGAAA GATGCAGAAA AGAAATAGGC
 8801  AATAATGACT CTGCCCTCTG GGGCTTCCTA AGCTTCTTAG ACATAAAATA
 8851  GCTTGAGAAT AATTAAGCAG TAGAGATCAA CGTCATGCTA ACAGGTGGGG
 8901  GTGGGGTGGG AACTGCATAA GCAAAGGCCC TGGGCTGGGC ATGTCCTGGA
 8951  GCAGTGAAGA CACTGTATAG AGTGGGGGGC AGGCAGGACC CACATTCAAT
 9001  AGAACTTTAA GATCCAGGAC TCTTAGGCTT TATCCAGAGA GCCCTGGGGA
 9051  GCCCAGAAAG GTTTTATATA GCGGAGAGAC ATGATCAGAT TTGGGTTCTA
 9101  GAAACCTGCC CTGGGCCAGG CATGGTGGCT CATGCCTGTA ATCCCATCAC
 9151  TTTGGGAGGC AGAAGCAGGT GGATCACTTG AGGCCAGGAG TTTGAGACGA
 9201  GACTGGCCAA CATGGTGAAA CCCAGTGTCT ATTAGAAATA CAATAAAATT
 9251  AGCTGGGTGT GGTGGCACAC GCCTGTAGTC CCAGCTACTT AGAAGGCTGA
 9301  GGCATGAGAA TATGAGAATC GCTTGAACTT GGGAGGTGGA GGTTGCAGTG
 9351  AGCTGAGATT GCCTTACTGC ACTTTAGCCT GGGGGTGACA AAGTGAGACT
 9401  CTGTCTCAAA AAAAGAAAAA AAAAAGAAGA AGAAAAATAA AGAAACCTGC
 9451  CTCGGTGGCA TTGTCTGGGT TGAACTGGAA GAGAGAGGTG GGGCCAGGAG
 9501  GCTAGAGTGG AGGCCAAGCC AATACAGGGG TCAGTGAGTT CTGGAGCTTT
 9551  TTGAGAACTT GGGAAAGGCT GGATAGATGA GAACAGGGAA GGGAATGTCT
 9601  AGGTGGCTCA GGCTTGGACT GGGGTCAGGG GTGTAGTGCA GACATCTCAG
 9651  TAAGTCAGGA TCTCATGAGG GAAAAGGCTC ATGGAAGGCT CAGGAAAGCT
 9701  GGGCGTGGGT GGGCTGAGGT AGTGGGAGAG ATCTTTGTAG TGTTTCTAGC
 9751  TAGGATGCAG AGGGTCAGAG ATCATGGAGC CATCTCTTGC CAGACAGGGA
 9801  AACTGAGACT ATGGCTTCAT CACTATCCTT TGGCTGCAAG GCTGGGGCTC
 9851  AACCTCTTCA TCAGACCTGA CCCTCAATAT CATTCTCCTT CAGGCCCTGC
 9901  CCGGAACCTC TTGGTTGCTG AGCTTGGTCA GCTCAGTGAG GGTTAATTGT
 9951  CTTTATGCTC CCTGCACCCC CACCCCCCGC AGTCATTCCC CCTGCCCACC
10001  AAGCAGCTCC TGCCACTCTT CCTGCTTCCC ACTCCAGCCT CCTGTCCCCA
10051  GGGACTGCTG ATGGCTTGGC TGGGATCTAG CCAAATGGTG GGGGTGGGG
10101  GCGGGGTGG GGGGAAGAGC TCCCAGCAGT CCTTTACCCC TTGGTCTTAA
10151  TGGACTGGGA GTCTCACCCT CAGCCATGCT GCTGTCAGGC CAGGCCTGCG
10201  CTCCCCGGGC TTCTGCTGCT TGGGCCTATG AAATCTCCCG ACTCAGCATG
10251  ATTCCATTGC TGCATTCATT CATTCAACCA CTCAACAGGA ACTTCTCAGT
10301  AGCTGCTTGG TGCCCACTTG GCTTGTCACC GGGGACACAG AGCAGACACT
10351  GACTGAGTCC CTGTTCTCAG GGAGTGCCCA GTCTGATGAA GGAGAAAGAA
10401  ATGGAAAGCT GCAACCCTAC AGGGTGAGCA GTGCTGTGTA GGAGGTGGGG
10451  GGCCCACAGC AAGCCTGGGC TTCAGAGGAA GAGACATTTG AGCCGGACCT
10501  TGAAGGATGG GTAGGAATCA CCCAGGCAGG GAAGAGCAGA GGGAACAGTT
10551  TGTGAAGGTG GGTAGGAAAG GCACAGGGCT AGGCACCTGA CTCAGTGCAG
10601  CCTCTGGGTG GGAGAAGACA GTAAGGGCGT TTGGGTCATT TTCTAGCAGT
10651  TGTTTTAGTA CTCTCTACAA CTTGCCCTGC AGATCTATCC AGCCTGCTGT
10701  TTGCATACCC CCGGACATAG GATGTTCATC TCTTCCCTCC TGGGCAGCCC
10751  TTCCCTTGTG GTGGTTATAT CTGTCCTGGG TCTTCTCCGC AGGGCCCAGC
10801  AACTCCAGGC TACCCAGCCT GGCCTTATGT CCTTTCTCCG TCCTGTGTCA
10851  CTGTCCCCTG AAGTAGGGCC AGGCTGGGGC ACAATGATCC AGGAGTGGCA
10901  AGAACACATC TAGGCAGAGA GTGGGAGAAA TGCGCAGCCT TTATTAACAA
10951  AAATCTGAGA TGGGTGCAGG CCCTGACTCC TCTCCAAAAA TAATGATAAA
11001  GAAGCAGGCA TGGCCAAATA AGGGAGTGAG GACAGACAGC AGGAAGAACT
11051  TCCTACCAAT GCAGAAGGGC TGTGAGTCTC TTGGTTTTAT GAGAGTGGGC
11101  TGTACGTGTG AAAGGGAGGG TCTCAGAGGA CAAGAGGGGG AATTGGAGGC
11151  AGAGGCACTG TCAGCCTCTG ACTCTCCCAT AGGTGAGTGA GTGAAGTCAT
11201  CCAGGGAGAG GGAACAGAGG AGGGAGATCA GGACTCATCA TTCATTCATT
11251  CAGCAGCCGT TCACTGGCCC TACCAAACAT GACACCCTG GGGGCAGATG
11301  GACAGAGCCA GTGACCACGT GGATGGAAGC TCCGAGTCTT TCCTACCTGT
11351  GTTAATGTCG CAGGAAGGTA TTTAGGAGGA GGGGCCATTG GGGCTGGCCT
11401  TATAAGGAAG AGCCACTTCA GGCTGAGTTG AGGGACAGCA CTAGGAAGAT
11451  GGAAGAGCAT TTGCAAAGGC CTCAAGGTAA GGGCAAGCAG GATTTTGTTC
11501  ACTTAGCACT ATAGGAGTTC AGAGTGGCCT AGGCATGAAG TGCCAGGCTG
11551  GGGGGAAGCC CTGGGCCGTG GTGGAGCAGG AGAGGAGTGG GGAATTGAGC
```

FIGURE 3-4

```
11601  CTAGACTGTA GGAAGCACTT TCTTCCGTGA AGGTGTCTCC AACAGGCTTG
11651  ATGTGTAGGC ATTATTGTAA GTTTGCAACT TCTTGGTCTC TCCTGGTGCT
11701  CGTGACCAGA GCTTGCTGAG GGACCCAGCC TTGCTTGAGA AAGGGGTGTT
11751  CAGTGAACAA AAGAGACCCT GGAAATGAGA GAGAAGCAGT GGCTGAAGAA
11801  TGTGGGCCCC TTCCAGAAAG TGGCGTGCAA ACAAATACAA AGCAATATGC
11851  AAATCAGCTG GCTAGGGCTT GGCAGCTTTG GTTGGAAGAA ATGAGCCATC
11901  ACCCCTTATT ATGCCGGCCT CCTACCCCCT CTGCCCCAGC CTCCAGGACA
11951  GCCGGAACAG CCTTGTCTGC TCCTTGGAGC GCCCCAGCTT TTCTGAGACA
12001  CAGGATTGTG GCCTCCAGGG TGGTGGCCGT GGGCTCCCTG TCAGCACCCT
12051  CGTCCTCCTG GGAAGTCGAT ATATTTAGTA ACAGAAATGT TTTCACACAT
12101  TTATCTCCTA TTGTTCAGCT GCTTGCTCCC TGGGAAAGGC CAGGTCCCCA
12151  GTGATGTGAC CCACTTCTTG AAGTCCCTGA AGTCACCCTT CTCACTGCCC
12201  CCCCACCCCG AAAAACAGGA GGCAACTGGG GCTTGGTGCA GCAGAACAGA
12251  TTTGAGTCAA ATATCTGGGA GGACTTCCCA ACAGTGTGGT TGCTGAGATG
12301  TGTGGACCCT GGATTTCTGG GCTTTCATTC TTTGGATGGT TGCCTTGGGC
12351  GCAGAGGAGG CTTTGAAGAT AGAGCAGAGA AGGTGGCAGG CAGGCTTATG
12401  CTCAAATTTC AGCATACTGA AAGATGTACT GTTACTCTGT AGCTGTGTGG
12451  TCCTGGGCAA GTTACTTAAC TTCTCTGAAC CTTGTGTGAA TAGTGGGGTG
12501  GAGATAATTA TCCTTTCTTG GCAGGATGAT TCTGAAGAAT CTGGAAGTGC
12551  AGAGCTTAGC CCCTGGCATG CGGCAGGTGC TCACAAAGGT TAGCTACTGT
12601  CATTATGAAC CACCCACGAT CAGCCACACT TTCAGAAAGA TTTAGCGGGG
12651  CCTGGAGAGG GAGAGACCAG AGCTAGGAGC TCAGGGCTGT CATCGTGTGG
12701  GAGGGACCAG GAGGCCTGAA ACAGAGCTGT GGTTGTGGCT ACGGTGAGAA
12751  GCACAAAGCT CTGTGGGAGG GACCGAGGTT TCTCAGAGAA GTGTGGCCAC
12801  CTCATTAAGT TGTTCTGACT GGTCTGAGAC CAATCCCCAG ATAATACAAT
12851  GGAAGAAAGG GCTTGGTGAA GAAGGGGTTA AGTCTGTGGC CACACCCATG
12901  CAGTCTGTGA GCCATTCTGG GAGCTGTAGT CTGTTGTGAA TTTGCAGTAA
12951  GCATAGTTTG TACTGCCTCT TTTGATCCAA ATCCACACCC TGCTGCCAAG
13001  GCTGGCCGAG GGCCGGCCCT GGTGGGTGCT GGGCTGTGTG GAGCCCAAAG
13051  GTGAAGCAGC ATCGACCTCT TCCCTCAGGG ACCCCCTGGC TTGCTATGTG
13101  TTGGGGGGTG CAGGTAGGAG CAGGGATAGA AGTATTAAGC CATAATTACG
13151  ACTTCTCACA TGTTCACACA GAAGTTTACA GCTTCCTGAG CACTGTTTCC
13201  ACACCTGTGA TCTCATTTAA TCCTCACCAC AAACCCAAGA GACTGCTGTT
13251  TTCTGGATGA AGAAACAGAG GATCCAGGAG GGGAAATCGC TTGCCCACAG
13301  GTATTCAGCC AGTGGAGCCA GACCTGGGGC ACAAATCTGT CTGCTTCCAG
13351  AGCTCCTGCT CTTTCCATAC ATTACTGTTC CAGATGGCAG ACAGGCAAGA
13401  TGTGGACAAC TAAAGTTGGA TGTGAGACAT CTCGGCAGAG GAACAGCTGA
13451  GCAGAGAGCT GCTGATTCCA GGCTGAGAGT TTGGACTTTG TGTTGTGGCC
13501  CACCAGGATC CACCCAAGGG TTTTCTGATT AGAGCTGAGC TTTGAGAGAA
13551  TTGGTCTTGC AGCTTAGGCT GAATGGATTG AACTGGAGAA ACCAAAGTCA
13601  GACTGAGGCT TCTAAATCCC ATCCTTGGTG CACCCAGCAC TTTGCTGCTG
13651  TCCCTCCTCC ATGCTTCTTC TCAGTTTCTT CCTTCTCCTC TCCTTCATCT
13701  TCTTCCCTCA CCCTTTTTTT TTTTTTTTTT AATAGAGACA GTGTCTTGCT
13751  GGCTGGAGTA CAGTGGTGCC ATAATAGCTC ACTGCAGCCT CAAATTCCTG
13801  GGCTGAAGCT ATCCTCCTGC CTGGGCCTCC CAAAGTGCTG GGATTACAGG
13851  TGTGAGCCAC TGCACCCAGC TCATCTTCCT CTTTCTCTCC TACTCCTCTC
13901  TGCCTCAGGC TGAGGAGTGA TGACTTTTAT ACCATAGAGC TGTGCTGTAA
13951  TATCACATGT CTCCAGAAGG GGGTGCTGTC ACATACAGTC CATTCCAGCC
14001  TGAATCTTCG TTGTGTTTGA AGGGCCAGTA GAAGTGTTGG ACAAGTGGCA
14051  GAGATGAAGG ATGGAGAGAA GGATAGCCCA TTGTTCTCCA CCTCCATTGA
14101  GCCCAGGACA TGAGGGCCCT GCTGAAATGG CACTGGGAGG AATGAAGGCT
14151  GAGGAGAGGT TGGACCCCAA CCAGAAGGGA CAGACATACT GAGTTAAGCC
14201  AGAGGAAATT TTCTCCTCAT GGTTCTGGGA CAGGCTAAGA TTTGGAAATG
14251  CATCTAGAAT GACATTGCAG TTGGGGTCTG GTTTTCTTTT GGGTCATGAC
14301  TTGCTTGATA CTGAGGTGCT GGGGATATTG CTTGTGTCTC AGTGTGTGTA
14351  TGTGTACCTG AATGTGAGCT TCCAGTTGTG CATATGTGTA TGCTGATCTG
14401  AGAGGGTGAG AATGTGTGGG TCAGTGTTCG TATAAAAGTG TGAACATACT
14451  CACATGTGTG AGCATGTGAG TGTCCTTTTT TTTAGTTTAG TTTTGAGACA
```

FIGURE 3-5

```
14501  GGGTCTCACA CTCTCACCCA GACTGGAGTG CAGTGGCGTG ATCTCGGCTC
14551  ACCGCAACCT CCGCATCCCA GGCTCAAGCT ATTCTCCTGC CTCAGCCTCC
14601  TGAGTAGCTG GGACTACAGG CATGCACCAC CACACCTGCA TAATTTTTGT
14651  ATTTTTAGTA GAGATGGGGT TTCACCATGT TGGCCAGGCT GGTCTTGAAC
14701  TCCTGACCTC AAATGATCCA CCCACCTTGG CCTCCCAAAG TACTGGGATT
14751  ACAGGCATGA GCCACTGCAC CCGGCTGTGA CTGTCCATCT TTATGTCTGA
14801  TTTTGGTAAA CAGTTATATG CATGTGACTG TGGCTTGTGT GTGTGTACAT
14851  GTATGTAGAG TGCCATATAC ATATGTTCTA GTGAAACCGT ATGTGTGTTC
14901  CCTGTGTATA CAGATGCCTG TGTCTCAATG TGAGCACAGG GATGAGGGGA
14951  TATGTGTGTG TGAAGGCCCA GACACCTGCT GTGCTAACCT TTAAGGCCGC
15001  GCCTAATGTC TGGCTATTCA ATACTTTTTC TCCTGGGTCG CGCTTTCCTG
15051  TAGGTAGAGA CCCTTGAAGG GCTGGGCTTC CTTCAGGGGA CTCTGGGCCA
15101  GAGTCAGGCT TTGTGTTCAG TCTCAGGTTG GGCCAGCCAG GGTCCTAGTC
15151  TATCGGATTG GGCAGCTAGA CATGGCTGGG AAGTGTCTAG GTTCCATTCT
15201  CCCCAGGAAC TCTTAATGGT CACACTTAAA GAGTTTCAGG GACTCCCAGC
15251  ACGGTCCTCT TGTACTGATG CAACTACTGA AGTTCAGAGA GGTGCAGTGA
15301  TTAACCCAAG GTCACCCAGC AGGACCCAGG ATGAGATGAT AGGGCTTGCA
15351  GCAGAGAGGG GAGTGTCTGA CCTGGAAGGC TGCCCTCCCT CCAGCCCCTA
15401  GAGCAGGTGG GGAGCTCAGA GGAGAGCCAA GTCTGTGGTG TGAAGCCACC
15451  TCCTGCACCT GGCTATTTCC ATGCCTCCTG GCCTCAGAG GCTGCCTTTG
15501  AAGTTTTTAC CAGAGCTTCT GCATGCTGTG AGATTCCTCC TGGGGACGTG
15551  TGAAGTCGAC TGTTCCATGG AGCATGGAGA CTCGATGGAG AGGAGCCCAG
15601  TGGTGAAGTG AGGCCAGAGG AGGGGCTTCC TCTGGAAGCC TCAATTTCTT
15651  CTTTGCAGTA GTTGCTTTTT TTTTCGTGTT TTTTTTTGTT GTTGTTTTTT
15701  AGGTTTTCAC CGTTCTAACA TTCAAGGCTT TCTCTGTTAT CTCTCTTTGA
15751  GCTCTTAGTA CTGAGACAGT GCTGGGGTTT GGGGCAGTCC TGGAGGCCTA
15801  TCTGGGCTCA AAGTGAGGGT GGCAGGGCAG TCCCTTAGGG AAAGGGCTGC
15851  GTGGGAGACA GGGATGAGCT TCCTGCCCAT AGTGGGGAGG CATGAGCAGG
15901  GGCTGGACAG CCTGGTTAGC AAGGCTGTAT ACAAGGTACC TACCCTAGTG
15951  AGGAAGTTGG TTGCAGATTA TCTTGAGTCC CTTCAAGCTG TAGCTGCCAT
16001  GGGGGGCCAG AGAAGAACGT GCCTCAGCTC TCTTGGGCCT GGGGAGGATT
16051  GAGTCCACAG AGTGCTCCTG GTGTCCTGGG CAGTGGAAGG TGCAAGGTTA
16101  GACTGTGCAC CTGGAAGCAG AGAGATCCCA TTCCCTGGAG AACTGAAGGG
16151  AAATTTGTCT TCCTGGAGGT TTGGGGCTGG AGGCAGGGGC TGGATGGGAG
16201  GACACTCTGG GGTGGAGTGG GGGTGGGATG GGGAGGACTG GGCAAGTCCG
16251  AGGCGGCTCT GCTGTTCAGC ACCCGCAGGA AGGAGCAGGG AGGCATATCC
16301  TGAATCATGC AGGGCTCTAG GGTGGGAGGC CCATGGTTGT GGGGCTCAAA
16351  CATGGGCTCT GGTTGGGGCA GAGGAGAGGC TTCCTGGGGT TGGGGTCTGG
16401  GCAGGAATTG GGGTAGAAAA GGAGAGAAGC AGCAATTGGG TACCACCTCC
16451  TTCCCAGGTC AGGTAATTCG GAGTTGTCTT AAAACTCTCA GTGGGCCAGG
16501  CATAGTGGCT CGCGCCTGTA ACCCAAGCAC TTTGGGAGGC TGAGGTGGGT
16551  GGATCACCTG AGGTTGGGAG TTCAAGACCA GCCTGGCCAA CCTGGAGAAA
16601  CTCTGTCTTT ACTAAAAATA CAGAATTAGC TGGGCGTGGT GGTGGATGCC
16651  TGTAATCCCA GCTACTCGGG GGGCTGAGGC AGGAGAATTG CTTGAACCCA
16701  GGAGGCGGAG GTTGCAGTGA GCCTAGATTG TGCCATTGCA TTCCAGCCTA
16751  GGCAACAAGA GCAAAACTCT GCCTCAAACA AAGAAACAAA CAAAACCTCT
16801  CAGTGAGGGG GGATCTGGGG TCCAGATGGA GAGAACTAAT GTTTACAGAG
16851  TGACCTTTAA GTTTTAAAAA TGATTATTTA AGGAGGCGAT TAAACAAATC
16901  GCCTCCTTAA ATAATCCTTC CAGGGAGGCC GGGCACGGTG GCTCACACCT
16951  GTAATCCCAG TACTTTGGGA GGCTGAGGTG GGCGGATCAC GAGGTCNNNN
17001  NNNNNNNNNN NNNNNNNNNN NNNNNNNNNN NNNNNNNNNN NNNNNGGAA
17051  AAGAGATATT AGNTGGAGTA TTAGTAAGAG ATAAAAGAGA AAAACAACGA
17101  AAAAAAAGCA GAGTGATAGA AGGGAAATAG AATAAGGAAG AATAGATTGA
17151  TAGTAGCGGC GGACGAAGAA AAAGACGAAA AACAGCGAGT ACGGAGGCGG
17201  GGGCGGTATA ATGAGAAAAT AGAAGATGAA CGCGATACGA AGGATGAGGG
17251  CGGAGGGAAA GTACAATGGT GGTGGGGTAT GGAGGCGAGA GTGAAAGGGA
17301  GGTAAATGAC GCACAAAAAC AAAAGACGGA AGGGAACAG GAGGAGGGGG
17351  TGGTAGGGGG GNATCGCCTC CTTAAATAAT CCTTCCAGGG AGGCCGGGCA
```

FIGURE 3-6

17401 CGGTGGCTCA CACCTGTAAT CCCAGTACTT TGGGAGGCTG AGGTGGGCGG
17451 ATCACGAGGT CAGGAGATCG AGACCATCCT GGCTAACACG GTGAAACCCC
17501 GTCTCTACTA AAAATACAAA AAATTAACCG GGCGTGGTGG GGGGCGCCTG
17551 TAGTCCCAGC TACTCGGGAG GCTGAGGCAG GATAATGGCA TGAACTCAGG
17601 AGGCGGAGCT TGCAGTGAGC CGAGATTGTG CCACTGCACT CCAAGCCTGA
17651 GGGACAGAGC AAGACTCCGT CTCAAAAAAA AAAAAAAAAA AAAAAAAAAT
17701 CCTTCAAGGG GCTAGCCCTA TTTTGTAGAG GGGAAACAGA TGACAAACTT
17751 AAATGGTTTA ACTGAAGACA GTTAGTGAAG CAAGTATTAT GGAGATGGGG
17801 AAGGCTTAAG GGAACCAGCA GGACATGTCA AGTTACTCAG GACTGGCATC
17851 CAAGGGGCCA GGGGCGTTGG CAGAGGGGGG CCGAGGAGAG TGCCCCAGCT
17901 CCATGAGCCA GAGCCCTGGA GATGGGCTG CCCTGCAGGA GCTGTGGCTG
17951 CAGCCACTGC TTGTCGAAGG AGGCAGGTGG GTGAGGGGGT GAATACCCAC
18001 CATGAGCCTG CATGCTTCTC ACCCTTTGCT CTCCTGCCAG TACCCTGACC
18051 CTCACTGGCA GAATTTCTCT GGATGCCAGG GGGCAAGGGA GCCCTGGATG
18101 AAGCTGCCAC TTAGAAGTCG GCCTCTGGGG CACACAACCC AGCAGCAAAA
18151 GTTAGAGATT GGATGTGGAG GGACAAAGAG ATGATGGGAA ACCGAAGAAC
18201 AGAGAGGGCA TGGACTTGCC CAAGGTCACA CAGCCTGTTG ATATCAGAAT
18251 TGGAGTCAGA AGCCAGGCTC TGCCTCTGAA CACTCACTTT TTTGTTTGTT
18301 TGGTTTTCTT TTTTTTCTTT CTTTTTTTTT TTTTTTGAGA CAGTCTTGCT
18351 CTGTCGCCCA GGCTGGAGTG CAGTGGTGCG ATCTTGTCTC ACTGCAACCT
18401 CCACCTCCTG GGTTCAAGTG ATTGTCCTGC CTCAGCCTCC CAAGTAGCTG
18451 GGATCACAGG CACCTGCCAG CATGCCCGGC TAATTTTTGT ACTTTTGGTA
18501 GAGACGGGGT TTCACCATAT TGGCCAGGCT GGTCTCGAAC TCCTGCCCTC
18551 AGGTGATCTG CCCGCCTTGA CCTCCCAAAG TGCTGGGATT ACAGGCGTGA
18601 GCCACTGCAC CTGGCCTGAA CACTCACTTT GTCACATTCA CTGAGGTCTC
18651 CTGAGTGGAC TCATATGCGC ATTATCTACT CTCTGGCTGA GAGCTGCTTC
18701 CTGCCGTGAT CACCGCGCTC TGTATCTGGG CAGCACAGGG GCTGCTGAAG
18751 AATGTCATTC TCAGAACGCA GTGTGCCCTG GAGCCCCCCA AGCCACCTGT
18801 TCATTCATCC CAACTGGCCT TGAGGGTGCC CTGGTGTGCC CTGCCTGTGC
18851 TTGTCACCCT GGCCATGGAG ATGGACCCAA AAGCCCTTGC TCTCCGCTTC
18901 ATTAGAGACA GGCACACCCA GACGCAGGCA ATCAATTTTG TCGGGTGAGT
18951 GCTGGGACCG CTGATGAGGA CCCTTCCTGA GGAGGCGATG CTGGGTCTTA
19001 GCCTTAAAGA ACAACTGAGA GTTTTCCAGG TGGAGGAGAA AAGGAAGGGT
19051 ATTCCAGGCA AAAATCCCCA TAAGAGCAAA GGTGTGAGCA GCAAGAAATC
19101 AAGGGTGGCA GGTTCAGGGC TCCTGGGCTG GAGGAAGGGC CTGGCGGTGG
19151 AGAGGAAGGG AGTGAAGGCC CAGCTCACAA AGGGAAGCAG AGGAAAGTTT
19201 AAGCAGGGTC AGGCCATGGT TAGCTTTGGG GTTAGGAAGC TCCAAATGAT
19251 GGGTGAAGTA GGGGGGCTAG ACCCAGGTGA GAGGCAGTAT TGCGGTTGGC
19301 CAAGGACACG TGAGTTGCAT AAATGGGCCA GAGGAGGGGT GACAGCCGCT
19351 ACTTCCCGGC TCACCTGCCT GAGCTAAGGC CCTAGTTCCT CAGTGTCTGC
19401 CCACCAATGC AGGTGTGTGG CAGCTCTAGA CCCTCCTCTA GGGACATCCC
19451 TCCCTGCCTC ATGCTGCCTA TGGCTTTCAC TCTCTGGAGC ACTCATCCAT
19501 GGCACCCATA AGCCACCCCC TCAGACAATG GCCCCTAAAG CAAAACTGTG
19551 TCACCGTTGC ATATCTCTTG ATAACACTCT GACCCCTCCA CTGCCAAATC
19601 TGATAAAAGA CCTCCCTTTG AAGACCTTCC TCCTGGAGTC GGATCTCAGT
19651 CCTTCTTGCT GTCCAGAGCC TGGGCCTTGG GCCTCCCTGG GAGGCGAGTC
19701 AGTGAGGGCA GCCCCCTTAT GGTGCTGGGA GTTGAGGGAC CTTGGCCCAG
19751 CCAACTCATC CCTGTTGTGT CAGCCTCTCT GGGCCTGGGC AGCCAACTCA
19801 TTTTCAGTGC TAATTAGCAT CTCCCCTGCA GCTTTCTGCC CCACTCTAAG
19851 TGCTTGACAA TCATTAGGTG TTACTGTGTG CAACTGGATC CCAGCTCCGG
19901 CACCTCCCTG CCCCAGCTTC TCCTCCAGAC CCCAGCTGCC TGAGATAAGG
19951 GACCTGGCCA CAAACATACA ACACACCGAA ACCGGACACG AATCTAGGCA
20001 TAGGGACTTG AACACCAACA TAAATATACA AAGAGGAAAA ACCCAATAAC
20051 ACAGAAGAAC TCCCCATACC AGGAAGCAGA CCATAGCACA GACAGAGACC
20101 CACAGTACAC ACACAACACA GACACCAACA GATGCTGAAA AGCAGACACA
20151 GGATCATTCC AAAAAGTGAC CCAGAAACGA AAACAGAACA AATGGGAACA
20201 TCAATGCACA TGACACAGGT ATACACATCT AGATATGCAA CACAGGTACG
20251 ATTCAGCACA TGTGTGGCGC ATCGCAGGGA AGCACTTGCA CTTGAAGTAT

FIGURE 3-7

```
20301  ACACAGATGC CAAGATAGTC AGAGGGAGCC GCCTGTGGTT CCCCACCTGT
20351  GCAGCGTCTC TCGCCTCTGG GCTGCCGCAC ATGCTGTTGC CCGGAATTCC
20401  CTTCCCCAAG GCCCTCCTCT TTTTACCTGG CTAATTCCTG TCATTCTTCA
20451  GATCTTCTAG GAAGACTTCT GCCTCCTTGA TAGGGGCCTT TCCATACTCC
20501  CCAGCCTTGG AGTGCTTCCT GCCACATGGC ATCACTGACT GTTTTCCAAT
20551  GAGTTTCTGT CAAGTTTTGG GATGAAGGAT TTTGCCTGTG CTCGTTGAGG
20601  TGGTGACTGT GGGTGTGAGT GGGTGATTAG GGCCAAAAAA ACCCCCCAAA
20651  AAACTGGACA GAGGCAAATT TGGGGGGAAA TGAGTTAGGA ATAGCTGTGA
20701  GGAGCCCCAG CTACTCAGGG CCTCAGAAGA TATTTATTTC TGTATTTATT
20751  TATTTATTGA GACAGAGTCT TGCTCTGTCA CCCAGGCTGG AGGGCAGTGG
20801  CGCTATCCTG GCCCACTGCA ACCTCCACCT CCCAGGTTCA GGCGATTCTC
20851  CTTCCTCAGC CTCCCGAGTA GCTGGGATTA CAGGTGCGCA CCACCATGCC
20901  TGGCTAATTT TTCTATTTTT AGCAGAGACG GGGTTTCACC ATGTTGGCCA
20951  GGCTGGTCTT CAACTTCTGA GCTCAGGTGA TCCTCCTGCC TCGGCCTCCC
21001  AAAGTGCTGA GATTACAGGT GTGAGCCACT GCACCCGACC TCAGAAGACA
21051  TTGAAACCCA CAGAGAGGAC ACAGCCAGAT GCCCTCTGCC TCATTTTCTC
21101  AGACCCTGCC TGATTTCTCT TATGTTTCTT CTAGGCTTGC TCCCTGACCC
21151  AGTTCCCTCC TTCCCAGAGC TGGCCTTGCC CCTTGCCACC TCTCGGAGCT
21201  CACACATACT CACTCACCTT CTCTGCTTGG CTGTGCCCTA CCCCTACTTC
21251  TACGTGCAGT GAAATCCTTG TTATTCAAGG CCTGAGGTCA GTGGGCACAT
21301  CATCCATGCC TGGCGTCCTA ACCCGTGCCA CTGAGTATCG TGAAGGGAGG
21351  TAGTGGAGGG ACGTGCTTGG GAGCACAAGC CTTGAGGACT GTCTCTTGGT
21401  TCAGATCTCT GCTCCTCTAC TTCTTAGCTG CAGGATTGTG CAAGTTCTGC
21451  CACCTTTGTT CCCTCATCTG TAGAAAGGAG AGGATAATAG AGCCCACCTC
21501  ATTAGGGCAG CCATGAGGAT TAAATGAGAC ACAGTGTGTA ATGTACCTGG
21551  CTCCCTCTCC AGGTTGCGTG AGAGCAGGGA GAAAGCTAAT GAGATCAAGG
21601  ATGTGCAAAT GCACTCAGAA GGTGCCTAGT GAGTCCTTGC TAACTGGCAC
21651  TTAGTGAAAC AAACACCTCC TGTGTGAGCA CCTAATATGT GCCTCTGTAG
21701  TGGGCTCTGT GACCCGCCCC TCCTTAGTTT CTGCATGGCT GCCAGTTCTG
21751  CACAGCTGTT ACTGCTGTGG GGGCTTAGAA GGTGGGGGTA TGACTACTTT
21801  TTCTGAATTT ATTTTTAATT TTTTACATCT GTTTTATGGA GGCATAATTT
21851  ACATACAGTA AAATCACCAA TTTAAAGTGT ATAATGAGTT TTGATAAATA
21901  TATATGGTCA TAACCACCAT GACAATTAAG AAAAGAATAT TTTTATCCTG
21951  GCAAACTTCC CTTGTGCCCT TTGTAGTCAG TCCCTTTGAG GGGGACTTCT
22001  TATAGGAGTG TGAGAAGTAC TGGGTTTTCC TTGGGCTGCA AACCTGGGCA
22051  CATGGAGTGG GGGTGCCTCC AACATGCTGG AAGTTGCCAG GGAACTGCTG
22101  ACCCTCTCTG GGCCTTGGTT CCTGGCAGAG GCAGTGCAGC CAGGCAGGGG
22151  AAGGGATGCT TAGGCCTTGG TCTCCTGAGG GCAAGCTTG GATGTGAGGG
22201  TTGGATCAGC TGGAAGTGGT GGCTTCAGAA ACCCATAGAG TGGGTGACAG
22251  GGTAGGGACT TGGTGTTTCC ACAAACCCGC CCCTCCTTTG ACCAGGTGTG
22301  CCCTGTGGTC CTGGTGGAAA TGGCTATATA TTGTCCAGAC TGTAGCAGGG
22351  GCTGGCCAAG ATGGTCCACT CCTCTCCCCA TCCTCCTCCA ACCAGAGGCC
22401  ATAAACCCCA CTCTATAGAT TAACAATTCC CTGAAAAGAA GGGGGTCACT
22451  TTTGTTCCCC AGTTCTAGAA CTAAATATTA AAGCAATTAT GTAACTAGCA
22501  ATAAATTACT TAAAGTAGTG ACTCACTCAG CTTAATTAGA GCGCAAGCAA
22551  GGAGGGATTA AGGTATTTTT AGAGCACACA CCTCACTCTC TCCTGTGGGG
22601  GAGGCCTCTG TGCAAGGTGG GGGTGGAAAA AAGGCTGGGA ACTCATGGGA
22651  GCACCCCAGG TGTCTGCAAG GAGATGAAAG CTGATCCTCC GCCCCACTGA
22701  GGTCCTAAGG AAGAAAGGCC GAGTCAGAGC TGCAGCAGGA GGGATTCGGA
22751  TCAGACTCAA GAACACTTCC CAGTGGTGCT TATTTGAGAA CTGGGACGGC
22801  AACACTAGAT TGTAAACTCT GTGAGGGCAG GGATTAGGTC TGTGACCGCC
22851  TCCTCACCCA GCGGGAGACC AAGAATGAGA CTTGGGAGTC AGACACAACT
22901  GGGTGTGACT CCTGCCTTTG CGGGTTGCCA GCACGTGGGC TTGGGCAGGT
22951  TCCTTTATCA CCAGAAGCTT TGCCGTCTCC TCCACTATAA AGTGGGCACA
23001  ATAACATCCA CCTGCATGCA TATTATAAGG ATTGAGTGGG TTAAAATGTG
23051  CAAAGCAAGA CTTTGTGCTC AGCTGGGCAC AGCGGCTCAC ACCTGTAATC
23101  CCAGTACTTT GGGAGGCTGA GACAGAGTGC TTCAGCCCAG TAGTTTTGAG
23151  ACCAGCCTGG GAAACATAGG GAGACCCTGT CTCTTAAAAG AAAAAAAAAA
```

FIGURE 3-8

```
23201  TTAGAAGACT CGGTGCTGAC TCTGCTAGAC CAAAAGCCCA CAAAGGCAGG
23251  GATTAGGTTT GGTTTGTGTT GTTCATTGTT GTATCTCAAG CTTCATTCAT
23301  AGGACTGCAC AAAGTAGGTG TTCAGTAAAT GCTTTGTTGT GTGACTGCGT
23351  GTTAATTTTG TTCCCATTCT CCTGCTCCAA AAAAAAGTTC ATTTTCCTGA
23401  GGTTGTGAGT GAAGAAAATA GGCAGTGTGG GCTGGGTGTG GTGTCTCATG
23451  CCTGTAATCC CCAGCACTTT GGGAAGCTGA GGCGGGAGGA TCACTTGAGG
23501  CCAGGAGTTC AAGACCAGCC TGGGTAACTT AGCGAGATCC CATCTCTACT
23551  TCAAAAAAAT TTAAAACAGA AAAAATCTAG GGTGTGTGGG GGGGCAGGTG
23601  GGGAGGTTGC AGGGGTGCCT CACAGGTGGG AGTCTGGCAT TTCTCCTCCA
23651  GGCTGAGGAG GTGGTGACTT CCAGGGAAAG TCCTGGGAGG GATCAGAACC
23701  ACAGCTCCAG CCTGCTTGGA TAAGGGTGGT CTTCTGGCTG CCAGGAGGGT
23751  AGCTAGGTGG GAAGATCTGC CCTTGTTTCC TCCATAACCT GGGGTGGGAG
23801  GAGGAGGAGC TCCCAGCCCA ATCTGATGGG GGAGACCAGA ACCCTCACCC
23851  ACCATTGCTG GCAGTTCAGA GAAGGCAGCG ATAAGTCGGG GTGGGGCATC
23901  CTGAAAGGCT TCCCAGAGGA TTGGATGGGA GGATTAGCTG AGAAGACATC
23951  CGGCATCCGT AAAATGGAGT AATGATTCTG ACCCTGCAGG TTTTCTGGGA
24001  GGATTAAATG AGTTACATTT TAAAGATGCC TGGTACATGC CTGCCAGGAG
24051  AAGGCACAAC ATATGAACTC CCTCCCTCTT CCCTCCACCC CTCCTCAGCT
24101  CCTGTGACAT CAGGAGGGAC ATGCCCTGCC CTGCTCACAG AGGCTGGGTG
24151  GGAGGCTCCC ATCATGGCCT TCACTGAGGC TGCCTCTGCA GTTGGACCAA
24201  GCTGGACACA CAGTAGGTGC ACATAACAGA TGGGGCAGG TCTGTGCTTG
24251  TTTTACCAGG GTGTTGGGAG GCTGAGGGAA GGGCACAGCT GGATTGGGGT
24301  GATGGAGTTC AATCCCTGCT CCTCCCCCAG ATCCAAGATC CTAAGACGCC
24351  TATGTCCAGT GGCTGCTCTG ATCAGCTCTG ACCAGCTCTC CTCACACCTC
24401  ATAGGCCTTC CAGGGTTCAG GTGATGAATT AGTGATGACA GCATCCAGCA
24451  TCGCTATGAC AACCACATGG CACTCTTAGC CTCCAGTCAG GGCTCAGCCG
24501  CAGAGGCCAG AGACCCCTTT GGCTCTGGGC CTTTGTACTG GCGTGTGTGA
24551  GCGGGGCTGG GGCCTGAGGG AGATGGAGGA GTGGGAGGGG CAGGGGCCGG
24601  GGCATGGGGC TGCATCTGGC ATGGACTGGA GTTCATTCAG ATTGTTCCAT
24651  CCAGAGGGAC CTTGGGGACA GTTGTTTCTC TCCTTCCTTC CCCCTTTCTT
24701  TTCATTCCTC CATCCCTCCT CTTTCCCCTC CTCCCACTTC TTCTGAGCCT
24751  TGTTCCTGTT TGAGGCCCTG GGCTGCCAAC CCTTTTCCCC TCCTCTGGGA
24801  ATAAAGCCAG GCTCAGCCCT CACCCCGGGG AGCTGAGTGA GGTGGGGGAC
24851  AGCCACCTTC TGGTCTAGGC CTCAGGGAAG GTGTGTGGGG ACCACTGATG
24901  GCTTGGTGAG AGGGCCTGAC CCAGCTGGGC CAGGGGCTGT GCAAGTGGCT
24951  GCTGACCCTG ATGAGTGGGG AGGAGGTTTT CAGTAGAGAG GCAGGGTCAG
25001  AGATGAAGCA GCGTGGGATG GGGGAGCGAC AGATGTTCAG AGTGGCCTAA
25051  GTGTGAGATG CGGAGCAGAG AACGTGGGAG GAATCGAGGC TCGAGAAGGA
25101  CTGGGAGAGA GTGGATGCAG TGAGGAGTTT GAAGTTTGTC CCTGGGGGAA
25151  GAGGAGCCCT GAAGATTTTT GTTGTTGCTT CTTTGATTTT TAAATGGGAG
25201  GGTTCATTTT AGAGATGGGG AAACAGGCCC AGGGTGGGAA AGTGACTTGC
25251  TCAAGCTTAA GTCACTAGAG ACAGACTGAG AGTACAGGCT CTGCTTGGGT
25301  CCTGCTGGAC TCTAGCTGGG ACCTCTTGCC CCAGACTTGC TGGCCAGGAT
25351  TTTCCCAGGT AATCACTACC TCCGAGAAAG GCGAGGAGAG CCCATGGGTG
25401  ACTTTGCCCT CAGTTTGAAT GAAATTTGCA TCAGCAAGGG CTATGCCGAT
25451  AGTCCTTTCT GCTCGTGTCT GGCCTGTTTG GGGGTGGGAG TGGGGTGGAG
25501  GTGAGCATCC AGGGAAGGAT CTGGGAAGTC AGGGGCTTGC CAGGGCCAGC
25551  AAGGCATTAG GGTCAGAGAT GGATTCAAAC TTGGGTCTTT GGAGACCCAG
25601  CCCAGACTCT GTGCTCCATC TCCTTCCTCC GTCTCTCAGG AGCCTTTGGC
25651  TGAGTTAGGC ACCTACAGGA GGCAAGGGCC CCCCGAGCC CCTCACATTC
25701  TCCTCAGGGC TCCTTCTGGC CCTGGGCCT GATATTGGGC CTGCTGTGCT
25751  GGAACTTATC CAGGCAGAAT AAACCTTTAG CCCCATTGTC CTGATGAAGA
25801  AACTGAGGTC CCGAGGTAAC AGTGACTCAT TCAGGGTTAC AACAGGTCAG
25851  TGGCTGGGCT GGGCCTAGCG TCTGGCCCTC AGCTTGTCTA CATGGCCCCC
25901  CTCGTGGCTC TCCCCTTGCC TCTCGCACCC CACTGTGCAG CATGGTTGGG
25951  CCTGCCAGCC TTGATGGATG GCTCTGCAGC TCAACCTCCC TCCCATTCCT
26001  CTCCAGATGC CGGGCCGTGA GCCTCCTAAT CACCAGTCCT GCCTGGTGGC
26051  CGCCAAGCCA TCCATCTCCC CACACAGCCT TGCCCAGCAC AGGTGATTTT
```

FIGURE 3-9

```
26101  GTTTGGGGAG AAGGGGGGCA CAGCAGGTCT TCCTCTGAGG CTGAGCCAAG
26151  AGTTTGGCTG CAGCCCCCAC TCTGGGGTGC CCGAGGGTTA GGGAATAGCC
26201  TGCACTCCCT TGCTGGAGTG TCAGAAATCC CTCCTGAATC TCCCTAGGGC
26251  ACGTGCACAT GCACACACAG GCACACACAC TCACAGTAAC ACTAATAAAA
26301  GCTCTCGTGT AGCAAAAGAA TATTGTATGG CAAGTATTGT TGCAGAGCCA
26351  TATGTATCAT CTCATTCATC ACTCCACTGT AGAGATACAG AAACTCAGGC
26401  TCAGAGAGGT TAAGTGACTT GCATAGGCTC CATATCCAGG AAATGGAGGA
26451  GCTGGGATTT GAACCCACAT CCTTATGGCT CACATCTTGC ATTCACAACT
26501  CCTGCTCTAC TGACTCACCT GTGCACACAC ACACACATGC ACACACACAC
26551  ACGTGCGTGC ACACACACAC ACAGGCACTC ACTTGCATGC ATGAGCACGA
26601  GCCACCATTT TGGCTCTTGT ACCATCCATC TACCTGGGCC AGGTTCTTGA
26651  GGAGTGAGGA GAATGCTGGG CTGCAGAGGG CATGAGGGGT CACTGCTCAT
26701  TGTCCCCAGG CTGCCCCAAG CTGGCTGTGG CACTGGCTGG CTGGGGAGCT
26751  GCAGGGAGGC AGCAGCCTCC AGGCAGTGGA AAGGGGAGGC TGGGAGACAG
26801  TCGATCGATC ATCCCTGCAG TGCCTCCTTC CAGGAACTGG GGCCCAGGGG
26851  AGTGTGGCGC CACGGGTCGA TGTTCTGGGC AGCAGCACAG TCTCTGAGTG
26901  CGTACAGGGT GTGTGTGGGG CGAGGCTGGT GTGCAGCTGC CCGCCTTCCC
26951  CTGGCTCCCT TCCCCTGCTC CTGCCTTCCT CCTGCCATTC ACCTGCCAGC
27001  CCCACACCTT CCCCTGATTC CCCCACTGTC CCCAACCTGG GCACTACAGA
27051  GGCTGAGAAT CAAACTCCCA GTTCCCAGGC ACCTGTGTGC CTGCTGCTAC
27101  CATCCCGCCC TGCCCTAGAG GCAGGTCTCG GGTGGGTGCT GCAAGAGTCA
27151  CCCTATGGTG GTTGGGGATG GGTGGGTAGG GGGACCGGGG GCTGGAGCTG
27201  TGGGGATGTG AGGCAAGCCC ACCTCAGAGC CTTTGGAGAC CTCGACAGAC
27251  AATACGATGA GTTAAGAAAT GTAAAGGGGC ACATAGTGGG TGCTGAATTC
27301  ATCTTGTCTC GTTCCTCCAG TAAGAGTCTG GAGAAACCAA GAGCAGCTGG
27351  GTGCCTCTGA GGGCACAGGA GCTCCCAGGG CTGGCTGGCA GGTGCAGCTA
27401  ACAGTGTTAG CAATCCCAAG GACAGGTAGC TTGGGGCGGA GGACAGCATG
27451  CTGTCACCCA TCCTGATGAG GGGAGAGATG TCTGGTGCTA GGAGCAGTGG
27501  TGGCCGGAGG AGGGCTGGGG ACCCTCCCCA GGCCACCCCA CACTCTCCCT
27551  CTGGGAGGGG CTCCTGAGCA GGCCTGGTCA CCTTGCTTCT TGGCTGCTTC
27601  TTCCCCGGCG GAGGAGCCTC CCCCAGGCTC TCCCACCTGC ACTGGCCTCA
27651  AGAGAGCTGG GATTGAGCCC CAGTTCAGGC ACCTGCTGGC TGGCGGAGGT
27701  TAGGGCAAAT CACTTTCCTC AGCCCTCTCA TCCGTGACAG GCTCTGGTGA
27751  GGGTTAAATG AGATGTTGCC CGTCAAGTGC CTGCCACTTC CCTGACGCCG
27801  AGCAGCTAGG CTGCTCTGGG TTCTCTAGCA CCTGCCTCCC CTGGTCCCAG
27851  CACTGGGTGG GCGGCTGTGT TCTACCGGTC ACTGGTGGGT CCTCAGGGCC
27901  CCGACACAGG GCCTGCTATT GGGAAAGAGG GAAGTAAACA TCCCAGGGCT
27951  GGAGCTCTGC CCACTATGGA GGTGTTCCAT CTTAGGCTCT GTAATCTCCT
28001  CATTCACTCT GGTATGGGGA CAAATGTGCC TCTCTGCACT AACTGAGCCC
28051  CCATGGGCAA CTAGGAGTGG TGTCACTTGG GGTGGAGGTG GGCAAGGATC
28101  TCTGGACTGG GATTTCCAAG CCCTGACTTC CTGTTATTTC AGGCACTACC
28151  TCATTGTTCC ATCTTGGGCA AGACCTGTCC CCTTGAGGGT AAGAGACACA
28201  TGTGACCTCT GACCTCCAGA GTCTCTCTTC TGAGCTTCTG TGCCCAGATG
28251  ATTCTGTGTT CTAGGGGACA GGCGAGGCTG GGGGGTGACC CCCATGCCAC
28301  TGATGGGCAG ACTAAGGAGC AGGGGCCCAG GACTGGGGCC AGCTCAGGAC
28351  TCTGGTGGCC TCGGTGCCCT TGACCTGGTA TTGCTGCCGT TTTGCCCCAC
28401  TGCTGTCTGT CTCCGCGTCC GAGTCACCAC CTGTCCCTCT CCAGTCCTCT
28451  CCTCTCTTCC TTTATTACTA TCTCTATATT GCCTCCTGCC TCAGGCTTAT
28501  CTCCTCCTGT CATGCCTCTA TCCACCTCTG TCACTCCCCT GCGACTCTGC
28551  CTCACTCCCT GGCACACCCT CTCCCTCCCT GGGAGTCGGG AGTGGAGCCT
28601  CGCTGGGAAT CAGGACCCCC CTGCCTCTGG TCTCTGTCTA AGCAGTCTCT
28651  GCGATTCTGG CCAGCTCTTA TCTTTTTCCA CCTTCCCGAA TCTCTCTTGC
28701  TGTCTGATGG TGTCTCTGCC TTTCACTGTC TCTGAACTCC CTTTGTTTTT
28751  CTCTATATGC TTCTCTCTGC TCTTATCTCT GGGCCTCTGT CTCTCAGGGC
28801  CTGACTGGTC TTGACCTCTT TGCCTCCTTC TTCCCCTCGA GAGCCCAGCC
28851  AGGCAGCAGG TCCAGCCCTC CAGCCCAGAG AACAGATGGA GTCCACCCTC
28901  CCTCTCTCTT GCTGGCTGCC TCGGAAGCCC CAAACAATGG CCTCCGCCCT
28951  GCACCGTGCC TTGTTGCTAG GCCTTGGGCT GGCAGCACCT GGCTTCCATA
```

FIGURE 3-10

```
29001  GCGACGGGTG CTTAGAAACA GAATGCCACA TCTCCCAGTC CCACCACAGG
29051  AGCCTTTGCC GATTGAGCGA GTGCCTTTTG ATCAATCAGG AAGTGTGGCC
29101  AGGCTCTAGG TTGCCTCCAA CTTGAGGAGG CAAGAGAGGA GGGGACTGTG
29151  GTCTCTGCCT TCTGGAGCTG GGGGACTGC TGGGCTGGGA GGAGTTGCTC
29201  AAGTACAGCC CTGAAGCCAA GGAAGGACTG GGGGAGGCCC TGGGCTCTTT
29251  TCCCCAAGTC AGCCTGCTGC AAGAGGCACA AGCTTGGGAG CTGGAAGGGG
29301  CTGTGTTGAA ATTGCTGTTC CATCATTTCT AGCTGCATGA CTTTGGATGA
29351  ATGACCTCAG GTCCCAGGGC CTCAGTTTCA TCAACTGTAA AATTGGGCTA
29401  ATAATATCAT GAAGATTAAA TGAGAGAATA GATCTGGCAC TTAGTAGGTG
29451  GTCATCAATG GCCATTCCCC TCCCTTCCCC TTTAAAGTTG TTTAAAATTT
29501  AATTGACAGA GAGGAGAAGG AGGGTTCTTC AGGCCTGTGG AATGGTGTAA
29551  GCAAAGGGGT GGAGGCTGGC ATGCACCTCA CATATGCTGG AGTATTTAGG
29601  GAGGACCAGG GGCCATATCT GGAAATGGTT CTGCCAGAAG CAGCCAGGCC
29651  AAGCTGGGTG CCATGTCATG CACCTGTAAT TCCAGCTACT AGGGAGGCTG
29701  AGGCAGGAGG ATCACTTGAG CCCTGGAGTT CCAGATCAGC CTGGGCAACA
29751  TAGTGAGACC CCATCTCAAA AAAACAAAAC ACAACAGGCA GGCTGATGGG
29801  CCCATGGAGA AGGGACTCTG TCTCCTGGGA GGTATATTCT TGCCAGGTGC
29851  AAAGGGATGG GCTTGACTAA TTTCTCCTCT AGCATTTGGG GCTGCTGGGT
29901  AGGGAGCTAC ATTGGGGTCC CCTTGCTTAT TCTCATGCTG CTCCCTACTT
29951  CTGCCCTGTC ACTTGGTCCC AGGAGAGGGG CTCCCACTGG TTCCTTTTCC
30001  CTGCCAGGCC TGCCCACCAA GGCCACCATG GCCACACAGC CTGAATCCTG
30051  GGGCCAGCAA GTGTCCATGG AAGGCCCCAC TCTGTCATCG TAGAGATCAG
30101  GAAACAGGCT CAGAAGTAGG AGGGCTTCCT GGTCCTAGGG CCCAGCTCTT
30151  CCCTCTTTTC AGGCCTGTCT TCTGCACTAA GGACTTCAGG CCACCAGGGA
30201  AGGTGGGGAG GGAGGAAAGG AGATGAGATA GACTTGGGCG GGGGCCTGAG
30251  GACAGAGTTT CATGTCACTT GGGCAGCCAG GAAAGGGTTA AAGATCCCTT
30301  ATCCCAAGCC ATGGGCACTG GCACTGCCAG AGGATGCTGA GGCCTGCTGG
30351  GGCATAAGGA CAACAAGCAA CATCCTTTTC TGAGCTGTTG GGAGTGCCAA
30401  GCTCTCTGTT AAATACTTTT GAGCCTCTTC TCATGTATTC ACAGCCACCT
30451  TTCAAGGAAG GCCAGTTGAT CCCCAGTTTA GAAGTGAGAA AACGGGGTCT
30501  CCAGGAGGCA CTTGTCTAAG GTGACACAGC TGGAGAGTTG GAGATGGTGG
30551  TTAGACCGAG TCACCCCCCC AGACCCTGGC CTCTCCCTGC GTGCCCCTTC
30601  CAGGACACCC ATCACTCCCT TGACACCCCT TGGGAGTGGG TGTTCATTTC
30651  CTTGGGCTCT CCCAATCCCA GTCCTTGGTA TCCCCAACTG CAGGCAGACA
30701  CAGGTGCTTG CTGCTGTGCC CTCCCCTTTA CCTGGCATCA CAGAGACTCA
30751  AGCCCACTGA CCATTAGGCT CTCAGGGCA TAGAAACCAG GTGCTGGAGT
30801  CTTAGAGTCC TGCAATCAGG CATCTCAGGC AGTCAGGACA TTAGAATGTT
30851  AGAATCTTGG GCTTCTACAT TCTCAAGACC CCAGGTTCTC GCATTCACAG
30901  AATGTAAGAA AAACAGACTT TTTGAATGAT GGGGTGTTAT AACAGAAGCT
30951  TTGATTTTCT AAGAACATGA AGCTCTGGGA GTTCTTGGAG CCTTGAAGCC
31001  ATAGACTGGG GCCTCCCTGT GTGATGGTTT CTGAGTTAGC AGGGAGTGTT
31051  CAGAGTATGG GGCCTTGGTC CCTGTTGCTT AGACCTTCTT GCCTTGGTAT
31101  CTCTGATGGG CTCAGCTCTT AGTAGCCTTT GTGTATGTGT GTGTGTATGT
31151  GTGTGTGTGT GTGTGTGTGT GTGTGTGTGT GTGTGTGTGT AGTGGGGACT
31201  GGGGTCAGGG GTCAGGGACT GACTCTAACC TGAGGCACCC CTGGAGTGGG
31251  GCCAGCCCAG GAATAGCAGG TGGAGGAAAG CCGGGCAGCC TCAGGGCTGC
31301  AGCTGTCTGG TGGTACAGGG CAGGGCTCTG GGTGGCTGCC TTTGGCAGAG
31351  GACCAGCCTG CCTCCTTCGT CCCCTACCCA GCCTGCTACC AGGATCAGGA
31401  GGAGGCATCT CCATGGGACT CCTAGGGCTG GAGTCAGAGC AGCCCCTCCA
31451  GGTTCTGCAG CCTGGACGGT AGGAGGTGCC ACTAAGGGA GGAGATTGGG
31501  GAAGGATTGG GACCTTTATC TGCGGTGAGG TGGGCACGG GGGGATGAGA
31551  GATATAGTGG GAGTCTTTGA AGGGTGTGGG ATCAGTGAAG GGGCTGGGGA
31601  TTTAGTGATG GGCTGGGGCT TAGGATGGAG CCAAGGGCTC TGTGGGTGGG
31651  AGACCTTTTG AGAGGGTGGA GACTCAGAGA GAAGGATGGG GGCTCAGCAA
31701  GGGGATGTGG CTCAGTGGAG GTTGCTGAAG AGTTTCTTGG GGTTGGCTAC
31751  ACGCGGTGGC TCACGCCTGT AATCCCAGCA CTTTGGGAGG CCAAGGCGGA
31801  TGGATCACTT GAGGTCAGGA CTTCAAGACC AGCCTGGCCA ACATGGTGAA
31851  ACCCTGCCTC TACCAAAAAA TACAAATATT AGCCGGGCGT AATGGCAGGC
```

FIGURE 3-11

```
31901  GCCTGTAATC TCAGCTACTC GGGAGGCTGA GGCAGGAGAA TTGCTTGAAC
31951  CTGAGAGGCG GAGGTTGCAG TGAGTCGAGA TTGTACCACT GCATTCCAGC
32001  CCTGGGCGAC AGAGCAAGAC TCCATCTAAA AAAAAAAAAA AAAAAAAGTC
32051  TCAGGGCTGT CTCTGCACTG CTCCAGGTTC CTGAGGACGG CGGTTGGGGC
32101  TGGGGGAGTC TTCTGTCCCT GGGGTAGGCT GAGAAGCAAG AGCTCCTTTT
32151  CCCAACTCTG CCCAAAGCTG GAAAGGTTGT TAGAGCTGCT AAGAAAGCTG
32201  GCATCTGCCT CTCCTTTTGC TCATCTTCCT TTCTGGTTTC CATGGGAATC
32251  TGTGGCTCAG GATGATCAGG GGTTGACAGG ATGGCGCTGT GGAAGGAGTC
32301  TGTGTCAGGC ACAGCCATCC CACATGGGAA GGAGCCGGCT GGTAAGAAAG
32351  TGAGTTCCCT GTCCCTGGGA GTGTGCAAGC AGGGTAGGGG CTGAATGGCT
32401  AGAGTGACTC CAGAAAGGGG TTCAGATGGG GCAGAGGAAG CAGTCTGGAG
32451  GCCACTTCCC TGAGACAATC ATGTTTTGTG TGATTGGCTC TGGGGGCCCC
32501  ACCAGCCCCA CCTTCCAGAC GTCCCTGGGC CTCACAAAGG GGGTTGCTGC
32551  ACCCTAGGCA CTGCCTCTGA TCCAGCCCCA ACTCCTGTGC TCTGTGCCTG
32601  GCCTATGCTG AACACGGACA TGTGCAGCTG AATCAGATTC AGTCTCTGCC
32651  TAGAGGAGCC CCAGTCTGAT GGGGGAGGCA CACAGGGACA CAAATATAGC
32701  TGGGTAAGTC CTACAAAAGG GGGCATACCT GGCTGGGAGG CAGTTCCATC
32751  ACTGATTCCT GTAGTCTGTA GATGTCTTTT TGAGCAATTC TTCTGGGTCA
32801  AGACTTGTTC TTATTTGCTG GGATAAAACA GCAGTGAGCA AAACAGAGCT
32851  GACAGCATGG TGGGAAGGTT GAGCTCTTCC AGACCGTGAT GAGAAGTATT
32901  GGTGAGTGGT GGGGAGAGTG GCCAGAAGGC AGAGTGTGGG CGCAGCATGA
32951  GAGGAGGCTT TGTCCAGACT TAAGGACCTG GAAGGCCTTG AAGGCCAGGA
33001  CCAGGGCTCC AATTGTCCTG CTGGCAATAG GAAGCCATAT GGGTGGGGGT
33051  GAGGCAGAAT CAGATTTAGG TGTGGAAAAG ATGACTCCAG CCAGTGTGGG
33101  CATCGAAGAG GAGGCACAGA AGCAGGCGTG GCCACCTGTG CCTCTGTGTA
33151  GGAGCTGTGT GAGCATGTGC TTGAGGATGT GTGTCTGTGT AGAGGACTGG
33201  GGTGTAGGCG TGATAGGAAC ATGGACGTGT ATCTATGGAA AGACTCCAAT
33251  TGTGCATAGG GGTGTATGTG TGTAAGATTC TGTGGCCCAG GGCAGCCTGT
33301  GAAAAGGAAG GATCTTGGGG TCTCTGGATG ATGGGGAGCA GAGACTAAGG
33351  CCTAAGGTAT GCTGGGGCTC GAGCCCCCTG GACTTTATCC CCTGTGAGCT
33401  GGCAGGTCTT AGACTAGTCC TGGACTAGAA TCCTATGGGT TCCCTTCCCC
33451  CAGAGGGTCA TGGGGCCAGC CATCTGCTGC AGACAAGACA AACATGCATG
33501  CAAATCACAT GAAAATGGAT GAGGCCTGTG GCTGACCCAC CCTACAGCCC
33551  CCATCCCCTG GGCCTGAGTT CACTCAGCCT GTACCCTTCC TGACCCAGAG
33601  CTGCTGCCAG GGCTCTGGGA ACAGGCCTTG CCCACTAGGA GCTGAAATTC
33651  ACATTGTCCC CAGCACCTGC CCGTGGCCAC ATCCTCTCTC TGTGAGGGCT
33701  ACCCCCACAT CTGGAGCCAT AGCCAGCGGA CACAGAGCTG GATCTGGACT
33751  GGTGGCCATG GGCAGCACCT CTGGCAGGTG CTGAGGTGGA GGAGGCAGTA
33801  TCCAGGCAGG CATCCCTGGG CAGAAGGTAC CTCTCCTGAG CAGACAGGCC
33851  TACCCAGGCA CCAGGCCCAA AGATAGGGGC AAGGGCTAGA TCCTGGTATT
33901  GGAGGACCCT CAGGAGAGGC TGTGTGTGAC TTGCTCTCTC TCTGACCTGG
33951  GCTAGAGCAT AAACACGTGT CACATACTTG CACACACATT CACACGTGAA
34001  AGCACGCACA TGCTATTCCT GGACACTTGT GTACACACAC CACTGCACAC
34051  ATATACCTGC ATGTGTGAAT ATACACTCAC TTCTGCACAC AGACACATGC
34101  CTATCTGCAT AGACACACCC GTGCCAACCC CTATAGATAC ACAGACATAT
34151  CTGTGTATAC ACATATAAGT TCAGCTATAC CACTGCAGTA TCACACACCC
34201  TCACAAGGAT ACAAACCTGT GCTCACACTC TCTTCCACCC TCACACACAT
34251  CATGCTTACA AGCCTGTGTG CAGCCTTACA CACATGCACA CACGTACAGA
34301  GCAGCCTAAG GGTGGCTCAC CCCTGCCCAG GTGAACACCT GTGCCCACTC
34351  CAGGGCTGGA GTGTTGAGGA AAGGGTCTGG ATGGAGGCAG AACCTGCAGA
34401  GATGTCAGTT TCTTCCAGGA AGCATCTTGG ATTGTCCCTT CACAGAGCCC
34451  TTGGAAGTGG GGCCCTCTTT TAGTCCATGG GCTCTAGCCC AGGTCACAGA
34501  GAGAGCAAGT CACACACAGC CTCTCCTGAG GGTCCTCCAA TACCAGGATC
34551  CAGCCCTTGT CCATATCTTT GGGCCTGGTG CCTGCGTAGG ACCATCTGCT
34601  CAGGAGAGGT ACCTTCTGCC CAGGGAGGCC TGCCTGGATA CTGCCTCCTC
34651  CACCTCAGCT TCCTGAGCAC TCAAAGAGAA GCAGGCCAAG CTTCACGGCT
34701  GCTGAGAAGT CTGAGACCAG GGAGGGCCAA AGCCTTGCCT GAGGTCACCC
34751  AGCATGTCAG GGAAGGGCTA GGGTTTGAAC CTGGGCTTCC AGGTGGGGGT
```

FIGURE 3-12

```
34801  GTAACCATGG TCCATGGCAA CAGGATAGAT GCATGTCAGG CAGCAGACAG
34851  GCCCTTGGAA GCAAGACATG TGGTCATGGG GGATAGGAAA AGACTTACAG
34901  TCTATGGAGA TCTGCCAGGA CCAAGTGTGT GAGATGGAGA GATGGTGCTT
34951  CTTCACCAGA GCTCACTGGG CACCACAGGG CTCCCAGCTT GGCTGGACCA
35001  TGGGGACTCA GGGAAGAATC AGACAGGCCC TGCTCTTGAG GGAGGGCTGG
35051  GGATAGGTGA AGAAGGAAGA GGGCATTATA GACTGGGGAG ATGGTGGGGG
35101  CTACTTCTCG TTGGATGGCA GTTTTCTTCC TGCATCTTGA AAGATCTAAC
35151  TTTCAAATTT CTTTACCCTC AAAACTCGGC ATGGAGTACA TTCTCAGTAA
35201  ATATTTATGG CATGAATGAA TTAATGAAAG TATGATATTG GCAGGCAGAT
35251  ATGCCTTTGG AAGGGTATTC AAAATGGGAG GGCAACAGGT TGGGCAAAGG
35301  CAAAGAGGTG GAAGAAAAGC CAGAGGTTCA GGGTACAGCT GAGTCAGGCA
35351  TGGCTGGACG GGAAGTGGTA GGAGAAGCAG CAGGAAAAAG TCACGTGGGG
35401  ATGAGCCTTG CATCTTATAC TGAGTTTGGA TGTTGCCTTG GAGGCCATGG
35451  GGAGCCCAGT GAAGATTATG AGCAGAGGGT GAACATGGTC AGAGTGAACC
35501  TGCCCTGGCT TTGGGGGGTC CTGGGCTACA TAGTAGCTGC TTATCCTTGG
35551  TGCAAAGAGC ACTGGGTTTG GAGTCTATAG GCCAGGGTTC ACATTCCTAT
35601  AGTAACCAGC TGTGCCATCT CAGGTAAGCA TCTACATTTC TCTGAGCCTC
35651  ACTTTCCTTA TTTGTAAAAT GGGGCTAATG CCGTGCCTCC TGAGGCTGTT
35701  GGATCTGGCC TGGGTGAGGA AATGCTTTGC CAGCACAAGG CCCTACCAAT
35751  GAGAGGTGTC ATTTTTATTA GGAACAAGGC AGGGCTGGTT CCTAGACAGG
35801  GCCTGAGGTT GAGTGGGCCC AGGACCCAGG CTGACAGCTG AGTCACCTTT
35851  TCCAGGCCAA GTGGCCTCTA AGGTGGGAAG ACAAAAAGAG TTGGCTAGAG
35901  GGGCTGGGCT ATGCATTCCT AAGCTGGAGC TGGGAGGAAA GCTGGGGCTG
35951  GGACTGGGCT TCCTGGTGTC CGAGATGGGC AGAGGGTGCA GACACCGGGA
36001  TAGTAGGACC CTCAGCCACT GCATTCTTGG GGACAAAAGA GGAGCTGGGA
36051  AATCTGATTT CCTTACCTGG CTTTGCTCAA GAAGCAAGGA ATGTATTTAA
36101  GGCACAGACT GGAGTGAGAT GGCCTGGGTT TGAATTTTGA CTACTTACAA
36151  GCTATGTGAC TGTGGGCAGT TTACTTTGTG CCTGAGTTTT CCTTATCTGT
36201  GAAGTGTGAC TAATAATAGA TCCCACCCTA TAACATTGTT GAGAAGATGA
36251  AATGTGAGGC ACACAGTATG TGCTCAATAA ATGCGAAAGC CTCCCAGCCC
36301  CAGATGTATA CACTCGGCCA GTAGGGGCCA GCCCTGGCCC TCACCTCCAT
36351  GGGACAGAGG TCAGCCAGGG AGGAGATGCA TCTACTCCAG GGTTCTCTGA
36401  CCTGGCAGCA AATTAGAATC ACCGGGGGAC ATTCACAAAC ATCTGGGATG
36451  GGGGTTCCAG ATATCAGTAT TTAAAATGCT CCCAGGCAAT TCTAACATGA
36501  GTCAGGGTGA GAACCCAGAA CAGGATCACA GATTGTGCAG TTGGAGTGAG
36551  GTAGGGATCT GCGTGTGAGT GGAGGAGTCC TTGGAGTGGG GTCACTCCTA
36601  GCTATAAGAG CTCGGCAAGG CCTTTAAATG TGCCAACTCA AGGAGCCTTG
36651  GTTGCCCCCT CAGGAAGGGT GCTGGTTGGG GAATTTCAAG GATTGTGTGA
36701  GAGGGTTTTT CTGAAAGGGC TCTGCACTCT ACCAAGCACT GGAAGAAAGC
36751  AGTGCACTTG TTTATTGAGT CTAGTGTAAT AACATTTCAC AGATGGGGAA
36801  ATAGAGGCCT AGAGAGGTGC TGTGGCCTGC TCAGAATCCC ACAGCAAGTC
36851  TATGGCACAG TTAGGACTCA AACCCTCTGA GGAATGCTTG GATCTGAAAG
36901  GTTGACACAG AAAGACTCTT TGAGCTGAGG GACACATAGA GCACACACCA
36951  GGGACCCCAG TCATTGAGCT GTAGTTTGAG AGATTCAAGT AAGACTGAAG
37001  AAATAACTTC TTGGCTGGGT GCAGTGGCTC ACACCTGTAA TCCCAACACT
37051  TTGGGAGGCT GAGGTGGGTG GATCATGAGG TCAAGAGATC GAGACCATCC
37101  TGGCCAACAT GGCGAAATCC CATCTGTACT AAAAATATAA AAATTAGCTG
37151  GGCATGGTGG TGCATGCCTG TAGTCCCATC TACTCGGAG GCTGAGGCAG
37201  GAGAATTGCT TGAACCCGGG AGGCGGAGGT TGCAGTGAGC TGAGATCGCG
37251  CCACTGCGCT CCAGCCTGGT GACAGAGCGA GACTCCGTCT CAAAAAAATA
37301  AAATAAAATA AAATAAAATA AAATAAAATA AAATAAAATA AAATAAATAA
37351  AATAACTTCT CAAGAGGTGA GTGCCATGGA GGTGGTGCCT GGAGTTGGGA
37401  GCCCAAGAGA TGGTGGCGGT GCCAGGCCAG GGTCGGCTGT TGACCATGGT
37451  CTGAGGTGGC CTCCCCTGAA GAACAAGTAA CTCTGGCCAG TGGCTGTAAC
37501  AGATACCTCC CGGGCACCTG TATCTCACCC AGCCTTGTCC AGAGCCCAGG
37551  ACTGAGCCAG TGACACATGC TCAGAATTTA CCAAGAGACT TGTGCACTGA
37601  GCTCAGACTC AGACCTAGTC CTTCCAACAG CCCTTACATG GGTCATCCCC
37651  TTTTACGGAA GAGAAAACTG AGGCCAAAAA TAGGAAGGGA GGCCCTGTGG
```

FIGURE 3-13

```
37701  GGGCCAGAAC CTTTACACAT CTTAGCCCAG GTAATTTTTT CTACAGTGTT
37751  AATAAGTAGG ATGAATTGCC CCTGTTTGGA AGATTCAGTA AAATACATTG
37801  ACTTGGCCCA GATCACTTAC TCTACACCTC TCCTAAGTCC CCAGATGTGA
37851  CTCCCAGGAA AGACACAAAA AAGGGCTACC CAGAGGGATA AGATAGTAAC
37901  CAGGGAAGCC CTCCCAGAGG AGGTGGGCCT TCAAATGGCC CCTAAATGAC
37951  AGGCAGGAGG GAAGGATCTG GGAGGGTATT GGGGGTGGGG TGGCATGGGC
38001  AAAGGCCTGG AGGTGAGAGT CAGTCAGTCA TTGATGTGAG AAGAGCAAGA
38051  AGTAGAAATG TAAGGAATGG TGGGGAGGGG AGTCAGAGCT GGATGACCAA
38101  GCAAGGGTTC AGCTGTAGAG GGTCTGGCCC GCCAGGCTCA GGGCTCGGGC
38151  TTTATTGTGC TGGTGGTAGG GAGCCACTGA GGGTGAGTGG GGGAGAGCAT
38201  GCCAGAGCAT GCCTCAGAAA GAAAGGTGGG AGAAACGCTG GCATGGAGGG
38251  CCGCCCCCTG AGTTGGTGGG GTGGCCGGGC TCTGCCAAGG CTATGTGCCA
38301  GCTGCCTGGA CTGTGTCCAG GAATGGGCAC AATGACTCAA CATTGAGAAA
38351  ATCACTCCCC AGGGAGAAAG GGCCCTGATG AATCACCCAG CTGAGGTGGG
38401  GAGGCTGGGA GGCTGGGAGG CTGGGAGGCT GGGAGCTCAC TGAGTCACCG
38451  TCCAAGAGTT GGTGAGGAGG GGAGCTGCAG AGAGAGGGGC CGGCAGTGCA
38501  GTTGACGGGG GGATTCAGGT CAGACCACAT TGAGGGCTGT CGGGGGACTC
38551  TACCTTCCCG CCATTCCCGG GTTTGGTCCT CCTGGCCGTC CTGTGAGGGA
38601  GATGAGAAAA CTGAGGCCCA GGAAGTGGGG GGAGGGGATC CGAGCAAGGT
38651  CATGCGGCAA GTCGCTGGCA AAGGCCTAGC GAGACCCAAG CGCACCCTCC
38701  AGTCCAGACA CGTCCTGCCG CCCCAGCCGC TTTCATGCCA AGCAGAGGCC
38751  TAAGAACCGG GTCGGTCCGG GCAGGGAGCT GACCCCGGTG ACCCGCTGAA
38801  TCCCCGGACG CGGCCCCTCC GGGCAGCCGG CAACTGAGGC CGGATTGCGC
38851  CGCCGCGATG GGACGGCAGG GGGCGCAGGA GCGTCGCGGC TGCCGCAGGC
38901  TCCTGAACCC AGAAGCCGCT CTGCGGAGAA ACGCGCTCCC GGAGCGCGGG
38951  TCCCACCGCG GAACTGCGGA CCGTGTGGCC CTGGGGCCTG CACCCTCTCC
39001  GGCTCCGGGG ACGGCGACAG AGACCTGCCC ACCCAGGCCT GGGGGCCCCA
39051  GTCAGTGGCG GCCGCCGTGT GTGCGCTCGG TGTCTGTTCG CACGTGTCTC
39101  CCTCGCAGAT GGGCGACTGC TCCAGGGCCT GTCCGTCTCA CAGCGACCTC
39151  CAACATTCTC CCGACTTCCC CCTGCCTCCT AGGCTGAGGG AGAGGAGCAA
39201  GCCCGAGGCT CCTGCGGTGT CCGCGGCCCC TGCCCCCCTT CCCCTTCCCT
39251  CCCCACCCCA CCCCACTGCG CCGGTCTCTG CCTGGGCTC TGGCCGGGCC
39301  CCGGACCCCA GAGTGGTGGC GGGGAAACAG GGTGCGATCA GACAGGGTGG
39351  AGGCTCTGAG AGCGGCCCCT GCGAGATGCG AGAGAAGTGG CGACGGGGCG
39401  AGGGGCAGCG AGCGCAGGCT GACAGCAGGC CAGCTGGAAG GGCCGAGGGA
39451  ACCCAGGGCG AGACAGAAGC GGGGTGACAG CGGCCGGGTG TCCGGTGGGG
39501  TCGGAGGATC CGACGGGCCG AGAGGTGCGG TCCGCGGTGG CGGGGACATA
39551  GGCGGGGCCG GGGCGGGCCG GGGGCGGGCG GGGGCGGGGC CGGGGCGGGG
39601  CCGGGGCGGA CACTCGGGCG GACCAGGCGA AGCTGTCGCG GACGCGCTGA
39651  CCGAGCGCAG CGGCCGGGCC GGCGGGCGGG CGGGCGGCTG CGAGCATGGT
39701  CCTGGTGCTG CACCACATCC TCATCGCTGT TGTCCAATTC CTCAGGCGGG
39751  GCCAGCAGGT CTTCCTCAAG CCGGACGAGC CGCCGCCGCC GCCGCAGCCA
39801  TGCGCCGACA GCCTGCAGGT AGGGGGGCCC CCGCGCTGGG CACCAGGAGA
39851  ACGGGGTGTC CGGCGAGCGC CGGGCCGGGT CTGCCCGCCC CCGTAACCCT
39901  TCTCAGGGTA GGAGACCCCT CCTCTAGTTC TGAATTCTAC TCCTGTGCTG
39951  GACGGCAGC GCAGACCAAG AGCCCTTGAA GCCCCAGCTC TCAGTCCACA
40001  CGTCACCCCA GACTCTGAAC TCCTTTCGGA TCCGGGCTC CACCCCAAGC
40051  ACTGAGCTTC CAGTCCACGG TGGGACCGCA GTGCACACTG AGAGCTGTGC
40101  CCAAGCCTCG AATTCCCTTT CCTTAGATTA GTGGGACCC TGCCCACGCC
40151  TCGGAACCTT CACCATATAT GTGGGGCTCC CGGCACACCT GGAGCACCTG
40201  AACCCCCAGC TGTCATCCAG GACTCCACCT CAGAGCCGGC CTCACCCAAA
40251  GCCCCAAACC TCCATTCCAA GCCTCAACTG GACACCCGCT CAGATTCCCA
40301  CCCAAACATC TGGACTTCAG TCCTCAGCCT GGAACCTACC CCAGAGTCCA
40351  AATCTCTCCT TCCATCAGGG CTTCACTGGC TTTCTCTGTG GACCCACTC
40401  CCCGATCCCT TCCCTCCCTC CTGTGTTGGA GATCTCCGAG TCTTTCCTCG
40451  TGGGGGGCCC CTCCTCTTGT TCCTCTCCAG GTACAGTGGT CCCACTTTAT
40501  TCTCTGGGCT TCTCCTCTGG TTTCTCTTCA AGTATTTCTG GGCTCTCTAA
40551  TTTGGTCTGT TGCCCCATGT GCCCACCTCT CTTGGTCTAT CTTGGTCTCT
```

FIGURE 3-14

```
40601  CTCCTGTTTC TCTAGGTCTC CATCTTCGTT TTGGGGTCTC TTTCTGCAGC
40651  CACCCCTTCC TCTTGTATCT ACCTCTGCTT TGTGGTGAGG AGGGGGCAGG
40701  CTCAGAGAGC AGGGCTAGTG TCCCTGGGAC ACCCCCGCCC CCCATGTTCT
40751  CAGGCATGGC ATGGTGTGGG CTCAGGTGGA AGGGCCTAAA TGTGGAGTGT
40801  GCTGCCCTCA GGCGATGCCC AGGGATCTGA GGTGGTGGGG GGATGATGTG
40851  GTGGGCACTG GCTTTTGTAA CTTATAAAGC CCCTCATCCC AGCTGCCCTG
40901  GTCTTGACGG GGGCGGCTAG GGCTTGAGAT AGGGAAGAGT AAACTGCAAT
40951  CTGGTGTCAA CCTGCGGTGG GATGTGTCCA GGCTGGGTGG GTCTATAGTG
41001  TATGTGTTTG TGTGAGTGTT CCTGTCTGTG TGTAGCACGG GCTGGGTTGC
41051  ATGTGTTGGG TGTGTCTTGT GTGTAATCAT GTGTGTTGTG CCGTGTATGA
41101  ATGTGTCATC GAGAGTGGGA TTATTTGTGG GGAGATTATG GGAATTATGG
41151  GTCTATGGCA TTGTGTGCTA TGTGTGGCTG GGGAGGCAGT GTTGTGGCTG
41201  TGGAGTGGTA GCTGGGTGTG TGGCTGTTGT GTGTGTAGAG AACTTGTGTG
41251  TATGTGGCTG TATGTCTGTT ATTGTACAGT GGAGTTGTTG TAGGGACAGC
41301  TTGCATACAG GATTCTATAT GTAGTTGTGT GTGTTACTGG CTGTTGTGTG
41351  TGGCCAGGAA GGGCCACTGC AGGGGCCTGA TGGTTTCCAC TGGGTGTCTT
41401  GTCAGAGAGG AGTTGGGGCA GGGGGTGCCG TGTGTGCCAA TGTGTTTGCA
41451  GCCTAGGTGG CTGGCTTAGA GTCACTATGG CACATCCTGG GATTGCTTGG
41501  GTAATATATC TATTAGGACC TGAGTGCTGG TGTTTGAATG TCATGTGTCT
41551  GTGTGGTGGC TGCTCCCGCG ATTCTGGACA GGAAAGGGTT GCAGCCAGGG
41601  CTGAGGGGTC TGAGGTGAGG AGCCAGTTGA CAAGTGTGTG AGTGTGTGAG
41651  TGTGTGTGTG TGCGTGCATG TACACGTGCA TATGGGAATG GGGTGGGGTG
41701  GGAGGAGGCA GTGGGCCAGC AGCGCTGTCT ATGCTGAGGG GCTGTGTGTG
41751  CCCACAAACG TGTGACATTA GGTGTGCACA TTATCTATGC AGGTTGTGTC
41801  TGCATGTGTC TCTGTGTCTA GGTGGCGTGC GTATTGAATT TAATTGGATG
41851  CATACACCTG TGGCTGGGGA GGTGAGAGGT GTGTGAGGTG CGTGGTGGGA
41901  GACGGTGTGA GTGTGGTGTG AAGTGAGGGT GTGTGAGCTG GGTGACTTTT
41951  TGGTGTGACG TGTGAATTAT GTGATCTTTT CTCCCCATGA GCTGTGTGTG
42001  CCTGTGGTGA GGAGTGAGTG GAGGATGGCC AGTGAGCTGG CGGTGTGTGT
42051  GTTGGGGGTG TTGAGGACTG TAGAATGTGC TGCGGTGGCA GTGTGTGCAT
42101  GAGGTGTGTG TGAGGAATGA GGTCTGTAAC ATTTGGGGCG TGTGGAATAT
42151  AGTGGGTGTC CCCATAAATG TCTGTGGAGT GACGCATGTG TGCAAAAGGG
42201  CTTGGCTGCC ATCCTGTTCT TGCTCCCCTC CTGATCAGGT CCCTAGAGAT
42251  GCCCTGGAAT GTTCTCCATG CCCCCCCAAC CCCAGCTGCC CCTACCCTTT
42301  GCCCTTCATC CTCCTTGCCT TGACCAAGCC CTTTGTTTTG GGTTTCCGGC
42351  GGAGCAGGCG CTGGACAGGC GGGCGGCAGG CAATGTCGTG GTCTGAGAAC
42401  CTTTGTTCTC TTAGTTTGAC TGGTGTTTGG GGCCTTGGTT TGGAGGAGGG
42451  TGTGGAGAGG ATGCACGTGG CAGCAAGGTC ACTGTGTTTA CTACACCACT
42501  TCGTGCTCCG CAGAGGGGAG GCGTACGGCG CAGGCAGTGA GGCCTGGGTG
42551  GTGTCTTTGG TGGCGCCTGT TGGTGTAAGA ACAGCTTAGG CTGGGCTTGG
42601  AGTTTGCCAG CCATGCAGTC TTAGTCCATA GTGGCCCAGC GCCCTTCCTG
42651  GCTCATGTCA GCGGGCTGA GCAGCCGAGC AGCCAAGCAC TCACTTCTCC
42701  AAGTTCACCT GCCCTCGCCC CTTCTCTGTG TGGCTGCAGC CCCTGGAGAC
42751  AACCAGGAAG ACCTCGATTT AGTTCTATTT GTGTTCACTC CAGGTCAGAT
42801  GGAGGAGAAA GAGTCCCCAT CCTCACAGAG ACACTTATCT GAAAGGAGAG
42851  AGCTGGTCAC ACCTTTGGGG ACCCTCTAGA CTGACGCAGT CTGTAGGGGG
42901  ATCGAGGTCA TACCTTCCAG AGAGAGCTGT GGGAAAACCC TACTGGGCTT
42951  CCTCCCAGCA GGTGCTTGAG AGAAGAAACA TCCAAGGTTC CTTGAGATTG
43001  GAAGGCTTAG AGAAGTCTGA GTCAGTCAGG GAAGGGGCTG GGTCGATGC
43051  CGCAGTGTCA CATACCAGAA GGTTCTCTGA AATGAATAGG CTTGAACTGG
43101  ACCTTGAAGG GGGTGTTGGG GTGGGCAGAG AAATGCAGCC TGGGGCTGAG
43151  GAAGGTTCTG GCCTGACTGG CAAAAGGGAT CTTGCTGGCC ATTCCCCAGG
43201  CAACACTGTC TGGCTTTGGG TAGCCATCCC TGGGCCTCCA GCCTTCTCAA
43251  GCTTTCACGG TACCTTTTTT ATCCCATTGT CTCTGGCTGG AATTATCTTC
43301  ATTGTCGTTG ACATTGTCAT CTTCATCATC TTTAGGCAG TTATTTCCAA
43351  ATTCCAGGGT CCTTTCACAA ATGTCTCATT TAGCAGGTTA ACTCATGCAA
43401  TTGTCCAAAA GTCTTTATGG AACACTGCTG TGTACCAGGC AGGCACAGTT
43451  TTAAGTGCCG GGGTCATGGT GGTGGCCAAA CTGGCCTCAT GGAGCTCCTA
```

FIGURE 3-15

```
43501  CCTTCTGTGT CCAGCCATGC TGTCAGTTGC CCACCCTTCT GTGTTTCCCC
43551  CAGTCTGGGG CGCCTGGTTC TGTGGGGCTC CGCATGTGCA CCCTCTGGTG
43601  CTGGGGTCTG GCTCCTACCA GAATGTGAGC TCTGCAGAGG CTGGGCCCGG
43651  GTCTCTCCTC TACCCACCGT GTGTGTCCTG AGCTGGGTCT GGCAGAGTCC
43701  AGATGCTCAC ACCTATCATC AAGTGACTGG AACTGCCATG TAGGGTTGGC
43751  AGTCCAGCTC TGTCTAGGGA AACTGGGGTC CATCGGATGA GGGGACTCTC
43801  ATCTCATCAG GCAGCATCTC ATCAGGCCCT TCTTTTACCA GTAGCTCCAG
43851  AGACCAAGAA GGGTCAGGTG ACTGGTGCAG GTCTCACAGC AGGGTGGCGC
43901  GGCTGGTGTC AGAAGACAGC ACTTCTTGCT GCCAGGTTGG GCTCTGGTCC
43951  TAGCACCATG CTGCTCTCTG GCTGGCCTCT GTGCTGCCTG CGGCGGGTAA
44001  ACGATTATTA ATGACCCCCC TGGCAAGGAG ACAGGAAATG TTTCCCAGCC
44051  ACAGCTGGGG ACCTGCTCCC TGCCAGCCCC AGCTATCCAT ACCCGTCCTG
44101  ACCATGGCAT CGGTGCTGAT GTTATCTTCA TTCTGCCTCA GTCTTCTTTA
44151  CTCCTTCTGC CCATCCCCCG ACCTCCCTGA TCTTGACATC CTAAGGGTAA
44201  ATGACGAGAA GCTACAGAGC TTTCTTTTCC ATATCCCTGT CCCTCACCAC
44251  TTTCTCCAAC CTGACTCATC TCTACCTTCT TCCTTGTCCC ATGCCAGCCA
44301  GAAGTAGCTC TTCCTCCAAG AAGGCTTCTC TGAATGCACA GCCAGCTCCT
44351  CCAGTGTCCA CTACCCTGAG CCCGAGGCAC TGAGTCCCCC TCATTGCAGA
44401  CTCTAGTCCT CCACTGATGG TTTGCTCTGA CAGCCCTAGG GCTGGCCTGG
44451  GCACTTCCCG CAGACTGTCC CTAATTGCTG CCTTAGGACT GACATATGAA
44501  GGGTCCTCCC AGATGCTACC TCCAGGAAGT CTCCAGTTCC ACTCAGCCCA
44551  GGGATTCTTA CCTCCTTTGA GCACAGTGCC CTTCCTGTCT GAGTCACACA
44601  TGTGTACTTC CAGGACTTCC TAGGTGGACA TTAGTGAACA CCTGCTATGT
44651  GCCCAGCACA GAGGGTGGGA AGAGATGAGC AGGATGCAGG CCTTAAAATC
44701  CCCACACCTT CCTCCAAGCC TGAGCAATGT TGCATCAGCC CCTTGGCAGG
44751  TGGCACAGAC CTAGGTACTA GGGCTGGGGG AGGGGAGGCG GAGAAACAGG
44801  GAGTGATGTT GGTAGAGTGT GTGGGGAGGG CAACGAGGGA GATAAACTCA
44851  GGGGCCATGG TGATATAAAG CAGGGACCCC TATTTCAGCC CAGAGTGGGA
44901  GGGAGGGGCA TGTTGGGGAG CTTCCAGGAG GAAACAAATC TGAACTGAGA
44951  GCTAAGGTCA AGCCAGGAGA AAGTTCTGGA CAGAGGGGAG AGAATGGTTA
45001  CTGTGAAGGT TCGCTGGTGG CAGACAGAGG GAGGAGAGCC TGTGGCAGCA
45051  CCACTCCATG GAGCAGGCCC CTGGGTGCCA GCCGGCTGGG TCCGGGGGGA
45101  TGGGGACTGG TAAAGCTGGC CCAGCCAGAT GGTGCAGGAC TTGTAAGCCA
45151  TGTTAAGGAC TGCGGACTTA TTCTGGAGGG AAATTGACCC TGGGGAAGAG
45201  TTGAGAGAAC GGATATGACA GATCAGATCT GCATGTTCAA TAGCTCCCTG
45251  GACCATGGTG TGGAGACTGA AGGGGAGGCT GGTGTGGTCC AGGTAAGCGG
45301  GGGTGATGAG GCCTGGACAG GGAAATGGCT GAAGAATGGA GGGGAGGGGA
45351  CGGAGTGGCC AGGGCTGGTG GAGGGAGCTG GACAGCTGTA GACGTGAAGG
45401  GCAAGGGAGG AGAATGCTGC CCCACCCAGG TGTCTGGATG GGTTTTGTGC
45451  AGTCTCTGAG ATGTATAGGA GGGAAGACAG GGGTTAGTGG CAGATGCCTG
45501  GGCCTGTGTC AGGGCCCTTT AAGGACCAAA AGGTCTTGGA AAAGCCTCAG
45551  AGGAGATCAT GAGCTTTGAG ATTAAAGGGA GACCTGAAGC CGGCCCAGGG
45601  CTGCTACAGC CTCACCTGTA ACATGGGAAC TTGAGATCTG CCCTGGGCAA
45651  AGGGTGTTCA GAATTCAATA ATCAAAACAA TCTGTGAAAT GTAATACTTA
45701  ATAAAATTCA AATCCAAAAA TGTCTGAGTA CATTCCAAAA TGAGTAAAAA
45751  TGTAAATTTA TGAAAATGCT AAACATGCGT GATTGTTCTA ATGTAAATTG
45801  TAAGCCTCAG CTGCTTCCCA GAACTTTGGA TCTGGCTCCC TTGAAGCTGC
45851  TGCCTCTGAT GTGGCTGCCC CCTGCAGCTC CAGGACCTTC CTGTTCAGCT
45901  CCCTTGAGAG TAGCCGGCAG GGCCCCTCCT CTGCAGAGCC TGTACTCTGG
45951  CTGGTGGCTT CAGGGGGCAG GCATTCTGCC TTTCCTGTCT CCCACCCTAA
46001  GGGAGTTGGC CTTGCATGCC TCCCATCCAC GGTTGCCTCT ACTGGGGGCT
46051  GCCACTGGGA GACAGGAAGG GCATGGGAGT TTCGGGAGCT CAGGGTAAGA
46101  GGGGCTGAGA TCTCGTGGTG TGGAGGGGGA GCGGGAAGGT CGGGTGGCCG
46151  AAAGAATGGA GAGGGCCGGG AGTGAGAGCA AAGGGAGACA GGCAGAGCTG
46201  AAGAGCAGTA TCGCCCCAAC ATCAATACTG GTATTTCAGA ATGGGAAAGC
46251  TGTTCCATTT CCCGAAATAT CAGAATGCTG AGGTCCGATC TTGCAGTCTC
46301  TGAGCTGGGC ATTCCTTGGC CCCCACTCTC GGGTATTCTT GCACAAGACC
46351  ATTTTTCTGG GCTGCATTTT CTCACTTGTA AAAGGAGGAA GTTGGGGGTC
```

FIGURE 3-16

```
46401  AATATCTCCA AGCGATATAT GAGCTCTAGC TCTAGGAGTA TAGGATTTTG
46451  AGAATCTGGA ATTGTTAGTC TGTGGGGTTC TAACTGGGAC AATTCTAGCA
46501  TTCCTTGACT CTCAGCTCCC AGCCAGGGCT GTGTGGATGC GTGGTTGTGT
46551  GATTCCGACA TTCTGAGACT TTAAGATGCT GAGGCTCTAG GAGCTAGAGA
46601  TACGGACATT CTGTGAATCT AGGATTCTAG GATTTGATGG TTTGATGATT
46651  CAATGATTCT AAATGGGGCT GCTGGGAAGA GCTGCAACCA CCTGCCTTGT
46701  TAATGTCAAT GTTCAGTTAT TAAAAACATA ACAAGAAGCA ATGGAGACAG
46751  ATAGCTCAGA ATGGTGGGCG CTCCCTCCAC TCCCAGTGAG GGAGGACAGA
46801  AGAGGCTGGG CTGGCCTTAG AGAATAGAGA CCTTTTCAAC CTGGGTCACA
46851  CAGGTTGTTT CTCCTGTCAC AACAGAACTG GTGTGTGTAC ATTCGAGAGA
46901  GCTTCCACTC CCAAAGCTTG CAGGGTAAGG GGCTCATTTC CTTCAGCACT
46951  GGCCTCTATT CCTTAACCAT TTCAGACTGG GCAGAGAGAG GGGTAACTAC
47001  CCTTTCCTCC CAGCCCTCGA AGTCTCTGGG CAGAAATGGC AGCAGTGGAG
47051  GAAGGAGAGG TCTGCTCACC CCCGCCCCTT CCCTGACAGC CTGAGGGGGA
47101  AAACAGGACA TGAATACTTC CTGGACACAG ACATGGAAAT GCATGAACCC
47151  CTGCCTTCGA GGGCCCCGCG TCCAAAGGCT CAGACAAGGG CAGAGGCCAG
47201  GACAGCCAGT GGGGTCCCAT CAGCACCCTC TCAGTATAGG CTGAGGAGGG
47251  AAGACCCTGT TCTTGCCCCA AGGGTGACAG TGAGAAGGGG TCAAGGAAAG
47301  GAGTCCCAGG TCAGGGACTG GAAGTGCTGA CAGGTCCTCC CCTGTGTGCA
47351  AGGCCACAGT CCAGCCTGGC AGAAGGCCAG CCCAATTGTC CAGTGTTTCA
47401  CTGCCTCCTG AGTCCTTCTT ATGCCTTGGC ACCCAGGCCA GAGTTGGGGA
47451  GGGGTCCAGG CTGCAGGGGA GGGTTTCCTT CCAGAGTGCC CATCCCTGAT
47501  GGATCCTTAG AAGCCCAGTA CAGCTGCACA GTTCCAAGGG CTTCCGCTGC
47551  CTGGTAGGTT CACAGACCAA AGCTGGCCCT GGTCACACAG CACAACGGGG
47601  CCTGAAATCA GGCTTCCTGA TTCCCAGTCC TGGGTGTTCC TTTTTGCCCA
47651  CAGCCTCCCC CACTTCCCCT GGGACACCTG AGGGGCAGGA GTGGAGGTGG
47701  GGCTCAGGTT AGGGAGCAGA GCCTCTGTCC ATCATCCCTC CGTCTTCCTC
47751  TTCCCACAGG CCAGAAGCAG GTGTGGTGGT GACAGCTGCC CCCAGTCCTC
47801  CACAAGGCTC CATTGTCCCC GGCAGGGAGC CCCTCCCCAG CTGCAGGCCA
47851  GAAGTGTGCC TCCCCGGGCC CTCCTGTCGT GACTCTGCCA CCCGCTTCCT
47901  CCTGCTGCCC CTTCCCTCTT CTCATCTCCG CTTGCCCTCA GGCCCTCCCC
47951  ATCCCCGTGA GGTCTCGTCT CTGGCGCTCT CTGGGTTTAA GCCTCTCTCC
48001  AGTGAAAGTT AGATTTGGAA GGGCCCTGGG AGATCACCAA GTCCAACCCT
48051  TTTATTCTTC GGATAAGGAG GCCAGGTCAG AGAGGGAAG GTCCTGTCCA
48101  AAGCTGCACA GTAGGCTGAG GCAGAGCCCA GTGCTGTGCT CCCTTCAGCG
48151  CTGGGTCATG GGTGCACACT GCCCTTGGCA TCAGGCGTCC AGGGTTTGAG
48201  AACTGACTGT GATGATCAGC GCTAAGCACA CAGGCACCTA CAGAAATGCG
48251  GTAGGGGGCT TCTCTCCTCA GCCCTTCTTC ACAGCCCTGA GCTGCCCTCC
48301  CTTCCTCTTC TTTGCCCAGC TCCTCTCTCC TTCACTATCC CTGCTGTCTG
48351  CTGACTCCTG CCTCTGGCCA ACACTGTCCT TGGACACAG ACTAGAGCTC
48401  AGGCCTCCAG GACTGGGATG CACACCCATG CACCCAGACA CAGACACATA
48451  AACATGTGCA AGCGTGTCAC GGGGTCCATA AATCCCAGCT GAAAACTGGT
48501  CAGACCATCA GGAGGCCACC CTGGAACCCA GTGTCCTCCT CTTCCTGTCA
48551  GGCCTCACAC ACCTCCTCCA GGAAGCCCCT TAGGACCCCT GAAGACCATC
48601  TTCATCCAAC TAGCCCCTTT GTGACAACTG AACTCTGTGA GCCTAGGTTC
48651  CTCCTGTGAC TCGAAGGGCA AGGCTGAGTC CCCCCTTCAG TCCTGGGGCC
48701  ACTCCTTCAG TGTCTTCAGG AGGGGCTCAG CTTCCTGTTG CTGGGTGGGG
48751  AGAGCCCTGA GGTCCCCACA GGACGTGGGA CAATGGGGAG GCGGTGACAG
48801  ATGAGAGGCT GAGTCTTCCC TAAAGCAGAC TCCACCCTCC CCTGACCTCC
48851  CTGGCTGGTG GCTTGGACAC AGCCCTGGCC TGGACTAGGG TCCTGGTCTG
48901  ACCCCACAAT GCAGAGGTCT GGGAATCAGA AGCCCTGGTT CTCCAGCAGC
48951  AGTTCTCTAA CTGGCGGCTA TGGAGTCCAG GCCTCCAGGG CACTGGTAGG
49001  TTATTGGCGG GTTGGTGCAG ATTCCAGTGT CCAGGAGGGG TGAGCTGGCC
49051  TGGGGGGCCT ATGTACAGGA GATAGGAGGG TGATAAACAC AGGCTAGGTG
49101  GGATTACAGG GAGCTGGGAA TACCTAGCTA AGAATCCCCT CATCCTAGGC
49151  ACTTTCCCCA CACTTGAAAT TGGCTGGAGG GGAACCAGA AGTTAGGTGG
49201  GGTTGGGGAG GGACAGGAGC CAGCACCCTG CCTCCACCTC CGGGCAGTGC
49251  CTCTGCTGGG GGGAGGGAAC CTGTCCTGGG GGTGGTGGGA GGTGTGAGGG
```

FIGURE 3-17

```
49301  GGGAGCTGGA TTCTCCAGTG AAACTGGCCC TCCCTCCTCT CAGGGGAGGG
49351  GAGGGGGCTG TCCCTGGCTG CTCAGCAGGT AGCCCATCTG GCTGTGGGTG
49401  GAAAAGAAGA CTCAGGCTTT GTGGATAAAA GGGACAGCCC TGGGTCAGGC
49451  ACTTATCTCA ACCCTCGTCA TTTCCTCTGC CGGACATGAC TGGGTGAGTG
49501  GGGTCATTGC ACAGAGGGAA GGAACAGGCC AGGGCCAGTG CATACCAGGC
49551  CCTACAGGAG AGTCAGGCAC ATGGGTGACC CTGCCACACC CTGGGCTGCA
49601  GTCAGCCCCT CATAGAGGCC CAGACACACA CCACAGTCAC TGCCGGAGAT
49651  GGCCACACCT AGACCATCAC ACCACACACA GACCCAGTCT CTCCAGGTGA
49701  CACTCAGGCC CAGCTGCAGG CGCAGCTAAG AGGGAAGACC CTGCAGGGCA
49751  CAGGGACACG TGGGACAACC AGACGCCCTG CTTCGGCCAC ACCACAAGCC
49801  TCCACACACC AGGTGCAGCT CCTGTCACCC CTACGGTCAA CCCAAGGAGA
49851  GCCAGAGATT CCAGTAGTCG TGGGCAGGTA TCCAGTGCCC AGGCGAGAAG
49901  AGGGGGACAC CAGCAGGGAA CCCAGAACCT CCTCCATGCC AGACTGTGCC
49951  CTCCCCCCAG CTCACAGAAG GAGTGCCTCA GGCTGTTTAT TTCCTAGCAG
50001  GGACTAGCAG GGATGGGTGT CTCATCCCCC TCCCCCTCCC AGTCCCCACC
50051  ACACGATTCT GAAGCTGCCA AATCAAATCA GCCCCTGCAC CCGCGCCAGG
50101  CTGGCATGGC GGCCAGCAGC TGACGGGAAC GAAGCCAGGC TCAGAATATC
50151  CCACCGCCTG TCCGATGCCT GAGTAGGCTT GTTGGGTGGG GGTGGGGAGG
50201  GGCAGGAGCC TGGCAGCCAG GCCCTGGGCA GTGCCCCTCA GAGAGGCTGG
50251  GGGTTTGGAA TGCTGCAGGG TGGTGGGCTT CTGGAGAATG AGTGAGCAGG
50301  TCTCTGTTGT GTCTCCAGGC TGCTGTGGCA GTGTCTCCAC CGCTAGCATT
50351  CCGGGAACTG TGGAAGTGGT GCTGGTAGGA TACAGGTCGG GGGTCTGATC
50401  CCAGTCCAGA TGACTGGGCG CCAGGCTGGG GTAGGGGGGC TCCCACATGG
50451  TCTCACATTC ATTTGAGACT CACAGCACCC AGGTTGGAAG CCCCTTGGTT
50501  GTCTGTCAGT AAAGGCCCAA CTCACTGTGG AGGCCCAGTG ACTGTGTGAG
50551  GTGGACATTA CGGATCCCAT TTTACAGACA GAGAAACTGA GGCTTAGAGA
50601  GGGCTAGTAG AGCTCCCTGG AGAGAAGCAG AAGTGGAGGA GGCCTCAGAA
50651  AGAGTAAAGA GGTGGTCATT TCCACTCCTT AGGAGCCCTA GGTGGAAAGA
50701  AGGAATATGG CTCTGTTCTC AGAGTCAAGG AACAGAGAAT ATGGCAGAGC
50751  CAGAGGTGCC CATGGGAAGC AGAGAACAAG GAGGGAGTCT TGGGAGAGAG
50801  CAGGGTGCAA GCAGGCAAGG CTCCCTGGAG GAGGGGGCCA TCCGTGGGCT
50851  TGCTGGGGGC TAATGGGAGG ACAGTCTGGG GAGAAGGGGA GAAGGCCTGG
50901  CCGGCCTCAG CCCCTGACCT TCTTGTCTCT GCAGCCAGCC TGGACCCCCT
50951  TGCAAAGGAG CCAGGACCCC CAGGGAGTAG AGACGACCGA CTGGAGGTGA
51001  GAGCTCAGTG GAGGGAGAAG TGGGTGGGCT TGAGGGGGTG GGGCGCAGAC
51051  TGAAGATCAG TCTGAGTGGT GCCCTCCCCC TTGGGAGGAC GGGGAGGCTG
51101  GAGTCACATC CCAGCCCCAG CCCTCCAGAC TAGGACCACC CCTATATCAA
51151  GACCATCTCC CCTCACCCTA TATATCCCCA GCCTGGAAGT CCTCCCATGA
51201  GGATTCCTCC TCCCAACTCA CCTGGGGAGT CACTACAGAC TCCTCCCTTG
51251  TCCTCCCCAC CCTCACCCAA CAATTCCCGT TGATTCTCTG CCCTGAGTAT
51301  TTCCCGAGTT CCTCTCCTCT CCATTCTGCC GCCTGCTTGG GTCCAGGCTC
51351  CCTCAACTCT CCCCTGGGCC ACTCACTGGC TGCTTGCTTT CAGTTTCCCC
51401  CATCATCCAC GTGGCCACCA GGAGGATCTT TCTAATGCAC AGACCTGAAC
51451  TTGTCACTCT CTTGCCCCAG AATCCTCCAT GCTCCCCACC CCCATGCCCC
51501  CTCCACAACC CCAGCCTGGC AATCGTTCCC CTTCATCCAT TCCTGCCTCC
51551  CCCAAACTGC TCCTGCTGGC CTCTTCCCCA CTCAGCTTCC TAAATCCTTC
51601  GGGGATCAGC TCTAGCCTCC TTTCCTCTGG GAAGTCCTCT CTACCCCTTG
51651  ACCATGGGAC CAAGCTCACT CCTGCTCCCT CCTCTGAGCT CTCCTGCCCT
51701  GGCAGTCAGA TGCCAGGGCG CTCTGCTGTC TGTCGCCCAC TGTGCTGTGC
51751  CACGAGCACC CTGTTTTCTC CATCATGTGA CTCTGTATGT GTGTCTGCCT
51801  TGTCTTCTCT GCACTGTGAG CTCTTTGAGC CTCGGGACTG TGCTTTCTTC
51851  ATTCCTGAAC CTTCTACCAC CCTTGGATGG GTACCGGTGC AGGGCTCAGC
51901  CAGCGCATTT CCTGCCCTGC GAGGGGTGCC ATCCCCACCC CCCGACCATG
51951  CCTTCCTTCC CTGTGAGGGG TGCCTCATAG GACTCTTCAG TGCTCAAAGG
52001  GGCCTTGACG AGCAAACAAG GTGGGCTGCT GATGTTGAAG ATCGGCACAG
52051  AGGAGGGTGT GTGTGTGTGT GAGAGAGAGA GAGAGAACTG GACCCACAGC
52101  CAGAACAGAG TCTGCCCAGG CCTGGCTGAG AGGGAGAGGA AGATGATGCT
52151  TGTATCAGCC CTCCTGTGTG CCAGGAGCCT TTGACACCCA CCTTGTTTAA
```

FIGURE 3-18

```
52201  TTATTACAGC ACCCCCATGA GGTAGGGGCT GCTATTATTC CTATTTCACA
52251  TTTGGGGAAG CTGAGGCCCA GAGGGATCAT TCAGCAAGTG AGTTGGGACA
52301  GAGCTAAGAT TGGAGCCTAG ATGTGTCTCA GGCTCGAGGC TCACTCTTTC
52351  CCGGCCCCTG AGTAAGATGG GAAAGAAGGT GCCCACACAG GGCCTGGTGC
52401  ACAGGAGGGG CTCAGCACAG GTTCCCTGCT GGGACACAGG GCCAAGACCT
52451  GAGAATGTGC CTCCAAGTGG GGCTGGGCCC TGCTGCTGGG AGCTGGCAAA
52501  GGGAGCTGGG AGGGGAGGGC CTGGAAAGCC ACATTATTAA TTTATTTACT
52551  GCCATGGCAT TCCCCATGGG GCGGGGCTCC CCCCAGAGCT GGGACAGATG
52601  GTGTTCCTGG GAGCCTGCAG TGTCTCAGCA GCCTCGGCCA CCCGCCAGGA
52651  AAGACTGGAT TTGTCATCCA CCCAGGGAGC CACAAGAAGA GGGGGCTTTG
52701  GCAAAGCTGA GACCCTCCTG GGCAACGGGG ACTGTGCCCT GAGGGAAGGA
52751  GTATGGCTCC AGGCACCCTG CTATGCCTCT GGGGCAGCCC CCGCTGCCTA
52801  GGCCATCTGC CTGCCCTCTG CAGGTTCAAG TTCTGCTCTT TGTCCAGCTC
52851  CACCGGCCTC GTCCTTCCCA TGAGGCTTCC CTGGGTCGGC CCCACCTGCT
52901  CCTATCCCTG TATTTTCTCT GCCTTTCCTT GAGCTGGGTC CTGCTGCCTC
52951  TTCCCTCTGA CCGAGGATCT GGAGCCATGA GCTCCTCAGC CCTCAGCTCT
53001  GTCCTGACCC CATCCCCACA CTCATCCCCA AAACAGTTAG TGTCTGCCTG
53051  GACTCTTGGC AGGGCCTGCT GGATTTCTGG GTCCTGCCAG CACCCCACCC
53101  GAGTGCCCAG GCCTATACTC AGCACTGCTG GGAAGAGATG GGCTGCCTGA
53151  GGGGACGCTG CCAACATGGA GAGGGCAAGA CTGGAGAGAG TGGGGACCCG
53201  AGGGCATTGC TCAGACCACA GGGGCAGCTG GAGGGAAAAG GGACTGGGAG
53251  CCTGAGGGGC CCTCCTGTCA GGGTGGATCT GGGAAGCCAA GATGGCCTCA
53301  TATAGTGGAC AAGCCACAGG GTCAGATGAG CACGGGTTCA AGTCCCAACT
53351  CCCTTGCTTC CTAGGTGTGT GGCCTTGTGC CTGTCACTTA ACCAGCCTGA
53401  GCATCAGTCT CCTCACCTGC CAGGCGGGAT AAGAACGTCT ATCACTGCCG
53451  GGAGCGGTGG CTCACGCTTG TAATCTCAGC ACTTTGGGAG GCCAAGGCAG
53501  GTGGATCACA AGGTCAGGAG ATCGAGACCA TTCTGGTTAA CAGGGTGAAA
53551  CCTGTCTCTA CTAAAAATAC AAAAAATTAG CCGGTTGTGG TGGTGGGCGC
53601  CTGTAGTCCC AGCTACTTGG GAGGCTGAGG CAGGAGAATG GTGTGAACCC
53651  GGGAGGCAGA GCTTGCAGTG AGCCGAGATC GCGCCACTGC ACTTCAGCCT
53701  GGGTGACAGA GTGAGACTCC ATCTCAAAAA AAAAAAAAAA GAACCTCTAT
53751  CATTCTTGGA TGTAATCACT GTTATTCAAC ATTACCACAA TAGAGCTGTT
53801  GGGAGAAGTT ACAAAGACTG TATGTGTGGG GTGCCCGGCG CAGGCCTGGC
53851  ACATGGCAGA TCCTTGGGGA GAGTTAGCCT CCTCTCTGTT TCCCTCAAGG
53901  ATGACATCCT TAGAGCCAGG ACTAGGCTGT ACCCCTGTGA GACAGGATGC
53951  TCTGCAGAGC TGGGCTGAGG CTTATGGAAG TTCTATGGGC ATGGCACACT
54001  CTCCTGGCAC TGGCTGGGCA GCAGCCAAGA AAGCAGAGCT GCCAGCACCC
54051  ATCCCCACCC AGCAGGCGTG TGTTCAGCAC ACCCTCCTGG GATGGTTACC
54101  TAGCCCCTGT GCCAGCAGCT GACTTGGAGG AGGGGCTCTT CCAGCTCAGC
54151  CTGGCATCCT CCTTCAGGGC CAGGCCTCTG CATCATTACT GTCTCTCTGA
54201  AAGTCAGGTC TGGGGCAGTT CAAGTTGGTG AATTGAGCAT GCTGAGTCAA
54251  TGCCCTCTTT GTGATGGCTC TCAGGGCCCA GATGGCGGCT TGGGAGCCTT
54301  AGCTGGGATG GGGGCATGGG GAGAGGCGGA CGTGGATGAG GGCACTGACA
54351  TCCACAATAA GTACTGAAAT GCACTGCCCA ACACCGGCTC CTCTATTGCT
54401  GCCCTTGGGA CAAAGACCAC ACCCCTTGGC AGGGCATTGC TGGCCTTGCC
54451  TGCTGGGTCC CCTCATGTCC CCTTGTGTCC CCTTATGCCC TGAGACAGCC
54501  AGCGCTACAG CCACATTGTT GTGTTCACTC CCAGCACACA GCAGCTCCCC
54551  CTGCCTCCCT GCCTTTGCTC ACACTGACCA CCTGTCTGGA ATACCTTTCC
54601  TTTCTTTCTC CACCTACTCT CTTTTCAAGG CCCAGATGAA ATGTCACCTC
54651  CTTTGTGACG TTCCTCAGAC TGGTCCCTCT ACCTCAGGCC GAGCCAGTCT
54701  CCTCCCTTCC CTGGGCACTC ACAGTCCCCA TTTCCCTGAG CCCACAGTTG
54751  GGAAACCTGT TACCCCACGG GGTGCTGTGG GTAGTGTATC CTTCCCCATG
54801  GGGTTGTAAA CACCCAGGAG GCAGAGGCTG AGACTGAGTC TCCTTTGTCT
54851  CTCTTGGGCC CATGTGGTGC TTGGTATAGG CCTGGTATAT GGTAGGTGCT
54901  CAATAAATAC TTCTTGAATG AACAAGAGTG GCTGTGAGTA GGGCTGGAGT
54951  AGTTCCAAGA AGGGGCACAG TTGGGTTGGG CGGTCTTGGA GACTTGGAGG
55001  AGGCAACCTT AGAACTTTGA AGGATGGAGA GGGTCAAGGG CACCAACCGA
55051  AGAAGCCAGG GACCAGCTAG GCAGTCAGAG AGGTCCATGA GGTCAGCTTC
```

FIGURE 3-19

```
55101  TGACAGCAGC AGCTAAGGAC AACCAGGACC AGAACAGGAC TGGGAAAAAG
55151  CAGATAGAGG AGGCTGGAGC AAGGACTCAG CCCCAGAGGA GGCTGCAGGA
55201  GGTTGGCTCA TGCTCAGAAC CCGGCTCCAA AACACTCTGC CCATGAGTGC
55251  TGGGCTGAGG AAGGCTTGGT GCCAGAGTCA GGGTGAGGCT GAGGCCACCA
55301  GTGAATATGT GGGCCAGCT GCGGGGGTAG CACTAGGCAG GGGCGGGAGC
55351  CAGGTTGGAG GGGGTATTGC CATTGCCGCT GCAGGTGGAG TAGGGCTTCG
55401  CTGGGGAAGG AGCAGCTTGT GCGAGAGTGT GGGCAGGAGT GGGAGGGGAG
55451  AAGGCTCCGA GTATACGAGC ATAGCTTACC AGCAAGTCCT GGGGTGAGGC
55501  TGGAGGGGCC GCGCTGTAGG CAGCACTTTT CAGGCCCTTA TCTAACATTC
55551  TCAAGTGAGT GCTCCTAGCT GCCAGATGTG CTACTTCCTC CTGGATTCTG
55601  CACATCAGGA GCCAGTGGCC TCTACAATGC CCCATGGCCC CAAGGGAGTG
55651  GCTGCCAACA AGTTGGCCTT AGCATCTGGC ATCCATGGGG GTCCTGAGGC
55701  CCTGCCATCT GTCTGTGCCC CTGTTGGGCT GCACAGGCCC GGGGCGTGCA
55751  GGGACCTGGG ACCAGGGAGG CGGTCTCAGC TGCCACTCTA GCCTGTCTCT
55801  CTGCCTGCCC ATCCACTGTC CACACCCCTG GCTGACTGAG TAAAGAGAGA
55851  GATGGGCATC GCAGGTCCTG CCATCAAAGA AGCCTAGTCT AAAGGAGGAG
55901  GCATAAAGCA CCGGGGACTT ATACCCAGAG AAGACACATG CTGAGACCAC
55951  GCCAGGCTCG CGGGCAAGGC CTAGGCCCAG GGAGGGCCAG CCTCGTCAAG
56001  GGCCTGGAGT TGAGACTCAG GGAAAGGCAG GAGCTGGCTT AGAGGCGCAG
56051  GCAGGTCCAA GGCAGTGCCC AGGCCAGATG CGGCGGCCCC GGGCTGAGGT
56101  TGCTCCAGCC GGCCCACCC CCCACCGTCC TGCCTGGCCT TTGGCTGTAA
56151  ACACTGAGAG AACAAGTTCC GTTTCCCGGG AAATATTTAT CTCAGGCTGT
56201  GTGAAGAGCG TGTGCACTGG CCTCCGTGTG TCCTTCCTGC AGACCGGCTG
56251  GGGCAGGAGG AGAGGGAGCT TGGCAGCGCC CTTGCTGGGG GGAGTCTGTG
56301  GGGCTAGGAG GGAAGGGTGT GCCAGAGGCC CCTGCCTAGA GCCTGAATTT
56351  GAGTGCTGGC TGAGGGAGAG GTGGGAGCAG ATGGGAGAGA AGCCTGTTTT
56401  CTCCAAACCC CACAAATGCC CTCCGCCTCT CTCATGTTCC TTTCTTCTTC
56451  CTGGTCCATC CTGTCTCCTC CAGGTTCCGG CCTCCAGCCT GGTGTCCCCT
56501  CCTCAGGCTG CCTTTTCCTC CTCCTCCTCC CTGTTTCCTG GCTCTTAGCC
56551  GCTCCATCTG GGAAGTCTTC CTCAACTTTA AACCCTCGAA CCCTTGTCCT
56601  CTGCCCTCCA TCTCCCACTC CTCAGGCTTT CAGCAGCTTC ACGTGGAGCA
56651  TTGGGCTGGT CCTGTCCACA GTTGTTCAGT TGCTGTAACA GCTTGTGCAG
56701  GCTGCCCTGG AGCCCTGTTC TGGGAAGCAC AGGTCTGGGC ACCCTGGGGC
56751  TGGGGCGAGG CCCGGAGCTG ATCTCCTCTG TCCATCCCAG TAGAGCCAGC
56801  ACCAGTGCAG ACACATGGGG GATCCAGGTT GGTGGACCAG GGGAGGATGG
56851  AAAGTCCCAT GGATCCAGCC GGAATGTTGG AGTGGGGAGG CAGAGGGCCC
56901  AGGGTTCCTG CTGGCCAGCC TCTGGGCTTA GGGGTGTGTA TCCCAGACAG
56951  GCCAGGCCTG CCAGGGGCCC TGACAACAGG AAATCCTTGA AGGAACAAGC
57001  AGAGGCTGAG GACTCTGAGC ACAACAACAG GAAACAGCCG TGACATGGGG
57051  CAACAGCCCT GGCGACTGTG CCCAGTTGGG GTGGGGACGA GGGGCCAAGC
57101  TTGTGGGACC CAGGGTGATG CCAAGAGGGA CACTGAGACA CTGTGGGACA
57151  GGGGGCGTTC TGCACATGTG ACACGGAGCT TATGACGTGT AATATCAAGT
57201  ACGTGACCAT GATCATAGGG TACTGTGTGG AGTGTGGGTG AGTCACTGAG
57251  TATGTGACAC TGGCTGTGAG GCACTCCATG ATAGCAGATG TGTACAGTGG
57301  CTGTGCCACC AAGTGTGTAA CACTGTGTGA TATTGATTGT GTGATGCTGA
57351  CACCGAGTGT GTGACATTGC ACATTGCATG CTACCACGTG TGTGACACTG
57401  AAAGTGACAG TGAGCACATG GAGGGTGTGT CTCCATGAGA ATCAAATACA
57451  GAAACGTGAG CAAATGACGC TGCAGTAGCA GGTATGGTCC TGAGTCTGTG
57501  GCTCGAGTGT CTGACACTGA ATTGTGACAT TGAGTGTGTC CCAAGCATAT
57551  GATCTAGTGA GGCTGAGTGT GTAAACAAAG GCATGACATG GAGTGATAGC
57601  AAGTGTGTGG AAGTGGGTGT GTGATGCTGT GTGATCTTGG GCCTGACATT
57651  ACATGTGTGA TGCTCTGTAA TGGTTGTAAC AGTATGCAAT GTGCACATAC
57701  AGTGCTGTGT AGGACACTGT CATGGGAAGG CACCGATGGG TTCAGGCGGG
57751  AAAGTAACAC CGTCCAAAGG ATGGTTTTAA AAGATTGCTC TGGCCGGATG
57801  CAGTGGCTCA CACCTATAAT CCCAGCACTT TGGGAGGCTG AGCTGGGTGG
57851  ATCACCTGAG GTCAGGAGTT CAAGACCAGT CTGGTGAAAC CCCATCTCTA
57901  CTAAAAATAC AAAAATTAGC CAGGCATGGT GACAGGCGCC TGTAATCTCA
57951  GCTGCTCGGG AGGTTGAGAC AGGAGAATCA CTTGAACCCA GGGGGCAGAG
```

FIGURE 3-20

```
58001  GTTGCAGTGA GCCAAGATTG AGCCATTGCA CTCCAGCCTG GGTGACGAGT
58051  GAAATACCAT CTCAAAAAAA AAAAAAAGAA AAAGATTGCT CAGGTTGCAG
58101  AATATGTATG TGTGCGAGTG TGCATGGTGC GTGGCAGGGG AGGGGAGATA
58151  AGTTAGGGGG AGGCAGAGAG AAGGTGGGTA GAGCAACTGG AGGCTCCTGC
58201  AGCTGCCCAG GCAGGAGATG GTGGTGCCTG TGTTAATGGA ATGGCAGAAG
58251  AGTTAGAGAT ATGGAGCAAC TTTGGAGATA TTTGAAAACA GAAATGACAG
58301  AACTTGCTGA TAAATGAGAA GATGAGCAAG AGGGAAAACC AGAGAACAAT
58351  TTCCAGGGTT CTGGCTTGAA GAACCAAGCG ATGGATGGTG AAGATGTTTC
58401  TGAGATGGGC AAAGGCAAGG GGGAGGGTCA GCACTAGTGG GGTGGGAGGA
58451  CAAGGAGGCA GAAACCGAGT GAGCTGTTTT GGATGTGTTA AGGGAAGCAT
58501  CCAGGTGAAG GTGTGCAGTG GGCAGCGGGG CCAGGCTAGG GATACATCTG
58551  GGAGTCGACA GGCATGGGGG GTTTGTTAAG GTCGTGGACC TGGCTGGGAT
58601  AATGGAGAGA GGGAGCTTGG CAACAGAAGA GGTGGGGACT GAGGACCGAG
58651  CCTTAAACTC TGAATATTCC ATTGTCTAGA GGCCGGGGAG GTGAGAAGGA
58701  GCAGCAACGA GACAGAGGAG GAGGGCCAGG GAGGCAGAGG AGACCAGGAG
58751  TGTGAAGCCA GAAGCCAAGG GAGGAAAGAG GCTCAAGTGG GAGGGAGGGT
58801  CGGTGTGTGG ATGGTGCTGG CCCACAGGTA AGATGGGAAC CGGAAGATTG
58851  TGCTGTGCTG GGCACTGTGG GTGAGTCAGG CTAATGGGAG CCATTTCAGT
58901  GATGGGCTGG AGCCAGAAGT CAGACTGGCC TGTGTAGGAT GGTGAGGGAG
58951  GTGAAGACGT TAGCCTGGAG AGCCCTTTGG AGACGTTGGG CTGTGAGGGC
59001  TGCAGAGAAG GACATGATCG CTGGAAAGGG AGATTACATT TTTTTATTAT
59051  GGGTGATTCT AAGCAGACAC AATACCAGAG AGAAGCATAT AAGAAACTGC
59101  CATATACTCA TCACCCCAGT TCAACAGTTG CTGGGATTTG GCCTCATTTC
59151  TTCCTCTCTT GCCCCCTATC TGTTCTTTCA TTTTCCTTTG CTTAAGCTTA
59201  AAATTTTTTA AATTGTGGTA AAATATACAT AACTTAAACT TTACCATCAT
59251  AACCATTTCT AAGTGTACAG TTCAGTTGTG GTAGGTACAT TCACACTGTT
59301  TTGCAACCAA TCTCTGGAAC TCTTTCATCT TCTCAAACTG AAACTCTGCA
59351  CCTATTAAAC GACAGCCCCC ATCCTCCTCT GTCTCCAGCT CCTGGCACCC
59401  ACCATTCTAC TTTCTGTCTC TATGACTTGG ACTACTCTAG ATACCTCAAG
59451  TAATTGGAAT AATGTAGTAT CTGTCTTTTT GTGACTGGTT TTTAAGTTTA
59501  CTTAGCATAA CGTCTTCAAG TTTTACCCAT GTTGTAGCAT GTGACAGGAT
59551  TTCCTTCCTT TTTATGGCCA CATAATATTC CAGTGTATGG ACAGACCACA
59601  TCCATCCAAC ACCAGACACT TGGGTTGCTT TCACATTTTA GCTATTGTGA
59651  GTAATGCTGC TATGAACATA AGTGTACAAA TATCTCTTCA AGATCCTGCT
59701  TCCAATTCTT TCAGATGTAT ACCTAGAAGT ACGCTTGCTG GATCACACAG
59751  TCATTCTATT TTTTGGTTTT TGAGGAACTG CCATACTGTT TTCTGTATCT
59801  TTTTACATTC CCACGGACAG TGTACAGGGG TTTCAGTTTC TCCACATCCT
59851  TGCCAACATG TGTTATTTTC TGTTCTTTTT TTTCTTTTAT TTTTTTAATG
59901  GTAGCCATCC TAATGGGTGT GGGGTGACAT TTCATTGTGG TTTTGATTTG
59951  CATTTCCCTA ATGATTAGTG AAGTTGAGCA TCTTTTCATG TGCTGGTTGG
60001  CCACTTGTAT ATCTTCTTTG GGAAAATGTT GATTCAAGTC CTTTGCCCAT
60051  TTAAAACATT GGGTTGTTTG CTTTTTTGTT GTTATTGAAT TGCAGGGGTT
60101  CTTTATATAT TCCAGATATT ACCTCTTTAT CAGATAAAAG CTTTGCAAAT
60151  ATTTTTCTCC CATTTCATAG GTTGCTTCGC TGAAATATTT TAAAGCAAAT
60201  CCCAGACATG ATGTCATTTC ACCAAAGGTA GACTTTTTTT TTGGTGGGGG
60251  GAGCTTTCCG GTGAAGACTG AAAAACCTGC TAGACAAATT CTAAAATAGA
60301  TGTGACTTTG GATTTTTGTT TTTTAAGGCT AGGAGGTCCT GGATGATGCT
60351  GAAATGTAAC AGTGACACAG AGCCAGTGTG GAACTGTGTC TGATGCTGTG
60401  TGAGGGTGAC ATGGTGGCTT TGGGAACATG GGTGCAACAC TGAAGATATG
60451  GGAGACTCCA AGTGAGGGTG ACAGTGAGAG ATCACTGTGT GTGTGGCCCT
60501  GTGACACCCA GTGACATGGG ACAGTGGGAC GCTGTGGACC CTGAAATGAC
60551  TGTGTGTCAC CGAGCAGGTG GGACCTGCTG TGTGAAGGCC ACAGGTGTCA
60601  TGTCTTCTTG TGTCATCCTG GTTGATGAGT GTGACACAGT GCAGGACTCT
60651  GCATGGGAGT AAGAGGGACT GAAGCTGTGC TATAGGTGAC CGGGCTGCAT
60701  GTGATTCAAG TGGGCTCAGC CCCAGCTTCA GCTGCTGAGT ATGGGAGGGA
60751  GCATGGACAT TGTAGGGTAG ATGAGGAGAA ACACTGAATG GGAACAGAAA
60801  TGGTGTCTGT GCCCAGATGC GAGCTCCTCC CTTCTCTGAA TACCCAGGAA
60851  GGCTTCCTGG AGGCAGGATG TGGGCACTTC AGCAGGATGT TGTAGGTGCT
```

FIGURE 3-21

```
60901  GATTAAGAGC AGGGCCTGTG GTGTCAGACA GCCCTGTCTA GGCTCTGACA
60951  TTCAGCAGGT CATTTTATCT CTTGAGCCTC AATTTCCTCA AGTATAAAAT
61001  GGGAGCTCTT AGGAGGATTG CATGAAGCAG TGCTCCAATG CATGCAGTCT
61051  CTGGCACTTG GTAAATACTC TATGGTCTCT TGGGGAGCAG CAACCTCAAC
61101  ACCTGCACCC CAGGTCCCCA AATAACAGGA GCACCAGTAG GAGCACAGTG
61151  AAGGTGCGCT GAGTGAGGTG TCCTCTTACA CCCACAGCCC TCCTCTCTCC
61201  CTCTCCCCCA ACTTCTGTCC CCTGCTTGGT GTTGTCAGCG ATACCCCTC
61251  CTGCCCACTC ACTCCTGCCC CCTCCTCTCC CCTGCCGTCC TTACCACTGT
61301  CAGCCTCCAG CCCAGGCTCC TGCAGCCTCA TCCAATTAGG CCAATGCAAT
61351  TTGCTCAAGA AAAAGCCCCA TAATTTGGTT AATCACACCA GTAGGGGATC
61401  TGGTCCCGGT CGGGAGGGTG GGGGTGGATA GGAGTCCATA CCCGCAGCTG
61451  AGGCACAGGT GTCAAAGTGC CTGTCTTTTG GGACCTTTAC CCACTTCCTT
61501  GGGCTCCTTT CAGGAGCCAA CAGAGTCCCA AAGCTTGGGT CTTCTCAAAC
61551  CCCAACTACA GAGGCCTTGA AACAGGAGTC TGGACTTCCT GGGTTCGCTT
61601  GTGTTCCTGG GAGGGTCCCT GCTACTCTCT GGGCCTCAGT CTCCCTTTCC
61651  AAAAATGGGA GTGGAACTGG GGAGTCTCAG AGGCCCCAGT TGGCCTAGCT
61701  CTGCATCCCA GCTCTGGTCA GTCCCCCTTG TGGCTTCTGA GGGGCCTTCT
61751  CCTGGGCCTT GGGGAGGGAG CACTGAGGGG TAGGTGGAGA GCACAGGGCC
61801  CCAGGGAAGT GAGGAGGGGT AAGTGTCCTC TGAGTCTCAT CTGGAATGTG
61851  TCTACCCCAG TCCTATAATC AGAGACCCTC TAGTTCCAGG CTGCACACCT
61901  GAAGGTGGGG CAGGAAGAAA GGAAGCTGCC CTTTCTTGGT CACCTGCAAG
61951  GCCAAAGTCT CTTAACCGTG CAGGCTATAC CTTGCACAGG AGCTCCAGCA
62001  GAGGTGGGGT GGTGCTGAAA CTGAGCCCAC TCTCCCTCAC CAAGCCTTTC
62051  CCCTCAGGCC CGCATCTGCC CAGAGAATTG GGGTCCCTCC TTTCTAATGT
62101  GCACACAGGT GGCCCCAGCC CCCTGCTGGG AGTCAGCTTA GGCAAGGTTT
62151  GATGGCTCAG CTTAATCTTC TCAGCAGCTC TGGGGGAAGA GACCATTTTA
62201  CGGATGAGGA ACTGAGCCCA GGAAGGTCCA AAGACTTGTC CAGTACATGT
62251  GGTGTGTGGC AGGGCAGGCA GATGAGCCCG CATCTGAGGG AGGCGATGGG
62301  AGAAGTGACA GGGGTGCGCA GAGGAGGAGA ATTAGACCCT CTCAGATTCC
62351  ACCACTCTCA GCCACACGTT CACTCACTCA TTTGGAGACA AGACTAACCA
62401  CCAGCGCATT CACAGCCCCC CAGACAGCCA CATACTGACT ATACCACTGT
62451  CACATGGACA TCAATGACCT GAATCACATA TGCATAGATG CAGGCCCACA
62501  TGGTCACTCC CACGTGCAGA TGGCCAGTGC ACACACATAG ACACAGGGTA
62551  CTCACACATG TTTACACTCT CACGACCCAT GTGGGTTACA GATTCCTACA
62601  GAGACACAGA CCTACATACT TTCACAAGGA AATTCTCCCA GTGACCCAGG
62651  GAACATAGTC TGCCATGATG ATGTGATGGT CCGTAGGGGC TCGCCACTAT
62701  GGACCATTAA TGGGCAGGCT GCACACATGC TTAGGTCCCC AGCAAAGCGG
62751  GAGTTCTGCA CAGAGTGAGA GGAGAGGTCA GTTCTGATGA GTGTATCCAG
62801  AATTTTGCAA TCAGAAAAAC CACACAAAAA CTATTTTAAT TTTCATTTCC
62851  AAGATAAAAT TTAGTTTGAA TTGTATAGAG GGTCCGAGGG TCTGGTGGGA
62901  GGGCATCATC ATCTTTTCAA GGCTTTGGGG TTCTAAGGCA CCCACAGATT
62951  CACAACAGTC CCACAAGATA TCCCAGGCTG ACATATTTAC CCAGCCCAGT
63001  GTGTGCGTGT GTGTGTGTGT GTGTGCGCAC GCTGTGTGCA TGCTCATGCT
63051  GGCTCCAGA TCCTCGGGAT GTGAGGAAGG AAAGTAGGAG AGATTCCAGA
63101  GACTCCGGAT GTTTGTTCTC TGGCTTCCTG GGCCCTTCAA AGGAAAATAA
63151  CTCTGGATGT CAGCCTGCCT GCCTGGCGGG CTGGGTGGAG AGGTGGGCTG
63201  TTTTGGGAGG TGGGCTGTAT GACAGCCTGC CTCAGCCCCT GTGGCCCCAC
63251  TGACCGGGAC CCTGTGTAAT GAGGCAGAGT GACCAAGGCC CATGGCCAGC
63301  GTCCCATGGG CTCGTAGGCC CATCGCCTCC CCTCTCTGGG GCTTGGCTCT
63351  CTCATCTGAA AAATGGAGGT GGGAAGGAGA TGAGACTGGA TGGGCTTTCT
63401  CCTGGAGACT GATTAGAGAG ACAGAGACTC AGGCCCGGGG TCCAGAAAAG
63451  ACAACCAAAG CTGGGGAGGG CACATGAAGG GGGGCAAAGA AGGTCTGGGT
63501  TCAGGGGAGT GCGTGGGGCC CCAGAGCCTG CCATGTCTCC GCCAACTCTC
63551  TCCCTCACTG GAGGAGGGCT CTGTGCCTTG GTGCCCCACC TGCCCAGGGC
63601  CCTGTGGCTC AGCCCCTTGC TTGCTCTGTG AGGGGACGG GAGAAGGATG
63651  AGAGTCCCAG TGATAGGGGG AGGACAAGAC CAGGGGAGAG GGCTGGGGGT
63701  TTCTGGAGGG CCAGAGCAGG AAGAGCAGGA GAGAAGAGAG GACACCACAG
63751  TGCAGGAAAC GGAGGAGCAA AGGCTGGGAG TGGGGAGGCT GGAGGGGTGC
```

FIGURE 3-22

```
63801  AGGGAATCAG ACTGGGGCGC TGCGAAGAGG CCTGAGGCCA GAGCAGGCAG
63851  TGCCTGGATG GAGGGAGCGA GCAGCTCCTC ACCCTCAGCT CCTTGATGAG
63901  GTAAGGTGAC CACGAGCCCT GCTCCAGGCT GTGTGCTGAG CACTTTGCTC
63951  GGAGCCTGTC ACTCTGGAGG AGGGGAGGGG GTGTTCCCAG GAGCTATGAC
64001  AGTCTTGTGC AAGGGAGGGA CAGGGTCACA TTTATGTTTA ACAAAGCACT
64051  GCGCTGGGAG AGAGGAGCTG AGAGACCCCG GCCCTGGGGA GCATGGTGGC
64101  TGGGACCCCG GAGGGCAGGC GTGCCCCAGA CGGACCCCAC TCAGAAGATT
64151  GCTTATCCCA ACCCCCCAAA GAGAAAGGCT ATTTTTAGGA ACAATAAAAG
64201  TGCTCACACA TTCCTGCAGG GGCAGAGAGA GGGAAAGGGG GCAGGAGTCA
64251  GTGCAGAGGA AGAGGGTGGA CCCCGCTCTT CTCCCAACTC TGCCTTGGTC
64301  TTCAGGGACT TCTCCTCAGG GGCTTCCCCA GCCAGCCCTG CCTCTCCAGC
64351  CTCCGCCTGT CCCTGGGGTT CCCTACCGGC TCTTATGTCT ATCCCTCTGC
64401  TTCTGAATTG GTACTTGTTC TGTCCCTGTC TCTCTTTCTC ATACTTCCAC
64451  TTTCCCCCTC CCCCTGGGGT TTGGGGAACA GCTGGGATGG GCCAAGCTCT
64501  GTTGAGAGAG CCAAATACAG TCATAGGACA AAGCAGCGGG AGGCTGTGGG
64551  ATACACACAT GCCGCAGAGC ACAGACAGAG AGAGGTGGCC AGGCACAGAG
64601  AGAGCGCCCA GGGAGGCTGA GAGGCAGGGA GAAAACACGC TGGGACAGTC
64651  AGGGAGAGCC CCAGGGCAGG CATCACCGGG CAGCCAGCCT CTGTGCCCTG
64701  CTCTCTATCT TGTCCCTAAG AAGACCAGCA TGGCTGGGCT TGCCTCCCGC
64751  CATCCACCCC ACCAGCCCTA CCCCAGGCTG GCCCTTCCTC CCCGCCCTCT
64801  GCAGGCCCAC ACTAACCCTA GGCCAGGCCG CCTCCTTCAG CATTTACCTC
64851  CCACACACAA TGGGCACAGT GAGGACATAA GAGACCCAGT CTCTGGCCTG
64901  GAGGCAGATA CTCAGCCTTA CCCGACATCT GAGAGGGCTC AGCCCATCCC
64951  CTGGCCAAGG CAGGTATTAG AGGGGCCCCA AAGACAAGCA GGACTCTGGG
65001  ACAAGGTGTC CTAGTGTGGC CCAAAGGGCT GGGCTGAAGC ATGGGTCTCC
65051  TGGCTCCAGA TGAGAGCCTG GGTGAATCCT TCCCTGCCTC CTCTGGCCTT
65101  AGTCTACCCC ATCAAGCTTG GGATTGGACT ACATGAGGCC TGAGGCCCTG
65151  TAGCCCCTGG TCCCTGGGAA TTCTCAGAAG GCCTGGGAGG GGGACAGGTG
65201  ACCACGCAGG AAGGCTTCCT GGAGGAGGTG TCCTCACTCA TGAAAGAAGG
65251  TGATAGTGAC AGTGCTCCTC TTGGGGAAGA GCCCTCCATC CTGACCTGCT
65301  GCCCCCACCC GGTCTGCACG TGGAGATGAT CCTGAAGCAC AAAGGGCCTC
65351  CCGGCCTGCA GAGGTGCCTG GGAGAGGTTG CCAAAGGCTC TCAGTAGGAG
65401  ACACCCCATT CCTCAGGCTC CTTCTCTGAG ACTGTAACTG TGCCAGACTG
65451  GGGAGGCTTT GAGAGGTCTC AGCTATCTCC CCTGCCTAGA TCCTTCCTCC
65501  ACACCCCTCT TCTCCCTGAT GGCATGTAGC CCTCACAGTA CAGTAGTCCT
65551  GGGCACACAG GAGTTTACCC AGTCATTTAC AGCTCAGCAA ACACCTACCA
65601  ACACCTATGA GGGGCTGGGT AATGCTGGAG ACCCGGAGAG GGGCAGGACA
65651  CAATCTCTGC CCTCCAAAAG CTCCCAGTCT GTTGTGGGAG CCAGACGGGA
65701  AAGGGTGGCA CTGCATTGAT GCACACAGTG CATGCCATGG TGGGGGAAAG
65751  GGGGGCAGTG GGAGCCCCAG GTGGGAGGGT CAGACTTGCC TGGAGAGAGA
65801  ACAACAACAG ACTCTCCCTG GAGGGGATCC AGAGAAGGGA GATCACTTCA
65851  TTCATTCATT CGTCATTCAT CCATCCACCC ATTCAATTAT TCCTTTGGCC
65901  ATCATTTCCT GAGGGATGTA AACTCTCTTC TGACACTGAC CCAGCGGGAC
65951  ACTCAGCGTC CTCCTCCTCT CCTGCTTGAG CCACCATGCC TGCCTCTTGG
66001  AGGCTCCTGG ACTTGCTTTG CTCAGCTCCC AACCCACCCT GAGGGGGTGA
66051  GGCTGAGGAG GGTGTACAGA CATTCAGGGT CACCAAACTC AGAGCTGGAG
66101  GCCTGCCACC TCACCAGGGG CCTTTCTCAG GGCACAGGCT CCCTGGTGGC
66151  AGGGCCTTGG CCCTTGCTTG CACACCCTTG GGGACTAGGA GCCCCCTCAT
66201  CCATCCTGCT CAGGCTCTCT TTTGTGGCGC GACTCTGATT CACAGTGTGC
66251  CCAAATCTGC CTCCTTGTGA CTGCCGCGAG CTGCCTCGTG GGCCCCAGGC
66301  CAGAGGACAA GGATAGCTAG AATGCCAGGT GACCAGGATG ACTGTGATGG
66351  CATGGAGAGG GGGATGCTGT GATGTGTTTG GGAGGAAGTT TGTGGTGTCC
66401  AGGAGAATGT GGGCAGCAGA AATGGGACCA CTCTCGGTTC TTCCCTGTAG
66451  ATGAAGCAGC TGAAGGTGGG AGGGGGTGGG AGGAGACCTG AGCTGGCTCT
66501  GCCCCGCTTG ATCTGATGTC TGCCTTGCAG GGCCATCCTC CCCCTCCCCA
66551  CACTCAGCTC CTGCCTCCCT CCCTCTACCC ACTCTGACTG TTCCCTCCTT
66601  TCCTGACTCC AGACTCTGGG TGAGGGACTG AGGTGATTCC AGTGAGTCAG
66651  GCCCTCAGGG AACTGATCGT GCAGGCAACT CTTGCCTGCC TTCTCCTGCT
```

FIGURE 3-23

```
66701  CTTTCCCTCT TCCCATTCCT TCATCCACCC CCAAACCTAG CTCCTGATGG
66751  ATCCAAGGGT GCGGGGGACA ACCGGGAGGT CATTTTGGAG GAGGCAGGAG
66801  CTGGAATAGA AGCTGGGACT GGCTTGGGAA GGGCGAGAGG CCGGGGCGGA
66851  GCTGGTTGTG GGCGCTGGAA GGGAGGAGCC AACAGTGTGG GGTCAGGCTC
66901  CTGTGGACGG GGACACCCTT GGGAGGCACT GGGACTGGCT CAGGTGTATT
66951  CTACAGTGCA CGTGTCTCCA GTGTGGCTCG GAGGCTGGAG ACGCGGCCCT
67001  GTTGGAGTAA CAACTGAAGC CGGAGTCTGC GAAGGGTGGG CAGGAGGGTG
67051  GAGGGATGGG GGCATGGAGC GGGAGGGGGT AAGTAGAGGA GGGAGGGGAG
67101  GAAGAGAAAG AGGGAGGAGG AAAGGTCTCT GGCAGGTCCC TCCTTTAAGA
67151  CTGGGCTCCT GCGCTGCGAG TGGCCCCGTC CATACTGCCT TGTTATCCAT
67201  ATCTCCCCAC CACTAGTCTC CCTCTGTCCT TCCACCCCCA GCCTCTCCCC
67251  TCCATTGGGA CCTTCCCTGG GGCGTCCCCT CATTGGCTGT TCTCACCTGA
67301  GCAAGGCCCC TCCCCTCCAG TCCTTAGCCT CTTCACCTGT ACAATGGGAT
67351  GACCCAAACA GGCACCTCTT GGGCTTGTAG GAGGATCCAA GATAGTGTCA
67401  GTGGGTCTCG AGGTGTGGTC CCCCGACCAG CAGCATCAGT GTCATCTAGG
67451  AATGTTTGGA AACGCAAGTT CTTGGACCTC GTCCAGACC TACTGTATCA
67501  GAAACCCTGG GGGTGGGGCC AGCAATCTGC ACTTTAACAA GCACTCTGGG
67551  TGGGTTCTGG TGCACATGAA AATTGGGGAA CGGCTGGTGG AAACCTCTAG
67601  CCACAGGAGG TGCTTGGGAA AGGTACCTTC CCCTCCCCAA AGCCTGATGC
67651  CTCACTCAAG CATGACACTG ACAGTTGGGC TAGTTCAGCT GCGTTCTGGG
67701  TCTCTGTCTT GCCTCCTCCT TCAGACTAAG CCTCCCAAGG GTTGCCAAGC
67751  CTCTTTCCTC TATTCTCCTC ACCCTGATCC AGCTCAGCCT CATTGAGAGA
67801  AGTCTGGGGC TGCAAGATCT TCGCACTCAC AGGCAGTTCC TCTTTGCACA
67851  TCCAAGGCAC CAGTGTCTTT GAGAGGCGTC TCCTTGGCCA GGTGGCAGGC
67901  GTGGGTGTGT GGGGAGGAAG GAGGAGGAAC CGCCTTGTTC TGCTTTCTTG
67951  TCTCTGACTC TGCAGGCTGG GGGTGCTGTA AGGCTGCGAG GAGGCATAGA
68001  GTCAGCTTGG GTGCTGGGCT GAGGCCAGGG GCCGAGGCTC AGCTGAAGCG
68051  GGCTTCTCTG GTCTGAGCCT ACAGGATGCC TCCTTTGGGG CAGTTCTGCC
68101  AGTCACCCTG ACTGGGCGGC TGTGCTTGCT AGTGCCAGAC CCATGCTAGG
68151  CACAGAGGTC GATACGTTCT CCTGTGCTCT TGAAGGGCCC TGTCCTCTGG
68201  GAAGATAAGA GGCTGTGTAT ATTGCCCACC GGAACAGGAG GCAGGAAGCA
68251  AAAGAGGCGT AGATGACACT TGCCTGGCAC CCCCTGTTTC CCCTCTAGCT
68301  GCCTTCCTGG GTTTCCCATT CTGTGGGCGC TTCTCTTGAG TTAGGTGCTT
68351  TCTCCCAGTG TTCTCAAGGT GACTATTTGG AGGTTTGTGG GAGGAGTGGG
68401  CTGGAGACAC AGGAGTAGGT GGGGGCAGGA AGTATGCAGG AGAGAGATGG
68451  AGAGTGGGAG GAGAAGCTAT GAGAGGAAGA GAGGACGCGG AGGTGGGAAA
68501  AGACGTCAAG ACTCCTGGAG AGGAACAGGA GTGCAGCCTG GGACAGAGGT
68551  GGACGTCGGC CGGGGAGGC AGGGAGGAAG GCAGGGAGGT CCACCCGAAA
68601  GGAAGGGAAG GGATGATGGA CAGAGAATGA GAGGGCTCCG AGGTCCTGGG
68651  GGATCTAGAA GGACCCTTCC CTTTACAGAA GGGGACACCA AGGCCCAGAG
68701  AGAGAGGAGG GCCTCACAGA GGACCTAACA CAAGCAGAGT TGCATGAATC
68751  AGTGTGAACG GACAGTCCCA AGAGCACAGC CGGACCTTGG GAGGTACTTG
68801  ACTCTTGAGT TTGATGTTAT TGCCTTCCTG TAGGCCAGTG TGAGGGGCAC
68851  TGTGAGGCTT CCTTCCAGAG AAGGAGGCAT GGAGCCAGTG CCAGGCAGTG
68901  GGGTGAGCCA TAGGAGGACC TGTGGAGATG GGGAAAGGCA TAGAGACTCA
68951  TGAAGATGAA ACAGGAAAGA TCTTATGGCA GCGACCCCAA CCCTCAGGAA
69001  GGGCGTTGGT CTTGTGCTTG TGGCTCCAAA GGGGATAAGA CCAAGGTCTC
69051  TGGTTTCATA GAATCTTAGG CTTTAAGAAC GAGTTAGAAG TAATTTAGTC
69101  CAGACCCTCT CCTCTCCCCA GATAAGTGCA GAAATGCAGA TCTAGCCCAC
69151  GGCTGAGCCC CAACCCTGGC TTCAGAGGAG GCCTGACTCA GAACAGGCTC
69201  CCCTTTCTTG GTACCTGGGG TGAATGAAAG ATAAGTCTGT GGTAATGGTG
69251  CTGTCTGTGG TGCTGACTGG CCTTACCTTG GACTACAGAG CTGCAGGTGG
69301  AGCTGGAGAG AGCAGAAAGG CTCCATCTAT CCATCTACCC ACCCACCCAG
69351  CCACCCATCT ACCTATCCAC CCACCATCCA CCCACCCATC CATCCACCAT
69401  CCCTCCCCCA ACCCATCCTG CACCCATTCA TCTATCCACC TACCCACTCA
69451  TCCATCCAGC CTCATTGAAT TAAACCATAG AACTATATGC TGCAGAGCTA
69501  GAAAGATCCA TTTTTTAGTA ATGACAAAAC TGAGGCTCAG AAGAGGAAAG
69551  GTGTTGCGTA AGGCCACACA GAACTTCTGT AGTCAGTCTG GTACAGGATT
```

FIGURE 3-24

```
69601  GGAAATTGCG GCTCTTTTCT ACACACCACA AGTTCTCCTC TGTGGTCTGG
69651  GAAATTGCCT GGTTTTTATG CTGATATCTA TACTGATATT TGTTCCAAAA
69701  AGCTGTGAAG GCAGGAAATG TGACCTCCTT CACCCCATCC CGAGCCTGAG
69751  TTCTGTGTGT GTGTGTGTGT GTGTGTGTGT GTGTGTGTGT GTATGTGATG
69801  TGCATGTCTA AGTGCAACCT TGTATATGCA TTGAATATAT GATTGCCTTT
69851  TGATCTGTCT GTGTGCGTGT TTGTGTGAGA GCCTGTGCAT ATACGTATGA
69901  GTAGAGGAGT GCGTAGCAAT ATGTATTTGT GTGGCATGTG TAGATGGGCA
69951  TGTGAGCAGG TAAAGCTGTG TCTGTATTTT TCCTTTCCTC TTCCTTTTAA
70001  GATCGAAGCC CCCTGACTTG AGCCTTGCTC CCCATCTGTG CCTCCAATTC
70051  AGGAATCTCC CTGCTTCCCA TTAGCAGCTG CTCCCCACTG ATTCTCTCCT
70101  TCCTTCACTG AAGCAGCAAC TCTTCCCTCT GAGCCCACAC CTCATGGGCT
70151  TTGCAATTTG AGCTATTTCC TCCCCTGAGT TGGTGCAATG GGGGTGAAGT
70201  TGCTTTGAGA TCTGAGGAAG ATTCATGGAG GAGATGGCAT TTGAGCAAGC
70251  CTTGAAGGCC CCTTTGAGTG CCAGATCTGA AGTGGCCCTT CCCAGCTGCA
70301  GTTCCTGCAC CCAACACCCT CCATTCCTGG GGCATGCTGG GCAGGACCAG
70351  GAGGTGGATT GACAGAAGGA TGCCCACAAA GAGCCCTGGG CTTCATCAGT
70401  CACATTACCA TCCAGTCCGC TCTAGCACAG ATGGGAAGCC CTTCCCTGCT
70451  GCTGCCCCAA CTCTCCCCAA CTTTCCTTTC CTGCTCTCCT TATTGCTACT
70501  ATCCTGCACT TGGCCTGAAA AGTCACAGAA AACTGAACAA TCAGAGCAAA
70551  GGTCAGGCAG GCACCCACCA ATTCCAGTAA AGGACAGTTG AGGGCATTCC
70601  CCAATTGAAG CAAAGGGCAG GTTGAGGAGT CCACCAATCA GAATAAAGGA
70651  CAGACTGTTC TTTCTGAGCA CCCTAGGGTG GGAGCTGGGG ATCGGGTGCT
70701  GAGCAGGAAC CAGACAGGGC TAGAGATCCA GAGGTTTGGG TTCTGGACCT
70751  GGCTCTGCTC TGACTGGCTG TCTGACCACA GGTTGATCAT TGCTTCTCAT
70801  TGAACCTCAG CTTCCTCATC GGTCAAATGG GGAGACTTAG CTCTCTGAAG
70851  GCTGTGGCTT TGAAGAATTT CTCCCCCTGT ATCAGGCTCA CTCCGTCACC
70901  TGGGTCTCTC TTCCCCAAGT CCACATCACA TACATCAGAC TCCACCAAGG
70951  GCAGGGCCTC TCAGGAGTCA GCTTGTGGGC TCCTCTGCCT CCAAGAAGGA
71001  ATAGACACAA ACCAACACCA CCTTCTGTGC TGTCTTTAGA GCCCCCGTCT
71051  GGGGAGCGTG CATCTGGAAG ACTTTATCTT GGGAGTACTG GGGGCATCAG
71101  CTCTTCCTCC CCTTTTTAGT CTTCAGAATT GACCTTGGAA GGCCATAATA
71151  GCCTGCGTGT ATTGTGCACA GGTATCACTC GAGCTCTTGC CCTGTGAATC
71201  TTTAAGGAAC TGTACCAGTG AGAACGTGTG TGTGTGTGCG CACATGGATG
71251  GTGTCTGAAG GCCTGCTGGG ATGTCTGCGA GGACGTGGGA TCTGTGGCTG
71301  TGTGGTGCTG AAGTTGTCTG TGCTGTGATG AGGAGTGCCT AAGGGTCAAA
71351  AGACAAGTGA TCCAATTTGG GTATTGTGTT GTCTGGAATC AGTAGCTTCT
71401  GATGTCTGAG GGTAGACATC TTCCCATGAC CAAGATATGT GTCTTCATCC
71451  TTGAGCAGTG GGAGGGACCA AGGAAGCCTG GGGGTTGGGG AAAGCGATGC
71501  TGAGTAAGCA TCTGGGGAGA AGGCCCACTA CTGCCCTCCT CCTGGGAACA
71551  CTGGATTGGG TGGGGGAAGG GGAGGAAACT GCAGCCAAGA AGACCCAGGA
71601  GTGAAATTTG GAGCTGAAGC CTGGATGCAA GTCTTCATTG AGAGCCCAGC
71651  GTGGAACTTT CTGGCAAATA GGCATTCAGC CCACTCTTGT GCACCCTTGA
71701  GGATGGGAAG CTCACTTCCT CCCTCTCTCC TGGTGACCTG TGGCATGCCT
71751  TTGTAGCATG GCCCTACCTG GAAGAAGGTC CTTCAGCCCA CTAGACCAAG
71801  GCCAGCCTCC TGTGAAATCC TATGGGTCCC CAGGCTGTCC ATGGGGCCAC
71851  AGAGTTCAGA TCCCCCATCT AGGAGGGTCT GAGAGATTGG AGTTGGAGAC
71901  TGATAACCCT GGGTCTCCTC TGCTTTAGAT GAGGCATCCC TGGGTTATCC
71951  AGTCTTAGTC ACATGCAAAA CTTGGTTTCC AATTCCCTCG TTTCATAGGT
72001  CGCCTCCTCT GGATGAGTGT CATCTTGTCA GCCCCTGGGA CACAATGAAC
72051  AGGGGATGGT CTAACTAGAC TATAAAGTG  GGGGAACTGT CATCTTCCCA
72101  ATTGGGTTAA CAGACCTCTA TTAATATGGC CTGCAGTTTG AGCATTTTTA
72151  TTTCTTGCCA GTCATGCTTA CACTGTGGGC TCATGCTGAA CTGTGGTCTT
72201  TTAAGACCCT CAACCTCATA TCATGTTCAC ATGAATGGGG ACCCAGCCAT
72251  GTCTCCTTCA TCTTGCAGTT AATCACTTTG CTTTCTGAAC ACAGACCCAA
72301  CCTTCCACTG GAAGACATC  TGAAAGGACT TCCAAGGGCT TGCGGGAGGG
72351  CATGGCTGGT GGCTGGTATG AGTCACGATC TTGCCTTGGC CCTCGTTTCC
72401  TTTGTTCTGT TACCTTTCTC TTTGATCCCC ATGGCTCTGG CCAAGTTAAT
72451  AGAGCGAGAA GCAGGGACTT TTGTCTCCGT TCCGGCTCTG CAAGGACGAG
```

FIGURE 3-25

```
72501  TTCTGTTCCT GGGATGGGAA GGCTGTGAGA CAGTCAAGGC TGACGTCTCC
72551  TTCTCCTCCT ATAGTTGCCA GGGGTGGCCC AGCTGTTCTC CCACCTTATG
72601  GGTTATGCAC CCCATAGGCT CTTGCTACTC TCAACCCAGC CCCTCACTAG
72651  GCTGGAAAAT GAGACTAGGT GAGACCACCT TCCTTCTGGG GAAAGTGAGC
72701  GGGACCCAGC TTCAGCGAAT ATTCAGCTGA GCATCTACTC TGTGTTGGGC
72751  ATTCTGTGAG GCACTTTTAG GACTCTGATT TTTATTTTCA TTTTTAAGGG
72801  CTCAATTTCA TTTTATCTTC ATGTCAGCCT GTAGGGGGCA ATAGCCCCAG
72851  CTGCTTCCAA CTTACAGATA GGAGACTGAG GCTCAGTGAC TGAACCAAGA
72901  CACTCACTGC TCATACACAG CGGAGCTAGG ATTCAAATTT GGGTGTTTTT
72951  TTGTTTGCTT GTTTTGTTTT AATTTGGAGC CTTGTGGTTT CCCTACTGTG
73001  CCAGAATTGT CCTCGACTAG AGAACAAGAG ACCTGGGGTC TAGGCCAGGC
73051  TTGACCTGTT GACTCACTAT GAGGCCTTTG CTAAGTCCCT GGCCCTTCTC
73101  TGCGCCTCAG TTTCCCCACC TGTAAGATGA GGGTACTTGG ACATTCTGTG
73151  GCCTTAAGAC TGTTTGATTT TGAGATCCTA AGATCCTGGG ATTCCTGTGC
73201  CTGAAAGACT CGGGCTCTGG ACTAAGCTGG GGGGTTTTGC TCACAGTCCT
73251  TTGGGCAGAT GGGGCTGCCC TGGCCTGCCT GGCAAAGCCT CTCACTGCCC
73301  TCTCCTCTCT TCCAGGACGC CTTGCTGAGT CTGGGCTCTG TCATCGACAT
73351  TTCAGGCCTG CAACGTGCTG TCAAGGAGGC CCTGTCAGCT GTGCTCCCCC
73401  GAGTGGTAGG TGCCCGCCCT TGCCCCACGC TTCCCACCCC ACCCCCAAAT
73451  CCTTTGACCA GCTCTATGCT GTACCTCACT CAGGGCCAAG GAGGAAGGAA
73501  GAGGCAGGGT CCCTGCCCAG AGGACTTTCA TGGGGAAGTG AAGGGTCTGG
73551  ATGGGTGTTC TGAGACAGCT TTCTGGAGGA GGAAGCCTTA GGCTAAGCAT
73601  CAAGGAATGA ACTTGCATAG GAATCCTGCA ATGGCTGAGC CAGAAGGGGC
73651  CTTAGAGGTT AAGTGGAAAA GCTGTGTCTC AGATAATGAA AGGGATTCAC
73701  CTAGGATAAC AGGACGTGGT GGAGCCAGCT GAGTTTTGGA ATACATGCAG
73751  CAGGAGAAGT TGAGGGTAGA CATGTAGAAG AACTTCCTGG AAGCCAGGTC
73801  TGGGAGGTAC TAGAATAGGG CTCAGCTTTG ATGAATAGAC ATGCATTGGG
73851  TTAAAGTGCC CTGCCTGGAG ATGGGAGGCT GGAAAAATGG CCTCTAGCAG
73901  CCTTTTAGCA GCTTTCTTTC TGTCCCATCC CAATACCATG GATGAGTTGC
73951  AGGTTTGGGG CAGGTTTGGG GTGATCATGG TTGCCTGAGC CCAGAGTGCC
74001  TTACTGGGGA GATTGTGCCC CTCATCATCT GTTCCAGGCC ACTCCCCTAC
74051  CTGGCTTCAA TGGCCACTGT TCATCCCTTA GGCAGGAGGA TGGGTAAACC
74101  AGCCCTTGAG GCCCAAAGTA GCAGGGTGTT AGTTGCACCA GAAAGAGGGA
74151  AGCAGGGGAC GTTTGAAGCC TGGAGAAGGG AGTCTGATCC AGCCTAAGGG
74201  GCATGGAAGA CTTCCTGGAG GAGGAGATTC CCTAACTGAG TCCTGATAGC
74251  CTTGAATGTC CTCTTCCCTA CTCTAAACCC GGCCAAGGGC AGCCTCTGCT
74301  CCAGGAAATA TGGCCAACTC AGAATGTGAC CTTCCCATCC CTCCAGAGCC
74351  CATTGTCCCT GAATCTGCTT GATGGATGAA CCACCGGAGG CCCAGAGAGA
74401  GAGGGCACTT GTCCCAAGGT CACACAGCAT GACAGGGATA AATGGGACTT
74451  GGTATCTAAG CAGCCCCATT CCCTCTCTTC AGCTCTGCCT TCCCCAAACC
74501  TCCTAGAAGT TCAGAGCCCA GGAGGAGGGC TAATGAGTGA GCTTTATTGA
74551  GTGTGAAATT GGTAGGAAGT GGGTGGTGTG TTGGCGCCCA AAAATAAATC
74601  CTCCTGGAGA AGGACGGGAC TAAGGCAACA TCTGGCCTGG GGTGAAGGCA
74651  CATCTGGAAA GGGAGGGTGG TGGAAACTGG CAGGTCGGTT TCTGTAGGGC
74701  TGCCCCGAGA GCCTCTGTGG CCACTGAGGC TGCCGTAGGG TGGGAGGAGG
74751  AAGTGACTGG CTCTGTTTCA CAGGCAGGGT GCCCTGGCGG CTGTGCCAGC
74801  CTAGATGCTC TGCAACAGAT TAATTGTCTC CCCAAAGCTG GGGGCTGGGA
74851  TGACAGCTGT GGTCCAGGTT CCTGGGACAG TGGGAAATGT CAGCCCTGGC
74901  CCACCCAAGA GCCCTATAGG AGCTAGGGAA GCCCTGACTT TCGGGAGTCC
74951  TGGCTTGATT GCACGGAGGG GCTCAGCCCC CAGTGAGGTA AGGGAGCTGA
75001  GGTCTGCTCT GCTGCCCCCA GGGAGGGAAG CAGAGATGGG GAGGGGACCC
75051  CCGCCCAGGG AGGAGAGCTG CTGGCACCTG GCTTCCTCAT CAGCACCCAT
75101  TGTGGCAGGC AGCCCCGAAT GCAGATGGTG CTGATGTGTC TGAAATGGTT
75151  CCCTCCTTCT CTCCAATAGA CTCAGCTAAT TTTAACCCAG AGGGCTGAGA
75201  GTAAGGGGGT GGGAGACATA CGGACATGCG GAAGTGAAGC GAGAATCTGT
75251  CCCCCTCTGC CCCCATGGAC TACCCACCCC TCCCTCTGCC TGGGCAGGAC
75301  TTTCTGTATA ACCCCGGCTG GTCTCTTAAC CTCTTTGGGC CAAATAACTC
75351  AGGCCCCTCC CAGGCTGCTG GAAGAGATGG ATGACAAGGA GGCTAGATAT
```

FIGURE 3-26

```
75401  AGCCGAAGAG TGGGCGGCCT CCTTCCCACT GAATTCTTTA TCCCTGAACA
75451  TCCCACTTAG GTTTCCTTCC AGCCAAACAA GAGGGTGTCT GCCCCTCTCA
75501  CTCCCTTCAG GCCTTATCAT TCCCACCCCA TGCCACACCC ACCACGGAAC
75551  CTGGCTCAGT GTCTCTGGAA GTAGTGGCCA GGCATCTCCT GTGGTGGGGG
75601  CTGGCTGGCG ACAGCTGATG ACAAGAAGAG TGGCTGGCAG GATTGTGGAC
75651  GCTCTCAGAG TCATGGAAGG CAACTGCTTC TTCTGGGAAG GATTCCACAC
75701  TTACTGAGGG TGGGCCTTCA ACACGTAGCT CCACTGTCAG CTCCTCCCAA
75751  AGCCCTCCAG GATACCCTCA GCTGGGAGGC AAGCCCTTCT CCATCCTCCT
75801  GCGGAGAAAA CAGCAGAGTT GTGGACAAGG CTGCGTTGCA TGGGGGTTGG
75851  TCAGGGATCC CGAAGGGTTG CCAGTTCTGC TTGAAGGAA TGTGGATTTT
75901  TGCCTGTAGG TCAGTGAGGG CAACTACTTC TGCCAAGACA TGGCCTGGAA
75951  CTGAGGCCAG AGCTGCTCTG GGCCCTTGGG GAGGGAGGAT TAAAGAGCAA
76001  GAGCTTTGAT CTCCCTCTGA GGAGTAATCG GTCCAAAATA CAAATCTGCT
76051  CACGTCTCCC TGTGCACGTC CTGCCCTGCC CCAGTTCTGT TCGTAAGCCC
76101  ATCCCACTCA GCCCTACTGA CCTTGGGCCC AGCCCTGTG CCCCTTCCCT
76151  CACTGTCTGT TCCTAAATGC TCCATGCTTT ATACGCCTCT GGACCTACCT
76201  GTGTACCTGC TATAAGGCCT GGGAGCCCAT TCTGCACCCT GCCCACTCCC
76251  TGAATGTGTC TAATTCCCAC TCAGTGACAG CTGAAAGGTC ACTTCCTCCA
76301  GGAAGCCCTC TCCAGCCCCA CCGGAGGATG GCGCAGTGCC CTGCTCTGTG
76351  TTCCTCCCCT GGCTGGGGTT ATGGGTGTGT GGTTTCTTGT AGAGGTGAAG
76401  GAGGGATGCT TCCTAGAACA TTCTGAGCCC CATCCCTGGT ACAGCTCAGA
76451  GTGGATGCTC AGTTATTGTT TGCTGAATGC CTGAGGCTGG AGTCAGGCAG
76501  GGAAATATCC CAGGTGGGAG GTGATTTGTC TGCACCCTCA GTCCTTGAAA
76551  CTCTTTACCT GGCACATTGG GTTTTGGGTG GTAAAAAAGG TCATAGGTTC
76601  ATGAATCATT GCCTGCTTAG AATTCCTTCC AAGAGGAGAG GACGAGGTGC
76651  TTAGTTCACC GGGTGTTTTG CTGCCCTGGC TGCATCTTAG AATCACCTGG
76701  AGAGAAAAAC AAACAGATCA TTGCCAGAGC TCCACTCCCA CAGGTTCCAT
76751  GACCTTGCCC CACAGACCCC TGTGTACAGG CTGGGACTGG GCAGCTGGGA
76801  GGGCCTCTCC ACAGGGTCTC ATAAGTGCCT TCTGTCCTAG GAAACTGTCT
76851  ACACCTACCT ACTGGATGGT GAGTCCCAGC TGGTGTGTGA GGACCCCCCA
76901  CATGAGCTGC CCCAGGAGGG GAAAGTCCGG TGAGCCATTC TCTGCACCCC
76951  CATTGCCCTC TTGCATGGCC AAGGATTCTC AGGGCTGAGG CACCATCCAA
77001  GGTCATCTGG TCTGACCCTC CCCTTCCAAC ATTGATCCCC GCCTCCCTGC
77051  CAGGTGGGAT TCCTTGGCCA GGTTGCTGAC TCCAGCACAG AAGGGCAGAA
77101  GCAATGTCTT CTCTTCCTTG GGGAAATGGA TAGGCACAGA GAAAATACCA
77151  ATTGATGGTA AATTTTCTCC TTCTAATTGC TTCTAAATGG CTGCAGCCTC
77201  CTCAGAGCAG AGTCTCAGAA CATTGGGGCT ATGGGGTGTA TCAGTTAGAA
77251  CACCGGCATG CTGTGAGAAC TACTGCGAGG CTGGACCTGG AATCCCAGCA
77301  TGCTGGGCCT GCAGGAGCTC ACAGTGCCAA CTCCTTGCAT CTGAGAACAG
77351  GGAGATCACA GGCAGCGTCC TGCTGAGGGT TCTGGAGCCC CACTGCCTGG
77401  GTTCAAATCT CAGCTCCCTG TTTACTAGCT GTGTAACCTT GGGCAAATGA
77451  CACAACCTCT CTGTGCCTCA GTTTTGTTTA TGAAATGGTG ATAATAATGG
77501  TGCTTATAGG ATTGTGGGGA GGATTAAATG TGTCACACAT GTAAAGCATT
77551  TAAATCAGGC CTGATCCATG GTGAGGGCTG TCTGTTGGGG ATTACCATTG
77601  TGAGAGAATG CTGGAATCAC TGACTTCAGG ATCATGGGAT CAGGGCACTT
77651  GGCCCCCTGA TACCTTGATG CCCATTTAAT TCAGCCTCCT CATCTTCCAG
77701  ATGGGTGGAT ATCATGAGAC ATGACCAAGG CCACATGCCA GGTATGAGGC
77751  AGAGCCAGGC CTAGGACTCG GGTCTTCTGA CTCCTGGCTG TTTAGGGGAA
77801  AGTGAGAGGA AGTGGAACTC ATCAGATGAG AAAACCTTGG GGGCAGGCAT
77851  GCTGCTGGGA GGAGGCAGGC TCTGAAGGAT GTGGCCATTG CCTGCTAAGC
77901  ACTGAATGCA GGGCCATTGT GGGGCCCAGG GAGCACTGGG CAGGAGCTGA
77951  GGGCAGAGTG GGCACCAGTG GGGATGTCCC AAGAAGGCAG CTCTCTACCC
78001  CTGTGAGGAG GGCTTTTCCA GCAGGCCAGG TGGTCCAGGG ATGTGGCTTT
78051  TTCAGGTAGC AGCTGAGCCT GGCAAGCCAC TCACCTTTCA CAGGGACCAT
78101  GGAAAGAATT CCTGTTTGAG GATGCTGGAC TCATGGTCCT GAGGCCCCTC
78151  CTTGTGCTGG AAACCCTGGT TTCTAGGATG CTGGTCTCTC CTCAGCCCTT
78201  TCCCGTGGAA GGAGTTGGTT CTGCTCTGAT AGCCACCTTC CCATTTCCTA
78251  TTCTCCCACT GAGCTCCTTT CACCTTCCCC TAACAACTTC TCCGTCAAGG
```

FIGURE 3-27

```
78301  AGCATGGGAA CAAAGCCATT ACCACCTCTC TCTAGCCTTT GTGTCCCGTC
78351  TGTAAGAGGA TGGTCTGAAA GGTCTTTAGA ACCTTAAGGG GAAAAATGTG
78401  GTCATGTCCC CCTTTCTCCT CTAATTCCAA AGAACTTCGC TCTCCTCCAG
78451  CATCCCCCAC CTCTAATTCT AAAGAACTTT GCTTCATATA AGCTCCACTC
78501  CTCCAGGAAG GCTCCTCGGA GCAGCCTGGG AGGCCTTCCT GGGAGGGATG
78551  CAGGAAAACA GGCTCAGGAG GCAGCGGGGA GCAGCCTGCA GGTTTGCTTC
78601  ACTCCCTAGG ACCCACACAT GCTCCCCTCA GCTGTCTGGG CATGTAGAGT
78651  GGGTGCGTAT CTGCGGTCCA GGCATTTTTG AGAGGGCTCA GATCCTTGGC
78701  ATCAGCTGCC CTTTCAACAT CCTCCTTCCA ACCACTTCAG ACTCAGTAAG
78751  GCCTTTGGAA AAAATACCAA AAAAAAAGCA ATTAAAAGTG AATATTCAAA
78801  TCCAATTATC CCAGAGCTCA GTGGAGATGG GGAGGTGAGT GCCTGCTGGT
78851  AGACAGGGGC TGAAGATTCC AGGAGGAGGG CCAGGGGATG AGAAGGCAAG
78901  AGAGTGAGGA CAGCAAGGAC CTCCCAGGGG ACATACCCAT CATCAGGACA
78951  CACCCGTCAT CATCCCCAAA CAGGAATTCT TTCCATGGCC CCTGTGAAAG
79001  GTGAGTGGCT TGCCAGGCTC AGCTGCTACC TGAAAAAGGA TTGGGGGAAG
79051  GCCCAGGCCC AGTGCTCTCT CTGGTATCTG AGCTCTGCTT GCCCACCTTT
79101  GTGCCTGGTG TCTGGTGGTG AGCCCATCTC CACAATTAGG GCGGAGAGGC
79151  CCCAGGGTTG GCTGGGCCCT GCTCTCAGGA GCTCCCAGCA GGATGGGGAC
79201  TTGAGACCCA GGTGTATGGA CGAGGGAAGA GCACTGGAAT GGGATTCAGA
79251  CAGGTCTGGA TTCTAGCTCA GCCCCCTCCC TGTCTCTCTG CTTTCCTACC
79301  TGAGGCCCGG TCTATTGGCT TAATGGGGTA ACAGGGGCCA AGTGCTTGGC
79351  ACAGTGCCCA GCACACAGTA GGAGCTCAGT GATTGCTACT TGCACTCCCA
79401  AGTCCCAACC AATGATTAGC CTTGAGTGAC CTTGAGAAAA CGACTTCTCT
79451  TCTGGCCTTT TTTCTGTGAA ATGGGTGGGG TTGGGTACAG GGTCCTTCCG
79501  ATGGTGACCT TTGTGGCTCT GGTCCCCCCA GGAGGGAGAG GGACTGACCT
79551  ACAGGCTGCC GTGGAGCCTG AGGCTCTAGC AGTGCCCGAG GAGGTGGGGG
79601  TGTGGGGAGG GTGCTACTCC AGGAAACCCT GGACTGTGGG CAAACAGCAG
79651  CAGGTGTGGC GTGGAGGCTG GATCATAGAG ACAGATAAGG AGGCCCGAGG
79701  CAATGGGCAG GGAATGGGAT CAGGGCAGTG TGGGGAGAGA CAGGGTGGAA
79751  AAGGGTCAAG GCGGGAGTGA GGAGGCCCCC GCCAGCTCCC AGCCCACCT
79801  GTCCCTGTTC CTGCCGCTGT TTGGGCTCTC AGATGCCCAG CTGCATCCCC
79851  CCAGTGTGTT TGGCTTTCCT GTCTTCTTGT GCTTGTAAGG GCTGCTTGCT
79901  CCCTTGCAAA GACCGTCCCT GCTCCACTTT CATCTCAGCC AATCCCATTG
79951  TAATTATCTT TCATGCCTG ACCAGAAGCT GTCTTGGGA AGCCTGCTCC
80001  ACAGTTCCCT GACACTGAGA AGGAACCAAG TTTCAGAAAA GGGGTCTGGG
80051  CCATATTGGC CTCCCTTAGG GTTCTTCCAC AGGAAGAACC TTGGGCTGGG
80101  AGTCAGAGAC CTGGGATCCA GGACAACATG GCTGCAATCA CAATCCGATG
80151  CCCTCTTCCT GGGCCTCCAT ATGCCCTTCT GTAAAATGAT ACGCTGAACA
80201  TTCTGATATT GAGGGCTGGT GAGGCTCTGA ATTGTAAGGG CTGCAAACGA
80251  CCTTGGGGCT GGAGAGGAGA GAATCCTGGA AGGCTGCCTG GGCCAGGGTC
80301  TTCCTGAAAG GAGGCTTCAC TTCCCTCTTG TTGGTGCCCC ACCTCCATCT
80351  CCCAGACTGT TTCAGGCCCC AGCTCTGCCG CCTTCCTCTT CTTGTGTCTC
80401  CTGCTATCTT AAAGCCTCTG ATTACCTGAT GCTGAGTGCA GCAAAAATCT
80451  CAGGCCTTTC AGCTGCAACT GAAGCACCCA CCGCCCACCT CGGCCCAGGC
80501  TGGCTGTCTC CCTCTGCTAC CATTTTGGGG TCCCCAGGGC CCATCCCTAA
80551  GAAATTTCTT CCCCTAAGCT GACCAGGTCT TCTTTCATTG CAGAATCTGA
80601  CCATCCCTAG GGGTTGTCTC AGAGGACACC GGGAACGGTC TGCTCCCATC
80651  TCGGGATCCT CACATGCTGG GGGAAGGAGG GCAAGAAGAG GGTCCAGGTC
80701  CTGGGGGCTC AGTGAGAGTG GGGGGCTTAG TGAGGGGATG GGGGCCCAGT
80751  GACAGTGGGC AGCCTCAGTG AGGTGATGGG GGCCCAGTGA GGATATGAGG
80801  GCTCAGTGAG AGTGGGGTGG CCCAGTGAGG GGATTGGGGC ACAGTGAGAG
80851  TGAGGGGCTC TGTGAGGGGG TAGGGACTTA AGTGAGGGGA TGAGGCTGA
80901  GTGAGTGTGT GGGGGCTCAT TGAGAGGGTG GGGGCTAAGT GGGGAATGGG
80951  GGCTCAGTGA GGGGATGGAG GCTCAGTGAG AGGATGAGGG CTCAGTGAGG
81001  GGATGGGGGC TCGGTGAGGG GATGGGGGTT CAATGAGGGG ATGGGGGCTG
81051  AGTGAGGGGA TGGGGCTGA GTGAGGGGAT GGGGGCTGAG TGAGAGGATG
81101  GGGGCTGAGT GAGGGGATGG GGCTCAATGA GAGGATGAGG GCTAGGTGAG
81151  AGGATGAGGG TTCAGTGAGG GGATGGGGCT CAGTGAGGGG ATAGGGGCTC
```

FIGURE 3-28

```
81201  AGTGAGAGGT  TGGGGGCTCA  GAGAGGGGAT  GGGGACTCAG  TGGGGGATGA
81251  GGGCTCAATA  AGGGGATGGG  GGCTGAGTGA  GAGGATGGGG  GCTGAGTGAG
81301  GGGATGGGGG  CTGAGTGAGA  AGATGGGGGC  TGAGTGAGAG  GATGGGGGCT
81351  GAGTGAGGGG  ATGGGGGCTC  AGTGGGGGAT  GAGGGTTCAG  TGAGAGGATG
81401  GGGGCTCACT  CGAGGGGATG  GGGGCTCAGT  GAGGGGATGG  GGGCTCAGTG
81451  AGAAGTTGGG  GGCTCAGTGA  GGGGATGGGG  GCTCAGTGAG  AGGAAGAGGG
81501  CTAAGTAAGA  GGATGAGGGC  TCAATGAGGG  GATGGGGCT  GAGTGAGGGG
81551  ATGGGGCTCA  GTGAGAGGAT  GAGGGCTAGG  TGAGAGGATG  AGGGTTTGGT
81601  GATGGGATGG  GGGTTAGTGA  GGGGATAGGG  GTTCAGTGAG  AGGATGGGGG
81651  CTCAGTGAGG  TGATGGGGGC  TCAGTGGGGG  ATTAGGGCTC  AGTGAGAGGA
81701  TGGGGGCTCA  GTGAGAGGAT  GAGGGTTAGT  GAGGGGATGG  GGCTCAGTGA
81751  GAGGATGGGG  GCTTAGTGAA  ATGATGGGAG  CTCAGTGAGA  GGATGGGGGC
81801  TCAGTGAGGG  GATGAGGCCG  AGTGAGAGGT  TGCGGCTCAG  TGAGGGGATG
81851  GGGACTTAGT  GAGAGGATAG  GGGCTCAGTG  AGGGAATGGG  GGCTCAGTGA
81901  GAAGGTGGGG  GCTCAGTGCG  GGATTGGGTC  TCAGTGAGAA  GGTGGGGGCT
81951  CAGTGAGAGG  GTGAGGGCTT  AGTGAGGGTA  TTCGGGCTCA  GTGAGGGGAT
82001  GGGGGCTCAG  TGAGAGGATG  GGGGCTTGGT  GAGGAGATGG  GGGCTCAGTG
82051  GGGGATGGGG  GCTGAGTGAG  GGGATGGGGG  CTCAGTGAGA  GGATGAGACC
82101  TCGGTGAGGG  GATGGGGGCT  CAGTGGGGGA  TGAGGGCTAA  GTGGTAGATG
82151  GGGGCTGAGT  GGGGGGATGG  GGCTCAGTG  ACAGGGTGGG  GCTCAGTGAG
82201  AGGATGGGGG  CTCAGTGAGG  TGATGGGGCT  CAGTGAGAGG  GTGAGGGCTT
82251  AGTGAGGGGA  TTGGGTCTCA  GTGAGGGGAT  GGGGGCTCAG  TGGGGGATGG
82301  GGGCTCAGTG  GTAGATAGGG  GCTGAGTGGG  GGGATGGGGG  CTCAGTGAGA
82351  GGGTGAGGGC  CTGGCGAAGG  GATTGGGGCT  CAGTGAGGGG  GTGGGGAGTC
82401  AGCGGGGGAT  AGGAGCTCAG  TGGGGGATGG  AGGGTCAGTG  GGGGATGGGG
82451  GCTGAGTGGT  AGATGGGGGC  TGAGTGGGGG  GATGGAGGCT  CAGTGAGAGG
82501  ATGGGGGCTC  AGTGAGGGGA  TGGGGCTCAG  TGAAAGGGTG  AGGGCTTAGT
82551  GAGGGGATTG  GGGCTCAGTG  GTAGATGGGG  GCTCAATTGG  GGGATGGGGG
82601  CTCAGTGAGG  GGGTGGAGAC  TTAGTGAGAG  TCGGGGGCT  CAGTGAGGGT
82651  GGGGGTTCCC  CTGGGGGGAT  GGGGTTCCGT  GGGAGGATGG  GCTCAGCAAC
82701  AGGCTTGGCT  GCTTAATGAT  GCCTGGGACC  TAGTGGGTGT  TGGAGGGGGG
82751  CTTCTCCAAA  GTAGAGAACG  CGAGAAGGAC  ACACACAGGG  GCTCAGAGAA
82801  GTGCAGGGGA  CCCAGCTCTT  TCCAGGCTGT  TGGCCCTACC  AGCAGAGAAC
82851  CTTTCCCTCG  ATTCTTTTTC  CATTAAACAA  ATAGTTGTTA  AAGGGACGGA
82901  ACTGCCATAA  AGTCCACGCC  TGTTCCTCTC  TCCACTCTGT  GCCCATCTGT
82951  CCTTATCTTC  AGTGGGGCAG  GCCATGACCA  CCCAGGCACC  CAGTGCTGTC
83001  ATTAGCCTTC  GCCTGGGCAG  CTGGCCCTGG  GTTGTGGAGT  TCCCCACAAC
83051  CCCCAGCATG  AGCCTGGAAG  GCAGGGTGGG  GGTGGGGTAG  TAGTAAGGGA
83101  GGAACTGGAG  AGGAGCAGGG  AGCGGCTCTG  AGTTGAGCAA  GGAGCTATCG
83151  GGGGTCTGAG  CAGTGGACGA  AGCTCCCGCT  CCCATGTGGG  TGGGGGAGAC
83201  TCAGCCTTGG  CACATTCCCC  CTCGCAGTCT  GTGGGCATCT  TTGGAGACTT
83251  CAGGAGGACA  GCAGTTCTGG  GAGGGCTATG  GCAGAGGAAA  GGGGCTCCCA
83301  TGGGGGTAGG  TTGAGGTGAG  TGTGGGCTAT  GGGGTCCCGC  AAAGCCGGGG
83351  GAGGGCAGGC  TGCAGAGCAA  GGTGCCGAGG  CTGCCTAAGA  ATTGAGGGTC
83401  CTTGGAAGCC  CCAGTGCTTG  GGGGCATCTC  GGCTTATCAA  GATTGGTCTA
83451  TCCCAGCTCA  GCCTCTGTCT  TGTCCAGGGC  CACTAAGATG  ATAGGACCCT
83501  CACTGAGACC  AGGTTTCCAG  TGTCACAGTC  TCCTTATGTG  GAGAGTTTTA
83551  CCCAGGCAGC  ATGATCGTTC  TGAAATCATA  CCTGACCATT  ACCGTCCCTG
83601  CTCAAATCCC  TCCCAGGGCA  CCCCCTGCCC  TCAGGCTCAA  GCCCAGCTCC
83651  ATAGGGCCCT  GGCCCCTGTC  TAGCCTTGCT  CTCGGCTGTC  CAGTCACACC
83701  AACCTCCTTG  TGGCCATACC  TTTCAGCAGG  CACACAATCT  TCTCGCCTCC
83751  AAGCCTTCAC  AATTGCAATT  CCCTGGACAT  CCTTTCCTGT  CTGCCTCGAT
83801  AACCTCTGCC  TGTCCTTTAG  GACTCAACTC  AGGTGTCTCC  CTCTACAGGA
83851  AGCCTTCTCT  GACTCCATCA  CACCCTGCAC  CTGAGTGGGC  TGGGGCCTGC
83901  TCTTCCTGCC  TTTGGCAGAG  CTCTCATCTC  CCGACTGAAG  CGTGGGTCTG
83951  TACGTTGATC  TCTGCGTGTT  CTTGGCCTCC  TCAAGTGAGG  CATATGTCTG
84001  ACCCCTCTGC  TCATCTCAGC  CCTCAGCACT  GAACCTGACC  CAGAAGGACC
84051  CAGTGAAATG  AGAGACTTTA  AGTAGAATGC  TCCCCGAGGT  TTTTCATCTA
```

FIGURE 3-29

```
84101  GAACACTTAT TCTTGCTCTG CCATGGAGAA TGGATTGAAG AGACCCAGCT
84151  AGGAGGCTAG AGGCTTGGGG AGAGGCTGCT TCAGGGTTCA GGGAAAAGGT
84201  GTCTCCATGT GAGCTGGGCA GTGGCTTGGG CATAGAGAGC AGAGGACAGT
84251  TGTGAGAGAC AACTGGGAGG TGACTCACTG ATCGGATGGG GGAGGTGAGG
84301  AAAGAAGGCA GGTTTTTGGA CAAGCCGTGA AGGACCTGGT GGATGGTTGT
84351  GCTGCTTTGT TGTGAGGTGG AGGGAGTGGA GATAATAATT CAGATGGTAT
84401  GGGGGTCCCT GGGCCACCTC AGGGACGTGG TGGGGAGGCT CCAGGTGGCC
84451  TTTGGGTATC TGGGGTCTGG AGCTCATGAG TGAGGGCTGG AGAGTCATGA
84501  GGCCGTGAGC ACAGAGGAGG GGTTTTGTGC AAAAGAGAAG AAAGGCTGAG
84551  GACAGATTCC TTCATCAGGG TCCTGGGAAA GAGAGGCCAA GCAGCTCCAG
84601  TCCAGGGGTG GGAGGGGAAA TAGTTGGGAG TCGGCAGGAT GAGGCTGCAG
84651  TGCGCACTGA CCAGCAACGC AAGGACCAGT GCCACCTTGT GGCCTCCGGT
84701  TAACCAGATT GTCTGAGGCC AAGGAGCTGG GCAGGGTTTG GCCAGGGGTC
84751  ACCCCCTGCC TCCGTGAAGC CTCAGCCTTC ATCAGTTTAA TCATCAGGAA
84801  ACGTGGCTCC CGTTGCCCTC CTGCCACCCT ACGTCCCTCT CCTTCCCGGG
84851  GTGACTGGCA ATGTGGACAG CCGGGAACTG GAGCCCAGCA CTTCAGGAAC
84901  CTTAAAGGTC CTGGGTGTAG GGGCTGGAAG GTGGGAGACA CCACCGGTTC
84951  CTGTAGATCC TGGATTACTT AAAGTGGCCA GGAAGGAATG GGTTTGGTTC
85001  AGAATGCTGC GTGAGCTTGA ACGAGATGCT CAACCTCTTT GGTCCTCGAT
85051  TTGTCTAGAG TCTCTGACCT AGTGATCTCG TGACTTGCAG GCCACCCCCT
85101  CCTTTTCCTC ATGTGACCTT TGCTGGGCTT CCCTTAGTGA CCCTGTATGC
85151  ACACAGTTCC CCAAGTTTCT CTTCTGTCCA GGCCAGGCAG TTCCTACAAG
85201  CACAATTAAG TGGAGGCAGC ATGAGGGATG AAGAACCCAG GACAATTAAT
85251  CATCAAGGAG TGACATTTGG TGCAAACNTC AGGTGCTTAA TTAAGCGGGA
85301  TGAGCCAGAG GCTGGGGGGT AGAGGAGGTG GGTTGTGTGG TGGGACAGAG
85351  AGAAACTCAT TCTTCCCATA CCAACCTCCC CTGCCTTGGT TCCCACCACC
85401  CCTCTGCCAC TGTCATACCC TGCCACTCAC ACCTGCCCCC TGTTCAAAGC
85451  TCACACCTCC ACAGGTATTT GGGAAGGTTC CAGCATAGTG GTTAGACCTA
85501  GCCCTGGTGC CACCTACCTG GGTTCAAATC CTGGCTCTAC CGCTTATTCA
85551  CTGTGTAACC CTGGGCAAGT GAATTAGCCT CTTGGTGCCA TAGCTTCTCC
85601  ATCTGAAAAT GAAGATATCT AATTCATAGA ATTGCTGGGA ATTCTGAGTT
85651  CATCTATGTG AGTTGCTTGG GCTGTGCACG GACATAGGA AATGGCCAAT
85701  AAACTTTAGT TATGATGATT ACCTCCTGTG CTTAGCACTA AAAGCTGATC
85751  AACAATTGTT TTCTGAGGAT GGTGACAGGG AGGGTTCTTC TCTCTCCACC
85801  CTAGTTCTCC TTGGGAAGAT CAGAGAGGTC AGGTCATGTG CCTAAGGTCA
85851  GATTGTAGCA GGCAGCCTAG CTTTGAGCCC CTGCATTCAC TTCCTCTGCT
85901  CTCCCACTGC CTGGAAGATC TGCACTGGGC CCCACCCGAG CCTTTACCAG
85951  CAAGGGGCAC CAGAGGCCAA ACTGTGGCTG CCTGTTTCTC CACATAGGGT
86001  CCAGGGTCCC CTACTTTTTT ACTTGTGCTG TCATCGTGTC CAACCTGAGG
86051  CAGGTCAGCT TGCCCAGATC CTTGCACATG TGCAGGGTCC AAACTGTCCT
86101  GTGTTCCCAG GCCAGGCCTC GTTCCTCCCT GAGTCGGGGG CTCTCAAGGT
86151  GGCATCATGT CCTCTTTTCA GGGAGGCTAT CATCTCCCAG AAGCGGCTGG
86201  GCTGCAATGG GCTGGGCTTC TCAGACCTGC CAGGGGAAGC CCTTGGCCAG
86251  GCTGGTGGCT CCACTGGCTC CTGATACCCA AGGTAAGGGC TAGGGGCTGG
86301  GCAGGGGCAG GGGCAGGGAG GGACTGTGGC CCCTGCACTC CAGGTCATGT
86351  GTGTCTTCTA TTCCTCTTCA TCTCTGGCTC CTTNNNNNNN NNNNNNNNNN
86401  NNNNNNNNNN NNNNNNNNNN NNNNNNNNNN NNNNNNNNNN NNNNNNNNNN
86451  NNNNNNNNNN NNNNNNNNNN NNNNNNNNNN NNNNNNNNNN NNNNNNNNNN
86501  NNNNNNNNNN NNNNNNNNNN NNNNNNNNNN NNNNNNNNNN NNNNNNNNNN
86551  NNNNNNNNNN NNNNNNNNNN NNNNNNNNNN NNNNNNNNNN NNNNNNNNNN
86601  NNNNNNNNNN NNNNNNNNNN NNNNNNNNNN NNNNNNNNNN NNNNNNNNNN
86651  NNNNNNNNNN NNNNNNNNNN NNNNNNNNNN NNNNNNNNNN NNNNNNNNNN
86701  NNNNNNNNNN NNNNNNNNNN NNNNNNNNNN NNNNNNNNNN NNNNNNNNNN
86751  NNNNNNNNNN NNNNNNNNNN NNNNNNNNNN NNNNNNNNNN NNNNNNNNNN
86801  NNNNNNNNNN NNNNNNNNNN NNNNNNNNNN NNNNNNNNNN NNNNNNNNNN
86851  NNNNNNNNNN NNNNNNNNNN NNNNNNNNNN NNNNNNNNNN NNNNNNNNNN
86901  NNNNNNNNNN NNNNNNNNNN NNNNNNNNNN NNNNNNNNNN NNNNNNNNNN
86951  NNNNNNNNNN NNNNNNNNNN NNNNNNNNNN NNNNNNNNNN NNNNNNNNNN
```

FIGURE 3-30

```
87001 NNNNNNNNNN NNNNNNNNNN NNNNNNNNNN NNNNNNNNNN NNNNNNNNNN
87051 NNNNNNNNNN NNNNNNNNNN NNNNNNNNNN NNNNNNNNNN NNNNNNNNNN
87101 NNNNNNNNNN NNNNNNNNNN NNNNNNNNNN NNNNNNNNNN NNNNNNNNNN
87151 NNNNNNNNNN NNNNNNNNNN NNNNNNNNNN NNNNNNNNNN NNNNNNNNNN
87201 NNNNNNNNNN NNNNNNNNNN NNNNNNNNNN NNNNNNNNNN NNNNNNNNNN
87251 NNNNNNNNNN NNNNNNNNNN NNNNNNNNNN NNNNNNNNNN NNNNNNNNNN
87301 NNNNNNNNNN NNNNNNNNNN NNNNNNNNNN NNNNNNNNNN NNNNNNNNNN
87351 NNNNNNNNNN NNNNNNNNNN NNNNNNNNNN NNNNNNNNNN NNNNNNNNNN
87401 NNNNNNNNNN NNNNNNNNNN NNNNNNNNNN NNNNNNNNNN NNNNNNNNNN
87451 NNNNNNNNNN NNNNNNNNNN NNNNNNNNNN NNNNNNNNNN NNNNNNNNNN
87501 NNNNNNNNNN NNNNNNNNNN NNNNNNNNNN NNNNNNNNNN NNNNNNNNNN
87551 NNNNNNNNNN NNNNNNNNNN NNNNNNNNNN NNNNNNNNNN NNNNNNNNNN
87601 NNNNNNNNNN NNNNNNNNNN NNNNNNNNNN NNNNNNNNNN NNNNNNNNNN
87651 NNNNNNNNNN NNNNNNNNNN NNNNNNNNNN NNNNNNNNNN NNNNNNNNNN
87701 NNNNNNNNNN NNNNNNNNNN NNNNNNNNNN NNNNNNNNNN NNNNNNNNNN
87751 NNNNNNNNNN NNNNNNNNNN NNNNNNNNNN NNNNNNNNNN NNNNNNNNNN
87801 NNNNNNNNNN NNNNNNNNNN NNNNNNNNNN NNNNNNNNNN NNNNNNNNNN
87851 NNNNNNNNNN NNNNNNNNNN NNNNNNNNNN NNNNNNNNNN NNNNNNTCTG
87901 CCCCACCTCG AATAGGTAGG ATGAAGCCAT TGGCCCAGTC AGCAGCTTTC
87951 TGAGGGGTGT GCAAGCCCCT GCTGGACTCT CAGCCCCCAT AAGGTTAGAA
88001 GGCCCAGCCT TTGGCGTACG CAGCACTAAC CTTGGTTTCT CTTTGGGATC
88051 CTCCAGATGG GGTGGGGATA ATGTCCAGGA GGGCATGAAC CAAGTGAGGT
88101 GTGAAGAGAG ATGCTGCGGA GGGACAGATG GACATAAGGG CCTGACCAAT
88151 AGAGATAGTG TGGAAAACTA GCCAGAGATT TGGAGTGGCT GGAGCTGGGG
88201 GCCTTGAGGA GAGAAAGGCC ATGGTCAGGC CAGCCAGACC CAGGGCTGAG
88251 GCTGGGCGGA AGACAGGCAG CTAGGGGGGC TTTCTGGAGT GGCTGAGGAA
88301 GGAGTGTTAG TGGGAAGTGG TGGATGCTCT GCCAGAGCCC CAGAACCCAG
88351 ACAAGCCTCC CTCTGCAGCC CCTCGAGGAG TTCCCAGGGT TTCTGCTCCG
88401 TGGAGGGGAT TGTGGAAGTG CAGAGCCTGT GGGGACGGGA TTCTGCCGCT
88451 CTTTCCGTTT CTTCTCCTGT ATGGAGGTGG GGGTTCAAAC TCGTTCTATC
88501 CTAGTAACCA AAGGATGAGT TCCCCAAATT GCTATTATTG GGGGTCTGCT
88551 TCTGTCGAGG GGGCTGCCAT TCCAGTAAAG GGCAGGCTTG GGGGCATGGA
88601 CAGATAAATG AGCAGGTGTT GGTTCCCCGG GGACTCCTCT CCAGCTCATT
88651 AAAATGGAAT TAAACGCTTC CCAGGCGCCT GACCTTTCTG AGCTGCTGGC
88701 AGGAGAGGGC AGTGGGAGTC AGGGATGGCT GAGAGGGGAG GAGAGGGGGG
88751 AGGGGAGGGA GGGGTACTTG GCTGGGTCTC CTCTGCACCC ATCTTCCTGA
88801 CTGAGGGAGC CAAGGCCGCT GCTTGGTTTC TCCGCAAGCT GCTCCCCCCA
88851 CCCCCGGTTT CTGGAACGGA GCTGCTGTTG CACGGAGTTC TCAGGGGGTC
88901 GCCTCCCCCT ATTCTTTGCT CTTGGTCTGC CCCAGGGCTG GTCAGCTTTG
88951 AGGGGCACTG AGGTGAGGGG CTGTGTGCAG AGGTGGGGAT TGGGAGGTGG
89001 TGGCTGGGTC ACGCACCTCC TTCTCTGCTG AGGGCAAAGG GCCTGGGGTG
89051 CCAGGTGCCT GAGAAGGACT TCCTTAGATT GAGGCTATGA GGACTGGGTC
89101 AGGAGGGAAG TAAGGGGAAG ACATTTGGAA GGTTGCTTCC CTTGTGGGCG
89151 GAATGCTTGC CATGGCCGCT GCTCACCTTG GCTCAGGCTG GCCAGAGGC
89201 CAATGTGTGT GTGTGTGTGT GTGTGTGTGT GTCTCAGGGA CGCTGGTGGG
89251 ATCAGATCAC TTACACTTAA CTCACCCAGT AGAACTCTGG TCTGGTCCTG
89301 CGGCAGGCTG GGTGCTGGAG CCGACTCTGC CTTCAGGGAG CTCTCAGTCT
89351 GGGGGAAGGC AGGGACACCC TCCCCACCAC AGGCCAGATG AAATACTGTT
89401 GCCAGCAGGT GTTCTGGTGG CAAAGCCTGG AGCAGCAAGT GGTACCTCAT
89451 CACAGAGAAA GCATTTGTGT GGGGCCTTGG GGCACAGGTA GGAGGTCCAC
89501 AGGCAGGGAA GAAGGGAAAG GGATTCTAG GCAGAGGAGG AATGTGAGCA
89551 AGGCAGGAAG GAGGCCGGGG GAAGGGGTGG TGTGCTGAGG GGAGAGTGTG
89601 GTCCTGGGGA AGCTGAAGTA GGGGTGCATG CTGTTGAGCA GGATGCTAGC
89651 CAGCTGGGCT CTGGCTGCCA GGAGTTTTCA ACAACCGTCC CTTCACCTCC
89701 TCAAATACCC TGGGCAGGGA AGAACTCTTG AAAGGTGTTT AGATTATTCA
89751 CATCTGCCTC TCCTCTAAGC CTGCACCTTC CCACTCATGT GTAAATGCAC
89801 TTCCCTAGGA TGCCCCCTCC CCAAGGCATA CATGTCTGAC AGATGCACCC
89851 TGGCTCACAG GATCTCACTG CCTCCCAGAG GTAGCACAGG CAGCCCCAGA
```

FIGURE 3-31

| | |
|---|---|
| 89901 | CTTCCCAGCT GCTGCCAGAT CCTGAGGGCA GAGGGTGCAG AAGGAAGATG |
| 89951 | GAGAGCCACA GGGTCGGTTG ATCTTTTGGG AAGGCCGAGT CACCAGCTCC |
| 90001 | TTCCTGGACA AGCCCCATTC CCCTCTCTCA GTCTCTGCTC TTAGTATTCA |
| 90051 | TCCACTGATC CACCTACCCA TCCACCCCCT CATCCATCAG TTGAACAACT |
| 90101 | ATTTCTTGAG TACCCACTGT ATGTCAGGCA TGGAGTGCTA GGTGCTGGGA |
| 90151 | ACACAGAAGT GACCAAGACA GATTAGACAG GCCCTGCCTT CACAGACCAT |
| 90201 | ATGGTCTGGA GGGTTGGTGG TGAGAAGCAC TAAAGTGAGC ATAACCCCAG |
| 90251 | CTACTTGGGA GTATTCCTTG AGCTCAGGAG TTTGAATCTG GCCTGGAGAA |
| 90301 | TAGAGTGCGA CTCCATCTCT AAAGACAATA AAAATAACAA AAATACTGCA |
| 90351 | AAACAAGTGA GCAAAATAAG GATAGGATCA CACGTGATGG CAAGTGCTAG |
| 90401 | CAAGGAAACC CCTCGAGGGA GTCCTGCAAA GGAATGCTGG GGTCCAGTGG |
| 90451 | CGACGCCATC AGCGAGGGCT CTCTGAGGAA TATGCTGGCC AGGTGCAGGG |
| 90501 | CTGTGTGGCT GACTTCTGGG CCTTTACAGC TCACTGCTCA AAGCACCTTG |
| 90551 | ATTGCAAATT TTTTGTGTGG AAAGTCTTTG GCTCTGTTCC TTAATCCTGG |
| 90601 | GATAATAAGT CCCTTTGAGG AGTGGCAGCC CTTGGTCTCT GGCATTTGAT |
| 90651 | GCCTGATTTG TGCCCACTCT TCCCCCAGCT GCACCAGCCA CACCAGCTCC |
| 90701 | CTGCACGGGG ATGGGGTGTT CATGCCATTA ACCATTTTGA ACTTGGTTAG |
| 90751 | GGTGGGGACC TGGGGGCTGT GCTGGGTTTT AACCCTCTCT TACAGCCACA |
| 90801 | GTGCCCAATG TTGAGTGTTC CCACTGGGTC CCAGACACTT GCCCTGATTA |
| 90851 | GCAAGAGCAG GTGTAAGTGT GTGTTCCTGT TGGCGAACAA AAAGCCATGA |
| 90901 | GTGTGTGGGG GTGATTGTGT GTGTTTGTGT ATGGGGCGC CAGGTGCATG |
| 90951 | TGCATGGCTT TTGGGTAAGT GAACTATTTC CTGTGTACAG GCATGAATGT |
| 91001 | GCCTGTGGGG ATGCTGTGGA CACTGTAAGG GTGGGTGTGT GGATGTCTTT |
| 91051 | GTGTCTGTGA CTGCACCGTG TGTGTGTGTG TGTGTGTGTG TGTACCACCT |
| 91101 | CCATGGGAGA TTGAGTGTAA GTGCATGTGT GTGAGGGCCT GACGTTCTTC |
| 91151 | ATGAGAGTGT AGGTGTGTGT GTTTGTGCAC ATGCTGGGTG CAAGTAGGCC |
| 91201 | AAGGCAGCCC GAGAACTGGT TGCCCCCACA GCCTTAGAGG GGTCCCAGCC |
| 91251 | TTCTCTATTC TTGAGAGATG GGACCAGGTG GAAGGAACAA GAACCACGTC |
| 91301 | CTCCTCCATG TGCTAACAGT AAAATGCCAA CATATTTATA TAAGCCATAT |
| 91351 | GCAAATGAAC CATAGCCCCA GCTTCTCCTC CCTCCCGCCC CCGCTGTCCT |
| 91401 | GTAGGAGTCA CAGATTGAGC CTCATCCAGA GCTTAAGTTT AAACACCATC |
| 91451 | CTTGACAGCC CAGGTCTCTT CCAGGTCTTC CTGCCTCCAA TCTCCCTCCC |
| 91501 | TCAAATTCAC CCTACACCCC ACAGACAGTG GCCCTCAGAT GCTAAAGTCT |
| 91551 | GCCATGGCTC CCCAGTACTC TCAGGCTAAA GTCTAACTTC TTAGCCTGGC |
| 91601 | ACTCAAGGCC CTTCCTTCTG TGGTACCATG GACCACACCC CTACCTGGAT |
| 91651 | CCTCATCTCC CCGCACCACC TACCGCCAGT GTCCTGGTCT CTTCAAGGTC |
| 91701 | TACTTGTCCT CCCCATGCCA ATTCAGGAAG CCTTCCAAAT GTCCTCCCCT |
| 91751 | CTGAGCTACC CACCTAGTTT TCTCTCTCCT TCCTCAGGTA TGAGGCTCCA |
| 91801 | CACCTCCTCC CAGTCATGTC TCCCCACTCG TCCCACCCCA GACAGACTGT |
| 91851 | GAGCTTCCCG AGAACCTGCT GGTCTCCTCC TCCCCATCTG CTCCTGGCAG |
| 91901 | GAGACCCAGA GCTGAGGCAG GCATTGGCTG CTGACTGGGG AGGGAGGAGG |
| 91951 | AAGGAGGAGC CCCCAGTGCA GGCGCTGTGG GGAGCTCTGC AGGTGGTGAG |
| 92001 | CAGCTTTGAG TAAGCTCCGG AAGCTAGTGA CGCAGGTGGG GAGCCTTGCT |
| 92051 | GGCAGGGCCT GTAGTGGGTC CCTAGGCTGC CACCCTCCCT CCCCACCGTC |
| 92101 | TCTCATTTTC CTCGACAAGC ACCCAAGTAG GAGTGGGGGA AGGGACTTCA |
| 92151 | CAGAGTATGA AAGATGGGCT GAGTTCCCTG GTGACTGGCA CAGGGAGCTT |
| 92201 | GGAGAGGGAC AGGATGATGG GGGTGGTGGA GAGAGTGGAT CTAGAGGGGG |
| 92251 | GAAGGTGTGG GCAGAGAACG GGAGGGAGTG GGTGGTGCTG TCTTCACTCT |
| 92301 | GCCACTTTCT GCTATGTGAT TTTGGGCAAG TCACTCCACT TTTCTGGCCA |
| 92351 | TGGCTTGCCT GCCAGGTGGA GGCTTGCATC ACAGTGGTGA GAATCACATG |
| 92401 | TAAGGCAAAG CACTTCACGA ACCCATTTAT CCATTTATTC ATTCACCCGT |
| 92451 | CCATCCTCAC CATGGCAGGT GCATCATACT GAGCCCATTC CTTTATCCAA |
| 92501 | GACTTAGGGG CAGCTCAAAC CCTAACTCAG ACAGGATAGA GCCGGGAGGC |
| 92551 | TGAGGCTAAT ACCACCAATT CTAAAATCAG GACCTGCAGC GCTCCATAAT |
| 92601 | CTGTGAGCTA AAAAGGGGTC TAAGGTCCCT CCATCCCCTG AACCATACAC |
| 92651 | CCGGACTGTG CTCTTGATGA GACAGTGATT GAAAGGCAG AGACAAAAAA |
| 92701 | GTTTCACGTC CTTAGGTTAG TCCTAGGAGA CTTCCTACAG GAGGGATTTT |
| 92751 | CCTGGAGCTG TCTGAGTGGT CAGAAAGATG GGGTTATCAC TGAGGCCCAC |

FIGURE 3-32

```
92801  AGACTGGAGT GTGTATGTGT TGGTGGGGAC CAGTGTGTGC TGCGCATGGG
92851  GAGGGCACTC TGGCAGAGAC AGACACTGAG AGAGGTCACA GCTAGTTCCC
92901  TTCTCCCATC CCTCCAGGTG CACTGTGGCC AGCTGAGTGA TAATGAGGAA
92951  TGGAGCCTGC AGGCGGTGGA GAAGCATGTG AGTGGGAGTG GGGCCATGTG
93001  CAATGAGGCT GAAGACCCTT ATCACAGCTG GTGGGAAGAT GGCCTGGCCA
93051  GGGAGCTGGA CAGACCTGGG TTTCAGCTTC GGCTTTGCTG CTTTTGAGCT
93101  GTGTGACCTT GAGCAAGTCA CTAAACCTCT CTGGGCCTCA GTTTCACACC
93151  TGAAAATGGG GATAATGATA GCACCGACTG ACCTAGGGCA GTGGTGAAAC
93201  AAAACTGGTC AAATATCTTG TAAATACACA CGGTTGCCAA CTTACAATTT
93251  TCGACTTTTT GATGGATTTA TGGGGAAGCA ACCCTATCCT AAGTCCAGGA
93301  GCATCTGTAC TTAGAAAGAA CCCTCCACAT AATGATACTG AGGCTCTTTC
93351  ATGCCTGAGA CTTTATGATT TTGTGACTTT AACAAGGACT TACGACTTCC
93401  TGAGGGGGCT GGAGACAGAA ATCTGACATC TTGTCTTGGA AGAATCTAGG
93451  GGCTAGGGAT GGAGATAGAC CCTGTACCCT CCTGTTCCTG GACCGCCGGA
93501  CGCTCCAGGG GCTGTGGGAG CCCCCGGGGG AGCCCTCAGG AAGGTAGAGT
93551  CCAGGGATGA GGTGTTTGGG ACGGCGGCGG GGTCCCTGGG CCCGGCAGGC
93601  AGAGGGAACG GCGGGAGCAA AGGCAGGAAT CCCGCTGCAG CAAGCGCAGC
93651  GAGCTTGGGG CGAGCGGCGC GCTAACCGCT CGGCCTGCCC CAGACCCTGG
93701  TCGCCCTGCG GAGGGTGCAG GTCCTGCAGC AGCGCGGGCC CAGGGAGGCT
93751  CCCCGAGCCG TCCAGAACCC CCCGGAGGGG ACGGCGGAAG ACCAGAAGGG
93801  CGGGGCGGCG TACACCGACC GCGACCGCAA GATCCTCCAA CTGTGCGGTG
93851  AGGGCCCGGC CTGGACAGGT CACGAGGGCG GGCCGGGCA GAACTTGGAG
93901  GGGAGGTGGG CGGGTTAGGC GATCCCGGGA GCCGGCGGCG GGCCCGGCGC
93951  GGAGCTGAGC GGCGCCTGAG GGACCCGGAC ACGGAGGTGC GGAGGGGCCC
94001  TCTCTCTGAC CGGCGCCTGG CCCTTGCAGG GGAACTCTAC GACCTGGATG
94051  CCTCTTCCCT GCAGCTCAAA GTGCTCCAAT ACGTGAGTCC CTGCGCCCCT
94101  GCCGGCCACC TCCCCGTCCT GTCTCCCTCC GGGGACCAAC TTCCCCTTGA
94151  GCCCTCCATC TCAGTTCCAA TTACGATGTC CTTCCTTCCT CTCTCCTCCA
94201  CCCGCCTGAA GAGCCCCGGA GAGGGGAGCA GGTGGGGAGT GGGGTGACCC
94251  GGATCCGCGG TCACCCCCTC GCCCTGCCTG TCCCTCTCTC AGCTGCAGCA
94301  GGAGACCCGG GCATCCCGCT GCTGCCTCCT GCTGGTGTCG GAGGACAATC
94351  TCCAGCTTTC TTGCAAGGTG AGGGCCCAGG TCCACTGTAG AGCGGGGGCG
94401  GGGCTGGGCG AGGAACTCGG GTCTCCGAGG GGGAAATCCA TTGCCTTTCC
94451  TTTAACCAGC CCCCTGCACT CCGTTCCTCA GGTCATCGGA GACAAAGTGC
94501  TCGGGGAAGA GGTCAGCTTT CCCGTGAGTC CCGCGTCTGT CTTCTCGTTG
94551  GAGTCTGCAG GGGCGGTTGA GGCCGGGTAG ACACTCCTGG GATCTGCCTG
94601  GAGTATTTGG ATCTTCTAGA CTCTTGGAAT CCGATGGAAT TATCTGGATC
94651  TTGGGACTAC TTAGAAATGC TGCAGGGATC ACAACCTGTG ATCAGCAGGC
94701  TCTATTAGGA AGAATCTCTT AGCATCTACA GAAAGGCTTA CCTGGGACCT
94751  GTTCACTTCT GTTGGAGTAT TTCTGGATAT GGATCTGCTA GAATCTGTTG
94801  ACGAGAATCC TTGGAGTCTG CTTATCTCTC TCGTAGTTAG GGAAGACTCT
94851  AGAGTCCTTT ATAGCGAATT CTGCCAGACT CCCCTCCATC TCTGCTCATC
94901  AATGCTGACC CTGTCCACCA TTTGGACTGA CTGAAGGGTT CTTTGAAACT
94951  TCCAGATTTG AGGGTGGGGA CAGGTTGAGA TCCCCTGACC TGGGGAGTAC
95001  TGGGCCCTGA CTCAGTCTCT CCTCACCCCC TAGTTGACAG GATGCCTGGG
95051  CCAGGTGGTG GAAGACAAGA AGTCCATCCA GCTGAAGGAC CTCACCTCCG
95101  TAAGTCATGG CCTGGCTGAC CCAGAGGGGA AAGAGGAGAC CCCACTGCCA
95151  GCCCCTAGAG CCAGGGTCTC TGTTACAGAG CAGCCTAGGA ATGGGGCAGA
95201  TAAGACCTGG GGACTTTCTA CTGTCCCATC TCCATGACAC AGAGCTTCCA
95251  GCCTTGCATG AGTCCCTTAG AACTGCCTGT TGCAAAATGT GATGGAGGGC
95301  TGGAGGAGGG AAGCATACTG CGCCCTGCTT CCCTGCCCTG ACTTGCCTCG
95351  CCTTTGCAGG AGGATGTACA ACAGCTGCAG AGCATGTTGG GCTGTGAGCT
95401  GCAGGCCATG CTCTGTGTCC CTGTCATCAG CCGGGCCACT GACCAGGTGG
95451  TGGCCTTGGC CTGCGCCTTC AACAAGCTAG AAGGAGACTT GTGAGTCTTT
95501  GTGGGATGAT GCAGATCAGG AGATGTCACT GAGAGGCTGG CTAGGGCTCC
95551  ACGAGGGTAA CAATGTGGGA TGGGTACTGG GCAGGGGCTA CTGTCTCAGC
95601  AGCAGTGGGT TGAACAGTGT GTTAGTGCAA GAGAATGAAA GTCATGTTGA
95651  GGTCCAAGCT AGTTCCTCTT CTCTTCTCCT GCTTCCTGAA GTTTGGGTAA
```

FIGURE 3-33

```
95701  TCTGCTCTTG GGGTATTGGG TTCCCTCCCT TGCCATCCCT GTTTTTGCAT
95751  TACTGCTATA AACTGCTAGA TGGAGGGGTG GGTGTGCTCT GGGTTGGATG
95801  AACCCTCTGG GACCCACAAA GCATCATCAA CACAGTGGAC AGTGGCTAAA
95851  GGGAATATGC TTGGGGACTG GGAAAAGCTG TGGATCTTTT GAGCCCCTGA
95901  CAGGGCAGCT ATAAAAATGA TACACAAAAA TCTCTTTTTT TGTGGGCAGG
95951  GCACAGTGGA CAGGAAAGCA GGCTTGGAGG CTTAGTTGGA AAGGATATCT
96001  CGAGAACTGA GGACAAACCT GGGGTCTAGA AATGGTGTCA TAAATAAATT
96051  TCATATCCTA CACCAACTCA TAAACAGGCA GTAGGTGCCT GAATTTTATT
96101  GCAAATGGAT CTTAGTTCAG GGAGAAACAG TGCTGCGTCT GATGAGCCAT
96151  TTCTGTCCTG GGTGCAGGTT CACACTTGGG CTGGCAGGAT GAGCAGTTTG
96201  TGCTGTGTCA CATAGGTGGG GAGAAGTAGA CAGATGAGGG GCTGAGTCCT
96251  GATGCAAAGA GATGCTGATA GGATGCTGGT CTCTGGAGTC CAAGCAAACA
96301  GGCTGGGTTT CAGGGCCTGG AGCTCCTGCA GGAGGTGGAC ACTAGAGAGC
96351  CTGGGACTAG GTAGGTGTCA GAGCCCGGGC CTGAGGTCTG CTGGGGTAGG
96401  GTGGAGATCC AGGAGTCCTA GGTCTGAGCT GCAGAACCTA CCAGCATGGA
96451  ACTGTGTTGA CAGTTGGGTG GGCCTGGAGA AACAAAGATA GGGGCAAGGC
96501  AGAATCAGCT GAGGCAGGGA GAATGTGGGA TTGGTGGCAT TTGGAACTTG
96551  TGGGCATCCT AATGGTGGGA GAATTTATGC CATTCAGCAA ACAAATATTG
96601  AGCACTTAAT GTTGCCATCC CAGTGCTGAC CAGATGGCCT TGGGAAGGCC
96651  TTTGGGGAAG GGAAGGTAGA GTGAATGGGG GTCCAGCAGG GGCCATGACT
96701  TCTTGCTGCT GGCTGTGAGA TTGGGTTCTA GGATGGCCCC AGAGCTGGAG
96751  AAGAGGTGGT ATCAGCAGGA AATAAGGATG GGGCCTTGGT GGCAGCTTTG
96801  AGGCCCAGGG CAGGGGCAGG GCTATCTCTG GGTCCCACGC ATTTCAGGGA
96851  GTGAGTGTTG AATGACTGCA TGAGCCAGGG TGGGGCTCAG CTCAGTGCAG
96901  TGACTACAGA GAAGCTTCCT GAAACACAGC TAAGTAGCCA GAGAACAGGG
96951  GCTCCAGAAG CCCTTCAGCT GTGAGTGGGA TGGGGCTGGT GGCAAGGCCA
97001  GGGATAGGAT ACACTGACGA CATTAGCAAA GACCTCCGAA GTGTTTCCTC
97051  TGTACCAGGC TCTGCACTGG GCATGGGTGA TATAGTCATG GCCCCATTTC
97101  ATAAGACTCA AAGCTCATTT TCAGGGCATA GAGGGAAGAG AGTGAGAAGG
97151  GTATTCTAGG CCGAGGGAAC AGTGTAGAAA AAAAAGCATG AAGGTGTGAA
97201  AGAGCCCAAG GTTTTCTCAG AATGATGAGG ATCTTTGTGT GGCTGAAGCT
97251  GAGAGATGTT CTGGGTTGAG GGGTGACAGG TGGGTGGGGC TAGCTGAGGG
97301  ACCACAAATG TAAGAAAGGT GTGCAGACAG ACCCAGGATG GTGGGGATGG
97351  GATCTAGATC CGAATCACTG GATGGCAAGC ATGAATGGGG GATGCCCCAC
97401  CAGGGTGGAG CACCAAGGCC AGCCAAAAAG TGGGGAAGGG CTTAGGCAGG
97451  GACACCTCAG GGCAGCGTGA TGTGGGCTAA GGCAGGCTCT TCCCATGACC
97501  CACACCATTG GTCCACCCAG CCCCATGCAG CTCCCCAGTG ACAAATCATT
97551  TGGTGGCCAG ATTGAATGAC GTGAGCAGGA TTTGGGGCTT ATCTTGTCTC
97601  ACCAGAGCTA GCTCCATGAG CAGGGCAAGC AGTCCTCTCC ACACCACCAC
97651  CCTAAGATTT CTGGAGGCAC CGAATCAGGG CCAGCGGAGT CCAGGGAGAG
97701  TGGGGTAGTG ACAGGAGCTG CACAAGATAG GGCAGTGCCA CCGCCCCTCC
97751  CCAAGGCTGG AGGTGTGCCT GGGGAAGAGC AGAACACCAG CTTGAGCCCA
97801  GGCAATCTCT AGTCTGAGGG AGGAGACCCA GCTTTGGGCT GGGTAAATCC
97851  CAAATCAGAG ACGGGAGGTA TGGCTCTGGT TTCAAGCATC TAAGGAGGAC
97901  TGGAGCCCTC CCCTTGGGCA GCCCCCAGTC TGCAGGGTCA TGGGGGTGGG
97951  AAGCTGTTCC AAGGGCCTGT GCAGTGGTTA TATAGTTGGC AGGTGGGTAC
98001  CCCTGTGGGC TTCTGATGGA ACAGAAGTAA GGAGAGTGGG GAGAGAAGCC
98051  AGTCTTCCCT TCCCTCCTGA GTGAGCCCAC CCCCTCCTCC AGGTTCACCG
98101  ACGAGGACGA GCATGTGATC CAGCACTGCT TCCACTACAC CAGCACCGTG
98151  CTCACCAGCA CCCTGGCCTT CCAGAAGGAA CAGAAACTCA AGTGTGAGTG
98201  CCAGGTGAGT GACCTGCCTT CAGCCTCTCT CGGGCACCGA CTCGCTCAGT
98251  TTTCAGCCCC GAGAGCCATT CAGAAGGGAA ATGCCCATGT CTTTCTGGAC
98301  TGGTGGCAGC CCTTCCCCAG GTGGCTCCAT AACCTCATAA CTTGAAGGCT
98351  TGCAGTTGTT CAGGACCCGC GCCACTGCCC GCAGGCACTG TATGTGATCG
98401  CCCTCTAGTG TTCAATATGT GCACTACAGC AACACCTAGG CAGCTAGAGC
98451  TGGCGTGAAG GCGGCTGAGA CACTCAGGAG ACTCCTCACC TGCACCGGGG
98501  CTATTCCCTC ACTCCTTCAC TTAGTAGCCA AATGATATAA TTAGACACTG
98551  ACAGTTTCTG GCTTGTCCAG TGAGCCCTAG GGAAGGAAGG AGAAGACCCG
```

FIGURE 3-34

```
98601  GGTGCTGTTG GAGGCAGAAG GTTGGATAGG GTGACCCCTA CACCCCGACC
98651  CCCCTATGAT CTCCATTTCC TTCATTCCAG GCTCTTCTCC AAGTGGCAAA
98701  GAACCTCTTC ACCCACCTGG GTGAGTGCAC TGTTCTCTCT GCCTGGCTGT
98751  GTGTGGGCAT GGGGGCTGGC ATTTGCAGAG GAGAGGCGGG AGGTCTTGGC
98801  AGCCTGGTCT CACCCTGCCT GGTCTTCTCC CTTCCCCAGA TGACGTCTCT
98851  GTCCTGCTCC AGGAGATCAT CACGGAGGCC AGAAACCTCA GCAACGCAGA
98901  GATGTGAGTG ACTCTACCCA GGGGACAGGG CGAGAGAGGC TGTGGCCTTC
98951  AGTCCCCATC ATCTCCTTTC CTGCCCCACC CACTTCCCTT TCTCTGCCTT
99001  CTGCGGGACT TCATCACCTT TTGAGGGATC CTTTATTTCA TGCCTGTCTC
99051  CCTCGCTAGA CTGTAGGCTC CAATACAGCA GGGACAGGGC TGGCTTTGGA
99101  TCCTCAGCTC CTATCACAGT GCCTGGCACA TAGTAGGTGC TTCCAAAAAA
99151  AAAAAAAACA AAACACTTGA ATGGACACGT TTCTGGAGCC AGCCAGCCCT
99201  GAGCAGAGTG TCTTACCTTG GAGCACTCCT CCCAGGCCTC GGAAATCCGG
99251  CCTTTGCCTC CTTATGGGAC GTGAGGGCGA TCAGAGGGGG TTGTCAGGCC
99301  CCAGAGGACC AAACCCCTCC CTCCACAGCT GCTCTGTGTT CCTGCTGGAT
99351  CAGAATGAGC TGGTGGCCAA GGTGTTCGAC GGGGGCGTGG TGGATGATGA
99401  GGTGAGAGGG CGTGGAGGGA GTATGTGGCC CTAGGGGTGT CCGGGAGTCC
99451  GCCGGCGGCG CTGGGGAGCG GCCCGAGGTT TAACAGTCCC CTCTGTGGCC
99501  GGGTCACTAA CTTCTTCCTC TCGACTCCAT CTCTGCTCCG GCAGAGCTAT
99551  GAGATCCGCA TCCCGGCCGA TCAGGGCATC GCGGGACACG TGGCGACCAC
99601  GGGCCAGATC CTGAACATCC CTGACGCATA TGCCCATCCG CTTTTCTACC
99651  GCGGCGTGGA CGACAGCACC GGCTTCCGCA CGCGCAACAT CCTCTGCTTC
99701  CCCATCAAGA ACGAGAACCA GGGTGCGCGT GGCGGCCCGG GCGGAGGGGC
99751  GGGGCCTGCG CCGGGCGGGG CGGGTCCGAG CGAGCGGGGG TGGCAACACT
99801  TCCCCACCGC CTCCGGCGTC CCGGAGCATA AGGGAGTCGG GTTCCATGCC
99851  TGGGACGTAC GTAACCTGCG GAAACTGCGA GGGCAGGTCC CGGCCGGATC
99901  CCTCCCTCCA ACCGATCCCT CCCTCCACCG GTGGTTCCTT GCCCCTCTCC
99951  CTTCCCCAGA GGTCATCGGT GTGGCCGAGC TGGTGAACAA GATCAATGGG
100001 CCATGGTTCA GCAAGTTCGA CGAGGACCTG GCGACGGCCT TCTCCATCTA
100051 CTGCGGCATC AGCATCGCCC ATGTGAGGGC GGGGTTGGGA GTGGGGTGTG
100101 GGGTGATAGG GGGCGGGGCC CACGAAGGAC CCTCGGTTCT CCTCCTCCGA
100151 CTGACTCTCC TTGTGGATTG ATCCCTTGGT CTGGCACTCA GAGTCCCGCC
100201 GCTGGGGTGC AGCCTTCAGG ACACGCTGGC CACCTCTGGG CTCAGTTTCC
100251 CATCTAAAAA TTGGGCATAC GATTTCCTGC CCTGTCCACT CAGCCTCCTG
100301 GGACCATGAG AAACTCCCGT TGTCAAAACC TCCTCTCTTC CCTGGAAGCA
100351 GTCTCAACCC AAGCCGAGTG CTTTTTTGGA AGTGCTGGGT CTCGGTGTCC
100401 AGGCCTACTG GCGCTCTGGC CTGGGAATCC AGCCCCAAGG TCCCTGACAT
100451 GATCCCCTCC TTGCTTCTCC TTCCCTGCCA TGGGCCTTGG GCTCCATCAC
100501 TGAAGCCTGG ATCAGGTGTG GGGGAGTGCA AAGGGCCAGA CCAAATGCTG
100551 GGAGAACTTG ATGAGGAGGA ACCGGCGCGG GGGTCTGGAT GAAAGTGGGG
100601 GTGAGGTCTT TACTGTGGAC TGGAGCTTGA AGGTTTTGAC TGGGGCCAGA
100651 ATGGGACAGG AAGTGGGGTG TCTTTTTGAC CCCTTCATCC CAGTCCTGGG
100701 CATTGCTAAA TTTTCACAGC CACCTTCCTT GAGCCCCATC TTTCCCTCTT
100751 TCCCCTAGTC TCTCCTATAC AAAAAAGTGA ATGAGGCTCA GTATCGCAGC
100801 CACCTGGCCA ATGAGATGAT GATGTACCAC ATGAAGGTGA GGCTTGCAGA
100851 GACCTCTGGT CCTCCTCCCA GATTCCCCGG GGACCCAGGG CCAGGCAGGG
100901 CTTCCTGATC AATCTCTACT GAGGATGAGA GGATAGGCCC AGAGCCACAG
100951 CAGGCCTCCT GCCCTCCTTA GGGGCAGCTC CCACCCCTGC TTAGAGACCT
101001 CTCCTCCAAG CTGCTTCTGA GCTCAGTCCC AAGGCTGGAA GTAGCCAGAG
101051 GAACCAGCCC AGGGAGTAAT TGGTTCAGCC AGGTATTCCC CATGTTCAGG
101101 GAATAATTCC CATCTTGGGA ATTACTGAGG GCTAGGAAGC TCACCCAGGA
101151 CCCGTCCCCA TGGCTTCCCT AGGTACAATG CCCATGCAGC CCTGGGCAGT
101201 CTTAATTGCT GATAATCTAT CCCATTCCCT ACCCTGGGTC ACAAAAGCTG
101251 GCTTAGTTCC ATGTATATGG TAGTCGCTGT TCATTTGGAC ATTTCCTCTC
101301 ACCTGTGTCC AAACCAGAGA GGCCCAGACC TTGTGAGTTG GATCAAAACT
101351 GTAGTAGGAA GAGTTAAGGT TAGAGAGTAG AAAGGTCTCC ACAAAAGGAG
101401 GACTGCTACA GTTACTGTGT ATGAAATGCT GCCATGGTTT GGGGGTGTCA
101451 TGAAGGGGTG TTGTCGATCT TTGCCAAGGT TATGCTGTTA CAGATAAAGG
```

FIGURE 3-35

```
101501  GTGGTCACCT GCAGGAAGGC GCGCGGGGTG GGCTGCAGGG CTGTGAGGGG
101551  AGGGTGGTGA TTTCCTGCCC AGTTACAGTC CACAGCGTGG TGGCCCAACT
101601  GTGGTACATT CTGGGTGACG GATCCCCCAC CTGCCATGGG AATTTGAGGG
101651  TGAAGACACC AGATGGGGTG AAGGCTGTCT TCTAATGCTC TGGCTGGTCT
101701  CCTCTAGGTC TCCGACGATG AGTATACCAA ACTTCTCCAT GATGGGATCC
101751  AGCCTGTGGC TGCCATTGAC TCCAATTTTG CAAGTTTCAC CTATACCCCT
101801  CGTTCCCTGC CCGAGGATGA CACGTCCATG GTGAGTTGCT CTCCTCCACT
101851  TGACTGGCCA GGCCGAAGGT ATGTAGCCAG AGGCTTAAGT TAAATGCGCA
101901  TCAAGAACTT CCTGGGAAGA CAGAGTCATC AAGGAAGGCT GTGGAGGGTC
101951  CCTCAGAGAT GGAGGGGCTT GTAGTCTGCC ATCAGGAAGC CATGGGGCCT
102001  GCCCAGGGGC TAGAGGCTGG ACTGGATGAT CCCAAGGGCT GCTCTTGGAC
102051  CAACCATGCC CAGGGCATGT GACCTCAGGG TTTGCATCCC TCCCAACCCT
102101  GTTTTTCTAA CATTTTGTGT GGGCTTGGTT TCAAGAGTTC TTAGTTCTTA
102151  GATCTCTAAA AATGCATAGC TCTGAGAACG GTTGCTTCAA CTATTTTGTG
102201  GTTCTCTAGT TTAGATGTAA GTTTCTAAGA CTCCAGATCT TGAGTGTGGA
102251  GCTTGAAGAA GGACCCAGGC AAGGGCCCTG TCTTGATACT GGCAGCCCCT
102301  CTGATACCTC CCTCTGCCCT CTCCAGGCCA TCCTGAGCAT GCTGCAGGAC
102351  ATGAATTTCA TCAACAACTA CAAAATTGAC TGCCCGACCC TGGCCCGGTT
102401  CGTGCGCCCA CAGACAGCCC CAGTCTTCGC CTCCCTCTTT CCTCTACTGT
102451  CACATCCATT GCCCCCGGCA TTCTGGAGAG GATCTCTCTA AGGATGACTG
102501  GGGAGACCCA GTCTTATGGG GGTGGGGAGG ATCCATGAAT GAGAAGCAAT
102551  TCCTAGACAC TGAACTGTCA ATAAAGGCAA GAAATGAGGC AAGGCAAAGC
102601  CTGGAGGCAA GGCCGAGAGT GTGTAGCCAG AGGTTTAAGT TAGATGTGCA
102651  TAGGAACTTC CTGCTAAGAC AGAGTCATCA AGGAAGGCTG TGGAGGGTCC
102701  CTCAGGGATG GAGGGGACAT GTAGTTTGCC ATCATGGGGC CGTGATGGAG
102751  GAGGAGAGGC TGAGGCCCCT CTTCTGCCCT CTTCCCTCCC CCAGGTTCTG
102801  TTTGATGGTG AAGAAGGGCT ACCGGGATCC CCCCTACCAC AACTGGATGC
102851  ACGCCTTTTC TGTCTCCCAC TTCTGCTACC TGCTCTACAA GAACCTGGAG
102901  CTCACCAACT ACCTCGAGTG AGTGGCTGCA TCTCCCCCAC ATCTGGCAGC
102951  CACTGGGGTC CCCTTCCCTG GACAGGGAA GCACCCCCTG TGTGTCAGGC
103001  ACTTTACACG CACTGCCTCA TGGGATCTTC TTAGCCCCAG GGGACTAGAG
103051  GGGAAGGCTG TGAGCCCCAT CTTCCAGGAG GGGCTTGCTC ACAGCCAAGC
103101  AGCTAGTGAA GACTGAGCCT GATTTAAACC CGGGTCTGCT GGACTCCAAA
103151  CCAGTGCTTC TTTCCAGGAA GGGAACCCAG GTGTTCCAAC CTCCTGTCCC
103201  AGTGGCTCCT GGGCATGTCA TCTCCTGTCT GTCCTCTTGG GGATTTAGGG
103251  AGGGAACTGT GGGCTGACCT CTTTTTTTTC TCCTTTCTGC CTCTCAACCA
103301  GGGACATCGA GATCTTTGCC TTGTTTATTT CCTGCATGTG TCATGACCTG
103351  GACCACAGAG GCACAAACAA CTCTTTCCAG GTGGCCTCGG TGAGACCCTG
103401  CCCTGCTCAC AGTGGGACC CTCCATGGGG TGTCTTGGAT CTCATCCTCT
103451  CCCAGCCTGA ATAGGGTGGG AGCGAGTGAG ACCAGGAGCC AGGTTTAGAC
103501  ACAGGAGGAG GTTCCCCCAG GGTTTGCCCC TGGCTCTGAG ATAGGGAGGA
103551  GGGGAGAAAG GTGGAAGGGC AGGACACTGC TCAGCCTAAA GCAGTGGCAC
103601  TTGGATCCGG ATGTGAGGAG TGACCACAGT TTTCCTGGGC TTTTCCAGAA
103651  ATCTGTGCTG GCTGCGCTCT ACAGCTCTGA GGGCTCCGTC ATGGAGGTAT
103701  CACTCTTCTG TCCCACCCCG TCCTTCTTCC CCTTTAAGGC CAGTGACTTG
103751  CAAAGTTATG ACCCAGCTCC TCCTATTCCC AAACCATGCT CTCCAGACAG
103801  GCTGCGAGAG CTGCAGCCAC ACCTAGGACA TGTCTGGCTC ATTTTCCTGG
103851  AGTGGGCTTG GAAGGGTGCA GGTGCGGATG ATAGCAAGGA TTTGTGTTCA
103901  GCGTGTTTCC CTTTGGCTGC CTGGGAACAC CCCATTCAGC CCCCTCCTGC
103951  CAAACTTGGG ATGGGCTCCA CTCCCATCAC TTAGCGTCAC CTTAGATTGT
104001  TTGGTTTGGG TCTGCCTACC TCCTCGTGCA CAAGGTCTGA GCCATTTCTG
104051  AGTTCCCTGC ACTTGGCACA GGGCTTGGCA CAGAGTAGGA GACACATTTC
104101  CAAGGTCACC TTGCCTCATG CTACTTCCCA CAACACCTCT CCAGAGGCTG
104151  CCCCTGCTTG CACACCCCCA GAGACGAGGT TCTCTGTCTC TCTCCCAGGA
104201  GGCCTGGTGG CAGTGCTGGT TCTGCCCTCT GCCCCCCTGA GATAAGCTGC
104251  TCCTTTTCTG AGTGACAGCC CTTCAGCATC CGGAAATGGG GGCCTTGCCC
104301  TTGCCTCATC ACTGCCTCTC CTTGTCAGCA AACAAATGTG TTCTGCATGA
104351  TTTGGTGTCT AGGACTCCAA AGGATCATTT CAAAAATGTT CCAGCTTTCA
```

FIGURE 3-36

```
104401  GGGACCCCAG AGCTTACCTT GTTGGGTCCC TGCATGTGAC AGCTGAGGAG
104451  TCTGAGGCTC AGAGTGGTCT AGGGACTCAC CCTGGGTCAC ACAGAGGGTT
104501  GAAACAGAGC TCAGAAAGGG AACTGGGGCC CCTGACTCCC CCTTTCTGAC
104551  TGCTCTGCTT ACCTGGGGGC TGGAGCTGGA CGAGGCCCCT GCTTCCTCTC
104601  TTGGGGTCAA TGGTAAGGGA GCCCATCTGC CCCAGCTGGG CCCCCATCAC
104651  TCCTCTCCCC CCAGAGGCAC CACTTTGCTC AGGCCATCGC CATCCTCAAC
104701  ACCCACGGCT GCAACATCTT TGATCATTTC TCCCGGAAGG TGATGGGGTT
104751  GGGGGTGGGG TGGGGATTGA GGGGAGCTG GGAGCTGGCT GGAGGTGGGA
104801  TAAGGAGCCA AGGAGTGGAG GCTCACTGGG ATGGGCAAAT GGGTGGGGGT
104851  GTCCAGTAGG AGGGCATGAC ACCCCTGCCC TCGCCTCAGG ACTATCAGCG
104901  CATGCTGGAT CTGATGCGGG ACATCATCTT GGCCACAGAC CTGGCCCACC
104951  ATCTCCGCAT CTTCAAGGAC CTCCAGAAGA TGGCTGAGGG TGACTGCTGT
105001  TAGCCCCAGT CCTTGGGGCT GGGGAGGAAC AACCAGGGGA AGGATTTGCC
105051  AGGGGAGCAT TCCCAGGGTG CAGACCCATC CCCTGCAACA TCAACCCTTC
105101  TCTGGCTGCA CGGCCCCCCC CAGGCAGACC CAGCACTGGC CCCTTGGCTC
105151  CCATCAAGGG TGCCCAATTC CCTGGACCGC TCTGGGTTGG GCCCTGGGAG
105201  CCTTGTCCTC AGAAGGGCAA AGAGGCTGGG CCCCGCTCCT TGACCCCATC
105251  CTCCCCTCAA CAGTGGGCTA CGACCGAAAC AACAAGCAGC ACCACAGACT
105301  TCTCCTCTGC CTCCTCATGA CCTCCTGTGA CCTCTCTGAC CAGACCAAGG
105351  GCTGGAAGAC TACGAGAAAG ATCGCGGTAG GTGTAGTCCT CCCTGGGAAG
105401  GCACAGGCTG CCCACCCTGC CCAGCTTTGG GTGCCCCCTG TGCCTGAATA
105451  CCCTCTCTCT GCTCAGCTCA GCCTGGCTGT GTTCTGGGGA GACAGAAACC
105501  TAGACCATCT CAGGGTGACA AATGGAGACT CAGAGAGGGG AACAGACCTA
105551  GCAAGTCAGT GGCTGGTGGA AGGTGGGCCC CAACCCAGCC ACTCCCTGCC
105601  TCAGGCCATC CCACTGCCAA GCTGGGGCTG GTGGGGACGG CTCCTGAGCT
105651  GGGACTGAAT CCCTGGGCCT CAGTTTTCTC TCCTGGGAAC GGGCTGTCAG
105701  AGGAGCTTGG GTGGATGTAT CCTACATAGA GGATGTGATG AGAGTGTTGG
105751  CCTTTCAGGA GCTGATCTAC AAAGAATTCT TCTCCCAGGG AGACCTGGTA
105801  TGTGTGGAGT GACCCCAGGA TGTCCAGGAT GGGGGAGGGT TCCTGGCCTG
105851  GGACAGGGAG GGCTTGAACT AGCCTGACCC TGGTACCCGA TGGAGGAATG
105901  AGAGGGACAG GCCTGACGAC TCGATGCCTG CAGGAGAAGG CCATGGGCAA
105951  CAGGCCGATG GAGATGATGG ACCGGGAGAA GGCCTATATC CCTGAGCTGC
106001  AAATCAGCTT CATGGAGCAC ATTGCAATGC CCATCTACAA GTGAGTGAGC
106051  TCATGGGGAC AAGCTGCACC CTGCACAGAG AGGGTAGGCT GGAGTGGGGA
106101  CATCACAGGA AACACAGGTG CTGAGATTGG CCTGGCCCAG CTCCAACTGA
106151  TTCATCCCCT TGCCTCTGGG CATAACTGTC TCCCGCTGTG CCCCTCAGTG
106201  GGTCCTTCAC TTCATCCTTG GTCCTCAGTG GAAAGAGACC ATCATGCTTT
106251  CCTAGGTGTC CTCCTCTGTC TCACATTCTT GTGGAAGTTC TTGTTTTTTT
106301  TGAGATGGAG TCTCACTCTG TTGCCCAGGC TGGAGTGCAA TGGCACGATC
106351  TTGGCTCACT GCAACCTCCC CCTCCTGGGT TCAAGCGATT CTCCTGCCTC
106401  AGCCTCCCAA GTAGCTGGGA TTACAGGCAT GCACCACCAC GCCCAGCTAA
106451  TTTTGTATTT TTAGTAGAGA TGGGGCTTCA CCATTTTGGT CAGGCTGGTC
106501  TTGAACTCCT GACTTCAGGT GATCCACACA CCTCGGCATC TCTGAGTGTT
106551  GGGATTACAG GCGTGAGCTA CCGTACCTGG CCCTTGTGGA AATTCTATTT
106601  GTTGTGTAGC CCTAGTCTTT CTTGCTGCCC ATGGTCTGAT TTCTGGCCTC
106651  TCACCCTCTG CCCCCATGCA CCCGCAGGCT GTTGCAGGAC CTGTTCCCCA
106701  AAGCGGCAGA GCTGTACGAG CGCGTGGCCT CCAACCGTGA GCACTGGACC
106751  AAGGTGTCCC ACAAGTTCAC CATCCGCGGC CTCCCAAGTA ACAACTCGCT
106801  GGACTTCCTG GATGAGGAGT ACGAGGTGCC TGATCTGGAT GGCACTAGGG
106851  CCCCCATCAA TGGCTGCTGC AGCCTTGATG CTGAGTGATC CCCTCCAGGG
106901  ACACTTCCCT GCCCAGGCCA CCTCCCACAG CCCTCCACTG GTCTGGCCAG
106951  ATGCACTGGG AACAGAGCCA CGGGTCCTGG GTCCTAGACC AGGACTTCCT
107001  GTGTGACCCT GGACAAGTAC TACCTTCCTG GCCCTCAGCT TTCTCGTCTG
107051  TATAATGGAA GCAAGACTTC CAACCTCACG GAGACTTTGT AATTTGTTCT
107101  CTGAGAGCAC AGGGGTGACC AATGAGCAGT GGGCCCTACT CTGCACCTCT
107151  GACCACACCT TGGCAAGTCT TTCCCAAGCC ATTCTTTGTC TGAGCAGCTT
107201  GATGGTTTCT CCTTGCCCCA TTTCTGCCCC ACCAGATCTT TGCTCCTTTC
107251  CCTTTGAGGA CTCCCACCCT TTGGGGTCTC CAGGATCCTC ATGGAAGGGG
```

FIGURE 3-37

```
107301  AAGGTGAGAC ATCTGAGTGA GCAGAGTGTG GCATCTTGGA AACAGTCCTT
107351  AGTTCTGTGG GAGGACTAGA AACAGCCGCG GGGCGAAGGC CCCCTGAGGA
107401  CCACTACTAT ACTGATGGTG GGATTGGGAC CTGGGGGATA CAGGGGCCCC
107451  AGGAAGAAGC TGCCAGAGGG GCAGCTCAGT GCTCTGCAGA GAGGGGCCCT
107501  GGGGAGAAGC AGGATGGGAT TGATGGGCAG GAGGGATCCC CGCACTGGGA
107551  GACAGGCCCA GGTATGAATG AGCCAGCCAT GCTTCCTCCT GCCTGTGTGA
107601  CGCTGGGCGA GTCTCTTCCC CTGTCTGGGC CAAACAGGGA GCGGGTAAGA
107651  CAATCCATGC TCTAAGATCC ATTTTAGATC AATGTCTAAA ATAGCTCTAT
107701  CGCTCTGCGG AGTCCCAGCA GAGGCTATGG AATGTTTCTG CAACCCTAAG
107751  GCACAGAGAG CCCAACCCTG AGTGTCTCAG AGGCCCCCTG AGTGTTCCCC
107801  TTGGCCTGAG CCCCTTACCC ATTCCTGCAG CCAGTGAGAG ACCTGGCCTC
107851  AGCCCTGGCA GGGCTCTCTC TTCAAGGCCA TATCCACCTG TGCCCTGGGG
107901  CTTGGGAGAC CCCATAGGGC CGGGACTCTT GGGTCAGCCC GGCCACTGGC
107951  TTCTCTCTTT TTCTCCGTTT CATTCTGTGT GCGTTGTGGG GTGGGGGAGG
108001  GGGTCCACCT GCCTTACCTT TCTGAGTTGC CTTTAGAGAG ATGCGTTTTT
108051  CTAGGACTCT GTGCAACTGT CGTATATGGT CCCGTGGGCT GACCGCTTTG
108101  TACATGAGAA TAAATCTATT TCTTTCTACC AGTCCTCCCC CATGGGGCTG
108151  TTTGCAGACT TTGTGCTTGG GGTGGGTGGA GGGGGGGAAT AGAACTGGGA
108201  GAGGCAAACG CCCTTTGGAA CTCCATGGCT TCCAGGGTCC TCCACCCTTG
108251  GTGCCTAGCC CCCCTTCTGG GGAAGTCATA GACCTGTTGG GGTACTCCCT
108301  AGGCCAGATC GTGGAGGCTA AGGGGTGGGT GGCAGATGAG AAGGCCTGGC
108351  CATGGAGCAG TGATGGGACA TGTTGGCTGG CAGAGATTGT AGAATAGAGG
108401  AAAAACAAAG GTTGAGGCAA GCAGGCAGGC TGCCTGGAGG AGGTAGCCTG
108451  GAGCTTGTCC TAGACCCTCC CAGCGCTGGC CTGCCCTGGT CATGAGTGCC
108501  CATACGGCGA GGGCCTAGGC CTCTGAACTC TGTTTCTAGC TGCAGTGATG
108551  CCTGGCTGTG TCCCAGGAAG TCCCACATCC CAGTTACTCT GAGTCCTGCC
108601  GAAGGTGCAC GCCTGAGTCA GACTCCACAC CAGATCCAGC CCCGGGTTGT
108651  GTCTGAGGAG TTGCGTCTGT TCCTCTGCAT GAGAGTGTTT ACTTCCGCCC
108701  AGTCCAAGAT GGGCAGACTG CAGGTTGGGG CTACGCGGAG GCTCTGCCTG
108751  GCACAGTCTC CAGACCCTGT CCCCGACTTG CCTACCCCCC TCTGAGCTCC
108801  TCTCCGTGTT CATCTCTTCC TGGTCAGTAA AGGTTGATGT GTTAAGAGGG
108851  TGGGCACTGG GGTCTCCTTT CTTGGTGGGA GCAGGAAGGA GATGGACAGG
108901  GCCATCCTGT GACCATCAGC CATTGCCAGC TTTGCCTTTG GGACCACAGA
108951  GCCCATCTGC TTCCTCTGCA GCTCCCCCTG CCCCACTAGC CTGTCTGGGT
109001  TTGGAATCTG CTCCTCTGGC TGAATGGTCT CCAGGTTTCC AGCTTCCCTT
109051  AGCGTCATGG GGCTCCAGGC TCCTCCCATT CCCAGCTCCT GCTGTGGGCT
109101  CCCCAAGTCC GTCTCTATCC TCTCACAGCA CAGGACCCAG GCTTGGCCAG
109151  TGGGTCCCCG GGTGGGGGTG GGAGTGGTCA GTTTGTGGCC CACGGCCAAT
109201  AAGAGATGGC TATTCTAATG GTGCCTGGCT GACCCCAGGG TCACTGTGGG
109251  CTGATGTAGC TGCTCTTCTG CCTGACCCCT GACCCTGAGT GTGTGTGCGT
109301  GTTCCTCTTC CACAACTCTT CAGGCAAAGA GAACCTTGAC CCTGCATCTG
109351  TCTGTCCCCA GCCCAGCCCT CCTTTGAGGC TCATGCTGTG ACACATCCCT
109401  GTTTTTCACC AAATGGAGGG AACAACCACA GATATTTCCT TGTGCACGCA
109451  GGACCCTGTG CTAGGGCTGA GGGCTTTGTC TTTGTCCTGC TCTGGAAAGT
109501  CTCACAGTTT GATTGGAGAG CTAGATCTAA ACTCAGATGC AGGCCATGAC
109551  AACGCTGTGG GGTGCCCGGC CATGGGGCTC CAGGCAGGAT CATAACCCTG
109601  AGAACAACAA TGAGGTTTGA AAGATGAGCA GATGTTGTTT ATAGGCAAAA
109651  GGGGACAGGC ACTCCTGGTA GAAGAAACTG CTTTTGCAAA GGCCTCAGAGA
109701  ACAGAAGGGA CTGGCAGGTG GAGGAGCCGA GAGATGGAGG AGGAGGCAAG
109751  GCCAGATCCT GAAGGGCCTT AAATGCCAGG TTGTGGAGTT TGGCTTTATT
109801  CTGTGGGCAG TGGAGAACCA GAGAAAGGTT TTCAGTAGGA GAGTGACTCA
109851  GAAGTGCATT TTAGAAAGAT CCCCCTGGAG AGCAGGGAAG TGACTGCAAG
109901  GGGAGAGGGT GGGCAGGGAT TATTCTATGG GTGATGTGCT GTGCCCTGGG
109951  CTGGGCGAGG AGAGGAATTC GGAGATGCTA GGTTGGCAGA ACATGGTGAC
110001  CAGTGGGTCG GGGGATGCAG AGGGAGGACT TGGAGGGGCC CTGGGAGGTG
110051  GGGTCTATGC CACTCCATGA AGAGCTGTGG GGGCTCTGTT CAGCATCACC
110101  CTCACCCACA ACAGGTATTG GGTGGAGCCT CTGGCAGGGG TGAGCTCCCT
110151  GCAAAGGTGA GCAAAACAGC TATCTGAGGA TGCCCAGGGA GGAGAGGTGG
```

FIGURE 3-38

```
110201  GAGGAAGGGA GAGAGGACAG ATGGGAGGAG GCTCTGCACA GAGCCTGAGG
110251  ACAGCCCTCA CCAGGTTACA GAACACAAGG CTTGACCCCA TTGGCTTCCT
110301  GTAGCTGTCC TGCTCTCCCA ACTTAATGGT TTCATTTTGC ATTTTATTTA
110351  AATTTCACAA TGATTCTAGC AGATACCATT AGTCTATTCT GCAGCCAAGT
110401  TGTCTAAGGT TTGGAGAGGT TAAGTAATGC ACCAAGGTTA GGATTTGAGC
110451  CCTACCTGTC TGATTCCCCT CCGAGAGCTG TCTGATTCCT TTCTCCTCCT
110501  CTGGGATAGG GGAAGGAGAC TCAGAAGGAC GGGGTCTCCA TCTTCAGTCT
110551  TTGCAAGACT ATTGTAGGGC ATTGGGATGG TGAGCACAAA GTGGGTTGAA
110601  GCCCAGAGA AAGAGCTGAG AGCTGGGATC AACTGTGTGT GTGCATGTGT
110651  GTGTCTGTGT GTGTGTGAGT TGGAGTAGGG GGCAGGGAGA AAAGAGTGGG
110701  GTGGTGGTGG CTTGTAGTGC AGCTCAGGGC CACCAGGTGG TGTCCAGCCC
110751  TCGCTGTCCT CACCTCCCCA GAGGTCAGAG AAGGATATGG GAGGGGGTGG
110801  GGTGGGGTGA GGGGGACGCG GCGGGGACGG GGGGACGGT GGTTGGTAGT
110851  CTCACTCCTG TCCATTCACC TACAGGTTGA GTATCCCTTA TCCAAAATGC
110901  TTGGGGCCAG AAGTGTCTCA GATTTAAGAT TTTTTTCGGA TTTTGGAATA
110951  TTTGCATATA CATAATGAGA TATCTTGGGA ATGAGACCCC AGGCTAAACA
111001  GGAAATTCAT TTATGTTTTA TATACACACA GCCTGAAGCA GTTTTATATA
111051  ATATTTTGAA TAATTTTATG CATGAAACAA AGTTTGTGCA CATTGAAGCA
111101  AGTGTGGAAT TTTCCACTTG TGGCATTATG TCGGTGCTAA AAAATGTTTT
111151  AGATTTTGGA GCATTTTGGA TCTCAGAACT TTGCATTAGG AATTGAGGAC
111201  TAAGTCTGAT ATTCTGTCTT ACCCAGATTC CTACCTAAGA GGTCTAGGAA
111251  GTCATGCCCT ACAAACCATA CATTCTCATC AG (SEQ ID NO:3)
```

CHROMOSOME MAP POSITION:
Chromosome 11

ALLELIC VARIANTS (SNPs):
DNA

| Position | Major | Minor |   |   |
|---|---|---|---|---|
| 254 | G | A |   |   |
| 1997 | C | T |   |   |
| 2653 | C | A |   |   |
| 2986 | G | A |   |   |
| 3702 | G | A |   |   |
| 3710 | A | G |   |   |
| 4661 | G | T |   |   |
| 4734 | G | A |   |   |
| 5649 | A | G |   |   |
| 5957 | A | G |   |   |
| 6060 | A | C |   |   |
| 6133 | A | G |   |   |
| 6692 | A | G | C | T |
| 6911 | A | G |   |   |
| 7541 | C | T |   |   |
| 8173 | G | T | C | A |
| 8694 | A | G | T | C |
| 9072 | C | G |   |   |
| 9426 | - | A | G |   |
| 9426 | A | G | C | T |
| 9573 | A | G |   |   |
| 9826 | C | T |   |   |
| 10134 | C | T | A | G |
| 11014 | C | T |   |   |
| 12390 | G | A |   |   |
| 13720 | T | - |   |   |
| 14701 | C | T | A | G |
| 15679 | - | T |   |   |

FIGURE 3-39

| | | |
|---|---|---|
| 15687 | - | T |
| 18322 | - | T |
| 18606 | C | T |
| 19070 | A | G |
| 19470 | A | G |
| 19611 | C | A |
| 20641 | A | C |
| 20642 | A | C |
| 21036 | C | T |
| 21871 | T | C |
| 22907 | G | A |
| 23722 | A | G |
| 24121 | A | C |
| 24553 | G | C |
| 25917 | T | C |
| 26573 | - | A |
| 27525 | T | A |
| 27625 | T | C A |
| 27833 | C | T |
| 27852 | A | G |
| 28478 | C | A |
| 28514 | T | C G |
| 28702 | G | C |
| 28859 | A | C G T |
| 28960 | C | G |
| 29030 | A | G |
| 29348 | T | C |
| 29973 | T | C G A |
| 30153 | C | T |
| 30389 | T | C |
| 30581 | C | G |
| 31147 | G | A |
| 31224 | C | T |
| 31735 | G | A T C |
| 31739 | G | - |
| 31742 | G | - |
| 31798 | G | C A T |
| 31994 | A | G T |
| 32324 | A | T |
| 32891 | G | A |
| 33104 | C | T |
| 33296 | C | T |
| 33324 | C | G |
| 33533 | T | C |
| 33852 | A | T |
| 33907 | A | C |
| 34294 | A | G |
| 37090 | C | T |
| 37248 | C | T G |
| 37355 | A | - |
| 37893 | A | G |
| 38252 | A | G C |
| 38726 | G | T C A |
| 40472 | G | C |
| 40965 | C | T |
| 41664 | G | A |
| 41760 | G | T C A |
| 42523 | G | A |

FIGURE 3-40

| | | | | |
|---|---|---|---|---|
| 42904 | G | A | | |
| 43382 | - | C | A | |
| 43386 | - | C | G | |
| 43387 | - | G | | |
| 43728 | G | A | T | |
| 45012 | C | T | | |
| 45079 | C | T | | |
| 45247 | A | G | C | |
| 46267 | T | A | | |
| 46268 | T | C | | |
| 46414 | G | A | | |
| 46822 | G | A | C | T |
| 47169 | C | T | | |
| 47214 | G | C | A | T |
| 47431 | A | G | | |
| 47773 | G | T | G | T |
| 47821 | G | A | | |
| 48186 | C | T | | |
| 48544 | G | A | C | |
| 48577 | G | C | | |
| 48705 | G | A | C | |
| 48873 | - | C | | |
| 48874 | - | G | C | |
| 48876 | - | T | | |
| 48879 | - | C | | |
| 48880 | - | T | C | |
| 48881 | - | A | T | |
| 49008 | C | T | | |
| 49259 | G | C | | |
| 49821 | C | T | | |
| 52352 | C | T | | |
| 55378 | G | A | | |
| 55440 | T | G | | |
| 55532 | A | G | | |
| 56039 | T | A | | |
| 56082 | T | G | | |
| 56113 | G | C | | |
| 56425 | G | A | | |
| 56554 | C | T | | |
| 57097 | A | G | | |
| 57284 | G | A | | |
| 57618 | T | C | | |
| 57795 | C | T | | |
| 57796 | A | G | | |
| 57957 | C | T | | |
| 58064 | - | A | | |
| 58069 | - | A | | |
| 58108 | A | G | | |
| 58125 | T | C | | |
| 58171 | G | A | | |
| 58246 | A | G | | |
| 59173 | T | A | | |
| 60931 | G | C | | |
| 62318 | G | A | | |
| 62417 | C | T | G | A |
| 62655 | A | G | | |
| 62676 | A | G | | |
| 63504 | G | A | | |

FIGURE 3-41

| | | |
|---|---|---|
| 63823 | C | T |
| 64793 | T | C |
| 64829 | C | T |
| 65593 | G | C A T |
| 65634 | A | G C |
| 65848 | A | G T |
| 66187 | A | G |
| 66843 | T | C G |
| 66908 | A | G C |
| 67481 | G | A |
| 67637 | C | T |
| 69231 | A | C |
| 69238 | T | C |
| 70821 | G | A |
| 72136 | T | C G |
| 72285 | C | T |
| 72611 | C | A |
| 73103 | C | T |
| 73589 | G | T |
| 73591 | G | C A T |
| 74229 | T | A G C |
| 74478 | T | C |
| 74636 | C | G |
| 75308 | A | C T G |
| 75554 | G | C A T |
| 76209 | G | A |
| 76627 | T | C T C |
| 76767 | C | A |
| 77530 | G | A |
| 78642 | A | G |
| 78774 | A | - |
| 79135 | A | G |
| 79648 | C | T |
| 80969 | C | T A |
| 82103 | G | A |
| 83833 | G | A |
| 84945 | T | C |
| 84985 | A | G |
| 85295 | G | A |
| 89241 | C | T |
| 91827 | A | G C |
| 93127 | C | G |
| 93815 | C | T |
| 96136 | C | T |
| 96831 | T | G |
| 97038 | G | A T C |
| 97110 | G | A T C |
| 98446 | A | G |
| 98618 | G | A |
| 99145 | - | A |
| 99158 | A | - |
| 99278 | C | A |
| 99411 | G | A C |
| 99744 | G | C |
| 99815 | A | G |
| 100604 | G | A |
| 100878 | C | A G T |
| 101440 | A | T |

FIGURE 3-42

| | | | |
|---|---|---|---|
| 101516 | A | T | C G |
| 101994 | A | G | |
| 102173 | T | C | |
| 102239 | G | A | C |
| 102279 | A | G | T |
| 102458 | A | T | C G |
| 102522 | G | T | C A |
| 102687 | A | C | G |
| 103134 | G | T | |
| 103152 | C | A | |
| 103392 | G | A | |
| 103436 | G | T | |
| 104138 | T | C | |
| 104175 | C | T | |
| 104560 | T | G | |
| 104688 | T | C | |
| 105118 | C | T | |
| 105179 | G | A | |
| 106026 | A | G | |
| 106141 | C | G | |
| 106474 | G | A | |
| 106717 | T | C | |
| 107099 | C | T | |
| 107322 | C | G | |
| 108611 | G | C | |
| 108664 | A | G | C |
| 109160 | T | C | G |
| 110512 | G | A | |
| 110746 | A | G | |
| 110781 | A | T | |

Context:

DNA
Position
254  ACGTGGATGAACACCCACCCACACACAGCTCTCTAGGAAAATTGCTCCCCTTCCCTCCTG
CTCCTCCTCCACCCTGTCCTCCCACCACCACCCACTTCCAAATGCTGAGACCAAAGAGAT
GGGCTGGACGGTGCCTCTCACCACTTGTCAGCCTGGGACGCCCTCCTCCCTTTGTGACTA
GCATGCCCTCCTCCCCCTGCCCGTCTGCCTCCCCAGCTCTCTCTGCCTCCCTGTCGCCCT
GCCACCTCCCTGC
[G,A]
TTCCTGTGTATCTGCCCTCCACACAAGTCACTCTGAGGCCTCTCTTTGTTACTCTTGACT
CTGAAGTGGAAACTGCTCCTCCCAGCTCTCCTGAGAGGCTCAGGATGGGGACCTGACCTC
ATAGGGCTGATGGAGGCATAGGGACAAGTGAAAGGGACCCCAGGTCCCGAATCTCCTCAG
CTCCTGTCACCTTCAGTCCCTCCTATTGGGTTAGGGGAGGGCTGTGTGCCTGGCACCATG
GAGACCAGTGTCATGGCAACACAGTTCGGGTGGGCACAGCTTCCTCCTCCTGGGGTGTGG 1997  GGGGCCACTTCTGCCCTGACCCATCCCTGCTGGAATTCCACATTCCTGGGGGCCCTCCCC
AGAGTCACAAGCTATATGTACAGCCTTCTCTTGTGGGCTGCTGTCTCAGTTGGAGGAGGA
AGGAGAGGTGGAAGAGTATGAAGAGGGGAAGTAGTCCGGTGGGGCAATGGCCACCGTCT
TTGGTCCTAGGCTCAGCCTCGCCCTTCACTCACTGGGTTACCTGGGCACCCCTCTGACCT
CAGTTTTCCCATCTGCACAGTGAAGGATTAGATTAACTGGCTCTAGCGTCTCATTCTCTC
[C,T]
GATTTATAACCCTGGAGATGATCTCAACCTGAGGCTGAAGGCACTTCCGAGTGTCTGGCC
CAGCCGCGTTCCAGGCTGACTTCCCTCCCTCTTTTCTCTGCCATCCCTCCTAGACCAATG
CAGCCACCCCCACCCACAAGACAAAAGAGGCAGGAGAGGGCCCTGGACTCAGCTGGGGCT
GGGCGGCTTCTCCCTTCCCTGAACTCGCCATCTGTTCCAGCCCCCCAGCCCCCTGCCTAG
CAGCCATGGGTAGGTCACTGCCCTCACCTGGGGTCACCCCTTCCTCCCCGGAGAGCTCTG

FIGURE 3-43

2653    CCACCTTCCTGAGGTGTTGAAGAAGCTGCTCCACCTTGGAACTACTATAGGGGCTGTGGT
GGCCTTTCATTCCTTTATCAGCAAAAGCTTTTGTCACTTGTGTGGTGGGGGACATGCTTA
GTGTGAGAATGCAGAGACCCATGCCAGGCCCTACCCAAGGACATGGTGCTCCTTCAGCCA
TTGTCATCAGAGCCACAGAGGGGAGCTTCCTGGCAGAGGAGGAGTGGGGAGAAGCTGTGG
AATGGCTCCTTGAGCTCCCCACTCCACCCCTTCCCCATGCCTGGGCTCCCATTGCAAAGA
[C,A]
CCAGATGTGGGCTTATCCTGTCCCCCAGCCAGAGGGAGTCACCCAGGGGTGTTCAGGCCA
ACCCTTTGTGAAATCCATGTTCCACCAGTTACCAGCCTTTCTCCGGAGAGCTGAGGGCTG
TCTCACACTGGGTAGTCTCAGCCTGCCCTGGGGTTGGGGGGGTGCTCACAGAGCAGTAAG
CGTCACTGCCTGCATCCCCACACACCTGCATTATCTTGTCTGCAAGACACGTGTGCCCCT
GAGCTGAGCTCTGTTGTGCACCACCCGATTTCCGTCGGCCTCCTTTCTGACTTTTCTCCA

2986    AGGGAGTCACCCAGGGGTGTTCAGGCCAACCCTTTGTGAAATCCATGTTCCACCAGTTAC
CAGCCTTTCTCCGGAGAGCTGAGGGCTGTCTCACACTGGGTAGTCTCAGCCTGCCCTGGG
GTTGGGGGGGTGCTCACAGAGCAGTAAGCGTCACTGCCTGCATCCCCACACACCTGCATT
ATCTTGTCTGCAAGACACGTGTGCCCCTGAGCTGAGCTCTGTTGTGCACCACCCGATTTC
CGTCGGCCTCCTTTCTGACTTTTCTCCATCAACATTTCCTGCTTGGGCCTGTTGCGGGCT
[G,A]
CCCAAAGGCTGTGGACTGGGGCCGAGGTACATAGGACTTTGGCTTGTCTTTTGAGCTAAC
AGGATCCTGTAGAAGAAATGAGATGAGCCTGAGAGGGGTCGGGGGGTGAGACATTAGGG
AAGGGAGAGGCCACCAAGGGTCTCTAGCCCAGAATCCAATGCCCCTTCCTGCCTACCTGT
CCTTGTGGGTGGGAGGCAGGGTGTGTGCTGACTGGCCCAGCAATGGTGGGCTAGGATTTG
GGATAGGCAGAGAAAAGGAAGAGGAGGGGGAAGTCGGCCTGGGAGGAGAAACACTGTACA

3702    AGGAGCTTGGCCTTTATCCTGAGGGCACTGGGGAGCCCTGCAAAGGTTTTGAGAGGGAAT
TCCATTACCAGATAGATGTCTTTGGAAGCCGCCTCTAGGTGCAAGGAGGAGGTGGAGTAG
AGAGGTTGACCTGGGGTAAGGGTTGGAGCATGACCAGGGGAGGGGGAAGGAAGCAGGGGG
TGGGGATGGAGGGAGTGGATGGATCTAAGAGAATCTACTGTCCTTTGGAACAAACGATAC
AGGAAGTGTAGGAGAGGGATGGGGCAAGGCGACTTTGAAGTGTCCAGCTCAGAGATTGGA
[G,A]
GTTTGCTGATGCCTTTGGGAGGCCAAGGCAGGCAGATCACGAGGTCAGGAGTTGAAGACC
AGCCTGGCCAATATGGTGAAACCCCGTCTCTACTAAAAATACAAAAATTAGCCGGGCGTG
GTGCGGGTGCCTGTAGTCCCAGCTACTTAGGAGGCTGAGGCAGGAGAATTGCTTGAACCC
GGGAGGCAGAGGTTGCAGTGAGCCCAGATCGCACCACTGCACTCCCCACTCCACCCCTTC
CCCATGCCTGGGTGACAGAGCGAGACTCCGTCTCAAAAACAAAACAAAAACCCAAAAAAC

3710    GGCCTTTATCCTGAGGGCACTGGGGAGCCCTGCAAAGGTTTTGAGAGGGAATTCCATTAC
CAGATAGATGTCTTTGGAAGCCGCCTCTAGGTGCAAGGAGGAGGTGGAGTAGAGAGGTTG
ACCTGGGGTAAGGGTTGGAGCATGACCAGGGGAGGGGGAAGGAAGCAGGGGGTGGGGATG
GAGGGAGTGGATGGATCTAAGAGAATCTACTGTCCTTTGGAACAAACGATACAGGAAGTG
TAGGAGAGGGATGGGGCAAGGCGACTTTGAAGTGTCCAGCTCAGAGATTGGAGGTTTGCT
[A,G]
ATGCCTTTGGGAGGCCAAGGCAGGCAGATCACGAGGTCAGGAGTTGAAGACCAGCCTGGC
CAATATGGTGAAACCCCGTCTCTACTAAAAATACAAAAATTAGCCGGGCGTGGTGCGGGT
GCCTGTAGTCCCAGCTACTTAGGAGGCTGAGGCAGGAGAATTGCTTGAACCCGGGAGGCA
GAGGTTGCAGTGAGCCCAGATCGCACCACTGCACTCCCCACTCCACCCCTTCCCCATGCC
TGGGTGACAGAGCGAGACTCCGTCTCAAAAACAAAACAAAAACCCAAAAAACAAAAAACT

4661    GAGAAGAAGCCGCCTTCTTCGGCAAAGAGGTAGCTGAAGCCTGTGGAGCCTGCAGTCCTC
TCAAGGCTATGGGGGCAGCGCGGAGGCCGGATTCCAGAACTGAATCTTCCCATCGCTTTG
GGCAGCCACCCTACCTCCCAGGAGCATCCTTCCTGCCATCCCACCTCCAGTTCCCCAGCT
AACAAAAAACGGTGTTTCTTGACTCCCGGCAGGGCGGCGGGGCGGGCAGGTCTTGTGAAC
ACGGCTCGCAGGGTTCAGCACCCTGGAGAGAGGCCTGTGGCCGGGGCGGGGCCTGCGGCG
[G,T]
GGGTAGGGGCGCGCAGTCAGAGCAGTCGGGCCTTTGGCTCCGTCTGGGAGCGGTCTTGCA
GGCAGGCAATTGGTGGAGGAGGGAAAAACAATCTTGGATTTTCTCCAGCTCTCTCCCCTT
TATGCACCTCCCCCATCCCGGCACTGGCCTACAGGAGCCCCTATCCCAGCATTTGGGGCT

FIGURE 3-44

```
       ATTACTCTCCTGACGACTTCAGGAAATGAGATGGGAGGAGAGGGGCAACTATTTACTGGG
       AACTTTTCAGACATTCCCAAAACCTCACAACCTTTTGAGCTTGGAATTCGTGACCCCATA
```

4734
```
       GGCAGCGCGGAGGCCGGATTCCAGAACTGAATCTTCCCATCGCTTTGGGCAGCCACCCTA
       CCTCCCAGGAGCATCCTTCCTGCCATCCCACCTCCAGTTCCCCAGCTAACAAAAAACGGT
       GTTTCTTGACTCCCGGCAGGGCGGCGGGGCGGGCAGGTCTTGTGAACACGGCTCGCAGGG
       TTCAGCACCCTGGAGAGAGGCCTGTGGCCGGGGCGGGGCCTGCGGCGGGGGTAGGGGCGC
       GCAGTCAGAGCAGTCGGGCCTTTGGCTCCGTCTGGGAGCGGTCTTGCAGGCAGGCAATTG
       [G,A]
       TGGAGGAGGGAAAAACAATCTTGGATTTTCTCCAGCTCTCTCCCCTTTATGCACCTCCCC
       CATCCCGGCACTGGCCTACAGGAGCCCCTATCCCAGCATTTGGGGCTATTACTCTCCTGA
       CGACTTCAGGAAATGAGATGGGAGGAGAGGGGCAACTATTTACTGGGAACTTTTCAGACA
       TTCCCAAAACCTCACAACCTTTTGAGCTTGGAATTCGTGACCCCATATTTCAGATGAGGA
       AACTAAATTGAAGTTCAGGAAGGTGAAATACCTTGCCTAGGCACTTGGCAGAGCTGGGAT
```

5649
```
       TTCTTGCTGCCAGGTTCCTCCGACCAGTGAGCAGGTTCCCAGGACATGAAGGGGAGCTGT
       GAGGGAGCAGGACGCCATGGTCCAGGGCTGCAGCTTCCTGAGCCCAGAGAATGCCTTCCT
       AGCTGTCAGGAATGGAGCAGCGAGGCCCCAGTGATAGGTGAGGTGGAGAAGCAAGACATG
       AGTTCTGGGCTGGCTCAGCTGCTTTACAACCAGCCTGGGCCTCGTTCCCTTTGAGAAAAT
       GGTTTGCCCAGAGTTCAGAGATCTAAAATTCTATGATGCCTTCTGGGGCCACAGTGGGAA
       [A,G]
       CAAAGACTCCTCATATTTTCTTTCCTGACACTTCCCAGGCCACAAGACAACTGCTTTCTG
       CAGCACCCAGCCTGGGCAGGCCATCTACACAAGCTCAGTCATTTCTGACCTTGCCCCCTC
       CACCGTGCACCCCCATGTTCTTCAACATGGGTCAGGTTTCTATTCAGCCTCAGGGACTTC
       TCTGCTTGAAGCCTGTTGTGTGGCGGGGAGGTATTCTCCCCACAGCTCAGAGAGATGGGG
       TTGCTGTGGAGGGTTTGCTGTAGCTCCTCTACCCTGGAATATACCCTCTTCTGCCTTAAA
```

5957
```
       TCCTCATATTTTCTTTCCTGACACTTCCCAGGCCACAAGACAACTGCTTTCTGCAGCACC
       CAGCCTGGGCAGGCCATCTACACAAGCTCAGTCATTTCTGACCTTGCCCCCTCCACCGTG
       CACCCCCATGTTCTTCAACATGGGTCAGGTTTCTATTCAGCCTCAGGGACTTCTCTGCTT
       GAAGCCTGTTGTGTGGCGGGGAGGTATTCTCCCCACAGCTCAGAGAGATGGGGTTGCTGT
       GGAGGGTTTGCTGTAGCTCCTCTACCCTGGAATATACCCTCTTCTGCCTTAAAAGACCCA
       [A,G]
       CTTGGACCCTCTCTTCCAGAAATGCTTGCTAACCGCCCCCCCACCACCCAAACTAGGTCA
       GGGGTCCCTCTGGGCTTCACAGACCCTGTGCTTCTTTCTGTCACAGCCTGCAAGTCTCCC
       CTCCCCACTCCCCAGCCCGAGTGCTTCTCTGAGACAAGGGATAGTGTGAGCCATGAGCTC
       AGCCACTGGTAGGCCAATGAATAAGTAAGTTAATGGTGAAGCCAGGATCCAAATCCCCAT
       TTCCTGCCTCAAGGTGTGGAGCTGTTTCTCCTGCATACAATAGTAGCTCTGCTGTGACAA
```

6060
```
       TTGCCCCCTCCACCGTGCACCCCCATGTTCTTCAACATGGGTCAGGTTTCTATTCAGCCT
       CAGGGACTTCTCTGCTTGAAGCCTGTTGTGTGGCGGGGAGGTATTCTCCCCACAGCTCAG
       AGAGATGGGGTTGCTGTGGAGGGTTTGCTGTAGCTCCTCTACCCTGGAATATACCCTCTT
       CTGCCTTAAAAGACCCAACTTGGACCCTCTCTTCCAGAAATGCTTGCTAACCGCCCCCCC
       ACCACCCAAACTAGGTCAGGGGTCCCTCTGGGCTTCACAGACCCTGTGCTTCTTTCTGTC
       [A,C]
       CAGCCTGCAAGTCTCCCCCTCCCCACTCCCCAGCCCGAGTGCTTCTCTGAGACAAGGGATA
       GTGTGAGCCATGAGCTCAGCCACTGGTAGGCCAATGAATAAGTAAGTTAATGGTGAAGCC
       AGGATCCAAATCCCCATTTCCTGCCTCAAGGTGTGGAGCTGTTTCTCCTGCATACAATAG
       TAGCTCTGCTGTGACAACTCTCTATCTGTCCTAGGGCCTAAAATGCCTCTATTTCACTAG
       GTTATAGCTTTATCCTAGGGAGTCCTCTTTGGAAGCAGGGTGGGGGTGCAACAGGCCTTC
```

6133
```
       GCTTGAAGCCTGTTGTGTGGCGGGGAGGTATTCTCCCCACAGCTCAGAGAGATGGGGTTG
       CTGTGGAGGGTTTGCTGTAGCTCCTCTACCCTGGAATATACCCTCTTCTGCCTTAAAAGA
       CCCAACTTGGACCCTCTCTTCCAGAAATGCTTGCTAACCGCCCCCCCACCACCCAAACTA
       GGTCAGGGGTCCCTCTGGGCTTCACAGACCCTGTGCTTCTTTCTGTCACAGCCTGCAAGT
       CTCCCCTCCCCACTCCCCAGCCCGAGTGCTTCTCTGAGACAAGGGATAGTGTGAGCCATG
       [A,G]
       GCTCAGCCACTGGTAGGCCAATGAATAAGTAAGTTAATGGTGAAGCCAGGATCCAAATCC
```

FIGURE 3-45

```
     CCATTTCCTGCCCTCAAGGTGTGGAGCTGTTTCTCCTGCATACAATAGTAGCTCTGCTGTG
     ACAACTCTCTATCTGTCCTAGGGCCTAAAATGCCTCTATTTCACTAGGTTATAGCTTTAT
     CCTAGGGAGTCCTCTTTGGAAGCAGGGTGGGGGTGCAACAGGCCTTCCCCCATGCCTGTA
     GTCTGTGAGCAGCGAAGGCCATGTGGGGCAGGCTGTGGCCTAGGTCTCCACAGATCCTGG

6692 CCATGTGGGGCAGGCTGTGGCCTAGGTCTCCACAGATCCTGGTAGAAGTCCATGCTCACG
     CATCAGCTCCAAGTCCCAGCTAAACCAAGCCACCAAGAGGTGGGCCCTGTGACAAGGCTC
     TGAGTCCAAAGGCCATCAGTAAAGCCCCCTAAGTCTTCCGTGGACCCAGCTCCAGGCTGG
     GATGCACGCTAGGAGATGATACACACCGGGTGAGGGAGCCCAGAGGAGAGGGCAGCTAGC
     TGTGCATGGAGGCCTGATCTCTCAGACTTGAGGGCACAAGCGTGTCCCCTCATCCTGAAG
     [A,G,C,T]
     CTTCTGCGATGGGGCAGCAGAGGGTCTGGGTCTGCTGCCCCTCAAGTCCCCAGCCCCATC
     CTAGCCCATGAGGATTGTAAATCCCTCGTCCTCTCCCCTCTCTCCTCTGTCAGCCACTCC
     CCTTTCCCCCTACCCCACTCTCTTTCTATTTCTGCCTCTGATTTTTTTTCCTTTTCTGCC
     TTTGTTCCTCTGTGTGTGTGTTTCTCTATGCCTCTCTGATCTCTTTGTACTTCCATCTTG
     ATCTCGCTAAGGCTCTGATCCCTCTCTCCTCTCCCTCTTCATGTGTTACTGTCCCCCTTC

6911 CCAGAGGAGAGGGCAGCTAGCTGTGCATGGAGGCCTGATCTCTCAGACTTGAGGGCACAA
     GCGTGTCCCCTCATCCTGAAGGCTTCTGCGATGGGGCAGCAGAGGGTCTGGGTCTGCTGC
     CCCTCAAGTCCCCAGCCCCATCCTAGCCCATGAGGATTGTAAATCCCTCGTCCTCTCCCC
     TCTCTCCTCTGTCAGCCACTCCCCTTTCCCCCTACCCCACTCTCTTTCTATTTCTGCCTC
     TGATTTTTTTTCCTTTTCTGCCTTTGTTCCTCTGTGTGTGTGTTTCTCTATGCCTCTCTG
     [A,G]
     TCTCTTTGTACTTCCATCTTGATCTCGCTAAGGCTCTGATCCCTCTCTCCTCTCCCTCTT
     CATGTGTTACTGTCCCCCTTCCTGTCTCTGTTTATCTCTCAGTCTCTCTGTCTGTGAGTC
     TTTTTTCCTCTCTCCCAGTCAGACTCTCTCTCTACCCCTCCCTCTCTCCCTCTCTCCCTC
     TCTGTCTGGGCCTCTCTCTGTTCCTCCTCCCTCCTCCCTCCCCCTTCTGCATTATCAGAC
     CTGCTCCAACCTCCTCCCAGAGCCAGCCGAGCAGCAGAGGCAGTGGCAGCGGGAGAGGCG

7541 GGTGTTGAGTCCAGGCTGAGTAGGGGGCAGCCCACTGCTCTTGGTCCCTGTGCCTGCTGG
     GGGTGCCCTGCCCTGAACTCCAGGCAGCGGGGACAGGGCGAGGTGCCACCTTAGTCTGGC
     TGGGGAGGCGGACGATGAGGAGTGATGGGGCAGGCATGCGGCCACTCCATCCTCTGCAGG
     AGCCAGCAGTACCCGGCAGCGCGACCGGCTGAGCCGTGAGTATAGTGAGGGGCTGGGGTG
     GTGAGCGGCTGTGAGAGGTGCCACAGACAGGGTCCTGGGAGTCCCTCCAAGGAGCTGGGG
     [C,T]
     TGGCATGGAGCTGAGCCACGTGGAAGGATCGATCCTGTTCCTGGGCACCCCTCCTCCCCG
     CGTTGCCAGACTGCAGCCTGGGGTGGGGGCAGGTTACCTCTGAGCAGAATGAGGGTGTCT
     AACGTCAACCTAGTAGGTGATGAGGCTGGGGTCCCATGGAAGGGGCTGCTGGTTGGAGGA
     GGGGCTGATAATGAACCTGAACCGCTTCTTCAAGGGCTGAGGGTGTATGTGGGGAGGGGG
     AGGTCTGCCAAGTAGTTGGGAGGAGCTCTCGGGGCTGCAATAGGCTGGTTCAGGACCCTG

8173 ATGTGTGTGTGAAGGAGGTGGGGAGGGGGAAAGATGGAGAAAATATGAATAAGAGTGGCC
     CTGGAGCAAGAGAGGGTTAGAGGTAACCACCTTCCATGGAATTGGGAATTGGGGTTCAGG
     GACACCACTTTATGAAACTTTACCCCAAAGCGTCTGTCCCAGGATAGGGTTCTACGGAGC
     CAGATGGAATATGGTGCCAGCCTCGTGTGTGTCCACGTGCAGGGGGTGCATGTGCAAGT
     GAGTGGGGGGCGCCGTGGCGACACCCCTCTACTAAGGGCTGCCGAGGTGGTAGGCAGGGT
     [G,T,C,A]
     TGTGTGTGTGTGTGTGTGTGTGTGTATACATGTGGAATGTAAGGGACATGTTGGGTGT
     AGAGGGGCCTGTAGAGCTCTAGGGTCCTTGGTGGTTGGATGTAAAGCAGCCTGTCAGAGT
     TTGTGATCATCCCTGTGTGAGTGAGAGTTTATTCGCATGTGTCTGAGTGTGAGTGCAGGT
     TGGTCTGCATATGTATGTAGGTGTGTCTATTAGGTTGAGTTTGTATATTATGTGTGTTGT
     GTCTGCAAAATAGAGTGAATCAGTGTGCATTTTTTATCTGTTCCATGTGCATTTATGTGT

8694 TTGTATATTATGTGTGTTGTGTCTGCAAAATAGAGTGAATCAGTGTGCATTTTTTATCTG
     TTCCATGTGCATTTATGTGTGTGTATTTGTTAGTGTGTGAATAATAGCATTGCTGTGTGT
     GGAGGTGGATGTGGCTGTGTGCGTATAAGTATTCTGGTGTGGGTGTGTGATCATGGTGCT
     AGTGTGTATATCGGTGCTTCTGTGGCTGGTGTGTGTGTGTATCTATATGTGTGTATTCAT
     CTGAGTGTGTGTGGGTGGCTGTTTCCTTCCCCTGGCAATTGAGGATACAGCTGGGACACC
```

FIGURE 3-46

[A,G,T,C]
TGGCCCACTGATGCAGGGCAGGGAGGGGCTGAATGTATGACCGCCTCTTTGAACTCAGGA
CAATTCATTCTACACCCTGTGGGAAAGATGCAGAAAAGAAATAGGCAATAATGACTCTGC
CCTCTGGGGCTTCCTAAGCTTCTTAGACATAAAATAGCTTGAGAATAATTAAGCAGTAGA
GATCAACGTCATGCTAACAGGTGGGGGTGGGGTGGGAACTGCATAAGCAAAGGCCCTGGG
CTGGGCATGTCCTGGAGCAGTGAAGACACTGTATAGAGTGGGGGGCAGGCAGGACCCACA

9072    TGTGGGAAAGATGCAGAAAAGAAATAGGCAATAATGACTCTGCCCTCTGGGGCTTCCTAA
GCTTCTTAGACATAAAATAGCTTGAGAATAATTAAGCAGTAGAGATCAACGTCATGCTAA
CAGGTGGGGGTGGGGTGGGAACTGCATAAGCAAAGGCCCTGGGCTGGGCATGTCCTGGAG
CAGTGAAGACACTGTATAGAGTGGGGGGCAGGCAGGACCCACATTCAATAGAACTTTAAG
ATCCAGGACTCTTAGGCTTTATCCAGAGAGCCCTGGGGAGCCCAGAAAGGTTTTATATAG
[C,G]
GGAGAGACATGATCAGATTTGGGTTCTAGAAACCTGCCCTGGGCCAGGCATGGTGGCTCA
TGCCTGTAATCCCATCACTTTGGGAGGCAGAAGCAGGTGGATCACTTGAGGCCAGGAGTT
TGAGACGAGACTGGCCAACATGGTGAAACCCAGTGTCTATTAGAAATACAATAAAATTAG
CTGGGTGTGGTGGCACACGCCTGTAGTCCCAGCTACTTAGAAGGCTGAGGCATGAGAATA
TGAGAATCGCTTGAACTTGGGAGGTGGAGGTTGCAGTGAGCTGAGATTGCCTTACTGCAC

9426    TGGCTCATGCCTGTAATCCCATCACTTTGGGAGGCAGAAGCAGGTGGATCACTTGAGGCC
AGGAGTTTGAGACGAGACTGGCCAACATGGTGAAACCCAGTGTCTATTAGAAATACAATA
AAATTAGCTGGGTGTGGTGGCACACGCCTGTAGTCCCAGCTACTTAGAAGGCTGAGGCAT
GAGAATATGAGAATCGCTTGAACTTGGGAGGTGGAGGTTGCAGTGAGCTGAGATTGCCTT
ACTGCACTTTAGCCTGGGGGTGACAAAGTGAGACTCTGTCTCAAAAAAAGAAAAAAAAAA
[-,A,G]
AAGAAGAAAAATAAAGAAACCTGCCTCGGTGGCATTGTCTGGGTTGAACTGGAAGAGAGA
GGTGGGGCCAGGAGGCTAGAGTGGAGGCCAAGCCAATACAGGGGTCAGTGAGTTCTGGAG
CTTTTTGAGAACTTGGGAAAGGCTGGATAGATGAGAACAGGGAAGGGAATGTCTAGGTGG
CTCAGGCTTGGACTGGGGTCAGGGGTGTAGTGCAGACATCTCAGTAAGTCAGGATCTCAT
GAGGGAAAAGGCTCATGGAAGGCTCAGGAAAGCTGGGCGTGGGTGGGCTGAGGTAGTGGG

9426    TGGCTCATGCCTGTAATCCCATCACTTTGGGAGGCAGAAGCAGGTGGATCACTTGAGGCC
AGGAGTTTGAGACGAGACTGGCCAACATGGTGAAACCCAGTGTCTATTAGAAATACAATA
AAATTAGCTGGGTGTGGTGGCACACGCCTGTAGTCCCAGCTACTTAGAAGGCTGAGGCAT
GAGAATATGAGAATCGCTTGAACTTGGGAGGTGGAGGTTGCAGTGAGCTGAGATTGCCTT
ACTGCACTTTAGCCTGGGGGTGACAAAGTGAGACTCTGTCTCAAAAAAAGAAAAAAAAAA
[-,A,G]
AAGAAGAAAAATAAAGAAACCTGCCTCGGTGGCATTGTCTGGGTTGAACTGGAAGAGAGA
GGTGGGGCCAGGAGGCTAGAGTGGAGGCCAAGCCAATACAGGGGTCAGTGAGTTCTGGAG
CTTTTTGAGAACTTGGGAAAGGCTGGATAGATGAGAACAGGGAAGGGAATGTCTAGGTGG
CTCAGGCTTGGACTGGGGTCAGGGGTGTAGTGCAGACATCTCAGTAAGTCAGGATCTCAT
GAGGGAAAAGGCTCATGGAAGGCTCAGGAAAGCTGGGCGTGGGTGGGCTGAGGTAGTGGG

9426    TGGCTCATGCCTGTAATCCCATCACTTTGGGAGGCAGAAGCAGGTGGATCACTTGAGGCC
AGGAGTTTGAGACGAGACTGGCCAACATGGTGAAACCCAGTGTCTATTAGAAATACAATA
AAATTAGCTGGGTGTGGTGGCACACGCCTGTAGTCCCAGCTACTTAGAAGGCTGAGGCAT
GAGAATATGAGAATCGCTTGAACTTGGGAGGTGGAGGTTGCAGTGAGCTGAGATTGCCTT
ACTGCACTTTAGCCTGGGGGTGACAAAGTGAGACTCTGTCTCAAAAAAAGAAAAAAAAAA
[-,A,G]
AAGAAGAAAAATAAAGAAACCTGCCTCGGTGGCATTGTCTGGGTTGAACTGGAAGAGAGA
GGTGGGGCCAGGAGGCTAGAGTGGAGGCCAAGCCAATACAGGGGTCAGTGAGTTCTGGAG
CTTTTTGAGAACTTGGGAAAGGCTGGATAGATGAGAACAGGGAAGGGAATGTCTAGGTGG
CTCAGGCTTGGACTGGGGTCAGGGGTGTAGTGCAGACATCTCAGTAAGTCAGGATCTCAT
GAGGGAAAAGGCTCATGGAAGGCTCAGGAAAGCTGGGCGTGGGTGGGCTGAGGTAGTGGG

9426    TGGCTCATGCCTGTAATCCCATCACTTTGGGAGGCAGAAGCAGGTGGATCACTTGAGGCC
AGGAGTTTGAGACGAGACTGGCCAACATGGTGAAACCCAGTGTCTATTAGAAATACAATA
AAATTAGCTGGGTGTGGTGGCACACGCCTGTAGTCCCAGCTACTTAGAAGGCTGAGGCAT

FIGURE 3-47

```
      GAGAATATGAGAATCGCTTGAACTTGGGAGGTGGAGGTTGCAGTGAGCTGAGATTGCCTT
      ACTGCACTTTAGCCTGGGGGTGACAAAGTGAGACTCTGTCTCAAAAAAAGAAAAAAAAAA
      [A,GsC,T]
      AAGAAGAAAAATAAAGAAACCTGCCTCGGTGGCATTGTCTGGGTTGAACTGGAAGAGAGA
      GGTGGGGCCAGGAGGCTAGAGTGGAGGCCAAGCCAATACAGGGGTCAGTGAGTTCTGGAG
      CTTTTTGAGAACTTGGGAAAGGCTGGATAGATGAGAACAGGGAAGGGAATGTCTAGGTGG
      CTCAGGCTTGGACTGGGGTCAGGGGTGTAGTGCAGACATCTCAGTAAGTCAGGATCTCAT
      GAGGGAAAAGGCTCATGGAAGGCTCAGGAAAGCTGGGCGTGGGTGGGCTGAGGTAGTGGG

9573  CTGTAGTCCCAGCTACTTAGAAGGCTGAGGCATGAGAATATGAGAATCGCTTGAACTTGG
      GAGGTGGAGGTTGCAGTGAGCTGAGATTGCCTTACTGCACTTTAGCCTGGGGGTGACAAA
      GTGAGACTCTGTCTCAAAAAAAGAAAAAAAAAAGAAGAAGAAAAATAAAGAAACCTGCCT
      CGGTGGCATTGTCTGGGTTGAACTGGAAGAGAGAGGTGGGGCCAGGAGGCTAGAGTGGAG
      GCCAAGCCAATACAGGGGTCAGTGAGTTCTGGAGCTTTTTGAGAACTTGGGAAAGGCTGG
      [A,G]
      TAGATGAGAACAGGGAAGGGAATGTCTAGGTGGCTCAGGCTTGGACTGGGGTCAGGGGTG
      TAGTGCAGACATCTCAGTAAGTCAGGATCTCATGAGGGAAAAGGCTCATGGAAGGCTCAG
      GAAAGCTGGGCGTGGGTGGGCTGAGGTAGTGGGAGAGATCTTTGTAGTGTTTCTAGCTAG
      GATGCAGAGGGTCAGAGATCATGGAGCCATCTCTTGCCAGACAGGGAAACTGAGACTATG
      GCTTCATCACTATCCTTTGGCTGCAAGGCTGGGCTCAACCTCTTCATCAGACCTGACCC

9826  AGGGGTCAGTGAGTTCTGGAGCTTTTTGAGAACTTGGGAAAGGCTGGATAGATGAGAACA
      GGGAAGGGAATGTCTAGGTGGCTCAGGCTTGGACTGGGGTCAGGGGTGTAGTGCAGACAT
      CTCAGTAAGTCAGGATCTCATGAGGGAAAAGGCTCATGGAAGGCTCAGGAAAGCTGGGCG
      TGGGTGGGCTGAGGTAGTGGGAGAGATCTTTGTAGTGTTTCTAGCTAGGATGCAGAGGGT
      CAGAGATCATGGAGCCATCTCTTGCCAGACAGGGAAACTGAGACTATGGCTTCATCACTA
      [C,T]
      CCTTTGGCTGCAAGGCTGGGCTCAACCTCTTCATCAGACCTGACCCTCAATATCATTCT
      CCTTCAGGCCCTGCCCGGAACCTCTTGGTTGCTGAGCTTGGTCAGCTCAGTGAGGGTTAA
      TTGTCTTTATGCTCCCTGCACCCCCACCCCCCGCAGTCATTCCCCCTGCCCACCAAGCAG
      CTCCTGCCACTCTTCCTGCTTCCCACTCCAGCCTCCTGTCCCCAGGGACTGCTGATGGCT
      TGGCTGGGATCTAGCCAAATGGTGGGGGGTGGGGCGGGGGTGGGGGGAAGAGCTCCCAG

10134 CTGCAAGGCTGGGGCTCAACCTCTTCATCAGACCTGACCCTCAATATCATTCTCCTTCAG
      GCCCTGCCCGGAACCTCTTGGTTGCTGAGCTTGGTCAGCTCAGTGAGGGTTAATTGTCTT
      TATGCTCCCTGCACCCCCACCCCCCGCAGTCATTCCCCCTGCCCACCAAGCAGCTCCTGC
      CACTCTTCCTGCTTCCCACTCCAGCCTCCTGTCCCCAGGGACTGCTGATGGCTTGGCTGG
      GATCTAGCCAAATGGTGGGGGGTGGGGCGGGGGTGGGGGAAGAGCTCCCAGCAGTCCT
      [C,T,A,G]
      TACCCCTTGGTCTTAATGGACTGGGAGTCTCACCCTCAGCCATGCTGCTGTCAGGCCAGG
      CCTGCGCTCCCCGGGCTTCTGCTGCTTGGGCCTATGAAATCTCCCGACTCAGCATGATTC
      CATTGCTGCATTCATTCATTCAACCACTCAACAGGAACTTCTCAGTAGCTGCTTGGTGCC
      CACTTGGCTTGTCACCGGGGACACAGAGCAGACACTGACTGAGTCCCTGTTCTCAGGGAG
      TGCCCAGTCTGATGAAGGAGAAAGAAATGGAAAGCTGCAACCCTACAGGGTGAGCAGTGC

11014 GACATAGGATGTTCATCTCTTCCCTCCTGGGCAGCCCTTCCCTTGTGGTGGTTATATCTG
      TCCTGGGTCTTCTCCGCAGGGCCCAGCAACTCCAGGCTACCCAGCCTGGCCTTATGTCCT
      TTCTCCGTCCTGTGTCACTGTCCCCTGAAGTAGGGCCAGGCTGGGGCACAATGATCCAGG
      AGTGGCAAGAACACATCTAGGCAGAGAGTGGGAGAAATGCGCAGCCTTTATTAACAAAAA
      TCTGAGATGGGTGCAGGCCCTGACTCCTCTCCAAAAATAATGATAAAGAAGCAGGCATGG
      [C,T]
      CAAATAAGGGAGTGAGGACAGACAGCAGGAAGAACTTCCTACCAATGCAGAAGGGCTGTG
      AGTCTCTTGGTTTTATGAGAGTGGGCTGTACGTGTGAAAGGGAGGGTCTCAGAGGACAAG
      AGGGGGAATTGGAGGCAGAGGCACTGTCAGCCTCTGACTCTCCCATAGGTGAGTGAGTGA
      AGTCATCCAGGGAGAGGGAACAGAGGAGGGAGATCAGGACTCATCATTCATTCATTCAGC
      AGCCGTTCACTGGCCCTACCAAACATGACACCCCTGGGGCAGATGGACAGAGCCAGTGA

12390 TTTTCACACATTTATCTCCTATTGTTCAGCTGCTTGCTCCCTGGGAAAGGCCAGGTCCCC
```

FIGURE 3-48

```
        AGTGATGTGACCCACTTCTTGAAGTCCCTGAAGTCACCCTTCTCACTGCCCCCCCACCCC
        GAAAAACAGGAGGCAACTGGGGCTTGGTGCAGCAGAACAGATTTGAGTCAAATATCTGGG
        AGGACTTCCCAACAGTGTGGTTGCTGAGATGTGTGGACCCTGGATTTCTGGGCTTTCATT
        CTTTGGATGGTTGCCTTGGGCGCAGAGGAGGCTTTGAAGATAGAGCAGAGAAGGTGGCAG
        [G,A]
        CAGGCTTATGCTCAAATTTCAGCATACTGAAAGATGTACTGTTACTCTGTAGCTGTGTGG
        TCCTGGGCAAGTTACTTAACTTCTCTGAACCTTGTGTGAATAGTGGGGTGGAGATAATTA
        TCCTTTCTTGGCAGGATGATTCTGAAGAATCTGGAAGTGCAGAGCTTAGCCCCTGGCATG
        CGGCAGGTGCTCACAAAGGTTAGCTACTGTCATTATGAACCACCCACGATCAGCCACACT
        TTCAGAAAGATTTAGCGGGGCCTGGAGAGGGAGAGACCAGAGCTAGGAGCTCAGGGCTGT

13720   ATGTGAGACATCTCGGCAGAGGAACAGCTGAGCAGAGAGCTGCTGATTCCAGGCTGAGAG
        TTTGGACTTTGTGTTGTGGCCCACCAGGATCCACCCAAGGGTTTTCTGATTAGAGCTGAG
        CTTTGAGAGAATTGGTCTTGCAGCTTAGGCTGAATGGATTGAACTGGAGAAACCAAAGTC
        AGACTGAGGCTTCTAAATCCCATCCTTGGTGCACCCAGCACTTTGCTGCTGTCCCTCCTC
        CATGCTTCTTCTCAGTTTCTTCCTTCTCCTCTCCTTCATCTTCTTCCCTCACCCTTTTTT
        [T,-]
        TTTTTTTTTTTAATAGAGACAGTGTCTTGCTGGCTGGAGTACAGTGGTGCCATAATAGCTC
        ACTGCAGCCTCAAATTCCTGGGCTGAAGCTATCCTCCTGCCTGGGCCTCCCAAAGTGCTG
        GGATTACAGGTGTGAGCCACTGCACCCAGCTCATCTTCCTCTTTCTCTCCTACTCCTCTC
        TGCCTCAGGCTGAGGAGTGATGACTTTTATACCATAGAGCTGTGCTGTAATATCACATGT
        CTCCAGAAGGGGGTGCTGTCACATACAGTCCATTCCAGCCTGAATCTTCGTTGTGTTTGA

14701   AGAGGGTGAGAATGTGTGGGTCAGTGTTCGTATAAAAGTGTGAACATACTCACATGTGTG
        AGCATGTGAGTGTCCTTTTTTTTTAGTTTAGTTTTGAGACAGGGTCTCACACTCTCACCCA
        GACTGGAGTGCAGTGGCGTGATCTCGGCTCACCGCAACCTCCGCATCCCAGGCTCAAGCT
        ATTCTCCTGCCTCAGCCTCCTGAGTAGCTGGGACTACAGGCATGCACCACCACACCTGCA
        TAATTTTTGTATTTTTAGTAGAGATGGGGTTTCACCATGTTGGCCAGGCTGGTCTTGAAC
        [C,T,A,G]
        CCTGACCTCAAATGATCCACCCACCTTGGCCTCCCAAAGTACTGGGATTACAGGCATGAG
        CCACTGCACCCGGCTGTGACTGTCCATCTTTATGTCTGATTTTGGTAAACAGTTATATGC
        ATGTGACTGTGGCTTGTGTGTGTGTACATGTATGTAGAGTGCCATATACATATGTTCTAG
        TGAAACCGTATGTGTGTTCCCTGTGTATACAGATGCCTGTGTCTCAATGTGAGCACAGGG
        ATGAGGGGATATGTGTGTGTGAAGGCCCAGACACCTGCTGTGCTAACCTTTAAGGCCGCG

15679   GCTGCCCTCCCTCCAGCCCCTAGAGCAGGTGGGGAGCTCAGAGGAGAGCCAAGTCTGTGG
        TGTGAAGCCACCTCCTGCACCTGGCTATTTCCATGCCTCCTGGGCCTCAGAGGCTGCCTT
        TGAAGTTTTTACCAGAGCTTCTGCATGCTGTGAGATTCCTCCTGGGGACGTGTGAAGTCG
        ACTGTTCCATGGAGCATGGAGACTCGATGGAGAGGAGCCCAGTGGTGAAGTGAGGCCAGA
        GGAGGGGCTTCCTCTGGAAGCCTCAATTTCTTCTTTGCAGTAGTTGCTTTTTTTTTTCGTG
        [-,T]
        TTTTTTTTGTTGTTGTTTTTTAGGTTTTCACCGTTCTAACATTCAAGGCTTTCTCTGTTA
        TCTCTCTTTGAGCTCTTAGTACTGAGACAGTGCTGGGGTTTGGGGCAGTCCTGGAGGCCT
        ATCTGGGCTCAAAGTGAGGGTGGCAGGGCAGTCCCTTAGGGAAAGGGCTGCGTGGGAGAC
        AGGGATGAGCTTCCTGCCCATAGTGGGGAGGCATGAGCAGGGGCTGGACAGCCTGGTTAG
        CAAGGCTGTATACAAGGTACCTACCCTAGTGAGGAAGTTGGTTGCAGATTATCTTGAGTC

15687   CCCTCCAGCCCCTAGAGCAGGTGGGGAGCTCAGAGGAGAGCCAAGTCTGTGGTGTGAAGC
        CACCTCCTGCACCTGGCTATTTCCATGCCTCCTGGGCCTCAGAGGCTGCCTTTGAAGTTT
        TTACCAGAGCTTCTGCATGCTGTGAGATTCCTCCTGGGGACGTGTGAAGTCGACTGTTCC
        ATGGAGCATGGAGACTCGATGGAGAGGAGCCCAGTGGTGAAGTGAGGCCAGAGGAGGGGC
        TTCCTCTGGAAGCCTCAATTTCTTCTTTGCAGTAGTTGCTTTTTTTTTCGTGTTTTTTTT
        [-,T]
        GTTGTTGTTTTTTAGGTTTTCACCGTTCTAACATTCAAGGCTTTCTCTGTTATCTCTCTT
        TGAGCTCTTAGTACTGAGACAGTGCTGGGGTTTGGGGCAGTCCTGGAGGCCTATCTGGGC
        TCAAAGTGAGGGTGGCAGGGCAGTCCCTTAGGGAAAGGGCTGCGTGGGAGACAGGGATGA
        GCTTCCTGCCCATAGTGGGGAGGCATGAGCAGGGGCTGGACAGCCTGGTTAGCAAGGCTG
        TATACAAGGTACCTACCCTAGTGAGGAAGTTGGTTGCAGATTATCTTGAGTCCCTTCAAG
```

FIGURE 3-49

18322     CCCTTTGCTCTCCTGCCAGTACCCTGACCCTCACTGGCAGAATTTCTCTGGATGCCAGGG
          GGCAAGGGAGCCCTGGATGAAGCTGCCACTTAGAAGTCGGCCTCTGGGGCACACAACCCA
          GCAGCAAAAGTTAGAGATTGGATGTGGAGGGACAAAGAGATGATGGGAAACCGAAGAACA
          GAGAGGGCATGGACTTGCCCAAGGTCACACAGCCTGTTGATATCAGAATTGGAGTCAGAA
          GCCAGGCTCTGCCTCTGAACACTCACTTTTTTGTTTGTTTGGTTTTCTTTTTTTTCTTTC
          [-,T]
          TTTTTTTTTTTTTTGAGACAGTCTTGCTCTGTCGCCCAGGCTGGAGTGCAGTGGTGCGAT
          CTTGTCTCACTGCAACCTCCACCTCCTGGGTTCAAGTGATTGTCCTGCCTCAGCCTCCCA
          AGTAGCTGGGATCACAGGCACCTGCCAGCATGCCCGGCTAATTTTTTGTACTTTTGGTAGA
          GACGGGGTTTCACCATATTGGCCAGGCTGGTCTCGAACTCCTGCCCTCAGGTGATCTGCC
          CGCCTTGACCTCCCAAAGTGCTGGGATTACAGGCGTGAGCCACTGCACCTGGCCTGAACA

18606     TTCTTTTTTTTCTTTCTTTTTTTTTTTTTTGAGACAGTCTTGCTCTGTCGCCCAGGCTG
          GAGTGCAGTGGTGCGATCTTGTCTCACTGCAACCTCCACCTCCTGGGTTCAAGTGATTGT
          CCTGCCTCAGCCTCCCAAGTAGCTGGGATCACAGGCACCTGCCAGCATGCCCGGCTAATT
          TTTGTACTTTTGGTAGAGACGGGGTTTCACCATATTGGCCAGGCTGGTCTCGAACTCCTG
          CCCTCAGGTGATCTGCCCGCCTTGACCTCCCAAAGTGCTGGGATTACAGGCGTGAGCCAC
          [C,T]
          GCACCTGGCCTGAACACTCACTTTGTCACATTCACTGAGGTCTCCTGAGTGGACTCATAT
          GCGCATTATCTACTCTCTGGCTGAGAGCTGCTTCCTGCCGTGATCACCGCGCTCTGTATC
          TGGGCAGCACAGGGGCTGCTGAAGAATGTCATTCTCAGAACGCAGTGTGCCCTGGAGCCC
          CCCAAGCCACCTGTTCATTCATCCCAACTGGCCTTGAGGGTGCCCTGGTGTGCCCTGCCT
          GTGCTTGTCACCCTGGCCATGGAGATGGACCCAAAAGCCCTTGCTCTCCGCTTCATTAGA

19070     AGTGTGCCCTGGAGCCCCCCAAGCCACCTGTTCATTCATCCCAACTGGCCTTGAGGGTGC
          CCTGGTGTGCCCTGCCTGTGCTTGTCACCCTGGCCATGGAGATGGACCCAAAAGCCCTTG
          CTCTCCGCTTCATTAGAGACAGGCACACCCAGACGCAGGCAATCAATTTTGTCGGGTGAG
          TGCTGGGACCGCTGATGAGGACCCTTCCTGAGGAGGCGATGCTGGGTCTTAGCCTTAAAG
          AACAACTGAGAGTTTTCCAGGTGGAGGAGAAAAGGAAGGGTATTCCAGGCAAAAATCCCC
          [A,G]
          TAAGAGCAAAGGTGTGAGCAGCAAGAAATCAAGGGTGGCAGGTTCAGGGCTCCTGGGCTG
          GAGGAAGGGCCTGGCGGTGGAGAGGAAGGGAGTGAAGGCCCAGCTCACAAAGGGAAGCAG
          AGGAAAGTTTAAGCAGGGTCAGGCCATGGTTAGCTTTGGGGTTAGGAAGCTCCAAATGAT
          GGGTGAAGTAGGGGGGCTAGACCCAGGTGAGAGGCAGTATTGCGGTTGGCCAAGGACACG
          TGAGTTGCATAAATGGGCCAGAGGAGGGGTGACAGCCGCTACTTCCCGGCTCACCTGCCT

19470     CCAGCTCACAAAGGGAAGCAGAGGAAAGTTTAAGCAGGGTCAGGCCATGGTTAGCTTTGG
          GGTTAGGAAGCTCCAAATGATGGGTGAAGTAGGGGGGCTAGACCCAGGTGAGAGGCAGTA
          TTGCGGTTGGCCAAGGACACGTGAGTTGCATAAATGGGCCAGAGGAGGGGTGACAGCCGC
          TACTTCCCGGCTCACCTGCCTGAGCTAAGGCCCTAGTTCCTCAGTGTCTGCCCACCAATG
          CAGGTGTGTGGCAGCTCTAGACCCTCCTCTAGGGACATCCCTCCCTGCCTCATGCTGCCT
          [A,G]
          TGGCTTTCACTCTCTGGAGCACTCATCCATGGCACCCATAAGCCACCCCCTCAGACAATG
          GCCCCTAAAGCAAAACTGTGTCACCGTTGCATATCTCTTGATAACACTCTGACCCCTCCA
          CTGCCAAATCTGATAAAAGACCTCCCTTTGAAGACCTTCCTCCTGGAGTCGGATCTCAGT
          CCTTCTTGCTGTCCAGAGCCTGGGCCTTGGGCCTCCCTGGGAGGCGAGTCAGTGAGGGCA
          GCCCCCTTATGGTGCTGGGAGTTGAGGGACCTTGGCCCAGCCAACTCATCCCTGTTGTGT

19611     TGAGTTGCATAAATGGGCCAGAGGAGGGGTGACAGCCGCTACTTCCCGGCTCACCTGCCT
          GAGCTAAGGCCCTAGTTCCTCAGTGTCTGCCCACCAATGCAGGTGTGTGGCAGCTCTAGA
          CCCTCCTCTAGGGACATCCCTCCCTGCCTCATGCTGCCTATGGCTTTCACTCTCTGGAGC
          ACTCATCCATGGCACCCATAAGCCACCCCCTCAGACAATGGCCCCTAAAGCAAAACTGTG
          TCACCGTTGCATATCTCTTGATAACACTCTGACCCCTCCACTGCCAAATCTGATAAAAGA
          [C,A]
          CTCCCTTTGAAGACCTTCCTCCTGGAGTCGGATCTCAGTCCTTCTTGCTGTCCAGAGCCT
          GGGCCTTGGGCCTCCCTGGGAGGCGAGTCAGTGAGGGCAGCCCCCTTATGGTGCTGGGAG
          TTGAGGGACCTTGGCCCAGCCAACTCATCCCTGTTGTGTCAGCCTCTCTGGGCCTGGGCA

FIGURE 3-50

```
        GCCAACTCATTTTCAGTGCTAATTAGCATCTCCCCTGCAGCTTTCTGCCCCACTCTAAGT
        GCTTGACAATCATTAGGTGTTACTGTGTGCAACTGGATCCCAGCTCCGGCACCTCCCTGC

20641   CCCCACCTGTGCAGCGTCTCTCGCCTCTGGGCTGCCGCACATGCTGTTGCCCGGAATTCC
        CTTCCCCAAGGCCCTCCTCTTTTTACCTGGCTAATTCCTGTCATTCTTCAGATCTTCTAG
        GAAGACTTCTGCCTCCTTGATAGGGGCCTTTCCATACTCCCCAGCCTTGGAGTGCTTCCT
        GCCACATGGCATCACTGACTGTTTTCCAATGAGTTTCTGTCAAGTTTTGGGATGAAGGAT
        TTTGCCTGTGCTCGTTGAGGTGGTGACTGTGGGTGTGAGTGGGTGATTAGGGCCAAAAAA
        [A,C]
        CCCCCCAAAAAACTGGACAGAGGCAAATTTGGGGGGAAATGAGTTAGGAATAGCTGTGAG
        GAGCCCCAGCTACTCAGGGCCTCAGAAGATATTTATTTCTGTATTTATTTATTTATTGAG
        ACAGAGTCTTGCTCTGTCACCCAGGCTGGAGGGCAGTGGCGCTATCCTGGCCCACTGCAA
        CCTCCACCTCCCAGGTTCAGGCGATTCTCCTTCCTCAGCCTCCCGAGTAGCTGGGATTAC
        AGGTGCGCACCACCATGCCTGGCTAATTTTTCTATTTTTAGCAGAGACGGGGTTTCACCA

20642   CCCACCTGTGCAGCGTCTCTCGCCTCTGGGCTGCCGCACATGCTGTTGCCCGGAATTCCC
        TTCCCCAAGGCCCTCCTCTTTTTACCTGGCTAATTCCTGTCATTCTTCAGATCTTCTAGG
        AAGACTTCTGCCTCCTTGATAGGGGCCTTTCCATACTCCCCAGCCTTGGAGTGCTTCCTG
        CCACATGGCATCACTGACTGTTTTCCAATGAGTTTCTGTCAAGTTTTGGGATGAAGGATT
        TTGCCTGTGCTCGTTGAGGTGGTGACTGTGGGTGTGAGTGGGTGATTAGGGCCAAAAAAA
        [A,C]
        CCCCCAAAAAACTGGACAGAGGCAAATTTGGGGGGAAATGAGTTAGGAATAGCTGTGAGG
        AGCCCCAGCTACTCAGGGCCTCAGAAGATATTTATTTCTGTATTTATTTATTTATTGAGA
        CAGAGTCTTGCTCTGTCACCCAGGCTGGAGGGCAGTGGCGCTATCCTGGCCCACTGCAAC
        CTCCACCTCCCAGGTTCAGGCGATTCTCCTTCCTCAGCCTCCCGAGTAGCTGGGATTACA
        GGTGCGCACCACCATGCCTGGCTAATTTTTCTATTTTTAGCAGAGACGGGGTTTCACCAT

21036   ATTTCTGTATTTATTTATTTATTGAGACAGAGTCTTGCTCTGTCACCCAGGCTGGAGGGC
        AGTGGCGCTATCCTGGCCCACTGCAACCTCCACCTCCCAGGTTCAGGCGATTCTCCTTCC
        TCAGCCTCCCGAGTAGCTGGGATTACAGGTGCGCACCACCATGCCTGGCTAATTTTTCTA
        TTTTTAGCAGAGACGGGGTTTCACCATGTTGGCCAGGCTGGTCTTCAACTTCTGAGCTCA
        GGTGATCCTCCTGCCTCGGCCTCCCAAAGTGCTGAGATTACAGGTGTGAGCCACTGCACC
        [C,T]
        GACCTCAGAAGACATTGAAACCCACAGAGAGGACACAGCCAGATGCCCTCTGCCTCATTT
        TCTCAGACCCTGCCTGATTTCTCTTATGTTTCTTCTAGGCTTGCTCCCTGACCCAGTTCC
        CTCCTTCCCAGAGCTGGCCTTGCCCCTTGCCACCTCTCGGAGCTCACACATACTCACTCA
        CCTTCTCTGCTTGGCTGTGCCCTACCCCTACTTCTACGTGCAGTGAAATCCTTGTTATTC
        AAGGCCTGAGGTCAGTGGGCACATCATCCATGCCTGGCGTCCTAACCCGTGCCACTGAGT

21871   AGAGCAGGGAGAAAGCTAATGAGATCAAGGATGTGCAAATGCACTCAGAAGGTGCCTAGT
        GAGTCCTTGCTAACTGGCACTTAGTGAAACAAACACCTCCTGTGTGAGCACCTAATATGT
        GCCTCTGTAGTGGGCTCTGTGACCCGCCCCTCCTTAGTTTCTGCATGGCTGCCAGTTCTG
        CACAGCTGTTACTGCTGTGGGGCTTAGAAGGTGGGGTATGACTACTTTTTCTGAATTT
        ATTTTTAATTTTTTACATCTGTTTTATGGAGGCATAATTTACATACAGTAAAATCACCAA
        [T,C]
        TTAAAGTGTATAATGAGTTTTGATAAATATATATGGTCATAACCACCATGACAATTAAGA
        AAAGAATATTTTTATCCTGGCAAACTTCCCTTGTGCCCTTTGTAGTCAGTCCCTTTGAGG
        GGGACTTCTTATAGGAGTGTGAGAAGTACTGGGTTTTCCTTGGGCTGCAAACCTGGGCAC
        ATGGAGTGGGGGTGCCTCCAACATGCTGGAAGTTGCCAGGGAACTGCTGACCCTCTCTGG
        GCCTTGGTTCCTGGCAGAGGCAGTGCAGCCAGGCAGGGGAAGGGATGCTTAGGCCTTGGT

22907   TCTGTGCAAGGTGGGGGTGGAAAAAAGGCTGGGAACTCATGGGAGCACCCCAGGTGTCTG
        CAAGGAGATGAAAGCTGATCCTCCGCCCCACTGAGGTCCTAAGGAAGAAAGGCCGAGTCA
        GAGCTGCAGCAGGAGGGATTCGGATCAGACTCAAGAACACTTCCCAGTGGTGCTTATTTG
        AGAACTGGGACGGCAACACTAGATTGTAAACTCTGTGAGGGCAGGGATTAGGTCTGTGAC
        CGCCTCCTCACCCAGCGGGAGACCAAGAATGAGACTTGGGAGTCAGACACAACTGGGTGT
        [G,A]
        ACTCCTGCCTTTGCGGGTTGCCAGCACGTGGGCTTGGGCAGGTTCCTTTATCACCAGAAG
```

FIGURE 3-51

CTTTGCCGTCTCCTCCACTATAAAGTGGGCACAATAACATCCACCTGCATGCATATTATA
AGGATTGAGTGGGTTAAAATGTGCAAAGCAAGACTTTGTGCTCAGCTGGGCACAGCGGCT
CACACCTGTAATCCCAGTACTTTGGGAGGCTGAGACAGAGTGCTTCAGCCCAGTAGTTTT
GAGACCAGCCTGGGAAACATAGGGAGACCCTGTCTCTTAAAAGAAAAAAAAAAATTAGAAG

23722   GCAGTGTGGGCTGGGTGTGGTGTCTCATGCCTGTAATCCCCAGCACTTTGGGAAGCTGAG
        GCGGGAGGATCACTTGAGGCCAGGAGTTCAAGACCAGCCTGGGTAACTTAGCGAGATCCC
        ATCTCTACTTCAAAAAAATTTAAAACAGAAAAAATCTAGGGTGTGTGGGGGGGCAGGTGG
        GGAGGTTGCAGGGGTGCCTCACAGGTGGGAGTCTGGCATTTCTCCTCCAGGCTGAGGAGG
        TGGTGACTTCCAGGGAAAGTCCTGGGAGGGATCAGAACCACAGCTCCAGCCTGCTTGGAT
        [A,G]
        AGGGTGGTCTTCTGGCTGCCAGGAGGGTAGCTAGGTGGGAAGATCTGCCCTTGTTTCCTC
        CATAACCTGGGGTGGGAGGAGGAGGAGCTCCCAGCCCAATCTGATGGGGGAGACCAGAAC
        CCTCACCCACCATTGCTGGCAGTTCAGAGAAGGCAGCGATAAGTCGGGGTGGGGCATCCT
        GAAAGGCTTCCCAGAGGATTGGATGGGAGGATTAGCTGAGAAGACATCCGGCATCCGTAA
        AATGGAGTAATGATTCTGACCCTGCAGGTTTTCTGGGAGGATTAAATGAGTTACATTTTA

24121   ATCTGATGGGGGAGACCAGAACCCTCACCCACCATTGCTGGCAGTTCAGAGAAGGCAGCG
        ATAAGTCGGGGTGGGGCATCCTGAAAGGCTTCCCAGAGGATTGGATGGGAGGATTAGCTG
        AGAAGACATCCGGCATCCGTAAAATGGAGTAATGATTCTGACCCTGCAGGTTTTCTGGGA
        GGATTAAATGAGTTACATTTTAAAGATGCCTGGTACATGCCTGCCAGGAGAAGGCACAAC
        ATATGAACTCCCTCCCTCTTCCCTCCACCCCTCCTCAGCTCCTGTGACATCAGGAGGGAC
        [A,C]
        TGCCCTGCCCTGCTCACAGAGGCTGGGTGGGAGGCTCCCATCATGGCCTTCACTGAGGCT
        GCCTCTGCAGTTGGACCAAGCTGGACACACAGTAGGTGCACATAACAGATGGGGCAGGT
        CTGTGCTTGTTTTACCAGGGTGTTGGGAGGCTGAGGGAAGGGCACAGCTGGATTGGGGTG
        ATGGAGTTCAATCCCTGCTCCTCCCCCAGATCCAAGATCCTAAGACGCCTATGTCCAGTG
        GCTGCTCTGATCAGCTCTGACCAGCTCTCCTCACACCTCATAGGCCTTCCAGGGTTCAGG

24553   TTACCAGGGTGTTGGGAGGCTGAGGGAAGGGCACAGCTGGATTGGGGTGATGGAGTTCAA
        TCCCTGCTCCTCCCCCAGATCCAAGATCCTAAGACGCCTATGTCCAGTGGCTGCTCTGAT
        CAGCTCTGACCAGCTCTCCTCACACCTCATAGGCCTTCCAGGGTTCAGGTGATGAATTAG
        TGATGACAGCATCCAGCATCGCTATGACAACCACATGGCACTCTTAGCCTCCAGTCAGGG
        CTCAGCCGCAGAGGCCAGAGACCCCTTTGGCTCTGGGCCTTTGTACTGGCGTGTGTGAGC
        [G,C]
        GGGCTGGGGCCTGAGGGAGATGGAGGAGTGGGAGGGGCAGGGGCCGGGGCATGGGGCTGC
        ATCTGGCATGGACTGGAGTTCATTCAGATTGTTCCATCCAGAGGGACCTTGGGGACAGTT
        GTTTCTCTCCTTCCTTCCCCCTTTCTTTTCATTCCTCCATCCCTCCTCTTTCCCCTCCTC
        CCACTTCTTCTGAGCCTTGTTCCTGTTTGAGGCCCTGGGCTGCCAACCCTTTTCCCCTCC
        TCTGGGAATAAAGCCAGGCTCAGCCCTCACCCCGGGGAGCTGAGTGAGGTGGGGGACAGC

25917   CATCTCCTTCCTCCGTCTCTCAGGAGCCTTTGGCTGAGTTAGGCACCTACAGGAGGCAAG
        GGCCCCCCCGAGCCCCTCACATTCTCCTCAGGGCTCCTTCTGGCCCTGGGGCCTGATATT
        GGGCCTGCTGTGCTGGAACTTATCCAGGCAGAATAAACCTTTAGCCCCATTGTCCTGATG
        AAGAAACTGAGGTCCCGAGGTAACAGTGACTCATTCAGGGTTACAACAGGTCAGTGGCTG
        GGCTGGGCCTAGCGTCTGGCCCTCAGCTTGTCTACATGGCCCCCCTCGTGGCTCTCCCCT
        [T,C]
        GCCTCTCGCACCCCACTGTGCAGCATGGTTGGGCCTGCCAGCCTTGATGGATGGCTCTGC
        AGCTCAACCTCCCTCCCATTCCTCTCCAGATGCCGGGCCGTGAGCCTCCTAATCACCAGT
        CCTGCCTGGTGGCCGCCAAGCCATCCATCTCCCCACACAGCCTTGCCCAGCACAGGTGAT
        TTTGTTTGGGGAGAAGGGGGGCACAGCAGGTCTTCCTCTGAGGCTGAGCCAAGAGTTTGG
        CTGCAGCCCCCACTCTGGGGTGCCCGAGGGTTAGGGAATAGCCTGCACTCCCTTGCTGGA

26573   ACACACACTCACAGTAACACTAATAAAAGCTCTCGTGTAGCAAAAGAATATTGTATGGCA
        AGTATTGTTGCAGAGCCATATGTATCATCTCATTCATCACTCCACTGTAGAGATACAGAA
        ACTCAGGCTCAGAGAGGTTAAGTGACTTGCATAGGCTCCATATCCAGGAAATGGAGGAGC
        TGGGATTTGAACCCACATCCTTATGGCTCACATCTTGCATTCACAACTCCTGCTCTACTG
        ACTCACCTGTGCACACACACACACATGCACACACACACACGTGCGTGCACACACACACAC

FIGURE 3-52

[-,A]
GGCACTCACTTGCATGCATGAGCACGAGCCACCATTTTGGCTCTTGTACCATCCATCTAC
CTGGGCCAGGTTCTTGAGGAGTGAGGAGAATGCTGGGCTGCAGAGGGCATGAGGGGTCAC
TGCTCATTGTCCCCAGGCTGCCCCAAGCTGGCTGTGGCACTGGCTGGCTGGGGAGCTGCA
GGGAGGCAGCAGCCTCCAGGCAGTGGAAAGGGGAGGCTGGGAGACAGTCGATCGATCATC
CCTGCAGTGCCTCCTTCCAGGAACTGGGGCCCAGGGGAGTGTGGCGCCACGGGTCGATGT

27525    CAGAGCCTTTGGAGACCTCGACAGACAATACGATGAGTTAAGAAATGTAAAGGGGCACAT
AGTGGGTGCTGAATTCATCTTGTCTCGTTCCTCCAGTAAGAGTCTGGAGAAACCAAGAGC
AGCTGGGTGCCTCTGAGGGCACAGGAGCTCCCAGGGCTGGCTGGCAGGTGCAGCTAACAG
TGTTAGCAATCCCAAGGACAGGTAGCTTGGGGCGGAGGACAGCATGCTGTCACCCATCCT
GATGAGGGGAGAGATGTCTGGTGCTAGGAGCAGTGGTGGCCGGAGGAGGGCTGGGGACCC
[T,A]
CCCCAGGCCACCCCACACTCTCCCTCTGGGAGGGGCTCCTGAGCAGGCCTGGTCACCTTG
CTTCTTGGCTGCTTCTTCCCCGGCGGAGGAGCCTCCCCCAGGCTCTCCCACCTGCACTGG
CCTCAAGAGAGCTGGGATTGAGCCCCAGTTCAGGCACCTGCTGGCTGGCGGAGGTTAGGG
CAAATCACTTTCCTCAGCCCTCTCATCCGTGACAGGCTCTGGTGAGGGTTAAATGAGATG
TTGCCCGTCAAGTGCCTGCCACTTCCCTGACGCCGAGCAGCTAGGCTGCTCTGGGTTCTC

27625    AGTCTGGAGAAACCAAGAGCAGCTGGGTGCCTCTGAGGGCACAGGAGCTCCCAGGGCTGG
CTGGCAGGTGCAGCTAACAGTGTTAGCAATCCCAAGGACAGGTAGCTTGGGGCGGAGGAC
AGCATGCTGTCACCCATCCTGATGAGGGGAGAGATGTCTGGTGCTAGGAGCAGTGGTGGC
CGGAGGAGGGCTGGGGACCCTCCCCAGGCCACCCCACACTCTCCCTCTGGGAGGGGCTCC
TGAGCAGGCCTGGTCACCTTGCTTCTTGGCTGCTTCTTCCCCGGCGGAGGAGCCTCCCCC
[T,C,A]
GGCTCTCCCACCTGCACTGGCCTCAAGAGAGCTGGGATTGAGCCCCAGTTCAGGCACCTG
CTGGCTGGCGGAGGTTAGGGCAAATCACTTTCCTCAGCCCTCTCATCCGTGACAGGCTCT
GGTGAGGGTTAAATGAGATGTTGCCCGTCAAGTGCCTGCCACTTCCCTGACGCCGAGCAG
CTAGGCTGCTCTGGGTTCTCTAGCACCTGCCTCCCCTGGTCCCAGCACTGGGTGGGCGGC
TGTGTTCTACCGGTCACTGGTGGGTCCTCAGGGCCCCGACACAGGGCCTGCTATTGGGAA

27833    CCACCCCACACTCTCCCTCTGGGAGGGGCTCCTGAGCAGGCCTGGTCACCTTGCTTCTTG
GCTGCTTCTTCCCCGGCGGAGGAGCCTCCCCCAGGCTCTCCCACCTGCACTGGCCTCAAG
AGAGCTGGGATTGAGCCCCAGTTCAGGCACCTGCTGGCTGGCGGAGGTTAGGGCAAATCA
CTTTCCTCAGCCCTCTCATCCGTGACAGGCTCTGGTGAGGGTTAAATGAGATGTTGCCCG
TCAAGTGCCTGCCACTTCCCTGACGCCGAGCAGCTAGGCTGCTCTGGGTTCTCTAGCACC
[C,T]
GCCCTCCCCTGGTCCCAGCACTGGGTGGGCGGCTGTGTTCTACCGGTCACTGGTGGGTCCT
CAGGGCCCCGACACAGGGCCTGCTATTGGGAAAGAGGGAAGTAAACATCCCAGGGCTGGA
GCTCTGCCCACTATGGAGGTGTTCCATCTTAGGCTCTGTAATCTCCTCATTCACTCTGGT
ATGGGGACAAATGTGCCTCTCTGCACTAACTGAGCCCCCATGGGCAACTAGGAGTGGTGT
CACTTGGGGTGGAGGTGGGCAAGGATCTCTGGACTGGGATTTCCAAGCCCTGACTTCCTG

27852    TGGGAGGGGCTCCTGAGCAGGCCTGGTCACCTTGCTTCTTGGCTGCTTCTTCCCCGGCGG
AGGAGCCTCCCCCAGGCTCTCCCACCTGCACTGGCCTCAAGAGAGCTGGGATTGAGCCCC
AGTTCAGGCACCTGCTGGCTGGCGGAGGTTAGGGCAAATCACTTTCCTCAGCCCTCTCAT
CCGTGACAGGCTCTGGTGAGGGTTAAATGAGATGTTGCCCGTCAAGTGCCTGCCACTTCC
CTGACGCCGAGCAGCTAGGCTGCTCTGGGTTCTCTAGCACCTGCCTCCCCTGGTCCCAGC
[A,G]
CTGGGTGGGCGGCTGTGTTCTACCGGTCACTGGTGGGTCCTCAGGGCCCCGACACAGGGC
CTGCTATTGGGAAAGAGGGAAGTAAACATCCCAGGGCTGGAGCTCTGCCCACTATGGAGG
TGTTCCATCTTAGGCTCTGTAATCTCCTCATTCACTCTGGTATGGGGACAAATGTGCCTC
TCTGCACTAACTGAGCCCCCATGGGCAACTAGGAGTGGTGTCACTTGGGGTGGAGGTGGG
CAAGGATCTCTGGACTGGGATTTCCAAGCCCTGACTTCCTGTTATTTCAGGCACTACCTC

28478    TCCCCTTGAGGGTAAGAGACACATGTGACCTCTGACCTCCAGAGTCTCTCTTCTGAGCTT
CTGTGCCCAGATGATTCTGTGTTCTAGGGGACAGGCGAGGCTGGGGGTGACCCCCATGC
CACTGATGGGCAGACTAAGGAGCAGGGGCCCAGGACTGGGGCCAGCTCAGGACTCTGGTG

FIGURE 3-53

```
              GCCTCGGTGCCCTTGACCTGGTATTGCTGCCGTTTTGCCCCACTGCTGTCTGTCTCCGCG
              TCCGAGTCACCACCTGTCCCTCTCCAGTCCTCTCCTCTCTTCCTTTATTACTATCTCTAT
              [C,A]
              TTGCCTCCTGCCTCAGGCTTATCTCCTCCTGTCATGCCTCTATCCACCTCTGTCACTCCC
              CTGCGACTCTGCCTCACTCCCTGGCACACCCTCTCCCTCCCTGGGAGTCGGGAGTGGAGC
              CTCGCTGGGAATCAGGACCCCCCTGCCTCTGGTCTCTGTCTAAGCAGTCTCTGCGATTCT
              GGCCAGCTCTTATCTTTTTCCACCTTCCCGAATCTCTCTTGCTGTCTGATGGTGTCTCTG
              CCTTTCACTGTCTCTGAACTCCCTTTGTTTTTCTCTATATGCTTCTCTCTGCTCTTATCT

28514    CTCCAGAGTCTCTCTTCTGAGCTTCTGTGCCCAGATGATTCTGTGTTCTAGGGGACAGGC
              GAGGCTGGGGGGTGACCCCCATGCCACTGATGGGCAGACTAAGGAGCAGGGGCCCAGGAC
              TGGGGCCAGCTCAGGACTCTGGTGGCCTCGGTGCCCTTGACCTGGTATTGCTGCCGTTTT
              GCCCCACTGCTGTCTGTCTCCGCGTCCGAGTCACCACCTGTCCCTCTCCAGTCCTCTCCT
              CTCTTCCTTTATTACTATCTCTATATTGCCTCCTGCCTCAGGCTTATCTCCTCCTGTCAT
              [T,C,G]
              CCTCTATCCACCTCTGTCACTCCCCTGCGACTCTGCCTCACTCCCTGGCACACCCTCTCC
              CTCCCTGGGAGTCGGGAGTGGAGCCTCGCTGGGAATCAGGACCCCCCTGCCTCTGGTCTC
              TGTCTAAGCAGTCTCTGCGATTCTGGCCAGCTCTTATCTTTTTCCACCTTCCCGAATCTC
              TCTTGCTGTCTGATGGTGTCTCTGCCTTTCACTGTCTCTGAACTCCCTTTGTTTTTCTCT
              ATATGCTTCTCTCTGCTCTTATCTCTGGGCCTCTGTCTCTCAGGGCCTGACTGGTCTTGA

28702    GCTGTCTGTCTCCGCGTCCGAGTCACCACCTGTCCCTCTCCAGTCCTCTCCTCTCTTCCT
              TTATTACTATCTCTATATTGCCTCCTGCCTCAGGCTTATCTCCTCCTGTCATGCCTCTAT
              CCACCTCTGTCACTCCCCTGCGACTCTGCCTCACTCCCTGGCACACCCTCTCCCTCCCTG
              GGAGTCGGGAGTGGAGCCTCGCTGGGAATCAGGACCCCCCTGCCTCTGGTCTCTGTCTAA
              GCAGTCTCTGCGATTCTGGCCAGCTCTTATCTTTTTCCACCTTCCCGAATCTCTCTTGCT
              [G,C]
              TCTGATGGTGTCTCTGCCTTTCACTGTCTCTGAACTCCCTTTGTTTTTCTCTATATGCTT
              CTCTCTGCTCTTATCTCTGGGCCTCTGTCTCTCAGGGCCTGACTGGTCTTGACCTCTTTG
              CCTCCTTCTTCCCCTCGAGAGCCCAGCCAGGCAGCAGGTCCAGCCCTCCAGCCCAGAGAA
              CAGATGGAGTCCACCCTCCCTCTCTCTTGCTGGCTGCCTCGGAAGCCCCAAACAATGGCC
              TCCGCCCTGCACCGTGCCTTGTTGCTAGGCCTTGGGCTGGCAGCACCTGGCTTCCATAGC

28859    CTGGCACACCCTCTCCCTCCCTGGGAGTCGGGAGTGGAGCCTCGCTGGGAATCAGGACCC
              CCCTGCCTCTGGTCTCTGTCTAAGCAGTCTCTGCGATTCTGGCCAGCTCTTATCTTTTTC
              CACCTTCCCGAATCTCTCTTGCTGTCTGATGGTGTCTCTGCCTTTCACTGTCTCTGAACT
              CCCTTTGTTTTTCTCTATATGCTTCTCTCTGCTCTTATCTCTGGGCCTCTGTCTCTCAGG
              GCCTGACTGGTCTTGACCTCTTTGCCTCCTTCTTCCCCTCGAGAGCCCAGCCAGGCAGCA
              [A,C,G,T]
              GTCCAGCCCTCCAGCCCAGAGAACAGATGGAGTCCACCCTCCCTCTCTCTTGCTGGCTGC
              CTCGGAAGCCCCAAACAATGGCCTCCGCCCTGCACCGTGCCTTGTTGCTAGGCCTTGGGC
              TGGCAGCACCTGGCTTCCATAGCGACGGGTGCTTAGAAACAGAATGCCACATCTCCCAGT
              CCCACCACAGGAGCCTTTGCCGATTGAGCGAGTGCCTTTTGATCAATCAGGAAGTGTGGC
              CAGGCTCTAGGTTGCCTCCAACTTGAGGAGGCAAGAGAGGAGGGGACTGTGGTCTCTGCC

28960    GCCAGCTCTTATCTTTTTCCACCTTCCCGAATCTCTCTTGCTGTCTGATGGTGTCTCTGC
              CTTTCACTGTCTCTGAACTCCCTTTGTTTTTCTCTATATGCTTCTCTCTGCTCTTATCTC
              TGGGCCTCTGTCTCTCAGGGCCTGACTGGTCTTGACCTCTTTGCCTCCTTCTTCCCCTCG
              AGAGCCCAGCCAGGCAGCAGGTCCAGCCCTCCAGCCCAGAGAACAGATGGAGTCCACCCT
              CCCTCTCTCTTGCTGGCTGCCTCGGAAGCCCCAAACAATGGCCTCCGCCCTGCACCGTGC
              [C,G]
              TTGTTGCTAGGCCTTGGGCTGGCAGCACCTGGCTTCCATAGCGACGGGTGCTTAGAAACA
              GAATGCCACATCTCCCAGTCCCACCACAGGAGCCTTTGCCGATTGAGCGAGTGCCTTTTG
              ATCAATCAGGAAGTGTGGCCAGGCTCTAGGTTGCCTCCAACTTGAGGAGGCAAGAGAGGA
              GGGGACTGTGGTCTCTGCCTTCTGGAGCTGGGGGGACTGCTGGGCTGGGAGGAGTTGCTC
              AAGTACAGCCCTGAAGCCAAGGAAGGACTGGGGGAGGCCCTGGGCTCTTTTCCCCAAGTC

29030    CTCTGAACTCCCTTTGTTTTTCTCTATATGCTTCTCTCTGCTCTTATCTCTGGGCCTCTG
```

FIGURE 3-54

```
           TCTCTCAGGGCCTGACTGGTCTTGACCTCTTTGCCTCCTTCTTCCCCTCGAGAGCCCAGC
           CAGGCAGCAGGTCCAGCCCTCCAGCCCAGAGAACAGATGGAGTCCACCCTCCCTCTCTCT
           TGCTGGCTGCCTCGGAAGCCCCAAACAATGGCCTCCGCCCTGCACCGTGCCTTGTTGCTA
           GGCCTTGGGCTGGCAGCACCTGGCTTCCATAGCGACGGGTGCTTAGAAACAGAATGCCAC
           [A,G]
           TCTCCCAGTCCCACCACAGGAGCCTTTGCCGATTGAGCGAGTGCCTTTTGATCAATCAGG
           AAGTGTGGCCAGGCTCTAGGTTGCCTCCAACTTGAGGAGGCAAGAGAGGAGGGGACTGTG
           GTCTCTGCCTTCTGGAGCTGGGGGGACTGCTGGGCTGGGAGGAGTTGCTCAAGTACAGCC
           CTGAAGCCAAGGAAGGACTGGGGGAGGCCCTGGGCTCTTTTCCCCAAGTCAGCCTGCTGC
           AAGAGGCACAAGCTTGGGAGCTGGAAGGGGCTGTGTTGAAATTGCTGTTCCATCATTTCT

29348      AGGAGCCTTTGCCGATTGAGCGAGTGCCTTTTGATCAATCAGGAAGTGTGGCCAGGCTCT
           AGGTTGCCTCCAACTTGAGGAGGCAAGAGAGGAGGGGACTGTGGTCTCTGCCTTCTGGAG
           CTGGGGGGACTGCTGGGCTGGGAGGAGTTGCTCAAGTACAGCCCTGAAGCCAAGGAAGGA
           CTGGGGGAGGCCCTGGGCTCTTTTCCCCAAGTCAGCCTGCTGCAAGAGGCACAAGCTTGG
           GAGCTGGAAGGGGCTGTGTTGAAATTGCTGTTCCATCATTTCTAGCTGCATGACTTTGGA
           [T,C]
           GAATGACCTCAGGTCCCAGGGCCTCAGTTTCATCAACTGTAAAATTGGGCTAATAATATC
           ATGAAGATTAAATGAGAGAATAGATCTGGCACTTAGTAGGTGGTCATCAATGGCCATTCC
           CCTCCCTTCCCCTTTAAAGTTGTTTAAAATTTAATTGACAGAGAGGAGAAGGAGGGTTCT
           TCAGGCCTGTGGAATGGTGTAAGCAAAGGGGTGGAGGCTGGCATGCACCTCACATATGCT
           GGAGTATTTAGGGAGGACCAGGGGCCATATCTGGAAATGGTTCTGCCAGAAGCAGCCAGG

29973      CCTGTAATTCCAGCTACTAGGGAGGCTGAGGCAGGAGGATCACTTGAGCCCTGGAGTTCC
           AGATCAGCCTGGGCAACATAGTGAGACCCCATCTCAAAAAAACAAAACACAACAGGCAGG
           CTGATGGGCCCATGGAGAAGGGACTCTGTCTCCTGGGAGGTATATTCTTGCCAGGTGCAA
           AGGGATGGGCTTGACTAATTTCTCCTCTAGCATTTGGGGCTGCTGGGTAGGGAGCTACAT
           TGGGGTCCCCTTGCTTATTCTCATGCTGCTCCCTACTTCTGCCCTGTCACTTGGTCCCAG
           [T,C,G,A]
           AGAGGGGCTCCCACTGGTTCCTTTTCCCTGCCAGGCCTGCCCACCAAGGCCACCATGGCC
           ACACAGCCTGAATCCTGGGGCCAGCAAGTGTCCATGGAAGGCCCCACTCTGTCATCGTAG
           AGATCAGGAAACAGGCTCAGAAGTAGGAGGGCTTCCTGGTCCTAGGGCCCAGCTCTTCCC
           TCTTTTCAGGCCTGTCTTCTGCACTAAGGACTTCAGGCCACCAGGGAAGGTGGGGAGGGA
           GGAAAGGAGATGAGATAGACTTGGGCGGGGGCCTGAGGACAGAGTTTCATGTCACTTGGG

30153      AGGGATGGGCTTGACTAATTTCTCCTCTAGCATTTGGGGCTGCTGGGTAGGGAGCTACAT
           TGGGGTCCCCTTGCTTATTCTCATGCTGCTCCCTACTTCTGCCCTGTCACTTGGTCCCAG
           GAGAGGGGCTCCCACTGGTTCCTTTTCCCTGCCAGGCCTGCCCACCAAGGCCACCATGGC
           CACACAGCCTGAATCCTGGGGCCAGCAAGTGTCCATGGAAGGCCCCACTCTGTCATCGTA
           GAGATCAGGAAACAGGCTCAGAAGTAGGAGGGCTTCCTGGTCCTAGGGCCCAGCTCTTCC
           [C,T]
           TCTTTTCAGGCCTGTCTTCTGCACTAAGGACTTCAGGCCACCAGGGAAGGTGGGGAGGGA
           GGAAAGGAGATGAGATAGACTTGGGCGGGGGCCTGAGGACAGAGTTTCATGTCACTTGGG
           CAGCCAGGAAAGGGTTAAAGATCCCTTATCCCAAGCCATGGGCACTGGCACTGCCAGAGG
           ATGCTGAGGCCTGCTGGGGCATAAGGACAACAAGCAACATCCTTTTCTGAGCTGTTGGGA
           GTGCCAAGCTCTCTGTTAAATACTTTTGAGCCTCTTCTCATGTATTCACAGCCACCTTTC

30389      CGTAGAGATCAGGAAACAGGCTCAGAAGTAGGAGGGCTTCCTGGTCCTAGGGCCCAGCTC
           TTCCCTCTTTTCAGGCCTGTCTTCTGCACTAAGGACTTCAGGCCACCAGGGAAGGTGGGG
           AGGGAGGAAAGGAGATGAGATAGACTTGGGCGGGGGCCTGAGGACAGAGTTTCATGTCAC
           TTGGGCAGCCAGGAAAGGGTTAAAGATCCCTTATCCCAAGCCATGGGCACTGGCACTGCC
           AGAGGATGCTGAGGCCTGCTGGGGCATAAGGACAACAAGCAACATCCTTTTCTGAGCTGT
           [T,C]
           GGGAGTGCCAAGCTCTCTGTTAAATACTTTTGAGCCTCTTCTCATGTATTCACAGCCACC
           TTTCAAGGAAGGCCAGTTGATCCCCAGTTTAGAAGTGAGAAAACGGGGTCTCCAGGAGGC
           ACTTGTCTAAGGTGACACAGCTGGAGAGTTGGAGATGGTGGTTAGACCGAGTCACCCCCC
           CAGACCCTGGCCTCTCCCTGCGTGCCCCTTCCAGGACACCCATCACTCCCTTGACACCCC
           TTGGGAGTGGGTGTTCATTTCCTTGGGCTCTCCCAATCCCAGTCCTTGGTATCCCCAACT
```

FIGURE 3-55

30581 GAAAGGGTTAAAGATCCCTTATCCCAAGCCATGGGCACTGGCACTGCCAGAGGATGCTGA
GGCCTGCTGGGGCATAAGGACAACAAGCAACATCCTTTTCTGAGCTGTTGGGAGTGCCAA
GCTCTCTGTTAAATACTTTTGAGCCTCTTCTCATGTATTCACAGCCACCTTTCAAGGAAG
GCCAGTTGATCCCCAGTTTAGAAGTGAGAAAACGGGGTCTCCAGGAGGCACTTGTCTAAG
GTGACACAGCTGGAGAGTTGGAGATGGTGGTTAGACCGAGTCACCCCCCCAGACCCTGGC
[C,G]
TCTCCCTGCGTGCCCCTTCCAGGACACCCATCACTCCCTTGACACCCCTTGGGAGTGGGT
GTTCATTTCCTTGGGCTCTCCCAATCCCAGTCCTTGGTATCCCCAACTGCAGGCAGACAC
AGGTGCTTGCTGCTGTGCCCTCCCCTTTACCTGGCATCACAGAGACTCAAGCCCACTGAC
CATTAGGCTCTCAGGGGCATAGAAACCAGGTGCTGGAGTCTTAGAGTCCTGCAATCAGGC
ATCTCAGGCAGTCAGGACATTAGAATGTTAGAATCTTGGGCTTCTACATTCTCAAGACCC

31147 TGTTAGAATCTTGGGCTTCTACATTCTCAAGACCCCAGGTTCTCGCATTCACAGAATGTA
AGAAAAACAGACTTTTTGAATGATGGGGTGTTATAACAGAAGCTTTGATTTTCTAAGAAC
ATGAAGCTCTGGGAGTTCTTGGAGCCTTGAAGCCATAGACTGGGGCCTCCCTGTGTGATG
GTTTCTGAGTTAGCAGGGAGTGTTCAGAGTATGGGGCCTTGGTCCCTGTTGCTTAGACCT
TCTTGCCTTGGTATCTCTGATGGGCTCAGCTCTTAGTAGCCTTTGTGTATGTGTGTGTGT
[G,A]
TGTGTGTGTGTGTGTGTGTGTGTGTGTGTGTGTGTGTGTAGTGGGGACTGGGGTCA
GGGGTCAGGGACTGACTCTAACCTGAGGCACCCCTGGAGTGGGGCCAGCCCAGGAATAGC
AGGTGGAGGAAAGCCGGGCAGCCTCAGGGCTGCAGCTGTCTGGTGGTACAGGGCAGGGCT
CTGGGTGGCTGCCTTTGGCAGAGGACCAGCCTGCCTCCTTCGTCCCCTACCCAGCCTGCT
ACCAGGATCAGGAGGAGGCATCTCCATGGGACTCCTAGGGCTGGAGTCAGAGCAGCCCCT

31224 GAATGATGGGGTGTTATAACAGAAGCTTTGATTTTCTAAGAACATGAAGCTCTGGGAGTT
CTTGGAGCCTTGAAGCCATAGACTGGGGCCTCCCTGTGTGATGGTTTCTGAGTTAGCAGG
GAGTGTTCAGAGTATGGGGCCTTGGTCCCTGTTGCTTAGACCTTCTTGCCTTGGTATCTC
TGATGGGCTCAGCTCTTAGTAGCCTTTGTGTATGTGTGTGTGTATGTGTGTGTGTGTGTG
TGTGTGTGTGTGTGTGTGTGTGTGTGTAGTGGGGACTGGGGTCAGGGGTCAGGGACTGAC
[C,T]
CTAACCTGAGGCACCCCTGGAGTGGGGCCAGCCCAGGAATAGCAGGTGGAGGAAAGCCGG
GCAGCCTCAGGGCTGCAGCTGTCTGGTGGTACAGGGCAGGGCTCTGGGTGGCTGCCTTTG
GCAGAGGACCAGCCTGCCTCCTTCGTCCCCTACCCAGCCTGCTACCAGGATCAGGAGGAG
GCATCTCCATGGGACTCCTAGGGCTGGAGTCAGAGCAGCCCCTCCAGGTTCTGCAGCCTG
GACGGTAGGAGGTGCCACTAAGGGGAGGAGATTGGGGAAGGATTGGGACCTTTATCTGCG

31735 CAGAGCAGCCCCTCCAGGTTCTGCAGCCTGGACGGTAGGAGGTGCCACTAAGGGGAGGAG
ATTGGGGAAGGATTGGGACCTTTATCTGCGGTGAGGTGGGGCACGGGGGGATGAGAGATA
TAGTGGGAGTCTTTGAAGGGTGTGGGATCAGTGAAGGGGCTGGGGATTTAGTGATGGGCT
GGGGCTTAGGATGGAGCCAAGGGCTCTGTGGGTGGGAGACCTTTTGAGAGGGTGGAGACT
CAGAGAGAAGGATGGGGGCTCAGCAAGGGGATGTGGCTCAGTGGAGGTTGCTGAAGAGTT
[G,A,T,C]
CTTGGGGTTGGCTACACGCGGTGGCTCACGCCTGTAATCCCAGCACTTTGGGAGGCCAAG
GCGGATGGATCACTTGAGGTCAGGACTTCAAGACCAGCCTGGCCAACATGGTGAAACCCT
GCCTCTACCAAAAAATACAAATATTAGCCGGGCGTAATGGCAGGCGCCTGTAATCTCAGC
TACTCGGGAGGCTGAGGCAGGAGAATTGCTTGAACCTGAGAGGCGGAGGTTGCAGTGAGT
CGAGATTGTACCACTGCATTCCAGCCCTGGGCGACAGAGCAAGACTCCATCTAAAAAAAA

31739 GCAGCCCCTCCAGGTTCTGCAGCCTGGACGGTAGGAGGTGCCACTAAGGGGAGGAGATTG
GGGAAGGATTGGGACCTTTATCTGCGGTGAGGTGGGGCACGGGGGGATGAGAGATATAGT
GGGAGTCTTTGAAGGGTGTGGGATCAGTGAAGGGGCTGGGGATTTAGTGATGGGCTGGGG
CTTAGGATGGAGCCAAGGGCTCTGTGGGTGGGAGACCTTTTGAGAGGGTGGAGACTCAGA
GAGAAGGATGGGGGCTCAGCAAGGGGATGTGGCTCAGTGGAGGTTGCTGAAGAGTTTCTT
[G,-]
GGGTTGGCTACACGCGGTGGCTCACGCCTGTAATCCCAGCACTTTGGGAGGCCAAGGCGG
ATGGATCACTTGAGGTCAGGACTTCAAGACCAGCCTGGCCAACATGGTGAAACCCTGCCT
CTACCAAAAAATACAAATATTAGCCGGGCGTAATGGCAGGCGCCTGTAATCTCAGCTACT

FIGURE 3-56

```
            CGGGAGGCTGAGGCAGGAGAATTGCTTGAACCTGAGAGGCGGAGGTTGCAGTGAGTCGAG
            ATTGTACCACTGCATTCCAGCCCTGGGCGACAGAGCAAGACTCCATCTAAAAAAAAAAAA

31742   GCCCCTCCAGGTTCTGCAGCCTGGACGGTAGGAGGTGCCACTAAGGGGAGGAGATTGGGG
            AAGGATTGGGACCTTTATCTGCGGTGAGGTGGGGCACGGGGGGATGAGAGATATAGTGGG
            AGTCTTTGAAGGGTGTGGGATCAGTGAAGGGGCTGGGGATTTAGTGATGGGCTGGGGCTT
            AGGATGGAGCCAAGGGCTCTGTGGGTGGGAGACCTTTTGAGAGGGTGGAGACTCAGAGAG
            AAGGATGGGGGCTCAGCAAGGGGATGTGGCTCAGTGGAGGTTGCTGAAGAGTTTCTTGGG
            [G,-]
            TTGGCTACACGCGGTGGCTCACGCCTGTAATCCCAGCACTTTGGGAGGCCAAGGCGGATG
            GATCACTTGAGGTCAGGACTTCAAGACCAGCCTGGCCAACATGGTGAAACCCTGCCTCTA
            CCAAAAAATACAAATATTAGCCGGGCGTAATGGCAGGCGCCTGTAATCTCAGCTACTCGG
            GAGGCTGAGGCAGGAGAATTGCTTGAACCTGAGAGGCGGAGGTTGCAGTGAGTCGAGATT
            GTACCACTGCATTCCAGCCCTGGGCGACAGAGCAAGACTCCATCTAAAAAAAAAAAAAAA

31798   GGGGAAGGATTGGGACCTTTATCTGCGGTGAGGTGGGGCACGGGGGGATGAGAGATATAG
            TGGGAGTCTTTGAAGGGTGTGGGATCAGTGAAGGGGCTGGGGATTTAGTGATGGGCTGGG
            GCTTAGGATGGAGCCAAGGGCTCTGTGGGTGGGAGACCTTTTGAGAGGGTGGAGACTCAG
            AGAGAAGGATGGGGGCTCAGCAAGGGGATGTGGCTCAGTGGAGGTTGCTGAAGAGTTTCT
            TGGGGTTGGCTACACGCGGTGGCTCACGCCTGTAATCCCAGCACTTTGGGAGGCCAAGGC
            [G,C,AsT]
            GATGGATCACTTGAGGTCAGGACTTCAAGACCAGCCTGGCCAACATGGTGAAACCCTGCC
            TCTACCAAAAAATACAAATATTAGCCGGGCGTAATGGCAGGCGCCTGTAATCTCAGCTAC
            TCGGGAGGCTGAGGCAGGAGAATTGCTTGAACCTGAGAGGCGGAGGTTGCAGTGAGTCGA
            GATTGTACCACTGCATTCCAGCCCTGGGCGACAGAGCAAGACTCCATCTAAAAAAAAAAA
            AAAAAAAAAGTCTCAGGGCTGTCTCTGCACTGCTCCAGGTTCCTGAGGACGGCGGTTGGG

31994   TCAGCAAGGGGATGTGGCTCAGTGGAGGTTGCTGAAGAGTTTCTTGGGGTTGGCTACACG
            CGGTGGCTCACGCCTGTAATCCCAGCACTTTGGGAGGCCAAGGCGGATGGATCACTTGAG
            GTCAGGACTTCAAGACCAGCCTGGCCAACATGGTGAAACCCTGCCTCTACCAAAAAATAC
            AAATATTAGCCGGGCGTAATGGCAGGCGCCTGTAATCTCAGCTACTCGGGAGGCTGAGGC
            AGGAGAATTGCTTGAACCTGAGAGGCGGAGGTTGCAGTGAGTCGAGATTGTACCACTGCA
            [A,G,T]
            TCCAGCCCTGGGCGACAGAGCAAGACTCCATCTAAAAAAAAAAAAAAAAAAAAGTCTCAG
            GGCTGTCTCTGCACTGCTCCAGGTTCCTGAGGACGGCGGTTGGGGCTGGGGGAGTCTTCT
            GTCCCTGGGGTAGGCTGAGAAGCAAGAGCTCCTTTTCCCAACTCTGCCCAAAGCTGGAAA
            GGTTGTTAGAGCTGCTAAGAAAGCTGGCATCTGCCTCTCCTTTTGCTCATCTTCCTTTCT
            GGTTTCCATGGGAATCTGTGGCTCAGGATGATCAGGGGTTGACAGGATGGCGCTGTGGAA

32324   ATCTAAAAAAAAAAAAAAAAAAAAGTCTCAGGGCTGTCTCTGCACTGCTCCAGGTTCCTG
            AGGACGGCGGTTGGGGCTGGGGGAGTCTTCTGTCCCTGGGGTAGGCTGAGAAGCAAGAGC
            TCCTTTTCCCAACTCTGCCCAAAGCTGGAAAGGTTGTTAGAGCTGCTAAGAAAGCTGGCA
            TCTGCCTCTCCTTTTGCTCATCTTCCTTTCTGGTTTCCATGGGAATCTGTGGCTCAGGAT
            GATCAGGGGTTGACAGGATGGCGCTGTGGAAGGAGTCTGTGTCAGGCACAGCCATCCCAC
            [A,T]
            TGGGAAGGAGCCGGCTGGTAAGAAAGTGAGTTCCCTGTCCCTGGGAGTGTGCAAGCAGGG
            TAGGGGCTGAATGGCTAGAGTGACTCCAGAAAGGGGTTCAGATGGGGCAGAGGAAGCAGT
            CTGGAGGCCACTTCCCTGAGACAATCATGTTTTGTGTGATTGGCTCTGGGGCCCCACCA
            GCCCCACCTTCCAGACGTCCCTGGGCCTCACAAAGGGGTTGCTGCACCCTAGGCACTGC
            CTCTGATCCAGCCCCAACTCCTGTGCTCTGTGCCTGGCCTATGCTGAACACGGACATGTG

32891   TCTGTGCCTGGCCTATGCTGAACACGGACATGTGCAGCTGAATCAGATTCAGTCTCTGCC
            TAGAGGAGCCCCAGTCTGATGGGGGAGGCACACAGGGACACAAATATAGCTGGGTAAGTC
            CTACAAAAGGGGGCATACCTGGCTGGGAGGCAGTTCCATCACTGATTCCTGTAGTCTGTA
            GATGTCTTTTTGAGCAATTCTTCTGGGTCAAGACTTGTTCTTATTTGCTGGGATAAAACA
            GCAGTGAGCAAAACAGAGCTGACAGCATGGTGGGAAGGTTGAGCTCTTCCAGACCGTGAT
            [G,A]
            AGAAGTATTGGTGAGTGGTGGGGAGAGTGGCCAGAAGGCAGAGTGTGGGCGCAGCATGAG
```

FIGURE 3-57

```
         AGGAGGCTTTGTCCAGACTTAAGGACCTGGAAGGCCTTGAAGGCCAGGACCAGGGCTCCA
         ATTGTCCTGCTGGCAATAGGAAGCCATATGGGTGGGGGTGAGGCAGAATCAGATTTAGGT
         GTGGAAAAGATGACTCCAGCCAGTGTGGGCATCGAAGAGGAGGCACAGAAGCAGGCGTGG
         CCACCTGTGCCTCTGTGTAGGAGCTGTGTGAGCATGTGCTTGAGGATGTGTGTCTGTGTA

33104    CTTGTTCTTATTTGCTGGGATAAAACAGCAGTGAGCAAAACAGAGCTGACAGCATGGTGG
         GAAGGTTGAGCTCTTCCAGACCGTGATGAGAAGTATTGGTGAGTGGTGGGGAGAGTGGCC
         AGAAGGCAGAGTGTGGGCGCAGCATGAGAGGAGGCTTTGTCCAGACTTAAGGACCTGGAA
         GGCCTTGAAGGCCAGGACCAGGGCTCCAATTGTCCTGCTGGCAATAGGAAGCCATATGGG
         TGGGGGTGAGGCAGAATCAGATTTAGGTGTGGAAAAGATGACTCCAGCCAGTGTGGGCAT
         [C,T]
         GAAGAGGAGGCACAGAAGCAGGCGTGGCCACCTGTGCCTCTGTGTAGGAGCTGTGTGAGC
         ATGTGCTTGAGGATGTGTGTCTGTGTAGAGGACTGGGGTGTAGGCGTGATAGGAACATGG
         ACGTGTATCTATGGAAAGACTCCAATTGTGCATAGGGGTGTATGTGTGTAAGATTCTGTG
         GCCCAGGGCAGCCTGTGAAAAGGAAGGATCTTGGGGTCTCTGGATGATGGGGAGCAGAGA
         CTAAGGCCTAAGGTATGCTGGGGCTCGAGCCCCCTGGACTTTATCCCCTGTGAGCTGGCA

33296    CAGGACCAGGGCTCCAATTGTCCTGCTGGCAATAGGAAGCCATATGGGTGGGGGTGAGGC
         AGAATCAGATTTAGGTGTGGAAAAGATGACTCCAGCCAGTGTGGGCATCGAAGAGGAGGC
         ACAGAAGCAGGCGTGGCCACCTGTGCCTCTGTGTAGGAGCTGTGTGAGCATGTGCTTGAG
         GATGTGTGTCTGTGTAGAGGACTGGGGTGTAGGCGTGATAGGAACATGGACGTGTATCTA
         TGGAAAGACTCCAATTGTGCATAGGGGTGTATGTGTGTAAGATTCTGTGGCCCAGGGCAG
         [C,T]
         CTGTGAAAAGGAAGGATCTTGGGGTCTCTGGATGATGGGGAGCAGAGACTAAGGCCTAAG
         GTATGCTGGGGCTCGAGCCCCCTGGACTTTATCCCCTGTGAGCTGGCAGGTCTTAGACTA
         GTCCTGGACTAGAATCCTATGGGTTCCCTTCCCCCAGAGGGTCATGGGGCCAGCCATCTG
         CTGCAGACAAGACAAACATGCATGCAAATCACATGAAAATGGATGAGGCCTGTGGCTGAC
         CCACCCTACAGCCCCCATCCCCTGGGCCTGAGTTCACTCAGCCTGTACCCTTCCTGACCC

33324    GCAATAGGAAGCCATATGGGTGGGGGTGAGGCAGAATCAGATTTAGGTGTGGAAAAGATG
         ACTCCAGCCAGTGTGGGCATCGAAGAGGAGGCACAGAAGCAGGCGTGGCCACCTGTGCCT
         CTGTGTAGGAGCTGTGTGAGCATGTGCTTGAGGATGTGTGTCTGTGTAGAGGACTGGGGT
         GTAGGCGTGATAGGAACATGGACGTGTATCTATGGAAAGACTCCAATTGTGCATAGGGGT
         GTATGTGTGTAAGATTCTGTGGCCCAGGGCAGCCTGTGAAAAGGAAGGATCTTGGGGTCT
         [C,G]
         TGGATGATGGGGAGCAGAGACTAAGGCCTAAGGTATGCTGGGGCTCGAGCCCCCTGGACT
         TTATCCCCTGTGAGCTGGCAGGTCTTAGACTAGTCCTGGACTAGAATCCTATGGGTTCCC
         TTCCCCCAGAGGGTCATGGGGCCAGCCATCTGCTGCAGACAAGACAAACATGCATGCAAA
         TCACATGAAAATGGATGAGGCCTGTGGCTGACCCACCCTACAGCCCCCATCCCCTGGGCC
         TGAGTTCACTCAGCCTGTACCCTTCCTGACCCAGAGCTGCTGCCAGGGCTCTGGGAACAG

33533    CTATGGAAAGACTCCAATTGTGCATAGGGGTGTATGTGTGTAAGATTCTGTGGCCCAGGG
         CAGCCTGTGAAAAGGAAGGATCTTGGGGTCTCTGGATGATGGGGAGCAGAGACTAAGGCC
         TAAGGTATGCTGGGGCTCGAGCCCCCTGGACTTTATCCCCTGTGAGCTGGCAGGTCTTAG
         ACTAGTCCTGGACTAGAATCCTATGGGTTCCCTTCCCCCAGAGGGTCATGGGGCCAGCCA
         TCTGCTGCAGACAAGACAAACATGCATGCAAATCACATGAAAATGGATGAGGCCTGTGGC
         [T,C]
         GACCCACCCTACAGCCCCCATCCCCTGGGCCTGAGTTCACTCAGCCTGTACCCTTCCTGA
         CCCAGAGCTGCTGCCAGGGCTCTGGGAACAGGCCTTGCCCACTAGGAGCTGAAATTCACA
         TTGTCCCCAGCACCTGCCCGTGGCCACATCCTCTCTCTGTGAGGGCTACCCCCACATCTG
         GAGCCATAGCCAGCGGACACAGAGCTGGATCTGGACTGGTGGCCATGGGCAGCACCTCTG
         GCAGGTGCTGAGGTGGAGGAGGCAGTATCCAGGCAGGCATCCCTGGGCAGAAGGTACCTC

33852    CATCCCCTGGGCCTGAGTTCACTCAGCCTGTACCCTTCCTGACCCAGAGCTGCTGCCAGG
         GCTCTGGGAACAGGCCTTGCCCACTAGGAGCTGAAATTCACATTGTCCCCAGCACCTGCC
         CGTGGCCACATCCTCTCTCTGTGAGGGCTACCCCCACATCTGGAGCCATAGCCAGCGGAC
         ACAGAGCTGGATCTGGACTGGTGGCCATGGGCAGCACCTCTGGCAGGTGCTGAGGTGGAG
         GAGGCAGTATCCAGGCAGGCATCCCTGGGCAGAAGGTACCTCTCCTGAGCAGACAGGCCT
```

FIGURE 3-58

```
       [A,T]
       CCCAGGCACCAGGCCCAAAGATAGGGGCAAGGGCTAGATCCTGGTATTGGAGGACCCTCA
       GGAGAGGCTGTGTGTGACTTGCTCTCTCTCTGACCTGGGCTAGAGCATAAACACGTGTCA
       CATACTTGCACACACATTCACACGTGAAAGCACGCACATGCTATTCCTGGACACTTGTGT
       ACACACACCACTGCACACATATACCTGCATGTGTGAATATACACTCACTTCTGCACACAG
       ACACATGCCTATCTGCATAGACACACCCGTGCCAACCCCTATAGATACACAGACATATCT

33907  CCAGGGCTCTGGGAACAGGCCTTGCCCACTAGGAGCTGAAATTCACATTGTCCCCAGCAC
       CTGCCCGTGGCCACATCCTCTCTCTGTGAGGGCTACCCCCACATCTGGAGCCATAGCCAG
       CGGACACAGAGCTGGATCTGGACTGGTGGCCATGGGCAGCACCTCTGGCAGGTGCTGAGG
       TGGAGGAGGCAGTATCCAGGCAGGCATCCCTGGGCAGAAGGTACCTCTCCTGAGCAGACA
       GGCCTACCCAGGCACCAGGCCCAAAGATAGGGGCAAGGGCTAGATCCTGGTATTGGAGGA
       [A,C]
       CCTCAGGAGAGGCTGTGTGTGACTTGCTCTCTCTCTGACCTGGGCTAGAGCATAAACACG
       TGTCACATACTTGCACACACATTCACACGTGAAAGCACGCACATGCTATTCCTGGACACT
       TGTGTACACACACCACTGCACACATATACCTGCATGTGTGAATATACACTCACTTCTGCA
       CACAGACACATGCCTATCTGCATAGACACACCCGTGCCAACCCCTATAGATACACAGACA
       TATCTGTGTATACACATATAAGTTCAGCTATACCACTGCAGTATCACACACCCTCACAAG

34294  ACGTGAAAGCACGCACATGCTATTCCTGGACACTTGTGTACACACACCACTGCACACATA
       TACCTGCATGTGTGAATATACACTCACTTCTGCACACAGACACATGCCTATCTGCATAGA
       CACACCCGTGCCAACCCCTATAGATACACAGACATATCTGTGTATACACATATAAGTTCA
       GCTATACCACTGCAGTATCACACACCCTCACAAGGATACAAACCTGTGCTCACACTCTCT
       TCCACCCTCACACACATCATGCTTACAAGCCTGTGTGCAGCCTTACACACATGCACACAC
       [A,G]
       TACAGAGCAGCCTAAGGGTGGCTCACCCCTGCCCAGGTGAACACCTGTGCCCACTCCAGG
       GCTGGAGTGTTGAGGAAAGGGTCTGGATGGAGGCAGAACCTGCAGAGATGTCAGTTTCTT
       CCAGGAAGCATCTTGGATTGTCCCTTCACAGAGCCCTTGGAAGTGGGGCCCTCTTTTAGT
       CCATGGGCTCTAGCCCAGGTCACAGAGAGAGCAAGTCACACACAGCCTCTCCTGAGGGTC
       CTCCAATACCAGGATCCAGCCCTTGTCCATATCTTTGGGCCTGGTGCCTGCGTAGGACCA

37090  CAGATGGGGAAATAGAGGCCTAGAGAGGTGCTGTGGCCTGCTCAGAATCCCACAGCAAGT
       CTATGGCACAGTTAGGACTCAAACCCTCTGAGGAATGCTTGGATCTGAAAGGTTGACACA
       GAAAGACTCTTTGAGCTGAGGGACACATAGAGCACACACCAGGGACCCCAGTCATTGAGC
       TGTAGTTTGAGAGATTCAAGTAAGACTGAAGAAATAACTTCTTGGCTGGGTGCAGTGGCT
       CACACCTGTAATCCCAACACTTTGGGAGGCTGAGGTGGGTGGATCATGAGGTCAAGAGAT
       [C,T]
       GAGACCATCCTGGCCAACATGGCGAAATCCCATCTGTACTAAAAATATAAAAATTAGCTG
       GGCATGGTGGTGCATGCCTGTAGTCCCATCTACTCGGGAGGCTGAGGCAGGAGAATTGCT
       TGAACCCGGGAGGCGGAGGTTGCAGTGAGCTGAGATCGCGCCACTGCGCTCCAGCCTGGT
       GACAGAGCGAGACTCCGTCTCAAAAAAATAAAATAAAATAAAATAAAATAAAATAAAATA
       AAATAAAATAAAATAAAATAACTTCTCAAGAGGTGAGTGCCATGGAGGTGGTGCCT

37248  CCAGGGACCCCAGTCATTGAGCTGTAGTTTGAGAGATTCAAGTAAGACTGAAGAAATAAC
       TTCTTGGCTGGGTGCAGTGGCTCACACCTGTAATCCCAACACTTTGGGAGGCTGAGGTGG
       GTGGATCATGAGGTCAAGAGATCGAGACCATCCTGGCCAACATGGCGAAATCCCATCTGT
       ACTAAAAATATAAAAATTAGCTGGGCATGGTGGTGCATGCCTGTAGTCCCATCTACTCGG
       GAGGCTGAGGCAGGAGAATTGCTTGAACCCGGGAGGCGGAGGTTGCAGTGAGCTGAGATC
       [C,T,G]
       CGCCACTGCGCTCCAGCCTGGTGACAGAGCGAGACTCCGTCTCAAAAAAATAAAATAAAA
       TAAAATAAAATAAAATAAAATAAAATAAAATAAAATAAAATAACTTCTCAAGAGGT
       GAGTGCCATGGAGGTGGTGCCTGGAGTTGGGAGCCCAAGAGATGGTGGCGGTGCCAGGCC
       AGGGTCGGCTGTTGACCATGGTCTGAGGTGGCCTCCCCTGAAGAACAAGTAACTCTGGCC
       AGTGGCTGTAACAGATACCTCCCGGGCACCTGTATCTCACCCAGCCTTGTCCAGAGCCCA

37355  GAGGCTGAGGTGGGTGGATCATGAGGTCAAGAGATCGAGACCATCCTGGCCAACATGGCG
       AAATCCCATCTGTACTAAAAATATAAAAATTAGCTGGGCATGGTGGTGCATGCCTGTAGT
       CCCATCTACTCGGGAGGCTGAGGCAGGAGAATTGCTTGAACCCGGGAGGCGGAGGTTGCA
```

FIGURE 3-59

```
           GTGAGCTGAGATCGCGCCACTGCGCTCCAGCCTGGTGACAGAGCGAGACTCCGTCTCAAA
           AAAATAAAATAAAATAAAATAAAATAAAATAAAATAAAATAAAATAAAATAAAATAAAATA
           [A,-]
           CTTCTCAAGAGGTGAGTGCCATGGAGGTGGTGCCTGGAGTTGGGAGCCCAAGAGATGGTG
           GCGGTGCCAGGCCAGGGTCGGCTGTTGACCATGGTCTGAGGTGGCCTCCCCTGAAGAACA
           AGTAACTCTGGCCAGTGGCTGTAACAGATACCTCCCGGGCACCTGTATCTCACCCAGCCT
           TGTCCAGAGCCCAGGACTGAGCCAGTGACACATGCTCAGAATTTACCAAGAGACTTGTGC
           ACTGAGCTCAGACTCAGACCTAGTCCTTCCAACAGCCCTTACATGGGTCATCCCCTTTTA

37893      TGCACTGAGCTCAGACTCAGACCTAGTCCTTCCAACAGCCCTTACATGGGTCATCCCCTT
           TTACGGAAGAGAAAACTGAGGCCAAAAATAGGAAGGGAGGCCCTGTGGGGGCCAGAACCT
           TTACACATCTTAGCCCAGGTAATTTTTTTCTACAGTGTTAATAAGTAGGATGAATTGCCCC
           TGTTTGGAAGATTCAGTAAAATACATTGACTTGGCCCAGATCACTTACTCTACACCTCTC
           CTAAGTCCCCAGATGTGACTCCCAGGAAAGACACAAAAAAGGGCTACCCAGAGGGATAAG
           [A,G]
           TAGTAACCAGGGAAGCCCTCCCAGAGGAGGTGGGCCTTCAAATGGCCCCTAAATGACAGG
           CAGGAGGGAAGGATCTGGGAGGGTATTGGGGGTGGGGTGGCATGGGCAAAGGCCTGGAGG
           TGAGAGTCAGTCAGTCATTGATGTGAGAAGAGCAAGAAGTAGAAATGTAAGGAATGGTGG
           GGAGGGGAGTCAGAGCTGGATGACCAAGCAAGGGTTCAGCTGTAGAGGGTCTGGCCCGCC
           AGGCTCAGGGCTCGGGCTTTATTGTGCTGGTGGTAGGGAGCCACTGAGGGTGAGTGGGGG

38252      GGCAGGAGGGAAGGATCTGGGAGGGTATTGGGGGTGGGGTGGCATGGGCAAAGGCCTGGA
           GGTGAGAGTCAGTCAGTCATTGATGTGAGAAGAGCAAGAAGTAGAAATGTAAGGAATGGT
           GGGGAGGGGAGTCAGAGCTGGATGACCAAGCAAGGGTTCAGCTGTAGAGGGTCTGGCCCG
           CCAGGCTCAGGGCTCGGGCTTTATTGTGCTGGTGGTAGGGAGCCACTGAGGGTGAGTGGG
           GGAGAGCATGCCAGAGCATGCCTCAGAAAGAAAGGTGGGAGAAACGCTGGCATGGAGGGC
           [A,G,C]
           GCCCCCTGAGTTGGTGGGGTGGCCGGGCTCTGCCAAGGCTATGTGCCAGCTGCCTGGACT
           GTGTCCAGGAATGGGCACAATGACTCAACATTGAGAAAATCACTCCCCAGGGAGAAAGGG
           CCCTGATGAATCACCCAGCTGAGGTGGGGAGGCTGGGAGGCTGGGAGGCTGGGAGGCTGG
           GAGCTCACTGAGTCACCGTCCAAGAGTTGGTGAGGAGGGGAGCTGCAGAGAGAGGGGCCG
           GCAGTGCAGTTGACGGGGGGATTCAGGTCAGACCACATTGAGGGCTGTCGGGGGACTCTA

38726      AGGCTGGGAGCTCACTGAGTCACCGTCCAAGAGTTGGTGAGGAGGGGAGCTGCAGAGAGA
           GGGGCCGGCAGTGCAGTTGACGGGGGGATTCAGGTCAGACCACATTGAGGGCTGTCGGGG
           GACTCTACCTTCCCGCCATTCCCGGGTTTGGTCCTCCTGGCCGTCCTGTGAGGGAGATGA
           GAAAACTGAGGCCCAGGAAGTGGGGGGAGGGGATCCGAGCAAGGTCATGCGGCAAGTCGC
           TGGCAAAGGCCTAGCGAGACCCAAGCGCACCCTCCAGTCCAGACACGTCCTGCCGCCCCA
           [G,T,C,A]
           CCGCTTTCATGCCAAGCAGAGGCCTAAGAACCGGGTCGGTCCGGGCAGGGAGCTGACCCC
           GGTGACCCGCTGAATCCCCGGACGCGGCCCCTCCGGGCAGCCGGCAACTGAGGCCGGATT
           GCGCCGCCGCGATGGGACGGCAGGGGGCGCAGGAGCGTCGCGGCTGCCGCAGGCTCCTGA
           ACCCAGAAGCCGCTCTGCGGAGAAACGCGCTCCCGGAGCGCGGGTCCCACCGCGGAACTG
           CGGACCGTGTGGCCCTGGGGCCTGCACCCTCTCCGGCTCCGGGGACGGCGACAGAGACCT

40472      TGGGGCTCCCCGGCACACCTGGAGCACCTGAACCCCCAGCTGTCATCCAGGACTCCACCTC
           AGAGCCGGCCTCACCCAAAGCCCCAAACCTCCATTCCAAGCCTCAACTGGACACCCGCTC
           AGATTCCCACCCAAACATCTGGACTTCAGTCCTCAGCCTGGAACCTACCCCAGAGTCCAA
           ATCTCTCCTTCCATCAGGGCTTCACTGGCTTTCTCTGTGGGACCCACTCCCCGATCCCTT
           CCCTCCCTCCTGTGTTGGAGATCTCCGAGTCTTTCCTCGTGGGGGGCCCCTCCTCTTGTT
           [G,C]
           CTCTCCAGGTACAGTGGTCCCACTTTATTCTCTGGGCTTCTCCTCTGGTTTCTCTTCAAG
           TATTTCTGGGCTCTCTAATTTGGTCTGTTGCCCCATGTGCCCACCTCTCTTGGTCTATCT
           TGGTCTCTCTCCTGTTTCTCTAGGTCTCCATCTTCGTTTTGGGGTCTCTTTTCTGCAGCCA
           CCCCTTCCTCTTGTATCTACCTCTGCTTTGTGGTGAGGAGGGGGCAGGCTCAGAGAGCAG
           GGCTAGTGTCCCTGGGACACCCCCGCCCCCCATGTTCTCAGGCATGGCATGGTGTGGGCT

40965      GTATCTACCTCTGCTTTGTGGTGAGGAGGGGGCAGGCTCAGAGAGCAGGGCTAGTGTCCC
```

FIGURE 3-60

```
          TGGGACACCCCCGCCCCCCATGTTCTCAGGCATGGCATGGTGTGGGCTCAGGTGGAAGGG
          CCTAAATGTGGAGTGTGCTGCCCTCAGGCGATGCCCAGGGATCTGAGGTGGTGGGGGGAT
          GATGTGGTGGGCACTGGCTTTTGTAACTTATAAAGCCCCTCATCCCAGCTGCCCTGGTCT
          TGACGGGGGCGGCTAGGGCTTGAGATAGGGAAGAGTAAACTGCAATCTGGTGTCAACCTG
          [C,T]
          GGTGGGATGTGTCCAGGCTGGGTGGGTCTATAGTGTATGTGTTTGTGTGAGTGTTCCTGT
          CTGTGTGTAGCACGGGCTGGGTTGCATGTGTTGGGTGTGTCTTGTGTGTAATCATGTGTG
          TTGTGCCGTGTATGAATGTGTCATCGAGAGTGGGATTATTTGTGGGGAGATTATGGGAAT
          TATGGGTCTATGGCATTGTGTGCTATGTGTGGCTGGGGAGGCAGTGTTGTGGCTGTGGAG
          TGGTAGCTGGGTGTGTGGCTGTTGTGTGTGTAGAGAACTTGTGTGTATGTGGCTGTATGT

41664     CCACTGCAGGGGCCTGATGGTTTCCACTGGGTGTCTTGTCAGAGAGGAGTTGGGGCAGGG
          GGTGCCGTGTGTGCCAATGTGTTTGCAGCCTAGGTGGCTGGCTTAGAGTCACTATGGCAC
          ATCCTGGGATTGCTTGGGTAATATATCTATTAGGACCTGAGTGCTGGTGTTTGAATGTCA
          TGTGTCTGTGTGGTGGCTGCTCCCGCGATTCTGGACAGGAAAGGGTTGCAGCCAGGGCTG
          AGGGGTCTGAGGTGAGGAGCCAGTTGACAAGTGTGTGAGTGTGTGAGTGTGTGTGTGTGC
          [G,A]
          TGCATGTACACGTGCATATGGGAATGGGGTGGGGTGGGAGGAGGCAGTGGGCCAGCAGCG
          CTGTCTATGCTGAGGGGCTGTGTGTGCCCACAAACGTGTGACATTAGGTGTGCACATTAT
          CTATGCAGGTTGTGTCTGCATGTGTCTCTGTGTCTAGGTGGCGTGCGTATTGAATTTAAT
          TGGATGCATACACCTGTGGCTGGGGAGGTGAGAGGTGTGTGAGGTGCGTGGTGGGAGACG
          GTGTGAGTGTGGTGTGAAGTGAGGGTGTGTGAGCTGGGTGACTTTTTGGTGTGACGTGTG

41760     GCTGGCTTAGAGTCACTATGGCACATCCTGGGATTGCTTGGGTAATATATCTATTAGGAC
          CTGAGTGCTGGTGTTTGAATGTCATGTGTCTGTGTGGTGGCTGCTCCCGCGATTCTGGAC
          AGGAAAGGGTTGCAGCCAGGGCTGAGGGGTCTGAGGTGAGGAGCCAGTTGACAAGTGTGT
          GAGTGTGTGAGTGTGTGTGTGTGCGTGCATGTACACGTGCATATGGGAATGGGGTGGGT
          GGGAGGAGGCAGTGGGCCAGCAGCGCTGTCTATGCTGAGGGGCTGTGTGTGCCCACAAAC
          [G,T,C,A]
          TGTGACATTAGGTGTGCACATTATCTATGCAGGTTGTGTCTGCATGTGTCTCTGTGTCTA
          GGTGGCGTGCGTATTGAATTTAATTGGATGCATACACCTGTGGCTGGGGAGGTGAGAGGT
          GTGTGAGGTGCGTGGTGGGAGACGGTGTGAGTGTGGTGTGAAGTGAGGGTGTGTGAGCTG
          GGTGACTTTTTGGTGTGACGTGTGAATTATGTGATCTTTTCTCCCCATGAGCTGTGTGTG
          CCTGTGGTGAGGAGTGAGTGGAGGATGGCCAGTGAGCTGGCGGTGTGTGTGTTGGGGGTG

42523     CTCCCCTCCTGATCAGGTCCCTAGAGATGCCCTGGAATGTTCTCCATGCCCCCCCAACCC
          CAGCTGCCCCTACCCTTTGCCCTTCATCCTCCTTGCCTTGACCAAGCCCTTTGTTTTGGG
          TTTCCGGCGGAGCAGGCGCTGGACAGGCGGGCGGCAGGCAATGTCGTGGTCTGAGAACCT
          TTGTTCTCTTAGTTTGACTGGTGTTTGGGGCCTTGGTTTGGAGGAGGGTGTGGAGAGGAT
          GCACGTGGCAGCAAGGTCACTGTGTTTACTACACCACTTCGTGCTCCGCAGAGGGGAGGC
          [G,A]
          TACGGCGCAGGCAGTGAGGCCTGGGTGGTGTCTTTGGTGGCGCCTGTTGGTGTAAGAACA
          GCTTAGGCTGGGCTTGGAGTTTGCCAGCCATGCAGTCTTAGTCCATAGTGGCCCAGCGCC
          CTTCCTGGCTCATGTCAGCGGGGCTGAGCAGCCGAGCAGCCAAGCACTCACTTCTCCAAG
          TTCACCTGCCCTCGCCCCTTCTCTGTGTGGCTGCAGCCCCTGGAGACAACCAGGAAGACC
          TCGATTTAGTTCTATTTGTGTTCACTCCAGGTCAGATGGAGGAGAAAGAGTCCCCATCCT

42904     TTGCCAGCCATGCAGTCTTAGTCCATAGTGGCCCAGCGCCCTTCCTGGCTCATGTCAGCG
          GGGCTGAGCAGCCGAGCAGCCAAGCACTCACTTCTCCAAGTTCACCTGCCCTCGCCCCTT
          CTCTGTGTGGCTGCAGCCCCTGGAGACAACCAGGAAGACCTCGATTTAGTTCTATTTGTG
          TTCACTCCAGGTCAGATGGAGGAGAAAGAGTCCCCATCCTCACAGAGACACTTATCTGAA
          AGGAGAGAGCTGGTCACACCCTTTGGGGACCCTCTAGACTGACGCAGTCTGTAGGGGGATC
          [G,A]
          AGGTCATACCTTCCAGAGAGAGCTGTGGGAAAACCCTACTGGGCTGCCTCCCAGCAGGTG
          CTTGAGAGAAGAAACATCCAAGGTTCCTTGAGATTGGAAGGCTTAGAGAAGTCTGAGTCA
          GTCAGGGAAGGGGCTGGGGTCGATGCCGCAGTGTCACATACCAGAAGGTTCTCTGAAATG
          AATAGGCTTGAACTGGACCTTGAAGGGGTGTTGGGTGGGCAGAGAAATGCAGCCTGGG
          GCTGAGGAAGGTTCTGGCCTGACTGGCAAAAGGGATCTTGCTGGCCATTCCCCAGGCAAC
```

FIGURE 3-61

43382  ATGAATAGGCTTGAACTGGACCTTGAAGGGGGTGTTGGGGTGGGCAGAGAAATGCAGCCT
GGGGCTGAGGAAGGTTCTGGCCTGACTGGCAAAAGGGATCTTGCTGGCCATTCCCCAGGC
AACACTGTCTGGCTTTGGGTAGCCATCCCTGGGCCTCCAGCCTTCTCAAGCTTTCACGGT
ACCTTTTTTATCCCATTGTCTCTGGCTGGAATTATCTTCATTGTCGTTGACATTGTCATC
TTCATCATCTTTTAGGCAGTTATTTCCAAATTCCAGGGTCCTTTCACAAATGTCTCATTT
[-,C,A]
GCAGGTTAACTCATGCAATTGTCCAAAAGTCTTTATGGAACACTGCTGTGTACCAGGCAG
GCACAGTTTTAAGTGCCGGGGTCATGGTGGTGGCCAAACTGGCCTCATGGAGCTCCTACC
TTCTGTGTCCAGCCATGCTGTCAGTTGCCCACCCTTCTGTGTTTCCCCCAGTCTGGGGCG
CCTGGTTCTGTGGGGCTCCGCATGTGCACCCTCTGGTGCTGGGGTCTGGCTCCTACCAGA
ATGTGAGCTCTGCAGAGGCTGGGCCCGGGTCTCTCCTCTACCCACCGTGTGTGTCCTGAG

43386  ATAGGCTTGAACTGGACCTTGAAGGGGGTGTTGGGGTGGGCAGAGAAATGCAGCCTGGGG
CTGAGGAAGGTTCTGGCCTGACTGGCAAAAGGGATCTTGCTGGCCATTCCCCAGGCAACA
CTGTCTGGCTTTGGGTAGCCATCCCTGGGCCTCCAGCCTTCTCAAGCTTTCACGGTACCT
TTTTTATCCCATTGTCTCTGGCTGGAATTATCTTCATTGTCGTTGACATTGTCATCTTCA
TCATCTTTTAGGCAGTTATTTCCAAATTCCAGGGTCCTTTCACAAATGTCTCATTTAGCA
[-,C,G]
GTTAACTCATGCAATTGTCCAAAAGTCTTTATGGAACACTGCTGTGTACCAGGCAGGCAC
AGTTTTAAGTGCCGGGGTCATGGTGGTGGCCAAACTGGCCTCATGGAGCTCCTACCTTCT
GTGTCCAGCCATGCTGTCAGTTGCCCACCCTTCTGTGTTTCCCCCAGTCTGGGGCGCCTG
GTTCTGTGGGGCTCCGCATGTGCACCCTCTGGTGCTGGGGTCTGGCTCCTACCAGAATGT
GAGCTCTGCAGAGGCTGGGCCCGGGTCTCTCCTCTACCCACCGTGTGTGTCCTGAGCTGG

43387  TAGGCTTGAACTGGACCTTGAAGGGGGTGTTGGGGTGGGCAGAGAAATGCAGCCTGGGGC
TGAGGAAGGTTCTGGCCTGACTGGCAAAAGGGATCTTGCTGGCCATTCCCCAGGCAACAC
TGTCTGGCTTTGGGTAGCCATCCCTGGGCCTCCAGCCTTCTCAAGCTTTCACGGTACCTT
TTTTATCCCATTGTCTCTGGCTGGAATTATCTTCATTGTCGTTGACATTGTCATCTTCAT
CATCTTTTAGGCAGTTATTTCCAAATTCCAGGGTCCTTTCACAAATGTCTCATTTAGCAG
[-,G]
TTAACTCATGCAATTGTCCAAAAGTCTTTATGGAACACTGCTGTGTACCAGGCAGGCACA
GTTTTAAGTGCCGGGGTCATGGTGGTGGCCAAACTGGCCTCATGGAGCTCCTACCTTCTG
TGTCCAGCCATGCTGTCAGTTGCCCACCCTTCTGTGTTTCCCCCAGTCTGGGGCGCCTGG
TTCTGTGGGGCTCCGCATGTGCACCCTCTGGTGCTGGGGTCTGGCTCCTACCAGAATGTG
AGCTCTGCAGAGGCTGGGCCCGGGTCTCTCCTCTACCCACCGTGTGTGTCCTGAGCTGGG

43728  CTGTGTACCAGGCAGGCACAGTTTTAAGTGCCGGGGTCATGGTGGTGGCCAAACTGGCCT
CATGGAGCTCCTACCTTCTGTGTCCAGCCATGCTGTCAGTTGCCCACCCTTCTGTGTTTC
CCCCAGTCTGGGGCGCCTGGTTCTGTGGGGCTCCGCATGTGCACCCTCTGGTGCTGGGGT
CTGGCTCCTACCAGAATGTGAGCTCTGCAGAGGCTGGGCCCGGGTCTCTCCTCTACCCAC
CGTGTGTGTCCTGAGCTGGGTCTGGCAGAGTCCAGATGCTCACACCTATCATCAAGTGAC
[G,A,T]
GGAACTGCCATGTAGGGTTGGCAGTCCAGCTCTGTCTAGGGAAACTGGGGTCCATCGGAT
GAGGGGACTCTCATCTCATCAGGCAGCATCTCATCAGGCCCTTCTTTTACCAGTAGCTCC
AGAGACCAAGAAGGGTCAGGTGACTGGTGCAGGTCTCACAGCAGGGTGGCGCGGCTGGTG
TCAGAAGACAGCACTTCTTGCTGCCAGGTTGGGCTCTGGTCCTAGCACCATGCTGCTCTC
TGGCTGGCCTCTGTGCTGCCTGCGGCGGGTAAACGATTATTAATGACCCCCCTGGCAAGG

45012  CTCCAAGCCTGAGCAATGTTGCATCAGCCCCTTGGCAGGTGGCACAGACCTAGGTACTAG
GGCTGGGGGAGGGGAGGCGGAGAAACAGGGAGTGATGTTGGTAGAGTGTGTGGGGAGGGC
AACGAGGGAGATAAACTCAGGGGCCATGGTGATATAAAGCAGGGACCCCTATTTCAGCCC
AGAGTGGGAGGGAGGGGCATGTTGGGGAGCTTCCAGGAGGAAACAAATCTGAACTGAGAG
CTAAGGTCAAGCCAGGAGAAAGTTCTGGACAGAGGGGAGAGAATGGTTACTGTGAAGGTT
[C,T]
GCTGGTGGCAGACAGAGGGAGGAGAGCCTGTGGCAGCACCACTCCATGGAGCAGGCCCCT
GGGTGCCAGCCGGCTGGGTCCGGGGGGATGGGGACTGGTAAAGCTGGCCCAGCCAGATGG
TGCAGGACTTGTAAGCCATGTTAAGGACTGCGGACTTATTCTGGAGGGAAATTGACCCTG

FIGURE 3-62

| | |
|---|---|
| | GGGAAGAGTTGAGAGAACGGATATGACAGATCAGATCTGCATGTTCAATAGCTCCCTGGA
CCATGGTGTGGAGACTGAAGGGGAGGCTGGTGTGGTCCAGGTAAGCGGGGGTGATGAGGC |
| 45079 | GGAGGGGAGGCGGAGAAACAGGGAGTGATGTTGGTAGAGTGTGTGGGGAGGGCAACGAGG
GAGATAAACTCAGGGGCCATGGTGATATAAAGCAGGGACCCCTATTTCAGCCCAGAGTGG
GAGGGAGGGGCATGTTGGGGAGCTTCCAGGAGGAAACAAATCTGAACTGAGAGCTAAGGT
CAAGCCAGGAGAAAGTTCTGGACAGAGGGGAGAGAATGGTTACTGTGAAGGTTCGCTGGT
GGCAGACAGAGGGAGGAGAGCCTGTGGCAGCACCACTCCATGGAGCAGGCCCCTGGGTGC
[C,T]
AGCCGGCTGGGTCCGGGGGATGGGGACTGGTAAAGCTGGCCCAGCCAGATGGTGCAGGA
CTTGTAAGCCATGTTAAGGACTGCGGACTTATTCTGGAGGGAAATTGACCCTGGGGAAGA
GTTGAGAGAACGGATATGACAGATCAGATCTGCATGTTCAATAGCTCCCTGGACCATGGT
GTGGAGACTGAAGGGGAGGCTGGTGTGGTCCAGGTAAGCGGGGGTGATGAGGCCTGGACA
GGGAAATGGCTGAAGAATGGAGGGGAGGGGACGGAGTGGCCAGGGCTGGTGGAGGGAGCT |
| 45247 | GAGAGCTAAGGTCAAGCCAGGAGAAAGTTCTGGACAGAGGGGAGAGAATGGTTACTGTGA
AGGTTCGCTGGTGGCAGACAGAGGGAGGAGAGCCTGTGGCAGCACCACTCCATGGAGCAG
GCCCCTGGGTGCCAGCCGGCTGGGTCCGGGGGATGGGGACTGGTAAAGCTGGCCCAGCC
AGATGGTGCAGGACTTGTAAGCCATGTTAAGGACTGCGGACTTATTCTGGAGGGAAATTG
ACCCTGGGGAAGAGTTGAGAGAACGGATATGACAGATCAGATCTGCATGTTCAATAGCTC
[A,G,C]
CTGGACCATGGTGTGGAGACTGAAGGGGAGGCTGGTGTGGTCCAGGTAAGCGGGGGTGAT
GAGGCCTGGACAGGGAAATGGCTGAAGAATGGAGGGGAGGGGACGGAGTGGCCAGGGCTG
GTGGAGGGAGCTGGACAGCTGTAGACGTGAAGGGCAAGGGAGGAGAATGCTGCCCCACCC
AGGTGTCTGGATGGGTTTTGTGCAGTCTCTGAGATGTATAGGAGGGAAGACAGGGGTTAG
TGGCAGATGCCTGGGCCTGTGTCAGGGCCCTTTAAGGACCAAAAGGTCTTGGAAAAGCCT |
| 46267 | GCAGGCATTCTGCCTTTCCTGTCTCCCACCCTAAGGGAGTTGGCCTTGCATGCCTCCCAT
CCACGGTTGCCTCTACTGGGGGCTGCCACTGGGAGACAGGAAGGGCATGGGAGTTTCGGG
AGCTCAGGGTAAGAGGGGCTGAGATCTCGTGGTGTGGAGGGGGAGCGGGAAGGTCGGGTG
GCCGAAAGAATGGAGAGGGCCGGGAGTGAGAGCAAAGGGAGACAGGCAGAGCTGAAGAGC
AGTATCGCCCCAACATCAATACTGGTATTTCAGAATGGGAAAGCTGTTCCATTTCCCGAA
[T,A]
TATCAGAATGCTGAGGTCCGATCTTGCAGTCTCTGAGCTGGGCATTCCTTGGCCCCCACT
CTCGGGTATTCTTGCACAAGACCATTTTTCTGGGCTGCATTTTCTCACTTGTAAAAGGAG
GAAGTTGGGGGTCAATATCTCCAAGCGATATATGAGCTCTAGCTCTAGGAGTATAGGATT
TTGAGAATCTGGAATTGTTAGTCTGTGGGGTTCTAACTGGGACAATTCTAGCATTCCTTG
ACTCTCAGCTCCCAGCCAGGGCTGTGTGGATGCGTGGTTGTGTGATTCCGACATTCTGAG |
| 46268 | CAGGCATTCTGCCTTTCCTGTCTCCCACCCTAAGGGAGTTGGCCTTGCATGCCTCCCATC
CACGGTTGCCTCTACTGGGGGCTGCCACTGGGAGACAGGAAGGGCATGGGAGTTTCGGGA
GCTCAGGGTAAGAGGGGCTGAGATCTCGTGGTGTGGAGGGGGAGCGGGAAGGTCGGGTGG
CCGAAAGAATGGAGAGGGCCGGGAGTGAGAGCAAAGGGAGACAGGCAGAGCTGAAGAGCA
GTATCGCCCCAACATCAATACTGGTATTTCAGAATGGGAAAGCTGTTCCATTTCCCGAAA
[T,C]
ATCAGAATGCTGAGGTCCGATCTTGCAGTCTCTGAGCTGGGCATTCCTTGGCCCCCACTC
TCGGGTATTCTTGCACAAGACCATTTTTCTGGGCTGCATTTTCTCACTTGTAAAAGGAGG
AAGTTGGGGGTCAATATCTCCAAGCGATATATGAGCTCTAGCTCTAGGAGTATAGGATTT
TGAGAATCTGGAATTGTTAGTCTGTGGGGTTCTAACTGGGACAATTCTAGCATTCCTTGA
CTCTCAGCTCCCAGCCAGGGCTGTGTGGATGCGTGGTTGTGTGATTCCGACATTCTGAGA |
| 46414 | CGTGGTGTGGAGGGGGAGCGGGAAGGTCGGGTGGCCGAAAGAATGGAGAGGGCCGGGAGT
GAGAGCAAAGGGAGACAGGCAGAGCTGAAGAGCAGTATCGCCCCAACATCAATACTGGTA
TTTCAGAATGGGAAAGCTGTTCCATTTCCCGAAATATCAGAATGCTGAGGTCCGATCTTG
CAGTCTCTGAGCTGGGCATTCCTTGGCCCCCACTCTCGGGTATTCTTGCACAAGACCATT
TTTCTGGGCTGCATTTTCTCACTTGTAAAAGGAGGAAGTTGGGGGTCAATATCTCCAAGC
[G,A]
ATATATGAGCTCTAGCTCTAGGAGTATAGGATTTTGAGAATCTGGAATTGTTAGTCTGTG |

FIGURE 3-63

```
         GGGTTCTAACTGGGACAATTCTAGCATTCCTTGACTCTCAGCTCCCAGCCAGGGCTGTGT
         GGATGCGTGGTTGTGTGATTCCGACATTCTGAGACTTTAAGATGCTGAGGCTCTAGGAGC
         TAGAGATACGGACATTCTGTGAATCTAGGATTCTAGGATTTGATGGTTTGATGATTCAAT
         GATTCTAAATGGGGCTGCTGGGAAGAGCTGCAACCACCTGCCTTGTTAATGTCAATGTTC

46822    GCCAGGGCTGTGTGGATGCGTGGTTGTGTGATTCCGACATTCTGAGACTTTAAGATGCTG
         AGGCTCTAGGAGCTAGAGATACGGACATTCTGTGAATCTAGGATTCTAGGATTTGATGGT
         TTGATGATTCAATGATTCTAAATGGGGCTGCTGGGAAGAGCTGCAACCACCTGCCTTGTT
         AATGTCAATGTTCAGTTATTAAAAACATAACAAGAAGCAATGGAGACAGATAGCTCAGAA
         TGGTGGGCGCTCCCTCCACTCCCAGTGAGGGAGGACAGAAGAGGCTGGGCTGGCCTTAGA
         [G,A,C,T]
         AATAGAGACCTTTTCAACCTGGGTCACACAGGTTGTTTCTCCTGTCACAACAGAACTGGT
         GTGTGTACATTCGAGAGAGCTTCCACTCCCAAAGCTTGCAGGGTAAGGGGCTCATTTCCT
         TCAGCACTGGCCTCTATTCCTTAACCATTTCAGACTGGGCAGAGAGAGGGTAACTACCC
         TTTCCTCCCAGCCCTCGAAGTCTCTGGGCAGAAATGGCAGCAGTGGAGGAAGGAGAGGTC
         TGCTCACCCCCGCCCCTTCCCTGACAGCCTGAGGGGGAAAACAGGACATGAATACTTCCT

47169    ACAACAGAACTGGTGTGTGTACATTCGAGAGAGCTTCCACTCCCAAAGCTTGCAGGGTAA
         GGGGCTCATTTCCTTCAGCACTGGCCTCTATTCCTTAACCATTTCAGACTGGGCAGAGAG
         AGGGGTAACTACCCTTTCCTCCCAGCCCTCGAAGTCTCTGGGCAGAAATGGCAGCAGTGG
         AGGAAGGAGAGGTCTGCTCACCCCCGCCCCTTCCCTGACAGCCTGAGGGGGAAAACAGGA
         CATGAATACTTCCTGGACACAGACATGGAAATGCATGAACCCCTGCCTTCGAGGGCCCCG
         [C,T]
         GTCCAAAGGCTCAGACAAGGGCAGAGGCCAGGACAGCCAGTGGGGTCCCATCAGCACCCT
         CTCAGTATAGGCTGAGGAGGGAAGACCCTGTTCTTGCCCCAAGGGTGACAGTGAGAAGGG
         GTCAAGGAAAGGAGTCCCAGGTCAGGGACTGGAAGTGCTGACAGGTCCTCCCCTGTGTGC
         AAGGCCACAGTCCAGCCTGGCAGAAGGCCAGCCCAATTGTCCAGTGTTTCACTGCCTCCT
         GAGTCCTTCTTATGCCTTGGCACCCAGGCCAGAGTTGGGGAGGGTCCAGGCTGCAGGGG

47214    AAGCTTGCAGGGTAAGGGGCTCATTTCCTTCAGCACTGGCCTCTATTCCTTAACCATTTC
         AGACTGGGCAGAGAGAGGGGTAACTACCCTTTCCTCCCAGCCCTCGAAGTCTCTGGGCAG
         AAATGGCAGCAGTGGAGGAAGGAGAGGTCTGCTCACCCCCGCCCCTTCCCTGACAGCCTG
         AGGGGGAAAACAGGACATGAATACTTCCTGGACACAGACATGGAAATGCATGAACCCCTG
         CCTTCGAGGGCCCCGCGTCCAAAGGCTCAGACAAGGGCAGAGGCCAGGACAGCCAGTGGG
         [G,C,AsT]
         TCCCATCAGCACCCTCTCAGTATAGGCTGAGGAGGGAAGACCCTGTTCTTGCCCCAAGGG
         TGACAGTGAGAAGGGGTCAAGGAAAGGAGTCCCAGGTCAGGGACTGGAAGTGCTGACAGG
         TCCTCCCCTGTGTGCAAGGCCACAGTCCAGCCTGGCAGAAGGCCAGCCCAATTGTCCAGT
         GTTTCACTGCCTCCTGAGTCCTTCTTATGCCTTGGCACCCAGGCCAGAGTTGGGGAGGGG
         TCCAGGCTGCAGGGGAGGGTTTCCTTCCAGAGTGCCCATCCCTGATGGATCCTTAGAAGC

47431    ACATGGAAATGCATGAACCCCTGCCTTCGAGGGCCCCGCGTCCAAAGGCTCAGACAAGGG
         CAGAGGCCAGGACAGCCAGTGGGGTCCCATCAGCACCCTCTCAGTATAGGCTGAGGAGGG
         AAGACCCTGTTCTTGCCCCAAGGGTGACAGTGAGAAGGGGTCAAGGAAAGGAGTCCCAGG
         TCAGGGACTGGAAGTGCTGACAGGTCCTCCCCTGTGTGCAAGGCCACAGTCCAGCCTGGC
         AGAAGGCCAGCCCAATTGTCCAGTGTTTCACTGCCTCCTGAGTCCTTCTTATGCCTTGGC
         [A,G]
         CCCAGGCCAGAGTTGGGGAGGGGTCCAGGCTGCAGGGGAGGGTTTCCTTCCAGAGTGCCC
         ATCCCTGATGGATCCTTAGAAGCCCAGTACAGCTGCACAGTTCCAAGGGCTTCCGCTGCC
         TGGTAGGTTCACAGACCAAAGCTGGCCCTGGTCACACAGCACAACGGGGCCTGAAATCAG
         GCTTCCTGATTCCCAGTCCTGGGTGTTCCTTTTTGCCCACAGCCTCCCCCACTTCCCCTG
         GGACACCTGAGGGGCAGGAGTGGAGGTGGGGCTCAGGTTAGGGAGCAGAGCCTCTGTCCA

47773    GTTTCCTTCCAGAGTGCCCATCCCTGATGGATCCTTAGAAGCCCAGTACAGCTGCACAGT
         TCCAAGGGCTTCCGCTGCCTGGTAGGTTCACAGACCAAAGCTGGCCCTGGTCACACAGCA
         CAACGGGGCCTGAAATCAGGCTTCCTGATTCCCAGTCCTGGGTGTTCCTTTTTGCCCACA
         GCCTCCCCCACTTCCCCTGGGACACCTGAGGGGCAGGAGTGGAGGTGGGGCTCAGGTTAG
         GGAGCAGAGCCTCTGTCCATCATCCCTCCGTCTTCCTCTTCCCACAGGCCAGAAGCAGGT
```

FIGURE 3-64

[G,T,GsT]
TGGTGGTGACAGCTGCCCCCAGTCCTCCACAAGGCTCCATTGTCCCCGGCAGGGAGCCCC
TCCCCAGCTGCAGGCCAGAAGTGTGCCTCCCCGGGCCCTCCTGTCGTGACTCTGCCACCC
GCTTCCTCCTGCTGCCCCTTCCCTCTTCTCATCTCCGCTTGCCCTCAGGCCCTCCCCATC
CCCGTGAGGTCTCGTCTCTGGCGCTCTCTGGGTTTAAGCCTCTCTCCAGTGAAAGTTAGA
TTTGGAAGGGCCCTGGGAGATCACCAAGTCCAACCCTTTTATTCTTCGGATAAGGAGGCC

47821   CAGCTGCACAGTTCCAAGGGCTTCCGCTGCCTGGTAGGTTCACAGACCAAAGCTGGCCCT
GGTCACACAGCACAACGGGGCCTGAAATCAGGCTTCCTGATTCCCAGTCCTGGGTGTTCC
TTTTTGCCCACAGCCTCCCCCACTTCCCCTGGGACACCTGAGGGGCAGGAGTGGAGGTGG
GGCTCAGGTTAGGGAGCAGAGCCTCTGTCCATCATCCCTCCGTCTTCCTCTTCCCACAGG
CCAGAAGCAGGTGTGGTGGTGACAGCTGCCCCCAGTCCTCCACAAGGCTCCATTGTCCCC
[G,A]
GCAGGGAGCCCCTCCCCAGCTGCAGGCCAGAAGTGTGCCTCCCCGGGCCCTCCTGTCGTG
ACTCTGCCACCCGCTTCCTCCTGCTGCCCCTTCCCTCTTCTCATCTCCGCTTGCCCTCAG
GCCCTCCCCATCCCCGTGAGGTCTCGTCTCTGGCGCTCTCTGGGTTTAAGCCTCTCTCCA
GTGAAAGTTAGATTTGGAAGGGCCCTGGGAGATCACCAAGTCCAACCCTTTTATTCTTCG
GATAAGGAGGCCAGGTCAGAGAGGGGAAGGTCCTGTCCAAAGCTGCACAGTAGGCTGAGG

48186   TGCCACCCGCTTCCTCCTGCTGCCCCTTCCCTCTTCTCATCTCCGCTTGCCCTCAGGCCC
TCCCCATCCCCGTGAGGTCTCGTCTCTGGCGCTCTCTGGGTTTAAGCCTCTCTCCAGTGA
AAGTTAGATTTGGAAGGGCCCTGGGAGATCACCAAGTCCAACCCTTTTATTCTTCGGATA
AGGAGGCCAGGTCAGAGAGGGGAAGGTCCTGTCCAAAGCTGCACAGTAGGCTGAGGCAGA
GCCCAGTGCTGTGCTCCCTTCAGCGCTGGGTCATGGGTGCACACTGCCCTTGGCATCAGG
[C,T]
GTCCAGGGTTTGAGAACTGACTGTGATGATCAGCGCTAAGCACACAGGCACCTACAGAAA
TGCGGTAGGGGGCTTCTCTCCTCAGCCCTTCTTCACAGCCCTGAGCTGCCCTCCCTTCCT
CTTCTTTGCCCAGCTCCTCTCTCCTTCACTATCCCTGCTGTCTGCTGACTCCTGCCTCTG
GCAGACACTGTCCTTGGGACACAGACTAGAGCTCAGGCCTCCAGGACTGGGATGCACACC
CATGCACCCAGACACAGACACATAAACATGTGCAAGCGTGTCACGGGGTCCATAAATCCC

48544   AAATGCGGTAGGGGGCTTCTCTCCTCAGCCCTTCTTCACAGCCCTGAGCTGCCCTCCCTT
CCTCTTCTTTGCCCAGCTCCTCTCTCCTTCACTATCCCTGCTGTCTGCTGACTCCTGCCT
CTGGCAGACACTGTCCTTGGGACACAGACTAGAGCTCAGGCCTCCAGGACTGGGATGCAC
ACCCATGCACCCAGACACAGACACATAAACATGTGCAAGCGTGTCACGGGGTCCATAAAT
CCCAGCTGAAAACTGGTCAGACCATCAGGAGGCCACCCTGGAACCCAGTGTCCTCCTCTT
[G,A,C]
CTGTCAGGCCTCACACACCTCCTCCAGGAAGCCCCTTAGGACCCCTGAAGACCATCTTCA
TCCAACTAGCCCCTTTGTGACAACTGAACTCTGTGAGCCTAGGTTCCTCCTGTGACTCGA
AGGGCAAGGCTGAGTCCCCCCTTCAGTCCTGGGGCCACTCCTTCAGTGTCTTCAGGAGGG
GCTCAGCTTCCTGTTGCTGGGTGGGGAGAGCCCTGAGGTCCCCACAGGACGTGGGACAAT
GGGGAGGCGGTGACAGATGAGAGGCTGAGTCTTCCCTAAAGCAGACTCCACCCTCCCCTG

48577   CTTCACAGCCCTGAGCTGCCCTCCCTTCCTCTTCTTTGCCCAGCTCCTCTCTCCTTCACT
ATCCCTGCTGTCTGCTGACTCCTGCCTCTGGCAGACACTGTCCTTGGGACACAGACTAGA
GCTCAGGCCTCCAGGACTGGGATGCACACCCATGCACCCAGACACAGACACATAAACATG
TGCAAGCGTGTCACGGGGTCCATAAATCCCAGCTGAAAACTGGTCAGACCATCAGGAGGC
CACCCTGGAACCCAGTGTCCTCCTCTTCCTGTCAGGCCTCACACACCTCCTCCAGGAAGC
[G,C]
CCTTAGGACCCCTGAAGACCATCTTCATCCAACTAGCCCCTTTGTGACAACTGAACTCTG
TGAGCCTAGGTTCCTCCTGTGACTCGAAGGGCAAGGCTGAGTCCCCCCTTCAGTCCTGGG
GCCACTCCTTCAGTGTCTTCAGGAGGGGCTCAGCTTCCTGTTGCTGGGTGGGGAGAGCCC
TGAGGTCCCCACAGGACGTGGGACAATGGGGAGGCGGTGACAGATGAGAGGCTGAGTCTT
CCCTAAAGCAGACTCCACCCTCCCCTGACCTCCCTGGCTGGTGGCTTGGACACAGCCCTG

48705   CTCCAGGACTGGGATGCACACCCATGCACCCAGACACAGACACATAAACATGTGCAAGCG
TGTCACGGGGTCCATAAATCCCAGCTGAAAACTGGTCAGACCATCAGGAGGCCACCCTGG
AACCCAGTGTCCTCCTCTTCCTGTCAGGCCTCACACACCTCCTCCAGGAAGCCCCTTAGG

FIGURE 3-65

```
            ACCCCTGAAGACCATCTTCATCCAACTAGCCCCTTTGTGACAACTGAACTCTGTGAGCCT
            AGGTTCCTCCTGTGACTCGAAGGGCAAGGCTGAGTCCCCCCTTCAGTCCTGGGGCCACTC
            [G,A,C]
            TTCAGTGTCTTCAGGAGGGGCTCAGCTTCCTGTTGCTGGGTGGGGAGAGCCCTGAGGTCC
            CCACAGGACGTGGGACAATGGGGAGGCGGTGACAGATGAGAGGCTGAGTCTTCCCTAAAG
            CAGACTCCACCCTCCCCTGACCTCCCTGGCTGGTGGCTTGGACACAGCCCTGGCCTGGAC
            TAGGGTCCTGGTCTGACCCCACAATGCAGAGGTCTGGGAATCAGAAGCCCTGGTTCTCCA
            GCAGCAGTTCTCTAACTGGCGGCTATGGAGTCCAGGCCTCCAGGGCACTGGTAGGTTATT

48873     AAGCCCCTTAGGACCCCTGAAGACCATCTTCATCCAACTAGCCCCTTTGTGACAACTGAA
            CTCTGTGAGCCTAGGTTCCTCCTGTGACTCGAAGGGCAAGGCTGAGTCCCCCCTTCAGTC
            CTGGGGCCACTCCTTCAGTGTCTTCAGGAGGGGCTCAGCTTCCTGTTGCTGGGTGGGGAG
            AGCCCTGAGGTCCCCACAGGACGTGGGACAATGGGGAGGCGGTGACAGATGAGAGGCTGA
            GTCTTCCCTAAAGCAGACTCCACCCTCCCCTGACCTCCCTGGCTGGTGGCTTGGACACAG
            [-,C]
            CCTGGCCTGGACTAGGGTCCTGGTCTGACCCCACAATGCAGAGGTCTGGGAATCAGAAGC
            CCTGGTTCTCCAGCAGCAGTTCTCTAACTGGCGGCTATGGAGTCCAGGCCTCCAGGGCAC
            TGGTAGGTTATTGGCGGGTTGGTGCAGATTCCAGTGTCCAGGAGGGGTGAGCTGGCCTGG
            GGGGCCTATGTACAGGAGATAGGAGGGTGATAAACACAGGCTAGGTGGGATTACAGGGAG
            CTGGGAATACCTAGCTAAGAATCCCCTCATCCTAGGCACTTTCCCCACACTTGAAATTGG

48874     AGCCCCTTAGGACCCCTGAAGACCATCTTCATCCAACTAGCCCCTTTGTGACAACTGAAC
            TCTGTGAGCCTAGGTTCCTCCTGTGACTCGAAGGGCAAGGCTGAGTCCCCCCTTCAGTCC
            TGGGGCCACTCCTTCAGTGTCTTCAGGAGGGGCTCAGCTTCCTGTTGCTGGGTGGGGAGA
            GCCCTGAGGTCCCCACAGGACGTGGGACAATGGGGAGGCGGTGACAGATGAGAGGCTGAG
            TCTTCCCTAAAGCAGACTCCACCCTCCCCTGACCTCCCTGGCTGGTGGCTTGGACACAGC
            [-,G,C]
            CTGGCCTGGACTAGGGTCCTGGTCTGACCCCACAATGCAGAGGTCTGGGAATCAGAAGCC
            CTGGTTCTCCAGCAGCAGTTCTCTAACTGGCGGCTATGGAGTCCAGGCCTCCAGGGCACT
            GGTAGGTTATTGGCGGGTTGGTGCAGATTCCAGTGTCCAGGAGGGGTGAGCTGGCCTGGG
            GGGCCTATGTACAGGAGATAGGAGGGTGATAAACACAGGCTAGGTGGGATTACAGGGAGC
            TGGGAATACCTAGCTAAGAATCCCCTCATCCTAGGCACTTTCCCCACACTTGAAATTGGC

48876     CCCCTTAGGACCCCTGAAGACCATCTTCATCCAACTAGCCCCTTTGTGACAACTGAACTC
            TGTGAGCCTAGGTTCCTCCTGTGACTCGAAGGGCAAGGCTGAGTCCCCCCTTCAGTCCTG
            GGGCCACTCCTTCAGTGTCTTCAGGAGGGGCTCAGCTTCCTGTTGCTGGGTGGGGAGAGC
            CCTGAGGTCCCCACAGGACGTGGGACAATGGGGAGGCGGTGACAGATGAGAGGCTGAGTC
            TTCCCTAAAGCAGACTCCACCCTCCCCTGACCTCCCTGGCTGGTGGCTTGGACACAGCCC
            [-,T]
            GGCCTGGACTAGGGTCCTGGTCTGACCCCACAATGCAGAGGTCTGGGAATCAGAAGCCCT
            GGTTCTCCAGCAGCAGTTCTCTAACTGGCGGCTATGGAGTCCAGGCCTCCAGGGCACTGG
            TAGGTTATTGGCGGGTTGGTGCAGATTCCAGTGTCCAGGAGGGGTGAGCTGGCCTGGGGG
            GCCTATGTACAGGAGATAGGAGGGTGATAAACACAGGCTAGGTGGGATTACAGGGAGCTG
            GGAATACCTAGCTAAGAATCCCCTCATCCTAGGCACTTTCCCCACACTTGAAATTGGCTG

48879     CTTAGGACCCCTGAAGACCATCTTCATCCAACTAGCCCCTTTGTGACAACTGAACTCTGT
            GAGCCTAGGTTCCTCCTGTGACTCGAAGGGCAAGGCTGAGTCCCCCCTTCAGTCCTGGGG
            CCACTCCTTCAGTGTCTTCAGGAGGGGCTCAGCTTCCTGTTGCTGGGTGGGGAGAGCCCT
            GAGGTCCCCACAGGACGTGGGACAATGGGGAGGCGGTGACAGATGAGAGGCTGAGTCTTC
            CCTAAAGCAGACTCCACCCTCCCCTGACCTCCCTGGCTGGTGGCTTGGACACAGCCCTGG
            [-,C]
            CTGGACTAGGGTCCTGGTCTGACCCCACAATGCAGAGGTCTGGGAATCAGAAGCCCTGGT
            TCTCCAGCAGCAGTTCTCTAACTGGCGGCTATGGAGTCCAGGCCTCCAGGGCACTGGTAG
            GTTATTGGCGGGTTGGTGCAGATTCCAGTGTCCAGGAGGGGTGAGCTGGCCTGGGGGGCC
            TATGTACAGGAGATAGGAGGGTGATAAACACAGGCTAGGTGGGATTACAGGGAGCTGGGA
            ATACCTAGCTAAGAATCCCCTCATCCTAGGCACTTTCCCCACACTTGAAATTGGCTGGAG

48880     TTAGGACCCCTGAAGACCATCTTCATCCAACTAGCCCCTTTGTGACAACTGAACTCTGTG
```

FIGURE 3-66

```
       AGCCTAGGTTCCTCCTGTGACTCGAAGGGCAAGGCTGAGTCCCCCCTTCAGTCCTGGGGC
       CACTCCTTCAGTGTCTTCAGGAGGGGCTCAGCTTCCTGTTGCTGGGTGGGGAGAGCCCTG
       AGGTCCCCACAGGACGTGGGACAATGGGGAGGCGGTGACAGATGAGAGGCTGAGTCTTCC
       CTAAAGCAGACTCCACCCTCCCCTGACCTCCCTGGCTGGTGGCTTGGACACAGCCCTGGC
       [-,T,C]
       TGGACTAGGGTCCTGGTCTGACCCCACAATGCAGAGGTCTGGGAATCAGAAGCCCTGGTT
       CTCCAGCAGCAGTTCTCTAACTGGCGGCTATGGAGTCCAGGCCTCCAGGGCACTGGTAGG
       TTATTGGCGGGTTGGTGCAGATTCCAGTGTCCAGGAGGGGTGAGCTGGCCTGGGGGGCCT
       ATGTACAGGAGATAGGAGGGTGATAAACACAGGCTAGGTGGGATTACAGGGAGCTGGGAA
       TACCTAGCTAAGAATCCCCTCATCCTAGGCACTTTCCCCACACTTGAAATTGGCTGGAGG

48881  TAGGACCCCTGAAGACCATCTTCATCCAACTAGCCCCTTTGTGACAACTGAACTCTGTGA
       GCCTAGGTTCCTCCTGTGACTCGAAGGGCAAGGCTGAGTCCCCCCTTCAGTCCTGGGGCC
       ACTCCTTCAGTGTCTTCAGGAGGGGCTCAGCTTCCTGTTGCTGGGTGGGGAGAGCCCTGA
       GGTCCCCACAGGACGTGGGACAATGGGGAGGCGGTGACAGATGAGAGGCTGAGTCTTCCC
       TAAAGCAGACTCCACCCTCCCCTGACCTCCCTGGCTGGTGGCTTGGACACAGCCCTGGCC
       [-,A,T]
       GGACTAGGGTCCTGGTCTGACCCCACAATGCAGAGGTCTGGGAATCAGAAGCCCTGGTTC
       TCCAGCAGCAGTTCTCTAACTGGCGGCTATGGAGTCCAGGCCTCCAGGGCACTGGTAGGT
       TATTGGCGGGTTGGTGCAGATTCCAGTGTCCAGGAGGGGTGAGCTGGCCTGGGGGGCCTA
       TGTACAGGAGATAGGAGGGTGATAAACACAGGCTAGGTGGGATTACAGGGAGCTGGGAAT
       ACCTAGCTAAGAATCCCCTCATCCTAGGCACTTTCCCCACACTTGAAATTGGCTGGAGGG

49008  CAGTGTCTTCAGGAGGGGCTCAGCTTCCTGTTGCTGGGTGGGGAGAGCCCTGAGGTCCCC
       ACAGGACGTGGGACAATGGGGAGGCGGTGACAGATGAGAGGCTGAGTCTTCCCTAAAGCA
       GACTCCACCCTCCCCTGACCTCCCTGGCTGGTGGCTTGGACACAGCCCTGGCCTGGACTA
       GGGTCCTGGTCTGACCCCACAATGCAGAGGTCTGGGAATCAGAAGCCCTGGTTCTCCAGC
       AGCAGTTCTCTAACTGGCGGCTATGGAGTCCAGGCCTCCAGGGCACTGGTAGGTTATTGG
       [C,T]
       GGGTTGGTGCAGATTCCAGTGTCCAGGAGGGGTGAGCTGGCCTGGGGGGCCTATGTACAG
       GAGATAGGAGGGTGATAAACACAGGCTAGGTGGGATTACAGGGAGCTGGGAATACCTAGC
       TAAGAATCCCCTCATCCTAGGCACTTTCCCCACACTTGAAATTGGCTGGAGGGGGAACCA
       GAAGTTAGGTGGGGTTGGGGAGGGACAGGAGCCAGCACCCTGCCTCCACCTCCGGGCAGT
       GCCTCTGCTGGGGGGAGGGAACCTGTCCTGGGGGTGGTGGGAGGTGTGAGGGGGGAGCTG

49259  AACTGGCGGCTATGGAGTCCAGGCCTCCAGGGCACTGGTAGGTTATTGGCGGGTTGGTGC
       AGATTCCAGTGTCCAGGAGGGGTGAGCTGGCCTGGGGGGCCTATGTACAGGAGATAGGAG
       GGTGATAAACACAGGCTAGGTGGGATTACAGGGAGCTGGGAATACCTAGCTAAGAATCCC
       CTCATCCTAGGCACTTTCCCCACACTTGAAATTGGCTGGAGGGGGAACCAGAAGTTAGGT
       GGGGTTGGGGAGGGACAGGAGCCAGCACCCTGCCTCCACCTCCGGGCAGTGCCTCTGCTG
       [G,C]
       GGGGAGGGAACCTGTCCTGGGGGTGGTGGGAGGTGTGAGGGGGGAGCTGGATTCTCCAGT
       GAAACTGGCCCTCCCTCCTCTCAGGGGAGGGGAGGGGGCTGTCCCTGGCTGCTCAGCAGG
       TAGCCCATCTGGCTGTGGGTGGAAAAGAAGACTCAGGCTTTGTGGATAAAAGGGACAGCC
       CTGGGTCAGGCACTTATCTCAACCCTCGTCATTTCCTCTGCCGGACATGACTGGGTGAGT
       GGGGTCATTGCACAGAGGGAAGGAACAGGCCAGGGCCAGTGCATACCAGGCCCTACAGGA

49821  GGAACAGGCCAGGGCCAGTGCATACCAGGCCCTACAGGAGAGTCAGGCACATGGGTGACC
       CTGCCACACCCTGGGCTGCAGTCAGCCCCTCATAGAGGCCCAGACACACACCACAGTCAC
       TGCCGGAGATGGCCACACCTAGACCATCACACCACACACAGACCCAGTCTCTCCAGGTGA
       CACTCAGGCCCAGCTGCAGGCGCAGCTAAGAGGGAAGACCCTGCAGGGCACAGGGACACG
       TGGGACAACCAGACGCCCTGCTTCGGCCACACCACAAGCCTCCACACACCAGGTGCAGCT
       [C,T]
       CTGTCACCCCTACGGTCAACCCAAGGAGAGCCAGAGATTCCAGTAGTCGTGGGCAGGTAT
       CCAGTGCCCAGGCGAGAAGAGGGGGACACCAGCAGGGAACCCAGAACCTCCTCCATGCCA
       GACTGTGCCCTCCCCCCAGCTCACAGAAGGAGTGCCTCAGGCTGTTTATTTCCTAGCAGG
       GACTAGCAGGGATGGGTGTCTCATCCCCCTCCCCCTCCCAGTCCCCACCACACGATTCTG
       AAGCTGCCAAATCAAATCAGCCCCTGCACCCGCGCCAGGCTGGCATGGCGGCCAGCAGCT
```

FIGURE 3-67

52352   GGAGGGTGTGTGTGTGTGTGAGAGAGAGAGAGAGAACTGGACCCACAGCCAGAACAGAGT
CTGCCCAGGCCTGGCTGAGAGGGAGAGGAAGATGATGCTTGTATCAGCCCTCCTGTGTGC
CAGGAGCCTTTGACACCCACCTTGTTTAATTATTACAGCACCCCCATGAGGTAGGGCTG
CTATTATTCCTATTTCACATTTGGGGAAGCTGAGGCCCAGAGGGATCATTCAGCAAGTGA
GTTGGGACAGAGCTAAGATTGGAGCCTAGATGTGTCTCAGGCTCGAGGCTCACTCTTTCC
[C,T]
GGCCCCTGAGTAAGATGGGAAAGAAGGTGCCCACACAGGGCCTGGTGCACAGGAGGGGCT
CAGCACAGGTTCCCTGCTGGGACACAGGGCCAAGACCTGAGAATGTGCCTCCAAGTGGGG
CTGGGCCCTGCTGCTGGGAGCTGGCAAAGGGAGCTGGGAGGGGAGGGCCTGGAAAGCCAC
ATTATTAATTTATTTACTGCCATGGCATTCCCCATGGGGCGGGGCTCCCCCCAGAGCTGG
GACAGATGGTGTTCCTGGGAGCCTGCAGTGTCTCAGCAGCCTCGGCCACCCGCCAGGAAA

55378   GAGAGGTCCATGAGGTCAGCTTCTGACAGCAGCAGCTAAGGACAACCAGGACCAGAACAG
GACTGGGAAAAAGCAGATAGAGGAGGCTGGAGCAAGGACTCAGCCCCAGAGGAGGCTGCA
GGAGGTTGGCTCATGCTCAGAACCCGGCTCCAAAACACTCTGCCCATGAGTGCTGGGCTG
AGGAAGGCTTGGTGCCAGAGTCAGGGTGAGGCTGAGGCCACCAGTGAATATGTGGGCCCA
GCTGCGGGGGTAGCACTAGGCAGGGGCGGGAGCCAGGTTGGAGGGGGTATTGCCATTGCC
[G,A]
CTGCAGGTGGAGTAGGGCTTCGCTGGGGAAGGAGCAGCTTGTGCGAGAGTGTGGGCAGGA
GTGGGAGGGGAGAAGGCTCCGAGTATACGAGCATAGCTTACCAGCAAGTCCTGGGGTGAG
GCTGGAGGGGCCGCGCTGTAGGCAGCACTTTTCAGGCCCTTATCTAACATTCTCAAGTGA
GTGCTCCTAGCTGCCAGATGTGCTACTTCCTCCTGGATTCTGCACATCAGGAGCCAGTGG
CCTCTACAATGCCCCATGGCCCCAAGGGAGTGGCTGCCAACAAGTTGGCCTTAGCATCTG

55440   CTGGGAAAAAGCAGATAGAGGAGGCTGGAGCAAGGACTCAGCCCCAGAGGAGGCTGCAGG
AGGTTGGCTCATGCTCAGAACCCGGCTCCAAAACACTCTGCCCATGAGTGCTGGGCTGAG
GAAGGCTTGGTGCCAGAGTCAGGGTGAGGCTGAGGCCACCAGTGAATATGTGGGCCCAGC
TGCGGGGGTAGCACTAGGCAGGGGCGGGAGCCAGGTTGGAGGGGGTATTGCCATTGCCGC
TGCAGGTGGAGTAGGGCTTCGCTGGGGAAGGAGCAGCTTGTGCGAGAGTGTGGGCAGGAG
[T,G]
GGGAGGGGAGAAGGCTCCGAGTATACGAGCATAGCTTACCAGCAAGTCCTGGGGTGAGGC
TGGAGGGGCCGCGCTGTAGGCAGCACTTTTCAGGCCCTTATCTAACATTCTCAAGTGAGT
GCTCCTAGCTGCCAGATGTGCTACTTCCTCCTGGATTCTGCACATCAGGAGCCAGTGGCC
TCTACAATGCCCCATGGCCCCAAGGGAGTGGCTGCCAACAAGTTGGCCTTAGCATCTGGC
ATCCATGGGGGTCCTGAGGCCCTGCCATCTGTCTGTGCCCCTGTTGGGCTGCACAGGCCC

55532   ACACTCTGCCCATGAGTGCTGGGCTGAGGAAGGCTTGGTGCCAGAGTCAGGGTGAGGCTG
AGGCCACCAGTGAATATGTGGGCCCAGCTGCGGGGGTAGCACTAGGCAGGGGCGGGAGCC
AGGTTGGAGGGGGTATTGCCATTGCCGCTGCAGGTGGAGTAGGGCTTCGCTGGGGAAGGA
GCAGCTTGTGCGAGAGTGTGGGCAGGAGTGGGAGGGGAGAAGGCTCCGAGTATACGAGCA
TAGCTTACCAGCAAGTCCTGGGGTGAGGCTGGAGGGGCCGCGCTGTAGGCAGCACTTTTC
[A,G]
GGCCCTTATCTAACATTCTCAAGTGAGTGCTCCTAGCTGCCAGATGTGCTACTTCCTCCT
GGATTCTGCACATCAGGAGCCAGTGGCCTCTACAATGCCCCATGGCCCCAAGGGAGTGGC
TGCCAACAAGTTGGCCTTAGCATCTGGCATCCATGGGGGTCCTGAGGCCCTGCCATCTGT
CTGTGCCCCTGTTGGGCTGCACAGGCCCGGGGCGTGCAGGGACCTGGGACCAGGGAGGCG
GTCTCAGCTGCCACTCTAGCCTGTCTCTCTGCCTGCCCATCCACTGTCCACACCCCTGGC

56039   CCGGGGCGTGCAGGGACCTGGGACCAGGGAGGCGGTCTCAGCTGCCACTCTAGCCTGTCT
CTCTGCCTGCCCATCCACTGTCCACACCCCTGGCTGACTGAGTAAAGAGAGAGATGGGCA
TCGCAGGTCCTGCCATCAAAGAAGCCTAGTCTAAAGGAGGAGGCATAAAGCACCGGGGAC
TTATACCCAGAGAAGACACATGCTGAGACCACGCCAGGCTCGCGGGCAAGGCCTAGGCCC
AGGGAGGGCCAGCCTCGTCAAGGGCCTGGAGTTGAGACTCAGGGAAAGGCAGGAGCTGGC
[T,A]
TAGAGGCGCAGGCAGGTCCAAGGCAGTGCCCAGGCCAGATGCGGCGGCCCCGGGCTGAGG
TTGCTCCAGCCGGCCCCACCCCCCACCGTCCTGCCTGGCCTTTGGCTGTAAACACTGAGA
GAACAAGTTCCGTTTCCCGGGAAATATTTATCTCAGGCTGTGTGAAGAGCGTGTGCACTG

FIGURE 3-68

GCCTCCGTGTGTCCTTCCTGCAGACCGGCTGGGGCAGGAGGAGAGGGAGCTTGGCAGCGC
CCTTGCTGGGGGGAGTCTGTGGGGCTAGGAGGGAAGGGTGTGCCAGAGGCCCCTGCCTAG

56082    GCCACTCTAGCCTGTCTCTCTGCCTGCCCATCCACTGTCCACACCCCTGGCTGACTGAGT
AAAGAGAGAGATGGGCATCGCAGGTCCTGCCATCAAAGAAGCCTAGTCTAAAGGAGGAGG
CATAAAGCACCGGGGACTTATACCCAGAGAAGACACATGCTGAGACCACGCCAGGCTCGC
GGGCAAGGCCTAGGCCCAGGGAGGGCCAGCCTCGTCAAGGGCCTGGAGTTGAGACTCAGG
GAAAGGCAGGAGCTGGCTTAGAGGCGCAGGCAGGTCCAAGGCAGTGCCCAGGCCAGATGC
[T,G]
GCGGCCCCGGGCTGAGGTTGCTCCAGCCGGCCCCACCCCCACCGTCCTGCCTGGCCTTT
GGCTGTAAACACTGAGAGAACAAGTTCCGTTTCCCGGGAAATATTTATCTCAGGCTGTGT
GAAGAGCGTGTGCACTGGCCTCCGTGTGTCCTTCCTGCAGACCGGCTGGGGCAGGAGGAG
AGGGAGCTTGGCAGCGCCCTTGCTGGGGGGAGTCTGTGGGGCTAGGAGGGAAGGGTGTGC
CAGAGGCCCCTGCCTAGAGCCTGAATTTGAGTGCTGGCTGAGGGAGAGGTGGGAGCAGAT

56113    CCACTGTCCACACCCCTGGCTGACTGAGTAAAGAGAGAGATGGGCATCGCAGGTCCTGCC
ATCAAAGAAGCCTAGTCTAAAGGAGGAGGCATAAAGCACCGGGGACTTATACCCAGAGAA
GACACATGCTGAGACCACGCCAGGCTCGCGGGCAAGGCCTAGGCCCAGGGAGGGCCAGCC
TCGTCAAGGGCCTGGAGTTGAGACTCAGGGAAAGGCAGGAGCTGGCTTAGAGGCGCAGGC
AGGTCCAAGGCAGTGCCCAGGCCAGATGCGGCGGCCCCGGGCTGAGGTTGCTCCAGCCGG
[G,C]
CCCACCCCCCACCGTCCTGCCTGGCCTTTGGCTGTAAACACTGAGAGAACAAGTTCCGTT
TCCCGGGAAATATTTATCTCAGGCTGTGTGAAGAGCGTGTGCACTGGCCTCCGTGTGTCC
TTCCTGCAGACCGGCTGGGGCAGGAGGAGAGGGAGCTTGGCAGCGCCCTTGCTGGGGGGA
GTCTGTGGGGCTAGGAGGGAAGGGTGTGCCAGAGGCCCCTGCCTAGAGCCTGAATTTGAG
TGCTGGCTGAGGGAGAGGTGGGAGCAGATGGGAGAGAAGCCTGTTTTCTCCAAACCCCAC

56425    CCGTCCTGCCTGGCCTTTGGCTGTAAACACTGAGAGAACAAGTTCCGTTTCCCGGGAAAT
ATTTATCTCAGGCTGTGTGAAGAGCGTGTGCACTGGCCTCCGTGTGTCCTTCCTGCAGAC
CGGCTGGGGCAGGAGGAGAGGGAGCTTGGCAGCGCCCTTGCTGGGGGGAGTCTGTGGGGC
TAGGAGGGAAGGGTGTGCCAGAGGCCCCTGCCTAGAGCCTGAATTTGAGTGCTGGCTGAG
GGAGAGGTGGGAGCAGATGGGAGAGAAGCCTGTTTTCTCCAAACCCCACAAATGCCCTCC
[G,A]
CCTCTCTCATGTTCCTTTCTTCTTCCTGGTCCATCCTGTCTCCTCCAGGTTCCGGCCTCC
AGCCTGGTGTCCCCTCCTCAGGCTGCCTTTTCCTCCTCCTCCTCCCTGTTTCCTGGCTCT
TAGCCGCTCCATCTGGGAAGTCTTCCTCAACTTTAAACCCTCGAACCCTTGTCCTCTGCC
CTCCATCTCCCACTCCTCAGGCTTTCAGCAGCTTCACGTGGAGCATTGGGCTGGTCCTGT
CCACAGTTGTTCAGTTGCTGTAACAGCTTGTGCAGGCTGCCCTGGAGCCCTGTTCTGGGA

56554    CAGGAGGAGAGGGAGCTTGGCAGCGCCCTTGCTGGGGGGAGTCTGTGGGGCTAGGAGGGA
AGGGTGTGCCAGAGGCCCCTGCCTAGAGCCTGAATTTGAGTGCTGGCTGAGGGAGAGGTG
GGAGCAGATGGGAGAGAAGCCTGTTTTCTCCAAACCCCACAAATGCCCTCCGCCTCTCTC
ATGTTCCTTTCTTCTTCCTGGTCCATCCTGTCTCCTCCAGGTTCCGGCCTCCAGCCTGGT
GTCCCCTCCTCAGGCTGCCTTTTCCTCCTCCTCCTCCCTGTTTCCTGGCTCTTAGCCGCT
[C,T]
CATCTGGGAAGTCTTCCTCAACTTTAAACCCTCGAACCCTTGTCCTCTGCCCTCCATCTC
CCACTCCTCAGGCTTTCAGCAGCTTCACGTGGAGCATTGGGCTGGTCCTGTCCACAGTTG
TTCAGTTGCTGTAACAGCTTGTGCAGGCTGCCCTGGAGCCCTGTTCTGGGAAGCACAGGT
CTGGGCACCCTGGGCTGGGGCGAGGCCCGGAGCTGATCTCCTCTGTCCATCCCAGTAGA
GCCAGCACCAGTGCAGACACATGGGGGATCCAGGTTGGTGGACCAGGGGAGGATGGAAAG

57097    CAGCACCAGTGCAGACACATGGGGGATCCAGGTTGGTGGACCAGGGGAGGATGGAAAGTC
CCATGGATCCAGCCGGAATGTTGGAGTGGGGAGGCAGAGGGCCCAGGGTTCCTGCTGGCC
AGCCTCTGGGCTTAGGGGTGTGTATCCCAGACAGGCCAGGCCTGCCAGGGGCCCTGACAA
CAGGAAATCCTTGAAGGAACAAGCAGAGGCTGAGGACTCTGAGCACAACAACAGGAAACA
GCCGTGACATGGGGCAACAGCCCTGGCGACTGTGCCCAGTTGGGGTGGGGACGAGGGGCC
[A,G]
AGCTTGTGGGACCCAGGGTGATGCCAAGAGGGACACTGAGACACTGTGGGACAGGGGGCG

FIGURE 3-69

TTCTGCACATGTGACACGGAGCTTATGACGTGTAATATCAAGTACGTGACCATGATCATA
GGGTACTGTGTGGAGTGTGGGTGAGTCACTGAGTATGTGACACTGGCTGTGAGGCACTCC
ATGATAGCAGATGTGTACAGTGGCTGTGCCACCAAGTGTGTAACACTGTGTGATATTGAT
TGTGTGATGCTGACACCGAGTGTGTGACATTGCACATTGCATGCTACCACGTGTGTGACA

57284  TCCTTGAAGGAACAAGCAGAGGCTGAGGACTCTGAGCACAACAACAGGAAACAGCCGTGA
CATGGGGCAACAGCCCTGGCGACTGTGCCCAGTTGGGGTGGGGACGAGGGGCCAAGCTTG
TGGGACCCAGGGTGATGCCAAGAGGGACACTGAGACACTGTGGGACAGGGGGCGTTCTGC
ACATGTGACACGGAGCTTATGACGTGTAATATCAAGTACGTGACCATGATCATAGGGTAC
TGTGTGGAGTGTGGGTGAGTCACTGAGTATGTGACACTGGCTGTGAGGCACTCCATGATA
[G,A]
CAGATGTGTACAGTGGCTGTGCCACCAAGTGTGTAACACTGTGTGATATTGATTGTGTGA
TGCTGACACCGAGTGTGTGACATTGCACATTGCATGCTACCACGTGTGTGACACTGAAAG
TGACAGTGAGCACATGGAGGGTGTGTCTCCATGAGAATCAAATACAGAAACGTGAGCAAA
TGACGCTGCAGTAGCAGGTATGGTCCTGAGTCTGTGGCTCGAGTGTCTGACACTGAATTG
TGACATTGAGTGTGTCCCAAGCATATGATCTAGTGAGGCTGAGTGTGTAAACAAAGGCAT

57618  TAACACTGTGTGATATTGATTGTGTGATGCTGACACCGAGTGTGTGACATTGCACATTGC
ATGCTACCACGTGTGTGACACTGAAAGTGACAGTGAGCACATGGAGGGTGTGTCTCCATG
AGAATCAAATACAGAAACGTGAGCAAATGACGCTGCAGTAGCAGGTATGGTCCTGAGTCT
GTGGCTCGAGTGTCTGACACTGAATTGTGACATTGAGTGTGTCCCAAGCATATGATCTAG
TGAGGCTGAGTGTGTAAACAAAGGCATGACATGGAGTGATAGCAAGTGTGTGGAAGTGGG
[T,C]
GTGTGATGCTGTGTGATCTTGGGCCTGACATTACATGTGTGATGCTCTGTAATGGTTGTA
ACAGTATGCAATGTGCACATACAGTGCTGTGTAGGACACTGTCATGGGAAGGCACCGATG
GGTTCAGGCGGGAAAGTAACACCGTCCAAAGGATGGTTTTAAAAGATTGCTCTGGCCGGA
TGCAGTGGCTCACACCTATAATCCCAGCACTTTGGGAGGCTGAGCTGGGTGGATCACCTG
AGGTCAGGAGTTCAAGACCAGTCTGGTGAAACCCCATCTCTACTAAAAATACAAAAATTA

57795  TCTGTGGCTCGAGTGTCTGACACTGAATTGTGACATTGAGTGTGTCCCAAGCATATGATC
TAGTGAGGCTGAGTGTGTAAACAAAGGCATGACATGGAGTGATAGCAAGTGTGTGGAAGT
GGGTGTGTGATGCTGTGTGATCTTGGGCCTGACATTACATGTGTGATGCTCTGTAATGGT
TGTAACAGTATGCAATGTGCACATACAGTGCTGTGTAGGACACTGTCATGGGAAGGCACC
GATGGGTTCAGGCGGGAAAGTAACACCGTCCAAAGGATGGTTTTAAAAGATTGCTCTGGC
[C,T]
GGATGCAGTGGCTCACACCTATAATCCCAGCACTTTGGGAGGCTGAGCTGGGTGGATCAC
CTGAGGTCAGGAGTTCAAGACCAGTCTGGTGAAACCCCATCTCTACTAAAAATACAAAAA
TTAGCCAGGCATGGTGACAGGCGCCTGTAATCTCAGCTGCTCGGGAGGTTGAGACAGGAG
AATCACTTGAACCCAGGGGGCAGAGGTTGCAGTGAGCCAAGATTGAGCCATTGCACTCCA
GCCTGGGTGACGAGTGAAATACCATCTCAAAAAAAAAAAAAGAAAAAGATTGCTCAGGT

57796  CTGTGGCTCGAGTGTCTGACACTGAATTGTGACATTGAGTGTGTCCCAAGCATATGATCT
AGTGAGGCTGAGTGTGTAAACAAAGGCATGACATGGAGTGATAGCAAGTGTGTGGAAGTG
GGTGTGTGATGCTGTGTGATCTTGGGCCTGACATTACATGTGTGATGCTCTGTAATGGTT
GTAACAGTATGCAATGTGCACATACAGTGCTGTGTAGGACACTGTCATGGGAAGGCACCG
ATGGGTTCAGGCGGGAAAGTAACACCGTCCAAAGGATGGTTTTAAAAGATTGCTCTGGCC
[A,G]
GATGCAGTGGCTCACACCTATAATCCCAGCACTTTGGGAGGCTGAGCTGGGTGGATCACC
TGAGGTCAGGAGTTCAAGACCAGTCTGGTGAAACCCCATCTCTACTAAAAATACAAAAAT
TAGCCAGGCATGGTGACAGGCGCCTGTAATCTCAGCTGCTCGGGAGGTTGAGACAGGAGA
ATCACTTGAACCCAGGGGGCAGAGGTTGCAGTGAGCCAAGATTGAGCCATTGCACTCCAG
CCTGGGTGACGAGTGAAATACCATCTCAAAAAAAAAAAAAGAAAAAGATTGCTCAGGTT

57957  GTGATGCTCTGTAATGGTTGTAACAGTATGCAATGTGCACATACAGTGCTGTGTAGGACA
CTGTCATGGGAAGGCACCGATGGGTTCAGGCGGGAAAGTAACACCGTCCAAAGGATGGTT
TTAAAAGATTGCTCTGGCCGGATGCAGTGGCTCACACCTATAATCCCAGCACTTTGGGAG
GCTGAGCTGGGTGGATCACCTGAGGTCAGGAGTTCAAGACCAGTCTGGTGAAACCCCATC
TCTACTAAAAATACAAAAATTAGCCAGGCATGGTGACAGGCGCCTGTAATCTCAGCTGCT

FIGURE 3-70

```
                [C,T]
                GGGAGGTTGAGACAGGAGAATCACTTGAACCCAGGGGGCAGAGGTTGCAGTGAGCCAAGA
                TTGAGCCATTGCACTCCAGCCTGGGTGACGAGTGAAATACCATCTCAAAAAAAAAAAAAA
                GAAAAAGATTGCTCAGGTTGCAGAATATGTATGTGTGCGAGTGTGCATGGTGCGTGGCAG
                GGGAGGGGAGATAAGTTAGGGGGAGGCAGAGAGAAGGTGGGTAGAGCAACTGGAGGCTCC
                TGCAGCTGCCCAGGCAGGAGATGGTGGTGCCTGTGTTAATGGAATGGCAGAAGAGTTAGA

58064    CCAAAGGATGGTTTTAAAAGATTGCTCTGGCCGGATGCAGTGGCTCACACCTATAATCCC
                AGCACTTTGGGAGGCTGAGCTGGGTGGATCACCTGAGGTCAGGAGTTCAAGACCAGTCTG
                GTGAAACCCCATCTCTACTAAAAATACAAAAATTAGCCAGGCATGGTGACAGGCGCCTGT
                AATCTCAGCTGCTCGGGAGGTTGAGACAGGAGAATCACTTGAACCCAGGGGGCAGAGGTT
                GCAGTGAGCCAAGATTGAGCCATTGCACTCCAGCCTGGGTGACGAGTGAAATACCATCTC
                [-,A]
                AAAAAAAAAAAAAGAAAAAGATTGCTCAGGTTGCAGAATATGTATGTGTGCGAGTGTGCA
                TGGTGCGTGGCAGGGGAGGGGAGATAAGTTAGGGGGAGGCAGAGAGAAGGTGGGTAGAGC
                AACTGGAGGCTCCTGCAGCTGCCCAGGCAGGAGATGGTGGTGCCTGTGTTAATGGAATGG
                CAGAAGAGTTAGAGATATGGAGCAACTTTGGAGATATTTGAAAACAGAAATGACAGAACT
                TGCTGATAAATGAGAAGATGAGCAAGAGGGAAAACCAGAGAACAATTTCCAGGGTTCTGG

58069    GGATGGTTTTAAAAGATTGCTCTGGCCGGATGCAGTGGCTCACACCTATAATCCCAGCAC
                TTTGGGAGGCTGAGCTGGGTGGATCACCTGAGGTCAGGAGTTCAAGACCAGTCTGGTGAA
                ACCCCATCTCTACTAAAAATACAAAAATTAGCCAGGCATGGTGACAGGCGCCTGTAATCT
                CAGCTGCTCGGGAGGTTGAGACAGGAGAATCACTTGAACCCAGGGGGCAGAGGTTGCAGT
                GAGCCAAGATTGAGCCATTGCACTCCAGCCTGGGTGACGAGTGAAATACCATCTCAAAAA
                [-,A]
                AAAAAAAAGAAAAAGATTGCTCAGGTTGCAGAATATGTATGTGTGCGAGTGTGCATGGTG
                CGTGGCAGGGGAGGGGAGATAAGTTAGGGGGAGGCAGAGAGAAGGTGGGTAGAGCAACTG
                GAGGCTCCTGCAGCTGCCCAGGCAGGAGATGGTGGTGCCTGTGTTAATGGAATGGCAGAA
                GAGTTAGAGATATGGAGCAACTTTGGAGATATTTGAAAACAGAAATGACAGAACTTGCTG
                ATAAATGAGAAGATGAGCAAGAGGGAAAACCAGAGAACAATTTCCAGGGTTCTGGCTTGA

58108    TCACACCTATAATCCCAGCACTTTGGGAGGCTGAGCTGGGTGGATCACCTGAGGTCAGGA
                GTTCAAGACCAGTCTGGTGAAACCCCATCTCTACTAAAAATACAAAAATTAGCCAGGCAT
                GGTGACAGGCGCCTGTAATCTCAGCTGCTCGGGAGGTTGAGACAGGAGAATCACTTGAAC
                CCAGGGGGCAGAGGTTGCAGTGAGCCAAGATTGAGCCATTGCACTCCAGCCTGGGTGACG
                AGTGAAATACCATCTCAAAAAAAAAAAAAAAGAAAAAGATTGCTCAGGTTGCAGAATATGT
                [A,G]
                TGTGTGCGAGTGTGCATGGTGCGTGGCAGGGGAGGGGAGATAAGTTAGGGGGAGGCAGAG
                AGAAGGTGGGTAGAGCAACTGGAGGCTCCTGCAGCTGCCCAGGCAGGAGATGGTGGTGCC
                TGTGTTAATGGAATGGCAGAAGAGTTAGAGATATGGAGCAACTTTGGAGATATTTGAAAA
                CAGAAATGACAGAACTTGCTGATAAATGAGAAGATGAGCAAGAGGGAAAACCAGAGAACA
                ATTTCCAGGGTTCTGGCTTGAAGAACCAAGCGATGGATGGTGAAGATGTTTCTGAGATGG

58125    GCACTTTGGGAGGCTGAGCTGGGTGGATCACCTGAGGTCAGGAGTTCAAGACCAGTCTGG
                TGAAACCCCATCTCTACTAAAAATACAAAAATTAGCCAGGCATGGTGACAGGCGCCTGTA
                ATCTCAGCTGCTCGGGAGGTTGAGACAGGAGAATCACTTGAACCCAGGGGGCAGAGGTTG
                CAGTGAGCCAAGATTGAGCCATTGCACTCCAGCCTGGGTGACGAGTGAAATACCATCTCA
                AAAAAAAAAAAAAGAAAAAGATTGCTCAGGTTGCAGAATATGTATGTGTGCGAGTGTGCA
                [T,C]
                GGTGCGTGGCAGGGGAGGGGAGATAAGTTAGGGGGAGGCAGAGAGAAGGTGGGTAGAGCA
                ACTGGAGGCTCCTGCAGCTGCCCAGGCAGGAGATGGTGGTGCCTGTGTTAATGGAATGGC
                AGAAGAGTTAGAGATATGGAGCAACTTTGGAGATATTTGAAAACAGAAATGACAGAACTT
                GCTGATAAATGAGAAGATGAGCAAGAGGGAAAACCAGAGAACAATTTCCAGGGTTCTGGC
                TTGAAGAACCAAGCGATGGATGGTGAAGATGTTTCTGAGATGGGCAAAGGCAAGGGGGAG

58171    CAAGACCAGTCTGGTGAAACCCCATCTCTACTAAAAATACAAAAATTAGCCAGGCATGGT
                GACAGGCGCCTGTAATCTCAGCTGCTCGGGAGGTTGAGACAGGAGAATCACTTGAACCCA
                GGGGGCAGAGGTTGCAGTGAGCCAAGATTGAGCCATTGCACTCCAGCCTGGGTGACGAGT
```

FIGURE 3-71

```
         GAAATACCATCTCAAAAAAAAAAAAAAGAAAAAGATTGCTCAGGTTGCAGAATATGTATG
         TGTGCGAGTGTGCATGGTGCGTGGCAGGGGAGGGGAGATAAGTTAGGGGGAGGCAGAGAG
         [G,A]
         AGGTGGGTAGAGCAACTGGAGGCTCCTGCAGCTGCCCAGGCAGGAGATGGTGGTGCCTGT
         GTTAATGGAATGGCAGAAGAGTTAGAGATATGGAGCAACTTTGGAGATATTTGAAAACAG
         AAATGACAGAACTTGCTGATAAATGAGAAGATGAGCAAGAGGGAAAACCAGAGAACAATT
         TCCAGGGTTCTGGCTTGAAGAACCAAGCGATGGATGGTGAAGATGTTTCTGAGATGGGCA
         AAGGCAAGGGGGAGGGTCAGCACTAGTGGGGTGGGAGGACAAGGAGGCAGAAACCGAGTG

58246    TCTCAGCTGCTCGGGAGGTTGAGACAGGAGAATCACTTGAACCCAGGGGGCAGAGGTTGC
         AGTGAGCCAAGATTGAGCCATTGCACTCCAGCCTGGGTGACGAGTGAAATACCATCTCAA
         AAAAAAAAAAAAGAAAAAGATTGCTCAGGTTGCAGAATATGTATGTGTGCGAGTGTGCAT
         GGTGCGTGGCAGGGGAGGGGAGATAAGTTAGGGGGAGGCAGAGAGAAGGTGGGTAGAGCA
         ACTGGAGGCTCCTGCAGCTGCCCAGGCAGGAGATGGTGGTGCCTGTGTTAATGGAATGGC
         [A,G]
         GAAGAGTTAGAGATATGGAGCAACTTTGGAGATATTTGAAAACAGAAATGACAGAACTTG
         CTGATAAATGAGAAGATGAGCAAGAGGGAAAACCAGAGAACAATTTCCAGGGTTCTGGCT
         TGAAGAACCAAGCGATGGATGGTGAAGATGTTTCTGAGATGGGCAAAGGCAAGGGGGAGG
         GTCAGCACTAGTGGGGTGGGAGGACAAGGAGGCAGAAACCGAGTGAGCTGTTTTGGATGT
         GTTAAGGGAAGCATCCAGGTGAAGGTGTGCAGTGGGCAGCGGGGCCAGGCTAGGGATACA

59173    GAGTCAGGCTAATGGGAGCCATTTCAGTGATGGGCTGGAGCCAGAAGTCAGACTGGCCTG
         TGTAGGATGGTGAGGGAGGTGAAGACGTTAGCCTGGAGAGCCCTTTGGAGACGTTGGGCT
         GTGAGGGCTGCAGAGAAGGACATGATCGCTGGAAAGGGAGATTACATTTTTTTTATTATGG
         GTGATTCTAAGCAGACACAATACCAGAGAGAAGCATATAAGAAACTGCCATATACTCATC
         ACCCCAGTTCAACAGTTGCTGGGATTTGGCCTCATTTCTTCCTCTCTTGCCCCCTATCTG
         [T,A]
         TCTTTCATTTTCCTTTGCTTAAGCTTAAAATTTTTTAAATTGTGGTAAAATATACATAAC
         TTAAACTTTACCATCATAACCATTTCTAAGTGTACAGTTCAGTTGTGGTAGGTACATTCA
         CACTGTTTTGCAACCAATCTCTGGAACTCTTTCATCTTCTCAAACTGAAACTCTGCACCT
         ATTAAACGACAGCCCCCATCCTCCTCTGTCTCCAGCTCCTGGCACCCACCATTCTACTTT
         CTGTCTCTATGACTTGGACTACTCTAGATACCTCAAGTAATTGGAATAATGTAGTATCTG

60931    GTGACACAGTGCAGGACTCTGCATGGGAGTAAGAGGGACTGAAGCTGTGCTATAGGTGAC
         CGGGCTGCATGTGATTCAAGTGGGCTCAGCCCCAGCTTCAGCTGCTGAGTATGGGAGGGA
         GCATGGACATTGTAGGGTAGATGAGGAGAAACACTGAATGGGAACAGAAATGGTGTCTGT
         GCCCAGATGCGAGCTCCTCCCTTCTCTGAATACCCAGGAAGGCTTCCTGGAGGCAGGATG
         TGGGCACTTCAGCAGGATGTTGTAGGTGCTGATTAAGAGCAGGGCCTGTGGTGTCAGACA
         [G,C]
         CCCTGTCTAGGCTCTGACATTCAGCAGGTCATTTTATCTCTTGAGCCTCAATTTCCTCAA
         GTATAAAATGGGAGCTCTTAGGAGGATTGCATGAAGCAGTGCTCCAATGCATGCAGTCTC
         TGGCACTTGGTAAATACTCTATGGTCTCTTGGGGAGCAGCAACCTCAACACCTGCACCCC
         AGGTCCCCAAATAACAGGAGCACCAGTAGGAGCACAGTGAAGGTGCGCTGAGTGAGGTGT
         CCTCTTACACCCACAGCCCTCCTCTCTCCCTCTCCCCCAACTTCTGTCCCCTGCTTGGTG

62318    AAACTGAGCCCACTCTCCCTCACCAAGCCTTTCCCCTCAGGCCCGCATCTGCCCAGAGAA
         TTGGGGTCCCTCCTTTCTAATGTGCACACAGGTGGCCCCAGCCCCCTGCTGGGAGTCAGC
         TTAGGCAAGGTTTGATGGCTCAGCTTAATCTTCTCAGCAGCTCTGGGGGAAGAGACCATT
         TTACGGATGAGGAACTGAGCCCAGGAAGGTCCAAAGACTTGTCCAGTACATGTGGTGTGT
         GGCAGGGCAGGCAGATGAGCCCGCATCTGAGGGAGGCGATGGGAGAAGTGACAGGGGTGC
         [G,A]
         CAGAGGAGGAGAATTAGACCCTCTCAGATTCCACCACTCTCAGCCACACGTTCACTCACT
         CATTTGGAGACAAGACTAACCACCAGCGCATTCACAGCCCCCCAGACAGCCACATACTGA
         CTATACCACTGTCACATGGACATCAATGACCTGAATCACATATGCATAGATGCAGGCCCA
         CATGGTCACTCCCACGTGCAGATGGCCAGTGCACACACATAGACACAGGGTACTCACACA
         TGTTTACACTCTCACGACCCATGTGGGTTACAGATTCCTACAGAGACACAGACCTACATA

62417    AGCCCCCTGCTGGGAGTCAGCTTAGGCAAGGTTTGATGGCTCAGCTTAATCTTCTCAGCA
```

FIGURE 3-72

```
        GCTCTGGGGGAAGAGACCATTTTACGGATGAGGAACTGAGCCCAGGAAGGTCCAAAGACT
        TGTCCAGTACATGTGGTGTGTGGCAGGGCAGGCAGATGAGCCCGCATCTGAGGGAGGCGA
        TGGGAGAAGTGACAGGGGTGCGCAGAGGAGGAGAATTAGACCCTCTCAGATTCCACCACT
        CTCAGCCACACGTTCACTCACTCATTTGGAGACAAGACTAACCACCAGCGCATTCACAGC
        [C,T,G,A]
        CCCCAGACAGCCACATACTGACTATACCACTGTCACATGGACATCAATGACCTGAATCAC
        ATATGCATAGATGCAGGCCCACATGGTCACTCCCACGTGCAGATGGCCAGTGCACACACA
        TAGACACAGGGTACTCACACATGTTTACACTCTCACGACCCATGTGGGTTACAGATTCCT
        ACAGAGACACAGACCTACATACTTTCACAAGGAAATTCTCCCAGTGACCCAGGGAACATA
        GTCTGCCATGATGATGTGATGGTCCGTAGGGGCTCGCCACTATGGACCATTAATGGGCAG

62655   CTCTCAGCCACACGTTCACTCACTCATTTGGAGACAAGACTAACCACCAGCGCATTCACA
        GCCCCCCAGACAGCCACATACTGACTATACCACTGTCACATGGACATCAATGACCTGAAT
        CACATATGCATAGATGCAGGCCCACATGGTCACTCCCACGTGCAGATGGCCAGTGCACAC
        ACATAGACACAGGGTACTCACACATGTTTACACTCTCACGACCCATGTGGGTTACAGATT
        CCTACAGAGACACAGACCTACATACTTTCACAAGGAAATTCTCCCAGTGACCCAGGGAAC
        [A,G]
        TAGTCTGCCATGATGATGTGATGGTCCGTAGGGGCTCGCCACTATGGACCATTAATGGGC
        AGGCTGCACACATGCTTAGGTCCCCAGCAAAGCGGGAGTTCTGCACAGAGTGAGAGGAGA
        GGTCAGTTCTGATGAGTGTATCCAGAATTTTTGCAATCAGAAAAACCACACAAAAACTATT
        TTAATTTTCATTTCCAAGATAAAATTTAGTTTGAATTGTATAGAGGGTCCGAGGGTCTGG
        TGGGAGGGCATCATCATCTTTTCAAGGCTTTGGGGTTCTAAGGCACCCACAGATTCACAA

62676   ACTCATTTGGAGACAAGACTAACCACCAGCGCATTCACAGCCCCCCAGACAGCCACATAC
        TGACTATACCACTGTCACATGGACATCAATGACCTGAATCACATATGCATAGATGCAGGC
        CCACATGGTCACTCCCACGTGCAGATGGCCAGTGCACACACATAGACACAGGGTACTCAC
        ACATGTTTACACTCTCACGACCCATGTGGGTTACAGATTCCTACAGAGACACAGACCTAC
        ATACTTTCACAAGGAAATTCTCCCAGTGACCCAGGGAACATAGTCTGCCATGATGATGTG
        [A,G]
        TGGTCCGTAGGGGCTCGCCACTATGGACCATTAATGGGCAGGCTGCACACATGCTTAGGT
        CCCCAGCAAAGCGGGAGTTCTGCACAGAGTGAGAGGAGAGGTCAGTTCTGATGAGTGTAT
        CCAGAATTTTGCAATCAGAAAAACCACACAAAAACTATTTTAATTTTCATTTCCAAGATA
        AAATTTAGTTTGAATTGTATAGAGGGTCCGAGGGTCTGGTGGGAGGGCATCATCATCTTT
        TCAAGGCTTTGGGGTTCTAAGGCACCCACAGATTCACAACAGTCCCACAAGATATCCCAG

63504   TGGGAGGTGGGCTGTATGACAGCCTGCCTCAGCCCCTGTGGCCCCACTGACCGGGACCCT
        GTGTAATGAGGCAGAGTGACCAAGGCCCATGGCCAGCGTCCCATGGGCTCGTAGGCCCAT
        CGCCTCCCCTCTCTGGGGCTTGGCTCTCTCATCTGAAAAATGGAGGTGGGAAGGAGATGA
        GACTGGATGGGCTTTCTCCTGGAGACTGATTAGAGAGACAGAGACTCAGGCCCGGGGTCC
        AGAAAAGACAACCAAAGCTGGGGAGGGCACATGAAGGGGGGCAAAGAAGGTCTGGGTTCA
        [G,A]
        GGGAGTGCGTGGGGCCCCAGAGCCTGCCATGTCTCCGCCAACTCTCTCCCTCACTGGAGG
        AGGGCTCTGTGCCTTGGTGCCCCACCTGCCCAGGGCCCTGTGGCTCAGCCCCTTGCTTGC
        TCTGTGAGGGGACGGGAGAAGGATGAGAGTCCCAGTGATAGGGGAGGACAAGACCAGG
        GGAGAGGGCTGGGGTTTCTGGAGGGCCAGAGCAGGAAGAGCAGGAGAGAAGAGAGGACA
        CCACAGTGCAGGAAACGGAGGAGCAAAGGCTGGGAGTGGGGAGGCTGGAGGGGTGCAGGG

63823   AGAGCCTGCCATGTCTCCGCCAACTCTCTCCCTCACTGGAGGAGGGCTCTGTGCCTTGGT
        GCCCCACCTGCCCAGGGCCCTGTGGCTCAGCCCCTTGCTTGCTCTGTGAGGGGACGGGA
        GAAGGATGAGAGTCCCAGTGATAGGGGAGGACAAGACCAGGGGAGAGGGCTGGGGTTT
        CTGGAGGGCCAGAGCAGGAAGAGCAGGAGAGAAGAGAGGACACCACAGTGCAGGAAACGG
        AGGAGCAAAGGCTGGGAGTGGGGAGGCTGGAGGGGTGCAGGGAATCAGACTGGGGCGCTG
        [C,T]
        GAAGAGGCCTGAGGCCAGAGCAGGCAGTGCCTGGATGGAGGGAGCGAGCAGCTCCTCACC
        CTCAGCTCCTTGATGAGGTAAGGTGACCACGAGCCCTGCTCCAGGCTGTGTGCTGAGCAC
        TTTGCTCGGAGCCTGTCACTCTGGAGGAGGGGAGGGGGTGTTCCCAGGAGCTATGACAGT
        CTTGTGCAAGGGAGGGACAGGGTCACATTTATGTTTAACAAAGCACTGCGCTGGGAGAGA
        GGAGCTGAGAGACCCCGGCCCTGGGGAGCATGGTGGCTGGGACCCCGGAGGGCAGGCGTG
```

FIGURE 3-73

| | |
|---|---|
| 64793 | CAAGCTCTGTTGAGAGAGCCAAATACAGTCATAGGACAAAGCAGCGGGAGGCTGTGGGAT |
| | ACACACATGCCGCAGAGCACAGACAGAGAGAGGTGGCCAGGCACAGAGAGAGCGCCCAGG |
| | GAGGCTGAGAGGCAGGGAGAAAACACGCTGGGACAGTCAGGGAGAGCCCCAGGGCAGGCA |
| | TCACCGGGCAGCCAGCCTCTGTGCCCTGCTCTCTATCTTGTCCCTAAGAAGACCAGCATG |
| | GCTGGGCTTGCCTCCCGCCATCCACCCCACCAGCCCTACCCCAGGCTGGCCCTTCCTCCC |
| | [T,C] |
| | GCCCTCTGCAGGCCCACACTAACCCTAGGCCAGGCCGCCTCCTTCAGCATTTACCTCCCA |
| | CACACAATGGGCACAGTGAGGACATAAGAGACCCAGTCTCTGGCCTGGAGGCAGATACTC |
| | AGCCTTACCCGACATCTGAGAGGGCTCAGCCCATCCCCTGGCCAAGGCAGGTATTAGAGG |
| | GGCCCCAAAGACAAGCAGGACTCTGGGACAAGGTGTCCTAGTGTGGCCCAAAGGGCTGGG |
| | CTGAAGCATGGGTCTCCTGGCTCCAGATGAGAGCCTGGGTGAATCCTTCCCTGCCTCCTC |
| 64829 | CAAAGCAGCGGGAGGCTGTGGGATACACACATGCCGCAGAGCACAGACAGAGAGAGGTGG |
| | CCAGGCACAGAGAGAGCGCCCAGGGAGGCTGAGAGGCAGGGAGAAAACACGCTGGGACAG |
| | TCAGGGAGAGCCCCAGGGCAGGCATCACCGGGCAGCCAGCCTCTGTGCCCTGCTCTCTAT |
| | CTTGTCCCTAAGAAGACCAGCATGGCTGGGCTTGCCTCCCGCCATCCACCCCACCAGCCC |
| | TACCCCAGGCTGGCCCTTCCTCCCCGCCCTCTGCAGGCCCACACTAACCCTAGGCCAGGC |
| | [C,T] |
| | GCCTCCTTCAGCATTTACCTCCCACACACAATGGGCACAGTGAGGACATAAGAGACCCAG |
| | TCTCTGGCCTGGAGGCAGATACTCAGCCTTACCCGACATCTGAGAGGGCTCAGCCCATCC |
| | CCTGGCCAAGGCAGGTATTAGAGGGGCCCCAAAGACAAGCAGGACTCTGGGACAAGGTGT |
| | CCTAGTGTGGCCCAAAGGGCTGGGCTGAAGCATGGGTCTCCTGGCTCCAGATGAGAGCCT |
| | GGGTGAATCCTTCCCTGCCTCCTCTGGCCTTAGTCTACCCCATCAAGCTTGGGATTGGAC |
| 65593 | GACCTGCTGCCCCCACCCGGTCTGCACGTGGAGATGATCCTGAAGCACAAAGGGCCTCCC |
| | GGCCTGCAGAGGTGCCTGGGAGAGGTTGCCAAAGGCTCTCAGTAGGAGACACCCCATTCC |
| | TCAGGCTCCTTCTCTGAGACTGTAACTGTGCCAGACTGGGGAGGCTTTGAGAGGTCTCAG |
| | CTATCTCCCCTGCCTAGATCCTTCCTCCACACCCCTCTTCTCCCTGATGGCATGTAGCCC |
| | TCACAGTACAGTAGTCCTGGGCACACAGGAGTTTACCCAGTCATTTACAGCTCAGCAAAC |
| | [G,C,AsT] |
| | CCTACCAACACCTATGAGGGGCTGGGTAATGCTGGAGACCCGGAGAGGGGCAGGACACAA |
| | TCTCTGCCCTCCAAAAGCTCCCAGTCTGTTGTGGGAGCCAGACGGGAAAGGGTGGCACTG |
| | CATTGATGCACACAGTGCATGCCATGGTGGGGGAAAGGGGGCAGTGGGAGCCCCAGGTG |
| | GGAGGGTCAGACTTGCCTGGAGAGAGAACAACAACAGACTCTCCCTGGAGGGGATCCAGA |
| | GAAGGGAGATCACTTCATTCATTCATTCGTCATTCATCCATCCACCCATTCAATTATTCC |
| 65634 | GAAGCACAAAGGGCCTCCCGGCCTGCAGAGGTGCCTGGGAGAGGTTGCCAAAGGCTCTCA |
| | GTAGGAGACACCCCATTCCTCAGGCTCCTTCTCTGAGACTGTAACTGTGCCAGACTGGGG |
| | AGGCTTTGAGAGGTCTCAGCTATCTCCCCTGCCTAGATCCTTCCTCCACACCCCTCTTCT |
| | CCCTGATGGCATGTAGCCCTCACAGTACAGTAGTCCTGGGCACACAGGAGTTTACCCAGT |
| | CATTTACAGCTCAGCAAACACCTACCAACACCTATGAGGGGCTGGGTAATGCTGGAGACC |
| | [A,G,C] |
| | GGAGAGGGGCAGGACACAATCTCTGCCCTCCAAAAGCTCCCAGTCTGTTGTGGGAGCCAG |
| | ACGGGAAAGGGTGGCACTGCATTGATGCACACAGTGCATGCCATGGTGGGGGAAAGGGGG |
| | GCAGTGGGAGCCCCAGGTGGGAGGGTCAGACTTGCCTGGAGAGAGAACAACAACAGACTC |
| | TCCCTGGAGGGGATCCAGAGAAGGGAGATCACTTCATTCATTCATTCGTCATTCATCCAT |
| | CCACCCATTCAATTATTCCTTTGGCCATCATTTCCTGAGGGATGTAAACTCTCTTCTGAC |
| 65848 | CCTGGGCACACAGGAGTTTACCCAGTCATTTACAGCTCAGCAAACACCTACCAACACCTA |
| | TGAGGGGCTGGGTAATGCTGGAGACCCGGAGAGGGGCAGGACACAATCTCTGCCCTCCAA |
| | AAGCTCCCAGTCTGTTGTGGGAGCCAGACGGGAAAGGGTGGCACTGCATTGATGCACACA |
| | GTGCATGCCATGGTGGGGGAAAGGGGGCAGTGGGAGCCCCAGGTGGGAGGGTCAGACTT |
| | GCCTGGAGAGAGAACAACAACAGACTCTCCCTGGAGGGGATCCAGAGAAGGGAGATCACT |
| | [A,G,T] |
| | CATTCATTCATTCGTCATTCATCCATCCACCCATTCAATTATTCCTTTGGCCATCATTTC |
| | CTGAGGGATGTAAACTCTCTTCTGACACTGACCCAGCGGGACACTCAGCGTCCTCCTCCT |
| | CTCCTGCTTGAGCCACCATGCCTGCCTCTTGGAGGCTCCTGGACTTGCTTTGCTCAGCTC |

FIGURE 3-74

```
         CCAACCCACCCCTGAGGGGGTGAGGCTGAGGAGGGTGTACAGACATTCAGGGTCACCAAAC
         TCAGAGCTGGAGGCCTGCCACCTCACCAGGGGCCTTTCTCAGGGCACAGGCTCCCTGGTG

66187    TTATTCCTTTGGCCATCATTTCCTGAGGGATGTAAACTCTCTTCTGACACTGACCCAGCG
         GGACACTCAGCGTCCTCCTCCTCTCCTGCTTGAGCCACCATGCCTGCCTCTTGGAGGCTC
         CTGGACTTGCTTTGCTCAGCTCCCAACCCACCCTGAGGGGGTGAGGCTGAGGAGGGTGTA
         CAGACATTCAGGGTCACCAAACTCAGAGCTGGAGGCCTGCCACCTCACCAGGGGCCTTTC
         TCAGGGCACAGGCTCCCTGGTGGCAGGGCCTTGGCCCTTGCTTGCACACCCTTGGGGACT
         [A,G]
         GGAGCCCCCTCATCCATCCTGCTCAGGCTCTCTTTTGTGGCGCGACTCTGATTCACAGTG
         TGCCCAAATCTGCCTCCTTGTGACTGCCGCGAGCTGCCTCGTGGGCCCCAGGCCAGAGGA
         CAAGGATAGCTAGAATGCCAGGTGACCAGGATGACTGTGATGGCATGGAGAGGGGGATGC
         TGTGATGTGTTTGGGAGGAAGTTTGTGGTGTCCAGGAGAATGTGGGCAGCAGAAATGGGA
         CCACTCTCGGTTCTTCCCTGTAGATGAAGCAGCTGAAGGTGGGAGGGGGTGGGAGGAGAC

66843    CCTCCCCACACTCAGCTCCTGCCTCCCTCCCTCTACCCACTCTGACTGTTCCCTCCTTTC
         CTGACTCCAGACTCTGGGTGAGGGACTGAGGTGATTCCAGTGAGTCAGGCCCTCAGGGAA
         CTGATCGTGCAGGCAACTCTTGCCTGCCTTCTCCTGCTCTTTCCCTCTTCCCATTCCTTC
         ATCCACCCCCAAACCTAGCTCCTGATGGATCCAAGGGTGCGGGGGACAACCGGGAGGTCA
         TTTTGGAGGAGGCAGGAGCTGGAATAGAAGCTGGGACTGGCTTGGGAAGGGCGAGAGGCC
         [T,C,G]
         GGGCGGAGCTGGTTGTGGGCGCTGGAAGGGAGGAGCCAACAGTGTGGGGTCAGGCTCCTG
         TGGACGGGGACACCCTTGGGAGGCACTGGGACTGGCTCAGGTGTATTCTACAGTGCACGT
         GTCTCCAGTGTGGCTCGGAGGCTGGAGACGCGGCCCTGTTGGAGTAACAACTGAAGCCGG
         AGTCTGCGAAGGGTGGGCAGGAGGGTGGAGGGATGGGGGCATGGAGCGGGAGGGGGTAAG
         TAGAGGAGGGAGGGGAGGAAGAGAAAGAGGGAGGAGGAAAGGTCTCTGGCAGGTCCCTCC

66908    TCCAGACTCTGGGTGAGGGACTGAGGTGATTCCAGTGAGTCAGGCCCTCAGGGAACTGAT
         CGTGCAGGCAACTCTTGCCTGCCTTCTCCTGCTCTTTCCCTCTTCCCATTCCTTCATCCA
         CCCCCAAACCTAGCTCCTGATGGATCCAAGGGTGCGGGGGACAACCGGGAGGTCATTTTG
         GAGGAGGCAGGAGCTGGAATAGAAGCTGGGACTGGCTTGGGAAGGGCGAGAGGCCGGGGC
         GGAGCTGGTTGTGGGCGCTGGAAGGGAGGAGCCAACAGTGTGGGGTCAGGCTCCTGTGGA
         [A,G,C]
         GGGGACACCCTTGGGAGGCACTGGGACTGGCTCAGGTGTATTCTACAGTGCACGTGTCTC
         CAGTGTGGCTCGGAGGCTGGAGACGCGGCCCTGTTGGAGTAACAACTGAAGCCGGAGTCT
         GCGAAGGGTGGGCAGGAGGGTGGAGGGATGGGGGCATGGAGCGGGAGGGGGTAAGTAGAG
         GAGGGAGGGGAGGAAGAGAAAGAGGGAGGAGGAAAGGTCTCTGGCAGGTCCCTCCTTTAA
         GACTGGGCTCCTGCGCTGCGAGTGGCCCCGTCCATACTGCCTTGTTATCCATATCTCCCC

67481    CATACTGCCTTGTTATCCATATCTCCCCACCACTAGTCTCCCTCTGTCCTTCCACCCCCA
         GCCTCTCCCCTCCATTGGGACCTTCCCTGGGGCGTCCCCTCATTGGCTGTTCTCACCTGA
         GCAAGGCCCCTCCCCTCCAGTCCTTAGCCTCTTCACCTGTACAATGGGATGACCCAAACA
         GGCACCTCTTGGGCTTGTAGGAGGATCCAAGATAGTGTCAGTGGGTCTCGAGGTGTGGTC
         CCCCGACCAGCAGCATCAGTGTCATCTAGGAATGTTTGGAAACGCAAGTTCTTGGACCTC
         [G,A]
         TCCCAGACCTACTGTATCAGAAACCCTGGGGGTGGGGCCAGCAATCTGCACTTTAACAAG
         CACTCTGGGTGGGTTCTGGTGCACATGAAAATTGGGGAACGGCTGGTGGAAACCTCTAGC
         CACAGGAGGTGCTTGGGAAAGGTACCTTCCCCTCCCCAAAGCCTGATGCCTCACTCAAGC
         ATGACACTGACAGTTGGGCTAGTTCAGCTGCGTTCTGGGTCTCTGTCTTGCCTCCTCCTT
         CAGACTAAGCCTCCCAAGGGTTGCCAAGCCTCTTTCCTCTATTCTCCTCACCCTGATCCA

67637    CTGTACAATGGGATGACCCAAACAGGCACCTCTTGGGCTTGTAGGAGGATCCAAGATAGT
         GTCAGTGGGTCTCGAGGTGTGGTCCCCCGACCAGCAGCATCAGTGTCATCTAGGAATGTT
         TGGAAACGCAAGTTCTTGGACCTCGTCCCAGACCTACTGTATCAGAAACCCTGGGGGTGG
         GGCCAGCAATCTGCACTTTAACAAGCACTCTGGGTGGGTTCTGGTGCACATGAAAATTGG
         GGAACGGCTGGTGGAAACCTCTAGCCACAGGAGGTGCTTGGGAAAGGTACCTTCCCCTCC
         [C,T]
         CAAAGCCTGATGCCTCACTCAAGCATGACACTGACAGTTGGGCTAGTTCAGCTGCGTTCT
```

FIGURE 3-75

```
       GGGTCTCTGTCTTGCCTCCTCCTTCAGACTAAGCCTCCCAAGGGTTGCCAAGCCTCTTTC
       CTCTATTCTCCTCACCCTGATCCAGCTCAGCCTCATTGAGAGAAGTCTGGGGCTGCAAGA
       TCTTCGCACTCACAGGCAGTTCCTCTTTGCACATCCAAGGCACCAGTGTCTTTGAGAGGC
       GTCTCCTTGGCCAGGTGGCAGGCGTGGGTGTGTGGGGAGGAAGGAGGAGGAACCGCCTTG

69231  GGGAAAGGCATAGAGACTCATGAAGATGAAACAGGAAAGATCTTATGGCAGCGACCCCAA
       CCCTCAGGAAGGGCGTTGGTCTTGTGCTTGTGGCTCCAAAGGGGATAAGACCAAGGTCTC
       TGGTTTCATAGAATCTTAGGCTTTAAGAACGAGTTAGAAGTAATTTAGTCCAGACCCTCT
       CCTCTCCCCAGATAAGTGCAGAAATGCAGATCTAGCCCACGGCTGAGCCCCAACCCTGGC
       TTCAGAGGAGGCCTGACTCAGAACAGGCTCCCCTTTCTTGGTACCTGGGGTGAATGAAAG
       [A,C]
       TAAGTCTGTGGTAATGGTGCTGTCTGTGGTGCTGACTGGCCTTACCTTGGACTACAGAGC
       TGCAGGTGGAGCTGGAGAGAGCAGAAAGGCTCCATCTATCCATCTACCCACCCACCCAGC
       CACCCATCTACCTATCCACCCACCATCCACCCACCCATCCATCCACCATCCCTCCCCCAA
       CCCATCCTGCACCCATTCATCTATCCACCTACCCACTCATCCATCCAGCCTCATTGAATT
       AAACCATAGAACTATATGCTGCAGAGCTAGAAAGATCCATTTTTTAGTAATGACAAAACT

69238  GCATAGAGACTCATGAAGATGAAACAGGAAAGATCTTATGGCAGCGACCCCAACCCTCAG
       GAAGGGCGTTGGTCTTGTGCTTGTGGCTCCAAAGGGGATAAGACCAAGGTCTCTGGTTTC
       ATAGAATCTTAGGCTTTAAGAACGAGTTAGAAGTAATTTAGTCCAGACCCTCTCCTCTCC
       CCAGATAAGTGCAGAAATGCAGATCTAGCCCACGGCTGAGCCCCAACCCTGGCTTCAGAG
       GAGGCCTGACTCAGAACAGGCTCCCCTTTCTTGGTACCTGGGGTGAATGAAAGATAAGTC
       [T,C]
       GTGGTAATGGTGCTGTCTGTGGTGCTGACTGGCCTTACCTTGGACTACAGAGCTGCAGGT
       GGAGCTGGAGAGAGCAGAAAGGCTCCATCTATCCATCTACCCACCCACCCAGCCACCCAT
       CTACCTATCCACCCACCATCCACCCACCCATCCATCCACCATCCCTCCCCCAACCCATCC
       TGCACCCATTCATCTATCCACCTACCCACTCATCCATCCAGCCTCATTGAATTAAACCAT
       AGAACTATATGCTGCAGAGCTAGAAAGATCCATTTTTTAGTAATGACAAAACTGAGGCTC

70821  AGTCACAGAAAACTGAACAATCAGAGCAAAGGTCAGGCAGGCACCCACCCAATTCCAGTAA
       AGGACAGTTGAGGGCATTCCCCAATTGAAGCAAAGGGCAGGTTGAGGAGTCCACCAATCA
       GAATAAAGGACAGACTGTTCTTTCTGAGCACCCTAGGGTGGGAGCTGGGGATCGGGTGCT
       GAGCAGGAACCAGACAGGGCTAGAGATCCAGAGGTTTGGGTTCTGGACCTGGCTCTGCTC
       TGACTGGCTGTCTGACCACAGGTTGATCATTGCTTCTCATTGAACCTCAGCTTCCTCATC
       [G,A]
       GTCAAATGGGGAGACTTAGCTCTCTGAAGGCTGTGGCTTTGAAGAATTTCTCCCCCTGTA
       TCAGGCTCACTCCGTCACCTGGGTCTCTCTTCCCCAAGTCCACATCACATACATCAGACT
       CCACCAAGGGCAGGGCCTCTCAGGAGTCAGCTTGTGGGCTCCTCTGCCTCCAAGAAGGAA
       TAGACACAAACCAACACCACCTTCTGTGCTGTCTTTAGAGCCCCCGTCTGGGGAGCGTGC
       ATCTGGAAGACTTTATCTTGGGAGTACTGGGGGCATCAGCTCTTCCTCCCCTTTTTAGTC

72136  TGTCCATGGGGCCACAGAGTTCAGATCCCCCATCTAGGAGGGTCTGAGAGATTGGAGTTG
       GAGACTGATAACCCTGGGTCTCCTCTGCTTTAGATGAGGCATCCCTGGGTTATCCAGTCT
       TAGTCACATGCAAAACTTGGTTTTCCAATTCCCTCGTTTCATAGGTCGCCTCCTCTGGATG
       AGTGTCATCTTGTCAGCCCCTGGGACACAATGAACAGGGGATGGTCTAACTAGACTATAA
       AAGTGGGGGAACTGTCATCTTCCCAATTGGGTTAACAGACCTCTATTAATATGGCCTGCA
       [T,C,G]
       TTTGAGCATTTTTATTTCTTGCCAGTCATGCTTACACTGTGGGCTCATGCTGAACTGTGG
       TCTTTTTAAGACCCTCAACCTCATATCATGTTCACATGAATGGGGACCCAGCCATGTCTCC
       TTCATCTTGCAGTTAATCACTTTGCTTTTCTGAACACAGACCCAACCTTCCACTGGGAAGA
       CATCTGAAAGGACTTCCAAGGGCTTGCGGGAGGGCATGGCTGGTGGCTGGTATGAGTCAC
       GATCTTGCCTTGGCCCTCGTTTCCTTTGTTCTGTTACCTTTCTCTTTGATCCCCATGGCT

72285  CCCTCGTTTCATAGGTCGCCTCCTCTGGATGAGTGTCATCTTGTCAGCCCCTGGGACACA
       ATGAACAGGGGATGGTCTAACTAGACTATAAAAGTGGGGGAACTGTCATCTTCCCAATTG
       GGTTAACAGACCTCTATTAATATGGCCTGCAGTTTGAGCATTTTTATTTCTTGCCAGTCA
       TGCTTACACTGTGGGCTCATGCTGAACTGTGGTCTTTTAAGACCCTCAACCTCATATCAT
       GTTCACATGAATGGGGACCCAGCCATGTCTCCTTCATCTTGCAGTTAATCACTTTGCTTT
```

FIGURE 3-76

[C,T]
TGAACACAGACCCAACCTTCCACTGGGAAGACATCTGAAAGGACTTCCAAGGGCTTGCGG
GAGGGCATGGCTGGTGGCTGGTATGAGTCACGATCTTGCCTTGGCCCTCGTTTCCTTTGT
TCTGTTACCTTTCTCTTTGATCCCCATGGCTCTGGCCAAGTTAATAGAGCGAGAAGCAGG
GACTTTTGTCTCCGTTCCGGCTCTGCAAGGACGAGTTCTGTTCCTGGGATGGGAAGGCTG
TGAGACAGTCAAGGCTGACGTCTCCTTCTCCTCCTATAGTTGCCAGGGGTGGCCCAGCTG

72611 GGAAGACATCTGAAAGGACTTCCAAGGGCTTGCGGGAGGGCATGGCTGGTGGCTGGTATG
AGTCACGATCTTGCCTTGGCCCTCGTTTCCTTTGTTCTGTTACCTTTCTCTTTGATCCCC
ATGGCTCTGGCCAAGTTAATAGAGCGAGAAGCAGGGACTTTTGTCTCCGTTCCGGCTCTG
CAAGGACGAGTTCTGTTCCTGGGATGGGAAGGCTGTGAGACAGTCAAGGCTGACGTCTCC
TTCTCCTCCTATAGTTGCCAGGGGTGGCCCAGCTGTTCTCCCACCTTATGGGTTATGCAC
[C,A]
CCATAGGCTCTTGCTACTCTCAACCCAGCCCCTCACTAGGCTGGAAAATGAGACTAGGTG
AGACCACCTTCCTTCTGGGGAAAGTGAGCGGGACCCAGCTTCAGCGAATATTCAGCTGAG
CATCTACTCTGTGTTGGGCATTCTGTGAGGCACTTTTAGGACTCTGATTTTTATTTTCAT
TTTTAAGGGCTCAATTTCATTTTATCTTCATGTCAGCCTGTAGGGGGCAATAGCCCCAGC
TGCTTCCAACTTACAGATAGGAGACTGAGGCTCAGTGACTGAACCAAGACACTCACTGCT

73103 CAATTTCATTTTATCTTCATGTCAGCCTGTAGGGGGCAATAGCCCCAGCTGCTTCCAACT
TACAGATAGGAGACTGAGGCTCAGTGACTGAACCAAGACACTCACTGCTCATACACAGCG
GAGCTAGGATTCAAATTTGGGTGTTTTTTTGTTTGCTTGTTTTGTTTTAATTTGGAGCCT
TGTGGTTTCCCTACTGTGCCAGAATTGTCCTCGACTAGAGAACAAGAGACCTGGGGTCTA
GGCCAGGCTTGACCTGTTGACTCACTATGAGGCCTTTGCTAAGTCCCTGGCCCTTCTCTG
[C,T]
GCCTCAGTTTCCCCACCTGTAAGATGAGGGTACTTGGACATTCTGTGGCCTTAAGACTGT
TTGATTTTGAGATCCTAAGATCCTGGGATTCCTGTGCCTGAAAGACTCGGGCTCTGGACT
AAGCTGGGGGGTTTTGCTCACAGTCCTTTGGGCAGATGGGGCTGCCCTGGCCTGCCTGGC
AAAGCCTCTCACTGCCCTCTCCTCTCTTCCAGGACGCCTTGCTGAGTCTGGGCTCTGTCA
TCGACATTTCAGGCCTGCAACGTGCTGTCAAGGAGGCCCTGTCAGCTGTGCTCCCCCGAG

73589 CTCTCACTGCCCTCTCCTCTCTTCCAGGACGCCTTGCTGAGTCTGGGCTCTGTCATCGAC
ATTTCAGGCCTGCAACGTGCTGTCAAGGAGGCCCTGTCAGCTGTGCTCCCCCGAGTGGTA
GGTGCCCGCCCTTGCCCCACGCTTCCCACCCCACCCCCAAATCCTTTGACCAGCTCTATG
CTGTACCTCACTCAGGGCCAAGGAGGAAGGAAGAGGCAGGGTCCCTGCCCAGAGGACTTT
CATGGGGAAGTGAAGGGTCTGGATGGGTGTTCTGAGACAGCTTTCTGGAGGAGGAAGCCT
[G,T]
AGGCTAAGCATCAAGGAATGAACTTGCATAGGAATCCTGCAATGGCTGAGCCAGAAGGGG
CCTTAGAGGTTAAGTGGAAAAGCTGTGTCTCAGATAATGAAAGGGATTCACCTAGGATAA
CAGGACGTGGTGGAGCCAGCTGAGTTTTGGAATACATGCAGCAGGAGAAGTTGAGGGTAG
ACATGTAGAAGAACTTCCTGGAAGCCAGGTCTGGGAGGTACTAGAATAGGGCTCAGCTTT
GATGAATAGACATGCATTGGGTTAAAGTGCCCTGCCTGGAGATGGGAGGCTGGAAAAATG

73591 CTCACTGCCCTCTCCTCTCTTCCAGGACGCCTTGCTGAGTCTGGGCTCTGTCATCGACAT
TTCAGGCCTGCAACGTGCTGTCAAGGAGGCCCTGTCAGCTGTGCTCCCCCGAGTGGTAGG
TGCCCGCCCTTGCCCCACGCTTCCCACCCCACCCCCAAATCCTTTGACCAGCTCTATGCT
GTACCTCACTCAGGGCCAAGGAGGAAGGAAGAGGCAGGGTCCCTGCCCAGAGGACTTTCA
TGGGGAAGTGAAGGGTCTGGATGGGTGTTCTGAGACAGCTTTCTGGAGGAGGAAGCCTTA
[G,C,AsT]
GCTAAGCATCAAGGAATGAACTTGCATAGGAATCCTGCAATGGCTGAGCCAGAAGGGGCC
TTAGAGGTTAAGTGGAAAAGCTGTGTCTCAGATAATGAAAGGGATTCACCTAGGATAACA
GGACGTGGTGGAGCCAGCTGAGTTTTGGAATACATGCAGCAGGAGAAGTTGAGGGTAGAC
ATGTAGAAGAACTTCCTGGAAGCCAGGTCTGGGAGGTACTAGAATAGGGCTCAGCTTTGA
TGAATAGACATGCATTGGGTTAAAGTGCCCTGCCTGGAGATGGGAGGCTGGAAAAATGGC

74229 CCCAATACCATGGATGAGTTGCAGGTTTGGGGCAGGTTTGGGGTGATCATGGTTGCCTGA
GCCCAGAGTGCCTTACTGGGGAGATTGTGCCCCTCATCATCTGTTCCAGGCCACTCCCCT
ACCTGGCTTCAATGGCCACTGTTCATCCCTTAGGCAGGAGGATGGGTAAACCAGCCCTTG

FIGURE 3-77

```
         AGGCCCAAAGTAGCAGGGTGTTAGTTGCACCAGAAAGAGGGAAGCAGGGGACGTTTGAAG
         CCTGGAGAAGGGAGTCTGATCCAGCCTAAGGGGCATGGAAGACTTCCTGGAGGAGGAGAT
         [T,A,GsC]
         CCCTAACTGAGTCCTGATAGCCTTGAATGTCCTCTTCCCTACTCTAAACCCGGCCAAGGG
         CAGCCTCTGCTCCAGGAAATATGGCCAACTCAGAATGTGACCTTCCCATCCCTCCAGAGC
         CCATTGTCCCTGAATCTGCTTGATGGATGAACCACCGGAGGCCCAGAGAGAGAGGGCACT
         TGTCCCAAGGTCACACAGCATGACAGGGATAAATGGGACTTGGTATCTAAGCAGCCCCAT
         TCCCTCTCTTCAGCTCTGCCTTCCCCAAACCTCCTAGAAGTTCAGAGCCCAGGAGGAGGG

74478    GGGAGTCTGATCCAGCCTAAGGGGCATGGAAGACTTCCTGGAGGAGGAGATTCCCTAACT
         GAGTCCTGATAGCCTTGAATGTCCTCTTCCCTACTCTAAACCCGGCCAAGGGCAGCCTCT
         GCTCCAGGAAATATGGCCAACTCAGAATGTGACCTTCCCATCCCTCCAGAGCCCATTGTC
         CCTGAATCTGCTTGATGGATGAACCACCGGAGGCCCAGAGAGAGAGGGCACTTGTCCCAA
         GGTCACACAGCATGACAGGGATAAATGGGACTTGGTATCTAAGCAGCCCCATTCCCTCTC
         [T,C]
         TCAGCTCTGCCTTCCCCAAACCTCCTAGAAGTTCAGAGCCCAGGAGGAGGGCTAATGAGT
         GAGCTTTATTGAGTGTGAAATTGGTAGGAAGTGGGTGGTGTGTTGGCGCCCAAAAATAAA
         TCCTCCTGGAGAAGGACGGGACTAAGGCAACATCTGGCCTGGGGTGAAGGCACATCTGGA
         AAGGGAGGGTGGTGGAAACTGGCAGGTCGGTTTCTGTAGGGCTGCCCCGAGAGCCTCTGT
         GGCCACTGAGGCTGCCGTAGGGTGGGAGGAGGAAGTGACTGGCTCTGTTTCACAGGCAGG

74636    CATCCCTCCAGAGCCCATTGTCCCTGAATCTGCTTGATGGATGAACCACCGGAGGCCCAG
         AGAGAGAGGGCACTTGTCCCAAGGTCACACAGCATGACAGGGATAAATGGGACTTGGTAT
         CTAAGCAGCCCCATTCCCTCTCTTCAGCTCTGCCTTCCCCAAACCTCCTAGAAGTTCAGA
         GCCCAGGAGGAGGGCTAATGAGTGAGCTTTATTGAGTGTGAAATTGGTAGGAAGTGGGTG
         GTGTGTTGGCGCCCAAAAATAAATCCTCCTGGAGAAGGACGGGACTAAGGCAACATCTGG
         [C,G]
         CTGGGGTGAAGGCACATCTGGAAAGGGAGGGTGGTGGAAACTGGCAGGTCGGTTTCTGTA
         GGGCTGCCCCGAGAGCCTCTGTGGCCACTGAGGCTGCCGTAGGGTGGGAGGAGGAAGTGA
         CTGGCTCTGTTTCACAGGCAGGGTGCCCTGGCGGCTGTGCCAGCCTAGATGCTCTGCAAC
         AGATTAATTGTCTCCCCAAAGCTGGGGCTGGGATGACAGCTGTGGTCCAGGTTCCTGGG
         ACAGTGGGAAATGTCAGCCCTGGCCCACCCAAGAGCCCTATAGGAGCTAGGGAAGCCCTG

75308    TCTGCTGCCCCCAGGGAGGGAAGCAGAGATGGGGAGGGGACCCCCGCCCAGGGAGGAGAG
         CTGCTGGCACCTGGCTTCCTCATCAGCACCCATTGTGGCAGGCAGCCCCGAATGCAGATG
         GTGCTGATGTGTCTGAAATGGTTCCCTCCTTCTCTCCAATAGACTCAGCTAATTTTAACC
         CAGAGGGCTGAGAGTAAGGGGGTGGGAGACATACGGACATGCGGAAGTGAAGCGAGAATC
         TGTCCCCCTCTGCCCCATGGACTACCCACCCCTCCCTCTGCCTGGGCAGGACTTTCTGT
         [A,C,T,G]
         TAACCCCGGCTGGTCTCTTAACCTCTTTGGGCCAAATAACTCAGGCCCCTCCCAGGCTGC
         TGGAAGAGATGGATGACAAGGAGGCTAGATATAGCCGAAGAGTGGGCGGCCTCCTTCCCA
         CTGAATTCTTTATCCCTGAACATCCCACTTAGGTTTCCTTCCAGCCAAACAAGAGGGTGT
         CTGCCCCTCTCACTCCCTTCAGGCCTTATCATTCCCACCCCATGCCACACCCACCACGGA
         ACCTGGCTCAGTGTCTCTGGAAGTAGTGGCCAGGCATCTCCTGTGGTGGGGGCTGGCTGG

75554    CCTCTGCCCCCATGGACTACCCACCCCTCCCTCTGCCTGGGCAGGACTTTCTGTATAACC
         CCGGCTGGTCTCTTAACCTCTTTGGGCCAAATAACTCAGGCCCCTCCCAGGCTGCTGGAA
         GAGATGGATGACAAGGAGGCTAGATATAGCCGAAGAGTGGGCGGCCTCCTTCCCACTGAA
         TTCTTTATCCCTGAACATCCCACTTAGGTTTCCTTCCAGCCAAACAAGAGGGTGTCTGCC
         CCTCTCACTCCCTTCAGGCCTTATCATTCCCACCCCATGCCACACCCACCACGGAACCTG
         [G,C,AsT]
         CTCAGTGTCTCTGGAAGTAGTGGCCAGGCATCTCCTGTGGTGGGGCTGGCTGGCGACAG
         CTGATGACAAGAAGAGTGGCTGGCAGGATTGTGGACGCTCTCAGAGTCATGGAAGGCAAC
         TGCTTCTTCTGGGAAGGATTCCACACTTACTGAGGGTGGGCCTTCAACACGTAGCTCCAC
         TGTCAGCTCCTCCCAAAGCCCTCCAGGATACCCTCAGCTGGGAGGCAAGCCCTTCTCCAT
         CCTCCTGCGGAGAAAACAGCAGAGTTGTGGACAAGGCTGCGTTGCATGGGGGTTGGTCAG

76209    GGTCAGTGAGGGCAACTACTTCTGCCAAGACATGGCCTGGAACTGAGGCCAGAGCTGCTC
```

FIGURE 3-78

```
        TGGGCCCTTGGGGAGGGAGGATTAAAGAGCAAGAGCTTTGATCTCCCTCTGAGGAGTAAT
        CGGTCCAAAATACAAATCTGCTCACGTCTCCCTGTGCACGTCCTGCCCTGCCCCAGTTCT
        GTTCGTAAGCCCATCCCACTCAGCCCTACTGACCTTGGGCCCAGCCCCTGTGCCCCTTCC
        CTCACTGTCTGTTCCTAAATGCTCCATGCTTTATACGCCTCTGGACCTACCTGTGTACCT
        [G,A]
        CTATAAGGCCTGGGAGCCCATTCTGCACCCTGCCCACTCCCTGAATGTGTCTAATTCCCA
        CTCAGTGACAGCTGAAAGGTCACTTCCTCCAGGAAGCCCTCTCCAGCCCCACCGGAGGAT
        GGCGCAGTGCCCTGCTCTGTGTTCCTCCCCTGGCTGGGGTTATGGGTGTGTGGTTTCTTG
        TAGAGGTGAAGGAGGGATGCTTCCTAGAACATTCTGAGCCCCATCCCTGGTACAGCTCAG
        AGTGGATGCTCAGTTATTGTTTGCTGAATGCCTGAGGCTGGAGTCAGGCAGGGAAATATC

76627   GATGGCGCAGTGCCCTGCTCTGTGTTCCTCCCCTGGCTGGGGTTATGGGTGTGTGGTTTC
        TTGTAGAGGTGAAGGAGGGATGCTTCCTAGAACATTCTGAGCCCCATCCCTGGTACAGCT
        CAGAGTGGATGCTCAGTTATTGTTTGCTGAATGCCTGAGGCTGGAGTCAGGCAGGGAAAT
        ATCCCAGGTGGGAGGTGATTTGTCTGCACCCTCAGTCCTTGAAACTCTTTACCTGGCACA
        TTGGGTTTTGGGTGGTAAAAAAGGTCATAGGTTCATGAATCATTGCCTGCTTAGAATTCC
        [T,C,TsC]
        TCCAAGAGGAGAGGACGAGGTGCTTAGTTCACCGGGTGTTTTGCTGCCCTGGCTGCATCT
        TAGAATCACCTGGAGAGAAAAACAAACAGATCATTGCCAGAGCTCCACTCCCACAGGTTC
        CATGACCTTGCCCCACAGACCCCTGTGTACAGGCTGGGACTGGGCAGCTGGGAGGGCCTC
        TCCACAGGGTCTCATAAGTGCCTTCTGTCCTAGGAAACTGTCTACACCTACCTACTGGAT
        GGTGAGTCCCAGCTGGTGTGTGAGGACCCCCCACATGAGCTGCCCCAGGAGGGGAAAGTC

76767   TGTTTGCTGAATGCCTGAGGCTGGAGTCAGGCAGGGAAATATCCCAGGTGGGAGGTGATT
        TGTCTGCACCCTCAGTCCTTGAAACTCTTTACCTGGCACATTGGGTTTTGGGTGGTAAAA
        AAGGTCATAGGTTCATGAATCATTGCCTGCTTAGAATTCCTTCCAAGAGGAGAGGACGAG
        GTGCTTAGTTCACCGGGTGTTTTGCTGCCCTGGCTGCATCTTAGAATCACCTGGAGAGAA
        AAACAAACAGATCATTGCCAGAGCTCCACTCCCACAGGTTCCATGACCTTGCCCCACAGA
        [C,A]
        CCCTGTGTACAGGCTGGGACTGGGCAGCTGGGAGGGCCTCTCCACAGGGTCTCATAAGTG
        CCTTCTGTCCTAGGAAACTGTCTACACCTACCTACTGGATGGTGAGTCCCAGCTGGTGTG
        TGAGGACCCCCCACATGAGCTGCCCCAGGAGGGGAAAGTCCGGTGAGCCATTCTCTGCAC
        CCCCATTGCCCTCTTGCATGGCCAAGGATTCTCAGGGCTGAGGCACCATCCAAGGTCATC
        TGGTCTGACCCTCCCCTTCCAACATTGATCCCCGCCTCCCTGCCAGGTGGGATTCCTTGG

77530   TATGGGGTGTATCAGTTAGAACACCGGCATGCTGTGAGAACTACTGCGAGGCTGGACCTG
        GAATCCCAGCATGCTGGGCCTGCAGGAGCTCACAGTGCCAACTCCTTGCATCTGAGAACA
        GGGAGATCACAGGCAGCGTCCTGCTGAGGGTTCTGGAGCCCCACTGCCTGGGTTCAAATC
        TCAGCTCCCTGTTTACTAGCTGTGTAACCTTGGGCAAATGACACAACCTCTCTGTGCCTC
        AGTTTTGTTTATGAAATGGTGATAATAATGGTGCTTATAGGATTGTGGGGAGGATTAAAT
        [G,A]
        TGTCACACATGTAAAGCATTTAAATCAGGCCTGATCCATGGTGAGGGCTGTCTGTTGGGG
        ATTACCATTGTGAGAGAATGCTGGAATCACTGACTTCAGGATCATGGGATCAGGGCACTT
        GGCCCCCTGATACCTTGATGCCCATTTAATTCAGCCTCCTCATCTTCCAGATGGGTGGAT
        ATCATGAGACATGACCAAGGCCACATGCCAGGTATGAGGCAGAGCCAGGCCTAGGACTCG
        GGTCTTCTGACTCCTGGCTGTTTAGGGGAAAGTGAGAGGAAGTGGAACTCATCAGATGAG

78642   TGTCCCGTCTGTAAGAGGATGGTCTGAAAGGTCTTTAGAACCTTAAGGGGAAAAATGTGG
        TCATGTCCCCCTTTCTCCTCTAATTCCAAAGAACTTCGCTCTCCTCCAGCATCCCCCACC
        TCTAATTCTAAAGAACTTTGCTTCATATAAGCTCCACTCCTCCAGGAAGGCTCCTCGGAG
        CAGCCTGGGAGGCCTTCCTGGGAGGGATGCAGGAAAACAGGCTCAGGAGGCAGCGGGGAG
        CAGCCTGCAGGTTTGCTTCACTCCCTAGGACCCACACATGCTCCCCTCAGCTGTCTGGGC
        [A,G]
        TGTAGAGTGGGTGCGTATCTGCGGTCCAGGCATTTTTGAGAGGGCTCAGATCCTTGGCAT
        CAGCTGCCCTTTCAACATCCTCCTTCCAACCACTTCAGACTCAGTAAGGCCTTTGGAAAA
        AATACCAAAAAAAAAGCAATTAAAAGTGAATATTCAAATCCAATTATCCCAGAGCTCAGT
        GGAGATGGGGAGGTGAGTGCCTGCTGGTAGACAGGGGCTGAAGATTCCAGGAGGAGGGCC
        AGGGGATGAGAAGGCAAGAGAGTGAGGACAGCAAGGACCTCCCAGGGGACATACCCATCA
```

FIGURE 3-79

78774  GAACTTTGCTTCATATAAGCTCCACTCCTCCAGGAAGGCTCCTCGGAGCAGCCTGGGAGG
CCTTCCTGGGAGGGATGCAGGAAAACAGGCTCAGGAGGCAGCGGGGAGCAGCCTGCAGGT
TTGCTTCACTCCCTAGGACCCACACATGCTCCCCTCAGCTGTCTGGGCATGTAGAGTGGG
TGCGTATCTGCGGTCCAGGCATTTTTGAGAGGGCTCAGATCCTTGGCATCAGCTGCCCTT
TCAACATCCTCCTTCCAACCACTTCAGACTCAGTAAGGCCTTTGGAAAAAATACCAAAAA
[A,-]
AAAGCAATTAAAAGTGAATATTCAAATCCAATTATCCCAGAGCTCAGTGGAGATGGGGAG
GTGAGTGCCTGCTGGTAGACAGGGGCTGAAGATTCCAGGAGGAGGGCCAGGGGATGAGAA
GGCAAGAGAGTGAGGACAGCAAGGACCTCCCAGGGGACATACCCATCATCAGGACACACC
CGTCATCATCCCCAAACAGGAATTCTTTCCATGGCCCCTGTGAAAGGTGAGTGGCTTGCC
AGGCTCAGCTGCTACCTGAAAAAGGATTGGGGGAAGGCCCAGGCCCAGTGCTCTCTCTGG

79135  GTGAGTGCCTGCTGGTAGACAGGGGCTGAAGATTCCAGGAGGAGGGCCAGGGGATGAGAA
GGCAAGAGAGTGAGGACAGCAAGGACCTCCCAGGGGACATACCCATCATCAGGACACACC
CGTCATCATCCCCAAACAGGAATTCTTTCCATGGCCCCTGTGAAAGGTGAGTGGCTTGCC
AGGCTCAGCTGCTACCTGAAAAAGGATTGGGGGAAGGCCCAGGCCCAGTGCTCTCTCTGG
TATCTGAGCTCTGCTTGCCCACCTTTGTGCCTGGTGTCTGGTGGTGAGCCCATCTCCACA
[A,G]
TTAGGGCGGAGAGGCCCCAGGGTTGGCTGGGCCCTGCTCTCAGGAGCTCCCAGCAGGATG
GGGACTTGAGACCCAGGTGTATGGACGAGGGAAGAGCACTGGAATGGGATTCAGACAGGT
CTGGATTCTAGCTCAGCCCCCTCCCTGTCTCTCTGCTTTCCTACCTGAGGCCCGGTCTAT
TGGCTTAATGGGGTAACAGGGGCCAAGTGCTTGGCACAGTGCCCAGCACACAGTAGGAGC
TCAGTGATTGCTACTTGCACTCCCAAGTCCCAACCAATGATTAGCCTTGAGTGACCTTGA

79648  GGCACAGTGCCCAGCACACAGTAGGAGCTCAGTGATTGCTACTTGCACTCCCAAGTCCCA
ACCAATGATTAGCCTTGAGTGACCTTGAGAAAACGACTTCTCTTCTGGCCTTTTTTCTGT
GAAATGGGTGGGGTTGGGTACAGGGTCCTTCCGATGGTGACCTTTGTGGCTCTGGTCCCC
CCAGGAGGGAGAGGGACTGACCTACAGGCTGCCGTGGAGCCTGAGGCTCTAGCAGTGCCC
GAGGAGGTGGGGGTGTGGGGAGGGTGCTACTCCAGGAAACCCTGGACTGTGGGCAAACAG
[C,T]
AGCAGGTGTGGCGTGGAGGCTGGATCATAGAGACAGATAAGGAGGCCCGAGGCAATGGGC
AGGGAATGGGATCAGGGCAGTGTGGGGAGAGACAGGGTGGAAAAGGGTCAAGGCGGGAGT
GAGGAGGCCCCCGCCAGCTCCCAGCCCCACCTGTCCCTGTTCCTGCCGCTGTTTGGGCTC
TCAGATGCCCAGCTGCATCCCCCCAGTGTGTTTGGCTTTCCTGTCTTCTTGTGCTTGTAA
GGGCTGCTTGCTCCCTTGCAAAGACCGTCCCTGCTCCACTTTCATCTCAGCCAATCCCAT

80969  GGGGGAAGGAGGGCAAGAAGAGGGTCCAGGTCCTGGGGGCTCAGTGAGAGTGGGGGGCTT
AGTGAGGGGATGGGGGCCCAGTGACAGTGGGCAGCCTCAGTGAGGTGATGGGGGCCCAGT
GAGGATATGAGGGCTCAGTGAGAGTGGGGTGCCCAGTGAGGGGATTGGGGCACAGTGAG
AGTGAGGGGCTCTGTGAGGGGGTAGGGACTTAAGTGAGGGGATGGAGGCTGAGTGAGTGT
GTGGGGGCTCATTGAGAGGGTGGGGGCTAAGTGGGGAATGGGGGCTCAGTGAGGGGATGG
[C,T,A]
GGCTCAGTGAGAGGATGAGGGCTCAGTGAGGGGATGGGGGCTCGGTGAGGGGATGGGGGT
TCAATGAGGGGATGGGGGCTGAGTGAGGGGATGGGGGCTGAGTGAGGGGATGGGGCTGA
GTGAGAGGATGGGGGCTGAGTGAGGGGATGGGGCTCAATGAGAGGATGAGGGCTAGGTGA
GAGGATGAGGGTTCAGTGAGGGGATGGGGCTCAGTGAGGGGATAGGGGCTCAGTGAGAGG
TTGGGGGCTCAGAGAGGGGATGGGGACTCAGTGGGGGATGAGGGCTCAATAAGGGGATGG

82103  AGTGAGGGGATGAGGCCGAGTGAGAGGTTGCGGCTCAGTGAGGGGATGGGGACTTAGTGA
GAGGATAGGGGCTCAGTGAGGGAATGGGGGCTCAGTGAGAAGGTGGGGGCTCAGTGCGGG
ATTGGGTCTCAGTGAGAAGGTGGGGGCTCAGTGAGAGGGTGAGGGCTTAGTGAGGGTATT
CGGGCTCAGTGAGGGGATGGGGGCTCAGTGAGAGGATGGGGCTTGGTGAGGAGATGGGG
GCTCAGTGGGGGATGGGGGCTGAGTGAGGGGATGGGGGCTCAGTGAGAGGATGAGACCTC
[G,A]
GTGAGGGGATGGGGGCTCAGTGGGGGATGAGGGCTAAGTGGTAGATGGGGGCTGAGTGGG
GGGATGGGGGCTCAGTGACAGGGTGGGGCTCAGTGAGAGGATGGGGGCTCAGTGAGGTGA
TGGGGCTCAGTGAGAGGGTGAGGGCTTAGTGAGGGGATTGGGTCTCAGTGAGGGGATGGG

FIGURE 3-80

```
        GGCTCAGTGGGGGATGGGGGCTCAGTGGTAGATAGGGGCTGAGTGGGGGGATGGGGGCTC
        AGTGAGAGGGTGAGGGCCTGGCGAAGGGATTGGGGCTCAGTGAGGGGGTGGGGAGTCAGC

83833   CTTATGTGGAGAGTTTTACCCAGGCAGCATGATCGTTCTGAAATCATACCTGACCATTAC
        CGTCCCTGCTCAAATCCCTCCCAGGGCACCCCCTGCCCTCAGGCTCAAGCCCAGCTCCAT
        AGGGCCCTGGCCCCTGTCTAGCCTTGCTCTCGGCTGTCCAGTCACACCAACCTCCTTGTG
        GCCATACCTTTCAGCAGGCACACAATCTTCTCGCCTCCAAGCCTTCACAATTGCAATTCC
        CTGGACATCCTTTCCTGTCTGCCTCGATAACCTCTGCCTGTCCTTTTAGGACTCAACTCAG
        [G,A]
        TGTCTCCCTCTACAGGAAGCCTTCTCTGACTCCATCACACCCTGCACCTGAGTGGGCTGG
        GGCCTGCTCTTCCTGCCTTTGGCAGAGCTCTCATCTCCCGACTGAAGCGTGGGTCTGTAC
        GTTGATCTCTGCGTGTTCTTGGCCTCCTCAAGTGAGGCATATGTCTGACCCCTCTGCTCA
        TCTCAGCCCTCAGCACTGAACCTGACCCAGAAGGACCCAGTGAAATGAGAGACTTTAAGT
        AGAATGCTCCCCGAGGTTTTTCATCTAGAACACTTATTCTTGCTCTGCCATGGAGAATGG

84945   CTGCAGTGCGCACTGACCAGCAACGCAAGGACCAGTGCCACCTTGTGGCCTCCGGTTAAC
        CAGATTGTCTGAGGCCAAGGAGCTGGGCAGGGTTTGGCCAGGGGTCACCCCCTGCCTCCG
        TGAAGCCTCAGCCTTCATCAGTTTAATCATCAGGAAACGTGGCTCCCGTTGCCCTCCTGC
        CACCCTACGTCCCTCTCCTTCCCGGGGTGACTGGCAATGTGGACAGCCGGGAACTGGAGC
        CCAGCACTTCAGGAACCTTAAAGGTCCTGGGTGTAGGGGCTGGAAGGTGGGAGACACCAC
        [T,C]
        GGTTCCTGTAGATCCTGGATTACTTAAAGTGGCCAGGAAGGAATGGGTTTGGTTCAGAAT
        GCTGCGTGAGCTTGAACGAGATGCTCAACCTCTTTGGTCCTCGATTTGTCTAGAGTCTCT
        GACCTAGTGATCTCGTGACTTGCAGGCCACCCCCTCCTTTTCCTCATGTGACCTTTGCTG
        GGCTTCCCTTAGTGACCCTGTATGCACACAGTTCCCCAAGTTTCTCTTCTGTCCAGGCCA
        GGCAGTTCCTACAAGCACAATTAAGTGGAGGCAGCATGAGGGATGAAGAACCCAGGACAA

84985   CCTTGTGGCCTCCGGTTAACCAGATTGTCTGAGGCCAAGGAGCTGGGCAGGGTTTGGCCA
        GGGGTCACCCCCTGCCTCCGTGAAGCCTCAGCCTTCATCAGTTTAATCATCAGGAAACGT
        GGCTCCCGTTGCCCTCCTGCCACCCTACGTCCCTCTCCTTCCCGGGGTGACTGGCAATGT
        GGACAGCCGGGAACTGGAGCCCAGCACTTCAGGAACCTTAAAGGTCCTGGGTGTAGGGGC
        TGGAAGGTGGGAGACACCACCGGTTCCTGTAGATCCTGGATTACTTAAAGTGGCCAGGAA
        [A,G]
        GAATGGGTTTGGTTCAGAATGCTGCGTGAGCTTGAACGAGATGCTCAACCTCTTTGGTCC
        TCGATTTGTCTAGAGTCTCTGACCTAGTGATCTCGTGACTTGCAGGCCACCCCCTCCTTT
        TCCTCATGTGACCTTTGCTGGGCTTCCCTTAGTGACCCTGTATGCACACAGTTCCCCAAG
        TTTCTCTTCTGTCCAGGCCAGGCAGTTCCTACAAGCACAATTAAGTGGAGGCAGCATGAG
        GGATGAAGAACCCAGGACAATTAATCATCAAGGAGTGACATTTGGTGCAAACNTCAGGTG

85295   TGGTTCAGAATGCTGCGTGAGCTTGAACGAGATGCTCAACCTCTTTGGTCCTCGATTTGT
        CTAGAGTCTCTGACCTAGTGATCTCGTGACTTGCAGGCCACCCCCTCCTTTTCCTCATGT
        GACCTTTGCTGGGCTTCCCTTAGTGACCCTGTATGCACACAGTTCCCCAAGTTTCTCTTC
        TGTCCAGGCCAGGCAGTTCCTACAAGCACAATTAAGTGGAGGCAGCATGAGGGATGAAGA
        ACCCAGGACAATTAATCATCAAGGAGTGACATTTGGTGCAAACNTCAGGTGCTTAATTAA
        [G,A]
        CGGGATGAGCCAGAGGCTGGGGGGTAGAGGAGGTGGGTTGTGTGGTGGGACAGAGAGAAA
        CTCATTCTTCCCATACCAACCTCCCCTGCCTTGGTTCCCACCACCCCTCTGCCACTGTCA
        TACCCTGCCACTCACACCTGCCCCCTGTTCAAAGCTCACACCTCCACAGGTATTTGGGAA
        GGTTCCAGCATAGTGGTTAGACCTAGCCCTGGTGCCACCTACCTGGGTTCAAATCCTGGC
        TCTACCGCTTATTCACTGTGTAACCCTGGGCAAGTGAATTAGCCTCTTGGTGCCATAGCT

89241   GTCAGCTTTGAGGGGCACTGAGGTGAGGGGCTGTGTGCAGAGGTGGGGATTGGGAGGTGG
        TGGCTGGGTCACGCACCTCCTTCTCTGCTGAGGGCAAAGGGCCTGGGGTGCCAGGTGCCT
        GAGAAGGACTTCCTTAGATTGAGGCTATGAGGACTGGGTCAGGAGGGAAGTAAGGGGAAG
        ACATTTGGAAGGTTGCTTCCCTTGTGGGCGGAATGCTTGCCATGGCCGCTGCTCACCTTG
        GCTCAGGCTGGGCCAGAGGCCAATGTGTGTGTGTGTGTGTGTGTGTGTGTCTCAGGGA
        [C,T]
        GCTGGTGGGATCAGATCACTTACACTTAACTCACCCAGTAGAACTCTGGTCTGGTCCTGC
```

FIGURE 3-81

```
        GGCAGGCTGGGTGCTGGAGCCGACTCTGCCTTCAGGGAGCTCTCAGTCTGGGGGAAGGCA
        GGGACACCCTCCCCACCACAGGCCAGATGAAATACTGTTGCCAGCAGGTGTTCTGGTGGC
        AAAGCCTGGAGCAGCAAGTGGTACCTCATCACAGAGAAAGCATTTGTGTGGGGCCTTGGG
        GCACAGGTAGGAGGTCCACAGGCAGGGAAGAAGGGAAAGGGGATTCTAGGCAGAGGAGGA

91827   AGTGGCCCTCAGATGCTAAAGTCTGCCATGGCTCCCCAGTACTCTCAGGCTAAAGTCTAA
        CTTCTTAGCCTGGCACTCAAGGCCCTTCCTTCTGTGGTACCATGGACCACACCCCTACCT
        GGATCCTCATCTCCCCGCACCACCTACCGCCAGTGTCCTGGTCTCTTCAAGGTCTACTTG
        TCCTCCCCATGCCAATTCAGGAAGCCTTCCAAATGTCCTCCCCTCTGAGCTACCCACCTA
        GTTTTCTCTCTCCTTCCTCAGGTATGAGGCTCCACACCTCCTCCCAGTCATGTCTCCCCA
        [A,G,C]
        TCGTCCCACCCCAGACAGACTGTGAGCTTCCCGAGAACCTGCTGGTCTCCTCCTCCCCAT
        CTGCTCCTGGCAGGAGACCCAGAGCTGAGGCAGGCATTGGCTGCTGACTGGGGAGGGAGG
        AGGAAGGAGGAGCCCCCAGTGCAGGCGCTGTGGGGAGCTCTGCAGGTGGTGAGCAGCTTT
        GAGTAAGCTCCGGAAGCTAGTGACGCAGGTGGGGAGCCTTGCTGGCAGGGCCTGTAGTGG
        GTCCCTAGGCTGCCACCCTCCCTCCCCACCGTCTCTCATTTTCCTCGACAAGCACCCAAG

93127   GGACCAGTGTGTGCTGCGCATGGGGAGGGCACTCTGGCAGAGACAGACACTGAGAGAGGT
        CACAGCTAGTTCCCTTCTCCCATCCCTCCAGGTGCACTGTGGCCAGCTGAGTGATAATGA
        GGAATGGAGCCTGCAGGCGGTGGAGAAGCATGTGAGTGGGAGTGGGGCCATGTGCAATGA
        GGCTGAAGACCCTTATCACAGCTGGTGGAAGATGGCCTGGCCAGGGAGCTGGACAGACC
        TGGGTTTCAGCTTCGGCTTTGCTGCTTTTGAGCTGTGTGACCTTGAGCAAGTCACTAAAC
        [C,G]
        TCTCTGGGCCTCAGTTTCACACCTGAAAATGGGGATAATGATAGCACCGACTGACCTAGG
        GCAGTGGTGAAACAAAACTGGTCAAATATCTTGTAAATACACACGGTTGCCAACTTACAA
        TTTTCGACTTTTTGATGGATTTATGGGGAAGCAACCCTATCCTAAGTCCAGGAGCATCTG
        TACTTAGAAAGAACCCTCCACATAATGATACTGAGGCTCTTTCATGCCTGAGACTTTATG
        ATTTTGTGACTTTAACAAG

93815   TGGGAGCCCCCGGGGGAGCCCTCAGGAAGGTAGAGTCCAGGGATGAGGTGTTTGGGACGG
        CGGCGGGGTCCCTGGGCCCGGCAGGCAGAGGGAACGGCGGGAGCAAAGGCAGGAATCCCG
        CTGCAGCAAGCGCAGCGAGCTTGGGGCGAGCGGCGCGCTAACCGCTCGGCCTGCCCCAGA
        CCCTGGTCGCCCTGCGGAGGGTGCAGGTCCTGCAGCAGCGCGGGCCCAGGGAGGCTCCCC
        GAGCCGTCCAGAACCCCCCGGAGGGGACGGCGGAAGACCAGAAGGGCGGGGCGGCGTACA
        [C,T]
        CGACCGCGACCGCAAGATCCTCCAACTGTGCGGTGAGGGCCCGGCCTGGACAGGTCACGA
        GGGCGGGGCCGGGCAGAACTTGGAGGGGAGGTGGGCGGGTTAGGCGATCCCGGGAGCCGG
        CGGCGGGCCCGGCGCGGAGCTGAGCGGCGCCTGAGGGACCCGGACACGGAGGTGCGGAGG
        GGCCCTCTCTCTGACCGGCGCCTGGCCCTTGCAGGGGAACTCTACGACCTGGATGCCTCT
        TCCCTGCAGCTCAAAGTGCTCCAATACGTGAGTCCCTGCGCCCCTGCCGGCCACCTCCCC

96136   TGGACAGTGGCTAAAGGGAATATGCTTGGGGACTGGGAAAAGCTGTGGATCTTTTGAGCC
        CCTGACAGGGCAGCTATAAAAATGATACACAAAAATCTCTTTTTTTGTGGGCAGGGCACA
        GTGGACAGGAAAGCAGGCTTGGAGGCTTAGTTGGAAAGGATATCTCGAGAACTGAGGACA
        AACCTGGGGTCTAGAAATGGTGTCATAAATAAATTTCATATCCTACACCAACTCATAAAC
        AGGCAGTAGGTGCCTGAATTTTATTGCAAATGGATCTTAGTTCAGGGAGAAACAGTGCTG
        [C,T]
        GTCTGATGAGCCATTTCTGTCCTGGGTGCAGGTTCACACTTGGGCTGGCAGGATGAGCAG
        TTTGTGCTGTGTCACATAGGTGGGGAGAAGTAGACAGATGAGGGGCTGAGTCCTGATGCA
        AAGAGATGCTGATAGGATGCTGGTCTCTGGAGTCCAAGCAAACAGGCTGGGTTTCAGGGC
        CTGGAGCTCCTGCAGGAGGTGGACACTAGAGAGCCTGGGACTAGGTAGGTGTCAGAGCCC
        GGGCCTGAGGTCTGCTGGGGTAGGGTGGAGATCCAGGAGTCCTAGGTCTGAGCTGCAGAA

96831   TTGGTGGCATTTGGAACTTGTGGGCATCCTAATGGTGGGAGAATTTATGCCATTCAGCAA
        ACAAATATTGAGCACTTAATGTTGCCATCCCAGTGCTGACCAGATGGCCTTGGGAAGGCC
        TTTGGGGAAGGGAAGGTAGAGTGAATGGGGGTCCAGCAGGGGCCATGACTTCTTGCTGCT
        GGCTGTGAGATTGGGTTCTAGGATGGCCCCAGAGCTGGAGAAGAGGTGGTATCAGCAGGA
        AATAAGGATGGGGCCTTGGTGGCAGCTTTGAGGCCCAGGGCAGGGCAGGGCTATCTCTG
```

FIGURE 3-82

[T,G]
GTCCCACGCATTTCAGGGAGTGAGTGTTGAATGACTGCATGAGCCAGGGTGGGGCTCAGC
TCAGTGCAGTGACTACAGAGAAGCTTCCTGAAACACAGCTAAGTAGCCAGAGAACAGGGG
CTCCAGAAGCCCTTCAGCTGTGAGTGGGATGGGGCTGGTGGCAAGGCCAGGGATAGGATA
CACTGACGACATTAGCAAAGACCTCCGAAGTGTTTCCTCTGTACCAGGCTCTGCACTGGG
CATGGGTGATATAGTCATGGCCCCATTTCATAAGACTCAAAGCTCATTTTCAGGGCATAG

97038　CCCAGAGCTGGAGAAGAGGTGGTATCAGCAGGAAATAAGGATGGGGCCTTGGTGGCAGCT
TTGAGGCCCAGGGCAGGGGCAGGGCTATCTCTGGGTCCCACGCATTTCAGGGAGTGAGTG
TTGAATGACTGCATGAGCCAGGGTGGGGCTCAGCTCAGTGCAGTGACTACAGAGAAGCTT
CCTGAAACACAGCTAAGTAGCCAGAGAACAGGGGCTCCAGAAGCCCTTCAGCTGTGAGTG
GGATGGGGCTGGTGGCAAGGCCAGGGATAGGATACACTGACGACATTAGCAAAGACCTCC
[G,A,T,C]
AAGTGTTTCCTCTGTACCAGGCTCTGCACTGGGCATGGGTGATATAGTCATGGCCCCATT
TCATAAGACTCAAAGCTCATTTTCAGGGCATAGAGGGAAGAGAGTGAGAAGGGTATTCTA
GGCCGAGGGAACAGTGTAGAAAAAAAAGCATGAAGGTGTGAAAGAGCCCAAGGTTTTCTC
AGAATGATGAGGATCTTTGTGTGGCTGAAGCTGAGAGATGTTCTGGGTTGAGGGGTGACA
GGTGGGTGGGGCTAGCTGAGGGACCACAAATGTAAGAAAGGTGTGCAGACAGACCCAGGA

97110　GCAGGGGCAGGGCTATCTCTGGGTCCCACGCATTTCAGGGAGTGAGTGTTGAATGACTGC
ATGAGCCAGGGTGGGGCTCAGCTCAGTGCAGTGACTACAGAGAAGCTTCCTGAAACACAG
CTAAGTAGCCAGAGAACAGGGGCTCCAGAAGCCCTTCAGCTGTGAGTGGGATGGGCTGG
TGGCAAGGCCAGGGATAGGATACACTGACGACATTAGCAAAGACCTCCGAAGTGTTTCCT
CTGTACCAGGCTCTGCACTGGGCATGGGTGATATAGTCATGGCCCCATTTCATAAGACTC
[G,A,T,C]
AAGCTCATTTTCAGGGCATAGAGGGAAGAGAGTGAGAAGGGTATTCTAGGCCGAGGGAAC
AGTGTAGAAAAAAAAGCATGAAGGTGTGAAAGAGCCCAAGGTTTTCTCAGAATGATGAGG
ATCTTTGTGTGGCTGAAGCTGAGAGATGTTCTGGGTTGAGGGGTGACAGGTGGGTGGGGC
TAGCTGAGGGACCACAAATGTAAGAAAGGTGTGCAGACAGACCCAGGATGGTGGGGATGG
GATCTAGATCCGAATCACTGGATGGCAAGCATGAATGGGGGATGCCCCACCAGGGTGGAG

98446　CCGTGCTCACCAGCACCCTGGCCTTCCAGAAGGAACAGAAACTCAAGTGTGAGTGCCAGG
TGAGTGACCTGCCTTCAGCCTCTCTCGGGCACCGACTCGCTCAGTTTTCAGCCCCGAGAG
CCATTCAGAAGGGAAATGCCCATGTCTTTCTGGACTGGTGGCAGCCCTTCCCCAGGTGGC
TCCATAACCTCATAACTTGAAGGCTTGCAGTTGTTCAGGACCCGCGCCACTGCCCGCAGG
CACTGTATGTGATCGCCCTCTAGTGTTCAATATGTGCACTACAGCAACACCTAGGCAGCT
[A,G]
GAGCTGGCGTGAAGGCGGCTGAGACACTCAGGAGACTCCTCACCTGCACCGGGGCTATTC
CCTCACTCCTTCACTTAGTAGCCAAATGATATAATTAGACACTGACAGTTTCTGGCTTGT
CCAGTGAGCCCTAGGGAAGGAAGGAGAAGACCCGGGTGCTGTTGGAGGCAGAAGGTTGGA
TAGGGTGACCCCTACACCCCGACCCCCCTATGATCTCCATTTCCTTCATTCCAGGCTCTT
CTCCAAGTGGCAAAGAACCTCTTCACCCACCTGGGTGAGTGCACTGTTCTCTCTGCCTGG

98618　CAGGTGGCTCCATAACCTCATAACTTGAAGGCTTGCAGTTGTTCAGGACCCGCGCCACTG
CCCGCAGGCACTGTATGTGATCGCCCTCTAGTGTTCAATATGTGCACTACAGCAACACCT
AGGCAGCTAGAGCTGGCGTGAAGGCGGCTGAGACACTCAGGAGACTCCTCACCTGCACCG
GGGCTATTCCCTCACTCCTTCACTTAGTAGCCAAATGATATAATTAGACACTGACAGTTT
CTGGCTTGTCCAGTGAGCCCTAGGGAAGGAAGGAGAAGACCCGGGTGCTGTTGGAGGCAG
[G,A]
AGGTTGGATAGGGTGACCCCTACACCCCGACCCCCCTATGATCTCCATTTCCTTCATTCC
AGGCTCTTCTCCAAGTGGCAAAGAACCTCTTCACCCACCTGGGTGAGTGCACTGTTCTCT
CTGCCTGGCTGTGTGTGGGCATGGGGGCTGGCATTTGCAGAGGAGAGGCGGGAGGTCTTG
GCAGCCTGGTCTCACCCTGCCTGGTCTTCTCCCTTCCCCAGATGACGTCTCTGTCCTGCT
CCAGGAGATCATCACGGAGGCCAGAAACCTCAGCAACGCAGAGATGTGAGTGACTCTACC

99145　GTCTCTGTCCTGCTCCAGGAGATCATCACGGAGGCCAGAAACCTCAGCAACGCAGAGATG
TGAGTGACTCTACCCAGGGGACAGGGCGAGAGAGGCTGTGGCCTTCAGTCCCCATCATCT
CCTTTCCTGCCCCACCCACTTCCCTTTCTCTGCCTTCTGCGGGACTTCATCACCTTTTGA

FIGURE 3-83

```
         GGGATCCTTTATTTCATGCCTGTCTCCCTCGCTAGACTGTAGGCTCCAATACAGCAGGGA
         CAGGGCTGGCTTTGGATCCTCAGCTCCTATCACAGTGCCTGGCACATAGTAGGTGCTTCC
         [-,A]
         AAAAAAAAAAAAACAAAACACTTGAATGGACACGTTTCTGGAGCCAGCCAGCCCTGAGCA
         GAGTGTCTTACCTTGGAGCACTCCTCCCAGGCCTCGGAAATCCGGCCTTTGCCTCCTTAT
         GGGACGTGAGGGCGATCAGAGGGGGTTGTCAGGCCCCAGAGGACCAAACCCCTCCCTCCA
         CAGCTGCTCTGTGTTCCTGCTGGATCAGAATGAGCTGGTGGCCAAGGTGTTCGACGGGGG
         CGTGGTGGATGATGAGGTGAGAGGGCGTGGAGGGAGTATGTGGCCCTAGGGGTGTCCGGG
```

99158
```
         TCCAGGAGATCATCACGGAGGCCAGAAACCTCAGCAACGCAGAGATGTGAGTGACTCTAC
         CCAGGGGACAGGGCGAGAGAGGCTGTGGCCTTCAGTCCCCATCATCTCCTTTCCTGCCCC
         ACCCACTTCCCTTTCTCTGCCTTCTGCGGGACTTCATCACCTTTTGAGGGATCCTTTATT
         TCATGCCTGTCTCCCTCGCTAGACTGTAGGCTCCAATACAGCAGGGACAGGGCTGGCTTT
         GGATCCTCAGCTCCTATCACAGTGCCTGGCACATAGTAGGTGCTTCCAAAAAAAAAAAAA
         [A,-]
         CAAAACACTTGAATGGACACGTTTCTGGAGCCAGCCAGCCCTGAGCAGAGTGTCTTACCT
         TGGAGCACTCCTCCCAGGCCTCGGAAATCCGGCCTTTGCCTCCTTATGGGACGTGAGGGC
         GATCAGAGGGGGTTGTCAGGCCCCAGAGGACCAAACCCCTCCCTCCACAGCTGCTCTGTG
         TTCCTGCTGGATCAGAATGAGCTGGTGGCCAAGGTGTTCGACGGGGGCGTGGTGGATGAT
         GAGGTGAGAGGGCGTGGAGGGAGTATGTGGCCCTAGGGGTGTCCGGGAGTCCGCCGGCGG
```

99278
```
         ACCCACTTCCCTTTCTCTGCCTTCTGCGGGACTTCATCACCTTTTGAGGGATCCTTTATT
         TCATGCCTGTCTCCCTCGCTAGACTGTAGGCTCCAATACAGCAGGGACAGGGCTGGCTTT
         GGATCCTCAGCTCCTATCACAGTGCCTGGCACATAGTAGGTGCTTCCAAAAAAAAAAAAA
         ACAAAACACTTGAATGGACACGTTTCTGGAGCCAGCCAGCCCTGAGCAGAGTGTCTTACC
         TTGGAGCACTCCTCCCAGGCCTCGGAAATCCGGCCTTTGCCTCCTTATGGGACGTGAGGG
         [C,A]
         GATCAGAGGGGGTTGTCAGGCCCCAGAGGACCAAACCCCTCCCTCCACAGCTGCTCTGTG
         TTCCTGCTGGATCAGAATGAGCTGGTGGCCAAGGTGTTCGACGGGGGCGTGGTGGATGAT
         GAGGTGAGAGGGCGTGGAGGGAGTATGTGGCCCTAGGGGTGTCCGGGAGTCCGCCGGCGG
         CGCTGGGGAGCGGCCCGAGGTTTAACAGTCCCCTCTGTGGCCGGGTCACTAACTTCTTCC
         TCTCGACTCCATCTCTGCTCCGGCAGAGCTATGAGATCCGCATCCCGGCCGATCAGGGCA
```

99411
```
         CTATCACAGTGCCTGGCACATAGTAGGTGCTTCCAAAAAAAAAAAAAACAAAACACTTGA
         ATGGACACGTTTCTGGAGCCAGCCAGCCCTGAGCAGAGTGTCTTACCTTGGAGCACTCCT
         CCCAGGCCTCGGAAATCCGGCCTTTGCCTCCTTATGGGACGTGAGGGCGATCAGAGGGGG
         TTGTCAGGCCCCAGAGGACCAAACCCCTCCCTCCACAGCTGCTCTGTGTTCCTGCTGGAT
         CAGAATGAGCTGGTGGCCAAGGTGTTCGACGGGGGCGTGGTGGATGATGAGGTGAGAGGG
         [G,A,C]
         GTGGAGGGAGTATGTGGCCCTAGGGGTGTCCGGGAGTCCGCCGGCGGCGCTGGGGAGCGG
         CCCGAGGTTTAACAGTCCCCTCTGTGGCCGGGTCACTAACTTCTTCCTCTCGACTCCATC
         TCTGCTCCGGCAGAGCTATGAGATCCGCATCCCGGCCGATCAGGGCATCGCGGGACACGT
         GGCGACCACGGGCCAGATCCTGAACATCCCTGACGCATATGCCCATCCGCTTTTCTACCG
         CGGCGTGGACGACAGCACCGGCTTCCGCACGCGCAACATCCTCTGCTTCCCCATCAAGAA
```

99744
```
         GGAGTCCGCCGGCGGCGCTGGGGAGCGGCCCGAGGTTTAACAGTCCCCTCTGTGGCCGGG
         TCACTAACTTCTTCCTCTCGACTCCATCTCTGCTCCGGCAGAGCTATGAGATCCGCATCC
         CGGCCGATCAGGGCATCGCGGGACACGTGGCGACCACGGGCCAGATCCTGAACATCCCTG
         ACGCATATGCCCATCCGCTTTTCTACCGCGGCGTGGACGACAGCACCGGCTTCCGCACGC
         GCAACATCCTCTGCTTCCCCATCAAGAACGAGAACCAGGGTGCGCGTGGCGGCCCGGGCG
         [G,C]
         AGGGGCGGGGCCTGCGCCGGGCGGGGCGGGTCCGAGCGAGCGGGGGTGGCAACACTTCCC
         CACCGCCTCCGGCGTCCCGGAGCATAAGGGAGTCGGGTTCCATGCCTGGGACGTACGTAA
         CCTGCGGAAACTGCGAGGGCAGGTCCCGGCCGGATCCCTCCCTCCAACCGATCCCTCCCT
         CCACCGGTGGTTCCTTGCCCCTCTCCCTTCCCCAGAGGTCATCGGTGTGGCCGAGCTGGT
         GAACAAGATCAATGGGCCATGGTTCAGCAAGTTCGACGAGGACCTGGCGACGGCCTTCTC
```

99815    TTCCTCTCGACTCCATCTCTGCTCCGGCAGAGCTATGAGATCCGCATCCCGGCCGATCAG

FIGURE 3-84

```
        GGCATCGCGGGACACGTGGCGACCACGGGCCAGATCCTGAACATCCCTGACGCATATGCC
        CATCCGCTTTTCTACCGCGGCGTGGACGACAGCACCGGCTTCCGCACGCGCAACATCCTC
        TGCTTCCCCATCAAGAACGAGAACCAGGGTGCGCGTGGCGGCCCGGGCGGAGGGGCGGGG
        CCTGCGCCGGGCGGGGCGGGTCCGAGCGAGCGGGGGTGGCAACACTTCCCCACCGCCTCC
        [A,G]
        GCGTCCCGGAGCATAAGGGAGTCGGGTTCCATGCCTGGGACGTACGTAACCTGCGGAAAC
        TGCGAGGGCAGGTCCCGGCCGGATCCCTCCCTCCAACCGATCCCTCCCTCCACCGGTGGT
        TCCTTGCCCCTCTCCCTTCCCCAGAGGTCATCGGTGTGGCCGAGCTGGTGAACAAGATCA
        ATGGGCCATGGTTCAGCAAGTTCGACGAGGACCTGGCGACGGCCTTCTCCATCTACTGCG
        GCATCAGCATCGCCCATGTGAGGGCGGGGTTGGGAGTGGGGTGTGGGGTGATAGGGGGCG

100604  CCATGAGAAACTCCCGTTGTCAAAACCTCCTCTCTTCCCTGGAAGCAGTCTCAACCCAAG
        CCGAGTGCTTTTTTGGAAGTGCTGGGTCTCGGTGTCCAGGCCTACTGGCGCTCTGGCCTG
        GGAATCCAGCCCCAAGGTCCCTGACATGATCCCCTCCTTGCTTCTCCTTCCCTGCCATGG
        GCCTTGGGCTCCATCACTGAAGCCTGGATCAGGTGTGGGGGAGTGCAAAGGGCCAGACCA
        AATGCTGGGAGAACTTGATGAGGAGGAACCGGCGCGGGGGTCTGGATGAAAGTGGGGGTG
        [G,A]
        GGTCTTTACTGTGGACTGGAGCTTGAAGGTTTTGACTGGGGCCAGAATGGGACAGGAAGT
        GGGGTGTCTTTTTGACCCCTTCATCCCAGTCCTGGGCATTGCTAAATTTTCACAGCCACC
        TTCCTTGAGCCCCATCTTTCCCTCTTTCCCCTAGTCTCTCCTATACAAAAAAGTGAATGA
        GGCTCAGTATCGCAGCCACCTGGCCAATGAGATGATGATGTACCACATGAAGGTGAGGCT
        TGCAGAGACCTCTGGTCCTCCTCCCAGATTCCCCGGGGACCCAGGGCCAGGCAGGGCTTC

100878  CGGGGGTCTGGATGAAAGTGGGGGTGAGGTCTTTACTGTGGACTGGAGCTTGAAGGTTTT
        GACTGGGGCCAGAATGGGACAGGAAGTGGGGTGTCTTTTTGACCCCTTCATCCCAGTCCT
        GGGCATTGCTAAATTTTCACAGCCACCTTCCTTGAGCCCCATCTTTCCCTCTTTCCCCTA
        GTCTCTCCTATACAAAAAAGTGAATGAGGCTCAGTATCGCAGCCACCTGGCCAATGAGAT
        GATGATGTACCACATGAAGGTGAGGCTTGCAGAGACCTCTGGTCCTCCTCCCAGATTCCC
        [C,A,G,T]
        GGGGACCCAGGGCCAGGCAGGGCTTCCTGATCAATCTCTACTGAGGATGAGAGGATAGGC
        CCAGAGCCACAGCAGGCCTCCTGCCCTCCTTAGGGGCAGCTCCCACCCCTGCTTAGAGAC
        CTCTCCTCCAAGCTGCTTCTGAGCTCAGTCCCAAGGCTGGAAGTAGCCAGAGGAACCAGC
        CCAGGGAGTAATTGGTTCAGCCAGGTATTCCCCATGTTCAGGGAATAATTCCCATCTTGG
        GAATTACTGAGGGCTAGGAAGCTCACCCAGGACCCGTCCCCATGGCTTCCCTAGGTACAA

101440  CTCACCCAGGACCCGTCCCCATGGCTTCCCTAGGTACAATGCCCATGCAGCCCTGGGCAG
        TCTTAATTGCTGATAATCTATCCCATTCCCTACCCTGGGTCACAAAAGCTGGCTTAGTTC
        CATGTATATGGTAGTCGCTGTTCATTTGGACATTTCCTCTCACCTGTGTCCAAACCAGAG
        AGGCCCAGACCTTGTGAGTTGGATCAAAACTGTAGTAGGAAGAGTTAAGGTTAGAGAGTA
        GAAAGGTCTCCACAAAAGGAGGACTGCTACAGTTACTGTGTATGAAATGCTGCCATGGTT
        [A,T]
        GGGGGTGTCATGAAGGGGTGTTGTCGATCTTTGCCAAGGTTATGCTGTTACAGATAAAGG
        GTGGTCACCTGCAGGAAGGCGCGCGGGGTGGGCTGCAGGGCTGTGAGGGGAGGGTGGTGA
        TTTCCTGCCCAGTTACAGTCCACAGCGTGGTGGCCCAACTGTGGTACATTCTGGGTGACG
        GATCCCCCACCTGCCATGGGAATTTGAGGGTGAAGACACCAGATGGGGTGAAGGCTGTCT
        TCTAATGCTCTGGCTGGTCTCCTCTAGGTCTCCGACGATGAGTATACCAAACTTCTCCAT

101516  TCTATCCCATTCCCTACCCTGGGTCACAAAAGCTGGCTTAGTTCCATGTATATGGTAGTC
        GCTGTTCATTTGGACATTTCCTCTCACCTGTGTCCAAACCAGAGAGGCCCAGACCTTGTG
        AGTTGGATCAAAACTGTAGTAGGAAGAGTTAAGGTTAGAGAGTAGAAAGGTCTCCACAAA
        AGGAGGACTGCTACAGTTACTGTGTATGAAATGCTGCCATGGTTTGGGGGTGTCATGAAG
        GGGTGTTGTCGATCTTTGCCAAGGTTATGCTGTTACAGATAAAGGGTGGTCACCTGCAGG
        [A,T,C,G]
        AGGCGCGCGGGGTGGGCTGCAGGGCTGTGAGGGGAGGGTGGTGATTTCCTGCCCAGTTAC
        AGTCCACAGCGTGGTGGCCCAACTGTGGTACATTCTGGGTGACGGATCCCCCACCTGCCA
        TGGGAATTTGAGGGTGAAGACACCAGATGGGGTGAAGGCTGTCTTCTAATGCTCTGGCTG
        GTCTCCTCTAGGTCTCCGACGATGAGTATACCAAACTTCTCCATGATGGGATCCAGCCTG
        TGGCTGCCATTGACTCCAATTTTTGCAAGTTTCACCTATACCCCTCGTTCCCTGCCCGAGG
```

FIGURE 3-85

101994 CTGGTCTCCTCTAGGTCTCCGACGATGAGTATACCAAACTTCTCCATGATGGGATCCAGC
CTGTGGCTGCCATTGACTCCAATTTTTGCAAGTTTCACCTATACCCCTCGTTCCCTGCCCG
AGGATGACACGTCCATGGTGAGTTGCTCTCCTCCACTTGACTGGCCAGGCCGAAGGTATG
TAGCCAGAGGCTTAAGTTAAATGCGCATCAAGAACTTCCTGGGAAGACAGAGTCATCAAG
GAAGGCTGTGGAGGGTCCCTCAGAGATGGAGGGGCTTGTAGTCTGCCATCAGGAAGCCAT
[A,G]
GGGCCTGCCCAGGGGCTAGAGGCTGGACTGGATGATCCCAAGGGCTGCTCTTGGACCAAC
CATGCCCAGGGCATGTGACCTCAGGGTTTGCATCCCTCCCAACCCTGTTTTTCTAACATT
TTGTGTGGGCTTGGTTTCAAGAGTTCTTAGTTCTTAGATCTCTAAAAATGCATAGCTCTG
AGAACGGTTGCTTCAACTATTTTGTGGTTCTCTAGTTTAGATGTAAGTTTCTAAGACTCC
AGATCTTGAGTGTGGAGCTTGAAGAAGGACCCAGGCAAGGGCCCTGTCTTGATACTGGCA

102173 GTAGCCAGAGGCTTAAGTTAAATGCGCATCAAGAACTTCCTGGGAAGACAGAGTCATCAA
GGAAGGCTGTGGAGGGTCCCTCAGAGATGGAGGGGCTTGTAGTCTGCCATCAGGAAGCCA
TGGGGCCTGCCCAGGGGCTAGAGGCTGGACTGGATGATCCCAAGGGCTGCTCTTGGACCA
ACCATGCCCAGGGCATGTGACCTCAGGGTTTGCATCCCTCCCAACCCTGTTTTTCTAACA
TTTTGTGTGGGCTTGGTTTCAAGAGTTCTTAGTTCTTAGATCTCTAAAAATGCATAGCTC
[T,C]
GAGAACGGTTGCTTCAACTATTTTGTGGTTCTCTAGTTTAGATGTAAGTTTCTAAGACTC
CAGATCTTGAGTGTGGAGCTTGAAGAAGGACCCAGGCAAGGGCCCTGTCTTGATACTGGC
AGCCCCTCTGATACCTCCCTCTGCCCTCTCCAGGCCATCCTGAGCATGCTGCAGGACATG
AATTTCATCAACAACTACAAAATTGACTGCCCGACCCTGGCCCGGTTCGTGCGCCCACAG
ACAGCCCCAGTCTTCGCCTCCCTCTTTCCTCTACTGTCACATCCATTGCCCCCGGCATTC

102239 CTGTGGAGGGTCCCTCAGAGATGGAGGGGCTTGTAGTCTGCCATCAGGAAGCCATGGGGC
CTGCCCAGGGGCTAGAGGCTGGACTGGATGATCCCAAGGGCTGCTCTTGGACCAACCATG
CCCAGGGCATGTGACCTCAGGGTTTGCATCCCTCCCAACCCTGTTTTTCTAACATTTTGT
GTGGGCTTGGTTTCAAGAGTTCTTAGTTCTTAGATCTCTAAAAATGCATAGCTCTGAGAA
CGGTTGCTTCAACTATTTTGTGGTTCTCTAGTTTAGATGTAAGTTTCTAAGACTCCAGAT
[G,A,C]
TTGAGTGTGGAGCTTGAAGAAGGACCCAGGCAAGGGCCCTGTCTTGATACTGGCAGCCCC
TCTGATACCTCCCTCTGCCCTCTCCAGGCCATCCTGAGCATGCTGCAGGACATGAATTTC
ATCAACAACTACAAAATTGACTGCCCGACCCTGGCCCGGTTCGTGCGCCCACAGACAGCC
CCAGTCTTCGCCTCCCTCTTTCCTCTACTGTCACATCCATTGCCCCCGGCATTCTGGAGA
GGATCTCTCTAAGGATGACTGGGGAGACCCAGTCTTATGGGGGTGGGGAGGATCCATGAA

102279 CCATCAGGAAGCCATGGGGCCTGCCCAGGGGCTAGAGGCTGGACTGGATGATCCCAAGGG
CTGCTCTTGGACCAACCATGCCCAGGGCATGTGACCTCAGGGTTTGCATCCCTCCCAACC
CTGTTTTTCTAACATTTTGTGTGGGCTTGGTTTCAAGAGTTCTTAGTTCTTAGATCTCTA
AAAATGCATAGCTCTGAGAACGGTTGCTTCAACTATTTTGTGGTTCTCTAGTTTAGATGT
AAGTTTCTAAGACTCCAGATCTTGAGTGTGGAGCTTGAAGAAGGACCCAGGCAAGGGCCC
[A,G,T]
GTCTTGATACTGGCAGCCCCTCTGATACCTCCCTCTGCCCTCTCCAGGCCATCCTGAGCA
TGCTGCAGGACATGAATTTCATCAACAACTACAAAATTGACTGCCCGACCCTGGCCCGGT
TCGTGCGCCCACAGACAGCCCCAGTCTTCGCCTCCCTCTTTCCTCTACTGTCACATCCAT
TGCCCCCGGCATTCTGGAGAGGATCTCTCTAAGGATGACTGGGGAGACCCAGTCTTATGG
GGGTGGGGAGGATCCATGAATGAGAAGCAATTCCTAGACACTGAACTGTCAATAAAGGCA

102458 AAAAATGCATAGCTCTGAGAACGGTTGCTTCAACTATTTTGTGGTTCTCTAGTTTAGATG
TAAGTTTCTAAGACTCCAGATCTTGAGTGTGGAGCTTGAAGAAGGACCCAGGCAAGGGCC
CTGTCTTGATACTGGCAGCCCCTCTGATACCTCCCTCTGCCCTCTCCAGGCCATCCTGAG
CATGCTGCAGGACATGAATTTCATCAACAACTACAAAATTGACTGCCCGACCCTGGCCCG
GTTCGTGCGCCCACAGACAGCCCCAGTCTTCGCCTCCCTCTTTCCTCTACTGTCACATCC
[A,T,CsG]
TTGCCCCCGGCATTCTGGAGAGGATCTCTCTAAGGATGACTGGGGAGACCCAGTCTTATG
GGGGTGGGGAGGATCCATGAATGAGAAGCAATTCCTAGACACTGAACTGTCAATAAAGGC
AAGAAATGAGGCAAGGCAAAGCCTGGAGGCAAGGCCGAGAGTGTGTAGCCAGAGGTTTAA

FIGURE 3-86

```
         GTTAGATGTGCATAGGAACTTCCTGCTAAGACAGAGTCATCAAGGAAGGCTGTGGAGGGT
         CCCTCAGGGATGGAGGGGACATGTAGTTTGCCATCATGGGGCCGTGATGGAGGAGGAGAG

102522   TTTCTAAGACTCCAGATCTTGAGTGTGGAGCTTGAAGAAGGACCCAGGCAAGGGCCCTGT
         CTTGATACTGGCAGCCCCTCTGATACCTCCCTCTGCCCTCTCCAGGCCATCCTGAGCATG
         CTGCAGGACATGAATTTCATCAACAACTACAAAATTGACTGCCCGACCCTGGCCCGGTTC
         GTGCGCCCACAGACAGCCCCAGTCTTCGCCTCCCTCTTTCCTCTACTGTCACATCCATTG
         CCCCCGGCATTCTGGAGAGGATCTCTCTAAGGATGACTGGGGAGACCCAGTCTTATGGGG
         [G,T,CsA]
         TGGGGAGGATCCATGAATGAGAAGCAATTCCTAGACACTGAACTGTCAATAAAGGCAAGA
         AATGAGGCAAGGCAAAGCCTGGAGGCAAGGCCGAGAGTGTGTAGCCAGAGGTTTAAGTTA
         GATGTGCATAGGAACTTCCTGCTAAGACAGAGTCATCAAGGAAGGCTGTGGAGGGTCCCT
         CAGGGATGGAGGGGACATGTAGTTTGCCATCATGGGGCCGTGATGGAGGAGGAGAGGCTG
         AGGCCCCTCTTCTGCCCTCTTCCCTCCCCAGGTTCTGTTTGATGGTGAAGAAGGGCTAC

102687   ACCCTGGCCCGGTTCGTGCGCCCACAGACAGCCCCAGTCTTCGCCTCCCTCTTTCCTCTA
         CTGTCACATCCATTGCCCCCGGCATTCTGGAGAGGATCTCTCTAAGGATGACTGGGGAGA
         CCCAGTCTTATGGGGGTGGGGAGGATCCATGAATGAGAAGCAATTCCTAGACACTGAACT
         GTCAATAAAGGCAAGAAATGAGGCAAGGCAAAGCCTGGAGGCAAGGCCGAGAGTGTGTAG
         CCAGAGGTTTAAGTTAGATGTGCATAGGAACTTCCTGCTAAGACAGAGTCATCAAGGAAG
         [A,C,G]
         CTGTGGAGGGTCCCTCAGGGATGGAGGGGACATGTAGTTTGCCATCATGGGGCCGTGATG
         GAGGAGGAGAGGCTGAGGCCCCTCTTCTGCCCTCTTCCCTCCCCAGGTTCTGTTTGATG
         GTGAAGAAGGGCTACCGGGATCCCCCCTACCACAACTGGATGCACGCCTTTTCTGTCTCC
         CACTTCTGCTACCTGCTCTACAAGAACCTGGAGCTCACCAACTACCTCGAGTGAGTGGCT
         GCATCTCCCCCACATCTGGCAGCCACTGGGGTCCCCTTCCCTGGGACAGGGAAGCACCCC

103134   CTACCACAACTGGATGCACGCCTTTTCTGTCTCCCACTTCTGCTACCTGCTCTACAAGAA
         CCTGGAGCTCACCAACTACCTCGAGTGAGTGGCTGCATCTCCCCCACATCTGGCAGCCAC
         TGGGGTCCCCTTCCCTGGGACAGGGAAGCACCCCCTGTGTGTCAGGCACTTTACACGCAC
         TGCCTCATGGGATCTTCTTAGCCCCAGGGGACTAGAGGGGAAGGCTGTGAGCCCCATCTT
         CCAGGAGGGGCTTGCTCACAGCCAAGCAGCTAGTGAAGACTGAGCCTGATTTAAACCCGG
         [G,T]
         TCTGCTGGACTCCAAACCAGTGCTTCTTTCCAGGAAGGGAACCCAGGTGTTCCAACCTCC
         TGTCCCAGTGGCTCCTGGGCATGTCATCTCCTGTCTGTCCTCTTGGGGATTTAGGGAGGG
         AACTGTGGGCTGACCTCTTTTTTTTTCTCCTTTCTGCCTCTCAACCAGGGACATCGAGATC
         TTTGCCTTGTTTATTTCCTGCATGTGTCATGACCTGGACCACAGAGGCACAAACAACTCT
         TTCCAGGTGGCCTCGGTGAGACCCTGCCCTGCTCACAGTGGGGACCCTCCATGGGGTGTC

103152   CGCCTTTTCTGTCTCCCACTTCTGCTACCTGCTCTACAAGAACCTGGAGCTCACCAACTA
         CCTCGAGTGAGTGGCTGCATCTCCCCCACATCTGGCAGCCACTGGGGTCCCCTTCCCTGG
         GACAGGGAAGCACCCCCTGTGTGTCAGGCACTTTACACGCACTGCCTCATGGGATCTTCT
         TAGCCCCAGGGGACTAGAGGGGAAGGCTGTGAGCCCCATCTTCCAGGAGGGGCTTGCTCA
         CAGCCAAGCAGCTAGTGAAGACTGAGCCTGATTTAAACCCGGGTCTGCTGGACTCCAAAC
         [C,A]
         AGTGCTTCTTTCCAGGAAGGGAACCCAGGTGTTCCAACCTCCTGTCCCAGTGGCTCCTGG
         GCATGTCATCTCCTGTCTGTCCTCTTGGGGATTTAGGGAGGGAACTGTGGGCTGACCTCT
         TTTTTTTCTCCTTTCTGCCTCTCAACCAGGGACATCGAGATCTTTGCCTTGTTTATTTCC
         TGCATGTGTCATGACCTGGACCACAGAGGCACAAACAACTCTTTCCAGGTGGCCTCGGTG
         AGACCCTGCCCTGCTCACAGTGGGGACCCTCCATGGGGTGTCTTGGATCTCATCCTCTCC

103392   CAGCCAAGCAGCTAGTGAAGACTGAGCCTGATTTAAACCCGGGTCTGCTGGACTCCAAAC
         CAGTGCTTCTTTCCAGGAAGGGAACCCAGGTGTTCCAACCTCCTGTCCCAGTGGCTCCTG
         GGCATGTCATCTCCTGTCTGTCCTCTTGGGGATTTAGGGAGGGAACTGTGGGCTGACCTC
         TTTTTTTCTCCTTTCTGCCTCTCAACCAGGGACATCGAGATCTTTGCCTTGTTTATTTC
         CTGCATGTGTCATGACCTGGACCACAGAGGCACAAACAACTCTTTCCAGGTGGCCTCGGT
         [G,A]
         AGACCCTGCCCTGCTCACAGTGGGGACCCTCCATGGGGTGTCTTGGATCTCATCCTCTCC
```

FIGURE 3-87

```
          CAGCCTGAATAGGGTGGGAGCGAGTGAGACCAGGAGCCAGGTTTAGACACAGGAGGAGGT
          TCCCCCAGGGTTTGCCCCTGGCTCTGAGATAGGGAGGAGGGGAGAAAGGTGGAAGGGCAG
          GACACTGCTCAGCCTAAAGCAGTGGCACTTGGATCCGGATGTGAGGAGTGACCACAGTTT
          TCCTGGGCTTTTCCAGAAATCTGTGCTGGCTGCGCTCTACAGCTCTGAGGGCTCCGTCAT

103436    CTGCTGGACTCCAAACCAGTGCTTCTTTCCAGGAAGGGAACCCAGGTGTTCCAACCTCCT
          GTCCCAGTGGCTCCTGGGCATGTCATCTCCTGTCTGTCCTCTTGGGGATTTAGGGAGGGA
          ACTGTGGGCTGACCTCTTTTTTTTCTCCTTTCTGCCTCTCAACCAGGGACATCGAGATCT
          TTGCCTTGTTTATTTCCTGCATGTGTCATGACCTGGACCACAGAGGCACAAACAACTCTT
          TCCAGGTGGCCTCGGTGAGACCCTGCCCTGCTCACAGTGGGGACCCTCCATGGGGTGTCT
          [G,T]
          GGATCTCATCCTCTCCCAGCCTGAATAGGGTGGGAGCGAGTGAGACCAGGAGCCAGGTTT
          AGACACAGGAGGAGGTTCCCCCAGGGTTTGCCCCTGGCTCTGAGATAGGGAGGAGGGGAG
          AAAGGTGGAAGGGCAGGACACTGCTCAGCCTAAAGCAGTGGCACTTGGATCCGGATGTGA
          GGAGTGACCACAGTTTTCCTGGGCTTTTCCAGAAATCTGTGCTGGCTGCGCTCTACAGCT
          CTGAGGGCTCCGTCATGGAGGTATCACTCTTCTGTCCCACCCCGTCCTTCTTCCCCTTTA

104138    CTCATTTTCCTGGAGTGGGCTTGGAAGGGTGCAGGTGCGGATGATAGCAAGGATTTGTGT
          TCAGCGTGTTTCCCTTTGGCTGCCTGGGAACACCCCATTCAGCCCCCTCCTGCCAAACTT
          GGGATGGGCTCCACTCCCATCACTTAGCGTCACCTTAGATTGTTTGGTTTGGGTCTGCCT
          ACCTCCTCGTGCACAAGGTCTGAGCCATTTCTGAGTTCCCTGCACTTGGCACAGGGCTTG
          GCACAGAGTAGGAGACACATTTCCAAGGTCACCTTGCCTCATGCTACTTCCCACAACACC
          [T,C]
          CTCCAGAGGCTGCCCCTGCTTGCACACCCCCAGAGACGAGGTTCTCTGTCTCTCTCCCAG
          GAGGCCTGGTGGCAGTGCTGGTTCTGCCCTCTGCCCCCCTGAGATAAGCTGCTCCTTTTC
          TGAGTGACAGCCCTTCAGCATCCGGAAATGGGGGCCTTGCCCTTGCCTCATCACTGCCTC
          TCCTTGTCAGCAAACAAATGTGTTCTGCATGATTTGGTGTCTAGGACTCCAAAGGATCAT
          TTCAAAAATGTTCCAGCTTTCAGGGACCCCAGAGCTTACCTTGTTGGGTCCCTGCATGTG

104175    CGGATGATAGCAAGGATTTGTGTTCAGCGTGTTTCCCTTTGGCTGCCTGGGAACACCCCA
          TTCAGCCCCCTCCTGCCAAACTTGGGATGGGCTCCACTCCCATCACTTAGCGTCACCTTA
          GATTGTTTGGTTTGGGTCTGCCTACCTCCTCGTGCACAAGGTCTGAGCCATTTCTGAGTT
          CCCTGCACTTGGCACAGGGCTTGGCACAGAGTAGGAGACACATTTCCAAGGTCACCTTGC
          CTCATGCTACTTCCCACAACACCTCTCCAGAGGCTGCCCCTGCTTGCACACCCCCAGAGA
          [C,T]
          GAGGTTCTCTGTCTCTCTCCCAGGAGGCCTGGTGGCAGTGCTGGTTCTGCCCTCTGCCCC
          CCTGAGATAAGCTGCTCCTTTTCTGAGTGACAGCCCTTCAGCATCCGGAAATGGGGCCT
          TGCCCTTGCCTCATCACTGCCTCTCCTTGTCAGCAAACAAATGTGTTCTGCATGATTTGG
          TGTCTAGGACTCCAAAGGATCATTTCAAAAATGTTCCAGCTTTCAGGGACCCCAGAGCTT
          ACCTTGTTGGGTCCCTGCATGTGACAGCTGAGGAGTCTGAGGCTCAGAGTGGTCTAGGGA

104560    GAGTGACAGCCCTTCAGCATCCGGAAATGGGGGCCTTGCCCTTGCCTCATCACTGCCTCT
          CCTTGTCAGCAAACAAATGTGTTCTGCATGATTTGGTGTCTAGGACTCCAAAGGATCATT
          TCAAAAATGTTCCAGCTTTCAGGGACCCCAGAGCTTACCTTGTTGGGTCCCTGCATGTGA
          CAGCTGAGGAGTCTGAGGCTCAGAGTGGTCTAGGGACTCACCCTGGGTCACACAGAGGGT
          TGAAACAGAGCTCAGAAAGGGAACTGGGGCCCCTGACTCCCCCTTTCTGACTGCTCTGCT
          [T,G]
          ACCTGGGGGCTGGAGCTGGACGAGGCCCCTGCTTCCTCTCTTGGGGTCAATGGTAAGGGA
          GCCCATCTGCCCCAGCTGGGCCCCCATCACTCCTCTCCCCCCAGAGGCACCACTTTGCTC
          AGGCCATCGCCATCCTCAACACCCACGGCTGCAACATCTTTGATCATTTCTCCCGGAAGG
          TGATGGGGTTGGGGGTGGGTGGGGATTGAGGGGGAGCTGGGAGCTGGCTGGAGGTGGGA
          TAAGGAGCCAAGGAGTGGAGGCTCACTGGGATGGGCAAATGGGTGGGGGTGTCCAGTAGG

104688    GTTCCAGCTTTCAGGGACCCCAGAGCTTACCTTGTTGGGTCCCTGCATGTGACAGCTGAG
          GAGTCTGAGGCTCAGAGTGGTCTAGGGACTCACCCTGGGTCACACAGAGGGTTGAAACAG
          AGCTCAGAAAGGGAACTGGGGCCCCTGACTCCCCCTTTCTGACTGCTCTGCTTACCTGGG
          GGCTGGAGCTGGACGAGGCCCCTGCTTCCTCTCTTGGGGTCAATGGTAAGGGAGCCCATC
          TGCCCCAGCTGGGCCCCCATCACTCCTCTCCCCCCAGAGGCACCACTTTGCTCAGGCCAT
```

FIGURE 3-88

```
            [T,C]
            GCCATCCTCAACACCCACGGCTGCAACATCTTTGATCATTTCTCCCGGAAGGTGATGGGG
            TTGGGGGTGGGGTGGGGATTGAGGGGGAGCTGGGAGCTGGCTGGAGGTGGGATAAGGAGC
            CAAGGAGTGGAGGCTCACTGGGATGGGCAAATGGGTGGGGGTGTCCAGTAGGAGGGCATG
            ACACCCCTGCCCTCGCCTCAGGACTATCAGCGCATGCTGGATCTGATGCGGGACATCATC
            TTGGCCACAGACCTGGCCCACCATCTCCGCATCTTCAAGGACCTCCAGAAGATGGCTGAG

105118    GAGGCTCACTGGGATGGGCAAATGGGTGGGGGTGTCCAGTAGGAGGGCATGACACCCCTG
            CCCTCGCCTCAGGACTATCAGCGCATGCTGGATCTGATGCGGGACATCATCTTGGCCACA
            GACCTGGCCCACCATCTCCGCATCTTCAAGGACCTCCAGAAGATGGCTGAGGGTGACTGC
            TGTTAGCCCCAGTCCTTGGGGCTGGGGAGGAACAACCAGGGGAAGGATTTGCCAGGGGAG
            CATTCCCAGGGTGCAGACCCATCCCCTGCAACATCAACCCTTCTCTGGCTGCACGGCCCC
            [C,T]
            CCCAGGCAGACCCAGCACTGGCCCCTTGGCTCCCATCAAGGGTGCCCAATTCCCTGGACC
            GCTCTGGGTTGGGCCCTGGGAGCCTTGTCCTCAGAAGGGCAAAGAGGCTGGGCCCCGCTC
            CTTGACCCCATCCTCCCCTCAACAGTGGGCTACGACCGAAACAACAAGCAGCACCACAGA
            CTTCTCCTCTGCCTCCTCATGACCTCCTGTGACCTCTCTGACCAGACCAAGGGCTGGAAG
            ACTACGAGAAAGATCGCGGTAGGTGTAGTCCTCCCTGGGAAGGCACAGGCTGCCCACCCT

105179    CCTCGCCTCAGGACTATCAGCGCATGCTGGATCTGATGCGGGACATCATCTTGGCCACAG
            ACCTGGCCCACCATCTCCGCATCTTCAAGGACCTCCAGAAGATGGCTGAGGGTGACTGCT
            GTTAGCCCCAGTCCTTGGGGCTGGGGAGGAACAACCAGGGGAAGGATTTGCCAGGGGAGC
            ATTCCCAGGGTGCAGACCCATCCCCTGCAACATCAACCCTTCTCTGGCTGCACGGCCCCC
            CCCAGGCAGACCCAGCACTGGCCCCTTGGCTCCCATCAAGGGTGCCCAATTCCCTGGACC
            [G,A]
            CTCTGGGTTGGGCCCTGGGAGCCTTGTCCTCAGAAGGGCAAAGAGGCTGGGCCCCGCTCC
            TTGACCCCATCCTCCCCTCAACAGTGGGCTACGACCGAAACAACAAGCAGCACCACAGAC
            TTCTCCTCTGCCTCCTCATGACCTCCTGTGACCTCTCTGACCAGACCAAGGGCTGGAAGA
            CTACGAGAAAGATCGCGGTAGGTGTAGTCCTCCCTGGGAAGGCACAGGCTGCCCACCCTG
            CCCAGCTTTGGGTGCCCCCTGTGCCTGAATACCCTCTCTCTGCTCAGCTCAGCCTGGCTG

106026    ATAGAGGATGTGATGAGAGTGTTGGCCTTTTCAGGAGCTGATCTACAAAGAATTCTTCTCC
            CAGGGAGACCTGGTATGTGTGGAGTGACCCCAGGATGTCCAGGATGGGGGAGGGTTCCTG
            GCCTGGGACAGGGAGGGCTTGAACTAGCCTGACCCTGGTACCCGATGGAGGAATGAGAGG
            GACAGGCCTGACGACTCGATGCCTGCAGGAGAAGGCCATGGGCAACAGGCCGATGGAGAT
            GATGGACCGGGAGAAGGCCTATATCCCTGAGCTGCAAATCAGCTTCATGGAGCACATTGC
            [A,G]
            ATGCCCATCTACAAGTGAGTGAGCTCATGGGGACAAGCTGCACCCTGCACAGAGAGGGTA
            GGCTGGAGTGGGGACATCACAGGAAACACAGGTGCTGAGATTGGCCTGGCCCAGCTCCAA
            CTGATTCATCCCCTTGCCTCTGGGCATAACTGTCTCCCGCTGTGCCCCTCAGTGGGTCCT
            TCACTTCATCCTTGGTCCTCAGTGGAAAGAGACCATCATGCTTTCCTAGGTGTCCTCCTC
            TGTCTCACATTCTTGTGGAAGTTCTTGTTTTTTTTGAGATGGAGTCTCACTCTGTTGCCC

106141    TCCTGGCCTGGGACAGGGAGGGCTTGAACTAGCCTGACCCTGGTACCCGATGGAGGAATG
            AGAGGGACAGGCCTGACGACTCGATGCCTGCAGGAGAAGGCCATGGGCAACAGGCCGATG
            GAGATGATGGACCGGGAGAAGGCCTATATCCCTGAGCTGCAAATCAGCTTCATGGAGCAC
            ATTGCAATGCCCATCTACAAGTGAGTGAGCTCATGGGGACAAGCTGCACCCTGCACAGAG
            AGGGTAGGCTGGAGTGGGGACATCACAGGAAACACAGGTGCTGAGATTGGCCTGGCCCAG
            [C,G]
            TCCAACTGATTCATCCCCTTGCCTCTGGGCATAACTGTCTCCCGCTGTGCCCCTCAGTGG
            GTCCTTCACTTCATCCTTGGTCCTCAGTGGAAAGAGACCATCATGCTTTCCTAGGTGTCC
            TCCTCTGTCTCACATTCTTGTGGAAGTTCTTGTTTTTTTTGAGATGGAGTCTCACTCTGT
            TGCCCAGGCTGGAGTGCAATGGCACGATCTTGGCTCACTGCAACCTCCCCCTCCTGGGTT
            CAAGCGATTCTCCTGCCTCAGCCTCCCAAGTAGCTGGGATTACAGGCATGCACCACCACG

106474    AACTGTCTCCCGCTGTGCCCCTCAGTGGGTCCTTCACTTCATCCTTGGTCCTCAGTGGAA
            AGAGACCATCATGCTTTCCTAGGTGTCCTCCTCTGTCTCACATTCTTGTGGAAGTTCTTG
            TTTTTTTTGAGATGGAGTCTCACTCTGTTGCCCAGGCTGGAGTGCAATGGCACGATCTTG
```

FIGURE 3-89

```
         GCTCACTGCAACCTCCCCCTCCTGGGTTCAAGCGATTCTCCTGCCTCAGCCTCCCAAGTA
         GCTGGGATTACAGGCATGCACCACCACGCCCAGCTAATTTTTGTATTTTTAGTAGAGATGG
         [G,A]
         GCTTCACCATTTTGGTCAGGCTGGTCTTGAACTCCTGACTTCAGGTGATCCACACACCTC
         GGCATCTCTGAGTGTTGGGATTACAGGCGTGAGCTACCGTACCTGGCCCTTGTGGAAATT
         CTATTTGTTGTGTAGCCCTAGTCTTTCTTGCTGCCCATGGTCTGATTTCTGGCCTCTCAC
         CCTCTGCCCCATGCACCCGCAGGCTGTTGCAGGACCTGTTCCCCAAAGCGGCAGAGCTG
         TACGAGCGCGTGGCCTCCAACCGTGAGCACTGGACCAAGGTGTCCCACAAGTTCACCATC

106717   GGGATTACAGGCATGCACCACCACGCCCAGCTAATTTTTGTATTTTTAGTAGAGATGGGGC
         TTCACCATTTTGGTCAGGCTGGTCTTGAACTCCTGACTTCAGGTGATCCACACACCTCGG
         CATCTCTGAGTGTTGGGATTACAGGCGTGAGCTACCGTACCTGGCCCTTGTGGAAATTCT
         ATTTGTTGTGTAGCCCTAGTCTTTCTTGCTGCCCATGGTCTGATTTCTGGCCTCTCACCC
         TCTGCCCCATGCACCCGCAGGCTGTTGCAGGACCTGTTCCCCAAAGCGGCAGAGCTGTA
         [T,C]
         GAGCGCGTGGCCTCCAACCGTGAGCACTGGACCAAGGTGTCCCACAAGTTCACCATCCGC
         GGCCTCCCAAGTAACAACTCGCTGGACTTCCTGGATGAGGAGTACGAGGTGCCTGATCTG
         GATGGCACTAGGGCCCCCATCAATGGCTGCTGCAGCCTTGATGCTGAGTGATCCCCTCCA
         GGGACACTTCCCTGCCCAGGCCACCTCCCACAGCCCTCCACTGGTCTGGCCAGATGCACT
         GGGAACAGAGCCACGGGTCCTGGGTCCTAGACCAGGACTTCCTGTGTGACCCTGGACAAG

107099   CTGGACTTCCTGGATGAGGAGTACGAGGTGCCTGATCTGGATGGCACTAGGGCCCCCATC
         AATGGCTGCTGCAGCCTTGATGCTGAGTGATCCCCTCCAGGGACACTTCCCTGCCCAGGC
         CACCTCCCACAGCCCTCCACTGGTCTGGCCAGATGCACTGGGAACAGAGCCACGGGTCCT
         GGGTCCTAGACCAGGACTTCCTGTGTGACCCTGGACAAGTACTACCTTCCTGGGCCTCAG
         CTTTCTCGTCTGTATAATGGAAGCAAGACTTCCAACCTCACGGAGACTTTGTAATTTGTT
         [C,T]
         TCTGAGAGCACAGGGGTGACCAATGAGCAGTGGGCCCTACTCTGCACCTCTGACCACACC
         TTGGCAAGTCTTTCCCAAGCCATTCTTTGTCTGAGCAGCTTGATGGTTTCTCCTTGCCCC
         ATTTCTGCCCCACCAGATCTTTGCTCCTTTCCCTTTGAGGACTCCCACCCTTTGGGGTCT
         CCAGGATCCTCATGGAAGGGGAAGGTGAGACATCTGAGTGAGCAGAGTGTGGCATCTTGG
         AAACAGTCCTTAGTTCTGTGGGAGGACTAGAAACAGCCGCGGGGCGAAGGCCCCCTGAGG

107322   ACCTTCCTGGGCCTCAGCTTTCTCGTCTGTATAATGGAAGCAAGACTTCCAACCTCACGG
         AGACTTTGTAATTTGTTCTCTGAGAGCACAGGGGTGACCAATGAGCAGTGGGCCCTACTC
         TGCACCTCTGACCACACCTTGGCAAGTCTTTCCCAAGCCATTCTTTGTCTGAGCAGCTTG
         ATGGTTTCTCCTTGCCCCATTTCTGCCCCACCAGATCTTTGCTCCTTTCCCTTTGAGGAC
         TCCCACCCTTTGGGGTCTCCAGGATCCTCATGGAAGGGGAAGGTGAGACATCTGAGTGAG
         [C,G]
         AGAGTGTGGCATCTTGGAAACAGTCCTTAGTTCTGTGGGAGGACTAGAAACAGCCGCGGG
         GCGAAGGCCCCCTGAGGACCACTACTATACTGATGGTGGGATTGGGACCTGGGGATACA
         GGGGCCCCAGGAAGAAGCTGCCAGAGGGGCAGCTCAGTGCTCTGCAGAGAGGGGCCCTGG
         GGAGAAGCAGGATGGGATTGATGGGCAGGAGGGATCCCCGCACTGGGAGACAGGCCCAGG
         TATGAATGAGCCAGCCATGCTTCCTCCTGCCTGTGTGACGCTGGGCGAGTCTCTTCCCCT

108611   GTGGAGGCTAAGGGGTGGGTGGCAGATGAGAAGGCCTGGCCATGGAGCAGTGATGGGACA
         TGTTGGCTGGCAGAGATTGTAGAATAGAGGAAAAACAAAGGTTGAGGCAAGCAGGCAGGC
         TGCCTGGAGGAGGTAGCCTGGAGCTTGTCCTAGACCCTCCCAGCGCTGGCCTGCCCTGGT
         CATGAGTGCCCATACGGCGAGGGCCTAGGCCTCTGAACTCTGTTTCTAGCTGCAGTGATG
         CCTGGCTGTGTCCCAGGAAGTCCCACATCCCAGTTACTCTGAGTCCTGCCGAAGGTGCAC
         [G,C]
         CCTGAGTCAGACTCCACACCAGATCCAGCCCCGGGTTGTGTCTGAGGAGTTGCGTCTGTT
         CCTCTGCATGAGAGTGTTTACTTCCGCCCAGTCCAAGATGGGCAGACTGCAGGTTGGGGC
         TACGCGGAGGCTCTGCCTGGCACAGTCTCCAGACCCTGTCCCCGACTTGCCTACCCCCCT
         CTGAGCTCCTCTCCGTGTTCATCTCTTCCTGGTCAGTAAAGGTTGATGTGTTAAGAGGGT
         GGGCACTGGGGTCTCCTTTCTTGGTGGGAGCAGGAAGGAGATGGACAGGGCCATCCTGTG

108664   TGGGACATGTTGGCTGGCAGAGATTGTAGAATAGAGGAAAAACAAAGGTTGAGGCAAGCA
```

FIGURE 3-90

```
         GGCAGGCTGCCTGGAGGAGGTAGCCTGGAGCTTGTCCTAGACCCTCCCAGCGCTGGCCTG
         CCCTGGTCATGAGTGCCCATACGGCGAGGGCCTAGGCCTCTGAACTCTGTTTCTAGCTGC
         AGTGATGCCTGGCTGTGTCCCAGGAAGTCCCACATCCCAGTTACTCTGAGTCCTGCCGAA
         GGTGCACGCCTGAGTCAGACTCCACACCAGATCCAGCCCCGGGTTGTGTCTGAGGAGTTG
         [A,G,C]
         GTCTGTTCCTCTGCATGAGAGTGTTTACTTCCGCCCAGTCCAAGATGGGCAGACTGCAGG
         TTGGGGCTACGCGGAGGCTCTGCCTGGCACAGTCTCCAGACCCTGTCCCCGACTTGCCTA
         CCCCCCTCTGAGCTCCTCTCCGTGTTCATCTCTTCCTGGTCAGTAAAGGTTGATGTGTTA
         AGAGGGTGGGCACTGGGGTCTCCTTTCTTGGTGGGAGCAGGAAGGAGATGGACAGGGCCA
         TCCTGTGACCATCAGCCATTGCCAGCTTTGCCTTTGGGACCACAGAGCCCATCTGCTTCC

109160   GGGTCTCCTTTCTTGGTGGGAGCAGGAAGGAGATGGACAGGGCCATCCTGTGACCATCAG
         CCATTGCCAGCTTTGCCTTTGGGACCACAGAGCCCATCTGCTTCCTCTGCAGCTCCCCCT
         GCCCCACTAGCCTGTCTGGGTTTGGAATCTGCTCCTCTGGCTGAATGGTCTCCAGGTTTC
         CAGCTTCCCTTAGCGTCATGGGGCTCCAGGCTCCTCCCATTCCCAGCTCCTGCTGTGGGC
         TCCCCAAGTCCGTCTCTATCCTCTCACAGCACAGGACCCAGGCTTGGCCAGTGGGTCCCC
         [T,C,G]
         GGTGGGGGTGGGAGTGGTCAGTTTGTGGCCCACGGCCAATAAGAGATGGCTATTCTAATG
         GTGCCTGGCTGACCCCAGGGTCACTGTGGGCTGATGTAGCTGCTCTTCTGCCTGACCCCT
         GACCCTGAGTGTGTGTGCGTGTTCCTCTTCCACAACTCTTCAGGCAAAGAGAACCTTGAC
         CCTGCATCTGTCTGTCCCCAGCCCAGCCCTCCTTTGAGGCTCATGCTGTGACACATCCCT
         GTTTTTCACCAAATGGAGGGAACAACCACAGATATTTCCTTGTGCACGCAGGACCCTGTG

110512   AGAGGACAGATGGGAGGAGGCTCTGCACAGAGCCTGAGGACAGCCCTCACCAGGTTACAG
         AACACAAGGCTTGACCCCATTGGCTTCCTGTAGCTGTCCTGCTCTCCCAACTTAATGGTT
         TCATTTTGCATTTTATTTAAATTTCACAATGATTCTAGCAGATACCATTAGTCTATTCTG
         CAGCCAAGTTGTCTAAGGTTTGGAGAGGTTAAGTAATGCACCAAGGTTAGGATTTGAGCC
         CTACCTGTCTGATTCCCCTCCGAGAGCTGTCTGATTCCTTTCTCCTCCTCTGGGATAGGG
         [G,A]
         AAGGAGACTCAGAAGGACGGGGTCTCCATCTTCAGTCTTTGCAAGACTATTGTAGGGCAT
         TGGGATGGTGAGCACAAAGTGGGTTGAAGCCCCAGAGAAAGAGCTGAGAGCTGGGATCAA
         CTGTGTGTGTGCATGTGTGTGTCTGTGTGTGTGTGAGTTGGAGTAGGGGGCAGGGAGAAA
         AGAGTGGGGTGGTGGTGGCTTGTAGTGCAGCTCAGGGCCACCAGGTGGTGTCCAGCCCTC
         GCTGTCCTCACCTCCCCAGAGGTCAGAGAAGGATATGGGAGGGGGTGGGGTGGGGTGAGG

110746   TGAGCCCTACCTGTCTGATTCCCCTCCGAGAGCTGTCTGATTCCTTTCTCCTCCTCTGGG
         ATAGGGGAAGGAGACTCAGAAGGACGGGGTCTCCATCTTCAGTCTTTGCAAGACTATTGT
         AGGGCATTGGGATGGTGAGCACAAAGTGGGTTGAAGCCCCAGAGAAAGAGCTGAGAGCTG
         GGATCAACTGTGTGTGTGCATGTGTGTGTCTGTGTGTGTGTGAGTTGGAGTAGGGGGCAG
         GGAGAAAAGAGTGGGGTGGTGGTGGCTTGTAGTGCAGCTCAGGGCCACCAGGTGGTGTCC
         [A,G]
         GCCCTCGCTGTCCTCACCTCCCCAGAGGTCAGAGAAGGATATGGGAGGGGGTGGGGTGGG
         GTGAGGGGGACGCGGCGGGACGGGGGGGACGGTGGTTGGTAGTCTCACTCCTGTCCATT
         CACCTACAGGTTGAGTATCCCTTATCCAAAATGCTTGGGGCCAGAAGTGTCTCAGATTTA
         AGATTTTTTTCGGATTTTTGGAATATTTGCATATACATAATGAGATATCTTGGGAATGAGA
         CCCCAGGCTAAACAGGAAATTCATTTATGTTTTATATACACACAGCCTGAAGCAGTTTTA

110781   TCTGATTCCTTTCTCCTCCTCTGGGATAGGGGAAGGAGACTCAGAAGGACGGGGTCTCCA
         TCTTCAGTCTTTGCAAGACTATTGTAGGGCATTGGGATGGTGAGCACAAAGTGGGTTGAA
         GCCCCAGAGAAAGAGCTGAGAGCTGGGATCAACTGTGTGTGTGCATGTGTGTGTCTGTGT
         GTGTGTGAGTTGGAGTAGGGGGCAGGGAGAAAAGAGTGGGGTGGTGGTGGCTTGTAGTGC
         AGCTCAGGGCCACCAGGTGGTGTCCAGCCCTCGCTGTCCTCACCTCCCCAGAGGTCAGAG
         [A,T]
         AGGATATGGGAGGGGGTGGGGTGGGGTGAGGGGGACGCGGCGGGACGGGGGGGACGGTG
         GTTGGTAGTCTCACTCCTGTCCATTCACCTACAGGTTGAGTATCCCTTATCCAAAATGCT
         TGGGGCCAGAAGTGTCTCAGATTTAAGATTTTTTTCGGATTTTTGGAATATTTGCATATAC
         ATAATGAGATATCTTGGGAATGAGACCCCAGGCTAAACAGGAAATTCATTTATGTTTTAT
         ATACACACAGCCTGAAGCAGTTTTATATAATATTTTGAATAATT
```

FIGURE 3-91

Multiple alignment of isoform1 (11000567083206_pep), human PDE2A3 (gi4505657_pep) and bovine PDE2A1 (gi116569_pep).
```
        Name: 11000567083206_pep  Len:  943  Check: 2306  Weight: 1.00
        Name: gi4505657_pep       Len:  943  Check:  362  Weight: 1.00
        Name: gi116569_pep        Len:  943  Check: 5464  Weight: 1.00

//
                 1                                                        50
110005670832    ~~~~~~~~~~ ~~~~~~~~~~ ~~MRRQPAAS LDPLAKEPGP PGSRDDRLED
gi4505657_pe    MGQACGHSIL CRSQQYPAAR PAEPRGQQVF LKP.DEPPPP PQPCADSLQD
gi116569_pep    ~~~~~~~~~~ ~~~~~~~~~~ ~~MRRQPAAS RDLFAQEPVP PGSGDGALQD 51                                                       100
110005670832    ALLSLGSVID ISGLQRAVKE ALSAVLPRVE TVYTYLLDGE SQLVCEDPPH
gi4505657_pe    ALLSLGSVID ISGLQRAVKE ALSAVLPRVE TVYTYLLDGE SQLVCEDPPH
gi116569_pep    ALLSLGSVID VAGLQQAVKE ALSAVLPKVE TVYTYLLDGE SRLVCEEPPH 101                                                      150
110005670832    ELPQEGKVRE AIISQKRLGC NGLGFSDLPG KPLARLVAPL APDTQVLVMP
gi4505657_pe    ELPQEGKVRE AIISQKRLGC NGLGFSDLPG KPLARLVAPL APDTQVLVMP
gi116569_pep    ELPQEGKVRE AVISRKRLGC NGLGPSDLPG KPLARLVAPL APDTQVLVIP 151                                                      200
110005670832    LADKEAGAVA AVILVHCGQL SDNEEWSLQA VEKHTLVALR RVQVLQQRGP
gi4505657_pe    LADKEAGAVA AVILVHCGQL SDNEEWSLQA VEKHTLVALR RVQVLQQRGP
gi116569_pep    LVDKEAGAVA AVILVHCGQL SDNEEWSLQA VEKHTLVALK RVQALQQRES 201                                                      250
110005670832    REAPRAVQNP PEGTAEDQKG GAAYIDRDRK ILQLCGELYD LDASSLQLKV
gi4505657_pe    REAPRAVQNP PEGTAEDQKG GAAYTDRDRK ILQLCGELYD LDASSLQLKV
gi116569_pep    SVAPEATQNP PEEAAGDQKG GVAYTNQDRK ILQLCGELYD LDASSLQLKV 251                                                      300
110005670832    LQYLQQETRA SRCCLLLVSE DNLQLSCKVI GDKVLGEEVS FPL.TGCLGQ
gi4505657_pe    LQYLQQETRA SRCCLLLVSE DNLQLSCKVI GDKVLGEEVS FPL.TGCLGQ
gi116569_pep    LQYLQQETQA SRCCLLLVSE DNLQLSCKVI GDKVLEEEIS FPLTTGRLGQ 301                                                      350
110005670832    WEDKKSIQL  KDLTSEDVQQ LQSMLGCELQ AMLCVPVISR ATDQVVALAC
gi4505657_pe    WEDKKSIQL  KDLTSEDVQQ LQSMLGCELQ AMLCVPVISR ATDQVVALAC
gi116569_pep    WEDKKSIQL  KDLTSEDMQQ LQSMLGCEVQ AMLCVPVISR ATDQVVALAC 351                                                      400
110005670832    AFNKLEGDLF TDEDEHVIQH CFHYTSTVLT STLAFQKEQK LKCECQALLQ
gi4505657_pe    AFNKLEGDLF TDEDEHVIQH CFHYTSTVLT STLAFQKEQK LKCECQALLQ
gi116569_pep    AFNKLGGDLF TDQDEHVIQH CFHYTSTVLT STLAFQKEQK LKCECQALLQ 401                                                      450
110005670832    VAKNLFTHLD DVSVLLQEII TEARNLSNAE ICSVFLLDQN ELVAKVFDGG
gi4505657_pe    VAKNLFTHLD DVSVLLQEII TEARNLSNAE ICSVFLLDQN ELVAKVFDGG
gi116569_pep    VAKNLFTHLD DVSVLLQEII TEARNLSNAE ICSVFLLDQN ELVAKVFDGG 451                                                      500
110005670832    WDDESYEIR  IPADQGIAGH VATTGQILNI PDAYAHPLFY RGVDDSTGFR
gi4505657_pe    WDDESYEIR  IPADQGIAGH VATTGQILNI PDAYAHPLFY RGVDDSTGFR
gi116569_pep    WEDESYEIR  IPADQGIAGH VATTGQILNI PDAYAHPLFY RGVDDSTGFR
```

```
                  501                                                          550
110005670832  TRNILCFPIK  NENQEVIGVA  ELVNKINGPW  FSKFDEDLAT  AFSIYCGISI
gi4505657_pe  TRNILCFPIK  NENQEVIGVA  ELVNKINGPW  FSKFDEDLAT  AFSIYCGISI
gi116569_pep  TRNILCFPIK  NENQEVIGVA  ELVNKINGPW  FSKFDEDLAT  AFSIYCGISI 551                                                          600
110005670832  AHSLLYKKVN  EAQYRSHLAN  EMMMYHMKVS  DDEYTKLLHD  GIQPVAAIDS
gi4505657_pe  AHSLLYKKVN  EAQYRSHLAN  EMMMYHMKVS  DDEYTKLLHD  GIQPVAAIDS
gi116569_pep  AHSLLYKKVN  EAQYRSHLAN  EMMMYHMKVS  DDEYTKLLHD  GIQPVAAIDS 601                                                          650
110005670832  NFASFTYTPR  SLPEDDTSMA  ILSMLQDMNF  INNYKIDCPT  LARFCLMVKK
gi4505657_pe  NFASFTYTPR  SLPEDDTSMA  ILSMLQDMNF  INNYKIDCPT  LARFCLMVKK
gi116569_pep  NFASFTYTPR  SLPEDDTSMA  ILSMLQDMNF  INNYKIDCPT  LARFCLMVKK 651                                                          700
110005670832  GYRDPPYHNW  MHAFSVSHFC  YLLYKNLELT  NYLEDIEIFA  LFISCMCHDL
gi4505657_pe  GYRDPPYHNW  MHAFSVSHFC  YLLYKNLELT  NYLEDIEIFA  LFISCMCHDL
gi116569_pep  GYRDPPYHNW  MHAFSVSHFC  YLLYKNLELT  NYLEDMEIFA  LFISCMCHDL 701                                                          750
110005670832  DHRGTNNSFQ  VASKSVLAAL  YSSEGSVMER  HHFAQAIAIL  NTHGCNIFDH
gi4505657_pe  DHRGTNNSFQ  VASKSVLAAL  YSSEGSVMER  HHFAQAIAIL  NTHGCNIFDH
gi116569_pep  DHRGTNNSFQ  VASKSVLAAL  YSSEGSVMER  HHFAQAIAIL  NTHGCNIFDH 751                                                          800
110005670832  FSRKDYQRML  DLMRDIILAT  DLAHHLRIFK  DLQKMAEVGY  DRNNKQHHRL
gi4505657_pe  FSRKDYQRML  DLMRDIILAT  DLAHHLRIFK  DLQKMAEVGY  DRNNKQHHRL
gi116569_pep  FSRKDYQRML  DLMRDIILAT  DLAHHLRIFK  DLQKMAEVGY  DRTNKQHHSL 801                                                          850
110005670832  LLCLLMTSCD  LSDQTKGWKT  TRKIAELIYK  EFFSQGDLEK  AMGNRPMEMM
gi4505657_pe  LLCLLMTSCD  LSDQTKGWKT  TRKIAELIYK  EFFSQGDLEK  AMGNRPMEMM
gi116569_pep  LLCLLMTSCD  LSDQTKGWKT  TRKIAELIYK  EFFSQGDLEK  AMGNRPMEMM 851                                                          900
110005670832  DREKAYIPEL  QISFMEHIAM  PIYKLLQDLF  PKAAELYERV  ASNREHWTKV
gi4505657_pe  DREKAYIPEL  QISFMEHIAM  PIYKLLQDLF  PKAAELYERV  ASNREHWTKV
gi116569_pep  DREKAYIPEL  QISFMEHIAM  PIYKLLQDLF  PKAAELYERV  ASNREHWTKV 901                                             943
110005670832  SHKFTIRGLP  SNNSLDFLDE  EYEVPDLDGT  RAPINGCCSL  DAE
gi4505657_pe  SHKFTIRGLP  SNNSLDFLDE  EYEVPDLDGT  RAPINGCCSL  DAE
gi116569_pep  SHKFTIRGLP  SNNSLDFLDE  EYEVPDLDGA  RAPINGCCSL  DAE
```

FIGURE 3-93

SEQUENCE LISTING

<160> NUMBER OF SEQ ID NOS: 5

<210> SEQ ID NO 1
<211> LENGTH: 4171
<212> TYPE: DNA
<213> ORGANISM: Human

<400> SEQUENCE: 1

```
gggccggcgg gcgggcgggc ggctgcgagc atggtcctgg tgctgcacca c atcctcatc      60 gctgttgtcc aattcctcag gcggggccag caggtcttcc tcaagccgga c gagccgccg     120 ccgccgccgc agccatgcgc cgacagcctg cagccagcct ggacccccctt g caaaggagc     180 caggaccccc agggagtaga gacgaccgac tggaggacgc cttgctgagt c tgggctctg     240 tcatcgacat ttcaggcctg caacgtgctg tcaaggaggc cctgtcagct g tgctccccc     300 gagtggaaac tgtctacacc tacctactgg atggtgagtc ccagctggtg t gtgaggacc     360 ccccacatga gctgcccag gaggggaaag tccgggaggc tatcatctcc c agaagcggc     420
```

-continued

| | |
|---|---|
| tgggctgcaa tgggctgggc ttctcagacc tgccagggaa gcccttggcc a ggctggtgg | 480 |
| ctccactggc tcctgatacc caagtgctgg tcatgccgct agcggacaag g aggctgggg | 540 |
| ccgtggcagc tgtcatcttg gtgcactgtg gccagctgag tgataatgag g aatggagcc | 600 |
| tgcaggcggt ggagaagcat accctggtcg ccctgcggag ggtgcaggtc c tgcagcagc | 660 |
| gcgggcccag ggaggctccc cgagccgtcc agaaccccc ggaggggacg g cggaagacc | 720 |
| agaagggcgg ggcggcgtac atcgaccgcg accgcaagat cctccaactg t gcggggaac | 780 |
| tctacgacct ggatgcctct tccctgcagc tcaaagtgct ccaatacctg c agcaggaga | 840 |
| cccgggcatc ccgctgctgc ctcctgctgg tgtcggagga caatctccag c tttcttgca | 900 |
| aggtcatcgg agacaaagtg ctcggggaag aggtcagctt tcccttgaca g gatgcctgg | 960 |
| gccaggtggt ggaagacaag aagtccatcc agctgaagga cctcacctcc g aggatgtac | 1020 |
| aacagctgca gagcatgttg ggctgtgagc tgcaggccat gctctgtgtc c ctgtcatca | 1080 |
| gccgggccac tgaccaggtg gtggccttgg cctgcgcctt caacaagcta g aaggagact | 1140 |
| tgttcaccga cgaggacgag catgtgatcc agcactgctt ccactacacc a gcaccgtgc | 1200 |
| tcaccagcac cctggccttc cagaaggaac agaaactcaa gtgtgagtgc c aggctcttc | 1260 |
| tccaagtggc aaagaacctc ttcacccacc tggatgacgt ctctgtcctg c tccaggaga | 1320 |
| tcatcacgga ggccagaaac ctcagcaacg cagagatctg ctctgtgttc c tgctggatc | 1380 |
| agaatgagct ggtggccaag gtgttcgacg ggggcgtggt ggatgatgag a gctatgaga | 1440 |
| tccgcatccc ggccgatcag ggcatcgcgg acacgtggc gaccacgggc c agatcctga | 1500 |
| acatccctga cgcatatgcc catccgcttt ctaccgcgg cgtggacgac a gcaccggct | 1560 |
| tccgcacgcg caacatcctc tgcttcccca tcaagaacga gaaccaggag g tcatcggtg | 1620 |
| tggccgagct ggtgaacaag atcaatgggc catggttcag caagttcgac g aggacctgg | 1680 |
| cgacggcctt ctccatctac tgcggcatca gcatcgccca ttctctccta t acaaaaaag | 1740 |
| tgaatgaggc tcagtatcgc agccacctgg ccaatgagat gatgatgtac c acatgaagg | 1800 |
| tctccgacga tgagtatacc aaacttctcc atgatgggat ccagcctgtg g ctgccattg | 1860 |
| actccaattt tgcaagtttc acctatacc ctcgttccct gcccgaggat g acacgtcca | 1920 |
| tggccatcct gagcatgctg caggacatga atttcatcaa caactacaaa a ttgactgcc | 1980 |
| cgaccctggc ccggttctgt ttgatggtga agaagggcta ccgggatccc c cctaccaca | 2040 |
| actggatgca cgccttttct gtctcccact tctgctacct gctctacaag a acctggagc | 2100 |
| tcaccaacta cctcgaggac atcgagatct ttgccttgtt tatttcctgc a tgtgtcatg | 2160 |
| acctggacca cagaggcaca aacaactctt tccaggtggc ctcgaaatct g tgctggctg | 2220 |
| cgctctacag ctctgagggc tccgtcatgg agaggcacca ctttgctcag g ccattgcca | 2280 |
| tcctcaacac ccacgctgc aacatctttg atcatttctc ccggaaggac t atcagcgca | 2340 |
| tgctggatct gatgcgggac atcatcttgg ccacagacct ggcccaccat c tccgcatct | 2400 |
| tcaaggacct ccagaagatg ctgaggtgg ctacgaccg aaacaacaag c agcaccaca | 2460 |
| gacttctcct ctgcctcctc atgacctcct gtgacctctc tgaccagacc a gggctgga | 2520 |
| agactacgag aaagatcgcg gagctgatct acaaagaatt cttctcccag g gagacctgg | 2580 |
| agaaggccat gggcaacagg ccgatggaga tgatggaccg ggagaaggcc t atatccctg | 2640 |
| agctgcaaat cagcttcatg gagcacattg caatgcccat ctacaagctg t tgcaggacc | 2700 |
| tgttccccaa agcggcagag ctgtatgagc gcgtggcctc caaccgtgag c actggacca | 2760 |
| aggtgtccca caagttcacc atccgcggcc tcccaagtaa caactcgctg g acttcctgg | 2820 |

```
atgaggagta cgaggtgcct gatctggatg gcactagggc ccccatcaat g gctgctgca    2880
gccttgatgc tgagtgatcc cctccaggga cacttccctg cccaggccac c tcccacagc    2940
cctccactgg tctggccaga tgcactggga acagagccac gggtcctggg t cctagacca    3000
ggacttcctg tgtgaccctg gacaagtact accttcctgg gcctcagctt t ctcgtctgt    3060
ataatggaag caagacttcc aacctcacgg agactttgta atttgttctc t gagagcaca    3120
ggggtgacca atgagcagtg ggccctactc tgcacctctg accacacctt g gcaagtctt    3180
tcccaagcca ttctttgtct gagcagcttg atggtttctc cttgccccat t tctgcccca    3240
ccagatcttt gctcctttcc ctttgaggac tcccaccctt tggggtctcc a ggatcctca    3300
tggaagggga aggtgagaca tctgagtgag cagagtgtgg catcttggaa a cagtcctta    3360
gttctgtggg aggactagaa acagccgcgg ggcgaaggcc ccctgaggac c actactata    3420
ctgatggtgg gattgggacc tggggggatac aggggccccca ggaagaagct g ccagagggg    3480
cagctcagtg ctctgcagag aggggccctg gggagaagca ggatgggatt g atgggcagg    3540
aggatccccc gcactgggag acaggcccag gtatgaatga gccagccatg c ttcctcctg    3600
cctgtgtgac gctgggcgag tctcttcccc tgtctgggcc aaacagggag c gggtaagac    3660
aatccatgct ctaagatcca ttttagatca atgtctaaaa tagctctatc g ctctgcgga    3720
gtcccagcag aggctatgga atgtttctgc aaccctaagg cacagagagc c caaccctga    3780
gtgtctcaga ggccccctga gtgttcccct tggcctgagc cccttaccca t tcctgcagc    3840
cagtgagaga cctggcctca gccctggcag ggctctctct tcaaggccat a tccacctgt    3900
gccctgggc ttgggagacc ccatagggcc gggactcttg ggtcagcccg g ccactggct    3960
tctctcttt tctccgtttc attctgtgtg cgttgtgggg tgggggaggg g gtccacctg    4020
ccttaccttt ctgagttgcc tttagagaga tgcgttttc taggactctg t gcaactgtc    4080
gtatatggtc ccgtgggctg accgctttgt acatgagaat aaatctattt c tttctacca    4140
gaaaaaaaa aaaaaaaaa aaaaaaaaa a                                       4171
```

<210> SEQ ID NO 2
<211> LENGTH: 920
<212> TYPE: PRT
<213> ORGANISM: Human

<400> SEQUENCE: 2

```
Met Arg Arg Gln Pro Ala Ala Ser Leu Asp P ro Leu Ala Lys Glu Pro
 1               5                  10                  15

Gly Pro Pro Gly Ser Arg Asp Asp Arg Leu G lu Asp Ala Leu Leu Ser
            20                  25                  30

Leu Gly Ser Val Ile Asp Ile Ser Gly Leu G ln Arg Ala Val Lys Glu
        35                  40                  45

Ala Leu Ser Ala Val Leu Pro Arg Val Glu T hr Val Tyr Thr Tyr Leu
    50                  55                  60

Leu Asp Gly Glu Ser Gln Leu Val Cys Glu A sp Pro Pro His Glu Leu
65                  70                  75                  80

Pro Gln Glu Gly Lys Val Arg Glu Ala Ile I le Ser Gln Lys Arg Leu
                85                  90                  95

Gly Cys Asn Gly Leu Gly Phe Ser Asp Leu P ro Gly Lys Pro Leu Ala
            100                 105                 110

Arg Leu Val Ala Pro Leu Ala Pro Asp Thr G ln Val Leu Val Met Pro
        115                 120                 125
```

-continued

```
Leu Ala Asp Lys Glu Ala Gly Ala Val Ala Val Ile Leu Val His
    130                 135                 140
Cys Gly Gln Leu Ser Asp Asn Glu Glu Trp Ser Leu Gln Ala Val Glu
145                 150                 155                 160
Lys His Thr Leu Val Ala Leu Arg Arg Val Gln Val Leu Gln Gln Arg
                165                 170                 175
Gly Pro Arg Glu Ala Pro Arg Ala Val Gln Asn Pro Pro Glu Gly Thr
            180                 185                 190
Ala Glu Asp Gln Lys Gly Gly Ala Ala Tyr Ile Asp Arg Asp Arg Lys
        195                 200                 205
Ile Leu Gln Leu Cys Gly Glu Leu Tyr Asp Leu Asp Ala Ser Ser Leu
    210                 215                 220
Gln Leu Lys Val Leu Gln Tyr Leu Gln Gln Glu Thr Arg Ala Ser Arg
225                 230                 235                 240
Cys Cys Leu Leu Leu Val Ser Glu Asp Asn Leu Gln Leu Ser Cys Lys
                245                 250                 255
Val Ile Gly Asp Lys Val Leu Gly Glu Glu Val Ser Phe Pro Leu Thr
            260                 265                 270
Gly Cys Leu Gly Gln Val Val Glu Asp Lys Lys Ser Ile Gln Leu Lys
        275                 280                 285
Asp Leu Thr Ser Glu Asp Val Gln Gln Leu Gln Ser Met Leu Gly Cys
    290                 295                 300
Glu Leu Gln Ala Met Leu Cys Val Pro Val Ile Ser Arg Ala Thr Asp
305                 310                 315                 320
Gln Val Val Ala Leu Ala Cys Ala Phe Asn Lys Leu Glu Gly Asp Leu
                325                 330                 335
Phe Thr Asp Glu Asp Glu His Val Ile Gln His Cys Phe His Tyr Thr
            340                 345                 350
Ser Thr Val Leu Thr Ser Thr Leu Ala Phe Gln Lys Glu Gln Lys Leu
        355                 360                 365
Lys Cys Glu Cys Gln Ala Leu Leu Gln Val Ala Lys Asn Leu Phe Thr
    370                 375                 380
His Leu Asp Asp Val Ser Val Leu Leu Gln Glu Ile Ile Thr Glu Ala
385                 390                 395                 400
Arg Asn Leu Ser Asn Ala Glu Ile Cys Ser Val Phe Leu Leu Asp Gln
                405                 410                 415
Asn Glu Leu Val Ala Lys Val Phe Asp Gly Gly Val Val Asp Asp Glu
            420                 425                 430
Ser Tyr Glu Ile Arg Ile Pro Ala Asp Gln Gly Ile Ala Gly His Val
        435                 440                 445
Ala Thr Thr Gly Gln Ile Leu Asn Ile Pro Asp Ala Tyr Ala His Pro
    450                 455                 460
Leu Phe Tyr Arg Gly Val Asp Asp Ser Thr Gly Phe Arg Thr Arg Asn
465                 470                 475                 480
Ile Leu Cys Phe Pro Ile Lys Asn Glu Asn Gln Glu Val Ile Gly Val
                485                 490                 495
Ala Glu Leu Val Asn Lys Ile Asn Gly Pro Trp Phe Ser Lys Phe Asp
            500                 505                 510
Glu Asp Leu Ala Thr Ala Phe Ser Ile Tyr Cys Gly Ile Ser Ile Ala
        515                 520                 525
His Ser Leu Leu Tyr Lys Lys Val Asn Glu Ala Gln Tyr Arg Ser His
    530                 535                 540
Leu Ala Asn Glu Met Met Met Tyr His Met Lys Val Ser Asp Asp Glu
```

-continued

```
545                 550                 555                 560

Tyr Thr Lys Leu Leu His Asp Gly Ile Gln P ro Val Ala Ala Ile Asp
                565                 570                 575

Ser Asn Phe Ala Ser Phe Thr Tyr Thr Pro A rg Ser Leu Pro Glu Asp
                580                 585                 590

Asp Thr Ser Met Ala Ile Leu Ser Met Leu G ln Asp Met Asn Phe Ile
                595                 600                 605

Asn Asn Tyr Lys Ile Asp Cys Pro Thr Leu A la Arg Phe Cys Leu Met
    610                 615                 620

Val Lys Lys Gly Tyr Arg Asp Pro Tyr H is Asn Trp Met His Ala
625                 630                 635                 640

Phe Ser Val Ser His Phe Cys Tyr Leu Leu T yr Lys Asn Leu Glu Leu
                645                 650                 655

Thr Asn Tyr Leu Glu Asp Ile Glu Ile Phe A la Leu Phe Ile Ser Cys
                660                 665                 670

Met Cys His Asp Leu Asp His Arg Gly Thr A sn Asn Ser Phe Gln Val
                675                 680                 685

Ala Ser Lys Ser Val Leu Ala Ala Leu Tyr S er Ser Glu Gly Ser Val
                690                 695                 700

Met Glu Arg His His Phe Ala Gln Ala Ile A la Ile Leu Asn Thr His
705                 710                 715                 720

Gly Cys Asn Ile Phe Asp His Phe Ser Arg L ys Asp Tyr Gln Arg Met
                725                 730                 735

Leu Asp Leu Met Arg Asp Ile Ile Leu Ala T hr Asp Leu Ala His His
                740                 745                 750

Leu Arg Ile Phe Lys Asp Leu Gln Lys Met A la Glu Val Gly Tyr Asp
                755                 760                 765

Arg Asn Asn Lys Gln His His Arg Leu Leu L eu Cys Leu Leu Met Thr
    770                 775                 780

Ser Cys Asp Leu Ser Asp Gln Thr Lys Gly T rp Lys Thr Thr Arg Lys
785                 790                 795                 800

Ile Ala Glu Leu Ile Tyr Lys Glu Phe Phe S er Gln Gly Asp Leu Glu
                805                 810                 815

Lys Ala Met Gly Asn Arg Pro Met Glu Met M et Asp Arg Glu Lys Ala
                820                 825                 830

Tyr Ile Pro Glu Leu Gln Ile Ser Phe Met G lu His Ile Ala Met Pro
                835                 840                 845

Ile Tyr Lys Leu Leu Gln Asp Leu Phe Pro L ys Ala Ala Glu Leu Tyr
    850                 855                 860

Glu Arg Val Ala Ser Asn Arg Glu His Trp T hr Lys Val Ser His Lys
865                 870                 875                 880

Phe Thr Ile Arg Gly Leu Pro Ser Asn Asn S er Leu Asp Phe Leu Asp
                885                 890                 895

Glu Glu Tyr Glu Val Pro Asp Leu Asp Gly T hr Arg Ala Pro Ile Asn
                900                 905                 910

Gly Cys Cys Ser Leu Asp Ala Glu
                915                 920

<210> SEQ ID NO 3
<211> LENGTH: 111282
<212> TYPE: DNA
<213> ORGANISM: Human
<220> FEATURE:
<221> NAME/KEY: misc_feature
<222> LOCATION: (1)...(111282)
```

-continued

<223> OTHER INFORMATION: n = A,T,C or G

<400> SEQUENCE: 3

| | | | | | |
|---|---|---|---|---|---|
| acgtggatga | acacccaccc | acacacagct | ctctaggaaa | attgctcccc t | tccctcctg | 60 |
| ctcctcctcc | accctgtcct | cccaccacca | cccacttcca | aatgctgaga c | caaagagat | 120 |
| gggctggacg | gtgcctctca | ccacttgtca | gcctgggacg | ccctcctccc t | ttgtgacta | 180 |
| gcatgccctc | ctcccctgc | ccgtctgcct | cccagctct | ctctgcctcc c | tgtcgccct | 240 |
| gccacctccc | tgcgttcctg | tgtatctgcc | ctccacacaa | gtcactctga g | gcctctctt | 300 |
| tgttactctt | gactctgaag | tggaaactgc | tcctcccagc | tctcctgaga g | gctcaggat | 360 |
| ggggacctga | cctcataggg | ctgatggagg | cataggaca | agtgaaaggg a | ccccaggtc | 420 |
| ccgaatctcc | tcagctcctg | tcaccttcag | tccctcctat | tgggttaggg g | agggctgtg | 480 |
| tgcctggcac | catggagacc | agtgtcatgg | caacacagtt | cggtgggca c | agcttcctc | 540 |
| ctcctgggt | gtgggtcca | taagaggagg | tgccgaggag | gtgggccttg t | gctggtgcc | 600 |
| caccatggct | gcctccagct | caccattccc | aggacagccc | accccatcc c | cccagccaa | 660 |
| ctttgcttgc | cactgcagct | tccagtgcca | caagtcactg | atcccatttg g | gaaatcctc | 720 |
| tctcaaacac | cagctccaga | gctgggcgcc | agagagggca | ggggcttgcc c | aggtcaca | 780 |
| cagcaagtct | ggccaagctc | ctgactctca | gacctgtttt | ctcctccggt c | tcccacctt | 840 |
| ccacccagaa | aggggactgg | ggcagaggg | gtcagtccaa | cctcagttcc c | accacgatc | 900 |
| ttcagccagc | ccttagagtt | ggcagtggga | gtgaagatgc | aagtgatagt g | ccgagaaac | 960 |
| catcatgggg | cgcccaccac | ctgctgtgcc | aaggctttgc | atgtgtcatc c | cattttatt | 1020 |
| ccaagaccca | ggaggaagat | gactggtaag | tggagtagct | gggacaggaa c | acaggtccc | 1080 |
| tctcagatgg | ggcaggtgag | tcaaggctcg | tgtgtattgc | tgtctccatc a | ggcgctctt | 1140 |
| ttaaaagaat | ggcaaagctt | ttaatcccat | ctttattacc | ggtaagagtg t | aggggagg | 1200 |
| atctggggca | tagcctgggt | ctggccttag | ggtttctaga | aaccagggga t | attttctca | 1260 |
| agaagataga | gaatagagct | ttcctagtgt | ggttagacct | agggaagacc t | tccttgcag | 1320 |
| tgcagcaatg | cagaccgact | tccaatccct | aggtcaagct | ggagtctagg g | acagagggg | 1380 |
| aggagacccc | tgcctcctgt | gcccagcctc | aacttgtctc | ctgaccttca t | ggagtcacg | 1440 |
| ttgcagctgc | ctccctcctg | gcttatgtaa | taattcaaat | atagcagctg c | ctttatccc | 1500 |
| actgagtcac | acccccctgca | tccccctca | ggtgcgggga | gttatggggg a | gaggtggt | 1560 |
| tcagggctga | gtgggaggtt | cggggcctcc | tggcaaggaa | gatccctagt g | tgctggatt | 1620 |
| ggagggtggt | ggtggtgagg | gggctggtgc | tgaggcccca | agaagagcag a | gccttcgcc | 1680 |
| agaatatgaa | gccacagggg | ccacttctgc | cctgacccat | ccctgctgga a | ttccacatt | 1740 |
| cctgggggcc | ctcccagag | tcacaagcta | tatgtacagc | cttctcttgt g | gctgctgt | 1800 |
| ctcagttgga | ggaggaagga | gaggtggaag | agtatgaaga | gggggaagta g | tccggtggg | 1860 |
| gcaatggcca | ccgtctttgg | tcctaggctc | agcctcgccc | ttcactcact g | gttacctg | 1920 |
| ggcacccctc | tgacctcagt | tttcccatct | gcacagtgaa | ggattagatt a | actggctct | 1980 |
| agcgtctcat | tctctccgat | ttataaccct | ggagatgatc | tcaacctgag g | ctgaaggca | 2040 |
| cttccgagtg | tctggcccag | ccgcgttcca | ggctgacttc | cctccctctt t | tctctgcca | 2100 |
| tccctcctag | accaatgcag | ccaccccac | ccacaagaca | aaagaggcag g | agagggccc | 2160 |
| tggactcagc | tggggctggg | cggcttctcc | cttccctgaa | ctcgccatct g | ttccagccc | 2220 |
| cccagccccc | tgcctagcag | ccatgggtag | gtcactgccc | tcacctgggg t | caccccttc | 2280 |

```
ctccccggag agctctgaca gatatcctgg aacctgaagt ggatccttca t gccccatcc    2340 tgaatcccaa agccaccttc ctgaggtgtt gaagaagctg ctccaccttg g aactactat    2400 aggggctgtg gtggccttc attcctttat cagcaaaagc ttttgtcact t gtgtggtgg    2460 gggacatgct tagtgtgaga atgcagagac ccatgccagg ccctacccaa g gacatggtg    2520 ctccttcagc cattgtcatc agagccacag aggggagctt cctggcagag a aggagtggg    2580 gagaagctgt ggaatggctc cttgagctcc ccactccacc ccttcccat g cctgggctc    2640 ccattgcaaa gacccagatg tgggcttatc ctgtccccca gccagaggga g tcacccagg    2700 ggtgttcagg ccaacccttt gtgaaatcca tgttccacca gttaccagcc t ttctccgga    2760 gagctgaggg ctgtctcaca ctgggtagtc tcagcctgcc ctggggttgg g ggggtgctc    2820 acagagcagt aagcgtcact gcctgcatcc ccacacacct gcattatctt g tctgcaaga    2880 cacgtgtgcc cctgagctga gctctgttgt gcaccacccg atttccgtcg g cctcctttc    2940 tgactttct ccatcaacat ttcctgcttg ggcctgttgc gggctgccca a aggctgtgg    3000 actggggccg aggtacatag gactttggct tgtcttttga gctaacagga t cctgtagaa    3060 gaaatgagat gagcctgaga gggggtcggg gggtgagaca ttagggaagg g agaggccac    3120 caagggtctc tagcccagaa tccaatgccc cttcctgcct acctgtcctt g tgggtggga    3180 ggcagggtgt gtgctgactg gcccagcaat ggtgggctag gatttgggat a ggcagagaa    3240 aaggaagagg aggggggaagt cggcctggga ggagaaaaac tgtacaaagt c gaggaggag    3300 agaaccagag tgtgcttagg gaccagacct ggccccacct ggagcagagg a tggtgaggt    3360 cagtcaggc tggatcacaa gggacctcaa atgccaggct gaggagcttg g cctttatcc    3420 tgagggcact ggggagccct gcaaaggtt tgagagggaa ttccattacc a gatagatgt    3480 ctttggaagc cgcctctagg tgcaaggagg aggtggagta gagaggttga c ctgggtaa    3540 gggttggagc atgaccaggg gaggggggaag gaagcagggg gtggggatgg a gggagtgga    3600 tggatctaag agaatctact gtcctttgga acaaacgata caggaagtgt a ggagaggga    3660 tggggcaagg cgactttgaa gtgtccagct cagagattgg aggtttgctg a tgcctttgg    3720 gaggccaagg caggcagatc acgaggtcag gagttgaaga ccagcctggc c aatatggtg    3780 aaaccccgtc tctactaaaa atacaaaaat tagccgggcg tggtgcgggt g cctgtagtc    3840 ccagctactt aggaggctga ggcaggagaa ttgcttgaac ccgggaggca g aggttgcag    3900 tgagcccaga tcgcaccact gcactcccca ctccaccct tccccatgcc t gggtgacag    3960 agcgagactc cgtctcaaaa acaaacaaa acccaaaaa acaaaaaact a gaagtttg    4020 ctgatgcctt taatagtaac aaaaggtgta ttggatgttc aatatttgag g gacctacgg    4080 gttgttccca gaggagatgt ccaagagaca gcctggacac ctggagctcc a gggagaggg    4140 atgggcagca ggggacaccc ggagttgttg gtatgctggg agaaggctgc a tgctccgtg    4200 ggagtagggt ggagaatgag gagagacagg gccgccgtcc tgcaaggagc a tccatattg    4260 aggggggcgaa gatagggtgc accagtgagg gagacagagg aggggccgtc t ggaaggtgg    4320 gagggaaaca gccgcgcagg acgggcggg ggcgggcgct gagaagaagc c gccttcttc    4380 ggcaaagagg tagctgaagc ctgtggagcc tgcagtcctc tcaaggctat g ggggcagcg    4440 cggaggccgg attccagaac tgaatcttcc catcgctttg ggcagccacc c tacctccca    4500 ggagcatcct tcctgccatc ccacctccag ttccccagct aacaaaaaac g gtgtttctt    4560 gactcccggc agggcggcgg ggcgggcagg tcttgtgaac acggctcgca g ggttcagca    4620
```

```
ccctggagag aggcctgtgg ccggggcggg gcctgcggcg ggggtagggg c gcgcagtca   4680 gagcagtcgg gcctttggct ccgtctggga gcggtcttgc aggcaggcaa t tggtggagg   4740 agggaaaaac aatcttggat tttctccagc tctctcccct ttatgcacct c ccccatccc   4800 ggcactggcc tacaggagcc cctatcccag catttgggc tattactctc c tgacgactt   4860 caggaaatga gatgggagga gaggggcaac tatttactgg gaacttttca g acattccca   4920 aaacctcaca acctttttgag cttggaattc gtgacccccat atttcagatg a ggaaactaa   4980 attgaagttc aggaaggtga aataccttgc ctaggcactt gcagagctg g gatttgaat   5040 tccacctgcc gggctctaag tcctgagtgc ccattagccc ttctgagtcc t gaatcttgc   5100 agtttgttcc tgcagactct ccacttctgg gtggctgtgg agtctggtgt g gcagtggga   5160 tggggaggag accttccctt ccacctgctt gcttgagtgt attcccagga g atttctgaa   5220 gatgaggcca ccaccattgt ttctgaagtg ggagggcaga aaggaggctg a gggccaggt   5280 gagacctcgt cacacctgca cccatgcatg cccaggagga accctccttt g aactcttct   5340 gactcagctt cttgctgcca ggttcctccg accagtgagc aggttcccag g acatgaagg   5400 ggagctgtga gggagcagga cgccatggtc cagggctgca gcttcctgag c ccagagaat   5460 gccttcctag ctgtcaggaa tggagcagcg aggccccagt gataggtgag g tggagaagc   5520 aagacatgag ttctgggctg gctcagctgc tttacaacca gcctgggcct c gttcccttt   5580 gagaaaatgg tttgcccaga gttcagagat ctaaaattct atgatgcctt c tggggccac   5640 agtgggaaac aaagactcct catatttct ttcctgacac ttcccaggcc a caagacaac   5700 tgctttctgc agcacccagc ctgggcaggc catctacaca agctcagtca t ttctgacct   5760 tgcccccctcc accgtgcacc cccatgttct tcaacatggg tcaggtttct a ttcagcctc   5820 agggacttct ctgcttgaag cctgttgtgt ggcggggagg tattctcccc a cagctcaga   5880 gagatggggt tgctgtggag ggtttgctgt agctcctcta ccctggaata t accctcttc   5940 tgccttaaaa gacccaactt ggaccctctc ttccagaaat gcttgctaac c gccccccca   6000 ccacccaaac taggtcaggg gtccctctgg gcttcacaga ccctgtgctt c tttctgtca   6060 cagcctgcaa gtctcccctc cccactcccc agcccgagtg cttctctgag a caagggata   6120 gtgtgagcca tgagctcagc cactggtagg ccaatgaata agtaagttaa t ggtgaagcc   6180 aggatccaaa tccccatttc ctgcctcaag gtgtggagct gtttctcctg c atacaatag   6240 tagctctgct gtgacaactc tctatctgtc ctagggccta aaatgcctct a tttcactag   6300 gttatagctt tatcctaggg agtcctcttt ggaagcaggg tgggggtgca a caggccttc   6360 ccccatgcct gtagtctgtg agcagcgaag gccatgtggg gcaggctgtg g cctaggtct   6420 ccacagatcc tggtagaagt ccatgctcac gcatcagctc caagtcccag c taaaccaag   6480 ccaccaagag gtgggccctg tgacaaggct ctgagtccaa aggccatcag t aaagccccc   6540 taagtcttcc gtgacccag ctccaggctg ggatgcacgc taggagatga t acacaccgg   6600 gtgagggagc ccagaggaga gggcagctag ctgtgcatgg aggcctgatc t ctcagactt   6660 gagggcacaa gcgtgtcccc tcatcctgaa ggcttctgcg atggggcagc a gagggtctg   6720 ggtctgctgc ccctcaagtc cccagcccca tcctagccca tgaggattgt a aatccctcg   6780 tcctctcccc tctctcctct gtcagccact ccctttccc cctacccac t ctctttcta   6840 tttctgcctc tgattttttt tccttttctg cctttgttcc tctgtgtgtg t gtttctcta   6900 tgcctctctg atctctttgt acttccatct tgatctcgct aaggctctga t ccctctctc   6960 ctctcccctct tcatgtgtta ctgtccccct tcctgtctct gtttatctct c agtctctct   7020
```

-continued

```
gtctgtgagt cttttttcct ctctcccagt cagactctct ctctacccct c cctctctcc      7080
ctctctccct ctctgtctgg gcctctctct gttcctcctc cctcctccct c ccccttctg      7140
cattatcaga cctgctccaa cctcctccca gagccagccg agcagcagag g cagtggcag      7200
cgggagaggc gggagcagcg gggcagcaga gctggattgg ggtgttgagt c caggctgag      7260
taggggggcag cccactgctc ttggtccctg tgcctgctgg gggtgccctg c cctgaactc      7320
caggcagcgg ggacagggcg aggtgccacc ttagtctggc tggggaggcg g acgatgagg      7380
agtgatgggg caggcatgcg gccactccat cctctgcagg agccagcagt a cccggcagc      7440
gcgaccggct gagccgtgag tatagtgagg ggctggggtg gtgagcggct g tgagaggtg      7500
ccacagacag ggtcctggga gtccctccaa ggagctgggg ctggcatgga g ctgagccac      7560
gtggaaggat cgatcctgtt cctgggcacc cctcctcccc gcgttgccag a ctgcagcct      7620
ggggtggggg caggttacct ctgagcagaa tgaggtgtgt taacgtcaac c tagtaggtg      7680
atgaggctgg ggtcccatgg aagggctgc tggttggagg agggggctgat a atgaacctg      7740
aaccgcttct tcaagggctg aggggtgtatg tggggagggg gaggtctgcc a agtagttgg      7800
gaggagctct cggggctgca ataggctggt tcaggaccct ggagagggag a gtgtcttgg      7860
cccaccaagg ctatgtgtgt gtgaaggagg tggggagggg gaaagatgga g aaaatatga      7920
ataagagtgg ccctggagca agagagggtt agaggtaacc accttccatg g aattgggaa      7980
ttggggttca gggacaccac tttatgaaac tttaccccaa agcgtctgtc c caggatagg      8040
gttctacgga gccagatgga atatggtgcc agcctcgtgt gtgtccacgt g caggggggt      8100
gcatgtgcaa gtgagtgggg ggcgccgtgg cgacacccct ctactaaggg c tgccgaggt      8160
ggtaggcagg gtgtgtgtgt gtgtgtgtgt gtgtgtgtgt atacatgtgg a atgtaaggg      8220
acatgttggg tgtagagggg cctgtagagc tctagggtcc ttggtggttg g atgtaaagc      8280
agcctgtcag agtttgtgat catccctgtg tgagtgagag tttattcgca t gtgtctgag      8340
tgtgagtgca ggttggtctg catatgtatg taggtgtgtc tattaggttg a gtttgtata      8400
ttatgtgtgt tgtgtctgca aaatagagtg aatcagtgtg cattttttat c tgttccatg      8460
tgcatttatg tgtgtgtatt tgttagtgtg tgaataatag cattgctgtg t gtggaggtg      8520
gatgtggctg tgtgcgtata agtattctgg tgtgggtgtg tgatcatggt g ctagtgtgt      8580
atatcggtgc ttctgtggct ggtgtgtgtg tgtatctata tgtgtgtatt c atctgagtg      8640
tgtgtgggtg gctgttttcct tcccctggca attgaggata cagctgggac a ccatggccc      8700
actgatgcag ggcaggggagg ggctgaatgt atgaccgcct ctttgaactc a ggacaattc      8760
attctacacc ctgtgggaaa gatgcagaaa agaaataggc aataatgact c tgccctctg      8820
gggcttccta agcttcttag acataaaata gcttgagaat aattaagcag t agagatcaa      8880
cgtcatgcta acaggtgggg gtggggtggg aactgcataa gcaaaggccc t gggctgggc      8940
atgtcctgga gcagtgaaga cactgtatag agtggggggc aggcaggacc c acattcaat      9000
agaactttaa gatccaggac tcttaggctt tatccagaga gccctgggga g cccagaaag      9060
gttttatata gcggagagac atgatcagat ttgggttcta gaaacctgcc c tgggccagg      9120
catggtggct catgcctgta atcccatcac tttgggaggc agaagcaggt g gatcacttg      9180
aggccaggag tttgagacga gactggccaa catggtgaaa cccagtgtct a ttagaaata      9240
caataaaatt agctgggtgt ggtggcacac gcctgtagtc ccagctactt a gaaggctga      9300
ggcatgagaa tatgagaatc gcttgaactt gggaggtgga ggttgcagtg a gctgagatt      9360
```

|  |  |  |  |  |
|---|---|---|---|---|
| gccttactgc | actttagcct | ggggtgaca | aagtgagact | ctgtctcaaa a aaagaaaaa 9420 |
| aaaagaaga | agaaaaataa | agaaacctgc | ctcggtggca | ttgtctgggt t gaactggaa 9480 |
| gagagaggtg | gggccaggag | gctagagtgg | aggccaagcc | aatacagggg t cagtgagtt 9540 |
| ctggagcttt | ttgagaactt | gggaaaggct | ggatagatga | aacagggaa g ggaatgtct 9600 |
| aggtggctca | ggcttggact | ggggtcaggg | gtgtagtgca | gacatctcag t aagtcagga 9660 |
| tctcatgagg | gaaaaggctc | atggaaggct | caggaaagct | gggcgtgggt g ggctgaggt 9720 |
| agtgggagag | atctttgtag | tgtttctagc | taggatgcag | agggtcagag a tcatggagc 9780 |
| catctcttgc | cagacaggga | aactgagact | atggcttcat | cactatcctt t ggctgcaag 9840 |
| gctgggctc | aacctcttca | tcagacctga | ccctcaatat | cattctcctt c aggccctgc 9900 |
| ccggaacctc | ttggttgctg | agcttggtca | gctcagtgag | ggttaattgt c tttatgctc 9960 |
| cctgcacccc | caccccccgc | agtcattccc | cctgcccacc | aagcagctcc t gccactctt 10020 |
| cctgcttccc | actccagcct | cctgtcccca | gggactgctg | atggcttggc t gggatctag 10080 |
| ccaaatggtg | gggggtgggg | gcgggggtgg | ggggaagagc | tcccagcagt c ctttacccc 10140 |
| ttggtcttaa | tggactggga | gtctcaccct | cagccatgct | gctgtcaggc c aggcctgcg 10200 |
| ctccccgggc | ttctgctgct | tgggcctatg | aaatctcccg | actcagcatg a ttccattgc 10260 |
| tgcattcatt | cattcaacca | ctcaacagga | acttctcagt | agctgcttgg t gcccacttg 10320 |
| gcttgtcacc | ggggacacag | agcagacact | gactgagtcc | ctgttctcag g gagtgccca 10380 |
| gtctgatgaa | ggagaaagaa | atggaaagct | gcaaccctac | agggtgagca g tgctgtgta 10440 |
| ggaggtgggg | ggcccacagc | aagcctgggc | ttcagaggaa | gagacatttg a gccggacct 10500 |
| tgaaggatgg | gtaggaatca | cccaggcagg | gaagagcaga | gggaacagtt t gtgaaggtg 10560 |
| ggtaggaaag | gcacagggct | aggcacctga | ctcagtgcag | cctctgggtg g gagaagaca 10620 |
| gtaagggcgt | ttgggtcatt | ttctagcagt | tgttttagta | ctctctacaa c ttgccctgc 10680 |
| agatctatcc | agcctgctgt | ttgcatacc | ccggacatag | gatgttcatc t cttccctcc 10740 |
| tgggcagccc | ttcccttgtg | gtggttatat | ctgtcctggg | tcttctccgc a gggcccagc 10800 |
| aactccaggc | tacccagcct | ggccttatgt | cctttctccg | tcctgtgtca c tgtcccctg 10860 |
| aagtagggcc | aggctgggc | acaatgatcc | aggagtggca | agaacacatc t aggcagaga 10920 |
| gtgggagaaa | tgcgcagcct | ttattaacaa | aaatctgaga | tgggtgcagg c cctgactcc 10980 |
| tctccaaaaa | taatgataaa | gaagcaggca | tggccaaata | agggagtgag g acagacagc 11040 |
| aggaagaact | tcctaccaat | gcagaagggc | tgtgagtctc | ttggttttat g agagtgggc 11100 |
| tgtacgtgtg | aaagggaggg | tctcagagga | caagaggggg | aattggaggc a gaggcactg 11160 |
| tcagcctctg | actctcccat | aggtgagtga | gtgaagtcat | ccagggagag g gaacagagg 11220 |
| agggagatca | ggactcatca | ttcattcatt | cagcagccgt | tcactggccc t accaaacat 11280 |
| gacacccctg | ggggcagatg | gacagagcca | gtgaccacgt | ggatggaagc t ccgagtctt 11340 |
| tcctacctgt | gttaatgtcg | caggaaggta | tttaggagga | gggccattg g ggctggcct 11400 |
| tataaggaag | agccacttca | ggctgagttg | agggacagca | ctaggaagat g gaagagcat 11460 |
| ttgcaaaggc | ctcaaggtaa | gggcaagcag | gattttgttc | acttagcact a taggagttc 11520 |
| agagtggcct | aggcatgaag | tgccaggctg | ggggaagcc | ctgggccgtg g tggagcagg 11580 |
| agaggagtgg | ggaattgagc | ctagactgta | ggaagcactt | tcttccgtga a ggtgtctcc 11640 |
| aacaggcttg | atgtgtaggc | attattgtaa | gtttgcaact | tcttggtctc t cctggtgct 11700 |
| cgtgaccaga | gcttgctgag | ggacccagcc | ttgcttgaga | aagggtgtt c agtgaacaa 11760 |

-continued

```
aagagaccct ggaaatgaga gagaagcagt ggctgaagaa tgtgggcccc t tccagaaag   11820 tggcgtgcaa acaaatacaa agcaatatgc aaatcagctg ctagggcttg g gcagctttg   11880 gttggaagaa atgagccatc accccttatt atgccggcct cctacccctc t gccccagc   11940 ctccaggaca gccggaacag ccttgtctgc tccttggagc gccccagctt t tctgagaca   12000 caggattgtg gcctccaggg tggtggccgt gggctccctg tcagcaccct c gtcctcctg   12060 ggaagtcgat atatttagta acagaaatgt tttcacacat ttatctccta t tgttcagct   12120 gcttgctccc tgggaaaggc caggtcccca gtgatgtgac ccacttcttg a agtccctga   12180 agtcacccct ctcactgccc ccccaccccg aaaaacagga ggcaactggg g cttggtgca   12240 gcagaacaga tttgagtcaa atatctggga ggacttccca acagtgtggt t gctgagatg   12300 tgtggaccct ggatttctgg gctttcattc tttggatggt tgccttgggc g cagaggagg   12360 ctttgaagat agagcagaga aggtggcagg caggcttatg ctcaaatttc a gcatactga   12420 aagatgtact gttactctgt agctgtgtgg tcctgggcaa gttacttaac t tctctgaac   12480 cttgtgtgaa tagtggggtg gagataatta cctttcttg gcaggatgat t ctgaagaat   12540 ctggaagtgc agagcttagc ccctggcatg cggcaggtgc tcacaaaggt t agctactgt   12600 cattatgaac cacccacgat cagccacact ttcagaaaga tttagcgggg c ctggagagg   12660 gagagaccag agctaggagc tcagggctgt catcgtgtgg gagggaccag g aggcctgaa   12720 acagagctgt ggttgtggct acggtgagaa gcacaaagct ctgtgggagg g accgaggtt   12780 tctcagagaa gtgtggccac ctcattaagt tgttctgact ggtctgagac c aatccccag   12840 ataatacaat ggaagaaagg gcttggtgaa gaaggggtta agtctgtggc c acacccatg   12900 cagtctgtga gccattctgg gagctgtagt ctgttgtgaa tttgcagtaa g catagtttg   12960 tactgcctct tttgatccaa atccacaccc tgctgccaag gctggccgag g gccggccct   13020 ggtgggtgct gggctgtgtg gagcccaaag gtgaagcagc atcgacctct t ccctcaggg   13080 accccctggc ttgctatgtg ttgggggggtg caggtaggag cagggataga a gtattaagc   13140 cataattacg acttctcaca tgttcacaca gaagtttaca gcttcctgag c actgtttcc   13200 acacctgtga tctcatttaa tcctcaccac aaacccaaga gactgctgtt t tctggatga   13260 agaaacagag gatccaggag gggaaatcgc ttgcccacag gtattcagcc a gtggagcca   13320 gacctggggc acaaatctgt ctgcttccag agctcctgct ctttccatac a ttactgttc   13380 cagatggcag acaggcaaga tgtggacaac taaagttgga tgtgagacat c tcggcagag   13440 gaacagctga gcagagagct gctgattcca ggctgagagt ttggactttg t gttgtggcc   13500 caccaggatc cacccaaggg ttttctgatt agagctgagc tttgagagaa t tggtcttgc   13560 agcttaggct gaatggattg aactggagaa accaaagtca gactgaggct t ctaaatccc   13620 atccttggtg cacccagcac tttgctgctg tccctcctcc atgcttcttc t cagtttctt   13680 ccttctcctc tccttcatct tcttccctca ccctttttt tttttttttt a atagagaca   13740 gtgtcttgct ggctggagta cagtggtgcc ataatagctc actgcagcct c aaattcctg   13800 ggctgaagct atcctcctgc ctgggcctcc caaagtgctg ggattacagg t gtgagccac   13860 tgcacccagc tcatcttcct cttctctcc tactcctctc tgcctcaggc t gaggagtga   13920 tgacttttat accatagagc tgtgctgtaa tatcacatgt ctccagaagg g ggtgctgtc   13980 acatacagtc cattccagcc tgaatcttcg ttgtgtttga agggccagta g aagtgttgg   14040 acaagtggca gagatgaagg atggagagaa ggatagccca ttgttctcca c ctccattga   14100
```

```
gcccaggaca tgagggccct gctgaaatgg cactgggagg aatgaaggct g aggagaggt    14160 tggaccccaa ccagaaggga cagacatact gagttaagcc agaggaaatt t tctcctcat    14220 ggttctggga caggctaaga tttgaaatg catctagaat gacattgcag t tggggtctg     14280 ggtttctttt gggtcatgac ttgcttgata ctgaggtgct ggggatattg c ttgtgtctc    14340 agtgtgtgta tgtgtacctg aatgtgagct tccagttgtg catatgtgta t gctgatctg    14400 agagggtgag aatgtgtggg tcagtgttcg tataaaagtg tgaacatact c acatgtgtg    14460 agcatgtgag tgtcctttt tttagtttag ttttgagaca gggtctcaca c tctcaccca    14520 gactggagtg cagtggcgtg atctcggctc accgcaacct ccgcatccca g gctcaagct    14580 attctcctgc ctcagcctcc tgagtagctg ggactacagg catgcaccac c acacctgca    14640 taatttttgt attttagta gagatggggt ttcaccatgt tggccaggct g gtcttgaac    14700 tcctgacctc aaatgatcca cccaccttgg cctcccaaag tactgggatt a caggcatga    14760 gccactgcac ccggctgtga ctgtccatct ttatgtctga ttttggtaaa c agttatatg    14820 catgtgactg tggcttgtgt gtgtgtacat gtatgtagag tgccatatac a tatgttcta    14880 gtgaaaccgt atgtgtgttc cctgtgtata cagatgcctg tgtctcaatg t gagcacagg    14940 gatgagggga tatgtgtgtg tgaaggccca gacacctgct gtgctaacct t taaggccgc    15000 gcctaatgtc tggctattca atactttttc tcctgggtcg cgctttcctg t aggtagaga    15060 cccttgaagg gctgggcttc cttcagggga ctctgggcca gagtcaggct t tgtgttcag    15120 tctcaggttg ggcagccag ggtcctagtc tatcggattg gcagctaga c atggctggg    15180 aagtgtctag gttccattct ccccaggaac tcttaatggt cacacttaaa g agtttcagg    15240 gactcccagc acggtcctct tgtactgatg caactactga agttcagaga g gtgcagtga    15300 ttaacccaag gtcacccagc aggacccagg atgagatgat agggcttgca g cagagaggg    15360 gagtgtctga cctggaaggc tgccctccct ccagcccta gcagtggg g gagctcaga    15420 ggagagccaa gtctgtggtg tgaagccacc tcctgcacct ggctatttcc a tgcctcctg    15480 ggcctcagag gctgccttg aagttttac cagagcttct gcatgctgtg a gattcctcc    15540 tggggacgtg tgaagtcgac tgttccatgg agcatggaga ctcgatggag a ggagcccag    15600 tggtgaagtg aggccagagg aggggcttcc tctggaagcc tcaatttctt c tttgcagta    15660 gttgctttt ttttcgtgtt tttttttgtt gttgttttt aggttttcac c gttctaaca    15720 ttcaaggctt tctctgttat ctctctttga gctcttagta ctgagacagt g ctggggttt    15780 ggggcagtcc tggaggccta tctgggctca aagtgagggt ggcagggcag t cccttaggg    15840 aaagggctgc gtgggagaca gggatgagct tcctgcccat agtggggagg c atgagcagg    15900 ggctggacag cctggttagc aaggctgtat acaaggtacc taccctagtg a ggaagttgg    15960 ttgcagatta tcttgagtcc cttcaagctg tagctgccat gggggccag a gaagaacgt    16020 gcctcagctc tcttgggcct gggaggatt gagtccacag agtgctcctg t gtcctggg    16080 cagtggaagg tgcaaggtta gactgtgcac ctggaagcag agagatccca t tccctggag    16140 aactgaaggg aaatttgtct tcctggaggt ttggggctgg aggcagggc t ggatgggag    16200 gacactctgg ggtggagtgg gggtgggatg ggaggactg gcaagtccg a ggcggctct    16260 gctgttcagc acccgcagga aggagcaggg aggcatatcc tgaatcatgc a gggctctag    16320 ggtgggaggc ccatggttgt ggggctcaaa catgggctct ggttgggca g aggagaggc    16380 ttcctggggt tggggtctgg gcaggaattg gggtagaaaa ggagagaagc a gcaattggg    16440 taccacctcc ttcccaggtc aggtaattcg gagttgtctt aaaactctca g tgggccagg    16500
```

```
catagtggct cgcgcctgta acccaagcac tttgggaggc tgaggtgggt g gatcacctg    16560 aggttgggag ttcaagacca gcctggccaa cctggagaaa ctctgtcttt a ctaaaaata    16620 cagaattagc tgggcgtggt ggtggatgcc tgtaatccca gctactcggg g ggctgaggc    16680 aggagaattg cttgaaccca ggaggcgagg ttgcagtga gcctagattg t gccattgca    16740 ttccagccta ggcaacaaga gcaaaactct gcctcaaaca aagaaacaaa c aaaacctct    16800 cagtgagggg ggatctgggg tccagatgga gagaactaat gtttacagag t gacctttaa    16860 gttttaaaaa tgattattta aggaggcgat taaacaaatc gcctccttaa a taatccttc    16920 cagggaggcc gggcacggtg gctcacacct gtaatcccag tactttggga g gctgaggtg    16980 ggcggatcac gaggtcnnnn nnnnnnnnnn nnnnnnnnnn nnnnnnnnnn n nnnnnnnnn    17040 nnnnnnggaa aagagatatt agntggagta ttagtaagag ataaaagaga a aaacaacga    17100 aaaaaaagca gagtgataga agggaaatag aataaggaag aatagattga t agtagcggc    17160 ggacgaagaa aaagacgaaa aacagcgagt acggaggcgg gggcggtata a tgagaaaat    17220 agaagatgaa cgcgatacga aggatgaggg cggagggaaa gtacaatggt g gtggggtat    17280 ggaggcgaga gtgaaaggga ggtaaatgac gcacaaaaac aaaagacgga a ggggaacag    17340 gaggaggggg tggtaggggg gnatcgcctc cttaaataat ccttccaggg a ggcccgggca    17400 cggtggctca cacctgtaat cccagtactt tgggaggctg aggtgggcgg a tcacgaggt    17460 caggagatcg agaccatcct ggctaacacg gtgaaacccc gtctctacta a aaatacaaa    17520 aaattaaccg ggcgtggtgg ggggcgcctg tagtcccagc tactcgggag g ctgaggcag    17580 gataatggca tgaactcagg aggcggagct tgcagtgagc cgagattgtg c cactgcact    17640 ccaagcctga gggacagagc aagactccgt ctcaaaaaaa aaaaaaaaaa a aaaaaaat    17700 ccttcaaggg gctagcccta ttttgtagag gggaaacaga tgacaaactt a aatggttta    17760 actgaagaca gttagtgaag caagtattat ggagatgggg aaggcttaag g gaaccagca    17820 ggacatgtca agttactcag gactggcatc caagggccca ggggcgttgg c agaggggg    17880 ccgaggagag tgcccagct ccatgagcca gagccctgga gatgggctg c cctgcagga    17940 gctgtggctg cagccactgc ttgtcgaagg aggcaggtgg gtgaggggt g aatacccac    18000 catgagcctg catgcttctc acccttcgct ctcctgccag taccctgacc c tcactggca    18060 gaatttctct ggatgccagg gggcaaggga gccctggatg aagctgccac t tagaagtcg    18120 gcctctgggg cacacaaccc agcagcaaaa gttagagatt ggatgtggag g acaaagag    18180 atgatgggaa accgaagaac agagagggca tggacttgcc caaggtcaca c agcctgttg    18240 atatcagaat tggagtcaga agccaggctc tgcctctgaa cactcacttt t ttgtttgtt    18300 tggttttctt ttttttcttt ctttttttt tttttgaga cagtcttgct c tgtcgccca    18360 ggctggagtg cagtggtgcg atcttgtctc actgcaacct ccacctcctg g gttcaagtg    18420 attgtcctgc ctcagcctcc caagtagctg ggatcacagg cacctgccag c atgcccggc    18480 taattttgt acttttggta gagacggggt ttcaccatat tggccaggct g gtctcgaac    18540 tcctgccctc aggtgatctg cccgccttga cctcccaaag tgctgggatt a caggcgtga    18600 gccactgcac ctggcctgaa cactcacttt gtcacattca ctgaggtctc c tgagtggac    18660 tcatatgcgc attatctact ctctggctga gagctgcttc ctgccgtgat c accgcgctc    18720 tgtatctggg cagcacaggg gctgctgaag aatgtcattc tcagaacgca g tgtgccctg    18780 gagcccccca agccacctgt tcattcatcc caactggcct tgagggtgcc c tggtgtgcc    18840
```

-continued

```
ctgcctgtgc ttgtcaccct ggccatggag atggacccaa aagcccttgc t ctccgcttc      18900 attagagaca ggcacaccca gacgcaggca atcaattttg tcgggtgagt g ctgggaccg      18960 ctgatgagga cccttcctga ggaggcgatg ctgggtctta gccttaaaga a caactgaga      19020 gttttccagg tggaggagaa aaggaagggt attccaggca aaaatcccca t aagagcaaa      19080 ggtgtgagca gcaagaaatc aagggtggca ggttcagggc tcctgggctg g aggaagggc      19140 ctggcggtgg agaggaaggg agtgaaggcc cagctcacaa agggaagcag a ggaaagttt      19200 aagcagggtc aggccatggt tagctttggg gttaggaagc tccaaatgat g ggtgaagta      19260 gggggggctag acccaggtga gaggcagtat tgcggttggc caaggacacg t gagttgcat      19320 aaatgggcca gaggaggggt gacagccgct acttcccggc tcacctgcct g agctaaggc      19380 cctagttcct cagtgtctgc ccaccaatgc aggtgtgtgg cagctctaga c cctcctcta      19440 gggacatccc tccctgcctc atgctgccta tggctttcac tctctggagc a ctcatccat      19500 ggcacccata agccacccc tcagacaatg gcccctaaag caaaactgtg t caccgttgc      19560 atatctcttg ataacactct gacccctcca ctgccaaatc tgataaaaga c ctcccttg      19620 aagaccttcc tcctggagtc ggatctcagt ccttcttgct gtccagagcc t gggccttgg      19680 gcctccctgg gaggcgagtc agtgagggca gcccccttat ggtgctggga g ttgagggac      19740 cttggcccag ccaactcatc cctgttgtgt cagcctctct gggcctgggc a gccaactca      19800 ttttcagtgc taattagcat ctccccctgca gctttctgcc ccactctaag t gcttgacaa      19860 tcattaggtg ttactgtgtg caactggatc ccagctccgg cacctccctg c cccagcttc      19920 tcctccagac cccagctgcc tgagataagg gacctggcca caaacataca a cacaccgaa      19980 acccggacac aatctaggca tagggacttg aacaccaaca taaatataca a agaggaaaa      20040 acccaataac acagaagaac tccccatacc aggaagcaga ccatagcaca g acagagacc      20100 cacagtacac acacaacaca gacaccaaca gatgctgaaa agcagacaca g gatcattcc      20160 aaaagtgac ccagaaacga aaacagaaca aatgggaaca tcaatgcaca t gacacaggt      20220 atacacatct agatatgcaa cacaggtacg attcagcaca tgtgtggcgc a tcgcaggga      20280 agcacttgca cttgaagtat acacagatgc caagatagtc agagggagcc g cctgtggtt      20340 ccccacctgt gcagcgtctc tcgcctctgg gctgccgcac atgctgttgc c cggaattcc      20400 cttccccaag gccctcctct ttttacctgg ctaattcctg tcattcttca g atcttctag      20460 gaagacttct gcctccttga tagggggcctt tccatactcc ccagccttgg a gtgcttcct      20520 gccacatggc atcactgact gttttccaat gagtttctgt caagttttgg g atgaaggat      20580 tttgcctgtg ctcgttgagg tggtgactgt gggtgtgagt gggtgattag g gccaaaaaa      20640 acccccaaa aaactggaca gaggcaaatt tgggggaaa tgagttagga a tagctgtga      20700 ggagcccag ctactcaggg cctcagaaga tatttatttc tgtatttatt t atttattga      20760 gacagagtct tgctctgtca cccaggctgg agggcagtgg cgctatcctg g cccactgca      20820 acctccacct cccaggttca ggcgattctc cttcctcagc ctcccgagta g ctgggatta      20880 caggtgcgca ccaccatgcc tggctaattt ttctattttt agcagagacg g gtttcacc      20940 atgttggcca ggctggtctt caacttctga gctcaggtga tcctcctgcc t cggcctccc      21000 aaagtgctga gattacaggt gtgagccact gcacccgacc tcagaagaca t gaaaccca      21060 cagagaggac acagccagat gccctctgcc tcatttctc agaccctgcc t gatttctct      21120 tatgtttctt ctaggcttgc tccctgaccc agttccctcc ttcccagagc t ggccttgcc      21180 ccttgccacc tctcggagct cacacatact cactcacctt ctctgcttgg c tgtgcccta      21240
```

```
cccctacttc tacgtgcagt gaaatccttg ttattcaagg cctgaggtca g tgggcacat    21300 catccatgcc tggcgtccta acccgtgcca ctgagtatcg tgaagggagg t agtggaggg    21360 acgtgcttgg gagcacaagc cttgaggact gtctcttggt tcagatctct g ctcctctac   21420 ttcttagctg caggattgtg caagttctgc cacctttgtt ccctcatctg t agaaaggag   21480 aggataatag agcccacctc attagggcag ccatgaggat taaatgagac a cagtgtgta   21540 atgtacctgg ctccctctcc aggttgcgtg agagcaggga gaaagctaat g agatcaagg   21600 atgtgcaaat gcactcagaa ggtgcctagt gagtccttgc taactggcac t tagtgaaac   21660 aaacacctcc tgtgtgagca cctaatatgt gcctctgtag tgggctctgt g acccgcccc   21720 tccttagttt ctgcatggct gccagttctg cacagctgtt actgctgtgg g gcttagaa    21780 ggtgggggta tgactacttt ttctgaattt atttttaatt ttttacatct g ttttatgga   21840 ggcataattt acatacagta aaatcaccaa tttaaagtgt ataatgagtt t tgataaata   21900 tatatggtca taaccaccat gacaattaag aaaagaatat ttttatcctg g caaacttcc   21960 cttgtgccct ttgtagtcag tcccttttgag ggggacttct tataggagtg t gagaagtac  22020 tgggttttcc ttgggctgca aacctgggca catggagtgg gggtgcctcc a acatgctgg   22080 aagttgccag ggaactgctg accctctctg ggccttggtt cctggcagag g cagtgcagc   22140 caggcagggg aagggatgct taggccttgg tctcctgagg gcaagccttg a tgtgaggg    22200 ttggatcagc tggaagtggt ggcttcagaa acccatagag tgggtgacag g gtagggact   22260 tggtgtttcc acaaacccgc ccctcctttg accaggtgtg ccctgtggtc c tggtggaaa   22320 tggctatata ttgtccagac tgtagcaggg gctggccaag atggtccact c ctctcccca   22380 tcctcctcca accagaggcc ataaacccca ctctatagat taacaattcc c tgaaaagaa   22440 gggggtcact tttgttcccc agttctagaa ctaaatatta aagcaattat g taactagca   22500 ataaattact taaagtagtg actcactcag cttaattaga gcgcaagcaa g gagggatta   22560 aggtatttt agagcacaca cctcactctc tcctgtgggg gaggcctctg t gcaaggtgg    22620 gggtggaaaa aaggctggga actcatggga gcaccccagg tgtctgcaag g agatgaaag   22680 ctgatcctcc gccccactga ggtcctaagg aagaaaggcc gagtcagagc t gcagcagga   22740 gggattcgga tcagactcaa gaacacttcc cagtggtgct tatttgagaa c tgggacggc   22800 aacactagat tgtaaactct gtgagggcag ggattaggtc tgtgaccgcc t cctcaccca   22860 gcgggagacc aagaatgaga cttgggagtc agacacaact gggtgtgact c ctgcctttg   22920 cgggttgcca gcacgtgggc ttgggcaggt tcctttatca ccagaagctt t gccgtctcc   22980 tccactataa agtgggcaca ataacatcca cctgcatgca tattataagg a ttgagtggg   23040 ttaaaatgtg caaagcaaga ctttgtgctc agctgggcac agcggctcac a cctgtaatc   23100 ccagtacttt gggaggctga gacagagtgc ttcagcccag tagttttgag a ccagcctgg   23160 gaaacatagg gagaccctgt ctcttaaaag aaaaaaaaaa ttagaagact c ggtgctgac   23220 tctgctagac caaaagccca caaggcagg gattaggttt ggtttgtgtt t tcattgtt     23280 gtatctcaag cttcattcat aggactgcac aaagtaggtg ttcagtaaat g ctttgttgt   23340 gtgactgcgt gttaattttg ttcccattct cctgctccaa aaaaagttc a ttttcctga    23400 ggttgtgagt gaagaaaata ggcagtgtgg gctgggtgtg gtgtctcatg c ctgtaatcc   23460 ccagcacttt gggaagctga ggcgggagga tcacttgagg ccaggagttc a agaccagcc   23520 tgggtaactt agcgagatcc catctctact tcaaaaaaat ttaaaacaga a aaaatctag   23580
```

```
ggtgtgtggg ggggcaggtg gggaggttgc agggtgcct cacagtggg a gtctggcat    23640
ttctcctcca ggctgaggag gtggtgactt ccagggaaag tcctgggagg g atcagaacc   23700
acagctccag cctgcttgga taagggtggt cttctggctg ccaggagggt a gctaggtgg   23760
gaagatctgc ccttgtttcc tccataacct ggggtgggag gaggaggagc t cccagccca   23820
atctgatggg ggagaccaga accctcaccc accattgctg gcagttcaga g aaggcagcg   23880
ataagtcggg gtggggcatc ctgaaaggct tcccagagga ttggatggga g gattagctg   23940
agaagacatc cggcatccgt aaaatggagt aatgattctg accctgcagg t tttctggga   24000
ggattaaatg agttacattt taaagatgcc tggtacatgc ctgccaggag a aggcacaac   24060
atatgaactc cctccctctt ccctccaccc ctcctcagct cctgtgacat c aggagggac   24120
atgccctgcc ctgctcacag aggctgggtg ggaggctccc atcatggcct t cactgaggc   24180
tgcctctgca gttggaccaa gctggacaca cagtaggtgc acataacaga t gggggcagg   24240
tctgtgcttg ttttaccagg gtgttgggag gctgagggaa gggcacagct g gattgggt    24300
gatggagttc aatccctgct cctcccccag atccaagatc ctaagacgcc t atgtccagt   24360
ggctgctctg atcagctctg accagctctc ctcacacctc ataggccttc c agggttcag   24420
gtgatgaatt agtgatgaca gcatccagca tcgctatgac aaccacatgg c actcttagc   24480
ctccagtcag ggctcagccg cagaggccag agacccctt ggctctgggc c tttgtactg   24540
gcgtgtgtga gcggggctgg ggcctgaggg agatggagga gtgggagggg c aggggccgg   24600
ggcatggggc tgcatctggc atggactgga gttcattcag attgttccat c cagagggac   24660
cttggggaca gttgtttctc tccttccttc ccctttctt ttcattcctc c atccctcct   24720
cttttcccctc ctcccacttc ttctgagcct tgttcctgtt tgaggccctg g gctgccaac   24780
ccttttcccc tcctctggga ataaagccag gctcagccct caccccgggg a gctgagtga   24840
ggtggggac agccaccttc tggtctaggc ctcaggaag gtgtgtgggg a ccactgatg   24900
gcttggtgag agggcctgac ccagctgggc caggggctgt gcaagtggct g ctgaccctg   24960
atgagtgggg aggagttttt cagtagagag gcagggtcag agatgaagca g cgtgggatg   25020
ggggagcgac agatgttcag agtggcctaa gtgtgagatg cggagcagag a acgtgggag   25080
gaatcgaggc tcgagaagga ctgggagaga gtggatgcag tgaggagttt g aagtttgtc   25140
cctgggggaa gaggagccct gaagattttt gttgttgctt ctttgatttt t aaatgggag   25200
ggttcatttt agagatgggg aaacaggccc agggtgggaa agtgacttgc t caagcttaa   25260
gtcactagag acagactgag agtacaggct ctgcttgggt cctgctggac t ctagctggg   25320
acctcttgcc ccagacttgc tggccaggat tttcccaggt aatcactacc t ccgagaaag   25380
gcgaggagag cccatgggtg actttgccct cagtttgaat gaaatttgca t cagcaaggg   25440
ctatgccgat agtcctttct gctcgtgtct ggcctgtttg ggggtgggag t ggggtggag   25500
gtgagcatcc agggaaggat ctgggaagtc aggggcttgc cagggccagc a aggcattag   25560
ggtcagagat ggattcaaac ttgggtcttt ggagacccag cccagactct g tgctccatc   25620
tccttcctcc gtctctcagg agcctttggc tgagttaggc acctacagga g caagggcc    25680
ccccgagcc cctcacattc tcctcagggc tccttctggc cctggggcct g atattgggc    25740
ctgctgtgct ggaacttatc caggcagaat aaacctttag ccccattgtc c tgatgaaga   25800
aactgaggtc ccgaggtaac agtgactcat tcagggttac aacaggtcag t ggctgggct   25860
gggcctagcg tctggccctc agcttgtcta catggccccc ctcgtggctc t cccttgcc    25920
tctcgcaccc cactgtgcag catggttggg cctgccagcc ttgatggatg g ctctgcagc   25980
```

-continued

```
tcaacctccc tcccattcct ctccagatgc cgggccgtga gcctcctaat c accagtcct   26040 gcctggtggc cgccaagcca tccatctccc cacacagcct tgcccagcac a ggtgatttt   26100 gtttggggag aagggggca cagcaggtct tcctctgagg ctgagccaag a gtttggctg   26160 cagcccccac tctgggtgc ccgagggtta gggaatagcc tgcactccct t gctggagtg   26220 tcagaaatcc ctcctgaatc tccctaggc acgtgcacat gcacacacag g cacacacac   26280 tcacagtaac actaataaaa gctctcgtgt agcaaaagaa tattgtatgg c aagtattgt   26340 tgcagagcca tatgtatcat ctcattcatc actccactgt agagatacag a aactcaggc   26400 tcagagaggt taagtgactt gcataggctc catatccagg aaatggagga g ctgggattt   26460 gaacccacat ccttatggct cacatcttgc attcacaact cctgctctac t gactcacct   26520 gtgcacacac acacacatgc acacacacac acgtgcgtgc acacacacac a caggcactc   26580 acttgcatgc atgagcacga gccaccattt tggctcttgt accatccatc t acctgggcc   26640 aggttcttga ggagtgagga gaatgctggg ctgcagaggg catgaggggt c actgctcat   26700 tgtccccagg ctgccccaag ctggctgtgg cactggctgg ctggggagct g cagggaggc   26760 agcagcctcc aggcagtgga aaggggaggc tgggagacag tcgatcgatc a tccctgcag   26820 tgcctccttc caggaactgg ggcccagggg agtgtggcgc cacgggtcga t gttctgggc   26880 agcagcacag tctctgagtg cgtacagggt gtgtgtgggg cgaggctggt g tgcagctgc   26940 ccgccttccc ctggctccct tccctgctc ctgccttcct cctgccattc a cctgccagc   27000 cccacacctt ccctgattc ccccactgtc cccaacctgg gcactacaga g gctgagaat   27060 caaactccca gttcccaggc acctgtgtgc ctgctgctac catcccgccc t gccctagag   27120 gcaggtctcg ggtgggtgct gcaagagtca ccctatggtg gttggggatg g gtgggtagg   27180 gggaccgggg gctggagctg tggggatgtg aggcaagccc acctcagagc c tttggagac   27240 ctcgacagac aatacgatga gttaagaaat gtaaaggggc acatagtggg t gctgaattc   27300 atcttgtctc gttcctccag taagagtctg gagaaaccaa gagcagctgg g tgcctctga   27360 gggcacagga gctcccaggg ctggctggca ggtgcagcta acagtgttag c aatcccaag   27420 gacaggtagc ttggggcgga ggacagcatg ctgtcaccca tcctgatgag g ggagagatg   27480 tctggtgcta ggagcagtgg tggccggagg agggctgggg accctcccca g gccacccca   27540 cactctccct ctgggagggg ctcctgagca ggcctggtca ccttgcttct t ggctgcttc   27600 ttccccggcg gaggagcctc ccccaggctc tcccacctgc actggcctca a gagagctgg   27660 gattgagccc cagttcaggc acctgctggc tgcggaggt tagggcaaat c actttcctc   27720 agccctctca tccgtgacag gctctggtga gggttaaatg agatgttgcc c gtcaagtgc   27780 ctgccacttc cctgacgccg agcagctagg ctgctctggg ttctctagca c ctgcctccc   27840 ctggtcccag cactgggtgg gcggctgtgt tctaccggtc actggtgggt c ctcagggcc   27900 ccgacacagg gcctgctatt gggaaagagg gaagtaaaca tcccagggct g gagctctgc   27960 ccactatgga ggtgttccat cttaggctct gtaatctcct cattcactct g gtatgggga   28020 caaatgtgcc tctctgcact aactgagccc ccatgggcaa ctaggagtgg t gtcacttgg   28080 ggtggaggtg ggcaaggatc tctggactgg gatttccaag ccctgacttc c tgttatttc   28140 aggcactacc tcattgttcc atcttgggca agacctgtcc ccttgagggt a agagacaca   28200 tgtgacctct gacctccaga gtctctcttc tgagcttctg tgcccagatg a ttctgtgtt   28260 ctaggggaca ggcgaggctg gggggtgacc cccatgccac tgatgggcag a ctaaggagc   28320
```

```
aggggcccag gactgggggcc agctcaggac tctggtggcc tcggtgccct t gacctggta    28380 ttgctgccgt tttgccccac tgctgtctgt ctccgcgtcc gagtcaccac c tgtccctct    28440 ccagtcctct cctctcttcc tttattacta tctctatatt gcctcctgcc t caggcttat    28500 ctcctcctgt catgcctcta tccacctctg tcactcccct gcgactctgc c tcactccct    28560 ggcacaccct ctccctccct gggagtcggg agtggagcct cgctgggaat c aggaccccc    28620 ctgcctctgg tctctgtcta agcagtctct gcgattctgg ccagctctta t ctttttcca    28680 ccttcccgaa tctctcttgc tgtctgatgg tgtctctgcc tttcactgtc t ctgaactcc    28740 ctttgttttt ctctatatgc ttctctctgc tcttatctct gggcctctgt c tctcagggc    28800 ctgactggtc ttgacctctt tgcctccttc ttcccctcga gagcccagcc a ggcagcagg    28860 tccagccctc cagcccagag aacagatgga gtccaccctc cctctctctt g ctggctgcc    28920 tcggaagccc caaacaatgg cctccgcccct gcaccgtgcc ttgttgctag g ccttgggct    28980 ggcagcacct ggcttccata gcgacggggtg cttagaaaca gaatgccaca t ctcccagtc    29040 ccaccacagg agccttttgcc gattgagcga gtgccttttg atcaatcagg a agtgtggcc    29100 aggctctagg ttgcctccaa cttgaggagg caagagagga ggggactgtg g tctctgcct    29160 tctggagctg gggggactgc tgggctggga ggagttgctc aagtacagcc c tgaagccaa    29220 ggaaggactg ggggaggccc tgggctcttt tccccaagtc agcctgctgc a agaggcaca    29280 agcttgggag ctggaagggg ctgtgttgaa attgctgttc catcatttct a gctgcatga    29340 cttttggatga atgacctcag gtcccagggc ctcagttcca tcaactgtaa a attgggcta    29400 ataatatcat gaagattaaa tgagagaata gatctggcac ttagtaggtg g tcatcaatg    29460 gccattcccc tcccttcccc tttaaagttg tttaaaattt aattgacaga g aggagaagg    29520 agggttcttc aggcctgtgg aatggtgtaa gcaaaggggt ggaggctggc a tgcacctca    29580 catatgctgg agtatttagg gaggaccagg ggccatatct ggaaatggtt c tgccagaag    29640 cagccaggcc aagctgggtg ccatgtcatg cacctgtaat tccagctact a gggaggctg    29700 aggcaggagg atcacttgag ccctggagtt ccagatcagc ctgggcaaca t agtgagacc    29760 ccatctcaaa aaacaaaac acaacaggca ggctgatggg cccatggaga a gggactctg    29820 tctcctggga ggtatattct tgccaggtgc aaagggatgg gcttgactaa t ttctcctct    29880 agcatttggg gctgctgggt agggagctac attggggtcc ccttgcttat t ctcatgctg    29940 ctccctactt ctgccctgtc acttggtccc aggagagggg ctcccactgg t tccttttcc    30000 ctgccaggcc tgcccaccaa ggccaccatg gccacacagc ctgaatcctg g ggccagcaa    30060 gtgtccatga aggccccac tctgtcatcg tagagatcag gaaacaggct c agaagtagg    30120 agggcttcct ggtcctaggg cccagctctt ccctcttttc aggcctgtct t ctgcactaa    30180 ggacttcagg ccaccaggga aggtggggag ggaggaaagg agatgagata g acttgggcg    30240 ggggcctgag gacagagttt catgtcactt gggcagccag gaaagggtta a agatcccctt   30300 atcccaagcc atgggcactg gcactgccag aggatgctga ggcctgctgg g gcataagga    30360 caacaagcaa catccttttc tgagctgttg ggagtgccaa gctctctgtt a aatactttt    30420 gagcctcttc tcatgtattc acagccacct ttcaaggaag gccagttgat c cccagttta    30480 gaagtgagaa aacgggtct ccaggaggca cttgtctaag gtgacacagc t ggagagttg    30540 gagatggtgg ttagaccgag tcaccccccc agaccctggc ctctccctgc g tgccccttc    30600 caggacaccc atcactccct tgacacccct tgggagtggg tgttcatttc c ttgggctct    30660 cccaatccca gtccttggta tccccaactg caggcagaca caggtgcttg c tgctgtgcc    30720
```

-continued

```
ctcccctttta cctggcatca cagagactca agcccactga ccattaggct c tcaggggca    30780 tagaaaccag gtgctggagt cttagagtcc tgcaatcagg catctcaggc a gtcaggaca    30840 ttagaatgtt agaatcttgg gcttctacat tctcaagacc ccaggttctc g cattcacag    30900 aatgtaagaa aaacagactt tttgaatgat ggggtgttat aacagaagct t tgattttct    30960 aagaacatga agctctggga gttcttggag ccttgaagcc atagactggg g cctccctgt    31020 gtgatggttt ctgagttagc agggagtgtt cagagtatgg ggccttggtc c ctgttgctt    31080 agaccttctt gccttggtat ctctgatggg ctcagctctt agtagccttt g tgtatgtgt    31140 gtgtgtatgt gtgtgtgtgt gtgtgtgtgt gtgtgtgtgt gtgtgtgtgt a gtgggact    31200 gggtcaggg gtcaggact gactctaacc tgaggcaccc ctggagtggg g ccagcccag    31260 gaatagcagg tggaggaaag ccgggcagcc tcagggctgc agctgtctgg t ggtacaggg    31320 cagggctctg ggtggctgcc tttggcagag gaccagcctc cctccttcgt c ccctaccca    31380 gcctgctacc aggatcagga ggaggcatct ccatgggact cctagggctg g agtcagagc    31440 agccctcca ggttctgcag cctggacggt aggaggtgcc actaagggga g gagattggg    31500 gaaggattgg gacctttatc tgcggtgagg tggggcacgg gggatgaga g atatagtgg    31560 gagtctttga agggtgtggg atcagtgaag gggctgggga tttagtgatg g gctggggct    31620 taggatggag ccaagggctc tgtgggtggg agacctttg agagggtgga g actcagaga    31680 gaaggatggg ggctcagcaa ggggatgtgg ctcagtggag gttgctgaag a gtttcttgg    31740 ggttggctac acgcggtggc tcacgcctgt aatcccagca ctttgggagg c caaggcgga    31800 tggatcactt gaggtcagga cttcaagacc agcctggcca acatggtgaa a ccctgcctc    31860 taccaaaaaa tacaaatatt agccgggcgt aatggcaggc gcctgtaatc t cagctactc    31920 gggaggctga gcaggagaa ttgcttgaac ctgagaggcg gaggttgcag t gagtcgaga    31980 ttgtaccact gcattccagc cctgggcgac agagcaagac tccatctaaa a aaaaaaaa    32040 aaaaaagtc tcagggctgt ctctgcactg ctccaggttc ctgaggacgg c ggttgggc    32100 tgggggagtc ttctgtccct ggggtaggct gagaagcaag agctccttt c ccaactctg    32160 cccaaagctg gaaaggttgt tagagctgct aagaaagctg gcatctgcct c tccttttgc    32220 tcatcttcct ttctggtttc catgggaatc tgtggctcag gatgatcagg g gttgacagg    32280 atggcgctgt ggaaggagtc tgtgtcaggc acagccatcc cacatgggaa g gagccggct    32340 ggtaagaaag tgagttccct gtccctggga gtgtgcaagc agggtagggg c tgaatggct    32400 agagtgactc cagaaagggg ttcagatggg gcagaggaag cagtctggag g ccacttccc    32460 tgagacaatc atgttttgtg tgattggctc tgggggcccc accagcccca c cttccagac    32520 gtccctgggc ctcacaaagg gggttgctgc accctaggca ctgcctctga t ccagcccca    32580 actcctgtgc tctgtgcctg gcctatgctg aacacggaca tgtgcagctg a atcagattc    32640 agtctctgcc tagaggagcc ccagtctgat gggggaggca cacagggaca c aaatatagc    32700 tgggtaagtc ctacaaaagg gggcatacct ggctgggagg cagttccatc a ctgattcct    32760 gtagtctgta gatgtctttt tgagcaattc ttctgggtca agacttgttc t tatttgctg    32820 ggataaaaca gcagtgagca aaacagagct gacagcatgt gggaaggtt g agctcttcc    32880 agaccgtgat gagaagtatt ggtgagtggt ggggagagtg gccagaaggc a gagtgtggg    32940 cgcagcatga gaggaggctt tgtccagact taaggacctg gaaggccttg a aggccagga    33000 ccagggctcc aattgtcctg ctggcaatag gaagccatat gggtgggggt g aggcagaat    33060
```

```
cagatttagg tgtggaaaag atgactccag ccagtgtggg catcgaagag g aggcacaga    33120 agcaggcgtg gccacctgtg cctctgtgta ggagctgtgt gagcatgtgc t tgaggatgt    33180 gtgtctgtgt agaggactgg ggtgtaggcg tgataggaac atggacgtgt a tctatggaa    33240 agactccaat tgtgcatagg ggtgtatgtg tgtaagattc tgtggcccag g gcagcctgt    33300 gaaaaggaag gatcttgggg tctctggatg atggggagca gagactaagg c ctaaggtat    33360 gctggggctc gagcccctg gactttatcc cctgtgagct ggcaggtctt a gactagtcc     33420 tggactagaa tcctatgggt tcccttcccc cagagggtca tggggccagc c atctgctgc    33480 agacaagaca aacatgcatg caaatcacat gaaaatggat gaggcctgtg g ctgacccac    33540 cctacagccc ccatcccctg ggcctgagtt cactcagcct gtaccttcc t gacccagag     33600 ctgctgccag ggctctggga acaggccttg cccactagga gctgaaattc a cattgtccc    33660 cagcacctgc ccgtggccac atcctctctc tgtgagggct accccacat c tggagccat     33720 agccagcgga cacagagctg gatctggact ggtggccatg ggcagcacct c tggcaggtg    33780 ctgaggtgga ggaggcagta tccaggcagg catccctggg cagaaggtac c tctcctgag    33840 cagacaggcc tacccaggca ccaggcccaa agataggggc aagggctaga t cctggtatt    33900 ggaggaccct caggagaggc tgtgtgtgac ttgctctctc tctgacctgg g ctagagcat    33960 aaacacgtgt cacatacttg cacacacatt cacacgtgaa agcacgcaca t gctattcct    34020 ggacacttgt gtacacacac cactgcacac atatacctgc atgtgtgaat a tacactcac    34080 ttctgcacac agacacatgc ctatctgcat agacacaccc gtgccaaccc c tatagatac    34140 acagacatat ctgtgtatac acatataagt tcagctatac cactgcagta t cacacaccc    34200 tcacaaggat acaaacctgt gctcacactc tcttccaccc tcacacacat c atgcttaca    34260 agcctgtgtg cagccttaca cacatgcaca cacgtacaga gcagcctaag g gtggctcac    34320 ccctgcccag gtgaacacct gtgcccactc cagggctgga gtgttgagga a agggtctgg    34380 atggaggcag aacctgcaga gatgtcagtt tcttccagga agcatcttgg a ttgtcccctt   34440 cacagagccc ttggaagtgg ggccctcttt tagtccatgg gctctagccc a ggtcacaga    34500 gagagcaagt cacacacagc ctctcctgag ggtcctccaa taccaggatc c agcccttgt    34560 ccatatcttt gggcctggtg cctgcgtagg accatctgct caggagaggt a ccttctgcc    34620 cagggaggcc tgcctggata ctgcctcctc cacctcagct tcctgagcac t caaagagaa    34680 gcaggccaag cttcacggct gctgagaagt ctgagaccag ggagggccaa a gccttgcct    34740 gaggtcaccc agcatgtcag ggaagggcta gggtttgaac ctgggcttcc a ggtgggggt    34800 gtaaccatgg tccatggcaa caggatagat gcatgtcagg cagcagacag g cccttggaa    34860 gcaagacatg tggtcatggg ggataggaaa agacttacag tctatggaga t ctgccagga    34920 ccaagtgtgt gagatggaga gatggtgctt cttcaccaga gctcactggg c accacaggg    34980 ctcccagctt ggctggacca tggggactca gggaagaatc agacaggccc t gctcttgag    35040 ggagggctgg ggataggtga agaaggaaga gggcattata gactggggag a tggtgggg     35100 ctacttctcg ttggatggca gttttcttcc tgcatcttga aagatctaac t ttcaaattt    35160 ctttacccctc aaaactcggc atggagtaca ttctcagtaa atatttatgg c atgaatgaa   35220 ttaatgaaag tatgatattg gcaggcagat atgcctttgg aagggtattc a aaatgggag    35280 ggcaacaggt tgggcaaagg caaagaggtg gaagaaaagc cagaggttca g ggtacagct    35340 gagtcaggca tggctggacg ggaagtggta ggagaagcag caggaaaaag t cacgtgggg    35400 atgagccttg catcttatac tgagtttgga tgttgccttg gaggccatgg g gagcccagt    35460
```

```
gaagattatg agcagagggt gaacatggtc agagtgaacc tgccctggct t tggggggtc    35520
ctgggctaca tagtagctgc ttatccttgg tgcaaagagc actgggtttg g agtctatag    35580
gccagggttc acattcctat agtaaccagc tgtgccatct caggtaagca t ctacatttc    35640
tctgagcctc actttcctta tttgtaaaat ggggctaatg ccgtgcctcc t gaggctgtt    35700
ggatctggcc tgggtgagga aatgctttgc cagcacaagg ccctaccaat g agaggtgtc    35760
atttttatta ggaacaaggc agggctggtt cctagacagg gcctgaggtt g agtgggccc    35820
aggacccagg ctgacagctg agtcaccttt tccaggccaa gtggcctcta a ggtgggaag    35880
acaaaaagag ttggctagag gggctgggct atgcattcct aagctggagc t gggaggaaa    35940
gctggggctg ggactgggct tcctggtgtc cgagatgggc agagggtgca g acaccggga    36000
tagtaggacc ctcagccact gcattcttgg ggacaaaaga ggagctggga a atctgattt    36060
ccttacctgg ctttgctcaa gaagcaagga atgtatttaa ggcacagact g gagtgagat    36120
ggcctggtt tgaattttga ctacttacaa gctatgtgac tgtgggcagt t tactttgtg    36180
cctgagtttt ccttatctgt gaagtgtgac taataataga tcccaccta t aacattgtt    36240
gagaagatga aatgtgaggc acacagtatg tgctcaataa atgcgaaagc c tcccagccc    36300
cagatgtata cactcggcca gtaggggcca gccctggccc tcacctccat g ggacagagg    36360
tcagccaggg aggagatgca tctactccag ggttctctga cctggcagca a attagaatc    36420
accgggggac attcacaaac atctgggatg ggggttccag atatcagtat t taaaatgct    36480
cccaggcaat tctaacatga gtcagggtga gaacccagaa caggatcaca a attgtgcag    36540
ttggagtgag gtagggatct gcgtgtgagt ggaggagtcc ttggagtggg g tcactccta    36600
gctataagag ctcggcaagg cctttaaatg tgccaactca aggagccttg g ttgcccct    36660
caggaagggt gctggttggg gaatttcaag gattgtgtga gagggttttt c tgaaagggc    36720
tctgcactct accaagcact ggaagaaagc agtgcacttg tttattgagt c tagtgtaat    36780
aacatttcac agatggggaa atagaggcct agagaggtgc tgtggcctgc t cagaatccc    36840
acagcaagtc tatggcacag ttaggactca aaccctctga ggaatgcttg g atctgaaag    36900
gttgacacag aaagactctt tgagctgagg gacacataga gcacacacca g gaccccag    36960
tcattgagct gtagtttgag agattcaagt aagactgaag aaataacttc t tggctgggt    37020
gcagtggctc acacctgtaa tcccaacact ttgggaggct gaggtgggtg g atcatgagg    37080
tcaagagatc gagaccatcc tggccaacat ggcgaaatcc catctgtact a aaaatataa    37140
aaattagctg gcatggtgg tgcatgcctg tagtcccatc tactcgggag g ctgaggcag    37200
gagaattgct tgaacccggg aggcggaggt tgcagtgagc tgagatcgcg c cactgcgct    37260
ccagcctggt gacagagcga gactccgtct caaaaaaata aaataaaata a aataaaata    37320
aaataaaata aaataaaata aaataaataa aataacttct caagaggtga g tgccatgga    37380
ggtggtgcct ggagttggga gcccaagaga tggtggcggt gccaggccag g gtcggctgt    37440
tgaccatggt ctgaggtggc ctcccctgaa gaacaagtaa ctctggccag t ggctgtaac    37500
agatacctcc cggcacctg tatctcaccc agccttgtcc agagcccagg a ctgagccag    37560
tgacacatgc tcagaattta ccaagagact tgtgcactga gctcagactc a gacctagtc    37620
cttccaacag cccttacatg ggtcatcccc ttttacggaa gagaaaactg a ggccaaaaa    37680
taggaaggga ggcctgtgtg ggccagaac ctttacacat cttagcccag g taatttttt    37740
ctacagtgtt aataagtagg atgaattgcc cctgtttgga agattcagta a aatacattg    37800
```

```
acttggccca gatcacttac tctacacctc tcctaagtcc ccagatgtga c tcccaggaa   37860 agacacaaaa aagggctacc cagagggata agatagtaac cagggaagcc c tcccagagg   37920 aggtgggcct tcaaatggcc cctaaatgac aggcaggagg gaaggatctg g gagggtatt   37980 gggggtgggg tggcatgggc aaaggcctgg aggtgagagt cagtcagtca t tgatgtgag   38040 aagagcaaga agtagaaatg taaggaatgg tgggagggg agtcagagct g gatgaccaa   38100 gcaagggttc agctgtagag ggtctggccc gccaggctca gggctcgggc t ttattgtgc   38160 tggtggtagg gagccactga gggtgagtgg gggagagcat gccagagcat g cctcagaaa   38220 gaaaggtggg agaaacgctg gcatggaggg ccgcccctg agttggtggg g tggccgggc   38280 tctgccaagg ctatgtgcca gctgcctgga ctgtgtccag gaatgggcac a atgactcaa   38340 cattgagaaa atcactcccc agggagaaag ggccctgatg aatcacccag c tgaggtggg   38400 gaggctggga ggctgggagg ctgggaggct ggagctcac tgagtcaccg t ccaagagtt   38460 ggtgaggagg ggagctgcag agagagggc cggcagtgca gttgacgggg g gattcaggt   38520 cagaccacat tgagggctgt cgggggactc taccttcccg ccattccggg tttggtcct   38580 cctggccgtc ctgtgaggga gatgagaaaa ctgaggccca ggaagtgggg g gagggggatc   38640 cgagcaaggt catgcggcaa gtcgctggca aaggcctagc gagacccaag c gcaccctcc   38700 agtccagaca cgtcctgccg ccccagccgc tttcatgcca agcagaggcc t aagaaccgg   38760 gtcggtccgg gcagggagct gaccccggtg acccgctgaa tccccggacg c ggcccctcc   38820 gggcagccgg caactgaggc cggattgcgc cgccgcgatg gacgcagg g ggcgcagga   38880 gcgtcgcggc tgccgcaggc tcctgaaccc agaagccgct ctgcggagaa a cgcgctccc   38940 ggagcgcggg tcccaccgcg gaactgcgga ccgtgtggcc ctggggcctg c accctctcc   39000 ggctccgggg acggcgacag agacctgccc acccaggcct gggggcccca g tcagtggcg   39060 gccgccgtgt gtgcgctcgg tgtctgttcg cacgtgtctc cctcgcagat g ggcgactgc   39120 tccagggcct gtccgtctca cagcgacctc caacattctc ccgacttccc c ctgcctcct   39180 aggctgaggg agaggagcaa gcccgaggct cctgcggtgt ccgcggcccc t gcccccctt   39240 ccccttccct ccccaccca ccccactgcg ccggtctctg cctgggctc t ggccgggcc   39300 ccggaccca gagtggtggc ggggaaacag ggtgcgatca gacagggtgg a ggctctgag   39360 agcggcccct gcgagatgcg agagaagtgg cgacgggcg aggggcagcg a gcgcaggct   39420 gacagcaggc cagctggaag ggccgaggga acccagggcg agacagaagc g gggtgacag   39480 cggccgggtg tccggtgggg tcggaggatc cgacgggccg agaggtgcgg t ccgcggtgg   39540 cggggacata ggcggggccg gggcggggcg ggggcgggg c ggggcgggg   39600 ccggggcgga cactcgggcg gaccaggcga agctgtcgcg gacgcgctga c cgagcgcag   39660 cggccgggcc ggcgggcggg cggcggctg cgagcatggt cctggtgctg c accacatcc   39720 tcatcgctgt tgtccaattc ctcaggcggg gccagcaggt cttcctcaag c cggacgagc   39780 cgccgccgcc gccgcagcca tgcgccgaca gcctgcaggt agggggccc c cgcgctggg   39840 caccaggaga acgggtgtc cggcgagcgc cgggccgggt ctgcccgccc c cgtaaccct   39900 tctcagggta ggagacccct cctctagttc tgaattctac tcctgtgctg g gacggcagc   39960 gcagaccaag agcccttgaa gccccagctc tcagtccaca cgtcacccca g actctgaac   40020 tcctttcgga tccggggctc caccccaagc actgagcttc cagtccacgg t gggaccgca   40080 gtgcacactg agagctgtgc ccaagcctcg aattccctt ccttagatta g tggggaccc   40140 tgcccacgcc tcggaacctt caccatatat gtggggctcc cggcacacct g gagcacctg   40200
```

-continued

```
aacccccagc tgtcatccag gactccacct cagagccggc ctcacccaaa g ccccaaacc   40260 tccattccaa gcctcaactg gacacccgct cagattccca cccaaacatc t ggacttcag   40320 tcctcagcct ggaacctacc ccagagtcca aatctctcct tccatcaggg c ttcactggc   40380 tttctctgtg ggacccactc cccgatccct tccctccctc ctgtgttgga g atctccgag   40440 tctttcctcg tggggggccc ctcctcttgt tcctctccag gtacagtggt c ccactttat   40500 tctctgggct tctcctctgg tttctcttca agtatttctg ggctctctaa t ttggtctgt   40560 tgccccatgt gcccacctct cttggtctat cttggtctct ctcctgtttc t ctaggtctc   40620 catcttcgtt ttggggtctc tttctgcagc cacccctttcc tcttgtatct a cctctgctt   40680 tgtggtgagg aggggggcagg ctcagagagc agggctagtg tccctgggac a ccccccgccc   40740 cccatgttct caggcatggc atggtgtggg ctcaggtgga agggcctaaa t gtggagtgt   40800 gctgccctca ggcgatgccc agggatctga ggtggtgggg ggatgatgtg g tgggcactg   40860 gcttttgtaa cttataaagc ccctcatccc agctgccctg gtcttgacgg g gcggctag    40920 ggcttgagat agggaagagt aaactgcaat ctggtgtcaa cctgcggtgg g atgtgtcca   40980 ggctgggtgg gtctatagtg tatgtgtttg tgtgagtgtt cctgtctgtg t gtagcacgg   41040 gctgggttgc atgtgttggg tgtgtcttgt gtgtaatcat gtgtgttgtg c cgtgtatga   41100 atgtgtcatc gagagtggga ttatttgtgg ggagattatg ggaattatgg g tctatggca   41160 ttgtgtgcta tgtgtggctg gggaggcagt gttgtggctg tggagtggta g ctgggtgtg   41220 tggctgttgt gtgtgtagag aacttgtgtg tatgtggctg tatgtctgtt a ttgtacagt   41280 ggagttgttg tagggacagc ttgcatacag gattctctat gtagttgtgt g tgttactgg   41340 ctgttgtgtg tggccaggaa gggccactgc aggggcctga tggtttccac t gggtgtctt   41400 gtcagagagg agttggggca ggggtgccg tgtgtgccaa tgtgtttgca g cctaggtgg   41460 ctggcttaga gtcactatgg cacatcctgg gattgcttgg gtaatatatc t attaggacc   41520 tgagtgctgg tgtttgaatg tcatgtgtct gtgtggtggc tgctcccgcg a ttctggaca   41580 ggaaagggtt gcagccaggg ctgagggtc tgaggtgagg agccagttga c aagtgtgtg   41640 agtgtgtgag tgtgtgtgtg tgcgtgcatg tacacgtgca tatgggaatg g ggtggggtg   41700 ggaggaggca gtgggccagc agcgctgtct atgctgaggg gctgtgtgtg c ccacaaacg   41760 tgtgacatta ggtgtgcaca ttatctatgc aggttgtgtc tgcatgtgtc t ctgtgtcta   41820 ggtggcgtgc gtattgaatt taattggatg catacacctg tggctgggga g tgagaggt    41880 gtgtgaggtc cgtggtggga gacggtgtga gtgtggtgtg aagtgagggt g tgtgagctg   41940 ggtgactttt tggtgtgacg tgtgaattat gtgatctttt ctccccatga g ctgtgtgtg   42000 cctgtggtga ggagtgagtg gaggatggcc agtgagctgg cggtgtgtgt g ttgggggtg   42060 ttgaggactg tagaatgtgc tgcggtggca gtgtgtgcat gaggtgtgtg t gaggaatga   42120 ggtctgtaac atttgggcg tgtggaatat agtgggtgtc cccataaatg t ctgtggagt    42180 gacgcatgtg tgcaaaaggg cttggctgcc atcctgttct tgctcccctc c tgatcaggt   42240 ccctagagat gccctggaat gttctccatg ccccccccaac cccagctgcc c taccccttt   42300 gcccttcatc ctccttgcct tgaccaagcc ctttgttttg ggtttccggc g gagcaggcg   42360 ctggacaggc gggcggcagg caatgtcgtg gtctgagaac ctttgttctc t tagtttgac   42420 tggtgttttg ggccttggtt tggaggaggg tgtggagagg atgcacgtgg c agcaaggtc   42480 actgtgttta ctacaccact tcgtgctccg cagaggggag gcgtacggcg c aggcagtga   42540
```

```
ggcctgggtg gtgtctttgg tggcgcctgt tggtgtaaga acagcttagg c tgggcttgg    42600 agtttgccag ccatgcagtc ttagtccata gtggcccagc gcccttcctg g ctcatgtca    42660 gcggggctga gcagccgagc agccaagcac tcacttctcc aagttcacct g ccctcgccc    42720 cttctctgtg tggctgcagc cctggagac aaccaggaag acctcgattt a gttctattt    42780 gtgttcactc caggtcagat ggaggagaaa gagtcccat cctcacagag a cacttatct    42840 gaaaggagag agctggtcac acctttgggg accctctaga ctgacgcagt c tgtaggggg    42900 atcgaggtca taccttccag agagagctgt gggaaaaccc tactgggctg c ctcccagca    42960 ggtgcttgag agaagaaaca tccaaggttc cttgagattg aaggcttag a gaagtctga    43020 gtcagtcagg gaagggggctg gggtcgatgc cgcagtgtca cataccagaa g gttctctga    43080 aatgaatagg cttgaactgg accttgaagg gggtgttggg gtgggcagag a aatgcagcc    43140 tggggctgag gaaggttctg gcctgactgg caaaagggat cttgctggcc a ttccccagg    43200 caacactgtc tggctttggg tagccatccc tgggcctcca gccttctcaa g ctttcacgg    43260 tacctttttt atcccattgt ctctggctgg aattatcttc attgtcgttg a cattgtcat    43320 cttcatcatc ttttaggcag ttatttccaa attccagggt cctttcacaa a tgtctcatt    43380 tagcaggtta actcatgcaa ttgtccaaaa gtctttatgg aacactgctg t gtaccaggc    43440 aggcacagtt ttaagtgccg gggtcatggt ggtggccaaa ctggcctcat g gagctccta    43500 ccttctgtgt ccagccatgc tgtcagttgc ccacccttct gtgtttcccc c agtctgggg    43560 cgcctggttc tgtggggctc cgcatgtgca ccctctggtg ctgggtctg g ctcctacca    43620 gaatgtgagc tctgcagagg ctgggcccgg gtctctcctc tacccaccgt g tgtgtcctg    43680 agctgggtct ggcagagtcc agatgctcac acctatcatc aagtgactgg a actgccatg    43740 tagggttggc agtccagctc tgtctaggga aactggggtc catcggatga g gggactctc    43800 atctcatcag gcagcatctc atcaggccct tcttttacca gtagctccag a gaccaagaa    43860 gggtcaggtg actggtgcag gtctcacagc agggtggcgc ggctggtgtc a gaagacagc    43920 acttcttgct gccaggttgg gctctggtcc tagcaccatg ctgctctctg g ctggcctct    43980 gtgctgcctg cggcgggtaa acgattatta atgaccccc tggcaaggag a caggaaatg    44040 tttcccagcc acagctgggg aacctgctcc tgccagcccc agctatccat a cccgtcctg    44100 accatggcat cggtgctgat gttatcttca ttctgcctca gtcttcttta c tccttctgc    44160 ccatcccccg acctccctga tcttgacatc ctaagggtaa atgacgagaa g ctacagagc    44220 tttcttttcc atatccctgt ccctcaccac tttctccaac ctgactcatc t ctaccttct    44280 tccttgtccc atgccagcca gaagtagctc ttcctccaag aaggcttctc t gaatgcaca    44340 gccagctcct ccagtgtcca ctaccctgag cccgaggcac tgagtccccc t cattgcaga    44400 ctctagtcct ccactgatgg tttgctctga cagccctagg gctggcctgg g cacttcccg    44460 cagactgtcc ctaattgctg ccttaggact gacatatgaa gggtcctccc a gatgctacc    44520 tccaggaagt ctccagttcc actcagccca gggattctta cctcctttga g cacagtgcc    44580 cttcctgtct gagtcacaca tgtgtacttc caggacttcc taggtggaca t tagtgaaca    44640 cctgctatgt gccagcacag gagggtggga agagatgagc aggatgcagg c cttaaaatc    44700 cccacacctt cctccaagcc tgagcaatgt tgcatcagcc ccttggcagg t ggcacagac    44760 ctaggtacta gggctggggg agggaggcg gagaaacagg gagtgatgtt g gtagagtgt    44820 gtggggaggg caacgaggga gataaactca ggggccatgg tgatataaag c agggacccc    44880 tatttcagcc cagagtggga gggagggca tgttggggag cttccaggag g aaacaaatc    44940
```

-continued

```
tgaactgaga gctaaggtca agccaggaga aagttctgga cagaggggag a gaatggtta    45000
ctgtgaaggt tcgctggtgg cagacagagg gaggagagcc tgtggcagca c cactccatg    45060
gagcaggccc ctgggtgcca gccggctggg tccgggggga tgggactgg t aaagctggc    45120
ccagccagat ggtgcaggac ttgtaagcca tgttaaggac tgcggactta t tctggaggg    45180
aaattgaccc tggggaagag ttgagagaac ggatatgaca gatcagatct g catgttcaa    45240
tagctccctg gaccatggtg tggagactga aggggaggct ggtgtggtcc a ggtaagcgg    45300
gggtgatgag gcctggacag ggaaatggct gaagaatgga ggggagggga c ggagtggcc    45360
agggctggtg gagggagctg gacagctgta gacgtgaagg gcaagggagg a gaatgctgc    45420
cccacccagg tgtctggatg ggttttgtgc agtctctgag atgtatagga g ggaagacag    45480
gggttagtgg cagatgcctg ggcctgtgtc agggcccttt aaggaccaaa a ggtcttgga    45540
aaagcctcag aggagatcat gagctttgag attaaaggga gacctgaagc c ggcccaggg    45600
ctgctacagc ctcacctgta acatgggaac ttgagatctg ccctgggcaa a gggtgttca    45660
gaattcaata atcaaaacaa tctgtgaaat gtaatactta ataaaattca a atccaaaaa    45720
tgtctgagta cattccaaaa tgagtaaaaa tgtaaattta tgaaaatgct a aacatgcgt    45780
gattgttcta atgtaaattg taagcctcag ctgcttccca gaactttgga t ctggctccc    45840
ttgaagctgc tgcctctgat gtggctgccc cctgcagctc caggaccttc c tgttcagct    45900
cccttgagag tagccggcag ggcccctcct ctgcagagcc tgtactctgg c tggtggctt    45960
caggggggcag gcattctgcc tttcctgtct cccaccctaa gggagttggc c ttgcatgcc    46020
tcccatccac ggttgcctct actggggggct gccactggga gacaggaagg g catgggagt    46080
ttcgggagct cagggtaaga ggggctgaga tctcgtggtg tggaggggga c gggaaggt    46140
cgggtggccg aaagaatgga gagggccggg agtgagagca aagggagaca g gcagagctg    46200
aagagcagta tcgccccaac atcaatactg gtatttcaga atgggaaagc t gttccattt    46260
cccgaaatat cagaatgctg aggtccgatc ttgcagtctc tgagctgggc a ttccttggc    46320
ccccactctc gggtattctt gcacaagacc attttttctgg gctgcatttt c tcacttgta    46380
aaaggaggaa gttgggggtc aatatctcca agcgatatat gagctctagc t ctaggagta    46440
taggattttg agaatctgga attgttagtc tgtggggttc taactgggac a attctagca    46500
ttccttgact ctcagctccc agccagggct gtgtggatgc gtggttgtgt g attccgaca    46560
ttctgagact ttaagatgct gaggctctag gagctagaga tacggacatt c tgtgaatct    46620
aggattctag gatttgatgg tttgatgatt caatgattct aaatgggggct g ctgggaaga    46680
gctgcaacca cctgccttgt taatgtcaat gttcagttat taaaaacata a caagaagca    46740
atggagacag atagctcaga atggtgggcg ctccctccac tcccagtgag g gaggacaga    46800
agaggctggg ctggccttag agaatagaga cctttcaac ctgggtcaca c aggttgttt    46860
ctcctgtcac aacagaactg gtgtgtgtac attcgagaga gcttccactc c caaagcttg    46920
cagggtaagg ggctcatttc cttcagcact ggcctctatt ccttaaccat t tcagactgg    46980
gcagagagag gggtaactac ccttctctcc cagccctcga agtctctggg c agaaatggc    47040
agcagtggag gaaggagagg tctgctcacc cccgcccctt ccctgacagc c tgaggggaa    47100
aaacaggaca tgaatacttc ctggacacag acatggaaat gcatgaaccc c tgccttcga    47160
gggccccgcg tccaaaggct cagacaaggg cagaggccag acagccagt g gggtcccat    47220
cagcaccctc tcagtatagg ctgaggaggg aagaccctgt tcttgcccca a gggtgacag    47280
```

```
tgagaagggg tcaaggaaag gagtcccagg tcagggactg gaagtgctga c aggtcctcc    47340 cctgtgtgca aggccacagt ccagcctggc agaaggccag cccaattgtc c agtgtttca    47400 ctgcctcctg agtccttctt atgccttggc acccaggcca gagttgggga g gggtccagg    47460 ctgcagggga gggtttcctt ccagagtgcc catccctgat ggatccttag a agcccagta    47520 cagctgcaca gttccaaggg cttccgctgc tggtaggtt cacagaccaa a gctggccct    47580 ggtcacacag cacaacgggg cctgaaatca ggcttcctga ttcccagtcc t gggtgttcc    47640 tttttgccca cagcctcccc cacttcccct gggacacctg aggggcagga g tggaggtgg    47700 ggctcaggtt agggagcaga gcctctgtcc atcatccctc cgtcttcctc t tcccacagg    47760 ccagaagcag gtgtggtggt gacagctgcc cccagtcctc cacaaggctc c attgtcccc    47820 ggcagggagc ccctccccag ctgcaggcca gaagtgtgcc tccccgggcc c tcctgtcgt    47880 gactctgcca cccgcttcct cctgctgccc cttccctctt ctcatctccg c ttgccctca    47940 ggccctcccc atccccgtga ggtctcgtct ctggcgctct ctgggtttaa g cctctctcc    48000 agtgaaagtt agatttggaa gggccctggg agatcaccaa gtccaaccct t ttattcttc    48060 ggataaggag gccaggtcag agaggggaag gtcctgtcca aagctgcaca g taggctgag    48120 gcagagccca gtgctgtgct cccttcagcg ctgggtcatg ggtgcacact g cccttggca    48180 tcaggcgtcc agggtttgag aactgactgt gatgatcagc gctaagcaca c aggcaccta    48240 cagaaatgcg gtaggggct tctctcctca gcccttcttc acagccctga g ctgccctcc    48300 cttcctcttc tttgcccagc tcctctctcc ttcactatcc ctgctgtctg c tgactcctg    48360 cctctggcag acactgtcct tgggacacag actagagctc aggcctccag g actgggatg    48420 cacacccatg cacccagaca cagacacata aacatgtgca agcgtgtcac g ggtccata    48480 aatcccagct gaaaactggt cagaccatca ggaggccacc ctggaaccca g tgtcctcct    48540 cttcctgtca ggcctcacac acctcctcca ggaagcccct taggacccct g aagaccatc    48600 ttcatccaac tagccccttt gtgacaactg aactctgtga gcctaggttc c tcctgtgac    48660 tcgaagggca aggctgagtc cccccttcag tcctggggcc actccttcag t gtcttcagg    48720 agggctcag cttcctgttg ctgggtgggg agagccctga ggtccccaca g gacgtggga    48780 caatggggag gcggtgacag atgagaggct gagtcttccc taaagcagac t ccaccctcc    48840 cctgacctcc ctggctggtg gcttggacac agccctggcc tggactaggg t cctggtctg    48900 accccacaat gcagaggtct gggaatcaga agccctggtt ctccagcagc a gttctctaa    48960 ctggcggcta tggagtccag gcctccaggg cactggtagg ttattggcgg g ttggtgcag    49020 attccagtgt ccaggagggg tgagctggcc tgggggcct atgtacagga g ataggaggg    49080 tgataaacac aggctaggtg ggattacagg gagctgggaa tacctagcta a gaatcccct    49140 catcctaggc actttcccca cacttgaaat tggctgagg gggaaccaga a gttaggtgg    49200 ggttggggag ggacaggagc cagcaccctg cctccacctc cgggcagtgc c tctgctggg    49260 gggagggaac ctgtcctggg ggtggtggga ggtgtgaggg gggagctgga t tctccagtg    49320 aaactggccc tccctcctct caggggaggg gaggggctg tccctggctg c tcagcaggt    49380 agcccatctg gctgtgggtg gaaaagaaga ctcaggcttt gtggataaaa g ggacagccc    49440 tgggtcaggc acttatctca accctcgtca tttcctctgc cggacatgac t gggtgagtg    49500 gggtcattgc acagagggaa ggaacaggcc agggccagtg cataccaggc c tacaggag    49560 agtcaggcac atgggtgacc ctgccacacc ctggctgca gtcagcccct c atagaggcc    49620 cagacacaca ccacagtcac tgccggagat ggccacacct agaccatcac a ccacacaca    49680
```

```
gacccagtct ctccaggtga cactcaggcc cagctgcagg cgcagctaag a gggaagacc   49740 ctgcagggca cagggacacg tgggacaacc agacgccctg cttcggccac a ccacaagcc   49800 tccacacacc aggtgcagct cctgtcaccc ctacggtcaa cccaaggaga g ccagagatt   49860 ccagtagtcg tgggcaggta tccagtgccc aggcgagaag aggggacac c agcagggaa    49920 cccagaacct cctccatgcc agactgtgcc ctcccccag ctcacagaag g agtgcctca   49980 ggctgtttat ttcctagcag ggactagcag ggatgggtgt ctcatcccc t cccctccc    50040 agtccccacc acacgattct gaagctgcca aatcaaatca gcccctgcac c cgcgccagg   50100 ctggcatggc ggccagcagc tgacgggaac gaagccaggc tcagaatatc c caccgcctg   50160 tccgatgcct gagtaggctt gttgggtggg ggtgggggag ggcaggagcc t ggcagccag   50220 gccctgggca gtgcccctca gagaggctgg gggtttggaa tgctgcaggg t ggtgggctt   50280 ctggagaatg agtgagcagg tctctgttgt gtctccaggc tgctgtggca g tgtctccac   50340 cgctagcatt ccgggaactg tggaagtggt gctggtagga tacaggtcgg g ggtctgatc   50400 ccagtccaga tgactgggcg ccaggctggg gtaggggggc tcccacatgg t ctcacattc   50460 atttgagact cacagcaccc aggttggaag ccccttggtt gtctgtcagt a aaggcccaa   50520 ctcactgtgg aggcccagtg actgtgtgag gtggacatta cggatcccat t ttacagaca   50580 gagaaactga ggcttagaga gggctagtag agctccctgg agagaagcag a agtggagga   50640 ggcctcagaa agagtaaaga ggtggtcatt tccactcctt aggagcccta g gtggaaaga   50700 aggaatatgg ctctgttctc agagtcaagg aacagagaat atggcagagc c agaggtgcc   50760 catgggaagc agagaacaag gagggagtct tgggagagag caggggtgcaa g caggcaagg   50820 ctccctggag gaggggggcca tccgtgggct tgctgggggc taatgggagg a cagtctggg   50880 gagaagggga gaaggcctgg ccggcctcag cccctgacct tcttgtctct g cagccagcc   50940 tggacccct tgcaaaggag ccaggacccc cagggagtag agacgaccga c tggaggtga   51000 gagctcagtg gagggagaag tgggtgggct tgaggggtg gggcgcagac t gaagatcag   51060 tctgagtggt gccctccccc ttgggaggac ggggaggctg gagtcacatc c cagccccag   51120 ccctccagac taggaccacc cctatatcaa gaccatctcc cctcaccta t atatcccca   51180 gcctggaagt cctcccatga ggattcctcc tcccaactca cctggggagt c actacagac   51240 tcctcccttg tcctccccac cctcacccaa caattcccgt tgattctctg c cctgagtat   51300 ttcccgagtt cctctcctct ccattctgcc gcctgcttgg gtccaggctc c ctcaactct   51360 cccctgggcc actcactggc tgcttgcttt cagtttcccc catcatccac g tggccacca   51420 ggaggatctt tctaatgcac agacctgaac ttgtcactct cttgccccag a tcctccat    51480 gctccccacc cccatgcccc ctccacaacc ccagcctggc aatcgttccc c ttcatccat   51540 tcctgcctcc cccaaactgc tcctgctggc ctcttcccca ctcagcttcc t aaatccttc   51600 ggggatcagc tctagcctcc tttcctctgg gaagtcctct ctacccttg a ccatgggac    51660 caagctcact cctgctccct cctctgagct ctcctgcccc ggcagtcaga t gccagggcg   51720 ctctgctgtc tgtcgcccac tgtgctgtgc cacgagcacc ctgttttctc c atcatgtga   51780 ctctgtatgt gtgtctgcct tgtcttctct gcactgtgag ctctttgagc c tcgggactg   51840 tgctttcttc attcctgaac cttctaccac ccttggatgg gtaccggtgc a gggctcagc   51900 cagcgcattt cctgccctgc gagggggtgcc atccccaccc cccgaccatg c cttccttcc   51960 ctgtgagggg tgcctcatag gactcttcag tgctcaaagg ggccttgacg g gcaaacaag   52020
```

-continued

```
gtgggctgct gatgttgaag atcggcacag aggagggtgt gtgtgtgtgt g agagagaga    52080 gagagaactg gacccacagc cagaacagag tctgcccagg cctggctgag a gggagagga    52140 agatgatgct tgtatcagcc ctcctgtgtg ccaggagcct tgacaccca c cttgtttaa    52200 ttattacagc accccatga ggtaggggct gctattattc ctatttcaca t ttggggaag    52260 ctgaggccca gagggatcat tcagcaagtg agttgggaca gagctaagat t ggagcctag    52320 atgtgtctca ggctcgaggc tcactctttc ccggcccctg agtaagatgg g aaagaaggt    52380 gcccacacag ggcctggtgc acaggagggg ctcagcacag gttccctgct g ggacacagg    52440 gccaagacct gagaatgtgc ctccaagtgg ggctgggccc tgctgctggg a gctggcaaa    52500 gggagctggg aggggagggc ctggaaagcc acattattaa tttatttact g ccatggcat    52560 tccccatggg gcggggctcc ccccagagct gggacagatg gtgttcctgg g agcctgcag    52620 tgtctcagca gcctcggcca cccgccagga aagactggat ttgtcatcca c ccagggagc    52680 cacaagaaga gggggctttg gcaaagctga gaccctcctg ggcaacgggg a ctgtgccct    52740 gagggaagga gtatggctcc aggcaccctg ctatgcctct gggcagccc c cgctgccta    52800 ggccatctgc ctgccctctg caggttcaag ttctgctctt tgtccagctc c accggcctc    52860 gtccttccca tgaggcttcc ctgggtcggc cccacctgct cctatccctg t attttctct    52920 gcctttcctt gagctgggtc ctgctgcctc ttccctctga ccgaggatct g gagccatga    52980 gctcctcagc cctcagctct gtcctgaccc catccccaca ctcatcccca a aacagttag    53040 tgtctgcctg gactcttggc agggcctgct ggatttctgg gtcctgccag c accccaccc    53100 gagtgcccag gcctatactc agcactgctg ggaagagatg ggctgcctga g gggacgctg    53160 ccaacatgga gagggcaaga ctggagagag tggggacccg agggcattgc t cagaccaca    53220 ggggcagctg gagggaaaag ggactgggag cctgaggggc cctcctgtca g ggtggatct    53280 gggaagccaa gatggcctca tatagtggac aagcccacag gtcagatgag c acgggttca    53340 agtcccaact cccttgcttc ctaggtgtgt ggccttgtgc ctgtcactta a ccagcctga    53400 gcatcagtct cctcacctgc caggcgggat aagaacgtct atcactgccg g gagcggtgg    53460 ctcacgcttg taatctcagc actttgggag gccaaggcag gtggatcaca a ggtcaggag    53520 atcgagacca ttctggttaa cagggtgaaa cctgtctcta ctaaaaatac a aaaaattag    53580 ccggttgtgg tggtgggcgc ctgtagtccc agctacttgg gaggctgagg c aggagaatg    53640 gtgtgaaccc gggaggcaga gcttgcagtg agccgagatc gcgccactgc a cttcagcct    53700 gggtgacaga gtgagactcc atctcaaaaa aaaaaaaaaa gaacctctat c attcttgga    53760 tgtaatcact gttattcaac attaccacaa tagagctgtt gggagaagtt a caaagactg    53820 tatgtgtggg gtgcccggcg caggcctggc acatggcaga tccttgggga g agttagcct    53880 cctctctgtt tccctcaagg atgacatcct tagagccagg actaggctgt a ccctgtga    53940 gacaggatgc tctgcagagc tgggctgagg cttatggaag ttctatgggc a tggcacact    54000 ctcctggcac tggctgggca gcagccaaga aagcagagct gccagcaccc a tccccaccc    54060 agcaggcgtg tgttcagcac accctcctgg gatggttacc tagcccctgt g ccagcagct    54120 gacttggagg aggggctctt ccagctcagc ctggcatcct ccttcagggc c aggcctctg    54180 catcattact gtctctctga aagtcaggtc tggggcagtt caagttggtg a attgagcat    54240 gctgagtcaa tgccctcttt gtgatggctc tcagggccca gatggcggct t gggagcctt    54300 agctgggatg ggggcatggg gagaggcgga cgtggatgag ggcactgaca t ccacaataa    54360 gtactgaaat gcactgccca acaccggctc ctctattgct gcccttggga c aaagaccac    54420
```

```
accccttggc agggcattgc tggccttgcc tgctgggtcc cctcatgtcc c cttgtgtcc     54480 ccttatgccc tgagacagcc agcgctacag ccacattgtt gtgttcactc c cagcacaca     54540 gcagctcccc ctgcctccct gcctttgctc acactgacca cctgtctgga a taccttttcc    54600 tttctttctc cacctactct cttttcaagg cccagatgaa atgtcacctc c tttgtgacg    54660 ttcctcagac tggtccctct acctcaggcc gagccagtct cctcccttcc c tgggcactc    54720 acagtcccca tttccctgag cccacagttg ggaaacctgt taccccacgg g gtgctgtgg     54780 gtagtgtatc cttcccatg ggttgtaaa cacccaggag gcagaggctg a gactgagtc      54840 tcctttgtct ctcttgggcc catgtggtgc ttggtatagg cctggtatat g gtaggtgct    54900 caataaatac ttcttgaatg aacaagagtg gctgtgagta gggctggagt a gttccaaga    54960 agggcacag ttgggttggg cggtcttgga gacttggagg aggcaacctt a gaactttga     55020 aggatggaga gggtcaaggg caccaaccga agaagccagg gaccagctag g cagtcagag    55080 aggtccatga ggtcagcttc tgacagcagc agctaaggac aaccaggacc a gaacaggac    55140 tgggaaaaag cagatagagg aggctggagc aaggactcag ccccagagga g gctgcagga    55200 ggttggctca tgctcagaac ccggctccaa aacactctgc ccatgagtgc t gggctgagg    55260 aaggcttggt gccagagtca gggtgaggct gaggccacca gtgaatatgt g ggcccagct    55320 gcgggggtag cactaggcag gggcgggagc caggttggag ggggtattgc c attgccgct    55380 gcaggtggag tagggcttcg ctggggaagg agcagcttgt gcgagagtgt g ggcaggagt    55440 gggagggagg aaggctccga gtatacgagc atagcttacc agcaagtcct g gggtgaggc    55500 tggagggcc gcgctgtagg cagcactttt caggcccttta tctaacattc t caagtgagt    55560 gctcctagct gccagatgtg ctacttcctc ctggattctg cacatcagga g ccagtggcc    55620 tctacaatgc cccatggccc caagggagtg gctgccaaca agttggcctt a gcatctggc    55680 atccatgggg gtcctgaggc cctgccatct gtctgtgccc ctgttgggct g cacaggccc    55740 ggggcgtgca gggacctggg accagggagg cggtctcagc tgccactcta g cctgtctct    55800 ctgcctgccc atccactgtc cacacccctg gctgactgag taaagagaga g atgggcatc    55860 gcaggtcctg ccatcaaaga agcctagtct aaaggaggag gcataaagca c cggggactt    55920 atcccagag aagacacatg ctgagaccac gccaggctcg cgggcaaggc c taggcccag    55980 ggagggccag cctcgtcaag ggcctggagt tgagactcag ggaaaggcag g agctggctt    56040 agaggcgcag gcaggtccaa ggcagtgccc aggccagatg cggcggcccc g ggctgaggt    56100 tgctccagcc ggccccaccc cccaccgtcc tgcctggcct ttggctgtaa a cactgagag    56160 aacaagttcc gtttcccggg aaatatttat ctcaggctgt gtgaagagcg t gtgcactgg    56220 cctccgtgtg tccttcctgc agaccggctg gggcaggagg agagggagct t ggcagcgcc    56280 cttgctgggg ggagtctgtg gggctaggag ggaagggtgt gccagaggcc c tgcctaga    56340 gcctgaattt gagtgctggc tgagggagag gtgggagcag atgggagaga a gcctgtttt    56400 ctccaaaccc cacaaatgcc ctccgcctct tcatgttcc tttcttcttc c tggtccatc     56460 ctgtctcctc caggttccgg cctccagcct ggtgtcccct cctcaggctg c cttttcctc    56520 ctcctcctcc ctgtttcctg gctcttagcc gctccatctg ggaagtcttc c tcaacttta    56580 aaccctcgaa cccttgtcct ctgccctcca tctcccactc ctcaggcttt c agcagcttc    56640 acgtggagca ttgggctggt cctgtccaca gttgttcagt tgctgtaaca g cttgtgcag    56700 gctgccctgg agccctgttc tgggaagcac aggtctgggc accctggggt t ggggcgagg    56760
```

-continued

| | | | | |
|---|---|---|---|---|
| cccggagctg | atctcctctg | tccatcccag | tagagccagc accagtgcag a | cacatgggg 56820 |
| gatccaggtt | ggtggaccag | gggaggatgg | aaagtcccat ggatccagcc g | aatgttgg 56880 |
| agtggggagg | cagagggccc | aggttcctg | ctggccagcc tctgggctta g | ggtgtgta 56940 |
| tcccagacag | gccaggcctg | ccaggggccc | tgacaacagg aaatccttga a | ggaacaagc 57000 |
| agaggctgag | gactctgagc | acaacaacag | gaaacagccg tgacatgggg c | aacagccct 57060 |
| ggcgactgtg | cccagttggg | gtggggacga | ggggccaagc ttgtgggacc c | agggtgatg 57120 |
| ccaagaggga | cactgagaca | ctgtgggaca | ggggcgttc tgcacatgtg a | cacggagct 57180 |
| tatgacgtgt | aatatcaagt | acgtgaccat | gatcataggg tactgtgtgg a | gtgtgggtg 57240 |
| agtcactgag | tatgtgacac | tggctgtgag | gcactccatg atagcagatg t | gtacagtgg 57300 |
| ctgtgccacc | aagtgtgtaa | cactgtgtga | tattgattgt gtgatgctga c | accgagtgt 57360 |
| gtgacattgc | acattgcatg | ctaccacgtg | tgtgacactg aaagtgacag t | gagcacatg 57420 |
| gagggtgtgt | ctccatgaga | atcaaataca | gaaacgtgag caaatgacgc t | gcagtagca 57480 |
| ggtatggtcc | tgagtctgtg | gctcgagtgt | ctgacactga attgtgacat t | gagtgtgtc 57540 |
| ccaagcatat | gatctagtga | ggctgagtgt | gtaaacaaag gcatgacatg g | agtgatagc 57600 |
| aagtgtgtgg | aagtgggtgt | gtgatgctgt | gtgatcttgg gcctgacatt a | catgtgtga 57660 |
| tgctctgtaa | tggttgtaac | agtatgcaat | gtgcacatac agtgctgtgt a | ggacactgt 57720 |
| catgggaagg | caccgatggg | ttcaggcggg | aaagtaacac cgtccaaagg a | tggttttaa 57780 |
| aagattgctc | tggccggatg | cagtggctca | cacctataat cccagcactt t | gggaggctg 57840 |
| agctgggtgg | atcacctgag | gtcaggagtt | caagaccagt ctggtgaaac c | ccatctcta 57900 |
| ctaaaaatac | aaaaattagc | caggcatggt | gacaggcgcc tgtaatctca g | ctgctcggg 57960 |
| aggttgagac | aggagaatca | cttgaaccca | gggggcagag gttgcagtga g | ccaagattg 58020 |
| agccattgca | ctccagcctg | ggtgacgagt | gaaataccat ctcaaaaaaa a | aaaaagaa 58080 |
| aaagattgct | caggttgcag | aatatgtatg | tgtgcgagtg tgcatggtgc g | tggcagggg 58140 |
| aggggagata | agttagggggg | aggcagagag | aaggtgggta gagcaactgg a | ggctcctgc 58200 |
| agctgcccag | gcaggagatg | gtggtgcctg | tgttaatgga atggcagaag a | gttagagat 58260 |
| atggagcaac | tttggagata | tttgaaaaca | gaaatgacag aacttgctga t | aaatgagaa 58320 |
| gatgagcaag | agggaaaacc | agagaacaat | ttccagggtt ctggcttgaa g | aaccaagcg 58380 |
| atggatggtg | aagatgtttc | tgagatgggc | aaaggcaagg gggagggtca g | cactagtgg 58440 |
| ggtgggagga | caaggaggca | gaaaccgagt | gagctgtttt ggatgtgtta a | gggaagcat 58500 |
| ccaggtgaag | gtgtgcagtg | ggcagcgggg | ccaggctagg gatacatctg g | gagtcgaca 58560 |
| ggcatggggg | gtttgttaag | gtcgtggacc | tggctgggat aatggagaga g | ggagcttgg 58620 |
| caacagaaga | ggtgggggact | gaggaccgag | ccttaaactc tgaatattcc a | ttgtctaga 58680 |
| ggccggggag | gtgagaagga | gcagcaacga | gacagaggag gagggccagg g | aggcagagg 58740 |
| agaccaggag | tgtgaagcca | gaagccaagg | gaggaaagag gctcaagtgg g | agggaggt 58800 |
| cggtgtgtgg | atggtgctgg | cccacaggta | agatgggaac cggaagattg t | gctgtgctg 58860 |
| ggcactgtgg | gtgagtcagg | ctaatggag | ccatttcagt gatgggctgg a | gccagaagt 58920 |
| cagactggcc | tgtgtaggat | ggtgagggag | gtgaagacgt tagcctggag a | gccctttgg 58980 |
| agacgttggg | ctgtgagggc | tgcagagaag | gacatgatcg ctggaaaggg a | gattacatt 59040 |
| tttttattat | gggtgattct | aagcagacac | aataccagag agaagcatat a | agaaactgc 59100 |
| catatactca | tcaccccagt | tcaacagttg | ctgggatttg gcctcatttc t | tcctctctt 59160 |

```
gccccctatc tgttctttca ttttcctttg cttaagctta aaattttta a attgtggta   59220 aaatatacat aacttaaact ttaccatcat aaccatttct aagtgtacag t tcagttgtg   59280 gtaggtacat tcacactgtt ttgcaaccaa tctctggaac tctttcatct t ctcaaactg   59340 aaactctgca cctattaaac gacagccccc atcctcctct gtctccagct c ctggcaccc   59400 accattctac tttctgtctc tatgacttgg actactctag atacctcaag t aattggaat   59460 aatgtagtat ctgtctttt gtgactggtt tttaagttta cttagcataa c gtcttcaag   59520 ttttacccat gttgtagcat gtgacaggat ttccttcctt tttatggcca c ataatattc   59580 cagtgtatgg acagaccaca tccatccaac accagacact tgggttgctt t cacatttta   59640 gctattgtga gtaatgctgc tatgaacata agtgtacaaa tatctcttca a gatcctgct   59700 tccaattctt tcagatgtat acctagaagt acgcttgctg gatcacacag t cattctatt   59760 ttttggtttt tgaggaactg ccatactgtt ttctgtatct ttttacattc c cacggacag   59820 tgtacagggg tttcagtttc tccacatcct tgccaacatg tgttattttc t gttcttttt   59880 tttctttat tttttaatg gtagccatcc taatgggtgt ggggtgacat t tcattgtgg   59940 ttttgatttg catttcccta atgattagtg aagttgagca tcttttcatg t gctggttgg   60000 ccacttgtat atcttctttg ggaaaatgtt gattcaagtc ctttgcccat t taaaacatt   60060 gggttgtttg cttttttgtt gttattgaat tgcagggggt ctttatatat t ccagatatt   60120 acctctttat cagataaaag ctttgcaaat attttctcc catttcatag g ttgcttcgc   60180 tgaaatattt taaagcaaat cccagacatg atgtcatttc accaaaggta g acttttttt   60240 ttggtgggg gagctttccg gtgaagactg aaaaacctgc tagacaaatt c taaaataga   60300 tgtgactttg gattttgtt tttaaggct aggaggtcct ggatgatgct g aaatgtaac   60360 agtgacacag agccagtgtg gaactgtgtc tgatgctgtg tgagggtgac a tggtggctt   60420 tgggaacatg ggtgcaacac tgaagatatg ggagactcca agtgagggtg a cagtgagag   60480 atcactgtgt gtgtggccct gtgacaccca gtgcatgggg acagtgggac g ctgtggacc   60540 ctgaaatgac tgtgtgtcac cgagcaggtg ggacctgctg tgtgaaggcc a caggtgtca   60600 tgtcttcttg tgtcatcctg gttgatgagt gtgacacagt gcaggactct g catgggagt   60660 aagagggact gaagctgtgc tataggtgac cgggctgcat gtgattcaag t gggctcagc   60720 cccagcttca gctgctgagt atgggaggga gcatggacat tgtagggtag a tgaggagaa   60780 acactgaatg ggaacagaaa tggtgtctgt gcccagatgc gagctcctcc c ttctctgaa   60840 tacccaggaa ggcttcctgg aggcaggatg tgggcacttc agcaggatgt t gtaggtgct   60900 gattaagagc agggcctgtg gtgtcagaca gccctgtcta ggctctgaca t tcagcaggt   60960 cattttatct cttgagcctc aatttcctca agtataaaat gggagctctt a ggaggattg   61020 catgaagcag tgctccaatg catgcagtct ctggcacttg gtaaatactc t atggtctct   61080 tggggagcag caacctcaac acctgcaccc caggtcccca ataacagga g caccagtag   61140 gagcacagtg aaggtgcgct gagtgaggtg tcctcttaca cccacagccc t cctctctcc   61200 ctctccccca acttctgtcc cctgcttggt gttgtcagcg ataccccctc c tgcccactc   61260 actcctgccc cctcctctcc cctgccgtcc ttaccactgt cagcctccag c ccaggctcc   61320 tgcagcctca tccaattagg ccaatgcaat ttgctcaaga aaagccccca t aatttggtt   61380 aatcacacca gtaggggatc tggtcccggt cgggagggtg ggggtggata g gagtccata   61440 cccgcagctg aggcacaggt gtcaaagtgc ctgtcttttg ggacctttac c cacttccctt   61500
```

```
gggctccttt caggagccaa cagagtccca aagcttgggt cttctcaaac c ccaactaca   61560 gaggccttga aacaggagtc tggacttcct gggttcgctt gtgttcctgg g agggtccct   61620 gctactctct gggcctcagt ctcccttttcc aaaaatggga gtggaactgg g gagtctcag   61680 aggccccagt tggcctagct ctgcatccca gctctggtca gtccccttg t ggcttctga    61740 ggggccttct cctgggcctt ggggagggag cactgagggg taggtggaga g cacagggcc   61800 ccagggaagt gaggagggt aagtgtcctc tgagtctcat ctggaatgtg t ctaccccag    61860 tcctataatc agagaccctc tagttccagg ctgcacacct gaaggtgggg c aggaagaaa   61920 ggaagctgcc cttcttggt cacctgcaag gccaaagtct cttaaccgtg c aggctatac    61980 cttgcacagg agctccagca gaggtggggt ggtgctgaaa ctgagcccac t ctccctcac   62040 caagcctttc ccctcaggcc cgcatctgcc cagagaattg gggtccctcc t ttctaatgt   62100 gcacacaggt ggccccagcc ccctgctggg agtcagctta gcaaggtttt g atggctcag   62160 cttaatcttc tcagcagctc tgggggaaga gaccatttta cggatgagga a ctgagccca   62220 ggaaggtcca aagacttgtc cagtacatgt ggtgtgtggc agggcaggca g atgagcccg   62280 catctgaggg aggcgatggg agaagtgaca ggggtgcgca gaggaggaga a ttagacct   62340 ctcagattcc accactctca gccacacgtt cactcactca tttggagaca a gactaacca   62400 ccagcgcatt cacagcccc cagacagcca catactgact ataccactgt c acatggaca   62460 tcaatgacct gaatcacata tgcatagatg caggcccaca tggtcactcc c acgtgcaga   62520 tggccagtgc acacacatag acacaggta ctcacacatg tttacactct c acgacccat    62580 gtgggttaca gattcctaca gagacacaga cctacatact ttcacaagga a attctccca   62640 gtgacccagg gaacatagtc tgccatgatg atgtgatggt ccgtagggc t cgccactat    62700 ggaccattaa tgggcaggct gcacacatgc ttaggtcccc agcaaagcgg g agttctgca   62760 cagagtgaga ggagaggtca gttctgatga gtgtatccag aattttgcaa t cagaaaaac   62820 cacacaaaaa ctattttaat tttcatttcc aagataaaat ttagtttgaa t tgtatagag   62880 ggtccgaggg tctggtggga gggcatcatc atcttttcaa ggctttgggg t tctaaggca   62940 cccacagatt cacaacagtc ccacaagata tcccaggctg acatatttac c cagcccagt   63000 gtgtgcgtgt gtgtgtgtgt gtgtgcgcac gctgtgtgca tgctcatgct g gctcccaga   63060 tcctcgggat gtgaggaagg aaagtaggag agattccaga gactccggat g tttgttctc   63120 tggcttcctg ggcccttcaa aggaaaataa ctctggatgt cagcctgcct g cctggcggg   63180 ctgggtggag aggtgggctg ttttgggagg tgggctgtat gacagcctgc c tcagcccct   63240 gtggccccac tgaccgggac cctgtgtaat gaggcagagt gaccaaggcc c atggccagc   63300 gtcccatggg ctcgtaggcc catcgcctcc cctctctggg gcttggctct c tcatctgaa   63360 aaatggaggt gggaaggaga tgagactgga tgggctttct cctggagact g attagagag   63420 acagagactc aggcccgggg tccagaaaag acaaccaaag ctggggaggg c acatgaagg   63480 ggggcaaaga aggtctgggt tcaggggagt gcgtggggcc ccagagcctg c catgtctcc   63540 gccaactctc tccctcactg gaggagggct ctgtgccttg gtgccccacc t gcccagggc   63600 cctgtggctc agcccttgc ttgctctgtg aggggacgg gagaaggatg a gagtcccag    63660 tgataggggg aggacaagac caggggagag ggctgggggt ttctggaggg c cagagcagg   63720 aagagcagga gagaagagag gacaccacag tgcaggaaac ggaggagcaa a ggctgggag   63780 tggggaggct ggaggggtgc agggaatcag actgggcgc tgcgaagagg c ctgaggcca    63840 gagcaggcag tgcctggatg gagggagcga gcagctcctc accctcagct c cttgatgag   63900
```

```
gtaaggtgac cacgagccct gctccaggct gtgtgctgag cactttgctc g gagcctgtc    63960 actctggagg aggggagggg gtgttcccag gagctatgac agtcttgtgc a agggaggga    64020 cagggtcaca tttatgttta acaaagcact gcgctgggag agaggagctg a gagacccg     64080 gccctgggga gcatggtggc tgggaccccg gagggcaggc gtgccccaga c ggaccccac    64140 tcagaagatt gcttatccca acccccaaa gagaaaggct atttttagga a caataaaag    64200 tgctcacaca ttcctgcagg ggcagagaga gggaaagggg gcaggagtca g tgcagagga   64260 agagggtgga ccccgctctt ctcccaactc tgccttggtc ttcagggact t ctcctcagg    64320 ggcttcccca gccagccctg cctctccagc ctccgcctgt ccctgggtt c cctaccggc    64380 tcttatgtct atccctctgc ttctgaattg gtacttgttc tgtccctgtc t ctctttctc    64440 atacttccac tttcccctc cccctggggt ttggggaaca gctgggatgg g ccaagctct    64500 gttgagagag ccaaatacag tcataggaca aagcagcggg aggctgtggg a tacacacat   64560 gccgcagagc acagacagag agaggtggcc aggcacagag agagcgccca g ggaggctga   64620 gaggcaggga gaaaacacgc tgggacagtc agggagagcc ccagggcagg c atcaccggg   64680 cagccagcct ctgtgccctg ctctctatct tgtccctaag aagaccagca t ggctgggct   64740 tgcctcccgc catccacccc accagcccta ccccaggctg gccttcctc c ccgccctct    64800 gcaggcccac actaaccta ggccaggccg cctccttcag catttacctc c cacacacaa    64860 tgggcacagt gaggacataa gagacccagt ctctggcctg gaggcagata c tcagcctta   64920 cccgacatct gagagggctc agcccatccc ctggccaagg caggtattag a ggggcccca   64980 aagacaagca ggactctggg acaaggtgtc ctagtgtggc ccaaagggct g ggctgaagc   65040 atgggtctcc tggctccaga tgagagcctg ggtgaatcct tccctgcctc c tctggcctt    65100 agtctacccc atcaagcttg ggattggact acatgaggcc tgaggccctg t agccctgg    65160 tccctgggaa ttctcagaag gcctgggagg gggacaggtg accacgcagg a aggcttcct   65220 ggaggaggtg tcctcactca tgaaagaagg tgatagtgac agtgctcctc t tggggaaga   65280 gccctccatc ctgacctgct gcccccaccc ggtctgcacg tggagatgat c ctgaagcac   65340 aaagggcctc ccggcctgca gaggtgcctg ggagaggttg ccaaaggctc t cagtaggag   65400 acaccccatt cctcaggctc cttctctgag actgtaactg tgccagactg g ggaggcttt   65460 gagaggtctc agctatctcc cctgcctaga tccttcctcc acaccctct t ctccctgat    65520 ggcatgtagc cctcacagta cagtagtcct gggcacacag gagtttaccc a gtcatttac    65580 agctcagcaa acacctacca acacctatga ggggctgggt aatgctggag a cccggagag   65640 gggcaggaca caatctctgc cctccaaaag ctcccagtct gttgtgggag c cagacggga   65700 aagggtggca ctgcattgat gcacacagtg catgccatgg tgggggaaag g ggggcagtg   65760 ggagcccag gtgggagggt cagacttgcc tgagagaga acaacaacag a ctctccctg    65820 gaggggatcc agagaaggga gatcacttca ttcattcatt cgtcattcat c catccaccc    65880 attcaattat tcctttggcc atcatttcct gagggatgta aactctcttc t gacactgac    65940 ccagcgggac actcagcgtc ctcctcctct cctgcttgag ccaccatgcc t gcctcttgg   66000 aggctcctgg acttgctttg ctcagctccc aacccacccct gaggggtga g gctgaggag   66060 ggtgtacaga cattcagggt caccaaactc agagctggag gcctgccacc t caccagggg   66120 cctttctcag ggcacaggct ccctggtggc agggccttgg cccttgcttg c acacccttg    66180 gggactagga gccccctcat ccatcctgct caggctctct tttgtggcgc g actctgatt    66240
```

-continued

```
cacagtgtgc ccaaatctgc ctccttgtga ctgccgcgag ctgcctcgtg g ccccaggc    66300 cagaggacaa ggatagctag aatgccaggt gaccaggatg actgtgatgg c atggagagg   66360 gggatgctgt gatgtgtttg ggaggaagtt tgtggtgtcc aggagaatgt g ggcagcaga   66420 aatgggacca ctctcggttc ttccctgtag atgaagcagc tgaaggtggg a gggggtggg   66480 aggagacctg agctggctct gccccgcttg atctgatgtc tgccttgcag g gccatcctc   66540 cccctcccca cactcagctc ctgcctccct ccctctaccc actctgactg t tccctcctt   66600 tcctgactcc agactctggg tgagggactg aggtgattcc agtgagtcag g ccctcaggg   66660 aactgatcgt gcaggcaact cttgcctgcc ttctcctgct ctttccctct t cccattcct   66720 tcatccaccc ccaaacctag ctcctgatgg atccaagggt gcggggggaca a ccgggaggt   66780 cattttggag gaggcaggag ctggaataga agctgggact ggcttgggaa g ggcgagagg   66840 ccggggcgga gctggttgtg ggcgctggaa gggaggagcc aacagtgtgg g gtcaggctc   66900 ctgtggacgg ggacacccct tgggaggcact gggactggct caggtgtatt c tacagtgca   66960 cgtgtctcca gtgtggctcg gaggctggag acgcggccct gttggagtaa c aactgaagc   67020 cggagtctgc gaagggtggg caggagggtg gagggatggg ggcatggagc g ggaggggt    67080 aagtagagga gggagggggag gaagagaaag agggaggagg aaaggtctct g gcaggtccc   67140 tcctttaaga ctgggctcct gcgctgcgag tggccccgtc catactgcct t gttatccat   67200 atctccccac cactagtctc cctctgtcct tccaccccca gcctctcccc t ccattggga   67260 ccttccctgg ggcgtcccct cattggctgt tctcacctga gcaaggcccc t cccctccag   67320 tccttagcct cttcacctgt acaatgggat gacccaaaca ggcacctctt g ggcttgtag   67380 gaggatccaa gatagtgtca gtgggtctcg aggtgtggtc ccccgaccag c agcatcagt   67440 gtcatctagg aatgtttgga aacgcaagtt cttggacctc gtcccagacc t actgtatca   67500 gaaaccctgg gggtggggcc agcaatctgc actttaacaa gcactctggg t gggttctgg   67560 tgcacatgaa aattggggaa cggctggtgg aaacctctag ccacaggagg t gcttgggaa   67620 aggtaccttc ccctccccaa agcctgatgc ctcactcaag catgcactg a cagttgggc    67680 tagttcagct gcgttctggg tctctgtctt gcctcctcct tcagactaag c ctcccaagg   67740 gttgccaagc ctcttttcctc tattctcctc accctgatcc agctcagcct c attgagaga   67800 agtctgggc tgcaagatct tcgcactcac aggcagttcc tctttgcaca t ccaaggcac    67860 cagtgtcttt gagaggcgtc tccttggcca ggtggcaggc gtgggtgtgt g gggaggaag   67920 gaggaggaac cgccttgttc tgctttcttg tctctgactc tgcaggctgg g ggtgctgta   67980 aggctgcgag gaggcataga gtcagcttgg gtgctgggct gaggccaggg g ccgaggctc   68040 agctgaagcg ggcttctctg gtctgagcct acaggatgcc tcctttgggg c agttctgcc   68100 agtcaccctg actgggcggc tgtgcttgct agtgccagac ccatgctagg c acagaggtc   68160 gatacgttct cctgtgctct tgaagggccc tgtcctctgg aagataaga g gctgtgtat    68220 attgcccacc ggaacaggag gcaggaagca aaagaggcgt agatgacact t gcctggcac   68280 cccctgtttc ccctctagct gccttcctgg gtttcccatt ctgtgggcgc t tctcttgag   68340 ttaggtgctt tctcccagtg ttctcaaggt gactatttgg aggtttgtgg g aggagtggg   68400 ctggagacac aggagtaggt gggggcagga agtatgcagg agagagatgg a gagtgggag   68460 gagaagctat gagaggaaga gaggacgcgg aggtgggaaa agacgtcaag a ctcctggag   68520 aggaacagga gtgcagcctg ggacagaggt ggacgtcggc cgggggaggc a gggaggaag   68580 gcagggaggt ccacccgaaa ggaagggaag ggatgatgga cagagaatga g agggctccg   68640
```

```
aggtcctggg ggatctagaa ggacccttcc ctttacagaa ggggacacca a ggcccagag    68700 agagaggagg gcctcacaga ggacctaaca caagcagagt tgcatgaatc a gtgtgaacg    68760 gacagtccca agagcacagc cggaccttgg gaggtacttg actcttgagt t tgatgttat    68820 tgccttcctg taggccagtg tgaggggcac tgtgaggctt ccttccagag a aggaggcat    68880 ggagccagtg ccaggcagtg gggtgagcca taggaggacc tgtggagatg g ggaaaggca    68940 tagagactca tgaagatgaa acaggaaaga tcttatggca gcgaccccaa c cctcaggaa    69000 gggcgttggt cttgtgcttg tggctccaaa ggggataaga ccaaggtctc t ggtttcata    69060 gaatcttagg ctttaagaac gagttagaag taatttagtc cagaccctct c ctctcccca    69120 gataagtgca gaaatgcaga tctagcccac ggctgagccc caaccctggc t tcagaggag    69180 gcctgactca gaacaggctc ccctttcttg gtacctgggg tgaatgaaag a taagtctgt    69240 ggtaatggtg ctgtctgtgg tgctgactgg ccttaccttg gactacagag c tgcaggtgg    69300 agctggagag agcagaaagg ctccatctat ccatctaccc acccacccag c cacccatct    69360 acctatccac ccaccatcca cccacccatc catccaccat ccctccccca a cccatcctg    69420 cacccattca tctatccacc tacccactca tccatccagc ctcattgaat t aaaccatag    69480 aactatatgc tgcagagcta gaaagatcca tttttttagta atgacaaaac t gaggctcag    69540 aagaggaaag gtgttgcgta aggccacaca gaacttctgt agtcagtctg g tacaggatt    69600 ggaaattgcg gctcttttct acacaccaca agttctcctc tgtggtctgg g aaattgcct    69660 ggtttttatg ctgatatcta tactgatatt tgttccaaaa agctgtgaag c caggaaatg    69720 tgacctcctt caccccatcc cgagcctgag ttctgtgtgt gtgtgtgtgt g tgtgtgtgt    69780 gtgtgtgtgt gtatgtgatg tgcatgtcta agtgcaacct tgtatatgca t tgaatatat    69840 gattgccttt tgatctgtct gtgtgcgtgt ttgtgtgaga gcctgtgcat a tacgtatga    69900 gtagaggagt gcgtagcaat atgtatttgt gtggcatgtg tagatgggca t gtgagcagg    69960 taaagctgtg tctgtatttt tcctttcctc ttccttttaa gatcgaagcc c cctgacttg    70020 agccttgctc cccatctgtg cctccaattc aggaatctcc ctgcttccca t tagcagctg    70080 ctccccactg attctctcct tccttcactg aagcagcaac tcttccctct g agcccacac    70140 ctcatgggct ttgcaatttg agctatttcc tcccctgagt tggtgcaatg g gggtgaagt    70200 tgctttgaga tctgaggaag attcatggag gagatggcat ttgagcaagc c ttgaaggcc    70260 cctttgagtg ccagatctga agtggcccctt cccagctgca gttcctgcac c caacaccct    70320 ccattcctgg ggcatgctgg gcaggaccag gaggtggatt gacagaagga t gcccacaaa    70380 gagccctggg cttcatcagt cacattacca tccagtccgc tctagcacag a tgggaagcc    70440 cttccctgct gctgccccaa ctctccccaa ctttcctttc tgctctcct t attgctact    70500 atcctgcact tggcctgaaa agtcacagaa aactgaacaa tcagagcaaa g gtcaggcag    70560 gcacccacca attccagtaa aggacagttg agggcattcc ccaattgaag c aaagggcag    70620 gttgaggagt ccaccaatca gaataaagga cagactgttc tttctgagca c cctagggtg    70680 ggagctgggg atcgggtgct gagcaggaac cagacagggc tagagatcca g aggtttggg    70740 ttctggacct ggctctgctc tgactggctg tctgaccaca ggttgatcat t gcttctcat    70800 tgaacctcag cttcctcatc ggtcaaatgg ggagacttag ctctctgaag g ctgtggctt    70860 tgaagaattt ctccccctgt atcaggctca ctccgtcacc tgggtctctc t tccccaagt    70920 ccacatcaca tacatcagac tccaccaagg gcagggcctc tcaggagtca g cttgtgggc    70980
```

-continued

```
tcctctgcct ccaagaagga atagacacaa accaacacca cctctgtgc t gtctttaga  71040
gcccccgtct ggggagcgtg catctggaag actttatctt gggagtactg g gggcatcag  71100
ctcttcctcc ccttttagt cttcagaatt gaccttggaa ggccataata g cctgcgtgt  71160
attgtgcaca ggtatcactc gagctcttgc cctgtgaatc tttaaggaac t gtaccagtg  71220
agaacgtgtg tgtgtgtgcg cacatggatg tgtctgaag gcctgctggg a tgtctgcga  71280
ggacgtggga tctgtggctg tgtggtgctg aagttgtctg tgctgtgatg a ggagtgcct  71340
aagggtcaaa agacaagtga tccaatttgg gtattgtgtt gtctggaatc a gtagcttct  71400
gatgtctgag ggtagacatc ttcccatgac caagatatgt gtcttcatcc t tgagcagtg  71460
ggagggacca aggaagcctg ggggttgggg aaagcgatgc tgagtaagca t ctggggaga  71520
aggcccacta ctgccctcct cctgggaaca ctggattggg tgggggaagg g gaggaaact  71580
gcagccaaga agacccagga gtgaaatttg gagctgaagc ctggatgcaa g tcttcattg  71640
agagcccagc gtggaacttt ctggcaaata ggcattcagc ccactcttgt g cacccttga  71700
ggatgggaag ctcacttcct ccctctctcc tggtgacctg tggcatgcct t tgtagcatg  71760
gccctacctg gaagaaggtc cttcagccca ctagaccaag gccagcctcc t gtgaaatcc  71820
tatgggtccc caggctgtcc atggggccac agagttcaga tccccatct a ggagggtct  71880
gagagattgg agttggagac tgataaccct gggtctcctc tgctttagat g aggcatccc  71940
tgggttatcc agtcttagtc acatgcaaaa cttggtttcc aattccctcg t ttcataggt  72000
cgcctcctct ggatgagtgt catcttgtca gcccctggga cacaatgaac a gggatggt  72060
ctaactagac tataaaagtg ggggaactgt catcttccca attgggttaa c agacctcta  72120
ttaatatggc ctgcagtttg agcattttta tttcttgcca gtcatgctta c actgtgggc  72180
tcatgctgaa ctgtggtctt ttaagaccct caacctcata tcatgttcac a tgaatgggg  72240
acccagccat gtctccttca tcttgcagtt aatcactttg ctttctgaac a cagacccaa  72300
ccttccactg ggaagacatc tgaaaggact tccaagggct tgcgggaggg c atggctggt  72360
ggctggtatg agtcacgatc ttgccttggc cctcgtttcc tttgttctgt t acctttctc  72420
tttgatcccc atggctctgg ccaagttaat agagcgagaa gcaggacttt t gtctccgt  72480
tccggctctg caaggacgag ttctgttcct gggatgggaa ggctgtgaga c agtcaaggc  72540
tgacgtctcc ttctcctcct atagttgcca ggggtggccc agctgttctc c cacctatg  72600
ggttatgcac cccataggct cttgctactc caacccagc ccctcactag g ctggaaaat  72660
gagactaggt gagaccacct tccttctggg gaaagtgagc gggacccagc t tcagcgaat  72720
attcagctga gcatctactc tgtgttgggc attctgtgag gcacttttag g actctgatt  72780
tttattttca ttttaaggg ctcaatttca ttttatcttc atgtcagcct g taggggca  72840
atagccccag ctgcttccaa cttacagata ggagactgag gctcagtgac t gaaccaaga  72900
cactcactgc tcatacacag cggagctagg attcaaattt gggtgttttt t tgtttgctt  72960
gttttgtttt aatttggagc cttgtggttt ccctactgtg ccagaattgt c ctcgactag  73020
agaacaagag acctggggtc taggccaggc ttgacctgtt gactcactat g aggcctttg  73080
ctaagtccct ggcccttctc tgcgcctcag tttccccacc tgtaagatga g ggtacttgg  73140
acattctgtg gccttaagac tgtttgattt tgagatccta agatcctggg a ttcctgtgc  73200
ctgaaagact cgggctctgg actaagctgg ggggttttgc tcacagtcct t tgggcagat  73260
ggggctgccc tggcctgcct ggcaaagcct ctcactgccc tctcctctct t ccaggacgc  73320
cttgctgagt ctgggctctg tcatcgacat ttcaggcctg caacgtgctg t caaggaggc  73380
```

```
cctgtcagct gtgctccccc gagtggtagg tgcccgccct tgccccacgc t tcccacccc    73440
accccccaaat cctttgacca gctctatgct gtacctcact cagggccaag g aggaaggaa   73500
gaggcagggt ccctgcccag aggactttca tggggaagtg aagggtctgg a tgggtgttc    73560
tgagacagct ttctggagga ggaagcctta ggctaagcat caaggaatga a cttgcatag    73620
gaatcctgca atggctgagc cagaagggc cttagaggtt aagtggaaaa g ctgtgtctc    73680
agataatgaa agggattcac ctaggataac aggacgtggt ggagccagct g agttttgga   73740
atacatgcag caggagaagt tgagggtaga catgtagaag aacttcctgg a agccaggtc   73800
tgggaggtac tagaataggg ctcagctttg atgaatagac atgcattggg t taaagtgcc   73860
ctgcctggag atgggaggct ggaaaaatgg cctctagcag ccttttagca g ctttcttc    73920
tgtcccatcc caataccatg gatgagttgc aggtttgggg caggtttggg g tgatcatgg   73980
ttgcctgagc ccagagtgcc ttactgggga gattgtgccc ctcatcatct g ttccaggcc   74040
actcccctac ctggcttcaa tggccactgt tcatcccta ggcaggagga t gggtaaacc    74100
agcccttgag gcccaaagta gcagggtgtt agttgcacca gaaagaggga a gcagggac    74160
gtttgaagcc tggagaaggg agtctgatcc agcctaaggg gcatggaaga c ttcctggag   74220
gaggagattc cctaactgag tcctgatagc cttgaatgtc ctcttcccta c tctaaaccc   74280
ggccaagggc agcctctgct ccaggaaata tggccaactc agaatgtgac c ttcccatcc   74340
ctccagagcc cattgtccct gaatctgctt gatgatgaa ccaccggagg c ccagagaga    74400
gagggcactt gtcccaaggt cacacagcat gacagggata aatgggactt g gtatctaag   74460
cagccccatt ccctctcttc agctctgcct tccccaaacc tcctagaagt t cagagccca   74520
ggaggagggc taatgagtga gctttattga gtgtgaaatt ggtaggaagt g ggtggtgtg   74580
ttggcgccca aaaataaatc ctcctggaga aggacgggac taaggcaaca t ctggcctgg   74640
ggtgaaggca catctggaaa gggagggtgg tggaaactgg caggtcggtt t ctgtagggc   74700
tgccccgaga gcctctgtgg ccactgaggc tgccgtaggg tgggaggagg a agtgactgg   74760
ctctgtttca caggcagggt gccctggcgg ctgtgccagc ctagatgctc t gcaacagat   74820
taattgtctc cccaaagctg ggggctggga tgacagctgt ggtccaggtt c ctgggacag   74880
tgggaaatgt cagccctggc ccacccaaga gccctatagg agctagggaa g ccctgactt   74940
tcgggagtcc tggcttgatt gcacggaggg gctcagcccc cagtgaggta a gggagctga   75000
ggtctgctct gctgccccca gggagggaag cagagatggg gagggaccc c cgcccaggg    75060
aggagagctg ctggcacctg gcttcctcat cagcacccat tgtggcaggc a gccccgaat   75120
gcagatggtg ctgatgtgtc tgaaatggtt ccctccttct ctccaataga c tcagctaat   75180
tttaacccag agggctgaga gtaaggggt gggagacata cggacatgcg g aagtgaagc    75240
gagaatctgt cccctctgc ccccatggac tacccacccc tccctctgcc t gggcaggac    75300
tttctgtata accccggctg gtctcttaac ctctttgggc caaataactc a ggcccctcc   75360
caggctgctg gaagagatgg atgacaagga ggctagatat agccgaagag t gggcggcct   75420
ccttcccact gaattcttta tccctgaaca tcccacttag gtttccttcc a gccaaacaa   75480
gagggtgtct gcccctctca ctcccttcag gccttatcat tcccacccca t gccacaccc   75540
accacggaac ctggctcagt gtctctggaa gtagtggcca ggcatctcct g tggtggggg   75600
ctggctggcg acagctgatg acaagaagag tggctggcag gattgtggac g ctctcagag   75660
tcatggaagg caactgcttc ttctgggaag gattccacac ttactgaggt t gggccttca   75720
```

-continued

| | | | | |
|---|---|---|---|---|
| acacgtagct | ccactgtcag | ctcctcccaa | agccctccag gatacccctca | g ctgggaggc 75780 |
| aagcccttct | ccatcctcct | gcggagaaaa | cagcagagtt gtggacaagg | c tgcgttgca 75840 |
| tgggggttgg | tcagggatcc | cgaagggttg | ccagttctgc ttggaaggaa | t gtggatttt 75900 |
| tgcctgtagg | tcagtgaggg | caactacttc | tgccaagaca tggcctggaa | c tgaggccag 75960 |
| agctgctctg | ggcccttggg | gagggaggat | taaagagcaa gagctttgat | c tccctctga 76020 |
| ggagtaatcg | gtccaaaata | caaatctgct | cacgtctccc tgtgcacgtc | c tgccctgcc 76080 |
| ccagttctgt | tcgtaagccc | atcccactca | gccctactga ccttgggccc | a gccctgtg 76140 |
| cccccttccct | cactgtctgt | tcctaaatgc | tccatgcttt atacgcctct | g gacctacct 76200 |
| gtgtacctgc | tataaggcct | gggagcccat | tctgcaccct gcccactccc | t gaatgtgtc 76260 |
| taattcccac | tcagtgacag | ctgaaaggtc | acttcctcca ggaagccctc | t ccagcccca 76320 |
| ccggaggatg | gcgcagtgcc | ctgctctgtg | ttcctcccct ggctgggtt | a tgggtgtgt 76380 |
| ggtttcttgt | agaggtgaag | gagggatgct | tcctagaaca ttctgagccc | c atccctggt 76440 |
| acagctcaga | gtggatgctc | agttattgtt | tgctgaatgc ctgaggctgg | a gtcaggcag 76500 |
| ggaaatatcc | caggtgggag | gtgatttgtc | tgcaccctca gtccttgaaa | c tctttacct 76560 |
| ggcacattgg | gttttgggtg | gtaaaaaagg | tcataggttc atgaatcatt | g cctgcttag 76620 |
| aattccttcc | aagaggagag | gacgaggtgc | ttagttcacc gggtgttttg | c tgccctggc 76680 |
| tgcatcttag | aatcacctgg | agagaaaaac | aaacagatca ttgccagagc | t ccactccca 76740 |
| caggttccat | gaccttgccc | cacagacccc | tgtgtacagg ctgggactgg | g cagctggga 76800 |
| gggcctctcc | acagggtctc | ataagtgcct | tctgtcctag gaaactgtct | a cacctacct 76860 |
| actggatggt | gagtcccagc | tggtgtgtga | ggaccccca catgagctgc | c ccaggaggg 76920 |
| gaaagtccgg | tgagccattc | tctgcacccc | cattgccctc ttgcatggcc | a aggattctc 76980 |
| agggctgagg | caccatccaa | ggtcatctgg | tctgaccctc ccttccaac | a ttgatcccc 77040 |
| gcctccctgc | caggtgggat | tccttggcca | ggttgctgac tccagcacag | a agggcagaa 77100 |
| gcaatgtctt | ctcttccttg | gggaaatgga | taggcacaga gaaatacca | a ttgatggta 77160 |
| aattttctcc | ttctaattgc | ttctaaatgg | ctgcagcctc ctcagagcag | a gtctcagaa 77220 |
| cattgggget | atgggtgta | tcagttagaa | caccggcatg ctgtgagaac | t actgcgagg 77280 |
| ctggacctgg | aatcccagca | tgctgggcct | gcaggagctc acagtgccaa | c tccttgcat 77340 |
| ctgagaacag | ggagatcaca | ggcagcgtcc | tgctgagggt tctggagccc | c actgcctgg 77400 |
| gttcaaatct | cagctcccctg | tttactagct | gtgtaacctt gggcaaatga | c acaacctct 77460 |
| ctgtgcctca | gttttgttta | tgaaatggtg | ataataatgg tgcttatagg | a ttgtgggga 77520 |
| ggattaaatg | tgtcacacat | gtaaagcatt | taaatcaggc ctgatccatg | g tgagggctg 77580 |
| tctgttgggg | attaccattg | tgagagaatg | ctggaatcac tgacttcagg | a tcatgggat 77640 |
| cagggcactt | ggccccctga | taccttgatg | cccatttaat tcagcctcct | c atcttccag 77700 |
| atgggtggat | atcatgagac | atgaccaagg | ccacatgcca ggtatgaggc | a gagccaggc 77760 |
| ctaggactcg | ggtcttctga | ctcctggctg | tttagggaa agtgagagga | a gtggaactc 77820 |
| atcagatgag | aaaaccttgg | gggcaggcat | gctgctggga ggaggcaggc | t ctgaaggat 77880 |
| gtggccattg | cctgctaagc | actgaatgca | gggccattgt ggggcccagg | g agcactggg 77940 |
| caggagctga | gggcagagtg | ggcaccagtg | gggatgtccc aagaaggcag | c tctctaccc 78000 |
| ctgtgaggag | ggcttttcca | gcaggccagg | tggtccaggg atgtggcttt | t tcaggtagc 78060 |
| agctgagcct | ggcaagccac | tcacctttca | cagggaccat ggaaagaatt | c ctgtttgag 78120 |

```
gatgctggac tcatggtcct gaggcccctc cttgtgctgg aaaccctggt t tctaggatg   78180 ctggtctctc ctcagccctt tcccgtggaa ggagttggtt ctgctctgat a gccaccttc   78240 ccatttccta ttctcccact gagctccttt caccttcccc taacaacttc t ccgtcaagg   78300 agcatgggaa caaagccatt accacctctc tctagccttt gtgtcccgtc t gtaagagga   78360 tggtctgaaa ggtctttaga accttaaggg gaaaaatgtg gtcatgtccc c ctttctcct   78420 ctaattccaa agaacttcgc tctcctccag catccccac ctctaattct a aagaactttt  78480 gcttcatata agctccactc ctccaggaag gctcctcgga gcagcctggg a ggccttcct   78540 gggagggatg caggaaaaca ggctcaggag gcagcgggga gcagcctgca g gtttgcttc   78600 actccctagg acccacacat gctcccctca gctgtctggg catgtagagt g ggtgcgtat   78660 ctgcggtcca ggcattttg agagggctca gatccttggc atcagctgcc c tttcaacat    78720 cctccttcca accacttcag actcagtaag gcctttggaa aaataccaa a aaaaaagca   78780 attaaaagtg aatattcaaa tccaattatc ccagagctca gtggagatgg g gaggtgagt   78840 gcctgctggt agacagggc tgaagattcc aggaggaggg ccaggggatg a aaggcaag    78900 agagtgagga cagcaaggac ctcccagggg acatacccat catcaggaca c acccgtcat   78960 catccccaaa caggaattct ttccatggcc cctgtgaaag gtgagtggct t gccaggctc   79020 agctgctacc tgaaaagga ttgggggaag gcccaggccc agtgctctct c tggtatctg    79080 agctctgctt gcccacctt gtgcctggtg tctggtggtg agcccatctc c acaattagg    79140 gcggagaggc cccagggttg gctgggccct gctctcagga gctcccagca g gatgggac    79200 ttgagaccca ggtgtatgga cgaggaaga gcactggaat gggattcaga c aggtctgga   79260 ttctagctca gcccctccc tgtctctctg ctttcctacc tgaggcccgg t ctattggct    79320 taatggggta acaggggcca agtgcttggc acagtgccca gcacacagta g gagctcagt   79380 gattgctact tgcactccca agtcccaacc aatgattagc cttgagtgac c ttgagaaaa   79440 cgacttctct tctggccttt tttctgtgaa atgggtgggg ttgggtacag g gtccttccg   79500 atggtgacct ttgtggctct ggtcccccca ggagggagag ggactgacct a caggctgcc   79560 gtggagcctg aggctctagc agtgcccgag gaggtggggg tgtggggagg g tgctactcc   79620 aggaaaccct ggactgtggg caaacagcag caggtgtggc gtggaggctg g atcatagag   79680 acagataagg aggcccgagg caatgggcag ggaatgggat cagggcagtg t ggggagaga   79740 cagggtggaa aagggtcaag gcgggagtga ggaggccccc gccagctccc a gccccacct   79800 gtccctgttc ctgccgctgt ttgggctctc agatgcccag ctgcatcccc c cagtgtgtt   79860 tggctttcct gtcttcttgt gcttgtaagg gctgcttgct cccttgcaaa g accgtccct   79920 gctccacttt catctcagcc aatcccattg taattatctt tcatggcctg a ccagaagct   79980 gtcttgggga agcctgctcc acagttccct gacactgaga aggaaccaag t tcagaaaa    80040 ggggtctggg ccatattggc ctcccttagg gttcttccac aggaagaacc t tgggctggg   80100 agtcagagac ctgggatcca ggacaacatg gctgcaatca caatccgatg c cctcttcct   80160 gggcctccat atgcccttct gtaaaatgat acgctgaaca ttctgatatt g agggctggt   80220 gaggctctga attgtaaggg ctgcaaacga ccttggggct ggagaggaga g aatcctgga   80280 aggctgcctg ggccagggtc ttcctgaaag gaggcttcac ttccctcttg t tggtgcccc   80340 acctccatct cccagactgt ttcaggcccc agctctgccg ccttcctctt c ttgtgtctc   80400 ctgctatctt aaagcctctg attacctgat gctgagtgca gcaaaaatct c aggcctttc   80460
```

```
agctgcaact gaagcaccca ccgcccacct cggcccaggc tggctgtctc c ctctgctac   80520 cattttgggg tccccagggc ccatccctaa gaaatttctt ccccctaagct g accaggtct   80580 tctttcattg cagaatctga ccatccctag gggttgtctc agaggacacc g ggaacggtc   80640 tgctcccatc tcgggatcct cacatgctgg gggaaggagg gcaagaagag g gtccaggtc   80700 ctggggctc agtgagagtg gggggcttag tgaggggatg ggggcccagt g acagtgggc   80760 agcctcagtg aggtgatggg ggcccagtga ggatatgagg gctcagtgag a gtggggtgg   80820 cccagtgagg ggattgggc acagtgagag tgaggggctc tgtgaggggg t aggactta   80880 agtgagggga tggaggctga gtgagtgtgt ggggctcat tgagagggtg g gggctaagt   80940 ggggaatggg ggctcagtga gggatggag gctcagtgag aggatgaggg c tcagtgagg   81000 ggatggggc tcggtgaggg gatggggtt caatgaggg atggggctg a gtgagggga   81060 tggggctga gtgagggat gggggctgag tgagaggatg ggggctgagt g agggatgg   81120 ggctcaatga gaggatgagg gctaggtgag aggatgaggg ttcagtgagg g gatggggct   81180 cagtgaggg ataggggctc agtgagaggt tgggggctca gagaggggat g gggactcag   81240 tgggggatga gggctcaata aggggatggg ggctgagtga gaggatgggg g ctgagtgag   81300 gggatggggg ctgagtgaga agatggggc tgagtgagag gatggggct g agtgagggg   81360 atggggctc agtgggggat gagggttcag tgagaggatg ggggctcact c gagggggatg   81420 ggggctcagt gagggatgg gggctcagtg agaagttggg ggctcagtga g gggatgggg   81480 gctcagtgag aggaagaggg ctaagtaaga ggatgagggc tcaatgaggg g atggggct   81540 gagtgagggg atgggctca gtgagaggat gagggctagg tgaggatg a gggtttggt   81600 gatgggatgg gggtagtga ggggataggg gttcagtgag aggatgggg c tcagtgagg   81660 tgatggggc tcagtggggg attagggctc agtgagagga tggggctca g tgagaggat   81720 gagggttagt gagggatgg ggctcagtga gaggatgggg gcttagtgaa a tgatgggag   81780 ctcagtgaga ggatggggc tcagtgaggg gatgaggccg agtgagaggt t gcggctcag   81840 tgagggatgg gggacttagt gagaggatag ggctcagtg agggaatggg g gctcagtga   81900 gaaggtgggg gctcagtgcg ggattggtc tcagtgagaa ggtgggggct c agtgagagg   81960 gtgaggctt agtgaggta ttcgggctca gtgagggat ggggctcag t gagaggatg   82020 ggggcttggt gaggagatgg gggctcagtg ggggatgggg gctgagtgag g gatggggg   82080 ctcagtgaga ggatgagacc tcggtgaggg gatggggggct cagtggggga t gagggctaa   82140 gtggtagatg ggggctgagt gggggatgg gggctcagtg acagggtggg g ctcagtgag   82200 aggatggggg ctcagtgagg tgatggggct cagtgagagg gtgagggctt a gtgagggga   82260 ttgggtctca gtgagggat gggggctcag tgggggatgg gggctcagtg g tagataggg   82320 gctgagtggg gggatgggg ctcagtgaga gggtgagggc tggcgaagg g attggggct   82380 cagtgagggg gtggggagtc agcggggat aggagctcag tggggatgg a gggtcagtg   82440 ggggatgggg gctgagtggt agatggggc tgagtgggg atggaggct c agtgagagg   82500 atggggctc agtgagggga tggggctcag tgaaagggtg agggcttagt g agggattg   82560 gggctcagtg gtagatgggg gctcaattgg gggatgggg ctcagtgagg g ggtggagac   82620 ttagtgagag tcggggggct cagtgagggt ggggggttccc ctgggggat g gggttccgt   82680 gggaggatgg gctcagcaac aggcttggct gcttaatgat gcctgggacc t agtgggtgt   82740 tggagggggg cttctccaaa gtagagaacg cgagaaggac acacacaggg g ctcagagaa   82800 gtgcagggga cccagctctt tccaggctgt tggccctacc agcagagaac c tttccctcg   82860
```

```
attcttttc  cattaaacaa  atagttgtta  aagggacgga  actgccataa a  gtccacgcc    82920 tgttcctctc  tccactctgt  gcccatctgt  ccttatcttc  agtggggcag g  ccatgacca    82980 cccaggcacc  cagtgctgtc  attagccttc  gcctgggcag  ctggccctgg g  ttgtggagt    83040 tccccacaac  ccccagcatg  agcctggaag  gcagggtggg  ggtggggtag t  agtaaggga    83100 ggaactggag  aggagcaggg  agcggctctg  agttgagcaa  ggagctatcg g  gggtctgag    83160 cagtggacga  agctcccgct  cccatgtggg  tgggggagac  tcagccttgg c  acattcccc    83220 ctcgcagtct  gtgggcatct  ttggagactt  caggaggaca  gcagttctgg g  agggctatg    83280 gcagaggaaa  ggggctccca  tgggggtagg  ttgaggtgag  tgtgggctat g  gggtcccgc    83340 aaagccgggg  gagggcaggc  tgcagagcaa  ggtgccgagg  ctgcctaaga a  ttgagggtc    83400 cttggaagcc  ccagtgcttg  ggggcatctc  ggcttatcaa  gattggtcta t  cccagctca    83460 gcctctgtct  tgtccaggc  cactaagatg  ataggaccct  cactgagacc a  ggtttccag    83520 tgtcacagtc  tccttatgtg  gagagtttta  cccaggcagc  atgatcgttc t  gaaatcata    83580 cctgaccatt  accgtccctg  ctcaaatccc  tcccagggca  ccccctgccc t  caggctcaa    83640 gcccagctcc  atagggccct  ggccctgtc  tagccttgct  ctcggctgtc c  agtcacacc    83700 aacctccttg  tggccatacc  tttcagcagg  cacacaatct  tctcgcctcc a  agccttcac    83760 aattgcaatt  ccctggacat  ccttttcctgt  ctgcctcgat  aacctctgcc t  gtccttag    83820 gactcaactc  aggtgtctcc  ctctacagga  agccttctct  gactccatca c  accctgcac    83880 ctgagtgggc  tggggcctgc  tcttcctgcc  tttggcagag  ctctcatctc c  cgactgaag    83940 cgtgggtctg  tacgttgatc  tctgcgtgtt  cttggcctcc  tcaagtgagg c  atatgtctg    84000 accctctgc  tcatctcagc  cctcagcact  gaacctgacc  cagaaggacc c  agtgaaatg    84060 agagacttta  agtagaatgc  tccccgaggt  ttttcatcta  gaacacttat t  cttgctctg    84120 ccatggagaa  tggattgaag  agacccagct  aggaggctag  aggcttgggg a  gaggctgct    84180 tcagggttca  gggaaaaggt  gtctccatgt  gagctgggca  gtggcttggg c  atagagagc    84240 agaggacagt  tgtgagagac  aactgggagg  tgactcactg  atcggatggg g  gaggtgagg    84300 aaagaaggca  ggttttttgga  caagccgtga  aggacctggt  ggatggttgt g  ctgctttgt    84360 tgtgaggtgg  agggagtgga  gataataatt  cagatggtat  gggggtccct g  ggccacctc    84420 aggacgtgg  tggggaggct  ccaggtggcc  tttgggtatc  tggggtctgg a  gctcatgag    84480 tgagggctgg  agagtcatga  ggccgtgagc  acagaggagg  ggttttgtgc a  aaagagaag    84540 aaaggctgag  gacagattcc  ttcatcaggg  tcctgggaaa  gagaggccaa g  cagctccag    84600 tccagggtg  ggaggggaaa  tagttgggag  tcggcaggat  gaggctgcag t  gcgcactga    84660 ccagcaacgc  aaggaccagt  gccaccttgt  ggcctccggt  taaccagatt g  tctgaggcc    84720 aaggagctgg  gcagggtttg  gccaggggtc  acccctgcc  tccgtgaagc c  tcagccttc    84780 atcagtttaa  tcatcaggaa  acgtggctcc  cgttgccctc  ctgccaccct a  cgtccctct    84840 ccttcccggg  gtgactggca  atgtgacag  ccggaactg  gagcccagca c  ttcaggaac    84900 cttaaaggtc  ctgggtgtag  gggctggaag  gtgggagaca  ccaccggttc c  tgtagatcc    84960 tggattactt  aaagtggcca  ggaaggaatg  ggtttggttc  agaatgctgc g  tgagcttga    85020 acgagatgct  caacctcttt  ggtcctcgat  ttgtctagag  tctctgacct a  gtgatctcg    85080 tgacttgcag  gccaccccct  ccttttcctc  atgtgaccctt  tgctgggctt c  ccttagtga    85140 ccctgtatgc  acacagttcc  ccaagtttct  cttctgtcca  ggccaggcag t  tcctacaag    85200
```

```
cacaattaag tggaggcagc atgagggatg aagaacccag gacaattaat c atcaaggag   85260
tgacatttgg tgcaaacntc aggtgcttaa ttaagcggga tgagccagag g ctgggggt   85320
agaggaggtg ggttgtgtgg tgggacagag agaaactcat tcttcccata c caacctccc  85380
ctgccttggt tcccaccacc cctctgccac tgtcataccc tgccactcac a cctgccccc  85440
tgttcaaagc tcacacctcc acaggtattt gggaaggttc cagcatagtg g ttagaccta  85500
gccctggtgc cacctacctg ggttcaaatc ctggctctac cgcttattca c tgtgtaacc  85560
ctgggcaagt gaattagcct cttggtgcca tagcttctcc atctgaaaat g aagatatct  85620
aattcataga attgctggga attctgagtt catctatgtg agttgcttgg g ctgtgcacg  85680
ggacatagga aatggccaat aaactttagt tatgatgatt acctcctgtg c ttagcacta  85740
aaagctgatc aacaattgtt ttctgaggat ggtgacaggg agggttcttc t ctctccacc  85800
ctagttctcc ttgggaagat cagagaggtc aggtcatgtg cctaaggtca g attgtagca  85860
ggcagcctag ctttgagccc ctgcattcac ttcctctgct ctcccactgc c tggaagatc  85920
tgcactgggc cccacccgag cctttaccag caagggcac cagagccaa a ctgtggctg   85980
cctgtttctc cacatagggt ccagggtccc ctactttttt acttgtgctg t catcgtgtc  86040
caacctgagg caggtcagct tgcccagatc cttgcacatg tgcagggtcc a aactgtcct  86100
gtgttcccag gccaggcctc gttcctccct gagtcggggg ctctcaaggt g gcatcatgt  86160
cctcttttca gggaggctat catctcccag aagcggctgg gctgcaatgg g ctgggcttc  86220
tcagacctgc caggggaagc ccttggccag gctggtggct ccactggctc c tgatacca   86280
aggtaagggc taggggctgg gcaggggcag gggcagggag ggactgtggc c cctgcactc  86340
caggtcatgt gtgtcttcta ttcctcttca tctctggctc cttnnnnnnn n nnnnnnnn   86400
nnnnnnnnnn nnnnnnnnnn nnnnnnnnnn nnnnnnnnnn nnnnnnnnnn n nnnnnnnn   86460
nnnnnnnnnn nnnnnnnnnn nnnnnnnnnn nnnnnnnnnn nnnnnnnnnn n nnnnnnnn   86520
nnnnnnnnnn nnnnnnnnnn nnnnnnnnnn nnnnnnnnnn nnnnnnnnnn n nnnnnnnn   86580
nnnnnnnnnn nnnnnnnnnn nnnnnnnnnn nnnnnnnnnn nnnnnnnnnn n nnnnnnnn   86640
nnnnnnnnnn nnnnnnnnnn nnnnnnnnnn nnnnnnnnnn nnnnnnnnnn n nnnnnnnn   86700
nnnnnnnnnn nnnnnnnnnn nnnnnnnnnn nnnnnnnnnn nnnnnnnnnn n nnnnnnnn   86760
nnnnnnnnnn nnnnnnnnnn nnnnnnnnnn nnnnnnnnnn nnnnnnnnnn n nnnnnnnn   86820
nnnnnnnnnn nnnnnnnnnn nnnnnnnnnn nnnnnnnnnn nnnnnnnnnn n nnnnnnnn   86880
nnnnnnnnnn nnnnnnnnnn nnnnnnnnnn nnnnnnnnnn nnnnnnnnnn n nnnnnnnn   86940
nnnnnnnnnn nnnnnnnnnn nnnnnnnnnn nnnnnnnnnn nnnnnnnnnn n nnnnnnnn   87000
nnnnnnnnnn nnnnnnnnnn nnnnnnnnnn nnnnnnnnnn nnnnnnnnnn n nnnnnnnn   87060
nnnnnnnnnn nnnnnnnnnn nnnnnnnnnn nnnnnnnnnn nnnnnnnnnn n nnnnnnnn   87120
nnnnnnnnnn nnnnnnnnnn nnnnnnnnnn nnnnnnnnnn nnnnnnnnnn n nnnnnnnn   87180
nnnnnnnnnn nnnnnnnnnn nnnnnnnnnn nnnnnnnnnn nnnnnnnnnn n nnnnnnnn   87240
nnnnnnnnnn nnnnnnnnnn nnnnnnnnnn nnnnnnnnnn nnnnnnnnnn n nnnnnnnn   87300
nnnnnnnnnn nnnnnnnnnn nnnnnnnnnn nnnnnnnnnn nnnnnnnnnn n nnnnnnnn   87360
nnnnnnnnnn nnnnnnnnnn nnnnnnnnnn nnnnnnnnnn nnnnnnnnnn n nnnnnnnn   87420
nnnnnnnnnn nnnnnnnnnn nnnnnnnnnn nnnnnnnnnn nnnnnnnnnn n nnnnnnnn   87480
nnnnnnnnnn nnnnnnnnnn nnnnnnnnnn nnnnnnnnnn nnnnnnnnnn n nnnnnnnn   87540
nnnnnnnnnn nnnnnnnnnn nnnnnnnnnn nnnnnnnnnn nnnnnnnnnn n nnnnnnnn   87600
```

```
nnnnnnnnnn nnnnnnnnnn nnnnnnnnnn nnnnnnnnnn nnnnnnnnnn n nnnnnnnnn   87660 nnnnnnnnnn nnnnnnnnnn nnnnnnnnnn nnnnnnnnnn nnnnnnnnnn n nnnnnnnnn   87720 nnnnnnnnnn nnnnnnnnnn nnnnnnnnnn nnnnnnnnnn nnnnnnnnnn n nnnnnnnnn   87780 nnnnnnnnnn nnnnnnnnnn nnnnnnnnnn nnnnnnnnnn nnnnnnnnnn n nnnnnnnnn   87840 nnnnnnnnnn nnnnnnnnnn nnnnnnnnnn nnnnnnnnnn nnnnnnnnnn n nnnnntctg   87900 ccccacctcg aataggtagg atgaagccat tggcccagtc agcagctttc t gagggtgt    87960 gcaagcccct gctggactct cagccccat aaggttagaa ggcccagcct t tggcgtacg   88020 cagcactaac cttggtttct ctttgggatc ctccagatgg ggtggggata a tgtccagga   88080 gggcatgaac caagtgaggt gtgaagagag atgctgcgga gggacagatg g acataaggg   88140 cctgaccaat agagatagtg tggaaaacta gccagagatt tggagtggct g gagctgggg   88200 gccttgagga gagaaaggcc atggtcaggc cagccagacc cagggctgag g ctgggcgga   88260 agacaggcag ctaggggggc tttctggagt ggctgaggaa ggagtgttag t gggaagtgg   88320 tggatgctct gccagagccc cagaacccag acaagcctcc ctctgcagcc c ctcgaggag   88380 ttcccagggt ttctgctccg tggagggat tgtggaagtg cagagcctgt g gggacggga   88440 ttctgccgct ctttccgttt cttctcctgt atggaggtgg gggttcaaac t cgttctatc   88500 ctagtaacca aaggatgagt tccccaaatt gctattattg ggggtctgct t ctgtcgagg   88560 gggctgccat tccagtaaag gcaggcttg ggggcatgga cagataaatg a gcaggtgtt   88620 ggttccccgg ggactcctct ccagctcatt aaaatggaat taaacgcttc c caggcgcct   88680 gacctttctg agctgctggc aggagagggc agtgggagtc agggatggct g agaggggag   88740 gagaggggg agggagggga gggtacttg gctgggtctc ctctgcaccc a tcttcctga   88800 ctgagggagc caaggccgct gcttggtttc tccgcaagct gctccccca c cccggttt    88860 ctggaacgga gctgctgttg cacggagttc tcaggggtc gcctcccct a ttctttgct    88920 cttggtctgc cccagggctg gtcagctttg aggggcactg aggtgagggg c tgtgtgcag   88980 aggtggggat tgggaggtgg tggctgggtc acgcacctcc ttctctgctg a gggcaaagg   89040 gcctggggtg ccaggtgcct gagaaggact tccttagatt gaggctatga g gactgggtc   89100 aggagggaag taaggggaag acatttggaa ggttgcttcc cttgtgggcg g aatgcttgc   89160 catggccgct gctcaccttg gctcaggctg gccagaggc caatgtgtgt g tgtgtgtgt    89220 gtgtgtgtgt gtctcaggga cgctggtggg atcagatcac ttacacttaa c tcacccagt   89280 agaactctgt tctggtcctg cggcaggctg ggtgctggag ccgactctgc c ttcagggag   89340 ctctcagtct gggggaaggc agggacaccc tccccaccac aggccagatg a aatactgtt   89400 gccagcaggt gttctggtgg caaagcctgg agcagcaagt ggtacctcat c acagagaaa   89460 gcatttgtgt ggggccttgg ggcacaggta ggaggtccac aggcagggaa g aagggaaag   89520 gggattctag gcagaggagg aatgtgagca aggcaggaag gaggccgggg g aagggggtgg   89580 tgtgctgagg ggagagtgtg gtcctgggga agctgaagta ggggtgcatg c tgttgagca   89640 ggatgctagc cagctgggct ctggctgcca ggagttttca acaaccgtcc c ttcacctcc   89700 tcaaatacc tgggcaggga agaactcttg aaaggtgttt agattattca c atctgcctc   89760 tcctctaagc ctgcaccttc ccactcatgt gtaaatgcac ttccctagga t gccccctcc   89820 ccaaggcata catgtctgac agatgcaccc tggctcacag gatctcactg c ctcccagag   89880 gtagcacagg cagccccaga cttcccagct gctgccagat cctgagggca g agggtgcag   89940
```

```
aaggaagatg gagagccaca gggtcggttg atcttttggg aaggccgagt c accagctcc    90000 ttcctggaca agccccattc ccctctctca gtctctgctc ttagtattca t ccactgatc    90060 cacctaccca tccacccct catccatcag ttgaacaact atttcttgag t acccactgt    90120 atgtcaggca tggagtgcta ggtgctggga acacagaagt gaccaagaca g attagacag   90180 gccctgcctt cacagaccat atggtctgga gggttggtgg tgagaagcac t aaagtgagc   90240 ataaccccag ctacttggga gtattccttg agctcaggag tttgaatctg g cctggagaa   90300 tagagtgcga ctccatctct aaagacaata aaaataacaa aaatactgca a aacaagtga   90360 gcaaaataag gataggatca cacgtgatgg caagtgctag caaggaaacc c ctcgaggga   90420 gtcctgcaaa ggaatgctgg ggtccagtgg cgacgccatc agcgagggct c tctgaggaa   90480 tatgctggcc aggtgcaggg ctgtgtggct gacttctggg cctttacagc t cactgctca   90540 aagcaccttg attgcaaatt ttttgtgtgg aaagtctttg gctctgttcc t taatcctgg   90600 gataataagt ccctttgagg agtggcagcc cttggtctct ggcatttgat g cctgatttg   90660 tgcccactct tccccagct gcaccagcca ccagctcc ctgcacgggg a tggggtgtt      90720 catgccatta accatttga acttggttag ggtgggggacc tgggggctgt g ctgggtttt   90780 aaccctctct tacagccaca gtgcccaatg ttgagtgttc ccactgggtc c cagacactt   90840 gccctgatta gcaagagcag gtgtaagtgt gtgttcctgt tggcgaacaa a aagccatga   90900 gtgtgtgggg gtgattgtgt gtgtttgtgt atggggggcgc caggtgcatg t gcatggctt   90960 ttgggtaagt gaactatttc ctgtgtacag gcatgaatgt gcctgtgggg a tgctgtgga   91020 cactgtaagg gtgggtgtgt ggatgtctttt gtgtctgtga ctgcaccgtg t gtgtgtgtg   91080 tgtgtgtgtg tgtaccacct ccatgggaga ttgagtgtaa gtgcatgtgt g tgagggcct   91140 gacgttcttc atgagagtgt aggtgtgtgt gtttgtgcac atgctgggtg c aagtaggcc   91200 aaggcagccc gagaactggt tgcccccaca gccttagagg ggtccagcc t tctctattc    91260 ttgagagatg ggaccaggtg gaaggaacaa gaaccacgtc ctcctccatg t gctaacagt   91320 aaaatgccaa catatttata taagccatat gcaaatgaac catagcccca g cttctcctc   91380 cctcccgccc ccgctgtcct gtaggagtca cagattgagc ctcatccaga g cttaagttt   91440 aaacaccatc cttgacagcc caggtctctt ccaggtcttc ctgcctccaa t ctccctccc   91500 tcaaattcac cctacacccc acagacagtg gccctcagat gctaaagtct g ccatggctc   91560 cccagtactc tcaggctaaa gtctaacttc ttagcctggc actcaaggcc c ttccttctg   91620 tggtaccatg gaccacaccc ctacctggat cctcatctcc ccgcaccacc t accgccagt   91680 gtcctggtct cttcaaggtc tacttgtcct ccccatgcca attcaggaag c cttccaaat   91740 gtcctcccct ctgagctacc cacctagttt tctctctcct tcctcaggta t gaggctcca   91800 cacctcctcc cagtcatgtc tccccactcg tcccacccca gacagactgt g agcttcccg   91860 agaacctgct ggtctcctcc tccccatctg ctcctggcag gagacccaga g ctgaggcag   91920 gcattggctc ctgactgggg agggaggagg aaggaggagc cccagtgca g gcgctgtgg    91980 ggagctctgc aggtggtgag cagctttgag taagctccgg aagctagtga c gcaggtggg   92040 gagccttgct ggcagggcct gtagtgggtc cctaggctgc caccctccct c cccaccgtc   92100 tctcattttc ctcgacaagc acccaagtag gagtggggga agggacttca c agagtatga   92160 aagatgggct gagttccctg gtgactggca cagggagctt ggagagggac a ggatgatgg   92220 gggtggtgga gagagtggat ctagaggggg gaaggtgtgg gcagagaacg g gagggagtg   92280 ggtggtgctg tcttcactct gccactttct gctatgtgat tttgggcaag t cactccact   92340
```

```
tttctggcca tggcttgcct gccaggtgga ggcttgcatc acagtggtga g aatcacatg   92400 taaggcaaag cacttcacga acccatttat ccatttattc attcacccgt c catcctcac   92460 catggcaggt gcatcatact gagcccattc ctttatccaa gacttagggg c agctcaaac   92520 cctaactcag acaggataga gccggaggc tgaggctaat accaccaatt c taaaatcag    92580 gacctgcagc gctccataat ctgtgagcta aaaagggtc taaggtccct c catcccctg    92640 aaccatacac ccggactgtg ctcttgatga gacagtgatt gaaaaggcag a gacaaaaaa   92700 gtttcacgtc cttaggttag tcctaggaga cttcctacag gagggattt c ctggagctg     92760 tctgagtggt cagaaagatg gggttatcac tgaggcccac agactggagt g tgtatgtgt   92820 tggtggggac cagtgtgtgc tgcgcatggg gagggcactc tggcagagac a gacactgag   92880 agaggtcaca gctagttccc ttctcccatc cctccaggtg cactgtggcc a gctgagtga   92940 taatgaggaa tggagcctgc aggcggtgga gaagcatgtg agtgggagtg g ggccatgtg   93000 caatgaggct gaagacccctt atcacagctg gtgggaagat ggcctggcca g ggagctgga  93060 cagacctggg tttcagcttc ggctttgctg cttttgagct gtgtgacctt g agcaagtca   93120 ctaaacctct ctgggcctca gtttcacacc tgaaaatggg gataatgata g caccgactg   93180 acctagggca gtggtgaaac aaaactggtc aaatatcttg taaatacaca c ggttgccaa   93240 cttacaattt tcgactttt gatggattta tggggaagca accctatcct a agtccagga    93300 gcatctgtac ttagaaagaa ccctccacat aatgatactg aggctctttc a tgcctgaga   93360 ctttatgatt ttgtgactt aacaaggact tacgacttcc tgagggggct g gagacagaa    93420 atctgacatc ttgtcttgga agaatctagg ggctagggat ggagatagac c ctgtaccct   93480 cctgttcctg gaccgccgga cgctccaggg gctgtgggag cccccggggg a gccctcagg   93540 aagtagagt ccagggatga ggtgtttggg acggcggcgg ggtccctggg c ccggcaggc    93600 agagggaacg gcgggagcaa aggcaggaat cccgctgcag caagcgcagc a gcttgggg    93660 cgagcggcgc gctaaccgct cggcctgccc cagaccctgg tcgccctgcg g agggtgcag   93720 gtcctgcagc agcgcgggcc cagggaggct ccccgagccg tccagaaccc c ccggagggg   93780 acggcggaag accagaaggg cggggcggcg tacaccgacc gcgaccgcaa g atcctccaa   93840 ctgtgcggtg agggcccggc ctggacaggt cacgaggcg gggccgggca a aacttggag    93900 gggaggtggg cgggttaggc gatcccggga gccggcggcg ggcccggcgc g gagctgagc   93960 ggcgcctgag ggacccggac acggaggtgc ggaggggccc tctctctgac c ggcgcctgg   94020 cccttgcagg ggaactctac gacctggatg cctcttccct gcagctcaaa g tgctccaat   94080 acgtgagtcc ctgcgcccct gccggccacc tccccgtcct gtctccctcc g ggaccaac   94140 ttccccttga gccctccatc tcagttccaa ttacgatgtc cttccttcct c tctcctcca   94200 cccgcctgaa gagcccccgga gagggagca ggtgggagt gggggtgaccc g gatccgcgg   94260 tcaccccctc gccctgcctg tccctctctc agctgcagca ggagacccgg g catcccgct   94320 gctgcctcct gctggtgtcg gaggacaatc tccagctttc ttgcaaggtg a gggcccagg   94380 tccactgtag agcgggggcg gggctgggcg aggaactcgg gtctccgagg g ggaaatcca   94440 ttgcctttcc tttaaccagc ccctgcact ccgttcctca ggtcatcgga g acaaagtgc    94500 tcggggaaga ggtcagcttt cccgtgagtc ccgcgtctgt cttctcgttg g agtctgcag   94560 gggcggttga ggcggggtag acactcctgg gatctgcctg gagtatttgg a tcttctaga   94620 ctcttggaat ccgatggaat tatctggatc ttgggactac ttagaaatgc t gcagggatc   94680
```

-continued

```
acaacctgtg atcagcaggc tctattagga agaatctctt agcatctaca g aaaggctta  94740
cctgggacct gttcacttct gttggagtat ttctggatat ggatctgcta g aatctgttg  94800
acgagaatcc ttggagtctg cttatctctc tcgtagttag ggaagactct a gagtccttt  94860
atagcgaatt ctgccagact cccctccatc tctgctcatc aatgctgacc c tgtccacca  94920
tttggactga ctgaagggtt cttttgaaact tccagatttg agggtgggga c aggttgaga  94980
tccctgacc tggggagtac tgggccctga ctcagtctct cctcacccc t agttgacag  95040
gatgcctggg ccaggtggtg gaagacaaga agtccatcca gctgaaggac c tcacctccg  95100
taagtcatgg cctggctgac ccagagggga aagaggagac cccactgcca g ccctagag  95160
ccagggtctc tgttacagag cagcctagga atggggcaga taagacctgg g gactttcta  95220
ctgtcccatc tccatgacac agagcttcca gccttgcatg agtcccttag a actgcctgt  95280
tgcaaaatgt gatggagggc tggaggaggg aagcatactg cgccctgctt c cctgccctg  95340
acttgcctcg cctttgcagg aggatgtaca acagctgcag agcatgttgg g ctgtgagct  95400
gcaggccatg ctctgtgtcc ctgtcatcag ccgggccact gaccaggtgg t ggccttggc  95460
ctgcgccttc aacaagctag aaggagactt gtgagtcttt gtgggatgat g cagatcagg  95520
agatgtcact gagaggctgg ctagggctcc acgagggtaa caatgtggga t gggtactgg  95580
gcagggcta ctgtctcagc agcagtgggt tgaacagtgt gttagtgcaa g agaatgaaa  95640
gtcatgttga ggtccaagct agttcctctt ctcttctcct gcttcctgaa g tttgggtaa  95700
tctgctcttg gggtattggg ttccctccct tgccatccct gttttttgcat t actgctata  95760
aactgctaga tggaggggtg ggtgtgctct gggttggatg aaccctctgg g acccacaaa  95820
gcatcatcaa cacagtggac agtggctaaa gggaatatgc ttggggactg g gaaaagctg  95880
tggatctttt gagcccctga cagggcagct ataaaaatga tacacaaaaa t ctcttttt  95940
tgtgggcagg gcacagtgga caggaaagca ggcttggagg cttagttgga a aggatatct  96000
cgagaactga ggacaaacct ggggtctaga aatggtgtca taaataaatt t catatccta  96060
caccaactca taaacaggca gtaggtgcct gaatttatt gcaaatggat c ttagttcag  96120
ggagaaacag tgctgcgtct gatgagccat ttctgtcctg ggtgcaggtt c acacttggg  96180
ctggcaggat gagcagtttg tgctgtgtca cataggtggg gagaagtaga c agatgaggg  96240
gctgagtcct gatgcaaaga gatgctgata ggatgctggt ctctggagtc c aagcaaaca  96300
ggctgggttt cagggcctgg agctcctgca ggaggtggac actagagagc c tgggactag  96360
gtaggtgtca gagcccgggc ctgaggtctg ctggggtagg gtggagatcc a ggagtccta  96420
ggtctgagct gcagaaccta ccagcatgga actgtgttga cagttgggtg g gcctggaga  96480
aacaaagata ggggcaaggc agaatcagct gaggcaggga gaatgtggga t tggtggcat  96540
ttggaacttg tgggcatcct aatggtggga gaatttatgc cattcagcaa a caaatattg  96600
agcacttaat gttgccatcc cagtgctgac cagatggcct tgggaaggcc t ttggggaag  96660
ggaaggtaga gtgaatgggg gtccagcagg ggccatgact tcttgctgct g gctgtgaga  96720
ttgggttcta ggatggcccc agagctggag aagaggtggt atcagcagga a ataaggatg  96780
gggccttggt ggcagctttg aggcccaggg caggggcagg gctatctctg g gtcccacgc  96840
atttcaggga gtgagtgttg aatgactgca tgagccaggg tggggctcag c tcagtgcag  96900
tgactacaga gaagcttcct gaaacacagc taagtagcca gagaacaggg g ctccagaag  96960
cccttcagct gtgagtggga tggggctggt ggcaaggcca gggataggat a cactgacga  97020
cattagcaaa gacctccgaa gtgtttcctc tgtaccaggc tctgcactgg g catgggtga  97080
```

```
tatagtcatg gccccatttc ataagactca aagctcattt tcagggcata g agggaagag   97140 agtgagaagg gtattctagg ccgagggaac agtgtagaaa aaaaagcatg a aggtgtgaa   97200 agagcccaag gttttctcag aatgatgagg atctttgtgt ggctgaagct g agagatgtt   97260 ctggtttgag gggtgacagg tgggtggggc tagctgaggg accacaaatg t aagaaaggt   97320 gtgcagacag acccaggatg gtggggatgg gatctagatc cgaatcactg a tggcaagc    97380 atgaatgggg gatgccccac cagggtggag caccaaggcc agccaaaaag t ggggaaggg   97440 cttaggcagg gacacctcag ggcagcgtga tgtgggctaa ggcaggctct t cccatgacc   97500 cacaccattg gtccacccag ccccatgcag ctccccagtg acaaatcatt t ggtggccag   97560 attgaatgac gtgagcagga tttgggctt atcttgtctc accagagcta g ctccatgag    97620 caggcaagc agtcctctcc acaccaccac cctaagattt ctggaggcac c gaatcaggg    97680 ccagcggagt ccagggagag tggggtagtg acaggagctg cacaagatag g gcagtgcca   97740 ccgcccctcc ccaaggctgg aggtgtgcct ggggaagagc agaacaccag c ttgagccca   97800 ggcaatctct agtctgaggg aggagaccca gctttgggct gggtaaatcc c aaatcagag   97860 acgggaggta tggctctggt ttcaagcatc taaggaggac tggagccctc c ccttgggca   97920 gccccagtc tgcagggtca tggggtggg aagctgttcc aagggcctgt g cagtggtta    97980 tatagttggc aggtgggtac ccctgtgggc ttctgatgga acagaagtaa g gagagtggg   98040 gagagaagcc agtcttccct tccctcctga gtgagcccac ccctcctcc a ggttcaccg    98100 acgaggacga gcatgtgatc cagcactgct tccactacac cagcaccgtg c tcaccagca   98160 ccctggcctt ccagaaggaa cagaaactca agtgtgagtg ccaggtgagt g acctgcctt   98220 cagcctctct cgggcaccga ctcgctcagt tttcagcccc gagagccatt a agaagggaa   98280 atgcccatgt ctttctggac tggtggcagc ccttccccag gtggctccat a acctcataa   98340 cttgaaggct tgcagttgtt caggaccgc gccactgccc gcaggcactg t atgtgatcg    98400 ccctctagtt tcaatatgt gcactacagc aacacctagg cagctagagc t ggcgtgaag    98460 gcggctgaga cactcaggag actcctcacc tgcaccgggg ctattccctc a ctccttcac   98520 ttagtagcca aatgatataa ttagacactg acagtttctg gcttgtccag t gagccctag   98580 ggaaggaagg agaagacccg ggtgctgttg gaggcagaag gttggatagg g tgacccta    98640 caccccgacc cccctatgat ctccatttcc ttcattccag gctcttctcc a agtggcaaa   98700 gaacctcttc acccacctgg gtgagtgcac tgttctctct gcctggctgt g tgtgggcat   98760 gggggctggc atttgcagag gagaggcggg aggtcttggc agcctggtct c accctgcct   98820 ggtcttctcc cttccccaga tgacgtctct gtcctgctcc aggagatcat c acggaggcc   98880 agaaacctca gcaacgcaga gatgtgagtg actctaccca ggggacaggg c gagagaggc   98940 tgtggccttc agtccccatc atctcctttc ctgccccacc cacttccctt t ctctgcctt   99000 ctgcgggact tcatcacctt ttgagggatc ctttatttca tgcctgtctc c ctcgctaga   99060 ctgtaggctc aatacagca gggacagggc tggctttgga tcctcagctc c tatcacagt    99120 gcctggcaca tagtaggtgc ttccaaaaaa aaaaaaaca aaacacttga a tggacacgt    99180 ttctggagcc agccagccct gagcagagtg tcttaccttg gagcactcct c ccaggcctc   99240 ggaaatccgg cctttgcctc cttatgggac gtgagggcga tcagagggggg t tgtcaggcc   99300 ccagaggacc aaaccctcc ctccacagct gctctgtgtt cctgctggat c agaatgagc    99360 tggtggccaa ggtgttcgac ggggcgtgg tggatgatga ggtgagaggc g gtggaggga    99420
```

```
gtatgtggcc ctagggtgt ccgggagtcc gccggcggcg ctgggagcg g cccgaggtt  99480 taacagtccc ctctgtggcc gggtcactaa cttcttcctc tcgactccat c tctgctccg  99540 gcagagctat gagatccgca tcccggccga tcagggcatc gcgggacacg t ggcgaccac  99600 gggccagatc ctgaacatcc ctgacgcata tgcccatccg cttttctacc g cggcgtgga  99660 cgacagcacc ggcttccgca cgcgcaacat cctctgcttc cccatcaaga a cgagaacca  99720 gggtgcgcgt ggcggcccgg gcggaggggc ggggcctgcg ccgggcgggg c gggtccgag  99780 cgagcggggg tggcaacact tccccaccgc tccggcgtc ccgagcata a gggagtcgg  99840 gttccatgcc tggacgtac gtaacctgcg gaaactgcga gggcaggtcc c ggccggatc  99900 cctccctcca accgatccct ccctccaccg gtggttcctt gccctctcc c ttccccaga  99960 ggtcatcggt gtggccgagc tggtgaacaa gatcaatggg ccatggttca g caagttcga 100020 cgaggacctg gcgacggcct tctccatcta ctgcggcatc agcatcgccc a tgtgagggc 100080 ggggttggga gtggggtgtg gggtgatagg gggcggggcc cacgaaggac c ctcggttct 100140 cctcctccga ctgactctcc ttgtggattg atcccttggt ctggcactca g agtcccgcc 100200 gctggggtgc agccttcagg acacgctggc cacctctggg ctcagtttcc c atctaaaaa 100260 ttgggcatac gatttcctgc cctgtccact cagcctcctg ggaccatgag a aactcccgt 100320 tgtcaaaacc tcctctcttc cctggaagca gtctcaaccc aagccgagtg c ttttttgga 100380 agtgctgggt ctcggtgtcc aggcctactg gcgctctggc ctgggaatcc a gccccaagg 100440 tccctgacat gatcccctcc ttgcttctcc ttccctgcca tgggccttgg g ctccatcac 100500 tgaagcctgg atcaggtgtg ggggagtgca aagggccaga ccaaatgctg g gagaacttg 100560 atgaggagga accggcgcgg gggtctggat gaaagtgggg gtgaggtctt t actgtggac 100620 tggagcttga aggttttgac tggggccaga atgggacagg aagtgggtg t cttttgac 100680 cccttcatcc cagtcctggg cattgctaaa ttttcacagc caccttcctt g agccccatc 100740 tttccctctt tccctagtc tctcctatac aaaaagtga atgaggctca g tatcgcagc 100800 cacctggcca atgagatgat gatgtaccac atgaaggtga ggcttgcaga g acctctggt 100860 cctcctccca gattccccgg ggacccaggg ccaggcaggg cttcctgatc a atctctact 100920 gaggatgaga ggataggccc agagccacag caggcctcct gccctcctta g gggcagctc 100980 ccacccctgc ttagagacct ctcctccaag ctgcttctga gctcagtccc a aggctggaa 101040 gtagccagag gaaccagccc agggagtaat tggttcagcc aggtattccc c atgttcagg 101100 gaataattcc catcttggga attactgagg gctaggaagc tcacccagga c ccgtcccca 101160 tggcttccct aggtacaatg cccatgcagc cctgggcagt cttaattgct g ataatctat 101220 cccattccct accctgggtc acaaaagctg gcttagttcc atgtatatgg t agtcgctgt 101280 tcatttggac atttcctctc acctgtgtcc aaaccagaga ggcccagacc t tgtgagttg 101340 gatcaaaact gtagtaggaa gagttaaggt tagagagtag aaaggtctcc a caaaggag 101400 gactgctaca gttactgtgt atgaaatgct gccatggttt ggggggtgtca t gaagggtg 101460 ttgtcgatct ttgccaaggt tatgctgtta cagataaagg gtggtcacct g caggaaggc 101520 gcgcggggtg ggctgcaggg ctgtgagggg agggtggtga tttcctgccc a gttacagtc 101580 cacacgcgtgg tgcccaact gtggtacatt ctgggtgacg gatcccccac c tgccatggg 101640 aatttgaggg tgaagacacc agatggggtg aaggctgtct tctaatgctc t ggctggtct 101700 cctctaggtc tccgacgatg agtataccaa acttctccat gatgggatcc a gcctgtggc 101760 tgccattgac tccaattttg caagtttcac ctataccct cgttccctgc c cgaggatga 101820
```

```
cacgtccatg gtgagttgct ctcctccact tgactggcca ggccgaaggt a tgtagccag 101880 aggcttaagt taaatgcgca tcaagaactt cctgggaaga cagagtcatc a aggaaggct 101940 gtggagggtc cctcagagat ggaggggctt gtagtctgcc atcaggaagc c atgggcct 102000 gcccagggc tagaggctgg actggatgat cccaagggct gctcttggac c aaccatgcc 102060 cagggcatgt gacctcaggg tttgcatccc tcccaaccct gttttctaa c attttgtgt 102120 gggcttggtt tcaagagttc ttagttctta gatctctaaa aatgcatagc t ctgagaacg 102180 gttgcttcaa ctattttgtg gttctctagt ttagatgtaa gttctaaga c ccagatct 102240 tgagtgtgga gcttgaagaa ggacccaggc aagggccctg tcttgatact g gcagcccct 102300 ctgataccte cctctgccct ctccaggcca tcctgagcat gctgcaggac a tgaatttca 102360 tcaacaacta caaaattgac tgcccgaccc tggcccggtt cgtgcgccca c agacagccc 102420 cagtcttcgc ctccctcttt cctctactgt cacatccatt gcccccggca t tctggagag 102480 gatctctcta aggatgactg gggagaccca gtcttatggg ggtggggagg a tccatgaat 102540 gagaagcaat tcctagacac tgaactgtca ataaaggcaa gaaatgaggc a aggcaaagc 102600 ctggaggcaa ggccgagagt gtgtagccag aggtttaagt tagatgtgca t aggaacttc 102660 ctgctaagac agagtcatca aggaaggctg tggagggtcc ctcagggatg g aggggacat 102720 gtagtttgcc atcatggggc cgtgatggag gaggagaggc tgaggcccct c ttctgccct 102780 cttccctccc ccaggttctg tttgatggtg aagaagggc accgggatcc c cctaccac 102840 aactggatgc acgcctttc tgtctcccac ttctgctacc tgctctacaa g aacctggag 102900 ctcaccaact acctcgagtg agtggctgca tctcccccac atctggcagc c actggggtc 102960 cccttccctg ggacagggaa gcaccccctg tgtgtcaggc actttacacg c actgcctca 103020 tgggatcttc ttagccccag gggactagag gggaaggctg tgagccccat c ttccaggag 103080 gggcttgctc acagccaagc agctagtgaa gactgagcct gatttaaacc c gggtctgct 103140 ggactccaaa ccagtgcttc tttccaggaa gggaacccag gtgttccaac c tcctgtccc 103200 agtggctcct gggcatgtca tctcctgtct gtcctcttgg ggatttaggg a gggaactgt 103260 gggctgacct ctttttttc tcctttctgc ctctcaacca gggacatcga g atctttgcc 103320 ttgtttattt cctgcatgtg tcatgacctg gaccacagag gcacaaacaa c tctttccag 103380 gtggcctcgg tgagaccctg ccctgctcac agtgggggacc ctccatgggg t gtcttggat 103440 ctcatcctct cccagcctga atagggtggg agcgagtgag accaggagcc a ggtttagac 103500 acaggaggag gttcccccag ggtttgcccc tggctctgag atagggagga g gggagaaag 103560 gtggaagggc aggacactgc tcagcctaaa gcagtggcac ttgatccgg a tgtgaggag 103620 tgaccacagt tttcctgggc ttttccagaa atctgtgctg gctgcgctct a cagctctga 103680 gggctccgtc atggaggtat cactcttctg tcccaccccg tccttcttcc c ctttaaggc 103740 cagtgacttg caaagttatg acccagctcc tcctattccc aaaccatgct c tccagacag 103800 gctgcgagag ctgcagccac acctaggaca tgtctggctc attttcctgg a gtgggcttg 103860 gaagggtgca ggtgcggatg atagcaagga tttgtgttca gcgtgttcc c tttggctgc 103920 ctgggaacac cccattcagc ccctcctgc caaacttggg atgggctcca c tcccatcac 103980 ttagcgtcac cttagattgt ttggtttggg tctgcctacc tcctcgtgca c aaggtctga 104040 gccatttctg agttccctgc acttggcaca gggcttggca cagagtagga g acacatttc 104100 caaggtcacc ttgcctcatg ctacttccca caacacctct ccagaggctg c ccctgcttg 104160
```

-continued

```
cacaccccca gagacgaggt tctctgtctc tctcccagga ggcctggtgg c agtgctggt 104220 tctgccctct gcccccctga gataagctgc tccttttctg agtgacagcc c ttcagcatc 104280 cggaaatggg ggccttgccc ttgcctcatc actgcctctc cttgtcagca a acaaatgtg 104340 ttctgcatga tttggtgtct aggactccaa aggatcattt caaaaatgtt c cagctttca 104400 gggaccccag agcttacctt gttgggtccc tgcatgtgac agctgaggag t ctgaggctc 104460 agagtggtct agggactcac cctgggtcac acagagggtt gaaacagagc t cagaaaggg 104520 aactggggcc cctgactccc cctttctgac tgctctgctt acctggggc t ggagctgga 104580 cgaggcccct gcttcctctc ttggggtcaa tggtaaggga gcccatctgc c ccagctggg 104640 cccccatcac tcctctcccc ccagaggcac cactttgctc aggccatcgc c atcctcaac 104700 acccacggct gcaacatctt tgatcatttc tcccggaagg tgatggggtt g ggggtgggg 104760 tggggattga gggggagctg ggagctggct ggaggtggga taaggagcca a ggagtggag 104820 gctcactggg atgggcaaat gggtgggggt gtccagtagg agggcatgac a cccctgccc 104880 tcgcctcagg actatcagcg catgctggat ctgatgcggg acatcatctt g gccacagac 104940 ctggcccacc atctccgcat cttcaaggac ctccagaaga tggctgaggg t gactgctgt 105000 tagccccagt ccttggggct ggggaggaac aaccagggga aggatttgcc a ggggagcat 105060 tcccagggtg cagacccatc ccctgcaaca tcaacccttc tctggctgca c ggccccccc 105120 caggcagacc cagcactggc cccttggctc ccatcaaggg tgcccaattc c ctggaccgc 105180 tctgggttgg gccctgggag ccttgtcctc agaagggcaa agaggctggg c cccgctcct 105240 tgacccccatc ctcccctcaa cagtgggcta cgaccgaaac aacaagcagc a ccacagact 105300 tctcctctgc ctcctcatga cctcctgtga cctctctgac cagaccaagg g ctggaagac 105360 tacgagaaag atcgcggtag gtgtagtcct ccctgggaag gcacaggctg c ccaccctgc 105420 ccagctttgg gtgcccccctg tgcctgaata ccctctctct gctcagctca g cctggctgt 105480 gttctgggga gacagaaacc tagaccatct cagggtgaca aatggagact c agagagggg 105540 aacagaccta gcaagtcagt ggctggtgga aagtgggccc caacccagcc a ctccctgcc 105600 tcaggccatc ccactgccaa gctgggctg gtggggacgg ctcctgagct g ggactgaat 105660 ccctgggcct cagttttctc tcctgggaac gggctgtcag aggagcttgg g tggatgtat 105720 cctacataga ggatgtgatg agagtgttgg cctttcagga gctgatctac a aagaattct 105780 tctcccaggg agacctggta tgtgtggagt gaccccagga tgtccaggat g ggggagggt 105840 tcctggcctg ggacagggag ggcttgaact agcctgaccc tggtacccga t ggaggaatg 105900 agagggacag gcctgacgac tcgatgcctg caggagaagg ccatgggcaa c aggccgatg 105960 gagatgatgg accgggagaa ggcctatatc cctgagctgc aaatcagctt c atggagcac 106020 attgcaatgc ccatctacaa gtgagtgagc tcatggggac aagctgcacc c tgcacagag 106080 agggtaggct ggagtgggga catcacagga aacacaggtg ctgagattgg c ctggcccag 106140 ctccaactga ttcatcccct tgcctctggg cataactgtc tcccgctgtg c ccctcagtg 106200 ggtccttcac ttcatccttg gtcctcagtg gaaagagacc atcatgcttt c ctaggtgtc 106260 ctcctctgtc tcacattctt gtggaagttc ttgttttttt tgagatggag t ctcactctg 106320 ttgcccaggc tggagtgcaa tggcacgatc ttggctcact gcaacctccc c ctcctgggt 106380 tcaagcgatt ctcctgcctc agcctcccaa gtagctggga ttacaggcat g caccaccac 106440 gcccagctaa ttttgtattt ttagtagaga tggggcttca ccattttggt c aggctggtc 106500 ttgaactcct gacttcaggt gatccacaca cctcggcatc tctgagtgtt g ggattacag 106560
```

-continued

```
gcgtgagcta ccgtacctgg cccttgtgga aattctattt gttgtgtagc c ctagtcttt 106620
cttgctgccc atggtctgat ttctggcctc tcaccctctg ccccatgca c ccgcaggct 106680
gttgcaggac ctgttcccca aagcggcaga gctgtacgag cgcgtggcct c caaccgtga 106740
gcactggacc aaggtgtccc acaagttcac catccgcggc ctcccaagta a caactcgct 106800
ggacttcctg gatgaggagt acgaggtgcc tgatctggat ggcactaggg c ccccatcaa 106860
tggctgctgc agccttgatg ctgagtgatc ccctccaggg acacttccct g cccaggcca 106920
cctcccacag ccctccactg gtctggccag atgcactggg aacagagcca c gggtcctgg 106980
gtcctagacc aggacttcct gtgtgaccct ggacaagtac taccttcctg g gcctcagct 107040
ttctcgtctg tataatggaa gcaagacttc caacctcacg gagactttgt a atttgttct 107100
ctgagagcac agggtgacc aatgagcagt gggccctact ctgcacctct g accacacct 107160
tggcaagtct ttcccaagcc attctttgtc tgagcagctt gatggtttct c cttgcccca 107220
tttctgcccc accagatctt tgctcctttc cctttgagga ctcccaccct t tggggtctc 107280
caggatcctc atggaagggg aaggtgagac atctgagtga gcagagtgtg g catcttgga 107340
aacagtcctt agttctgtgg gaggactaga aacagccgcg gggcgaaggc c ccctgagga 107400
ccactactat actgatggtg ggattgggac ctggggata caggggcccc a ggaagaagc 107460
tgccagaggg gcagctcagt gctctgcaga gaggggccct ggggagaagc a ggatgggat 107520
tgatgggcag gagggatccc cgcactggga gacaggccca ggtatgaatg a gccagccat 107580
gcttcctcct gcctgtgtga cgctgggcga gtctcttccc ctgtctgggc c aaacaggga 107640
gcgggtaaga caatccatgc tctaagatcc attttagatc aatgtctaaa a tagctctat 107700
cgctctgcgg agtcccagca gaggctatgg aatgtttctg caaccctaag g cacagagag 107760
cccaaccctg agtgtctcag aggcccctg agtgttccc ttggcctgag c cccttaccc 107820
attcctgcag ccagtgagag acctggcctc agccctggca gggctctctc t tcaaggcca 107880
tatccacctg tgccctgggg cttgggagac cccatagggc cggactctt g gtcagccc 107940
ggccactggc ttctctcttt ttctccgttt cattctgtgt gcgttgtggg g tggggagg 108000
gggtccacct gccttacctt tctgagttgc ctttagagag atgcgttttt c taggactct 108060
gtgcaactgt cgtatatggt cccgtgggct daccgctttg tacatgagaa t aaatctatt 108120
tctttctacc agtcctcccc catggggctg tttgcagact ttgtgcttgg g gtgggtgga 108180
gggggggaat agaactggga gaggcaaacg ccctttggaa ctccatggct t ccagggtcc 108240
tccacccttg gtgcctagcc ccccttctgg ggaagtcata gacctgttgg g gtactccct 108300
aggccagatc gtggaggcta aggggtgggt ggcagatgag aaggcctggc c atggagcag 108360
tgatgggaca tgttggctgg cagagattgt agaatagagg aaaaacaaag g ttgaggcaa 108420
gcaggcaggc tgcctggagg aggtagcctg gagcttgtcc tagaccctcc c agcgctggc 108480
ctgccctggt catgagtgcc catacggcga gggcctaggc ctctgaactc t gtttctagc 108540
tgcagtgatg cctggctgtg tcccaggaag tcccacatcc cagttactct g agtcctgcc 108600
gaaggtgcac gcctgagtca gactccacac cagatccagc ccgggttgt g tctgaggag 108660
ttgcgtctgt tcctctgcat gagagtgttt acttccgccc agtccaagat g gcagactg 108720
caggttgggg ctacgcggag gctctgcctg gcacagtctc cagaccctgt c ccgacttg 108780
cctaccccc tctgagctcc tctccgtgtt catctcttcc tggtcagtaa a ggttgatgt 108840
gttaagaggg tgggcactgg ggtctccttt cttggtggga gcaggaagga g atggacagg 108900
```

```
gccatcctgt gaccatcagc cattgccagc tttgcctttg ggaccacaga g cccatctgc 108960 ttcctctgca gctcccccctg ccccactagc ctgtctgggt ttggaatctg c tcctctggc 109020 tgaatggtct ccaggtttcc agcttcccctt agcgtcatgg ggctccaggc t cctcccatt 109080 cccagctcct gctgtgggct ccccaagtcc gtctctatcc tctcacagca c aggacccag 109140 gcttggccag tgggtccccg ggtgggggtg ggagtggtca gtttgtggcc c acggccaat 109200 aagagatggc tattctaatg gtgcctggct gaccccaggg tcactgtggg c tgatgtagc 109260 tgctcttctg cctgacccct gaccctgagt gtgtgtgcgt gttcctcttc c acaactctt 109320 caggcaaaga gaaccttgac cctgcatctg tctgtcccca gcccagccct c ctttgaggc 109380 tcatgctgtg acacatccct gttttttcacc aaatggaggg aacaaccaca g atatttcct 109440 tgtgcacgca ggaccctgtg ctagggctga gggctttgtc tttgtcctgc t ctggaaagt 109500 ctcacagttt gattggagag ctagatctaa actcagatgc aggccatgac a acgctgtgg 109560 ggtgcccggc catgggctc caggcaggat cataaccctg agaacaacaa t gaggtttga 109620 aagatgagca gatgttgttt ataggcaaaa ggggacaggc actcctggta g aagaaactg 109680 cttttgcaaa ggcctcgaga acagaaggga ctggcaggtg gaggagccga g agatggagg 109740 aggaggcaag gccagatcct gaagggcctt aaatgccagg ttgtggagtt t ggctttatt 109800 ctgtgggcag tggagaacca gagaaaggtt ttcagtagga gagtgactca g aagtgcatt 109860 ttagaaagat cccctggag agcagggaag tgactgcaag gggagagggt g ggcagggat 109920 tattctatgg gtgatgtgct gtgccctggg ctgggcgagg agaggaattc g gagatgcta 109980 ggttggcaga acatggtgac cagtgggtcg ggggatgcag agggaggact t ggaggggcc 110040 ctgggaggtg gggtctatgc cactccatga agagctgtgg gggctctgtt c agcatcacc 110100 ctcacccaca acaggtattg ggtggagcct ctggcagggg tgagctccct g caaggtga 110160 gcaaaacagc tatctgagga tgcccaggga ggagaggtgg gaggaaggga g agaggacag 110220 atgggaggag gctctgcaca gagcctgagg acagccctca ccaggttaca g aacacaagg 110280 cttgaccccca ttggcttcct gtagctgtcc tgctctccca acttaatggt t tcattttgc 110340 atttttattta aatttcacaa tgattctagc agataccatt agtctattct g cagccaagt 110400 tgtctaaggt ttggagagagt taagtaatgc accaaggtta ggatttgagc c ctacctgtc 110460 tgattcccct ccgagagctg tctgattcct ttctcctcct ctgggatagg g aaggagac 110520 tcagaaggac gggtctcca tcttcagtct ttgcaagact attgtagggc a ttgggatgg 110580 tgagcacaaa gtgggttgaa gccccagaga aagagctgag agctgggatc a actgtgtgt 110640 gtgcatgtgt gtgtctgtgt gtgtgtgagt tggagtaggg ggcagggaga a aagagtggg 110700 gtggtggtgg cttgtagtgc agctcagggc caccaggtgg tgtccagccc t cgctgtcct 110760 cacctccccca gaggtcagag aaggatatgg gaggggggtgg ggtggggtga g gggacgcg 110820 gcggggacgg ggggacggt ggttggtagt ctcactcctg tccattcacc t acaggttga 110880 gtatccctta tccaaaatgc ttggggccag aagtgtctca gatttaagat t tttttcgga 110940 ttttggaata tttgcatata cataatgaga tatcttggga atgagacccc a ggctaaaca 111000 ggaaattcat ttatgttttta tatacacaca gcctgaagca gttttatata a tattttgaa 111060 taattttatg catgaaacaa gtttgtgca cattgaagca agtgtggaat t tccacttg 111120 tggcattatg tcggtgctaa aaaatgtttt agattttgga gcattttgga t ctcagaact 111180 ttgcattagg aattgaggac taagtctgat attctgtctt acccagattc c tacctaaga 111240 ggtctaggaa gtcatgccct acaaaccata cattctcatc ag         111282
```

<210> SEQ ID NO 4
<211> LENGTH: 905
<212> TYPE: PRT
<213> ORGANISM: Human

<400> SEQUENCE: 4

```
Pro Pro Pro Pro Gln Pro Cys Ala Asp Ser Leu Gln Asp Ala Leu Leu
 1               5                  10                  15
Ser Leu Gly Ser Val Ile Asp Ile Ser Gly Leu Gln Arg Ala Val Lys
                20                  25                  30
Glu Ala Leu Ser Ala Val Leu Pro Arg Val Glu Thr Val Tyr Thr Tyr
            35                  40                  45
Leu Leu Asp Gly Glu Ser Gln Leu Val Cys Glu Asp Pro Pro His Glu
        50                  55                  60
Leu Pro Gln Glu Gly Lys Val Arg Glu Ala Ile Ile Ser Gln Lys Arg
    65                  70                  75                  80
Leu Gly Cys Asn Gly Leu Gly Phe Ser Asp Leu Pro Gly Lys Pro Leu
                    85                  90                  95
Ala Arg Leu Val Ala Pro Leu Ala Pro Asp Thr Gln Val Leu Val Met
                100                 105                 110
Pro Leu Ala Asp Lys Glu Ala Gly Ala Val Ala Ala Val Ile Leu Val
            115                 120                 125
His Cys Gly Gln Leu Ser Asp Asn Glu Glu Trp Ser Leu Gln Ala Val
        130                 135                 140
Glu Lys His Thr Leu Val Ala Leu Arg Arg Val Gln Val Leu Gln Gln
    145                 150                 155                 160
Arg Gly Pro Arg Glu Ala Pro Arg Ala Val Gln Asn Pro Pro Glu Gly
                    165                 170                 175
Thr Ala Glu Asp Gln Lys Gly Gly Ala Ala Tyr Thr Asp Arg Asp Arg
                180                 185                 190
Lys Ile Leu Gln Leu Cys Gly Glu Leu Tyr Asp Leu Asp Ala Ser Ser
            195                 200                 205
Leu Gln Leu Lys Val Leu Gln Tyr Leu Gln Gln Glu Thr Arg Ala Ser
        210                 215                 220
Arg Cys Cys Leu Leu Leu Val Ser Glu Asp Asn Leu Gln Leu Ser Cys
    225                 230                 235                 240
Lys Val Ile Gly Asp Lys Val Leu Gly Glu Glu Val Ser Phe Pro Leu
                    245                 250                 255
Thr Gly Cys Leu Gly Gln Val Val Glu Asp Lys Lys Ser Ile Gln Leu
                260                 265                 270
Lys Asp Leu Thr Ser Glu Asp Val Gln Gln Leu Gln Ser Met Leu Gly
            275                 280                 285
Cys Glu Leu Gln Ala Met Leu Cys Val Pro Val Ile Ser Arg Ala Thr
        290                 295                 300
Asp Gln Val Val Ala Leu Ala Cys Ala Phe Asn Lys Leu Glu Gly Asp
    305                 310                 315                 320
Leu Phe Thr Asp Glu Asp Glu His Val Ile Gln His Cys Phe His Tyr
                    325                 330                 335
Thr Ser Thr Val Leu Thr Ser Thr Leu Ala Phe Gln Lys Glu Gln Lys
                340                 345                 350
Leu Lys Cys Glu Cys Gln Ala Leu Leu Gln Val Ala Lys Asn Leu Phe
            355                 360                 365
Thr His Leu Asp Asp Val Ser Val Leu Leu Gln Glu Ile Ile Thr Glu
```

```
           370                 375                 380
Ala Arg Asn Leu Ser Asn Ala Glu Ile Cys S er Val Phe Leu Leu Asp
385                 390                 395                 400

Gln Asn Glu Leu Val Ala Lys Val Phe Asp G ly Gly Val Val Asp Asp
                405                 410                 415

Glu Ser Tyr Glu Ile Arg Ile Pro Ala Asp G ln Gly Ile Ala Gly His
                420                 425                 430

Val Ala Thr Thr Gly Gln Ile Leu Asn Ile P ro Asp Ala Tyr Ala His
                435                 440                 445

Pro Leu Phe Tyr Arg Gly Val Asp Asp Ser T hr Gly Phe Arg Thr Arg
                450                 455                 460

Asn Ile Leu Cys Phe Pro Ile Lys Asn Glu A sn Gln Glu Val Ile Gly
465                 470                 475                 480

Val Ala Glu Leu Val Asn Lys Ile Asn Gly P ro Trp Phe Ser Lys Phe
                485                 490                 495

Asp Glu Asp Leu Ala Thr Ala Phe Ser Ile T yr Cys Gly Ile Ser Ile
                500                 505                 510

Ala His Ser Leu Leu Tyr Lys Lys Val Asn G lu Ala Gln Tyr Arg Ser
                515                 520                 525

His Leu Ala Asn Glu Met Met Met Tyr His M et Lys Val Ser Asp Asp
                530                 535                 540

Glu Tyr Thr Lys Leu Leu His Asp Gly Ile G ln Pro Val Ala Ala Ile
545                 550                 555                 560

Asp Ser Asn Phe Ala Ser Phe Thr Tyr Thr P ro Arg Ser Leu Pro Glu
                565                 570                 575

Asp Asp Thr Ser Met Ala Ile Leu Ser Met L eu Gln Asp Met Asn Phe
                580                 585                 590

Ile Asn Asn Tyr Lys Ile Asp Cys Pro Thr L eu Ala Arg Phe Cys Leu
                595                 600                 605

Met Val Lys Lys Gly Tyr Arg Asp Pro Pro T yr His Asn Trp Met His
                610                 615                 620

Ala Phe Ser Val Ser His Phe Cys Tyr Leu L eu Tyr Lys Asn Leu Glu
625                 630                 635                 640

Leu Thr Asn Tyr Leu Glu Asp Ile Glu Ile P he Ala Leu Phe Ile Ser
                645                 650                 655

Cys Met Cys His Asp Leu Asp His Arg Gly T hr Asn Asn Ser Phe Gln
                660                 665                 670

Val Ala Ser Lys Ser Val Leu Ala Ala Leu T yr Ser Ser Glu Gly Ser
                675                 680                 685

Val Met Glu Arg His His Phe Ala Gln Ala I le Ala Ile Leu Asn Thr
                690                 695                 700

His Gly Cys Asn Ile Phe Asp His Phe Ser A rg Lys Asp Tyr Gln Arg
705                 710                 715                 720

Met Leu Asp Leu Met Arg Asp Ile Ile Leu A la Thr Asp Leu Ala His
                725                 730                 735

His Leu Arg Ile Phe Lys Asp Leu Gln Lys M et Ala Glu Val Gly Tyr
                740                 745                 750

Asp Arg Asn Asn Lys Gln His His Arg Leu L eu Leu Cys Leu Leu Met
                755                 760                 765

Thr Ser Cys Asp Leu Ser Asp Gln Thr Lys G ly Trp Lys Thr Thr Arg
                770                 775                 780

Lys Ile Ala Glu Leu Ile Tyr Lys Glu Phe P he Ser Gln Gly Asp Leu
785                 790                 795                 800
```

-continued

```
Glu Lys Ala Met Gly Asn Arg Pro Met Glu M et Met Asp Arg Glu Lys
                805                 810                 815

Ala Tyr Ile Pro Glu Leu Gln Ile Ser Phe M et Glu His Ile Ala Met
        820                 825                 830

Pro Ile Tyr Lys Leu Leu Gln Asp Leu Phe P ro Lys Ala Ala Glu Leu
        835                 840                 845

Tyr Glu Arg Val Ala Ser Asn Arg Glu His T rp Thr Lys Val Ser His
    850                 855                 860

Lys Phe Thr Ile Arg Gly Leu Pro Ser Asn A sn Ser Leu Asp Phe Leu
865                 870                 875                 880

Asp Glu Glu Tyr Glu Val Pro Asp Leu Asp G ly Thr Arg Ala Pro Ile
                885                 890                 895

Asn Gly Cys Cys Ser Leu Asp Ala Glu
                900                 905

<210> SEQ ID NO 5
<211> LENGTH: 921
<212> TYPE: PRT
<213> ORGANISM: Bos taurus

<400> SEQUENCE: 5

Met Arg Arg Gln Pro Ala Ala Ser Arg Asp L eu Phe Ala Gln Glu Pro
1               5                   10                  15

Val Pro Pro Gly Ser Gly Asp Gly Ala Leu G ln Asp Ala Leu Leu Ser
            20                  25                  30

Leu Gly Ser Val Ile Asp Val Ala Gly Leu G ln Gln Ala Val Lys Glu
        35                  40                  45

Ala Leu Ser Ala Val Leu Pro Lys Val Glu T hr Val Tyr Thr Tyr Leu
    50                  55                  60

Leu Asp Gly Glu Ser Arg Leu Val Cys Glu G lu Pro Pro His Glu Leu
65                  70                  75                  80

Pro Gln Glu Gly Lys Val Arg Glu Ala Val I le Ser Arg Lys Arg Leu
                85                  90                  95

Gly Cys Asn Gly Leu Gly Pro Ser Asp Leu P ro Gly Lys Pro Leu Ala
            100                 105                 110

Arg Leu Val Ala Pro Leu Ala Pro Asp Thr G ln Val Leu Val Ile Pro
        115                 120                 125

Leu Val Asp Lys Glu Ala Gly Ala Val Ala A la Val Ile Leu Val His
    130                 135                 140

Cys Gly Gln Leu Ser Asp Asn Glu Glu Trp S er Leu Gln Ala Val Glu
145                 150                 155                 160

Lys His Thr Leu Val Ala Leu Lys Arg Val G ln Ala Leu Gln Gln Arg
                165                 170                 175

Glu Ser Ser Val Ala Pro Glu Ala Thr Gln A sn Pro Glu Glu Ala
            180                 185                 190

Ala Gly Asp Gln Lys Gly Gly Val Ala Tyr T hr Asn Gln Asp Arg Lys
        195                 200                 205

Ile Leu Gln Leu Cys Gly Glu Leu Tyr Asp L eu Asp Ala Ser Ser Leu
    210                 215                 220

Gln Leu Lys Val Leu Gln Tyr Leu Gln Gln G lu Thr Gln Ala Ser Arg
225                 230                 235                 240

Cys Cys Leu Leu Leu Val Ser Glu Asp Asn L eu Gln Leu Ser Cys Lys
                245                 250                 255

Val Ile Gly Asp Lys Val Leu Glu Glu Glu I le Ser Phe Pro Leu Thr
```

```
                    260             265             270
Thr Gly Arg Leu Gly Gln Val Glu Asp Lys Lys Ser Ile Gln Leu
            275             280             285
Lys Asp Leu Thr Ser Glu Asp Met Gln Gln Leu Gln Ser Met Leu Gly
            290             295             300
Cys Glu Val Gln Ala Met Leu Cys Val Pro Val Ile Ser Arg Ala Thr
305             310             315             320
Asp Gln Val Val Ala Leu Ala Cys Ala Phe Asn Lys Leu Gly Gly Asp
                325             330             335
Leu Phe Thr Asp Gln Asp Glu His Val Ile Gln His Cys Phe His Tyr
            340             345             350
Thr Ser Thr Val Leu Thr Ser Thr Leu Ala Phe Gln Lys Glu Gln Lys
            355             360             365
Leu Lys Cys Glu Cys Gln Ala Leu Leu Gln Val Ala Lys Asn Leu Phe
            370             375             380
Thr His Leu Asp Asp Val Ser Val Leu Leu Gln Glu Ile Ile Thr Glu
385             390             395             400
Ala Arg Asn Leu Ser Asn Ala Glu Ile Cys Ser Val Phe Leu Leu Asp
                405             410             415
Gln Asn Glu Leu Val Ala Lys Val Phe Asp Gly Gly Val Val Glu Asp
            420             425             430
Glu Ser Tyr Glu Ile Arg Ile Pro Ala Asp Gln Gly Ile Ala Gly His
            435             440             445
Val Ala Thr Thr Gly Gln Ile Leu Asn Ile Pro Asp Ala Tyr Ala His
        450             455             460
Pro Leu Phe Tyr Arg Gly Val Asp Asp Ser Thr Gly Phe Arg Thr Arg
465             470             475             480
Asn Ile Leu Cys Phe Pro Ile Lys Asn Glu Asn Gln Glu Val Ile Gly
                485             490             495
Val Ala Glu Leu Val Asn Lys Ile Asn Gly Pro Trp Phe Ser Lys Phe
            500             505             510
Asp Glu Asp Leu Ala Thr Ala Phe Ser Ile Tyr Cys Gly Ile Ser Ile
            515             520             525
Ala His Ser Leu Leu Tyr Lys Lys Val Asn Glu Ala Gln Tyr Arg Ser
        530             535             540
His Leu Ala Asn Glu Met Met Met Tyr His Met Lys Val Ser Asp Asp
545             550             555             560
Glu Tyr Thr Lys Leu Leu His Asp Gly Ile Gln Pro Val Ala Ala Ile
                565             570             575
Asp Ser Asn Phe Ala Ser Phe Thr Tyr Thr Pro Arg Ser Leu Pro Glu
            580             585             590
Asp Asp Thr Ser Met Ala Ile Leu Ser Met Leu Gln Asp Met Asn Phe
            595             600             605
Ile Asn Asn Tyr Lys Ile Asp Cys Pro Thr Leu Ala Arg Phe Cys Leu
        610             615             620
Met Val Lys Lys Gly Tyr Arg Asp Pro Pro Tyr His Asn Trp Met His
625             630             635             640
Ala Phe Ser Val Ser His Phe Cys Tyr Leu Leu Tyr Lys Asn Leu Glu
                645             650             655
Leu Thr Asn Tyr Leu Glu Asp Met Glu Ile Phe Ala Leu Phe Ile Ser
            660             665             670
Cys Met Cys His Asp Leu Asp His Arg Gly Thr Asn Asn Ser Phe Gln
            675             680             685
```

```
Val Ala Ser Lys Ser Val Leu Ala Ala Leu Tyr Ser Ser Glu Gly Ser
    690             695                 700
Val Met Glu Arg His His Phe Ala Gln Ala Ile Ala Ile Leu Asn Thr
705             710                 715                 720
His Gly Cys Asn Ile Phe Asp His Phe Ser Arg Lys Asp Tyr Gln Arg
                725                 730                 735
Met Leu Asp Leu Met Arg Asp Ile Ile Leu Ala Thr Asp Leu Ala His
                740                 745                 750
His Leu Arg Ile Phe Lys Asp Leu Gln Lys Met Ala Glu Val Gly Tyr
            755                 760                 765
Asp Arg Thr Asn Lys Gln His His Ser Leu Leu Leu Cys Leu Leu Met
    770                 775                 780
Thr Ser Cys Asp Leu Ser Asp Gln Thr Lys Gly Trp Lys Thr Thr Arg
785                 790                 795                 800
Lys Ile Ala Glu Leu Ile Tyr Lys Glu Phe Phe Ser Gln Gly Asp Leu
                805                 810                 815
Glu Lys Ala Met Gly Asn Arg Pro Met Glu Met Met Asp Arg Glu Lys
            820                 825                 830
Ala Tyr Ile Pro Glu Leu Gln Ile Ser Phe Met Glu His Ile Ala Met
            835                 840                 845
Pro Ile Tyr Lys Leu Leu Gln Asp Leu Phe Pro Lys Ala Ala Glu Leu
850                 855                 860
Tyr Glu Arg Val Ala Ser Asn Arg Glu His Trp Thr Lys Val Ser His
865                 870                 875                 880
Lys Phe Thr Ile Arg Gly Leu Pro Ser Asn Asn Ser Leu Asp Phe Leu
                885                 890                 895
Asp Glu Glu Tyr Glu Val Pro Asp Leu Asp Gly Ala Arg Ala Pro Ile
                900                 905                 910
Asn Gly Cys Cys Ser Leu Asp Ala Glu
            915                 920
```

ISOLATED HUMAN PHOSPHODIESTERASE PROTEINS, NUCLEIC ACID MOLECULES ENCODING HUMAN PHOSPHODIESTERASE PROTEINS, AND USES THEREOF

FIELD OF THE INVENTION

The present invention is in the field of phosphodiesterase proteins that are related to cGMP-stimulated 3',5'-cyclic nucleotide phosphodiesterase 2A (PDE2A), recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods. In particular, the phosphodiesterase protein provided by the present invention is a novel alternative splice form of PDE2A.

BACKGROUND OF THE INVENTION

Phosphodiesterases

In general, phosphodiesterases ("PDEs") catalyze the hydrolysis of a phosphodiester bond. Specific classes of phosphodiesterases include those catalyzing the degradation of cyclilc monophosphates.

The signaling pathways regulated by PDEs include the transduction of photon capture in the outer segment of a photoreceptor as well as changes in neurotransmitter release from its inner segment. PDEs also regulate the aldosterone production by atrial natriuretic peptide and platelet aggregation by endothelial relaxation factor.

Experimental data have demonstrated the role of phosphodiesterases in a range of diseases, including inflammatory diseases such as asthma, chronic obstructive pulmonary disease, rheumatoid arthritis and atopy. Drugs that selectively inhibit individual PDE isozymes have a wide variety of different effects on an animals, suggesting specific roles for most of the different PDEs.

Experimental evidence indicates the existence of several related gene families coding for different phosphodiesterases, and that each of these families contain more than one gene. Furthermore, each gene product is differentially spliced in different tissues to yield different isozymes. Isolation of cDNAs for many of the isozymes has allowed a series of structure/function studies to be initiated. Several of these isozymes are regulated by phosphorylation/dephosphorylation mechanisms.

Over 30 phosphodiesterases have been identified. Categories of phosphodiesterases include seven major classes. Class I phosphodiesterases include calmodulin-dependent phosphodiesterases which are expressed in tissues such as the brain, testes, sperm, coronary artery, lung, heart, and pancreas. Class II phosphodiesterases include cGMP-stimulated phosphodiesterases which are expressed in tissues such as the brain, adrenal gland, and the heart. Class III phosphodiesterases include cGMP-inhibited phosphodiesterases expressed in tissues such as T-lymphocytes, macrophages, platelets, smooth muscle, heart, and adipose tissue. Class IV phosphodiesterases include cAMP-specific phosphodiesterases which are expressed in tissues such as monocytes, leukocytes, and the central nervous system. Class V phosphodiesterases include cGMP-specific phosphodiesterases which are expressed in tissues such as lung, smooth muscle, platelets, and the aorta. Class VI phosphodiesterases include photoreceptor-specific phosphodiesterases expressed in the retina. Class VII phosphodiesterases include high affinity cAMP-specific phosphodiesterases.

Cyclic Nucleotide Phosphodiesterases

As is well-known in the art, a myriad of physiological processes are controlling by causing changes in the steady state levels of the second messengers cAMP and cGMP. One of the major mechanisms by which these levels are controlled is via the cyclic nucleotide PDEs that control their degradation by catalyzing the hydrolysis of a phosphodiester bond, yielding 5'-AMP and 5'-GMP, respectively.

Experimental data have demonstrated the role of cyclic nucleotide phosphodiesterases in a range of diseases, including inflammatory diseases such as asthma, chronic obstructive pulmonary disease, rheumatoid arthritis and atopy.

In mammals, four genes are known to code for cAMP-specific PDEs. These genes are known as PDE4A, PDE4B, PDE4C and PDE4D. This was first demonstrated in rats and later in humans and in mice. The four human and four rat genes show a one to one correspondence, in that each of the four human PDE4 genes is more closely related to its homologous rat gene than to any other human gene. The PDE4 genes are located on three different human chromosomes: PDE4B on chromosome 1, PDE4D on chromosome 5; PDE4A on p13.2 of chromosome 19 and PDE4C on p13.1 of chromosome 19. Their four murine homologues are each located in correspondingly conserved regions of the mouse genome. The mammalian PDE4 genes thus comprise a well-conserved multigene family.

The existence of a large number of mRNA transcripts from many of the mammalian PDE4 genes suggests that the genomic structure of these genes is likely to be complex. Partial genomic sequences have been published for the rat PDE4B and PDE4D genes. However, the published data indicate that sequences at the 5' end of the genes, which would include a number of upstream exons and promoter sites, were not included.

cGMP-stimulated 3',5'-cyclic nucleotide phosphodiesterase 2A (PDE2A)

The novel human protein, and encoding gene, provided by the present invention is an alternative splice form of cGMP-stimulated 3',5'-cyclic nucleotide phosphodiesterase 2A (PDE2A). Specifically, the phosphodiesterase provided by the present invention differs from known phosphodiesterases, particularly bovine PDE2A1 (gi116569) and human PDE2A3 (gi4505657), in exon 1. These difference are illustrated in the Figures, particularly in the amino acid sequence alignments shown in FIGS. 2 and 3.

For a further review of PDE2A and related proteins, see Rosman et al., *Gene* May 20, 1997;191(1):89–95; Sonnenburg et al., *J Biol Chem* Sep. 15, 1991;266(26):17655–61; Trong et al., *Biochemistry* Nov. 6, 1990;29(44):10280–8; and Charbonneau et al., *Proc Natl Acad Sci U S A* December 1986;83(24):9308–12.

Phosphodiesterase proteins, particularly alternative splice forms of PDE2A, are a major target for drug action and development. Accordingly, it is valuable to the field of pharmaceutical development to identify and characterize previously unknown splice forms of phosphodiesterase proteins. The present invention advances the state of the art by providing a previously unidentified human PDE2A alternative splice form.

SUMMARY OF THE INVENTION

The present invention is based in part on the identification of amino acid sequences of human phosphodiesterase peptides and proteins that are related to PDE2A, as well as allelic variants and other mammalian orthologs thereof. Specifically, the phosphodiesterase protein provided by the present invention is a novel alternative splice form of PDE2A. These unique peptide sequences, and nucleic acid sequences that encode these peptides, can be used as models for the development of human therapeutic targets, aid in the identification of therapeutic proteins, and serve as targets for the development of human therapeutic agents that modulate phosphodiesterase activity in cells and tissues that express the phosphodiesterase. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample.

DESCRIPTION OF THE FIGURE SHEETS

FIG. 1 provides the nucleotide sequence of a cDNA molecule that encodes the phosphodiesterase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample.

FIG. 2 provides the predicted amino acid sequence of the phosphodiesterase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the phosphodiesterase protein of the present invention (SEQ ID NO:3), allowing one to readily determine specific uses of inventions based on this molecular sequence. As illustrated in FIG. 3, SNPs were identified at 231 different nucleotide positions. FIG. 3 also provides a multiple alignment of isoform1 (11000567083206_pep), human PDE2A3 (gi4505657_pep) and bovine PDE2A1 (gi116569_pep) amino acid sequences, illustrating the differences in exon 1 between the phosphodiesterase of the present invention and known phosphodiesterases.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phosphodiesterase protein or part of a phosphodiesterase protein and are related to PDE2A. Specifically, the phosphodiesterase protein provided by the present invention is a novel alternative splice form of PDE2A. Utilizing these sequences, additional genomic sequences were assembled and transcript and/or cDNA sequences were isolated and characterized. Based on this analysis, the present invention provides amino acid sequences of human phosphodiesterase peptides and proteins that are related to the PDE2A subfamily, nucleic acid sequences in the form of transcript sequences, cDNA sequences and/or genomic sequences that encode these phosphodiesterase peptides and proteins, nucleic acid variation (allelic information), tissue distribution of expression, and information about the closest art known protein/peptide/domain that has structural or sequence homology to the phosphodiesterase of the present invention.

In addition to being previously unknown, the peptides that are provided in the present invention are selected based on their ability to be used for the development of commercially important products and services. Specifically, the present peptides are selected based on homology and/or structural relatedness to known phosphodiesterase proteins of the PDE2A subfamily and the expression pattern observed. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known PDE2A family or subfamily of phosphodiesterase proteins.

Specific Embodiments

Peptide Molecules

The present invention provides nucleic acid sequences that encode protein molecules that have been identified as being members of the phosphodiesterase family of proteins and are related to PDE2A (protein sequences are provided in FIG. 2, transcript/cDNA sequences are provided in FIG. 1 and genomic sequences are provided in FIG. 3). Specifically, the phosphodiesterase protein provided by the present invention is a novel alternative splice form of PDE2A. The peptide sequences provided in FIG. 2, as well as the obvious variants described herein, particularly allelic variants as identified herein and using the information in FIG. 3, will be referred herein as the phosphodiesterase peptides of the present invention, phosphodiesterase peptides, or peptides/proteins of the present invention.

The present invention provides isolated peptide and protein molecules that consist of, consist essentially of, or comprise the amino acid sequences of the phosphodiesterase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phosphodiesterase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phosphodiesterase peptide can be purified from cells that naturally express it, purified from cells that have been altered to express it (recombinant), or synthesized using known protein synthesis methods. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. For example, a nucleic acid molecule encoding the phosphodiesterase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phosphodiesterase peptides of the present invention are the naturally occurring mature proteins. A brief description of how various types of these proteins can be made/isolated is provided below.

The phosphodiesterase peptides of the present invention can be attached to heterologous sequences to form chimeric or fusion proteins. Such chimeric and fusion proteins comprise a phosphodiesterase peptide operatively linked to a heterologous protein having an amino acid sequence not substantially homologous to the phosphodiesterase peptide. "Operatively linked" indicates that the phosphodiesterase peptide and the heterologous protein are fused in-frame. The heterologous protein can be fused to the N-terminus or C-terminus of the phosphodiesterase peptide.

In some uses, the fusion protein does not affect the activity of the phosphodiesterase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phosphodiesterase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A phosphodiesterase peptide-encoding nucleic acid can be cloned into such an expression vector such that the fusion moiety is linked in-frame to the phosphodiesterase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phosphodiesterase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phosphodiesterase peptides of the present invention as well as being encoded by the same genetic locus as the phosphodiesterase peptide provided herein. The gene encoding the novel phosphodiesterase protein of the present invention is located on a genome component that has been mapped to human chromosome 11 (as indicated in FIG. 3), which is supported by multiple lines of evidence, such as STS and BAC map data.

Allelic variants of a phosphodiesterase peptide can readily be identified as being a human protein having a high degree (significant) of sequence homology/identity to at least a portion of the phosphodiesterase peptide as well as being encoded by the same genetic locus as the phosphodiesterase peptide provided herein. Genetic locus can readily be determined based on the genomic information provided in FIG. 3, such as the genomic sequence mapped to the reference human. The gene encoding the novel phosphodiesterase protein of the present invention is located on a genome component that has been mapped to human chromosome 11 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phosphodiesterase peptide encoding nucleic acid molecule under stringent conditions as more fully described below.

FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

Paralogs of a phosphodiesterase peptide can readily be identified as having some degree of significant sequence homology/identity to at least a portion of the phosphodiesterase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phosphodiesterase peptide encoding nucleic acid molecule under moderate to stringent conditions as more fully described below.

Orthologs of a phosphodiesterase peptide can readily be identified as having some degree of significant sequence homology/identity to at least a portion of the phosphodiesterase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phosphodiesterase peptide encoding nucleic acid molecule under moderate to stringent conditions, as more fully described below, depending on the degree of relatedness of the two organisms yielding the proteins.

Non-naturally occurring variants of the phosphodiesterase peptides of the present invention can readily be generated using recombinant techniques. Such variaits include, but are not limited to deletions, additions and substitutions in the amino acid sequence of the phosphodiesterase peptide. For example, one class of substitutions are conserved amino acid substitution. Such substitutions are those that substitute a given amino acid in a phosphodiesterase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phosphodiesterase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as phosphodiesterase activity or in assays such as an in vitro proliferative activity. Sites that are critical for binding partner/substrate binding can also be determined by structural analysis such as crystallization, nuclear magnetic resonance or photoaffinity labeling (Smith et al., *J Mol. Biol.* 224:899–904 (1992); de Vos et al. *Science* 255:306–312 (1992)).

The present invention further provides fragments of the phosphodiesterase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phosphodiesterase peptide. Such fragments can be chosen based on the ability to retain one or more of the biological activities of the phosphodiesterase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phosphodiesterase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available: to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phosphodiesterase: peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the phosphodiesterase peptides of the present invention also encompass derivatives or analogs in which a substituted amino acid residue is not one encoded by the genetic code, in which a substituent group is included, in which the mature phosphodiesterase peptide is fused with another compound, such as a compound to increase the half-life of the phosphodiesterase peptide (for example, polyethylene glycol), or in which the additional amino acids are fused to the mature phosphodiesterase peptide, such as a leader or secretory sequence or a sequence for purification of the mature phosphodiesterase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phosphodiesterase-effector protein interaction or phosphodiesterase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phosphodiesterases isolated from humans and their human/mammalian orthologs serve as targets for identifying agents for use in mammalian therapeutic applications, e.g. a human drug, particularly in modulating a biological or pathological response in a cell or tissue that expresses the phosphodiesterase. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. A large percentage of pharmaceutical agents are being developed that modulate the activity of phosphodiesterase proteins, particularly members of the PDE2A subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. Such uses can readily be determined using the information provided herein, that which is known in the art, and routine experimentation.

The proteins of the present invention (including variants and fragments that may have been disclosed prior to the present invention) are useful for biological assays related to phosphodiesterases that are related to members of the PDE2A subfamily. Such assays involve any of the known phosphodiesterase functions or activities or properties useful for diagnosis and treatment of phosphodiesterase-related conditions that are specific for the subfamily of phosphodiesterases that the one of the present invention belongs to, particularly in cells and tissues that express the phosphodiesterase. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain.

The proteins of the present invention are also useful in drug screening assays, in cell-based or cell-free systems. Cell-based systems can be native, i.e., cells that normally express the phosphodiesterase, as a biopsy or expanded in cell culture. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. In an alternate embodiment, cell-based assays involve recombinant host cells expressing the phosphodiesterase protein.

The polypeptides can be used to identify compounds that modulate phosphodiesterase activity of the protein in its natural state or an altered form that causes a specific disease or pathology associated with the phosphodiesterase. Both the phosphodiesterases of the present invention and appropriate variants and fragments can be used in high-throughput screens to assay candidate compounds for the ability to bind to the phosphodiesterase. These compounds can be further screened against a functional phosphodiesterase to determine the effect of the compound on the phosphodiesterase activity. Further, these compounds can be tested in animal or invertebrate systems to determine activity/effectiveness. Compounds can be identified that activate (agonist) or inactivate (antagonist) the phosphodiesterase to a desired degree.

Further, the proteins of the present invention can be used to screen a compound for the ability to stimulate or inhibit interaction between the phosphodiesterase protein and a molecule that normally interacts with the phosphodiesterase protein, e.g. a substrate or a component of the signal pathway that the phosphodiesterase protein normally interacts (for example, another phosphodiesterase). Such assays typically include the steps of combining the phosphodiesterase protein with a candidate compound under conditions that allow the phosphodiesterase protein, or fragment, to interact with the target molecule, and to detect the formation of a complex between the protein and the target or to detect the biochemical consequence of the interaction with the phosphodiesterase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phosphodiesterases or appropriate fragments containing mutations that affect phosphodiesterase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phosphodiesterase activity. The assays typically involve an assay of events in the signal transduction pathway that indicate phosphodiesterase activity. Thus, the phosphorylation of a substrate, activation of a protein, a change in the expression of genes that are up- or down-regulated in response to the phosphodiesterase protein dependent signal cascade can be assayed.

Any of the biological or biochemical functions mediated by the phosphodiesterase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phosphodiesterase can be assayed. Experirnental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain.

Binding and/or activating compounds can also be screened by using chimeric phosphodiesterase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phosphodiesterase. Accordingly, a different set of signal transduction components is available as an endpoint assay for activation. This allows for assays to be performed in other than the specific host cell from which the phosphodiesterase is derived.

The proteins of the present invention are also useful in competition binding assays in methods designed to discover compounds that interact with the phosphodiesterase (e.g. binding partners and/or ligands). Thus, a compound is exposed to a phosphodiesterase polypeptide under conditions that allow the compound to bind or to otherwise interact with the polypeptide. Soluble phosphodiesterase polypeptide is also added to the mixture. If the test compound interacts with the soluble phosphodiesterase polypeptide, it decreases the amount of complex formed or activity from the phosphodiesterase target. This type of assay is particularly useful in cases in which compounds are sought that interact with specific regions of the phosphodiesterase. Thus, the soluble polypeptide that competes with the target phosphodiesterase region is designed to contain peptide sequences corresponding to the region of interest.

To perform cell free drug screening assays, it is sometimes desirable to immobilize either the phosphodiesterase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phosphodiesterase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphodiesterase-binding protein and a candidate compound are incubated in the phosphodiesterase protein-presenting wells and the amount of complex trapped in the well can be quantitated. Methods for detecting such complexes, in addition to those described above for the GST-immobilized complexes, include immunodetection of complexes using antibodies reactive with the phosphodiesterase protein target molecule, or which are reactive with phosphodiesterase protein and compete with the target molecule, as well as enzyme-linked assays which rely on detecting an enzymatic activity associated with the target molecule.

Agents that modulate one of the phosphodiesterases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phosphodiesterase protein activity identified according to these drug screening assays can be used to treat a subject with a disorder mediated by the phosphodiesterase pathway, by treating cells or tissues that express the phosphodiesterase. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. These methods of treatment include the steps of administering a modulator of phosphodiesterase activity in a pharmaceutical composition to a subject in need of such treatment, the modulator being identified as described herein.

In yet another aspect of the invention, the phosphodiesterase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phosphodiesterase and are involved in phosphodiesterase activity. Such phosphodiesterase-binding proteins are also likely to be involved in the propagation of signals by the phosphodiesterase proteins or phosphodiesterase targets as, for example, downstream elements of a phosphodiesterase-mediated signaling pathway. Alternatively, such phosphodiesterase-binding proteins are likely to be phosphodiesterase inhibitors.

The two-hybrid system is based on the modular nature of most transcription factors, which consist of separable DNA-binding and activation domains. Briefly, the assay utilizes two different DNA constructs. In one construct, the gene that codes for a phosphodiesterase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phosphodiesterase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phosphodiesterase protein.

This invention further pertains to novel agents identified by the above-described screening assays. Accordingly, it is within the scope of this invention to further use an agent identified as described herein in an appropriate animal model. For example, an agent identified as described herein (e.g., a phosphodiesterase-modulating agent, an antisense phosphodiesterase nucleic acid molecule, a phosphodiesterase-specific antibody, or a phosphodiesterase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phosphodiesterase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The method involves contacting a biological sample with a compound capable of interacting with the phosphodiesterase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phosphodiesterase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharnacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphodiesterase protein in which one or more of the phosphodiesterase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phosphodiesterase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. Accordingly, methods for treatment include the use of the phosphodiesterase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phosphodiesterase proteins. Antibodies can be prepared from any region of the peptide as described herein. However, preferred regions will include those involved in function/activity and/or phosphodiesterase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. Thus, where a specific protein has been correlated with expression in a specific tissue, antibodies that are specific for this protein can be used to identify a tissue type.

The antibodies are also useful for inhibiting protein function, for example, blocking the binding of the phosphodiesterase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a phosphodiesterase peptide or protein of the present invention (cDNA, transcript and genomic sequence). Such nucleic acid molecules will consist of, consist essentially of, or comprise a nucleotide sequence that encodes one of the phosphodiesterase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention firther provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phosphodiesterase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genornic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the phosphodiesterase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are usefull in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel phosphodiesterase protein of the present invention is located on a genome component that has been mapped to human chromosome 11 (as indicated in FIG. 3), which is supported by multiple lines of evidence, such as STS and BAC map data.

FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 231 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel phosphodiesterase protein of the present invention is located on a genome component that has been mapped to human chromosome 11 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phosphodiesterase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phosphodiesterase protein, such as by measuring a level of a phosphodiesterase-encoding nucleic acid in a sample of cells from a subject e.g., mRNA or genomic DNA, or determining if a phosphodiesterase gene has been mutated. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain.

Nucleic acid expression assays are useful for drug screening to identify compounds that modulate phosphodiesterase nucleic acid expression.

The invention thus provides a method for identifying a compound that can be used to treat a disorder associated with nucleic acid expression of the phosphodiesterase gene, particularly biological and pathological processes that are mediated by the phosphodiesterase in cells and tissues that express it. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample. The method typically includes assaying the ability of the compound to modulate the expression of the phosphodiesterase nucleic acid and thus identifying a compound that can be used to treat a disorder characterized by undesired phosphodiesterase nucleic acid expression. The assays can be performed in cell-based and cell-free systems. Cell-based assays include cells naturally expressing the phosphodiesterase nucleic acid or recombinant cells genetically engineered to express specific nucleic acid sequences.

The assay for phosphodiesterase nucleic acid expression can involve direct assay of nucleic acid levels, such as mRNA levels, or on collateral compounds involved in the signal pathway. Further, the expression of genes that are up- or down-regulated in response to the phosphodiesterase protein signal pathway can also be assayed. In this embodiment the regulatory regions of these genes can be operably linked to a reporter gene such as luciferase.

Thus, modulators of phosphodiesterase gene expression can be identified in a method wherein a cell is contacted with a candidate compound and the expression of mRNA determined. The level of expression of phosphodiesterase mRNA in the presence of the candidate compound is compared to the level of expression of phosphodiesterase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phosphodiesterase nucleic acid expression in cells and tissues that express the phosphodiesterase. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. Modulation includes both up-regulation (i.e. activation or agonization) or down-regulation (suppression or antagonization) or nucleic acid expression.

Alternatively, a modulator for phosphodiesterase nucleic acid expression can be a small molecule or drug identified using the screening assays described herein as long as the drug or small molecule inhibits the phosphodiesterase nucleic acid expression in the cells and tissues that express the protein. Experimental data as provided in FIG. 1 indicates expression in humans in the amygdala, brain (including infant brain), uterus, testis, placenta choriocarcinomas, Hela cells, and a pooled melanocyte/fetal heart/pregnant uterus sample.

The nucleic acid molecules are also useful for monitoring the effectiveness of modulating compounds on the expression or activity of the phosphodiesterase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phosphodiesterase nucleic acid expression, and particularly in qualitative changes that lead to pathology. The nucleic acid molecules can be used to detect mutations in phosphodiesterase genes and gene expression products such as mRNA. The nucleic acid molecules can be used as hybridization probes to detect naturally occurring genetic mutations in the phosphodiesterase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphodiesterase gene associated with a dysfunction provides a diagnostic tool for an active disease or susceptibility to disease when the disease results from overexpression, underexpression, or altered expression of a phosphodiesterase protein.

Individuals carrying mutations in the phosphodiesterase gene can be detected at the nucleic acid level by a variety of techniques. FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements. The gene encoding the novel phosphodiesterase protein of the present invention is located on a genome component that has been mapped to human chromosome 11 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phosphodiesterase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phosphodiesterase gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phosphodiesterase gene in an individual in order to select an appropriate compound or dosage regimen for treatment. FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phosphodiesterase gene expression in cells, tissues, and organisms. A DNA antisense nucleic acid molecule is designed to be complementary to a region of the gene involved in transcription, preventing transcription and hence production of phosphodiesterase protein. An antisense RNA or DNA nucleic acid molecule would hybridize to the mRNA and thus block translation of mRNA into phosphodiesterase protein.

Alternatively, a class of antisense molecules can be used to inactivate mRNA in order to decrease expression of phosphodiesterase nucleic acid. Accordingly, these molecules can treat a disorder characterized by abnormal or undesired phosphodiesterase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphodiesterase protein, such as substrate binding.

The nucleic acid molecules also provide vectors for gene therapy in patients containing cells that are aberrant in phosphodiesterase gene expression. Thus, recombinant cells, which include the patient's cells that have been engineered ex vivo and returned to the patient, are introduced into an individual where the cells produce the desired phosphodiesterase protein to treat the individual.

The invention also encompasses kits for detecting the presence of a phosphodiesterase nucleic acid in a biological sample. Experimental data as provided in FIG. 1 indicates that phosphodiesterase proteins of the present invention are expressed in humans in the amygdala, brain (including infant brain), uterus, testis, placenta choriocarcinomas, Hela cells, and a pooled melanocyte/fetal heart/pregnant uterus sample, as indicated by virtual northern blot analysis. PCR-based tissue screening panels also indicate expression in the brain. For example, the kit can comprise reagents such as a labeled or labelable nucleic acid or agent capable of detecting phosphodiesterase nucleic acid in a biological sample; means for determining the amount of phosphodiesterase nucleic acid in the sample; and means for comparing the amount of phosphodiesterase nucleic acid in the sample with a standard. The compound or agent can be packaged in a suitable container. The kit can further comprise instructions for using the kit to detect phosphodiesterase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phosphodiesterase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phosphodiesterase gene of the present invention. FIG. 3 provides information on SNPs that have been found in the gene encoding the phosphodiesterase protein of the present invention. SNPs were identified at 231 different nucleotide positions. Changes in the amino acid sequence caused by these SNPs can readily be determined using the universal genetic code and the protein sequence provided in FIG. 2 as a reference. These SNPs may also affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phosphodiesterase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or mdre cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phosphodiesterases, appropriate secretion signals are incorporated into the vector. The signal sequence can be endogenous to the peptides or heterologous to these peptides.

Where the peptide is not secreted into the medium, which is typically the case with phosphodiesterases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a phosphodiesterase protein or peptide that can be further purified to produce desired amounts of phosphodiesterase protein or fragments. Thus, host cells containing expression vectors are useful for peptide production.

Host cells are also useful for conducting cell-based assays involving the phosphodiesterase protein or phosphodiesterase protein fragments, such as those described above as well as other formats known in the art. Thus, a recombinant host cell expressing a native phosphodiesterase protein is useful for assaying compounds that stimulate or inhibit phosphodiesterase protein function.

Host cells are also useful for identifying phosphodiesterase protein mutants in which these functions are affected. If the mutants naturally occur and give rise to a pathology, host cells containing the mutations are useful to assay compounds that have a desired effect on the mutant phosphodiesterase protein (for example, stimulating or inhibiting function) which may not be indicated by their effect on the native phosphodiesterase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphodiesterase protein and identifying and evaluating modulators of phosphodiesterase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphodiesterase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phosphodiesterase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, phosphodiesterase protein activation, and signal transduction, may not be evident from in vitro cell-free or cell-based assays. Accordingly, it is useful to provide non-human transgenic animals to assay in vivo phosphodiesterase protein function, including substrate interaction, the effect of specific mutant phosphodiesterase proteins on phosphodiesterase protein function and substrate interaction, and the effect of chimeric phosphodiesterase proteins. It is also possible to assess the effect of null mutations, that is mutations that substantially or completely eliminate one or more phosphodiesterase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
    (a) a nucleotide sequence that encodes a protein comprising the amino acid sequence of SEQ ID NO:2;
    (b) a nucleic acid molecule consisting of the nucleic acid sequence of SEQ ID No: 1;
    (c) a nucleic acid molecule consisting of the nucleic acid sequence of SEQ ID No: 3; and
    (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. A vector according to claim 2, wherein said vector is selected from the group consisting of a plasmid, virus, and bacteriophage.

6. A vector according to claim 2, wherein said isolated nucleic acid molecule is inserted into said vector in proper orientation and correct reading frame such that the protein of SEQ ID NO: 2 may be expressed by a cell transformed with said vector.

7. A vector according to claim 6, wherein said isolated nucleic acid molecule is operatively linked to a promoter sequence.

8. An isolated polynucleotide consisting of a nucleotide sequence set forth in SEQ ID NO:1.

9. An isolated polynucleotide consisting of a nucleotide sequence set forth in SEQ ID NO:3.

10. A method for detecting the presence of a nucleic acid molecule of claim 1 in a sample, said method comprising
    contacting the sample with an oligonucleotide comprising at least 20 contiguous nucleotides that hybridizes to said nucleic acid molecule under stringent conditions, wherein the stringent condition is hybridization in 6×sodium chloride/sodium citrate (SSC) at about 45° C., followed by one or more washes in 0.2×SCC, 0.1% SDS at 50–65° C., and
    determining whether the oligonucleotide binds to said nucleic acid molecule in the sample.

* * * * *